US008686224B2

(12) United States Patent
Ryan et al.

(10) Patent No.: US 8,686,224 B2
(45) Date of Patent: Apr. 1, 2014

(54) PLANT DEFENSE SIGNAL PEPTIDES

(75) Inventors: Clarence A. Ryan, Pullman, WA (US); Patricia Louise Ryan, legal representative, Pullman, WA (US); Gregory L. Pearce, Palouse, WA (US); Alisa Huffaker, Pullman, WA (US); Yube Yamaguchi, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 13/592,971

(22) Filed: Aug. 23, 2012

(65) Prior Publication Data

US 2013/0061352 A1 Mar. 7, 2013

Related U.S. Application Data

(63) Continuation of application No. 12/386,247, filed on Apr. 14, 2009, now abandoned, which is a continuation-in-part of application No. 11/795,733, filed as application No. PCT/US2006/002661 on Jan. 24, 2006, now abandoned.

(60) Provisional application No. 60/647,708, filed on Jan. 26, 2005.

(51) Int. Cl.

| | |
|---|---|
| *A01H 5/00* | (2006.01) |
| *A01H 5/10* | (2006.01) |
| *C12N 15/09* | (2006.01) |
| *C12N 15/82* | (2006.01) |

(52) U.S. Cl.
USPC .......... 800/279; 800/298; 800/278; 435/69.1; 435/69.7; 536/23.6

(58) Field of Classification Search
None
See application file for complete search history.

(56) References Cited

U.S. PATENT DOCUMENTS

2004/0123343 A1* 6/2004 La Rosa et al. ............... 800/278

FOREIGN PATENT DOCUMENTS

| | | | |
|---|---|---|---|
| WO | WO-94/16077 | A1 | 7/1994 |
| WO | WO-95/28423 | A1 | 10/1995 |
| WO | WO-98/06748 | A1 | 2/1998 |
| WO | WO-98/26082 | A1 | 6/1998 |

OTHER PUBLICATIONS

Feng et al. Accession No. Q7X6RO; Deposited Oct. 1, 2003.*
Sasaki et al . Accession Nos: Q6Z4W0 and Q6Z4V8; Deposited Jul. 5, 2004.*
Sasaki et al. Accession Nos: Q6Z4W0 and Q6Z4V8; Deposited Jul. 5, 2004.*
Altschul, S. et al. (1997). "Gapped BLAST and PSI-BLAST: a new generation of protein database search programs," *Nucleic Acids Research* 25(17):3389-3402.
An, G. et al. (1988). "Organ-Specific and Developmental Regulation of the Nopaline Synthase Promoter in Transgenic Tobacco Plants," *Plant Physiology* 88(3):547-552.
An, G. et al. (1989). "Functional Analysis of the 3' Control Region of the Potato Wound-Inducible Proteinase Inhibitor II Gene," *The Plant Cell* 1(1):115-122.
Beaucage, S. L. and Caruthers, M. H. (1981). "Deoxynucleoside Phosphoramidites—A New Class of Key Intermediates for Deoxypolynucleotide Synthesis," *Tetrahedron Letters* 22(20):1859-1862.
Bisgrove, S. et al. (1994) "A Disease Resistance Gene in *Arabidopsis* with Specificity for Two Different Pathogen Avirulence Genes," *The Plant Cell* 6:927-933.
Bustos, M. et al. (1989). "Regulation of β-Glucuronidase Expression in Transgenic Tobacco Plants by an A/T-Rich, cis- Acting Sequence Found Upstream of a French Bean β-Phaseolin Gene," *The Plant Cell* 1(9):839-853.
Callis, J. et al. (1988). "Heat Inducible Expression of a Chimeric Maize hsp7oCAT Gene in Maize Protoplasts," *Plant Physiology* 88(4):965-968.
Clark, S. et al. (1997.) "The CLAVATA1 Gene Encodes a Putative Receptor Kinase That Controls Shoot and Floral Meristem Size in *Arabidopsis," Cell* 89:575-585.
Clough, S. and Bent, A. (1998). "The CLAVATA1 Gene Encodes a Putative Receptor Kinase That Controls Shoot and Floral Meristem Size in *Arabidopsis," The Plant Journal* 16(6):735-743.
Coego, A. et al. (2005). "An *Arabidopsis* Homeodomain Transcription Factor, Overexpressor of Cationic Peroxidase 3, Mediates Resistance to Infection by Necrotrophic Pathogens," *The Plant Cell* 17(7):2123-2137.
Craigon, D. et al. (2004). "NASCArrays: a repository for microarray data generated by NASC's transcriptomics service," *Nucleic Acids Research* 32:D575-D577.
Dangl, J. (1995). "Piece de Resistance: Novel Classes of Plant Disease Resistance Genes," *Cell* 80:363-366.
Dekeyser, R. et al. (1990). "Transient Gene Expression in Intact and Organized Rice Tissues,". *The Plant Cell* 2(7):591-602.
Dixon, R. (1990). "Molecular Communication in Interactions Between Plants and Microbial Pathogens," *Annu. Rev. Plant Physiol. Plant Mol. Bioi.* 41:339-67.

(Continued)

*Primary Examiner* — Medina A Ibrahim
(74) *Attorney, Agent, or Firm* — Whitham Curtis Christofferson & Cook, P.C.

(57) ABSTRACT

A 23 amino acid peptide, AtPep1, plays an important role as a signaling component of the innate immune system of *Arabidopsis*. The peptide precursor gene is transcribed in response to elicitors generated by pathogens, and AtPep1 is produced to amplify the signaling pathways. Seven paralogs of the AtproPep1 gene have been identified in the *Arabidopsis* genome, and orthologs have been identified in species of several agriculturally important families. AtPep1 and its paralogs and orthologs play important roles as endogenous signals to amplify innate immunity. The sequences of two AtPep1 receptors from *Arabidopsis* are also provided.

11 Claims, 51 Drawing Sheets

(56) References Cited

OTHER PUBLICATIONS

Draper, J. et al. (1982). "Ti Plasmid Homologous Sequences Present in Tissues from *Agrobacterium* Plasmid-transformed Petunia Protoplasts," *Plant and Cell Physiology* 23(3):451-458.
Ellingboe, A. (1981). "Changing Concepts in Host-Pathogen Genetics," *Ann. Rev. Phytopathol* 19:125-143.
Emanuelsson, O. et al. (1999). "ChloroP, a neural network-based method for predicting chloroplast transit peptides and their cleavage sites," *Protein Science* 8:978-984.
Emanuelsson, O. et al. (2000). "Predicting Subcellular Localization of Proteins Based on their N-terminal Amino Acid Sequence," *J. Mol. Biol.* 300:1005-1016.
Felix, G. and Boller, T. (1995). "Systemin induces rapid ion fluxes and ethylene biosynthesis in L ycopersicon peruvianum cells," *The Plant Journal* 7(3):381-389.
Fellbrich, G. et al. (2002). "NPP1, a Phytophthora-associated trigger of plant defense in parsley and *Arabidopsis," The Plant Journal* 32:375-390.
Flor, H. H. (1971). "Current Status of the Gene-For-Gene Concept," *Annu. Rev. Phytopathol.* 9:275-296.
Freeman, J.P. et al. (1984). "A Comparison of Methods for Plasmid Delivery into Plant Protoplasts," *Plant and Cell Physiol* 25(8):1353-1365.
Fromm, H. et al. (1989). "An Octopine Synthase Enhancer Element Directs Tissue-Specific Expression and Binds ASF-1, a Factor from Tobacco Nuclear Extracts," *The Plant Cell* 1(10):977-984.
Fromm, M. et al. (1986). "Stable transformation of maize after gene transfer by electroporation," *Nature* 319:791-793.
Gleave, A. (1992). "A versatile binary vector system with a T-DNA organisational structure conducive to efficient integration of cloned DNA into the plant genome," *Plant Molecular Biology* 20:1203-1207.
Gomez-Gomez, L. and Boller, T. (2002). "Flagellin perception: a paradigm for innate immunity," *TRENDS in Plant Science* 7(6):251-256.
Gordon-Kamm, W. et al. (1990). "Transformation of Maize Cells and Regeneration of Fertile Transgenic Plants," *The Plant Cell* 2:603-618.
Grant, M. et al. (1995). "Structure of the *Arabidopsis* RPM1 Gene Enabling Dual Specificity Disease Resistance," *Science* 269:843-846.
Guttman, D. (2004). "Plants as models for the study of human pathogenesis," *Biotechnology Advances* 22:363-382.
Guzman, P. and Ecker, J. (1990). "Exploiting the Triple Response of *Arabidopsis* to Identify Ethylene-Related Mutants," *The Plant Cell* 2(6):513-523.
Haas, B. et al. (2002). "Full-length messenger RNA sequences greatly improve genome annotation," *Genome Biology* 2002, 3(6):research0029.1-0029.12.
Hahlbrock, K. et al. (1995). "Oligopeptide elicitor-mediated defense gene activation in cultured parsley cells," *Proc. Natl. Acad. Sci. USA* 92:4150-4157.
Hammond-Kosack, K. and Parker, J. (2003). "Deciphering plant-pathogen communication: fresh perspectives for molecular resistance breeding," *Current Opinion in Biotechnology* 14:177-193.
He, S. et al. (1993). "*Pseudomonas syringae* pv. syringae HarpinPSS: A Protein That Is Secreted via the Hrp Pathway and Elicits the Hypersensitive Response in Plants," *Cell* 73:1255-1266.
Jones, D. and Takemoto, D. (2004). "Plant innate immunity—direct and indirect recognition of general and specific pathogen-associated molecules," *Current Opinion in Immunology* 16:48-62.
Kamoun, S. (2001). "Nonhost resistance to *Phytophthora*: novel prospects for a classical problem," *Current Opinion in Plant Biology* 4:295-300.
Kanehisa, M. (1984). "Use of statistical criteria for screening potential homologies in nucleic acid sequences," *Nucleic Acids Research* 12(1):203-213.
Kanehisa, M. et al. (1984). "Computer analysis and structure prediction of nucleic acid and proteins," *Nucleic Acids Research* 12(1):417-428.
Keen, N. T. (2004). "Gene-For-Gene Complementarity in Plant -Pathogen Interactions," *Annu. Rev. Genet.* 24:447-463.
Kindle, K. (1990). "High-frequency nuclear transformation of *Chlamydomonas reinhardtii," Proc. Natl. Acad. Sci. USA* 87:1228-1232.
Kobe, B. and Deisenhofer, J. (1994). "The leucine-rich repeat: a versatile binding motif," *Trends in Biochemical Sciences* 19(10):415-421.
Kuhlemeier, C. et al. (1989). "The Pea rbcS-3A Promoter Mediates Light Responsiveness but Not Organ Specificity," *The Plant Cell* 1(4):471-478.
Kunze, G. et al. (2004). "The N Terminus of Bacterial Elongation Factor Tu Elicits Innate Immunity in *Arabidopsis* Plants," *The Plant Cell* 16(12):3496-3507.
Lazo, G. et al. (1991). "A DNA Transformation Competent *Arabidopsis* Genomic Library in *Agrobacterium," Nature Biotechnology* 9:963-967.
Lorenzo, O. et al. (2003). "Ethylene Response Factor1 Integrates Signals from Ethylene and Jasmonate Pathways in Plant Defense," *The Plant Cell* 15(1):165-178.
Lorenzo, O. et al. (2004). "Jasmonate-Insensitive1 Encodes a MYC Transcription Factor Essential to Discriminate between Different Jasmonate-Regulated Defense Responses in *Arabidopsis," The Plant Cell* 16(7):1938-1950.
Lorenzo, O. and Solano, R. (2005). "Molecular players regulating the jasmonate signalling network," *Current Opinion in Plant Biology* 8:532-540.
Mackerness, S.A.-H. et al. (1999). "Ultraviolet-B-induced stress and changes in gene expression in *Arabidopsis thaliana*: role of signaling pathways controlled by jasmonic acid, ethylene and reactive oxygen species," *Plant, Cell and Environment* 22:1413-1423.
Marcotte, W. et al. (1989). "Abscisic Acid-Responsive Sequences from the Em Gene of Wheat," *The Plant Cell* 1(10):969-976.
Matsubayashi, Y. et al. (2002). "An LRR Receptor Kinase Involved in Perception of a Peptide Plant Hormone, Phytosulfokine," *Science, New Series* 296(5572):1470-1472.
Matteucci, M. D. and Caruthers, M. H. (1981). "Synthesis of Deoxyoligonucleotides on a Polymer Supportl," *J. Am. Chem. Soc.* 103:3185-3191.
Mauch-Mani, B. and Metraux, J. (1998). "Salicylic Acid and Systemic Acquired Resistance to Pathogen Attack," *Annals of Botany* 82:535-540.
McGurl, B. et al. (1994). "Overexpression of the prosystemin gene in transgenic tomato plants generates a systemic signal that constitutively induces proteinase inhibitor synthesis," *Proc. Natl. Acad. Sci. USA* 91:9799-9802.
Moyen, C. and Johannes, E. (1996). "Systemin transiently depolarizes the tomato mesophyll cell membrane and antagonizes fusicoccin-induced extracellular acidification of mesophyll tissue," *Plant, Cell and Environment* 19:464-470.
Nakai, K. and Kanehisa, M. (1991). "Expert system for predicting protein localization sites in gram-negative bacteria," *Proteins* 11(2):95-110.
Navarro, L. et al. (2004). "The Transcriptional Innate Immune Response to flg22. Interplay and Overlap with Avr Gene- Dependent Defense Responses and Bacterial Pathogenesis," *Plant Physiology* 135(2)1113-1128.
Nimchuk, Z. et al. (2003). "Recognition and Response in the Plant Immune System," *Annu. Rev. Genet.* 37:579-609.
Nishimura, C. et al. (2004). "Histidine Kinase Homologs That Act as Cytokinin Receptors Possess Overlapping Functions in the Regulation of Shoot and Root Growth in *Arabidopsis," The Plant Cell* 16(6):1365-1377.
Nurnberger, T. and Scheel, D. (2001). "Signal transmission in the plant immune response," *TRENDS in Plant Science* 6(8):372-379.
Nurnberger, T. et al. (2004). "Innate immunity in plants and animals: striking similarities and obvious differences," *Immunological Reviews* 198:249-266.

(56) References Cited

OTHER PUBLICATIONS

Odel, J. et al. (1985). "Identification of DNA sequences required for activity of the cauliflower mosaic virus35S promoter," *Nature* 313(28):810-812.
O'Donnell, V. et al. (1993). "Studies on the inhibitory mechanism of iodonium compounds with special reference to neutrophil NADPH oxidase," *Biochem J.* 298:41-49.
Pearce, G. and Ryan, C. (2003). "Systemic Signaling in Tomato Plants for Defense against Herbivores," *J. Biol. Chem.* 278(32):30044-30050.
Pearce, G. et al. (1991). "A Polypeptide from Tomato Leaves Induces Wound-Inducible Proteinase Inhibitor Proteins," *Science, New Series* 253(5022):895-898.
Pearce, G. et al. (2001). "Production of multiple plant hormones from a single polyprotein precursor," *Nature* 411:817-820.
Pearce, G. et al. (2001). "RALF, a 5-kDa ubiquitous polypeptide in plants, arrests root growth and development," *PNAS* 98(22):12843-12847.
Penninckx, I. et al. (1996). "Pathogen-Induced Systemic Activation of a Plant Defensin Gene in *Arabidopsis* Follows a Salicylic Acid-Independent Pathway," *The Plant Cell* 8(12):2309-2323.
Penninckx, I. et al. (1998). "Concomitant Activation of Jasmonate and Ethylene Response Pathways Is Required for Induction of a Plant Defensin Gene in *Arabidopsis," The Plant Cell* 10(12):2103-2113.
Rosahl, S. et al. (1987). "Expression of a tuber-specific storage protein in transgenic; tobacco plants: Demonstration of an esterase activity," *EMBO Journal* 6:1155-1159.
Ryals, J. et al. (1995). "Signal transduction in systemic acquired resistance," *Proc. Natl. Acad. Sci. USA* 92:4202-4205.
Ryan, C. and Pearce, G. (2004). "Plant Signaling: Peptides," *Encycl Biol Chem* 3:381-384.
Ryan, C. et al. (2002). "Polypeptide Hormones," *The Plant Cell Signal Transduction* 14(Suppl):S251-S264.
Schnaffner, A. and Sheen, J. (1991). "Maize rbcS Promoter Activity Depends on Sequence Elements Not Found in Dicot rbcS Promoters," *The Plant Cell* 3(9):997-1012.
Scheer, J. and Ryan, C. (1999). "A 160-kD Systemin Receptor on the Surface of *Lycopersicon* peruvianum Suspension-Cultured Cells," *The Plant Cell* 11(8):1525-1535.
Scheer, J. and Ryan, C. (2002). "The systemin receptor SR160 from *Lycopersicon* peruvianum is a member of the LRR receptor kinase family," *PNAS* 99(14):9585-9590.
Schernthaner, M.A. et al. (1988). "Endosperm-specific activity of a zein gene promoter in transgenic tobacco plants," *EMBO Journal* 7:1249-1255.
Schneitz, K. (2002). "Plant biology Paper alert," *Current Opinion in Plant Biology* 5:1-7.
Shevchenko, A. et al. (1996). "Mass Spectrometric Sequencing of Proteins from Silver-Stained Polyacrylamide Gels," *Anal. Chem.* 68:850-858.
Siebertz, B. et al. (1989). "cis-Analysis of the Wound-Inducible Promoter wun1 in Transgenic Tobacco Plants and Histochemical Localization of Its Expression," *The Plant Cell* 1(10):961-968.
Simpson, J. et al. (1985). "Light-inducible and tissue-specific expression of a chimeric gene under control of the 5'-flanking sequence of a pea chlorophyll a/b binding protein gene," *The EMBO Journal* 4(11):2723-2729.
Staskawicz, B. et al. (1995). "Molecular Genetics of Plant Disease Resistance," *Science, New Series* 268(5211):661-667.
Staskawicz, B. et al. (2001). "Common and Contrasting Themes of Plant and Animal Diseases," *Science, New Series* 292(5525):2285-2289.
Staswick, P. et al. (1998). "Jasmonate signaling mutants of *Arabidopsis* are susceptible to the soil fungus Pythium irregulare," *The Plant Journal* 15(6):747-754.
Stratman, J. et al. (2000). "Suramin inhibits initiation of defense signaling by systemin, chitosan, and a β-glucan elicitor in suspension-cultured *Lycopersicon* peruvianum cells," *PNAS* 97(16):8862-8867.
Takayama, S. et al. (2001). "Direct ligand±receptor complex interaction controls *Brassica* self-incompatibility," *Nature* 413:534-538.
Thornberg, R. et al. (1987). "Wound-inducible expression of a potato inhibitor II-chloramphenicol acetyltransferase gene fusion in transgenic tobacco plants," *Proc. Natl. Acad. Sci. USA* 84:744-748.
Toufighi, K. et al. (2005). "The Botany Array Resource: e-Northerns, Expression Angling, and promoter analyses," *The Plant Journal* 43:153-163.
Van den Ackerveken, G. (1993). "The AVR9 Race-Specific Elicitor of *Cladosporium fulvum* Is Processed by Endogenous and Plant Proteases," *Plant Physiology* 103(1):91-96.
Vijayan, P. et al. (1998). "A role for jasmonate inpathogen defense of *Arabidopsis," Proc. Natl. Acad. Sci. USA* 95:7209-7214.
Wetmur and Davidson. (1968). "Kinetics of renaturation of DNA," *Journal of Molecular Biology* 31(3):349-370.
Zhang, W. and Wu, R. (1988). "Efficient regeneration of transgenic plants from rice protoplasts and correctly regulated expression of the foreign gene in the plants," *Theor Appl Genet* 76:835-840.
Zimmerli, L. et al. (2004). "Host and non-host pathogens elicit different jasmonate/ ethylene responses in *Arabidopsis," The Plant Journal* 40:633-646.

* cited by examiner

FIGURE 1a

AtproPep1 mRNA - 499 bp

```
  1 actcacatat aaaaaacagc ttcactcctc tcaccaaaac taatcagatt aataaaagtt
 61 ttcctctgtc ttatcagatc tcaatggaga aatcagatag acgaagcgaa gaaagtcacc
121 tatggattcc tcttcagtgc ctcgaccaaa ccctcagagc tatcttgaaa tgccttggtc
181 tttttcatca agattctccg acaacgtcct ctcccggaac ttcgaaacag ccgaaggagg
241 aaaaagaaga cgttaccatg gaaaaggagg aggtcgttgt gacgagtaga gccacaaagg
301 tcaaggcaaa gcaaaggggg aaggagaaag ttagctcagg ccgtcctggc caacataatt
361 aggcacttta agttacattg tttagtctaa ttatttgcag tcgaaatgtg ttaatttaat
421 atcactgttt tacttttttta ttatatcaac aatctacaga caaacaaaat ttcattaagt
481 tcttgttcac tatacgagt
```

Protein - 92 aa

```
 1 MEKSDRRSEE SHLWIPLQCL DQTLRAILKC LGLFHQDSPT TSSPGTSKQP KEEKEDVTME
61 KEEVVVTSRA TKVKAKQRGK EKVSSGRPGQ HN
```

FIGURE 1b

AtproPep3 mRNA - 568 bp

```
  1 acattgagag atacaaagtt gtctctctga catataccta gctgctcgat aactcaccaa
 61 actattggat ttcaatggag aaattagata aacggaggga agaagaaact tatctatgga
121 ttccagttca gtttctcgac caagctctca tagctgtctt gaaatgtatt ggtcttcttt
181 gtcagccagc gaagaaaact gcgccgtctc cggtaacttt taaccagccg gaggaacaag
241 aggaagacta tggtgttgct ctgaaagacg atgatgtcgt tgtgttgctt agggacaaca
301 aggccaaatc aaagaaaagg gataaagaaa agcctagttc aggtcgtcct ggccaaacta
361 atagtgtacc caacgcggca atacaagttt ataaggagga ttaagaagtc aaaaattgag
421 tcgaaaaatc caagaggcca atgagtcagt cattgctcct ttttttttt tactcaaact
481 tctatgaaaa actcgtacgt agtttatttt ggtttcctca tttttcaaga cagcaaaatt
541 gaccagaatg tatatacttt tgaatcgg
```

Protein - 109 aa

```
 1 MEKLDKRREE ETYLWIPVQF LDQALIAVLK CIGLLCQPAK KTAPSPVTFN QPEEQEEDYG
61 VALKDDDVVV LLRDNKAKSK KRDKEKPSSG RPGQTNSVPN AAIQVYKED
```

FIGURE 1c

AtproPep4 mRNA - 486 bp

```
  1 atcaacctaa taacacacaa cactaaatct ctttcccaaa aaaagattaa gaagtcaacg
 61 atggagaatc tcagaaatgg agaagataac ggttctttga tcccatttac gttctttgat
121 caatcttcag tgacgattcc tctcttgaag tgttccggtc tcgaaagttc atcatcatca
181 tcttcttctt gcgatctttc gtcatcacac agcgaggaag atgagagtat cgatataaag
241 gaggaggaag aagaagaaga agaagatggc atgaccattg aaatcaaagc gagagggaag
301 aacaagacta agcctacgcc aagttcagga aaaggaggca aacacaatta gagttcattc
361 atataccgag gaaattaaac aaataaatgc atttgtataa aatacttaga gctataatac
421 agtggagttt ttttatagtc atttgtttcg aatatgaatt ggattaataa agatcgagtt
481 ttattt
```

Protein - 96 aa

```
 1 MENLRNGEDN GSLIPFTFFD QSSVTIPLLK CSGLESSSSS SSSCDLSSSH SEEDESIDIK
61 EEEEEEEEDG MTIEIKARGK NKTKPTPSSG KGGKHN
```

FIGURE 1d

AtproPep5 mRNA - 460 bp

```
  1 acttagctct cacgaagcag aattgaagaa aaacatggag agaggagttt cttattatct
 61 atggattcct tttaagttca tccaccaaac tttcggatct cttttactca agcttctcgg
121 tttgcgatct ccatctgatc atagttttcc ggaggatggg gaggaggaag ttaaggttgt
181 ggaagtgtcg tcgaggggtc ttcccgggaa aaagaatgta ctaaagaagt cgagagaaag
241 ttccggcaag ccgggaggca ccaacaagaa gccgttttag tttttcactt caactaataa
301 tatttgacgg agaaattctt ccttacattt tcatctattt agtgtaagat ctaagagaat
361 agtttcatat ttgtatcgta taattcctga agattgcaac tcctacgagt cctttatttt
421 ttttctttaa gacaataact aaagagagac gtgaatcata
```

Protein - 81 aa

```
 1 MERGVSYYLW IPFKFIHQTF GSLLLKLLGL RSPSDHSFPE DGEEEVKVVE VSSRGLPGKK
61 NVLKKSRESS GKPGGTNKKP F
```

FIGURE 1e

AtproPep2 mRNA - 412 bp

```
  1 acaaagaaaa tttgaggaga aagtcacata tagaggaact tagaagatag cgaagatgca
 61 gcaagagaga gatcacaaaa gagattgttg caagctcatg cctcaaactg tcaaggcttt
121 cttcaagtgt ctgagattca gacgttcttc ttcttcttct tcagacatgg tgaaagctag
181 agcaagaaat gaagagaaag aagaaccttc atctatcgaa acttcaacta ggagtctcaa
241 cgtaatgagg aaagggataa ggaaacaacc agttagctcg ggaaaacgag gtggagttaa
301 cgactacgac atgtaactag aatcttgatg tagaattgga taatcttgtt tggtagttac
361 tctacaacat actttctttg catctcatga atcatcatga tatattgata tt
```

Protein - 86 aa

```
 1 MQQERDHKRD CCKLMPQTVK AFFKCLRFRR SSSSSSDMVK ARARNEEKEE PSSIETSTRS
61 LNVMRKGIRK QPVSSGKRGG VNDYDM
```

FIGURE 1f

AtproPep6 mRNA - 397 bp

```
  1 ggtcaaacta gacacaacac ttaatgcatt gagcagaaga agaagaagaa gaagaattaa
 61 gaagagaaag aaaacaaaaa acatggaagt taatggagaa gaagagagaa gaagtagaag
121 agaagatgaa gaaaaagaag attactacta ctctcttctc aactctccat gttctgtttg
181 taacaaattt gttcaagcca tattgaagtg tcttggtctt gagtcatcat caataccacc
241 atcttcatca tcatcatcac catccttagt agaagaagaa gattcaggaa ctgaaactgt
301 tgaagaaaca ggatttatgg cgaggataac agcagtgtta agaaggagac caagaccacc
361 accttatagc tcaggacgac ctggtcaaaa caattga
```

Protein - 104 aa

```
 1 MEVNGEEERR SRREDEEKED YYYSLLNSPC SVCNKFVQAI LKCLGLESSS IPPSSSSSSP
61 SLVEEEDSGT ETVEETGFMA RITAVLRRRP RPPPYSSGRP GQNN
```

FIGURE 1g

AtproPep7 mRNA - 226 bp open reading frame (ORF)

```
  1 atgaatgttt tttttttgt ttctgaatta ttgtcacatc tttcttttca atatgaaatt
 61 tctaatggaa aatgtgtata tgtaataatg ttggtgacga agatatcaca agaagtagag
121 gaagagacag aggtagtgaa tataccgagg agtgtggtgt cggggaacgt tgcagcgcga
181 aagggtaagc agcaaacgag ttccgggaag ggtggaggta ccaactag
```

Protein - 75 aa

```
 1 MNVFFFVSEL LSHLSFQYEI SNGKCVYVIM LVTKISQEVE EETEVVNIPR SVVSGNVAAR
61 KGKQQTSSGK GGGTN
```

FIGURE 1h

BnproPep1

Protein - 95 aa

```
 1 MEVNGEEKRS YRREDEEKEV YYPLLNSPCS AFHKTVQAIL KCLGLESSSI
51 SPSSSSSQDP GTETVQETGF MAMVARLTRR RPRPPYSSGQ PGQIN
```

FIGURE 1i

StproPep1

Protein - 116 aa

```
  1 MFYLQEGIKA ILKCLGFESS KLVHQASSSS SSSSMSDINK NEEEESEKQE
 51 QECVLFQEDG NKQGSDSTND NYKNDPPVEN DDEDPPQSET LILPTERRGR
101 PPSRPKVGSG PPPQNN
```

FIGURE 1j

PbproPep1

Protein - 121 aa

```
  1 MDKGSSTKEE IQGDVLQISH SPSIFVEAFN ALLRCLGLGT VDHQRITQES
 51 SSTSSSKQED DEKASEESPQ YPPPTRTSDP QADPPTDTSE DPSTDAAVSA
101 LARRTPPVSR GGGGQTNTTT S
```

FIGURE 1k

BeproPep1

Protein - 110 aa

```
  1 MEESSANDQA TTAHTKVVYF LEEALRAIFK CLGLETKPQD DPPSSQLEDA
 51 SSTTKQAVAD NSSTADPELA DPPSTTETSE VAATASIDLV MAVNAPPRPS
101 LTPGSGAQIN
```

FIGURE 1L

GmproPep1

Protein - 115 aa

```
  1 MEGSSPSIEE ERTATFYVYH PCYFLQQALR ALLKCVGIDE SENTMCSQAN
 51 KQEKSSLPQT PSADDPITNS PTHKSSPDAA DPPSTTNQTI IIASLMATRG
101 SRGSKISDGS GPQHN
```

FIGURE 1m

MsproPep1

Protein - 127 aa

```
  1 MEETTERLST KKEEKTMTFY VYHPCYCLEE IFKTFLRCFG IESTQTKEEE
 51 DSSTSLLKPH ACACASDSNV ALKDRYYSSS SNKKSSQEEG VADPPPSTST
101 QTINLSSMGR GGPRRTPLTQ GPPPQHN
```

FIGURE 1n

VvproPep1

Protein - 83 aa

```
  1 MNDDAEQRQR SHAGDDGQEG LDLGRLPPNP CGHGVDRSSW RPHGGGPFVF
 51 CFCPCLAGEK VREKQKKGED GESVGRPGKK NEIL
```

FIGURE 1o

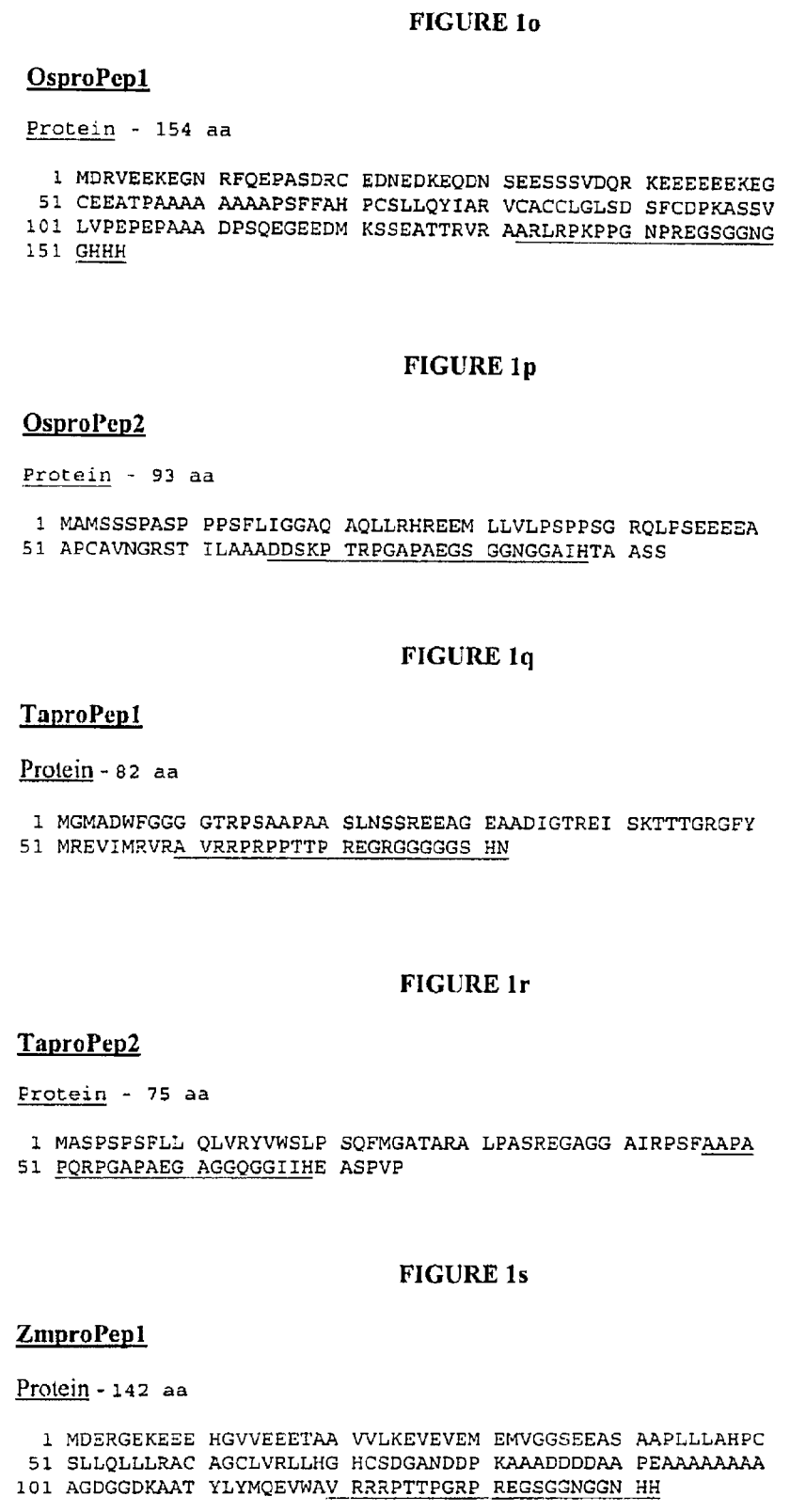

<u>OsproPep1</u>

<u>Protein</u> - 154 aa

```
  1 MDRVEEKEGN RFQEPASDRC EDNEDKEQDN SEESSSVDQR KEEEEEEKEG
 51 CEEATPAAAA AAAAPSFFAH PCSLLQYIAR VCACCLGLSD SFCDPKASSV
101 LVPEPEPAAA DPSQEGEEDM KSSEATTRVR AARLRPKPPG NPREGSGGNG
151 GHHH
```

FIGURE 1p

<u>OsproPep2</u>

<u>Protein</u> - 93 aa

```
 1 MAMSSSPASP PPSFLIGGAQ AQLLRHREEM LLVLPSPPSG RQLPSEEEEA
51 APCAVNGRST ILAAADDSKP TRPGAPAEGS GGNGGAIHTA ASS
```

FIGURE 1q

<u>TaproPep1</u>

<u>Protein</u> - 82 aa

```
 1 MGMADWFGGG GTRPSAAPAA SLNSSREEAG EAADIGTREI SKTTTGRGFY
51 MREVIMRVRA VRRPRPPTTP REGRGGGGGS HN
```

FIGURE 1r

<u>TaproPep2</u>

<u>Protein</u> - 75 aa

```
 1 MASPSPSFLL QLVRYVWSLP SQFMGATARA LPASREGAGG AIRPSFAAPA
51 PQRPGAPAEG AGGQGGIIHE ASPVP
```

FIGURE 1s

<u>ZmproPep1</u>

<u>Protein</u> - 142 aa

```
  1 MDERGEKEEE HGVVEEETAA VVLKEVEVEM EMVGGSEEAS AAPLLLAHPC
 51 SLLQLLLRAC AGCLVRLLHG HCSDGANDDP KAAADDDDAA PEAAAAAAAA
101 AGDGGDKAAT YLYMQEVWAV RRRPTTPGRP REGSGGNGGN HH
```

FIGURE 1t

HvproPep1

Protein - 93 aa

```
 1 MASSAPPAFL PQLVQPVSVL PDQPPSAPAE GTGGQVMVLN DASSLPLQLM
51 RTPPGEGAGG RIHRQLARPR PPGPPRQGHG GDGGAIHAIL LEL
```

FIGURE 2A

AtPEPRI (At1g73080)

```
   1 tgaaagaccc aaacctaatg aatgttaacc actaattgac cattcaccaa ccaattattt 61 aatgaaatat ctttgttagt ttcgttattt agtattgtta acggtttctt actcttttg 121 actacatcag acggacgtaa aacgacatcg ttgtcgaata ttcaaaagat tcacaatttg 181 acaaagagaa acagagacga cttgtttcta aaaaaaccac gtgtgtctga aaacggaaaa 241 aaagaagact gaatgagaaa cggcgtgtaa aaagaaaacg cgttgaaggt taggctctca 301 caatcgttgg tatacagaga gaccaaacat ctcgtcataa aaaacggcaa gaatcatcag 361 ttactttata cccatcaatc aagtcttgtc ctttttctcc ttctctctct catacgagct 421 tctttcctgc tgatgaggct tgagctttaa attttcaatc ttgattgaga ttctgcatgt 481 ttctcgatct ttaaactcag ATGAAGAATC TTGGGGGGTT GTTCAAAATT CTTCTGCTTT
                          M  K  N  L  G  G  L  F  K  I  L  L  L  F 541 TCTTCTGTCT CTTTCTATCG ACCCACATAA TTTCCGTTTC TTGTTTAAAC TCAGATGGGC
       F  C  L  F  L  S  T  H  I  I  S  V  S  C  L  N  S  D  G  L 601 TAACTCTACT CTCTCTTCTG AAGCATTTGG ATAGAGTACC ACCACAAGTT ACTTCGACAT
       T  L  L  S  L  L  K  H  L  D  R  V  P  P  Q  V  T  S  T  W 661 GGAAAATAAA CGCATCTGAA GCAACTCCAT GTAACTGGTT CGGTATCACT TGTGACGATT
       K  I  N  A  S  E  A  T  P  C  N  W  F  G  I  T  C  D  D  S 721 CTAAGAATGT TGCGTCTCTC AACTTCACTC GTTCTAGGGT TTCAGGTCAA TTGGGTCCGG
       K  N  V  A  S  L  N  F  T  R  S  R  V  S  G  Q  L  G  P  E 781 AAATTGGGGA GCTCAAAAGC TTGCAGATTT TGGATCTGAG TACTAACAAT TTCTCCGGGA
       I  G  E  L  K  S  L  Q  I  L  D  L  S  T  N  N  F  S  G  T 841 CTATACCTTC CACTTTAGGA AACTGTACCA AACTCGCTAC TCTAGATTTG TCTGAAAATG
       I  P  S  T  L  G  N  C  T  K  L  A  T  L  D  L  S  E  N  G 901 GATTCTCTGA TAAGATCCCA GATACTCTCG ATAGCTTGAA GAGGTTGGAG GTGCTTTATC
       F  S  D  K  I  P  D  T  L  D  S  L  K  R  L  E  V  L  Y  L 961 TTTACATAAA CTTCCTCACT GGTGAGTTAC CTGAATCCTT GTTTCGAATT CCGAAGCTGC
       Y  I  N  F  L  T  G  E  L  P  E  S  L  F  R  I  P  K  L  Q 1021 AGGTTTTATA TCTTGACTAT AACAATCTCA CCGGTCCGAT TCCTCAAAGT ATTGGTGATG
       V  L  Y  L  D  Y  N  N  L  T  G  P  I  P  Q  S  I  G  D  A 1081 CTAAGGAGCT TGTGGAGCTG AGTATGTATG CGAATCAGTT CTCTGGTAAC ATCCCTGAGT
       K  E  L  V  E  L  S  M  Y  A  N  Q  F  S  G  N  I  P  E  S 1141 CGATTGGGAA TAGCAGTAGT CTGCAGATTC TTTATTTGCA CAGGAACAAG TTAGTTGGTT
       I  G  N  S  S  S  L  Q  I  L  Y  L  H  R  N  K  L  V  G  S 1201 CATTACCTGA AAGTCTCAAT CTTTTGGGGA ATCTCACTAC TCTGTTTGTT GGTAACAACA
       L  P  E  S  L  N  L  L  G  N  L  T  T  L  F  V  G  N  N  S
```

FIGURE 2B

```
1261 GTCTACAAGG GCCGGTTCGT TTCGGATCAC CTAATTGCAA GAATTTGTTG ACTTTAGATT
      L  Q  G   P  V  R   F  G  S   P  N  C   K  N  L   L  T  L  D  L

1321 TGTCATACAA TGAATTCGAA GGCGGTGTTC CACCTGCATT GGGAAATTGC AGTAGCCTTG
      S  Y  N   E  F  E   G  G  V   P  P  A   L  G  N   C  S  S  L  D

1381 ACGCTTTAGT CATTGTGAGT GGTAACTTGT CAGGTACAAT CCCTTCCTCA TTGGGTATGT
      A  L  V   I  V  S   G  N  L   S  G  T   I  P  S   S  L  G  M  L

1441 TGAAGAATCT CACAATTCTT AACCTTTCCG AGAATCGTCT CTCTGGGAGT ATCCCCGCAG
      K  N  L   T  I  L   N  L  S   E  N  R   L  S  G   S  I  P  A  E

1501 AGCTCGGGAA CTGCAGTAGC TTGAACTTGT TGAAGCTGAA CGATAACCAG CTTGTAGGCG
      L  G  N   C  S  S   L  N  L   L  K  L   N  D  N   Q  L  V  G  G

1561 GAATACCGAG TGCATTAGGT AAGCTGAGGA AGCTAGAAAG TCTGGAGCTT TTCGAAAACC
      I  P  S   A  L  G   K  L  R   K  L  E   S  L  E   L  F  E  N  R

1621 GGTTTTCGGG TGAGATTCCT ATTGAGATAT GGAAGAGTCA GAGTCTTACG CAGTTGCTAG
      F  S  G   E  I  P   I  E  I   W  K  S   Q  S  L   T  Q  L  L  V

1681 TTTATCAAAA CAATCTCACT GGTGAACTAC CTGTGGAAAT GACTGAGATG AAGAAGCTAA
      Y  Q  N   N  L  T   G  E  L   P  V  E   M  T  E   M  K  K  L  K

1741 AGATCGCTAC GCTGTTCAAC AACAGCTTTT ATGGAGCGAT ACCACCGGGT TTAGGTGTGA
      I  A  T   L  F  N   N  S  F   Y  G  A   I  P  P   G  L  G  V  N

1801 ACAGCAGCTT AGAAGAGGTT GACTTTATTG GTAACAAACT TACAGGAGAG ATACCGCCAA
      S  S  L   E  E  V   D  F  I   G  N  K   L  T  G   E  I  P  P  N

1861 ATCTATGCCA TGGAAGGAAG TTGAGAATAC TCAACTTGGG TTCTAATCTG CTTCATGGTA
      L  C  H   G  R  K   L  R  I   L  N  L   G  S  N   L  L  H  G  T

1921 CAATACCAGC TTCTATTGGT CACTGTAAGA CCATCAGGAG ATTCATCCTT AGAGAAAATA
      I  P  A   S  I  G   H  C  K   T  I  R   R  F  I   L  R  E  N  N

1981 ACCTTTCAGG TCTTCTTCCT GAGTTTTCTC AGGATCATAG TCTTTCTTTT CTTGATTTCA
      L  S  G   L  L  P   E  F  S   Q  D  H   S  L  S   F  L  D  F  N

2041 ATAGCAACAA CTTCGAAGGA CCAATCCCGG GCAGCCTCGG AAGCTGTAAG AATCTCTCGA
      S  N  N   F  E  G   P  I  P   G  S  L   G  S  C   K  N  L  S  S

2101 GTATTAACCT ATCTCGAAAC AGATTCACGG GGCAGATACC TCCACAACTT GGGAATCTAC
      I  N  L   S  R  N   R  F  T   G  Q  I   P  P  Q   L  G  N  L  Q

2161 AAAACCTTGG TTACATGAAT CTTTCTCGTA ATCTTCTTGA AGGGTCTCTA CCAGCTCAGC
      N  L  G   Y  M  N   L  S  R   N  L  L   E  G  S   L  P  A  Q  L

2221 TATCTAACTG TGTGAGTTTA GAGCGTTTTG ATGTTGGCTT CAACTCATTA AACGGTTCAG
      S  N  C   V  S  L   E  R  F   D  V  G   F  N  S   L  N  G  S  V

2281 TTCCTTCAAA CTTTAGTAAC TGGAAAGGCT TGACGACTTT AGTTCTCAGC GAGAACCGGT
      P  S  N   F  S  N   W  K  G   L  T  T   L  V  L   S  E  N  R  F

2341 TTTCAGGAGG TATTCCACAG TTCTTGCCTG AGCTTAAGAA GCTGTCAACT CTGCAGATTG
      S  G  G   I  P  Q   F  L  P   E  L  K   K  L  S   T  L  Q  I  A
```

FIGURE 2C

```
2401 CTAGAAATGC TTTTGGTGGT GAGATTCCTT CGTCGATTGG GTTGATAGAG GATCTGATCT
        R  N  A   F  G  G   E  I  P  S   S  I  G   L  I  E   D  L  I  Y

2461 ATGACTTGGA CCTTAGTGGA AACGGATTGA CAGGTGAAAT TCCAGCCAAG TTGGGAGATC
        D  L  D   L  S  G   N  G  L  T   G  E  I   P  A  K   L  G  D  L

2521 TCATCAAGTT AACAAGACTC AACATATCTA ACAACAATTT GACAGGATCT TTATCGGTTC
        I  K  L   T  R  L   N  I  S  N   N  N  L   T  G  S   L  S  V  L

2581 TCAAAGGTCT TACCTCATTG CTACATGTTG ATGTCTCCAA CAATCAGTTC ACAGGTCCAA
        K  G  L   T  S  L   L  H  V  D   V  S  N   N  Q  F   T  G  P  I

2641 TACCAGATAA CTTGGAGGGT CAGTTGTTAT CTGAGCCGTC GTCGTTTTCA GGAAATCCAA
        P  D  N   L  E  G   Q  L  L  S   E  P  S   S  F  S   G  N  P  N

2701 ACCTCTGCAT TCCACATTCC TTCTCTGCTA GCAACAATAG CCGCAGCGCG TTAAAGTACT
        L  C  I   P  H  S   F  S  A  S   N  N  S   R  S  A   L  K  Y  C

2761 GTAAAGATCA ATCTAAAAGC AGGAAGAGTG GCCTTAGCAC CTGGCAAATC GTGCTAATAG
        K  D  Q   S  K  S   R  K  S  G   L  S  T   W  Q  I   V  L  I  A

2821 CGGTCTTATC GTCTTTATTA GTCTTGGTTG TGGTCCTTGC TCTTGTTTTC ATTTGCCTAC
        V  L  S   S  L  L   V  L  V  V   V  L  A   L  V  F   I  C  L  R

2881 GTCGTCGCAA AGGAAGACCA GAGAAAGATG CTTATGTCTT CACTCAGGAG GAAGGCCCAT
        R  R  K   G  R  P   E  K  D  A   Y  V  F   T  Q  E   E  G  P  S

2941 CTTTGTTGTT GAACAAAGTT CTTGCAGCAA CTGACAATCT AAATGAAAAG TACACCATTG
        L  L  L   N  K  V   L  A  A  T   D  N  L   N  E  K   Y  T  I  G

3001 GAAGAGGAGC TCATGGAATT GTGTACAGAG CTTCTTTAGG CTCCGGAAAG GTCTACGCTG
        R  G  A   H  G  I   V  Y  R  A   S  L  G   S  G  K   V  Y  A  V

3061 TGAAGAGACT TGTATTCGCG TCTCACATCC GCGCTAACCA GAGTATGATG AGGGAGATTG
        K  R  L   V  F  A   S  H  I  R   A  N  Q   S  M  M   R  E  I  D

3121 ATACAATCGG TAAAGTCAGG CACAGGAATC TGATTAAGTT AGAAGGGTTT TGGCTGAGGA
        T  I  G   K  V  R   H  R  N  L   I  K  L   E  G  F   W  L  R  K

3181 AAGACGACGG TTTAATGCTG TATAGATACA TGCCAAAAGG AAGTCTTTAC GACGTTCTCC
        D  D  G   L  M  L   Y  R  Y  M   P  K  G   S  L  Y   D  V  L  H

3241 ACGGTGTTAG CCCGAAAGAA AATGTGCTAG ACTGGTCTGC ACGGTACAAT GTAGCACTTG
        G  V  S   P  K  E   N  V  L  D   W  S  A   R  Y  N   V  A  L  G

3301 GTGTCGCTCA TGGACTAGCC TATCTACACT ATGACTGCCA TCCCCCGATT GTTCACCGTG
        V  A  H   G  L  A   Y  L  H  Y   D  C  H   P  P  I   V  H  R  D

3361 ACATCAAACC AGAGAACATA CTCATGGACT CAGATTTGGA GCCTCACATT GGGGATTTCG
        I  K  P   E  N  I   L  M  D  S   D  L  E   P  H  I   G  D  F  G

3421 GTTTGGCTCG CCTTCTTGAT GACTCAACGG TTTCAACTGC AACTGTTACA GGCACCACCG
        L  A  R   L  L  D   D  S  T  V   S  T  A   T  V  T   G  T  T  G

3481 GCTACATTGC ACCAGgtaat gcatcttctc attatacata gtggacttgg tataatctgg
        Y  I  A   P  E
```

FIGURE 2D

```
3541 tttagtgttc aaaccgagtt agttaccggt taaaaaagtc tgttaggaag atactctgtt 3601 tcttattagc taatttcaca attaaactgc agAAAACGCT TTCAAAACCG TGAGGGGAAG
                                        N  A   F  K  T  V   R  G  R 3661 AGAATCAGAC GTTTACAGTT ATGGAGTCGT GTTACTTGAG CTGGTTACGA GGAAGAGAGC
      E  S  D  V  Y  S  Y  G  V  V  L  L  E  L  V  T  R  K  R  A 3721 GGTGGACAAA TCTTTCCCGG AAAGTACAGA TATAGTAAGC TGGGTGAGAT CTGCCTTGAG
      V  D  K  S  F  P  E  S  T  D  I  V  S  W  V  R  S  A  L  S 3781 CAGCAGCAAC AACAATGTGG AGGATATGGT AACAACAATC GTCGATCCGA TTCTCGTGGA
      S  S  N  N  N  V  E  D  M  V  T  T  I  V  D  P  I  L  V  D 3841 CGAGCTTCTG GATTCGAGTC TTAGGGAGCA GGTGATGCAA GTGACGGAAC TGGCACTGAG
      E  L  L  D  S  S  L  R  E  Q  V  M  Q  V  T  E  L  A  L  S 3901 TTGTACACAG CAAGATCCGG CAATGAGACC AACGATGAGA GATGCGGTGA AACTGTTGGA
      C  T  Q  Q  D  P  A  M  R  P  T  M  R  D  A  V  K  L  L  E 3961 AGATGTGAAA CATCTGGCAA GAAGCTGCTC CTCTGATTCA GTTCGGTAAt ctcgttactt
      D  V  K  H  L  A  R  S  C  S  S  D  S  V  R  *

4021 tgtgcagagc agaaggagga aactaaagga ctgttatcag tggtaacgta actgggctta 4081 ccggtaatgt aactgggcca ataatgtaaa atatggctta ttgaaggccc aaatatgacg 4141 gcccctttaat tgtaaccgtg tttgtttgtg aaataaaatc tcgtttatca aatttctgtt 4201 tcctatttta tttttaaaaa aagtgttggg aaaatttttcg tttggccgga gatgaagata 4261 ggggcggttc aggagagttg gcttatacgg actccggtac ttaggccggc ggttcaaggc 4321 tcaattcgcc ggaatggaaa gccgcagctt gagtttcctc tctcgaacag tgagcttaag 4381 ctcttctttc ttccattgaa ttttttttt gggaacgcat tatcttgtgc acacttgtag 4441 taacttggtc tatatcaaat tgaggttgaa gatgaaagtt cagttatttc ctgtgatttg 4501 caatttcct
```

Signal sequense Residues 1-24

C C Cysteine paire Residues 64 and 71; and Residues 836 and 854

Leucine-rich repeat Residues 76-827

Transmembrane domain Residues 870-892

Kinase domain Residures 927-1208

Intron between 1099 and 1100.

FIGURE 3A

AtPEPR2 (At1g17750)

1 attctagtgt agacgacaga taccagagat cttgattaaa ttccaatata taatgtttat 61 gaaagattta aatctaacaa agtaacagta ggatgaaatg tcaatagaaa attagcgtcc 121 aaagaagctt tctcttgaat aagctaagaa aacaaaacgt ggaaaatgga atatttaaaa 181 ccacgaaaca gtctccgagt agtaatggaa atagcgagaa agaaacacga aacagcgttg 241 aaggtcgcca attcgtaaag ttaggttcac aatctctgac gaagagttaa ccaaaaagcg 301 cgctcttttt ctctctcacc aaactcatcg atcgtttctt aaataatgca atctgttcct 361 gtcactaaat ccagataccc tttcaaatcc aaaagctctc tcttttttt ttccgcctct 421 cattctgggt tcaagggttg ttgagtgagg ttactacgta cgagtgtttc atatttcagt 481 ctcttgagct ctaatctcaa ATGAGGAATC TTGGGTTACT CGAAATTACT CTGCTTTGCT
M R N L G L L E I T L L C S 541 CTCTCTTTGT CTATTTCCGT ATAGATTCTG TCTCTAGTTT AAACTCAGAT GGTTTGGCTT
L F V Y F R I D S V S S L N S D G L A L 601 TACTCTCGCT TCTCAAGCAC TTTGATAAAG TCCCACTTGA AGTAGCTTCG ACGTGGAAGG
L S L L K H F D K V P L E V A S T W K E 661 AGAACACATC TGAAACCACT CCATGTAATA ATAACTGGTT TGGTGTCATT TGTGATCTTT
N T S E T T P C N N N W F G V I C D L S 721 CTGGTAATGT CGTCGAGACC CTTAATTTGT CTGCTTCTGG GCTTTCAGGC CAATTAGGTT
G N V V E T L N L S A S G L S G Q L G S 781 CTGAAATTGG GGAGCTTAAG AGCTTGGTCA CATTGGATCT CAGTCTTAAC AGTTTCTCTG
E I G E L K S L V T L D L S L N S F S G 841 GTTTATTGCC TTCCACTTTA GGAAACTGTA CTTCACTTGA GTATTTGGAT TTGTCTAACA
L L P S T L G N C T S L E Y L D L S N N 901 ATGATTTTTC TGGAGAAGTT CCTGATATTT TTGGTAGCTT GCAGAATTTG ACGTTTCTGT
D F S G E V P D I F G S L Q N L T F L Y 961 ATCTTGATCG CAATAATCTT AGTGGTCTCA TTCCTGCAAG TGTTGGTGGG TTGATAGAGC
L D R N N L S G L I P A S V G G L I E L 1021 TCGTAGATCT GAGGATGTCA TATAATAACT TGTCTGGTAC CATTCCAGAG TTGCTTGGGA
V D L R M S Y N N L S G T I P E L L G N 1081 ACTGTAGTAA GCTGGAATAT CTGGCTTTGA ACAACAACAA GTTAAATGGT TCTTTGCCAG
C S K L E Y L A L N N N K L N G S L P A 1141 CAAGTCTCTA TCTACTCGAG AATCTTGGTG AGCTATTTGT CAGTAACAAC AGCCTTGGAG
S L Y L L E N L G E L F V S N N S L G G 1201 GGAGGCTTCA TTTTGGTTCT AGCAACTGCA AGAAATTGGT TTCTTTAGAT CTCTCGTTCA
R L H F G S S N C K K L V S L D L S F N

FIGURE 3B

```
1261 ATGATTTCCA AGGCGGTGTT CCACCTGAGA TAGGCAACTG CAGTAGCCTT CACTCTTTAG
       D  F  Q   G  G  V   P  P  E  I   G  N  C   S  S  L   H  S  L  V

1321 TCATGGTGAA ATGCAACTTG ACAGGTACAA TCCCATCATC AATGGGTATG TTGAGAAAGG
      M  V  K   C  N  L   T  G  T  I   P  S  S   M  G  M   L  R  K  V

1381 TTTCGGTTAT TGACCTTTCC GATAATCGTC TCTCGGGGAA TATCCCTCAA GAGCTTGGGA
      S  V  I   D  L  S   D  N  R  L   S  G  N   I  P  Q   E  L  G  N

1441 ACTGCAGCAG CTTGGAAACC TTGAAGCTGA ACGACAACCA GCTCCAAGGC GAGATACCAC
      C  S  S   L  E  T   L  K  L  N   D  N  Q   L  Q  G   E  I  P  P

1501 CTGCATTGAG TAAGCTAAAG AAGCTACAAA GCCTGGAGCT TTTTTTTAAT AAGCTGTCCG
      A  L  S   K  L  K   K  L  Q  S   L  E  L   F  F  N   K  L  S  G

1561 GTGAGATTCC TATTGGCATA TGGAAGATTC AGAGTCTGAC ACAGATGCTC GTTTATAACA
      E  I  P   I  G  I   W  K  I  Q   S  L  T   Q  M  L   V  Y  N  N

1621 ACACTCTCAC CGGGGAACTA CCAGTTGAAG TAACTCAGCT GAAGCACCTT AAGAAGCTTA
      T  L  T   G  E  L   P  V  E  V   T  Q  L   K  H  L   K  K  L  T

1681 CACTGTTTAA CAACGGCTTT TATGGAGATA TACCAATGAG TTTAGGCCTG AATCGAAGCT
      L  F  N   N  G  F   Y  G  D  I   P  M  S   L  G  L   N  R  S  L

1741 TAGAGGAGGT GGACCTTCTT GGTAACCGTT TTACAGGGGA GATACCACCC CATCTCTGCC
      E  E  V   D  L  L   G  N  R  F   T  G  E   I  P  P   H  L  C  H

1801 ATGGACAGAA GTTGAGATTG TTCATCTTGG GTTCTAATCA GCTTCATGGT AAGATACCAG
      G  Q  K   L  R  L   F  I  L  G   S  N  Q   L  H  G   K  I  P  A

1861 CGTCTATTCG TCAGTGTAAG ACCCTTGAGC GAGTCAGACT TGAAGATAAC AAACTTTCAG
      S  I  R   Q  C  K   T  L  E  R   V  R  L   E  D  N   K  L  S  G

1921 GTGTTCTTCC GGAATTCCCT GAGAGTCTTA GTCTTTCCTA TGTGAACCTC GGAAGCAATA
      V  L  P   E  F  P   E  S  L  S   L  S  Y   V  N  L   G  S  N  S

1981 GCTTTGAAGG ATCCATCCCG CGCAGCTTGG GAAGCTGTAA AAATCTCTTG ACTATTGACC
      F  E  G   S  I  P   R  S  L  G   S  C  K   N  L  L   T  I  D  L

2041 TTTCTCAAAA CAAACTCACG GGTCTGATAC CTCCAGAACT GGGAAATCTG CAAAGCCTTG
      S  Q  N   K  L  T   G  L  I  P   P  E  L   G  N  L   Q  S  L  G

2101 GACTGTTGAA CCTTTCACAT AATTATCTGG AAGGTCCTCT GCCATCCCAG CTATCAGGCT
      L  L  N   L  S  H   N  Y  L  E   G  P  L   P  S  Q   L  S  G  C

2161 GTGCGAGACT TCTGTATTTT GATGTTGGAT CCAACTCATT GAACGGTTCT ATTCCATCAA
      A  R  L   L  Y  F   D  V  G  S   N  S  L   N  G  S   I  P  S  S

2221 GCTTCAGAAG CTGGAAAAGC TTGTCCACTT TAGTTCTCAG TGACAATAAT TTTCTAGGAG
      F  R  S   W  K  S   L  S  T  L   V  L  S   D  N  N   F  L  G  A

2281 CTATTCCACA GTTCTTGGCA GAGCTTGACC GACTCTCAGA TCTGCGGATA GCTCGAAATG
      I  P  Q   F  L  A   E  L  D  R   L  S  D   L  R  I   A  R  N  A
```

FIGURE 3C

```
2341 CTTTTGGAGG TAAGATTCCT TCCTCGGTTG GCTTGTTGAA GAGTCTACGC TATGGCTTAG
       F  G  G   K  I  P   S  S  V  G   L  L  K   S  L  R   Y  G  L  D

2401 ACCTCAGTGC GAACGTATTT ACGGGTGAGA TTCCAACCAC ACTGGGGGCT CTTATCAATC
       L  S  A   N  V  F   T  G  E  I   P  T  T   L  G  A   L  I  N  L

2461 TTGAACGTCT CAACATATCC AACAACAAGT TGACAGGGCC TTTATCGGTT CTTCAAAGTC
       E  R  L   N  I  S   N  N  K  L   T  G  P   L  S  V   L  Q  S  L

2521 TTAAGTCATT GAATCAAGTT GACGTCTCGT ATAATCAGTT CACGGGTCCA ATACCCGTAA
       K  S  L   N  Q  V   D  V  S  Y   N  Q  F   T  G  P   I  P  V  N

2581 ATCTGTTATC AAATTCTTCA AAGTTTTCTG GAAATCCAGA CCTCTGCATT CAAGCTTCTT
       L  L  S   N  S  S   K  F  S  G   N  P  D   L  C  I   Q  A  S  Y

2641 ACTCAGTGAG TGCCATAATC CGCAAAGAGT TTAAATCTTG CAAAGGTCAA GTCAAACTTA
       S  V  S   A  I  I   R  K  E  F   K  S  C   K  G  Q   V  K  L  S

2701 GCACGTGGAA GATCGCCCTT ATAGCAGCTG GGTCCTCACT ATCCGTATTG GCTTTGCTTT
       T  W  K   I  A  L   I  A  A  G   S  S  L   S  V  L   A  L  L  F

2761 TTGCTCTCTT TTTGGTTTTA TGCCGGTGCA AAAGAGGAAC CAAGACAGAA GATGCTAATA
       A  L  F   L  V  L   C  R  C  K   R  G  T   K  T  E   D  A  N  I

2821 TCCTCGCAGA GGAAGGTCTG TCCTTGTTGC TGAACAAAGT TCTAGCAGCC ACTGACAATC
       L  A  E   E  G  L   S  L  L  L   N  K  V   L  A  A   T  D  N  L

2881 TAGATGACAA GTACATCATT GGAAGAGGAG CTCATGGAGT TGTTTACAGA GCTTCTTTAG
       D  D  K   Y  I  I   G  R  G  A   H  G  V   V  Y  R   A  S  L  G

2941 GATCAGGCGA AGAATACGCC GTGAAGAAAC TCATCTTTGC GGAACACATT CGCGCAAACC
       S  G  E   E  Y  A   V  K  K  L   I  F  A   E  H  I   R  A  N  Q

3001 AAAATATGAA GCGGGAGATC GAAACAATCG GGCTAGTCAG GCACAGAAAT CTCATTCGGT
       N  M  K   R  E  I   E  T  I  G   L  V  R   H  R  N   L  I  R  L

3061 TAGAAAGATT TTGGATGAGG AAAGAAGATG GCTTAATGCT GTATCAGTAC ATGCCCAATG
       E  R  F   W  M  R   K  E  D  G   L  M  L   Y  Q  Y   M  P  N  G

3121 GAAGCCTACA CGACGTTTTG CACAGAGGTA ATCAAGGAGA AGCAGTTCTT GACTGGTCTG
       S  L  H   D  V  L   H  R  G  N   Q  G  E   A  V  L   D  W  S  A

3181 CACGGTTCAA CATAGCCCTT GGGATTTCAC ATGGACTGGC GTATTTACAT CATGATTGTC
       R  F  N   I  A  L   G  I  S  H   G  L  A   Y  L  H   H  D  C  H

3241 ATCCACCAAT AATTCACCGC GACATCAAAC CAGAGAACAT ACTCATGGAC TCGGATATGG
       P  P  I   I  H  R   D  I  K  P   E  N  I   L  M  D   S  D  M  E

3301 AGCCTCACAT TGGAGATTTC GGATTGGCTC GGATTCTAGA TGACTCAACA GTTTCAACGG
       P  H  I   G  D  F   G  L  A  R   I  L  D   D  S  T   V  S  T  A

3361 CCACTGTTAC TGGCACAACT GGGTACATTG CACCAGgtat atatacttct caacataaca
       T  V  T   G  T  T   G  Y  I  A   P  E 3421 cgttcgtatt ttgttcaccg ttaccttatt catgctctga tgaccatatt tctatcaaac
```

FIGURE 3D

```
3481 agAAAATGCG TACAAGACGG TGAGGAGCAA GGAATCAGAT GTTTACAGTT ATGGAGTTGT
       N  A  Y  K  T  V  R  S  K  E  S  D  V  Y  S  Y  G  V  V

3541 TTTGCTCGAG CTGGTAACAG GAAAGAGAGC ACTGGACAGA TCTTTCCCGG AAGATATCAA
      L  L  E  L  V  T  G  K  R  A  L  D  R  S  F  P  E  D  I  N

3601 CATTGTGAGC TGGGTCAGAT CTGTATTAAG CAGCTACGAG GATGAAGACG ATACTGCTGG
      I  V  S  W  V  R  S  V  L  S  S  Y  E  D  E  D  D  T  A  G

3661 TCCAATCGTT GATCCAAAAC TTGTGGATGA GCTTCTGGAT ACGAAGCTCA GGGAACAAGC
      P  I  V  D  P  K  L  V  D  E  L  L  D  T  K  L  R  E  Q  A

3721 AATCCAAGTC ACAGACTTGG CTCTTAGATG TACAGACAAG AGGCCGGAGA ACAGACCATC
      I  Q  V  T  D  L  A  L  R  C  T  D  K  R  P  E  N  R  P  S

3781 GATGAGAGAT GTGGTGAAAG ATTTGACTGA TTTGGAAAGT TTTGTAAGAA GCACTTCGGG
      M  R  D  V  V  K  D  L  T  D  L  E  S  F  V  R  S  T  S  G

3841 TTCAGTTCAC TAGtttcata agttgcaggt ttatatagtg tactgttctt tgaaaccact
      S  V  H  *

3901 aatataattg taactaccat tgaataccgt gaagatttga gaaacatata tatccaaaga 3961 gacttaattt tattgcataa gttggaattg ttgggggaaa taaattacaa gtattaagag 4021 aggcttcaca aatttgccaa tctcagtata ttttagccag tgctaccaga aagctcgcca 4081 gagaaggcac taccatacga tgtggaaccg gttggtgtct gtgatgatgt tgcgatccct 4141 cgagctttcc gcatctgcct tagtctgaaa acatctgtgg gcaaaggctg gctttgtaca 4201 gttgctgtat catcttcttc ttgccctgtt aacagagaga tagaataaga taagtaacta 4261 tcatttaacg gttgttctaa gggatagtag aagttatatg catctgcagc taagaagtgc 4321 caaacatttg agtgatgaca tagtcatgag cca
```

_____ Signal sequense Residues 1-26

C C Cysteine paire Residues 62 and 71; and residues 709 and 727

Leucine-rich repeat Residues 99-697

Transmembrane domain Residues 738-760

Kinase domain Residues 793-1079

Intron between residues 966 and 967.

FIGURE 7A

RICE PROPEP8 (OsPep8)

Rice Genome Locus Os04g54620:
ATGGCCAGCTACGCGGCGCAGCTCAAGGACATGTTCTTCGGCCTCGTCGAGCGCGTCAC
CGGCTACGGACGCGGCGAGGACAAGGACGTCGCTGCAGGTGTAGATGAGCCCAGCAAGT
TGGCATCTGAAGAGGTTGCAGTAAGCAGCGAAGAGGTTGTGATTGTACAGCGCAATGAG
ATCAGATCAAGAGGCGTAGATCCCTCCGTGTCAGGCGGGAAACAGCCAGGGATCAATGC
GGCCGGTATCTAG Frame +1
MASYAAQLKDMFFGLVERVTGYGRGEDKDVAAGVDEPSKLASEEVAVSSEEVVIVQRNE
IRSRGVDPSVSGGKQPGINAAGI*

ALPINE PENNYCRESS PROPEP1 (TcPep1)

GenBank ID# DN923431
ACTTTAATTTCAGATCTCAATGGAGAAAGAGAGACGAAACGAAGAAGAAACTTATCGAT
GTTTTTCTTTTCAGTTCCTCGACCAAATTCTTAAAGCTAGCTTAAAGTGTTTTGGTCTT
CTTCATCATGATTCACCGCCGACGACGACGAAAACAGCGTCGTATCCCGTACCTTTAAA
CCAGCCGGAGGAAGAAGAAGAGGAAAATGTTGGCGTGAAAGACCACGTCGTTGTGACGC
CCAGTGGCAGTAAAAACGGCGTCGTTGTCACGAGTAGGGTCACAAAGTTCAAAGCAAAG
ATGAAGGAGAGGGAAAAAGTTAGCACTGGCCGGTCTGGCCAGCATAACTAGCACTTAAT
TAAAATTGTTTAGTTCAATTAATTCGCAGTCAATAATTCTATTTATTTTATAGTTGCAC
TTAATATAATGTTTAGTGGCATCATTGTACTTATTTGTATGAATTTATAAATGAAATTT
AACAGCTTACNGGCCCCAAATGATAAATCTAGTTCATCAATATGAAAACAACCTTAAAC
TTC Frame +2
L*FQISMEKERRNEEETYRCFSFQFLDQILKASLKCFGLLHHDSPPTTTKTASYPVPLN
QPEEEEEENVGVKDHVVVTPSGSKNGVVVTSRVTKFKAKMKEREKVSTGRSGQHN*HLI
KIV*FN*FAVNNSIYFIVALNIMFSGIIVLICMNL*MKFNSLXAPNDKSSSSI*KQP*T

COTTON PROPEP2 (GhPep2)

GenBank ID# BQ405970:
GGGAAGATACTTCATCAGCAAAGGAAGTAACGTTGCAAGGAACTCCAGCTAATTACTTC
CCCAGGTCCTTCCATGAAGTTGTAGGTGCCATTCTCAGGTGTTTGGGACTTGAAACTGG
ATTCCAACAAAACCCTAATCCATGTCCAAAGAAAGAAGATGACAGTAAAGCCAATCATA
ATCAATCTGTTTCTCAGAAGGAAAGTCCAGATCCACCTTCATCAACAGACAATTCAGAT
CCATCAACCACTGTGATCGACCCACCAGCTGATCCTCCTCCTTCCACCACTGGAGACAC
GAACGATGGCGAACTTCCCATGGTTTCTCTCTTTACTCCTAAAAGGCCAGGGACAAGCG
CCGGCAGTGGACCTCAGATTAATTAACTTGAGTTGTCAAGATCGACGCTTTGTGGGCAA
AAACAAGCTTTGGCAACTGCAGCGATATTCAAGAGAGGTTTATATGGGGTCCTTGACTG

FIGURE 7B

```
TTGTTTTCATCTTGTTCTTGGATGTTTTTTTTTAGGAGAATGGAAAATCGAGTGAGTT
GTGAATAATTTGTATAAAATATCATAAACCCATGTATTTTAAGAGTATATTAATTTCAA
TAACGTTGCNGAANAAAAAAAAAAAANNNAAANAANNNAAAAAAAANAAAANAAAANAA
AAAAAAAACTCGGAAAGTCCTTCTAC
```

Frame +3
EDTSSAKEVTLQGTPANYFPRSFHEVVGAILRCLGLETGFQQNPNPCPKKEDDSKANHN
QSVSQKESPDPPSSTDNSDPSTTVIDPPADPPPSTTGDTNDGE<u>LPMVSLFTPKRPGTSA</u>
<u>GSGPQIN</u>*LELSRSTLCGQKQALATAAIFKRGLYGVLDCCFHLVLGCFFFRRMENRVSC
E*V*NIINPCILRVY*FQ*RCXXKKKXXXXKKXKXXKKKTRKVLL

POPLAR PROPEP2 (PtPep2)

**JGI Populus trichocarpa v1.1 Gene Model ID: grail3.0041002801
Coordinates:Poptr1/scaffold_41:469909-470755, predicted transcript**
```
ATGGGTTCCTATCTCTCTTCCTTCTTTATTGAAGCTCATAATGCTCTTCTACAG
TTCTTGGGACTGGTTATGTTGATCATCAAAGTAAGACCCAAGAAGGCTCGTC
AACTTCCAGTTCAGAGAAACAAGAGGATGAAAAGCCTCTGAAGAAAGCTC
CCAAGATCCTCCTCCAACAACAACCGACCCAAAAGCTGATCCTCCCACAGAT
AACTCTGAAGATCCTCCTGCAGTCACTGTAAGTGCTCTTGCGAGGCGGACTCC
ACCAGTAAGCAGCGGGAGCGGTGGTCAGATTAATTAATTCCACCTCAGCTTA
AGAATCGCAGAAGCTCAAAGATCTGTCGGTCACACATGCTAGCTTCGCTAA
AGTCCAAAAAATCATCTTCTCTATAGATTTCACGAGTACTAGTTGTAATTATT
GTGTGTGCGCTTAGGGATACTCTCCCCCCCCCCCCCCCCCTTTTTTTTTTTGG
GGGAAATGAACTTGAAAATCTTGGACCCGTTATACCTATATGAATATTACAT
ATGTTTAG
```

Frame +1
MGSYLSSFFIEAHNALLQFLGLVIVDHQSKTQEGSSTSSSEKQEDEKASEESSQDP
PPTTTDPKADPPTDNSEDP<u>PAVTVSALARRTPPVSSGSGGQIN</u>*FHLSLRIAEAQ
RSVGHTMLASLKSKKSSSL*ISRVLVVIIVCALRDTLPPPPPLFFFWGK*T*KSWTR
YTYMNITYV*

GRAPE PROPEP2 (VvPep2)

GIDVvT00004519001; Chromosome 18:1019657-1020141
```
ATGTGTCAAAAACTGAAGCAGTATAGCATTCATTCAAAAGAAGGTACACCAC
CAAACCCCATTAAAGAGCTAGATATTGAAGGAGGAGGAGGAGAAGAAGAAG
AAAAATATGATCTAGAGATGGAGGAGCCATCAACCGGGGAGATGACACAGA
GACCAACAACTGTTTACTACTCTCACAATCCATGCTATTATCTTCAAGAAGCT
ATAAGGGCTATTCTCAAGTGTTTGGGCCTGGAATCTTCTACTTCTAGGGACTC
TTCGTCAAGCAGTTCAGAACAAAAGGATGATGACGACACTGAAGCAAGTCCC
CAACAATCTCGTTCTTCTACACAACAAGGAGCACACTCATCGTCAGCTGACTC
TCCTTCAACTACACAACAAGATAACAACACCTTCGAGGATGCTGAAAGTGCG
```

FIGURE 7C

CGTGTATTGAGGAGAGGGCCTACAAGGCCACCAATAAGTTTTGAAAGCAGGC
CTGGAGGTGGTTCTCAGATTAACTGA

Frame +1
MCQKLKQYSIHSKEGTPPNPIKELDIEGGGGEEEEKYDLEMEEPSTGEMTQRPTTVYYS
HNPCYYLQEAIRAILKCLGLESSTSRDSSSSSSEQKDDDDTEASPQQSRSSTQQGAHSS
SADSPSTTQQDNNTFEDAESARVLRRGPTRPPISFESRPGGGSQIN*

GRAPE PROPEP3 (VvPep3)

GIDVvT00034371001; Chromosome 7:12729384-12729620
ATGAAGTCTTGTGCAGAGAAGTGGATAAAAGTAGTAGAGTTCAACCAGAGCCGGGGCTA
TCTCCTGAAACTAGTCTTGAAGCCTTTCTTGAAGCGCCTTGGAGCTCATGCCTCAACTA
CTGATCAAGCCAAGCAAGAAAAGCTTGCAAGCAAGTCTAAAATGTCTTCAGATTTCAGA
CAGCCACCAAGACCGCCAATAGACCCTGGTCAAGGTGGGCAGATCAACTCTTCATCTTA
A Frame +1
MKSCAEKWIKVVEFNQSRGYLLKLVLKPFLKRLGAHASTTDQAKQEKLASKS**KMSSDFR
QPPRPPIDPGQGGQIN**SSS*

SUNFLOWER PROPEP1 (HaPep1)

GenBank ID# DY931166:
GCGGGGGATTTACATATCTAACCTTCCCTTCATTCTATTCATTCTCTTTGACTTGAAAA
AAGATATATGCAAACACATATATAAAATAATGGTGGAGGAAAGGGCTGAAGTTGTGTAT
GATATTGGATATGGTTATGGTAACCCTTGTAGGTATTTACAAGAAGTTTTTAGAAGCTT
TTTAAGGTGTTTGGGGTTAGAGAAACAAGAAGGAAAAGAAAGAAACACTAGTGGTGGTG
TTGGTGGCGGCGACACAGGCGGTGGTGACGGTGACGGTGACGGTGACGGTGACGGAGGT
GGAGGTGAGGTGGATCCACCTACAACTTCTCCTATTATGGATCCTACTGATGAACCTAT
GTCTACAAGGGGACTCACAAGAAGACCCCCTCCGCCAAGGGGGCCGATTAGCTCTGGAG
GAGGCGGTCAAACCAACTAACTAGTTAGATCGTTCGCTTTTCTCCCCTTCAACCAGTAT
ATCAATGTCGTAATTGTCGTTTTTAATGTTCTGAAATTTAGGATTTCTTAAACTATCAT
ATCCGATTTCATCGTAAATATGATTATATGTGCTTGATTTCAAAAAAACC Frame +2
MRGIYISNLPFILFILFDLKKDICKHIYKIMVEERAEVVYDIGYGYGNPCRYLQEVFRS
FLRCLGLEKQEGKERNTSGGVGGGDTGGGDGDGDGDGDGGGGEVDPPTTSPIMDPTDEP
MSTRGLTRRPPPPRGPISSGGGGQTN*LVRSFAFLPFNQYINVVIVVFNVLKFRIS*TI
ISDFIVNMIICA*FQKN

FIGURE 7D

SUNFLOWER PROPEP2 (HaPep2)

GenBank ID# DY910409:
GGGACAAGCGTTGGCATTCGCCGCCACCTCTACAACACCCCACGCGCCAATCATCCAAA
CCCCACGCGCCGCCCCCACCACCACCACATAGCAGCTCACCACCATCTCCCCACACCCT
TTTGCCCTCACATCTCCAAACCCACCTCAAAACCAAGATCTGAACACTCCAATTCTCAT
AAAGTTTCAAACTTTATTTATGAACAACAACAACAACAACAACAATAATCAATGGGAGG
AGTGACGTCATCAATTGCTGCAAAGTTTGCATTTTTCCCTCCCACTCCGCCGTCGTACA
CGGTGGAGGACGACGGTGGTGGTCAGCTGGTTATCCCGGAGGTGCCACGGAGGGAGGGT
GTGGATGTGTTGAAGCTTAGAACTAAAAAGGGGAATGAGATTGTGACTGTTTATATTAA
GCATCCTAAAGCTAATGCTACCCTTTTGTATTCTCATGGTAATGCTGCTGATTTGGGTC
AAATGTTTGAGCTTTTTGTGGAGTTGAGCCTTCGTCTCCGAGTTAATCTTGTTGGATAC
GACTACTCTGGCTATGGGCAATCAACCGGAAAGCCATCCGAGTGCAATACATACGCGGA
CGTTGACGCAGTGTATAAATGCCTCAAGGAGAAATACGGTGTTAAAGATGACCAACTAA
TCGTATACGGTCAATCTGTTGGTAGCGGTCCCACCATTGATCTTGCATCACGTATACCC
GACTTAAGAGGTGTGGTTCTACACAGTCCCATCCTCTCGGGCCTGAGGGTGCTATATCC
TGTCAAAAGAACCTATTGGTTTGATATTTATAAGAACATTGACAAGATCGGTTTAGTTA
ACTGCCCGGTTCTTGTCATACACGGTACGGCAGATGAAGTTGTTGATCATTCTCATGGG
AAACAGCTATGGGAACTTTGCAAGAACAAGTATGAACCGTTGTGGC Frame +1:
GTSVGIRRHLYNTPRANHPNPTRRPHHHHIAAHHHLPTPFCPHISKPTSKPRSEHSNSH
KVSNFIYEQQQQQQ*SMGGVTSSIAAKFAFFPPTPPSYTVEDDGGGQLVIPEVPRREG
VDVLKLRTKKGNEIVTVYIKHPKANATLLYSHGNAADLGQMFELFVELSLRLRVNLVGY
DYSGYGQSTGKPSECNTYADVDAVYKCLKEKYGVKDDQLIVYGQSVGSGPTIDLASRIP
DLRGVVLHSPILSGLRVLYPVKRTYWFDIYKNIDKIGLVNCPVLVIHGTADEVVDHSHG
KQLWELCKNKYEPLW

SUGARCANE PROPEP1 (SoPep1a)

TIGR Sugarcane Gene Index: SoGI TC70532
ATGGCGTTGTCGCCGTCTGCGCCAGCTAGCCCGCTCCGGCGGCAGCTGTTGCGCTACGT
GTCGTCCGGCCTTGTCGCCGCCCTTCACCGCCCAGCTCCAATCATCAGTCTTCCGATTG
CGCTGCGGGGAGTGGAAGCGGCGGCGTCCCAGCGGCTCCAAACCGCGAGCAGAGCCGCT
CCTTCCCCGAAAGGGAGCCCCGGCGCGCCGAGGCAAGGCAGTGGCGGACATGTCCATGC
CGCCGCTCCGGCGATGGCGACGATAGCGCGCATGGCTACGCCTATGCGACGGCCCACGC
CGCCTGGTCCCCCGGCACAGGGCAGCGGTGGCAAAACGAACGCCGTGACGACGGCGACG
ACTGCGCACATGGTGATACGAGGACCCGCCCGGCCTGGTCTCCCTGCACAAGGCAGCGG
TGGAAAAGTTCATGCCGTGTCGCTGGCGGCGACGGCGAGTGTGCTTCTGCGAGGGCCTG
CTCCGCCAGGTCGCCCTGTGGAAGGCAGCGGCGGAAAAGTTCATGCTGTGTCGCCGGCA
GCGACGGCCAGTGTGCTTATGCGAGGGCCCGCCCAGCCTGTTCCCCCGACAGAAGGCGC
CNGCGGGCGTGGTGGAGTCATC

FIGURE 7E

```
Frame +3
MALSPSAPASPLRRQLLRYVSSGLVAALHRPAPIISLPIALRGVEAAASQRLQTASRAA
PSPKGSPGAPRQGSGGHVHAAAPAMATIARMATPMRRPTPPGPPAQGSGGKTNAVTTAT
TAHMVIRGPARPGLPAQGSGGKVHAVSLAATASVLLRGPAPPGRPVEGSGGKVHAVSPA
ATASVLMRGPAQPVPPTEGAXGRGGVI
```

SUGARCANE PROPEP2 (SoPep2a)

TIGR Sugarcane Gene Index: SoGI TC71583

```
ATGGCGTTGTCGCCGTCTGCGCCAGCTAGCCCGCTCCGGCGGCAGCTGCTGCGCTACGT
GTCCTCCGGCCTTGTCGCCGCCCTCCACCGCCCAGCTCCAATCATCAGTCTGCCGATTG
CGCCGCGGGGAGTGGATTCGTCGGCGTCCCAGCGGCTCCAAACCGCGAGCAGAGCCGTT
CCTTCCCTGAAAGGGCGCCCCGGCGCGCCGAGGCAAGGCAGCGGCGGACATGTCCATGC
CGCCGCTCCGGCGTTGGCGACGATAGCGCGCATGGCTACGCCTATGCGACGGCCCACGT
CGCCTGGTCCCCCGGCACAGGGCAGCGGTGGCAAAACGAACGCCGTGACGACGGCGGCG
ACTGCGCACATGGTGATACGAGGACCCGCCCGGCCTGGTCTCCCTGCACAAGGCAGAGG
TGGAAAAGTTCATGTCGTGTCGCCGGCAGCAACGGCGAGTGTGCTTATGCGAGGGCCCG
CCCAGCCTGGTCCCCCGACAGAAGGCGCTGGACGGCGTGGTGGAGTCATCCATGCAATT
GCTTCTTG
```

```
Frame +2
MALSPSAPASPLRRQLLRYVSSGLVAALHRPAPIISLPIAPRGVDSSASQRLQTASRAV
PSLKGRPGAPRQGSGGHVHAAAPALATIARMATPMRRPTSPGPPAQGSGGKTNAVTTAA
TAHMVIRGPARPGLPAQGRGGKVHVVSPAATASVLMRGPAQPGPPTEGAGRRGGVIHAI
AS*
```

SWITCHGRASS PROPEP1 (PvPep1)

GenBank # DN148560

```
GCTCCGCGCCTGCGCCGGCTGCCTGGGCCTGCACGGCTACTGCAGCAGCGACGAGCCCG
ACCCGAAGCCGGCCGCTGTCGCTGCGCCGGACGCCGCGGCGGATGCGGCGTCGAAGGAA
GGAGAGGGCGGCGGCGAGGAGGCTAATAACTTCTTGTACATGCAGGAGGAGGTGGTGAC
CAGGGTGTGGGCGGTGAGGAGGCCGAGGGAGGGCAGCGGGGGCAATGGCGGAGTACACC
ACTAGACGGCGCGAACAAAACAAGCCGGTGATGAAACTACGGTGACGCGTCGGCCTCCG
CGGCAGGCGGCAGCTGATGTATTTTGTTCGTCGAAGCTATGGCCGTGTGTAGCATCTTT
TAACTTGGTATAAATAAAGTAGTAGGTGTGGCTATGGGGTTCTTGTTTGCGTAGGCTTC
TCTGATCTGAACTTGAAATAAGACTCTGAAAGTGTGTAGTTATCTGTATAGTTATCTTC
GTGTTTAAGCTGCAATACCCGATACGTGCGTTTGCTACTCGATGTGTGTGGGTGGTAGA
ATTAATTGTTTGTTGTCTTCAGAATTCAGATCATAGTTTGTTGCTGCTGGTGTATATAT
A
```

FIGURE 7F

Frame + 2
LRACAGCLGLHGYCSSDEPDPKPAAVAAPDAAADAASKEGEGGGEEANNFLYMQEEVVT
RVWAVRRPREGSGGNGGVHH*TARTKQAGDETTVTRRPPRQAAADVFCSSKLWPCVASF
NLV*IK**VWLWGSCLRRLL*S NOTE: This is from a single incomplete EST that does not contain the upstream start codon, A (*) indicates a stop codon.

Figure 8 ie. PROPEP3

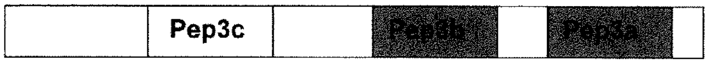

>Barley
MASSAPPAFLPQLVQPVSVLPDQPPSAPAEGTGGQVMVLNDASSLPLQLMRTPPGEGAGGRIHRQLARPRPPGPPRQG
HGGDGGAIHAILLEL

>Sugarcane1
MALSPSAPASPLRRQLLRYVSSGLVAALHRPAPIISLPIALRGVEAAASQRLQTASRAAPSPKGSPGAPRQGSGGHVH
AAAPAMATIARMATPMRRPTPPGPPAQGSGGKTNAVTTATTAHMVIRGPARPGLPAQGSGGKVHAVSLAATASVLLRG
PAPPGRPVEGSGGKVHAVSPAATASVLMRGPAQPVPPTEGAXGRGGVI

>Sugarcane2
MALSPSAPASPLRRQLLRYVSSGLVAALHRPAPIISLPIAPRGVDSSASQRLQTASRAVPSLKGRPGAPRQGSGGHVH
AAAPALATIARMATPMRRPTSPGPPAQGSGGKTNAVTTAATAHMVIRGPARPGLPAQGRGGKVHVVSPAATASVLMRG
PAQPGPPTEGAGRRGGVIHAIAS

```
ProAtPep1 --------------- --------------- ---MEKSDRRSEESH --------------- -------LWIPLQCL DQTLRAILKCLGLFH
ProAtPep2 --------------- --------------- ----MQQERDHKRDC --------------- -----------CKLM PQTVKAFFKCLRFRR
At2g22000 --------------- -----------MEVN GEEERRSRREDEEKE D-------------- --YYYSLLNSPCSVC NKFVQAILKCLGLES
Canola    --------------- -----------MEVN GEEKRSYRREDEEKE --------------- --VYYPLLNSPCSAF HKTVQAILKCLGLES
Potato    --------------- --------------- -MFYLQEGIKAILKC LGFESSKLVHQASSS SSSSSMSDINKNEEE ESEKQEQECVLFQE-
Rice      MDRVEEKEGNRFQEP ASDRCEDNEDKEQDN SEESSSVDQRKEEEE EEKEGCEEATPAAAA AAAAPSFFAHPCSLL QYIARVCACCLGLSD
Poplar    --------------- --------MDKGSST KEEIQGDVLQISHSP S-------------- IFVEAFNALLRCLGL GTVDHQRITQESSST
Medicago  --------------- --------MTFYVYH PCYCLEEIFKTFLRC FGIEST--------- -------QTKEEEDS STSLLKPHACACASD
Soybean   --------------- -------MEGSSPSI EEERTATFYVYHPCY --------------- --FLQQALRALLKCV GIDESENTMCSQANK Length
ProAtPep1 QDSPTTSSPGTSKQP K---EE----KEDVT MEKEEVVVTSRATKV KAKQRGKEKVSSGRP GQHN----          92
ProAtPep2 SSSSSSDMVKARAR- ----------NEEKE EPSSIETSTR-SLNV MRKGIRKQPVSSGKR GGVNDYDM          86
At2g22000 SSIPPSSSSSSPSL- V---EE----EDSGT ETVEETGFMARITAV LRRRPRPPPYSSGRP GQNN----         104
Canola    SSISPSSSSS----- ----------QDPGT ETVQETGFMAMVARL TRRRPRPP-YSSGQP GQIN----          95
Potato    DGNKQGSDSTNDNYK N---DPP---VENDD EDPPQSETLILPTER RGRPPSRPKVGSGPP PQNN----         116
Rice      SFCDPKASSVLVPEP EPAAADPSQEGEEDM KSSEATTRVRAARLR PKPPGNPREGSGGNG GHHH---         154
Poplar    SSSKQEDDEKASEES PQYPPPTRTSDPQAD PPTDTSEDPSTDAAV SALARRTPPVSRGGG GQTNTTTS        121
Medicago  SNVALKDRYYSSSSN KKSSQE----EGVAD PPPSTSTQTINLSSM GRGGPRRTPLTQGPP PQHN----         111
Soybean   QEKSSLPQTPSADDP ITNSPTHKSSPDAAD PPSTTNQTIIIASLM ATRGSRGSKISDGSG PQHN----         115
```

B.

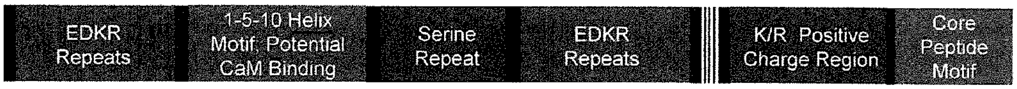

FIGURE 11A(1)

```
                              10        20        30        40        50        60        70        80        90       100
                      ....|....|....|....|....|....|....|....|....|....|....|....|....|....|....|....|....|....|....|....|
At1g73080(At)         MKNLGGLFKILLLFTCLFLSTHIISVSCLNS  LT  S LKHLDRV FQVTST KINA EA   N-- F IT DDSKNVAS- NFTRSRVS QL  EI E
At1g17750(At)         MRNLG--LLEITLLCSLFVYFRIDSVSSLNS  LA  S LKHFDKV LEVAST KENT ET   NNN F VI DLSGNV ET N SASGLS QL SEI E
Glyma20g33620(Gm)     -------MGYLYLLLISYLSALLYAASALNS  LA  S LRDWTIV SDINST KL-- DS   SS- A VH D-NANN VS N TSYSIF QL  DL R
Glyma10g33970(Gm)     -------MGYLYLLLLLCFSSLLYAASALNS  LA  S LRDWTTV SDINST RL-- DS   SS- A VH D-NANN VS N TSYSIL QL  DL R
Glyma15g00360(Gm)     -------MSMIWIVFFSLSCMSCAVVSSLTS  VT  S LRHWTSV PSINAT LA-- DT   SS- V VQ D-HSHH VN T PDYGIA QL  EI -
P93194(In)            -----MKVAVNTFLLFLCSTSSIYAAFALNS  AA  S TRHWTSI SDITQS NA-- DS   S-- L VE D-RRQF DT N SSYGIS EF  EISH
803073(Pt)            -------------------------------MS LRKWDSV TSITSS NS-- DS   S-- L IG DHRSHC VS N SGLGIS PL  ET Q
765043(Pt)            -----MSSVLNHVLLLCWYFVSVYTVSGLNY  ST  S LRQWNSV PSITSS NA-- DS   S-- L IG DSRTHS VS N SGYATS QL  EI L
CAO23192(Vv)          -------------------------------MA KSKW-AV TFMEES NA-- HS   S-- V VS D-ETHI VS NVSGLGIS IL  EIAD
Os08g0446200(Os)      ------MRLVVWHWFFFFFFTSVSSSWSLTS  LA  S SRDL-IL HSISST KA-- DT   N-- D VS N-KKNS VS D SSSGVS SL  QI L
Os08g0446400(Os)      ------MGLHIWCWLVVLFSL-APLCCSLSA  LA  D AKTL-IL SSISSN SA--DDA   T-- K VD D-EMSN VS N SYSGLS SL  QI L
GRMZM2G011806(Zm)     ------MKLVFWHWIFLFFVL-LSTSQGMSS  LA  A SKTL-IL SFIRTN SA-- DA   T-- N VG N-GRNR IS D SSSEVS FI  EI R
GRMZM2G128602(Zm)     ------MKLVLWHQFFLFFVL-VSTSQGMSS  LA  A SKSL-IL SPIRTN SD-- DA   T-- S VG N-GRNR IS D SSSGVS SI  AI R
Sb07g021950(Sb)       ------MKLV-WHWVFLFFLL-VSTSQGMSS  LA  A SKSL-IL SSIRSN ST-- -AN  T-- S VD N-GRNR IS D SSSEVS SI  DI R 110       120       130       140       150       160       170       180       190       200
                      ....|....|....|....|....|....|....|....|....|....|....|....|....|....|....|....|....|....|....|....|
At1g73080(At)         LKS QILD ST NFS TI STLG  TK AT D  E GFSDK  DTLDSLKRLEVLYLYINFLTGELPESLFRIPK QVLYLDY NLT PIPQSI DAKEL
At1g17750(At)         LKS VTLD SL SFS LL STLG  TS EY D  N DFSGEV DIFGSLQ-----------------------N TFLYLDR NLS LIPASV GLIEL
Glyma20g33620(Gm)     MVH QTID SY DLF KI PELD  TM EY D  V NFSGG  QSFKNLQNLKHIDLSSNPLNGEIPEPLFDIYH EEVYLSN SLT SISSSV NITKL
Glyma10g33970(Gm)     LVH QTID SY DFF KI PELE  SM EY N  V NFSGG  ESFKSLQNLKHIYLLSNHLNGEIPESLFEISH EEVDLSR SLT SIPLSV NITKL
Glyma15g00360(Gm)     ---------------------- LSR EY E AS NLTGQ  DAFKNMHNLNLLSLPYNQLSGEIPDSLTHAPQ NLVDLSH TLS SIPTSI NMTQL
P93194(In)            LKH KKVV SG GFF SI SQLG  SL EHID  S SFTGN  DTLGALQNLRNLSLFFNSLIGPFPESLLSIPH ETVYFTG GLN SIPSNI NMSEL
803073(Pt)            LKQ KTVD NT YFS DI SQLG  SL EY D  A SFTGG  DSFKYLQNLQTLIIFSNSLSGEIPESLFQDLA QVLYLDT KFN SIPRSV NLTEL
765043(Pt)            LKH KTID HTSNFS DI SQLG  SL EH D  I SFTRK  DGFKYLQN-----------------------------------------------
CAO23192(Vv)          LRH TSVDFSY SFS PI PEFG  SL MD D  V GFVGE  QNLNSLGKLEYLSFCNNSLTGAVPESLFRIPN EMLYLNS KLS SIPLNV NATQI
Os08g0446200(Os)      MKS QVLS SN SIS SI QELG  SM DQ D  S SFSGE  ASLGDIKKLSSLSLYSNSLTGEIPEGLFKNQF EQVYLHY KLS SIPLTV EMTSL
Os08g0446400(Os)      MKH KVID SG GIS---------------------------------------------------------------------------------
GRMZM2G011806(Zm)     LKY QVLI SA NIS LI LELG  SM EQ D  Q LLSGN  ASMGSLKKLSSLSLYYNSFHGTIPEELFKNQF EQVYLHG QLS WIPFSV EMTSL
GRMZM2G128602(Zm)     LKY RILI SA NIS LI LELGD NM EE D  Q LFSGN  ASLGNLKKLSSLSLYRNSFNGTIPEELFKNQF EQVYLHD QLS SVPLSV EMTSL
Sb07g021950(Sb)       LKY QVLI ST NIS SI LELG  SM EQ D  Q LLSGN  ASMGNLKKLSSLSLYSNSLNGSIPEELFKNQF EEVYLHD QLS SIPFAV EMTSL 210       220       230       240       250       260       270       280       290       300
                      ....|....|....|....|....|....|....|....|....|....|....|....|....|....|....|....|....|....|....|
At1g73080(At)         VE SMYA QF  NI E I  SSS QI Y HR K V SL ES NLLGN TTLFVGN SLQ PVRFG-SPN  N LTLD  Y EFE GV PA     SS DAL
At1g17750(At)         VD RMSY NL  TI ELL  CSK EY A NN K N SL AS YLLEN GELFVSN SLG RLHFG-SSN  K VSLD  F DFQ GV PEI    SS HSL
Glyma20g33620(Gm)     VT DLSY QL  TI M I  CSN EN Y ER Q E VI ES NNLKN QELFLNY NLG TVQLG-TGN  K SSLS  Y NFS GI SS     SG MEF
Glyma10g33970(Gm)     VT DLSY QL  TI I I  CSN EN Y ER Q E VI ES NNLKN QELYLNY NLG TVQLG-SGY  K SILSI Y NFS GI SS     SG IEF
Glyma15g00360(Gm)     LQ YLQS QL  TI S I  CSK QE F DK H E IL QS NNLND AYFDVAS RLK TIPFGSAAS  N KNLD  F DFS GL SS     SA SEF
P93194(In)            TT WLDD QF  PV S L  ITT QE Y ND N V TL VT NNLEN VYLDVRN SLV AIPLD-FVS  QIDTIS N QFT GL PG     TS REF
803073(Pt)            LE SLFG QL  TI E I  CRK QS P SY K S SL EI TNLES VELFVSH SLE RIPLG-FGK  N ETLD  F SYS GL PD     SS ATL
765043(Pt)            ---------------------- QY S SF S S EI ES TKLES AELLLDH SLE RIPTG-FSN  N DTLD  F SFS GF SD    FSS AIL
CAO23192(Vv)          IA WLYD AL  DI S I  CSE EE Y NH QFL VL ESINNLEN VYLDVSN NLE KIPLG-SGY  K DTLV  M GFG EI PG     TS SQF
Os08g0446200(Os)      RY WLHG KL  VL D I  CTK EE Y LD Q S SL KT SYIKG KIFDITA SFT EITFS-FED  - EVFI  F QISNEI SW    SS TQL
Os08g0446400(Os)      ----------- PM S I  CTK EV H LR R S IL DT SNIEA RVFDLSR SFT KVNFR-FEN  - EEFI  F YLR EI VWI    SS TQL
GRMZM2G011806(Zm)     KS WLHE ML  VL S I  CTK EE Y LH Q S SI ET SKIEG KVFDATA SFT EISFS-FEN  - EIFI  F NIK EI SW     RS QQL
GRMZM2G128602(Zm)     KS WLQE ML  VL S I  CTK ED Y LD Q S SI ET GMIKG KVFDATT SFT EISFS-FED  - EIFI  F NIK EI SW     MS QQL
Sb07g021950(Sb)       KS WLHV ML  VL S I  CTK EE Y LY Q S SL ET SEIKG RVFDATS SFT EINFS-FEN  - EIFI  F YIK EI SW V  RSMQQL 310       320       330       340       350       360       370       380       390       400
                      ....|....|....|....|....|....|....|....|....|....|....|....|....|....|....|....|....|....|....|
At1g73080(At)         VIVSGN S T  SSL M KN TI N SE R   S  A L N SS NL K ND   V GI SA GK RK ES E  E RFS EI IE  KSQS TQLLV Q
At1g17750(At)         VMVKCN T T  SSM M RKVSVID SD R   N  Q L N SS ET K ND   Q EI PA SK KK QS E  F K S EI IG  K QS TQMLV N
Glyma20g33620(Gm)     YAARSN V S  STL LMPN SL IIPE L   K   QI N KA EE R NS E E EI SE GN SK RD R YE L T EI LG  K QS EQIYL I
Glyma10g33970(Gm)     YASGNN V T  STF L PN SM FIPE L   K   QI N KS KE S NS   E EI SE GN SK RD R  E H T EI LG  K QS EQIHM I
Glyma15g00360(Gm)     SAVNCN D N  PSF L TK SI Y PE H   KV   I N MS TE H YS   E NI SE CK RK VD E  S Q T EI LS  K KS KHLLV N
P93194(In)            GAFSCA S P  SCF Q TK DT Y AG HF  R    L K KSMID Q QQ   E EI GE CM SQ QY H YT N S EV LS  K QS QSLQL Q
803073(Pt)            AIIHSN R A  SSF Q KK SV D SE R   T    LSN KS MT N YT E E KI SE GR NK ED E  N H S AI IS  K AS KYLLV N
```

FIGURE 11A(2)

```
765043(Pt)          AIINSH R A  SSF H KK SY D SQ Q   R    L D ES TT N YT   E EI GE GR SK EN E  D R S EI IS  K AS KSIYV N
CAO23192(Vv)        AALNNR S S  SSF L HK LL Y SE H   K    I Q KS RS H YM   E EI SE GM NE QD R  N R T EI IS  K PS ENVLV N
Os08g0446200(Os)    AFVNNNIS Q  SSL L RN SQ L SE S   P    I N QL VW E DA   N TV KE AN RK EK F  E R I EF ED  S KS QSVLI E
Os08g0446400(Os)    AFVNNSIT Q  SSI L RN SY V SQ S   T    I N QL IW H DA   E TI KE AN RN QK Y  E C T EF ED  G QS LSVDI K
GRMZM2G011806(Zm)   GFVNNS S K  NFI LFSN TY L SQ S T L    I N RL QW E DA   E TV EEFAN RY SK F  E H M DF ES  S QT ESVLL S
GRMZM2G128602(Zm)   GFVNNS Y K  NSL L SN TY L SQ S   P    I N QS QW E DA   D TV EEFAN RS SK F  E R M DF EN  S QT ESVLL S
Sb07g021950(Sb)     GFVNNS S K  NSL L SN TH L SQ S   P    ISN RL QW E DA   E TV EG AN RN SR F  E H M EF ES  S QT ESVLL R
                          410       420       430       440       450       460       470       480       490       500
                    ....|....|....|....|....|....|....|....|....|....|....|....|....|....|....|....|....|....|....|....|
At1g73080(At)        NLT E  VEMT M K KIAT FN S Y A  PG  V  S EEV FIG KLT E   NL H RK RI NL S L H T  ASIGH KTIR FI RE   S
At1g17750(At)        TLT E  VEVTQ  H KKLT FN G Y D  MS  L RS EEV LLG R T E   HL H QK RLFIL S Q H K  ASIRQ KT E VR ED K S
Glyma20g33620(Gm)    NLS E  FEMT   H KNIS FN Q S    QS  I  S VVL FMY N T TL  NL F KQ VK NM V QFY N  PDVGR TT T VR EE HFT
Glyma10g33970(Gm)    NLS E  LEMT   H KNVS FN Q S    QS  I  S VVL FMY N T TL  NL F KH VR NM G QFI S  PDVGR TT T LR ED   T
Glyma15g00360(Gm)    SLS E  LEMT   Q KNIS FS Q S    QS  I  S VLL FTN K T N   NL F KK NI NL I Q Q S  PDVGR TT R LI QQ  FT
P93194(In)           NLS E  VDMT   Q VSLA YE H T    QD  A  S EVL LTR M T H   NL SQKK KR LL Y Y E SV SDLGG ST E LI EE   R
803073(Pt)           SLS E  LEITH  N KNLS YN Q F    QS  I  S LQL FTD K T E   NL H KQ RV NM R Q Q S  SDVGG LT W LI KE   S
765043(Pt)           SLS E  LEMT  RQ QNIS AQ Q Y    QT  I  S LWL FFG K T E   NL Y QQ RI VM S Q Q S  SDVGG PT W LT EE   S
CAO23192(Vv)         TLS E  VEIT   H KNIS FN R S    QR  I  S VQL VTN K T E  KSI F KQ SV NM L L Q S  SAVGS ST R LI RK   T
Os08g0446200(Os)     SFT R  PVLA   F KNIT FN F T    PD  V  R TQI FTN S V G   NI S KR RI DL L L N S  SNVMD PS E FI QN   S
Os08g0446400(Os)     NFT Q  IVLA M Q QQIT FN S T    QG  V  S SVI FIN S V T   KI S GR EV NL S L N S  SGIAD PT R VI NQ   I
GRMZM2G011806(Zm)    KFT R  SVLA   S KNIT FD F T    QE  V  P VQI FTN S V G   NI S KA RI DL F H N S  SSVLD PS E VIVEN  V
GRMZM2G128602(Zm)    RFT K  SVLA   F KNIT FD F T    QE  V  P VQI FTN S V S   NI SRKA RI DL F H N S  SSVVD PS K VI QN   N
Sb07g021950(Sb)      RFT K  SVLA   Y ENIT FD F T    QE  V  P VQI FTN S V G   KI S KA RI DL F H N S  SNVVD PS E VIVEN  D 510       520       530       540       550       560       570       580       590       600
                    ....|....|....|....|....|....|....|....|....|....|....|....|....|....|....|....|....|....|....|....|
At1g73080(At)        LL E SQDHS SFLDFNS NFE P  G LGS KNLSSINL R RFT Q  PQL N QN GYMN  R L E SL A L N VSLERF VGF      VPS
At1g17750(At)        VL E PESLS SYVNLGS SFE S  R LGS KNLLTIDL Q KLT L  P L N QS GLLN  H Y E PL S L G ARLLYF VGS      IPS
Glyma20g33620(Gm)    SL D YINPN SYMSINN NIS A  S LGK TNLSLLNL M SLT LV S L N EN QTLD  H N E PL H L N AKMIKF VRF      VPS
Glyma10g33970(Gm)    AL D ETNPN SYMSINN NIS A  S LGN TNLSLLDL M SLT LV S L N VN QTLD  H N Q PL H L N AKMIKFNVGF      VPS
Glyma15g00360(Gm)    PL D KSNPN EHMDISS KIH E  S LRN RHITHLIL M KFN P  S L NIVN QTLN AH N E PL S L K TKMDRF VGF F    LPS
P93194(In)           GL D VEKQN LFFDLSG NFT P  P LGNLKNVTAIYL S QLS S  P L S VK EHLN  H I K IL SEL N HKLSEL ASH L    IPS
803073(Pt)           AL E SENPI YHMDVSK NIT P  P IGN SGLTSIHL M KLT F  S L N VN LVVD  S Q E SL S L K HNLGKF VGF      VPS
765043(Pt)           TL Q AENPI LYMDISK NIT P  P IGN SGLTFIRL M KLT S  S L N IN LVVD  S Q E SL S L R YKLGQF VGF     TIPS
CAO23192(Vv)         VL N AKNPN LLLDLSE GIN T  L LGN TNVTSINL M RLS L  Q L N NV QALN  H D G PL S L N KNLFKF VGF      FPS
Os08g0446200(Os)     PI Q RNCAN SYIDLSH SLS N  A LGR VNITMIKW E KLV P  S IRD VN RVLN  Q S Q VL V I S SKLYLL LSF      ALT
Os08g0446400(Os)     SI Q VNCSS NYIDLSY LLS D  A LSK INVTFVNW W KLA L  S I N GN SSLN  G R Y EL VEI G SKLYKL LSY      ALT
GRMZM2G011806(Zm)    SI Q INCAN SYMDLSH SLS N  S FSR VKIAEINW E NIF A  P I K VN KRLD  H L H SI V I S SKLYSL LGF      ALS
GRMZM2G128602(Zm)    SI Q VNCAN SYMDLSH SLS N  A FSR VNITEINW E KLF A  P I N VN KRLD  H I H SI V I S SKLYSL LSF      ALR
Sb07g021950(Sb)      SI Q KNCAN SYMDLSH SLS N  A FSR VNITEINW E KLS A  P I N VN KRLD  H V H SV V I S SKLYSL LSF      ALS 610       620       630       640       650       660       670       680       690       700
                    ....|....|....|....|....|....|....|....|....|....|....|....|....|....|....|....|....|....|....|....|
At1g73080(At)       NFSNWKG TT V S  R S  I QF PELKK ST  IAR AF  E  S I LIED IYD D  G G T EI AKL D IK TR NI N     SLSV KG
At1g17750(At)       SFRSWKS ST V SD N L AI QF AELDR SD RIAR AF  K  S V L KS RYG D  A VFT EI TTL A IN ER NI N K   PLSV QS
Glyma20g33620(Gm)   SFRSWTT TA I S  H N  I AF SEFKK NE      MF  N  R I E VN IYE    ATG I EL REI N KS LS DL W     SIQV DG
Glyma10g33970(Gm)   SFQSWTT TT I S  R N  I AF SEFKK NE R    TF  N  R I E VN IYE    A G I EL REI N KN LS DL W     SIQV DE
Glyma15g00360(Gm)   GLQSWTR TT I S  H S  L AF SEYKM SE      MF  R  R V A QS RYGM   S G I DI VEI N NF ER DL Q     SIEV GE
P93194(In)          TLGSLTE TK S G  S S  I TS FQSNK LN      LLA D  -PV A QA R-S    S K N QL IDL K KM EE DV H   S TLRV ST
803073(Pt)          SLRNWTS ST I K  H I  I PF SELEK TEI     FL  E  SWI S QS QYA    S G F EL SEL N IK EQ QL N     TLAP DK
765043(Pt)          SLRNWTS ST V S  H T  I PF PELGM TE      IL  V  S I SVRS KYA    S GFV KL SEL N KM ER DI N     TLAI DY
CAO23192(Vv)        SLRSLEN SV I R  R T  I SF SELQY SEI     FL  N  S I M QN IYS  I H R T SL LEL K IM ER DI H   S TLSA DG
Os08g0446200(Os)    TVSNLKF SQ R Q  K S  I DS SQLDM IE      VL  S  S L R VK GIA  ICS G V GI PLLSN VE QS DL L G   DLDM GN
Os08g0446400(Os)    TVSSLKF SQ R Q  K S  I DS SQLDM IE      IL  S  S L K VK GIA    R G V DI P-L N VE QS DL F     GLAS GN
GRMZM2G011806(Zm)   TVSSLKF TQ R Q  R S  L DPFSQLEM IE      IL  S  S L Q VK GTT    S G V DI SQF N VE QN DL F     GLAT RS
GRMZM2G128602(Zm)   TVSNLKF TQ R Q  R S  L DS SQLEM IE      IL  S  S L Q VK GTA    S G M DI TQL N VE QN DF F     GLAT RS
Sb07g021950(Sb)     TVSNLKY TQ R Q  R S  F KS SQLEM IE      II  S  S L Q VK GTA    S G I DI PQL N VD QN DL F     GLAT RS 710       720       730       740       750       760       770       780       790       800
                    ....|....|....|....|....|....|....|....|....|....|....|....|....|....|....|....|....|....|....|....|
At1g73080(At)       LTS LHVDV N Q T  I DN EGQ L EPSS S   N  IPHS----FSASNNSRSALKY KDQSKSRKSGLSTWQIVL AVL SLLVLVVVLALVFIC
At1g17750(At)       LKS NQVDV Y Q T  I VN---- L NSSK S   D  IQAS----YSVSAIIRKEFKS KGQVK-----LSTWKIAL AAG SLSVLA LFALFLVL
Glyma20g33620(Gm)   LSS SEFNI Y S E  V QQ TTLPN SLS- L   G  GSN---------FTESSYLK  DTNSKKSKK-LSKVATVM ALG AIFVVL LW-LVYIF
Glyma10g33970(Gm)   LSS SEFNI F S E  V QQ TTLPN SLS- L   G  DSN---------FTVSSYLQ  STNSKKSKK-LSKVEAVM ALG LVFVVL LG-LICIF
Glyma15g00360(Gm)   LLS VEVNI Y S H RV KK MKL K PLSS L   G  TTTRCSASDGLACTARSSIK  DDKSTKQKG-LSKVEIVM ALG SILVVL LLGLVYIF
P93194(In)          IQS TFINI H L S  V PS TKF N SPTS S  SD  INCP---ADGLACPESSILR  NMQSNTGKGGLSTLGIAM VLGALLFIIC FLFSAFLF
803073(Pt)          IHS VQVDI Y H S  I ET MNL N SPSS W   D  VSCL--PSGGLTCTKNRSIK  DSQSSKRDS-FSRVAVAL AIA VVAVFM VG-LVCMF
```

Figure 11A:
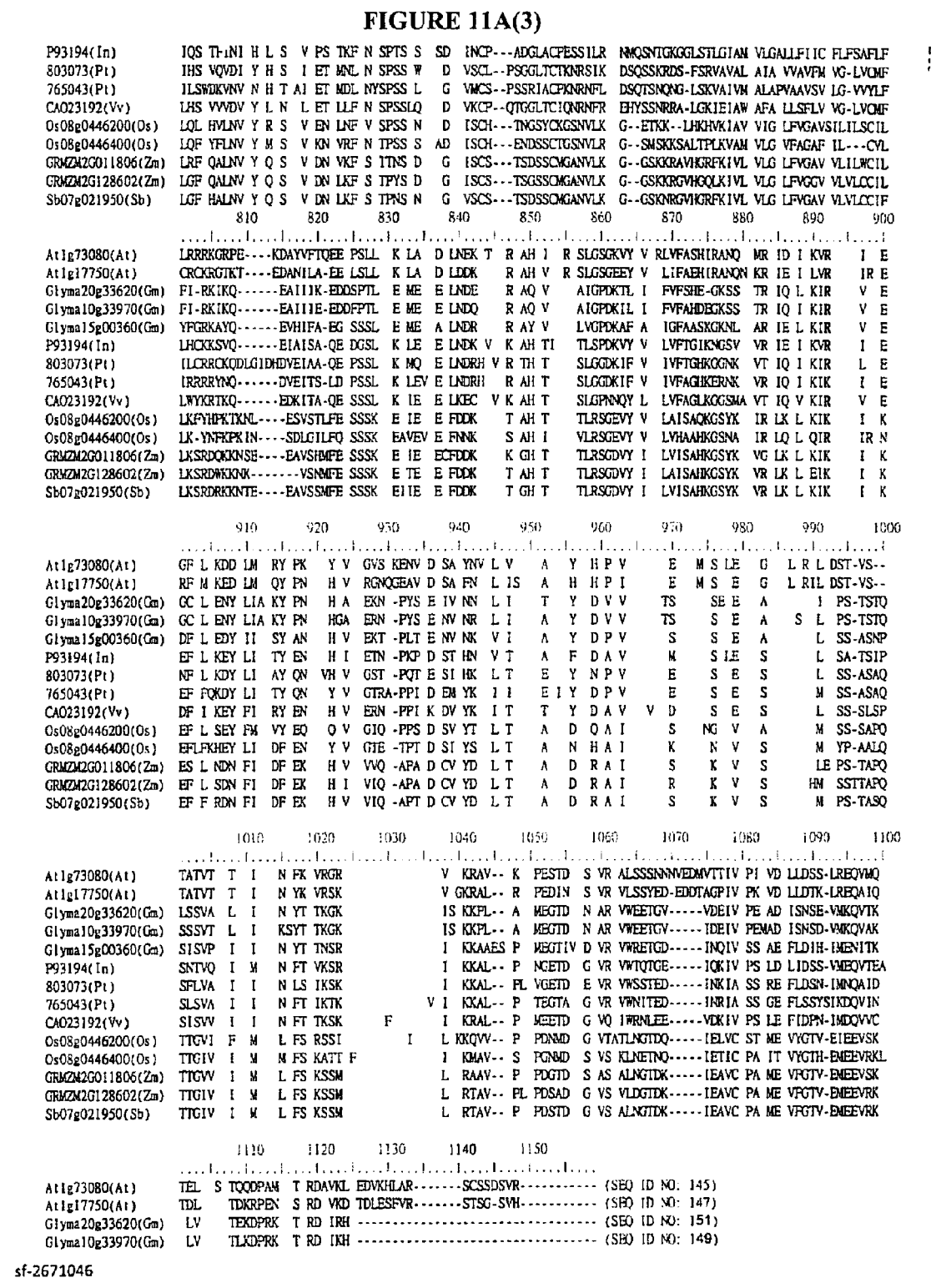

FIGURE 11A(3)

```
P93194(In)          IQS THNI H L S  V PS TKF N SPTS S  SD  INCP---ADGLACPESSILR  NMQSNTGKGGLSTLGIAN VLGALLFIIC FLFSAFLF
803073(Pt)          IHS VQVDI Y H S  I ET MNL N SPSS W  D  VSCL--PSGGLTCTKNRSIK  DSQSSKRDS-FSRVAVAL AIA VVAVFM VG-LVCMF
765043(Pt)          ILSWDKVNV N H T AI ET MDL NYSPSS L  G  VMCS--PSSRIACPKNRNFL  DSQTSNQNG-LSKVAIVM ALAPVAAVSV LG-VVYLF
CAO23192(Vv)        LHS VVVDV Y L N  L ET LLF N SPSSLQ  D  VKCP--QTGGLTCIQNRNFR  EHYSSNRRA-LGKIEIAW AFA LLSFLV VG-LVCMF
Os08g0446200(Os)    LQL HVLNV Y R S  V EN LNF V SPSS N  D  ISCH---TNGSYCKGSNVLK  G--ETKK--LHKHVKIAV VIG LFVGAVSILILSCIL
Os08g0446400(Os)    LQF YFLNV Y M S  V KN VRF N TPSS S  AD ISCH---ENDSSCTGSNVLR  G--SMSKKSALTPLKVAM VLG VFAGAF IL---CVL
GRMZM2G011806(Zm)   LRF QALNV Y Q S  V DN VKF S ITNS D  G  ISCS---TSDSSCMGANVLK  G--GSKKRAVHGRFKIVL VLG LFVGAV VLILWCIL
GRMZM2G128602(Zm)   LGF QALNV Y Q S  V DN LKF S TPYS D  G  ISCS---TSGSSCMGANVLK  G--GSKKRGVHGQLKIVL VLG LFVGGV VLVLCCIL
Sb07g021950(Sb)     LGF HALNV Y Q S  V DN LKF S TPNS N  G  VSCS---TSDSSCMGANVLK  G--GSKNRGVHGRFKIVL VLG LFVGAV VLVLCCIF
                           810       820       830       840       850       860       870       880       890       900

At1g73080(At)       LRRRKGRPE----KDAYVFTQEE PSLL  K LA  D LNEK T  R AH I  R SLGSGKVY V RLVFASHIRANQ  MR ID I KVR    I E
At1g17750(At)       CRCKRGTKT----EDANILA-EE LSLL  K LA  D LDDK    R AH V  R SLGSGEEY V  LIFAEHIRANQN KR IE I LVR    IR E
Glyma20g33620(Gm)   FI-RKIKQ------EAIIIK-EDDSPTL  E ME  E LNDE    R AQ V    AIGPDKTL I  FVFSHE-GKSS  TR IQ L KIR    V E
Glyma10g33970(Gm)   FI-RKIKQ------EAIIIE-EDDFPTL  E ME  E LNDQ    R AQ V    AIGPDKIL I  FVFAHDEGKSS  TR IQ I KIR    V E
Glyma15g00360(Gm)   YFGRKAYQ------EVHIFA-EG SSSL  E ME  A LNDR    R AY V    LVGPDKAF A  IGFAASKGKNL  AR IE L KIR    V E
P93194(In)          LHCKKSVQ------EIAISA-QE DGSL  K LE  E LNDK V  K AH TI   TLSPDKVY V  LVFTGIKNGSV  VR IE I KVR    I E
803073(Pt)          ILCRRCKQDLGIDHDVEIAA-QE PSSL  K MQ  E LNDRH V R TH T    SLGGDKIF V  IVFTGHKGGNK  VT IQ I KIR    L E
765043(Pt)          IRRRRYNQ------DVEITS-LD PSSL  K LEV E LNDRH   R AH T    SLGGDKIF V  IVFAGHKERNK  VR IQ I KIK    I E
CAO23192(Vv)        LWYKRTKQ------EDKITA-QE SSSL  K IE  E LKEC  V K AH T    SLGPNNQY L  LVFAGLKGGSMA VT IQ V KIR    V E
Os08g0446200(Os)    LKFYHPKTKNL----ESVSTLFE SSSK  E IE  E FDDK    T AH T    TLRSGEVY V  LAISAQKGSYK  IR LK L KIK    I K
Os08g0446400(Os)    LK-YNFKPKIN----SDLGILFQ SSSK  EAVEV E FNNK    S AH I    VLRSGEVY V  LVHAAHKGSNA  IR LQ L QIR    IR N
GRMZM2G011806(Zm)   LKSRDQKKNSE----EAVSHMFE SSSK  E IE  ECFDDK   K GH T    TLRSGDVY I  LVISAHKGSYK  VG LK L KIK    I K
GRMZM2G128602(Zm)   LKSRDWKKNK-------VSNMFE SSSK  E TE  E FDDK    T AH T    TLRSGDVY I  LAISAHKGSYK  VR LK L EIK    I K
Sb07g021950(Sb)     LKSRDRKKNTE----EAVSSMFE SSSK  EIIE  E FDDK    T GH T    TLRSGDVY I  LVISAHKGSYK  VR LK L KIK    I K 910       920       930       940       950       960       970       980       990      1000

At1g73080(At)       GF L KDD LM  RY PK   Y V  GVS KENV D SA YNV L V    A   Y  H P V      E   M S LE   G    L R L DST-VS--
At1g17750(At)       RF M KED LM  QY PN   H V  RGNQGEAV D SA FN  L IS   A   H  H P I      E   M S  E   G    L RIL DST-VS--
Glyma20g33620(Gm)   GC L ENY LIA KY PN   H A  EKN -PYS E IV NN  L I    T   Y  D V V      TS     SE E   A        I PS-TSTQ
Glyma10g33970(Gm)   GC L ENY LIA KY PN   HGA  ERN -PYS E NV NR  L I    A   Y  D V V      TS     S  E   A     S  L PS-TSTQ
Glyma15g00360(Gm)   DF L EDY II  SY AN   H V  EKT -PLT E NV NK  V I    A   Y  D P V      S      S  E   A        L SS-ASNP
P93194(In)          EF L KEY LI  TY EN   H I  ETN -PKP D ST HN  V T    A   F  D A V      M      S LE   S        L SA-TSIP
803073(Pt)          NF L KDY LI  AY QN  VH V  GST -PQT E SI HK  L T    E   Y  N P V      E      S  E   S        L SS-ASAQ
765043(Pt)          EF FQKDY LI  TY QN   Y V  GTRA-PPI D EM YK  I I    E I Y  D P V      E      S  E   S        M SS-ASAQ
CAO23192(Vv)        DF I KEY FI  RY EN   H V  ERN -PPI K DV YK  I T    T   Y  D A V   V  D      S  E   S        L SS-SLSP
Os08g0446200(Os)    EF L SEY FM  VY EQ   Q V  GIQ -PPS D SV YT  L T    A   D  Q A I      S     NG  V   A        M SS-SAPQ
Os08g0446400(Os)    EFLFKHEY LI  DF EN   Y V  GTE -TPT D SI YS  L T    A   N  H A I      K      N  V   S        M YP-AALQ
GRMZM2G011806(Zm)   ES L NDN FI  DF EK   H V  VVQ -APA D CV YD  L T    A   D  R A I      S      K  V   S       LE PS-TAPQ
GRMZM2G128602(Zm)   EF L SDN FI  DF EK   H I  VIQ -APA D CV YD  L T    A   D  R A I      R      K  V   S       HM SSTTAPQ
Sb07g021950(Sb)     EF F RDN FI  DF EK   H V  VIQ -APT D CV YD  L T    A   D  R A I      S      K  V   S        M PS-TASQ 1010      1020      1030      1040      1050      1060      1070      1080      1090      1100

At1g73080(At)       TATVT  T  I   N FK VRGR               V  KRAV-- K  PESTD  S VR ALSSSNNNVEDMVTTIV PI VD LLDSS-LREQVMQ
At1g17750(At)       TATVT  T  I   N YK VRSK               V GKRAL-- R  PEDIN  S VR VLSSYED-EDDTAGPIV PK VD LLDTK-LREQAIQ
Glyma20g33620(Gm)   LSSVA  L  I   N YT TKGK               IS KKPL-- A  MEGTD  N AR VWEETGV-----VDEIV PE AD ISNSE-VMKQVTK
Glyma10g33970(Gm)   SSSVT  L  I   KSYT TKGK               IS KKPL-- A  MEGTD  N AR VWEETGV-----IDEIV PEMAD ISNSD-VMKQVAK
Glyma15g00360(Gm)   SISVP  I  I   N YT TNSR               I  KKAAES P  MEGTIV D VR VWRETGD-----INQIV SS AE FLDIH-IMENITK
P93194(In)          SNTVQ  I  M   N FT VKSR               I  KKAL-- P  NGETD  G VR VWTQTGE-----IQKIV PS LD LIDSS-VMEQVTEA
803073(Pt)          SFLVA  I  I   N LS IKSK               I  KKAL-- PL VGETD  E VR VWSSTED-----INKIA SS RE FLDSN-IMNQAID
765043(Pt)          SLSVA  I  I   N FT IKTK              V I  KKAL-- P  TEGTA  G VR VWNITED-----INRIA SS GE FLSSYSIKDQVIN
CAO23192(Vv)        SISVV  I  I   N FT TKSK      F        I  KRAL-- P  MEETD  G VQ IWRNLEE-----VDKIV PS LE FIDPN-IMDQVVC
Os08g0446200(Os)    TTGVI  F  M   L FS RSSI          I    L KKQVV-- P  PDNMD  G VTATLNGTDQ-----IELVC ST ME VYGTV-EIEEVSK
Os08g0446400(Os)    TTGIV  I  M   M FS KATT F              I  KMAV-- S  PGNMD  S VS KLNETNQ-----IETIC PA IT VYGTH-EMEEVRKL
GRMZM2G011806(Zm)   TTGVV  I  M   L FS KSSM               L  RAAV-- P  PDGTD  S AS ALNGTDK-----IEAVC PA ME VFGTV-EMEEVSK
GRMZM2G128602(Zm)   TTGIV  I  M   L FS KSSM               L  RTAV-- PL PDSAD  G VS VLDGTDK-----IEAVC PA ME VFGTV-EMEEVRK
Sb07g021950(Sb)     TTGIV  I  M   L FS KSSM               L  RTAV-- P  PDSTD  G VS ALNGTDK-----IEAVC PA ME VFGTV-EMEEVRK 1110      1120      1130      1140      1150

At1g73080(At)       TEL  S TQQDPAM  T RDAVKL EDVKHLAR-------SCSSDSVR----------- (SEQ ID NO: 145)
At1g17750(At)       TDL    TDKRPEN  S RD VKD TDLESFVR-------STSG-SVH----------- (SEQ ID NO: 147)
Glyma20g33620(Gm)   LV     TEKDPRK  T RD IRH ---------------------------------- (SEQ ID NO: 151)
Glyma10g33970(Gm)   LV     TLKDPRK  T RD IKH ---------------------------------- (SEQ ID NO: 149)
``` sf-2671046

FIGURE 11A(4)

```
765043(Pt)          LM   TEEEPSK  S RD VRQ VKANDRRR-------RR---------------- (SEQ ID NO: 163)
CAO23192(Vv)        LV   TQKEASK  T RD VNQ TDANAPAR-------GKNS-------------- (SEQ ID NO: 165)
Os08g0446200(Os)    SL   AAKEASR  P AD VKE TDVRKSAG-----KLSKPE--KTASRSSS----- (SEQ ID NO: 155)
Os08g0446400(Os)    SL   TAKEASQ  S AV VKE TDARHVAG-----SYSKQNSGPSNS--------- (SEQ ID NO. 157)
GRMZM2G011806(Zm)   SV   AAREASQ  S TA VKE TDARPATG--GGRSLSKSKQGKPGSQSNSSAYRQ (SEQ ID NO: 167)
GRMZM2G128602(Zm)   SV   AAREVSQ  S TA VKE TDARPASASSGSRSLSKSREGKPGLQSSSSAYWQ (SEQ ID NO: 169)
Sb07g021950(Sb)     SV   AAREASQ  S AD VKE TGVRLATGSGGGRSLSKSKQGKPGSQSHSSAY— (SEQ ID NO: 171)
```

FIGURE 11B(1)

>At1g73080 (AtPEPR1) (SEQ ID NO: 144)

ATGAAGAATCTTGGGGGGTTGTTCAAAATTCTTCTGCTTTTCTTCTGTCTCTTTCTATCG
ACCCACATAATTTCCGTTTCTTGTTTAAACTCAGATGGGCTAACTCTACTCTCTCTTCTG
AAGCATTTGGATAGAGTACCACCACAAGTTACTTCGACATGGAAAATAAACGCATCTGAA
GCAACTCCATGTAACTGGTTCGGTATCACTTGTGACGATTCTAAGAATGTTGCGTCTCTC
AACTTCACTCGTTCTAGGGTTTCAGGTCAATTGGGTCCGGAAATTGGGGAGCTCAAAAGC
TTGCAGATTTTGGATCTGAGTACTAACAATTTCTCCGGGACTATACCTTCCACTTTAGGA
AACTGTACCAAACTCGCTACTCTAGATTTGTCTGAAAATGGATTCTCTGATAAGATCCCA
GATACTCTCGATAGCTTGAAGAGGTTGGAGGTGCTTTATCTTTACATAAACTTCCTCACT
GGTGAGTTACCTGAATCCTTGTTTCGAATTCCGAAGCTGCAGGTTTTATATCTTGACTAT
AACAATCTCACCGGTCCGATTCCTCAAAGTATTGGTGATGCTAAGGAGCTTGTGGAGCTG
AGTATGTATGCGAATCAGTTCTCTGGTAACATCCCTGAGTCGATTGGGAATAGCAGTAGT
CTGCAGATTCTTTATTTGCACAGGAACAAGTTAGTTGGTTCATTACCTGAAAGTCTCAAT
CTTTTGGGGAATCTCACTACTCTGTTTGTTGGTAACAACAGTCTACAAGGGCCGGTTCGT
TTCGGATCACCTAATTGCAAGAATTTGTTGACTTTAGATTTGTCATACAATGAATTCGAA
GGCGGTGTTCCACCTGCATTGGGAAATTGCAGTAGCCTTGACGCTTTAGTCATTGTGAGT
GGTAACTTGTCAGGTACAATCCCTTCCTCATTGGGTATGTTGAAGAATCTCACAATTCTT
AACCTTTCCGAGAATCGTCTCTCTGGGAGTATCCCCGCAGAGCTCGGGAACTGCAGTAGC
TTGAACTTGTTGAAGCTGAACGATAACCAGCTTGTAGGCGGAATACCGAGTGCATTAGGT
AAGCTGAGGAAGCTAGAAAGTCTGGAGCTTTTCGAAAACCGGTTTTCGGGTGAGATTCCT
ATTGAGATATGGAAGAGTCAGAGTCTTACGCAGTTGCTAGTTTATCAAAACAATCTCACT
GGTGAACTACCTGTGGAAATGACTGAGATGAAGAAGCTAAAGATCGCTACGCTGTTCAAC
AACAGCTTTTATGGAGCGATACCACCGGGTTTAGGTGTGAACAGCAGCTTAGAAGAGGTT
GACTTTATTGGTAACAAACTTACAGGAGAGATACCGCCAAATCTATGCCATGGAAGGAAG
TTGAGAATACTCAACTTGGGTTCTAATCTGCTTCATGGTACAATACCAGCTTCTATTGGT
CACTGTAAGACCATCAGGAGATTCATCCTTAGAGAAAATAACCTTTCAGGTCTTCTTCCT
GAGTTTTCTCAGGATCATAGTCTTTCTTTTCTTGATTTCAATAGCAACAACTTCGAAGGA
CCAATCCCGGGCAGCCTCGGAAGCTGTAAGAATCTCTCGAGTATTAACCTATCTCGAAAC
AGATTCACGGGGCAGATACCTCCACAACTTGGGAATCTACAAAACCTTGGTTACATGAAT
CTTTCTCGTAATCTTCTTGAAGGGTCTCTACCAGCTCAGCTATCTAACTGTGTGAGTTTA
GAGCGTTTTGATGTTGGCTTCAACTCATTAAACGGTTCAGTTCCTTCAAACTTTAGTAAC
TGGAAAGGCTTGACGACTTTAGTTCTCAGCGAGAACCGGTTTTCAGGAGGTATTCCACAG
TTCTTGCCTGAGCTTAAGAAGCTGTCAACTCTGCAGATTGCTAGAAATGCTTTTGGTGGT
GAGATTCCTTCGTCGATTGGGTTGATAGAGGATCTGATCTATGACTTGGACCTTAGTGGA
AACGGATTGACAGGTGAAATTCCAGCCAAGTTGGGAGATCTCATCAAGTTAACAAGACTC
AACATATCTAACAACAATTTGACAGGATCTTTATCGGTTCTCAAAGGTCTTACCTCATTG
CTACATGTTGATGTCTCCAACAATCAGTTCACAGGTCCAATACCAGATAACTTGGAGGGT
CAGTTGTTATCTGAGCCGTCGTCGTTTTCAGGAAATCCAAACCTCTGCATTCCACATTCC
TTCTCTGCTAGCAACAATAGCCGCAGCGCGTTAAAGTACTGTAAAGATCAATCTAAAAGC
AGGAAGAGTGGCCTTAGCACCTGGCAAATCGTGCTAATAGCGGTCTTATCGTCTTTATTA
GTCTTGGTTGTGGTCCTTGCTCTTGTTTTCATTTGCCTACGTCGTCGCAAAGGAAGACCA
GAGAAAGATGCTTATGTCTTCACTCAGGAGGAAGGCCCATCTTTGTTGTTGAACAAAGTT
CTTGCAGCAACTGACAATCTAAATGAAAAGTACACCATTGGAAGAGGAGCTCATGGAATT
GTGTACAGAGCTTCTTTAGGCTCCGGAAAGGTCTACGCTGTGAAGAGACTTGTATTCGCG
TCTCACATCCGCGCTAACCAGAGTATGATGAGGGAGATTGATACAATCGGTAAAGTCAGG
CACAGGAATCTGATTAAGTTAGAAGGGTTTTGGCTGAGGAAAGACGACGGTTTAATGCTG
TATAGATACATGCCAAAAGGAAGTCTTTACGACGTTCTCCACGGTGTTAGCCCGAAAGAA
AATGTGCTAGACTGGTCTGCACGGTACAATGTAGCACTTGGTGTCGCTCATGGACTAGCC
TATCTACACTATGACTGCCATCCCCCGATTGTTCACCGTGACATCAAACCAGAGAACATA
CTCATGGACTCAGATTTGGAGCCTCACATTGGGGATTTCGGTTTGGCTCGCCTTCTTGAT

FIGURE 11B(2)

GACTCAACGGTTTCAACTGCAACTGTTACAGGCACCACCGGCTACATTGCACCAGAAAAC
GCTTTCAAAACCGTGAGGGGAAGAGAATCAGACGTTTACAGTTATGGAGTCGTGTTACTT
GAGCTGGTTACGAGGAAGAGAGCGGTGGACAAATCTTTCCCGGAAAGTACAGATATAGTA
AGCTGGGTGAGATCTGCCTTGAGCAGCAGCAACAACAATGTGGAGGATATGGTAACAACA
ATCGTCGATCCGATTCTCGTGGACGAGCTTCTGGATTCGAGTCTTAGGGAGCAGGTGATG
CAAGTGACGGAACTGGCACTGAGTTGTACACAGCAAGATCCGGCAATGAGACCAACGATG
AGAGATGCGGTGAAACTGTTGGAAGATGTGAAACATCTGGCAAGAAGCTGCTCCTCTGAT
TCAGTTCGGTAA

>At1g73080 (AtPEPR1) (SEQ ID NO: 145)

MKNLGGLFKILLLFFCLFLSTHIISVSCLNSDGLTLLSLLKHLDRVPPQVTSTWKINASE
ATPCNWFGITCDDSKNVASLNFTRSRVSGQLGPEIGELKSLQILDLSTNNFSGTIPSTLG
NCTKLATLDLSENGFSDKIPDTLDSLKRLEVLYLYINFLTGELPESLFRIPKLQVLYLDY
NNLTGPIPQSIGDAKELVELSMYANQFSGNIPESIGNSSSLQILYLHRNKLVGSLPESLN
LLGNLTTLFVGNNSLQGPVRFGSPNCKNLLTLDLSYNEFEGGVPPALGNCSSLDALVIVS
GNLSGTIPSSLGMLKNLTILNLSENRLSGSIPAELGNCSSLNLLKLNDNQLVGGIPSALG
KLRKLESLELFENRFSGEIPIEIWKSQSLTQLLVYQNNLTGELPVEMTEMKKLKIATLFN
NSFYGAIPPGLGVNSSLEEVDFIGNKLTGEIPPNLCHGRKLRILNLGSNLLHGTIPASIG
HCKTIRRFILRENNLSGLLPEFSQDHSLSFLDFNSNNFEGPIPGSLGSCKNLSSINLSRN
RFTGQIPPQLGNLQNLGYMNLSRNLLEGSLPAQLSNCVSLERFDVGFNSLNGSVPSNFSN
WKGLTTLVLSENRFSGGIPQFLPELKKLSTLQIARNAFGGEIPSSIGLIEDLIYDLDLSG
NGLTGEIPAKLGDLIKLTRLNISNNNLTGSLSVLKGLTSLLHVDVSNNQFTGPIPDNLEG
QLLSEPSSFSGNPNLCIPHSFSASNNSRSALKYCKDQSKSRKSGLSTWQIVLIAVLSSLL
VLVVVLALVFICLRRRKGRPEKDAYVFTQEEGPSLLLNKVLAATDNLNEKYTIGRGAHGI
VYRASLGSGKVYAVKRLVFASHIRANQSMMREIDTIGKVRHRNLIKLEGFWLRKDDGLML
YRYMPKGSLYDVLHGVSPKENVLDWSARYNVALGVAHGLAYLHYDCHPPIVHRDIKPENI
LMDSDLEPHIGDFGLARLLDDSTVSTATVTGTTGYIAPENAFKTVRGRESDVYSYGVVLL
ELVTRKRAVDKSFPESTDIVSWVRSALSSSNNNVEDMVTTIVDPILVDELLDSSLREQVM
QVTELALSCTQQDPAMRPTMRDAVKLLEDVKHLARSCSSDSVR

>At1g17750 (AtPEPR2) (SEQ ID NO: 146)

ATGAGGAATCTTGGGTTACTCGAAATTACTCTGCTTTGCTCTCTCTTTGTCTATTTCCGT
ATAGATTCTGTCTCTAGTTTAAACTCAGATGGTTTGGCTTTACTCTCGCTTCTCAAGCAC
TTTGATAAAGTCCCACTTGAAGTAGCTTCGACGTGGAAGGAGAACACATCTGAAACCACT
CCATGTAATAATAACTGGTTTGGTGTCATTTGTGATCTTTCTGGTAATGTCGTCGAGACC
CTTAATTTGTCTGCTTCTGGGCTTTCAGGCCAATTAGGTTCTGAAATTGGGGAGCTTAAG
AGCTTGGTCACATTGGATCTCAGTCTTAACAGTTTCTCTGGTTTATTGCCTTCCACTTTA
GGAAACTGTACTTCACTTGAGTATTTGGATTTGTCTAACAATGATTTTTCTGGAGAAGTT
CCTGATATTTTTGGTAGCTTGCAGAATTTGACGTTTCTGTATCTTGATCGCAATAATCTT
AGTGGTCTCATTCCTGCAAGTGTTGGTGGGTTGATAGAGCTCGTAGATCTGAGGATGTCA
TATAATAACTTGTCTGGTACCATTCCAGAGTTGCTTGGGAACTGTAGTAAGCTGGAATAT
CTGGCTTTGAACAACAACAAGTTAAATGGTTCTTTGCCAGCAAGTCTCTATCTACTCGAG
AATCTTGGTGAGCTATTTGTCAGTAACAACAGCCTTGGAGGGAGGCTTCATTTTGGTTCT
AGCAACTGCAAGAAATTGGTTTCTTTAGATCTCTCGTTCAATGATTTCCAAGGCGGTGTT
CCACCTGAGATAGGCAACTGCAGTAGCCTTCACTCTTTAGTCATGGTGAAATGCAACTTG
ACAGGTACAATCCCATCATCAATGGGTATGTTGAGAAAGGTTTCGGTTATTGACCTTTCC
GATAATCGTCTCTCGGGGAATATCCCTCAAGAGCTTGGGAACTGCAGCAGCTTGGAAACC
TTGAAGCTGAACGACAACCAGCTCCAAGGCGAGATACCACCTGCATTGAGTAAGCTAAAG
AAGCTACAAAGCCTGGAGCTTTTTTTTAATAAGCTGTCCGGTGAGATTCCTATTGGCATA
TGGAAGATTCAGAGTCTGACACAGATGCTCGTTTATAACAACACTCTCACCGGGGAACTA
CCAGTTGAAGTAACTCAGCTGAAGCACCTTAAGAAGCTTACACTGTTTAACAACGGCTTT
TATGGAGATATACCAATGAGTTTAGGCCTGAATCGAAGCTTAGAGGAGGTGGACCTTCTT
GGTAACCGTTTTACAGGGGAGATACCACCCCATCTCTGCCATGGACAGAAGTTGAGATTG
TTCATCTTGGGTTCTAATCAGCTTCATGGTAAGATACCAGCGTCTATTCGTCAGTGTAAG
ACCCTTGAGCGAGTCAGACTTGAAGATAACAAACTTTCAGGTGTTCTTCCGGAATTCCCT
GAGAGTCTTAGTCTTTCCTATGTGAACCTCGGAAGCAATAGCTTTGAAGGATCCATCCCG
CGCAGCTTGGGAAGCTGTAAAAATCTCTTGACTATTGACCTTTCTCAAAACAAACTCACG
GGTCTGATACCTCCAGAACTGGGAAATCTGCAAAGCCTTGGACTGTTGAACCTTTCACAT
AATTATCTGGAAGGTCCTCTGCCATCCCAGCTATCAGGCTGTGCGAGACTTCTGTATTTT

FIGURE 11B(3)

GATGTTGGATCCAACTCATTGAACGGTTCTATTCCATCAAGCTTCAGAAGCTGGAAAAGC
TTGTCCACTTTAGTTCTCAGTGACAATAATTTTCTAGGAGCTATTCCACAGTTCTTGGCA
GAGCTTGACCGACTCTCAGATCTGCGGATAGCTCGAAATGCTTTTGGAGGTAAGATTCCT
TCCTCGGTTGGCTTGTTGAAGAGTCTACGCTATGGCTTAGACCTCAGTGCGAACGTATTT
ACGGGTGAGATTCCAACCACACTGGGGGCTCTTATCAATCTTGAACGTCTCAACATATCC
AACAACAAGTTGACAGGGCCTTTATCGGTTCTTCAAAGTCTTAAGTCATTGAATCAAGTT
GACGTCTCGTATAATCAGTTCACGGGTCCAATACCCGTAAATCTGTTATCAAATTCTTCA
AAGTTTTCTGGAAATCCAGACCTCTGCATTCAAGCTTCTTACTCAGTGAGTGCCATAATC
CGCAAAGAGTTTAAATCTTGCAAAGGTCAAGTCAAACTTAGCACGTGGAAGATCGCCCTT
ATAGCAGCTGGGTCCTCACTATCCGTATTGGCTTTGCTTTTTGCTCTCTTTTTGGTTTTA
TGCCGGTGCAAAAGAGGAACCAAGACAGAAGATGCTAATATCCTCGCAGAGGAAGGTCTG
TCCTTGTTGCTGAACAAAGTTCTAGCAGCCACTGACAATCTAGATGACAAGTACATCATT
GGAAGAGGAGCTCATGGAGTTGTTTACAGAGCTTCTTTAGGATCAGGCGAAGAATACGCC
GTGAAGAAACTCATCTTTGCGGAACACATTCGCGCAAACCAAAATATGAAGCGGGAGATC
GAAACAATCGGGCTAGTCAGGCACAGAAATCTCATTCGGTTAGAAAGATTTTGGATGAGG
AAAGAAGATGGCTTAATGCTGTATCAGTACATGCCCAATGGAAGCCTACACGACGTTTTG
CACAGAGGTAATCAAGGAGAAGCAGTTCTTGACTGGTCTGCACGGTTCAACATAGCCCTT
GGGATTTCACATGGACTGGCGTATTTACATCATGATTGTCATCCACCAATAATTCACCGC
GACATCAAACCAGAGAACATACTCATGGACTCGGATATGGAGCCTCACATTGGAGATTTC
GGATTGGCTCGGATTCTAGATGACTCAACAGTTTCAACGGCCACTGTTACTGGCACAACT
GGGTACATTGCACCAGAAAATGCGTACAAGACGGTGAGGAGCAAGGAATCAGATGTTTAC
AGTTATGGAGTTGTTTTGCTCGAGCTGGTAACAGGAAAGAGAGCACTGGACAGATCTTTC
CCGGAAGATATCAACATTGTGAGCTGGGTCAGATCTGTATTAAGCAGCTACGAGGATGAA
GACGATACTGCTGGTCCAATCGTTGATCCAAAACTTGTGGATGAGCTTCTGGATACGAAG
CTCAGGGAACAAGCAATCCAAGTCACAGACTTGGCTCTTAGATGTACAGACAAGAGGCCG
GAGAACAGACCATCGATGAGAGATGTGGTGAAAGATTTGACTGATTTGGAAAGTTTTGTA
AGAAGCACTTCGGGTTCAGTTCACTAG

>At1g17750 (AtPEPR2) (SEQ ID NO: 147)

MRNLGLLEITLLCSLFVYFRIDSVSSLNSDGLALLSLLKHFDKVPLEVASTWKENTSETT
PCNNNWFGVICDLSGNVVETLNLSASGLSGQLGSEIGELKSLVTLDLSLNSFSGLLPSTL
GNCTSLEYLDLSNNDFSGEVPDIFGSLQNLTFLYLDRNNLSGLIPASVGGLIELVDLRMS
YNNLSGTIPELLGNCSKLEYLALNNNKLNGSLPASLYLLENLGELFVSNNSLGGRLHFGS
SNCKKLVSLDLSFNDFQGGVPPEIGNCSSLHSLVMVKCNLTGTIPSSMGMLRKVSVIDLS
DNRLSGNIPQELGNCSSLETLKLNDNQLQGEIPPALSKLKKLQSLELFFNKLSGEIPIGI
WKIQSLTQMLVYNNTLTGELPVEVTQLKHLKKLTLFNNGFYGDIPMSLGLNRSLEEVDLL
GNRFTGEIPPHLCHGQKLRLFILGSNQLHGKIPASIRQCKTLERVRLEDNKLSGVLPEFP
ESLSLSYVNLGSNSFEGSIPRSLGSCKNLLTIDLSQNKLTGLIPPELGNLQSLGLLNLSH
NYLEGPLPSQLSGCARLLYFDVGSNSLNGSIPSSFRSWKSLSTLVLSDNNFLGAIPQFLA
ELDRLSDLRIARNAFGGKIPSSVGLLKSLRYGLDLSANVFTGEIPTTLGALINLERLNIS
NNKLTGPLSVLQSLKSLNQVDVSYNQFTGPIPVNLLSNSSKFSGNPDLCIQASYSVSAII
RKEFKSCKGQVKLSTWKIALIAAGSSLSVLALLFALFLVLCRCKRGTKTEDANILAEEGL
SLLLNKVLAATDNLDDKYIIGRGAHGVVYRASLGSGEEYAVKKLIFAEHIRANQNMKREI
ETIGLVRHRNLIRLERFWMRKEDGLMLYQYMPNGSLHDVLHRGNQGEAVLDWSARFNIAL
GISHGLAYLHHDCHPPIIHRDIKPENILMDSDMEPHIGDFGLARILDDSTVSTATVTGTT
GYIAPENAYKTVRSKESDVYSYGVVLLELVTGKRALDRSFPEDINIVSWVRSVLSSYEDE
DDTAGPIVDPKLVDELLDTKLREQAIQVTDLALRCTDKRPENRPSMRDVVKDLTDLESFV
RSTSGSVH

>Glyma10g33970 (GmPEPR1a) (SEQ ID NO: 148)

ATGGGGTATCTGTATCTCTTGCTGCTTCTATGTTTTTCTTCCTTGTTATATGCTGCTTCT
GCATTGAACTCTGATGGTTTGGCTTTGTTGTCCCTCTTGAGGGATTGGACTACTGTGCCT
AGTGACATAAACTCCACATGGAGGTTGTCTGATTCCACTCCATGCTCATCTTGGGCAGGA
GTGCATTGTGATAATGCCAACAATGTGGTTTCTCTAAACCTCACTAGTTATTCGATTTTG
GGTCAATTAGGACCTGATCTTGGACGTTTGGTTCACTTGCAAACCATAGACTTATCATAT
AATGATTTCTTTGGGAAAATCCCCCCAGAATTAGAGAACTGTAGCATGCTTGAGTACTTG
AACCTTTCTGTAAACAACTTTAGCGGAGGAATACCTGAGAGCTTCAAAAGCTTGCAAAAT
TTGAAGCATATATACCTTTTATCTAATCACCTTAATGGTGAAATTCCTGAATCCTTGTTT
GAAATTTCTCACCTGGAAGAAGTGGATCTTAGCAGAAACAGTTTAACTGGTTCAATCCCC

FIGURE 11B(4)

TTAAGTGTTGGGAATATCACTAAGCTTGTCACTCTGGATCTTTCTTATAATCAGTTGTCA
GGGACAATTCCAATATCCATTGGAAATTGTAGTAACTTAGAGAATCTGTATTTGGAAAGG
AATCAATTAGAGGGAGTTATTCCTGAGAGTCTAAATAATCTCAAAAATCTTCAAGAGTTA
TATCTCAATTATAATAACCTTGGAGGTACTGTTCAATTGGGATCTGGATATTGCAAAAAG
TTGTCTATTTTGAGTATTTCTTACAATAACTTTAGTGGGGGTATACCATCAAGCTTGGGG
AATTGTAGTGGTCTAATAGAGTTTTATGCTTCAGGGAATAACTTAGTTGGCACTATACCA
TCAACCTTCGGCCTCCTGCCCAACCTTTCTATGTTATTCATTCCGGAGAACCTATTGTCA
GGGAAAATACCTCCACAGATTGGTAATTGCAAATCACTGAAAGAGTTGAGTTTGAATTCC
AATCAACTTGAAGGAGAAATTCCAAGCGAATTAGGAAACTTGAGTAAATTGCGTGATCTT
AGATTGTTTGAAAACCATTTGACAGGAGAAATTCCACTTGGCATATGGAAAATTCAAAGC
CTTGAGCAGATCCATATGTACATTAATAACCTCTCGGGCGAGCTACCACTTGAGATGACA
GAGCTTAAACATCTTAAGAATGTCTCCTTGTTTAACAACCAGTTCTCCGGAGTCATACCT
CAAAGCTTAGGAATCAATAGCAGTTTGGTGGTGTTAGATTTTATGTATAATAATTTCACT
GGTACCCTCCCACCAAATCTTTGTTTTGGAAAGCACCTGGTCAGGCTGAATATGGGTGGC
AATCAATTTATTGGCAGCATACCTCCTGATGTAGGAAGGTGTACAACTCTTACAAGGTTG
AGACTTGAAGATAATAATTTAACTGGGGCACTTCCTGATTTTGAAACTAATCCAAACCTC
TCTTACATGAGCATCAACAACAACAATATCAGTGGAGCAATTCCATCAAGTTTGGGAAAC
TGCACAAATCTCTCTCTTTTAGATTTGTCCATGAACAGCTTGACGGGTCTTGTACCTTCA
GAGCTAGGAAACCTTGTGAATCTTCAGACTTTGGATCTTTCTCACAATAACTTGCAAGGT
CCTTTGCCACATCAGCTGTCAAACTGTGCCAAAATGATCAAGTTTAATGTCGGATTCAAT
TCTTTGAATGGTTCGGTTCCTTCAAGTTTTCAGAGCTGGACAACATTAACAACTTTAATT
CTCTCAGAGAATCGTTTTAATGGTGGTATTCCAGCTTTCTTGTCAGAATTTAAAAAGCTC
AACGAGTTACGACTTGGTGGAAATACGTTTGGAGGAAACATTCCTAGATCAATTGGAGAA
TTGGTGAATTTGATATATGAGCTAAATTTAAGTGCTAATGGGCTGATAGGTGAACTTCCT
AGGGAGATTGGAAACCTGAAGAATCTGCTAAGCCTGGATCTATCTTGGAACAATTTGACA
GGAAGTATACAAGTTCTTGATGAGCTCAGTTCATTATCTGAATTCAACATCTCATTTAAT
TCTTTTGAAGGTCCTGTGCCACAACAGCTAACAACATTACCAAATTCTTCTTTATCATTT
TTGGGCAATCCTGGTCTGTGTGACTCGAATTTCACTGTGAGCAGCTATTTACAGCCATGT
AGCACAAATTCAAAAAAGTCAAAAAAGCTGAGTAAAGTTGAAGCTGTGATGATAGCACTT
GGATCCTTAGTATTTGTTGTTCTGCTGCTGGGGTTAATCTGTATATTCTTTATCAGAAAA
ATTAAGCAGGAAGCCATAATCATTGAGGAGGATGATTTTCCAACACTTCTTAATGAAGTA
ATGGAAGCGACAGAAAATCTAAATGATCAATATATTATTGGCAGAGGAGCTCAAGGAGTG
GTTTACAAAGCAGCAATAGGTCCAGACAAAATTTTGGCTATAAAGAAATTTGTATTTGCT
CATGATGAAGGGAAAAGCTCAAGCATGACCAGAGAAATTCAAACCATTGGAAAGATTAGG
CATCGAAATTTGGTCAAATTGGAAGGGTGCTGGTTGAGAGAAAACTATGGTCTAATTGCA
TACAAATACATGCCAAATGGAAGCCTTCATGGTGCTTTGCATGAGAGGAATCCACCATAC
TCCTTAGAATGGAATGTCCGGAATAGGATAGCTCTTGGAATTGCTCATGGATTGGCTTAT
CTCCATTATGACTGTGATCCTGTCATAGTGCACAGAGACATCAAAACCAGCAATATACTT
CTAGATTCTGACATGGAGCCTCATATTGCAGATTTTGGTATTTCCAAGCTTTTAGATCAG
CCTTCTACCTCAACACAGTCGTCATCTGTTACTGGTACACTTGGATATATAGCACCAGAG
AAATCCTATACAACAACAAAGGGTAAGGAATCTGATGTATACAGTTATGGGGTAGTTTTG
CTGGAACTGATATCCAGAAAGAAGCCATTGGATGCATCATTTATGGAAGGGACGGATATA
GTTAATTGGGCTAGATCTGTCTGGGAGGAAACAGGAGTTATTGACGAAATTGTTGATCCA
GAGATGGCTGATGAAATTTCAAATTCTGATGTGATGAAACAAGTTGCCAAGGTGCTTTTG
GTGGCTTTGAGATGCACATTAAAGGATCCACGCAAGAGACCTACGATGAGGGATGTTATC
AAGCATTTGTAG

>Glyma10g33970 (GmPEPR1a) (SEQ ID NO: 149)

MGYLYLLLLLCFSSLLYAASALNSDGLALLSLLRDWTTVPSDINSTWRLSDSTPCSSWAG
VHCDNANNVVSLNLTSYSILGQLGPDLGRLVHLQTIDLSYNDFFGKIPPELENCSMLEYL
NLSVNNFSGGIPESFKSLQNLKHIYLLSNHLNGEIPESLFEISHLEEVDLSRNSLTGSIP
LSVGNITKLVTLDLSYNQLSGTIPISIGNCSNLENLYLERNQLEGVIPESLNNLKNLQEL
YLNYNNLGGTVQLGSGYCKKLSILSISYNNFSGGIPSSLGNCSGLIEFYASGNNLVGTIP
STFGLLPNLSMLFIPENLLSGKIPPQIGNCKSLKELSLNSNQLEGEIPSELGNLSKLRDL
RLFENHLTGEIPLGIWKIQSLEQIHMYINNLSGELPLEMTELKHLKNVSLFNNQFSGVIP

FIGURE 11B(5)

LGNPGLCDSNFTVSSYLQPCSTNSKKSKKLSKVEAVMIALGSLVFVVLLLGLICIFFIRK
IKQEAIIIEEDDFPTLLNEVMEATENLNDQYIIGRGAQGVVYKAAIGPDKILAIKKFVFA
HDEGKSSSMTREIQTIGKIRHRNLVKLEGCWLRENYGLIAYKYMPNGSLHGALHERNPPY
SLEWNVRNRIALGIAHGLAYLHYDCDPVIVHRDIKTSNILLDSDMEPHIADFGISKLLDQ
PSTSTQSSSVTGTLGYIAPEKSYTTTKGKESDVYSYGVVLLELISRKKPLDASFMEGTDI
VNWARSVWEETGVIDEIVDPEMADEISNSDVMKQVAKVLLVALRCTLKDPRKRPTMRDVI
KHL

>Glyma20g33620 (GmPEPR1b) (SEQ ID NO: 150)

ATGGGGTATTTGTATCTCTTGCTGATTTCATATTTGTCTGCCTTGTTGTATGCTGCTTCT
GCATTGAACTCTGATGGGTTGGCTTTGTTGTCCCTCTTGAGGGACTGGACTATTGTGCCT
AGTGACATAAACTCCACATGGAAGTTGTCTGATTCCACTCCGTGCTCATCTTGGGCAGGA
GTGCATTGTGATAATGCCAATAATGTGGTTTCTCTAAACCTCACTAACTTATCATATAAT
GATCTATTTGGAAAAATTCCCCCAGAATTAGACAACTGTACCATGCTTGAGTACTTGGAC
CTTTCTGTAAACAACTTTAGTGGAGGAATACCTCAGAGCTTCAAAAACTTGCAAAATTTG
AAGCATATAGACCTTTCATCTAATCCGCTGAATGGTGAAATTCCTGAACCCTTGTTTGAC
ATTTATCACCTGGAAGAAGTGTATCTTAGCAACAACAGTTTGACTGGTTCAATTTCCTCA
AGTGTTGGGAATATCACTAAGCTTGTCACACTGGATCTTTCTTATAATCAGCTGTCAGGG
ACAATTCCCATGTCCATTGGAAATTGTAGTAACTTAGAGAATCTATATTTGGAAAGGAAT
CAATTAGAGGGAGTTATTCCTGAGAGTCTAAATAATCTCAAAAATCTTCAGGAGTTATTT
CTCAATTATAATAACCTTGGAGGCACTGTTCAATTGGGAACTGGAAATTGCAAAAAGTTG
TCTAGTTTAAGTCTTTCTTACAATAACTTCAGTGGGGGTATACCATCAAGCTTGGGGAAT
TGTAGCGGTCTAATGGAGTTTTATGCTGCACGGAGTAACTTAGTTGGCAGTATACCATCA
ACCTTGGGCCTCATGCCCAACCTTTCTCTTCTAATCATTCCAGAGAACCTATTGTCTGGG
AAAATACCTCCACAGATTGGTAATTGCAAAGCACTGGAAGAGTTGCGTTTGAATTCCAAT
GAACTTGAGGGAGAAATTCCCAGTGAATTGGGAAACTTGAGTAAATTACGCGACCTTAGA
TTGTATGAAAACCTTTTGACAGGAGAAATTCCACTTGGCATATGGAAAATTCAAAGCCTT
GAGCAGATCTATCTGTACATTAATAACCTTTCGGGGGAGCTACCTTTTGAGATGACAGAG
CTCAAACATCTTAAGAATATCTCCTTGTTTAACAACCAGTTCTCCGGAGTCATACCTCAA
AGTTTAGGAATCAATAGCAGTTTGGTGGTGTTAGACTTCATGTATAATAATTTCACTGGT
ACCCTTCCACCAAATCTTTGTTTTGGAAAGCAACTGGTGAAGCTGAATATGGGTGTCAAT
CAATTTTATGGTAACATACCTCCAGATGTGGGAAGGTGTACAACTCTTACAAGGGTGAGA
CTTGAAGAAAATCATTTCACTGGGTCTCTTCCTGATTTTTATATTAATCCAAATCTCTCT
TACATGAGCATCAACAACAACAATATCAGTGGAGCAATTCCATCAAGTTTGGGAAAATGC
ACAAATCTCTCTCTTTTAAATTTGTCCATGAACAGCTTGACGGGTCTTGTACCTTCAGAG
CTTGGAAACCTTGAGAATCTCCAGACTTTGGATCTTTCTCACAATAACTTGGAAGGTCCT
TTGCCACATCAGCTGTCAAACTGTGCCAAAATGATCAAGTTTGATGTCAGATTCAATTCC
TTGAATGGTTCGGTTCCATCAAGTTTTCGGAGCTGGACAACATTAACAGCTTTAATTCTC
TCAGAGAATCATTTTAATGGTGGTATCCCAGCTTTCTTGTCAGAATTTAAAAAGCTCAAC
GAGTTACAACTTGGTGGAAACATGTTTGGAGGAAACATTCCTAGATCAATCGGAGAGCTG
GTGAATTTGATATATGAACTAAATCTAAGTGCTACTGGGCTGATAGGTGAGCTTCCTAGG
GAGATTGGAAACCTGAAGAGTCTGCTAAGCCTGGATCTATCTTGGAACAATTTGACAGGA
AGTATACAAGTTCTTGATGGGCTCAGTTCATTATCTGAATTCAACATCTCATATAATTCT
TTTGAAGGTCCTGTGCCACAACAGCTAACAACATTACCAAACTCTTCTTTATCATTTTTG
GGCAATCCTGGCCTGTGTGGCTCGAATTTCACTGAGAGCAGCTATTTAAAGCCTTGTGAC
ACAAATTCAAAAAAGTCAAAAAAGCTCAGTAAAGTTGCAACTGTGATGATAGCACTTGGA
TCTGCAATATTTGTTGTTCTGCTGCTGTGGTTAGTATATATATTCTTTATCAGAAAAATT
AAGCAAGAAGCCATAATCATTAAGGAAGATGATTCTCCAACCCTTCTTAACGAAGTGATG
GAAGCTACAGAAAATCTAAATGATGAGTATATTATTGGCAGAGGAGCTCAAGGAGTTGTT
TATAAAGCAGCAATAGGTCCAGACAAAACATTGGCTATAAAGAAGTTTGTATTTTCTCAT
GAAGGGAAAAGCTCAAGCATGACCAGAGAAATTCAAACCCTTGGAAAGATTAGGCATCGA
AATTTAGTCAAATTGGAAGGGTGCTGGTTGAGAGAAAACTATGGTCTAATTGCATACAAA
TACATGCCAAATGGAAGCCTACATGATGCTTTGCATGAGAAGAATCCACCATACTCCTTA
GAATGGATTGTTCGGAATAACATAGCACTTGGAATTGCTCACGGATTGACTTATCTCCAT
TATGACTGTGATCCTGTCATAGTGCACAGAGATATCAAAACAAGCAACATACTTCTAGAT
TCAGAAATGGAGCCTCATATTGCAGATTTTGGTATTGCTAAACTTATAGATCAGCCTTCT
ACCTCAACACAGTTATCATCTGTTGCTGGTACACTTGGTTATATAGCACCAGAGAATGCT
TATACAACAACAAAGGGTAAGGAATCTGATGTATACAGTTATGGGGTAGTTTTGCTGGAG
CTGATATCCAGAAAGAAGCCATTGGATGCATCATTTATGGAAGGAACGGATATAGTTAAT
TGGGCAAGATCTGTCTGGGAGGAAACGGGAGTTGTTGATGAAATTGTTGATCCAGAGCTG

FIGURE 11B(6)

GCTGATGAAATTTCAAATTCTGAAGTGATGAAACAAGTTACCAAGGTGCTTTTGGTGGCT
TTGAGATGCACTGAAAAGGATCCACGTAAGAGACCTACGATGAGGGATGTTATCAGGCAT
TTGTAG

>Glyma20g33620 (GmPEPR1b) (SEQ ID NO: 151)

MGYLYLLLISYLSALLYAASALNSDGLALLSLLRDWTIVPSDINSTWKLSDSTPCSSWAG
VHCDNANNVVSLNLTSYSIFGQLGPDLGRMVHLQTIDLSYNDLFGKIPPELDNCTMLEYL
DLSVNNFSGGIPQSFKNLQNLKHIDLSSNPLNGEIPEPLFDIYHLEEVYLSNNSLTGSIS
SSVGNITKLVTLDLSYNQLSGTIPMSIGNCSNLENLYLERNQLEGVIPESLNNLKNLQEL
FLNYNNLGGTVQLGTGNCKKLSSLSLSYNNFSGGIPSSLGNCSGLMEFYAARSNLVGSIP
STLGLMPNLSLLIIPENLLSGKIPPQIGNCKALEELRLNSNELEGEIPSELGNLSKLRDL
RLYENLLTGEIPLGIWKIQSLEQIYLYINNLSGELPFEMTELKHLKNISLFNNQFSGVIP
QSLGINSSLVVLDFMYNNFTGTLPPNLCFGKQLVKLNMGVNQFYGNIPPDVGRCTTLTRV
RLEENHFTGSLPDFYINPNLSYMSINNNNISGAIPSSLGKCTNLSLLNLSMNSLTGLVPS
ELGNLENLQTLDLSHNNLEGPLPHQLSNCAKMIKFDVRFNSLNGSVPSSFRSWTTLTALI
LSENHFNGGIPAFLSEFKKLNELQLGGNMFGGNIPRSIGELVNLIYELNLSATGLIGELP
REIGNLKSLLSLDLSWNNLTGSIQVLDGLSSLSEFNISYNSFEGPVPQQLTTLPNSSLSF
LGNPGLCGSNFTESSYLKPCDTNSKKSKKLSKVATVMIALGSAIFVVLLLWLVYIFFIRK
IKQEAIIIKEDDSPTLLNEVMEATENLNDEYIIGRGAQGVVYKAAIGPDKTLAIKKFVFS
HEGKSSSMTREIQTLGKIRHRNLVKLEGCWLRENYGLIAYKYMPNGSLHDALHEKNPPYS
LEWIVRNNIALGIAHGLTYLHYDCDPVIVHRDIKTSNILLDSEMEPHIADFGIAKLIDQP
STSTQLSSVAGTLGYIAPENAYTTTKGKESDVYSYGVVLLELISRKKPLDASFMEGTDIV
NWARSVWEETGVVDEIVDPELADEISNSEVMKQVTKVLLVALRCTEKDPRKRPTMRDVIR
HL

>Glyma15g00360 (GmPEPR2) (SEQ ID NO: 152)

ATGTCCATGATTTGGATTGTTTTCTTTTCCTTGTCTTGCATGTCTTGTGCTGTTGTTTCT
TCACTCACCTCCGATGGGGTGACTCTCTTGTCACTCTTGAGGCACTGGACATCCGTGCCT
CCTTCCATAAACGCCACCTGGCTTGCCTCCGATACCACTCCATGCTCCTCCTGGGTAGGA
GTACAATGTGACCATTCCCACCATGTCGTCAACCTTACCCTCCCAGATTATGGTATTGCT
GGTCAATTAGGACCTGAAATTGGAAATTTAAGTCGCCTAGAGTACTTAGAACTTGCTAGC
AACAACCTTACTGGTCAAATACCTGACGCCTTCAAAAACATGCACAACCTCAATTTACTC
AGCCTTCCATATAATCAACTGTCTGGTGAAATTCCAGATTCCTTGACTCATGCTCCCCAA
CTAAATCTTGTTGATCTTTCTCATAACACTTTAAGTGGATCCATCCCCACAAGTATTGGG
AACATGACTCAGCTCTTGCAGTTGTATCTTCAGAGTAACCAGTTGTCTGGGACAATTCCC
TCATCCATTGGGAACTGCAGCAAATTACAAGAATTGTTTTTGGATAAAAATCACTTGGAG
GGTATCCTGCCTCAGAGTCTTAACAATCTCAATGATCTTGCTTATTTTGATGTTGCCAGC
AATAGACTTAAGGGTACCATTCCTTTTGGTTCTGCTGCCAGTTGTAAAAATTTGAAGAAT
TTGGATCTCTCATTCAATGACTTTAGTGGAGGCCTTCCCTCAAGCTTGGGGAACTGTAGC
GCTTTATCTGAATTTTCTGCCGTGAACTGCAATTTGGATGGCAATATTCCTCCCTCCTTT
GGTCTACTGACCAAGCTTTCTATTCTATACCTTCCCGAGAACCACTTATCTGGAAAAGTA
CCTCCAGAAATTGGCAACTGCATGTCTTTGACAGAGTTACATCTGTATTCCAATCAACTT
GAGGGAAACATTCCAAGTGAACTGGGAAAACTAAGAAAACTAGTGGATCTTGAATTGTTT
TCAAATCAATTGACGGGTGAAATTCCACTCAGCATCTGGAAGATTAAATCTCTGAAGCAT
CTCCTTGTGTATAATAACAGTCTTTCTGGGGAACTTCCTTTGGAGATGACAGAGCTCAAG
CAACTGAAAAACATCTCATTGTTTAGCAACCAGTTCTCCGGAGTCATACCGCAAAGCTTG
GGAATTAACAGCAGTTTAGTTCTTTTGGATTTTACAAATAATAAATTCACTGGCAACATC
CCACCAAATCTGTGTTTTGGCAAGAAATTAAACATCCTGAATTTGGGCATCAACCAACTT
CAAGGCAGCATTCCTCCTGATGTTGGGAGATGTACAACCCTTAGAAGGTTAATTCTTCAA
CAAAATAACTTTACTGGGCCTCTTCCTGATTTCAAAAGCAATCCAAATCTCGAACATATG
GATATCAGCAGCAACAAAATCCATGGTGAAATTCCATCAAGTTTGCGAAATTGCAGACAT
ATCACTCACCTAATTTTGTCCATGAACAAATTTAATGGGCCTATACCCTCAGAGCTAGGG
AACATTGTCAATCTTCAAACTTTGAATCTCGCTCACAACAACTTAGAAGGTCCTTTGCCC
TCTCAGCTGTCAAAGTGTACCAAAATGGACAGGTTTGATGTTGGATTTAATTTCCTAAAT
GGTTCATTGCCATCAGGTCTGCAGAGCTGGACAAGGCTAACCACATTAATTTTGAGTGAG
AATCACTTTAGTGGGGGCCTCCCAGCTTTCTTGTCGGAATATAAAATGCTTTCTGAACTA
CAACTTGGTGGCAATATGTTTGGTGGCAGAATTCCTAGATCGGTTGGAGCATTGCAGAGT
TTGAGGTATGGTATGAATCTGAGTTCAAATGGGCTGATAGGAGACATTCCTGTTGAGATT
GGAAACTTGAACTTTTTGGAAAGACTGGATCTGTCTCAGAACAATTTGACCGGAAGCATA

FIGURE 11B(7)

GAAGTTCTTGGTGAACTCCTCTCCTTAGTTGAAGTCAATATTTCATACAATTCTTTTCAT
GGTCGTGTACCAAAGAAGCTAATGAAATTGCTCAAGTCTCCCTTGTCATCATTTTTGGGC
AATCCTGGCCTATGTACCACCACCAGGTGTTCAGCATCTGATGGCTTGGCTTGCACTGCA
AGAAGCTCTATAAAACCATGTGATGACAAATCTACTAAACAGAAAGGCCTCAGTAAAGTT
GAAATTGTGATGATAGCTCTCGGGTCCTCAATACTTGTTGTTTTGCTGTTGCTGGGATTA
GTTTATATTTTTTATTTTGGAAGAAAAGCTTACCAGGAAGTCCATATCTTTGCTGAAGGG
GGTTCTTCTTCCCTTCTTAACGAAGTCATGGAGGCTACAGCAAACCTAAATGATCGGTAT
ATTATTGGCAGAGGAGCCTATGGAGTTGTTTATAAAGCCCTGGTGGGTCCAGACAAAGCC
TTTGCTGCGAAGAAGATAGGATTTGCTGCGAGCAAAGGTAAGAACTTGAGCATGGCCAGA
GAAATTGAAACCCTTGGGAAAATTCGGCATCGAAATCTGGTCAAATTGGAAGACTTTTGG
TTGAGAGAAGATTATGGTATAATTTTGTACAGCTACATGGCAAATGGAAGTCTTCATGAT
GTTTTGCACGAAAAGACACCACCACTAACCTTAGAGTGGAATGTCCGGAATAAGATAGCT
GTTGGAATTGCTCATGGATTGGCTTATCTCCATTATGACTGTGATCCTCCCATAGTGCAC
CGAGACATCAAGCCAAGCAATATACTTCTAGACTCTGATATGGAGCCTCACATTGCTGAC
TTTGGTATTGCCAAACTTCTGGATCAGTCTTCTGCTTCAAATCCTTCCATTTCTGTTCCG
GGTACAATTGGTTATATTGCACCAGAGAATGCTTATACAACAACAAATAGTAGGGAGTCT
GATGTATACAGTTACGGGGTAGTTTTGCTTGAGCTGATAACCAGAAAGAAGGCAGCAGAA
TCAGATCCTTCCTTCATGGAGGGTACTATAGTAGTGGATTGGGTTAGGTCTGTGTGGAGG
GAAACAGGAGACATTAATCAAATTGTTGATTCAAGCCTTGCAGAGGAATTTCTAGATATC
CATATAATGGAAAATATTACCAAAGTGCTTATGGTGGCTCTGAGATGTACTGAGAAGGAT
CCACACAAGAGACCCACAATGAGAGATGTTACCAAGCAGTTAGCAGATGCTAATCCACGG
GCAAGAAGTACAAAGGGCTAG

>Glyma15g00360 (GmPEPR2) (SEQ ID NO: 153)

MSMIWIVFFSLSCMSCAVVSSLTSDGVTLLSLLRHWTSVPPSINATWLASDTTPCSSWVG
VQCDHSHHVVNLTLPDYGIAGQLGPEIGNLSRLEYLELASNNLTGQIPDAFKNMHNLNLL
SLPYNQLSGEIPDSLTHAPQLNLVDLSHNTLSGSIPTSIGNMTQLLQLYLQSNQLSGTIP
SSIGNCSKLQELFLDKNHLEGILPQSLNNLNDLAYFDVASNRLKGTIPFGSAASCKNLKN
LDLSFNDFSGGLPSSLGNCSALSEFSAVNCNLDGNIPPSFGLLTKLSILYLPENHLSGKV
PPEIGNCMSLTELHLYSNQLEGNIPSELGKLRKLVDLELFSNQLTGEIPLSIWKIKSLKH
LLVYNNSLSGELPLEMTELKQLKNISLFSNQFSGVIPQSLGINSSLVLLDFTNNKFTGNI
PPNLCFGKKLNILNLGINQLQGSIPPDVGRCTTLRRLILQQNNFTGPLPDFKSNPNLEHM
DISSNKIHGEIPSSLRNCRHITHLILSMNKFNGPIPSELGNIVNLQTLNLAHNNLEGPLP
SQLSKCTKMDRFDVGFNFLNGSLPSGLQSWTRLTTLILSENHFSGGLPAFLSEYKMLSEL
QLGGNMFGGRIPRSVGALQSLRYGMNLSSNGLIGDIPVEIGNLNFLERLDLSQNNLTGSI
EVLGELLSLVEVNISYNSFHGRVPKKLMKLLKSPLSSFLGNPGLCTTTRCSASDGLACTA
RSSIKPCDDKSTKQKGLSKVEIVMIALGSSILVVLLLLGLVYIFYFGRKAYQEVHIFAEG
GSSSLLNEVMEATANLNDRYIIGRGAYGVVYKALVGPDKAFAAKKIGFAASKGKNLSMAR
EIETLGKIRHRNLVKLEDFWLREDYGIILYSYMANGSLHDVLHEKTPPLTLEWNVRNKIA
VGIAHGLAYLHYDCDPPIVHRDIKPSNILLDSDMEPHIADFGIAKLLDQSSASNPSISVP
GTIGYIAPENAYTTTNSRESDVYSYGVVLLELITRKKAAESDPSFMEGTIVVDWVRSVWR
ETGDINQIVDSSLAEEFLDIHIMENITKVLMVALRCTEKDPHKRPTMRDVTKQLADANPR
ARSTKG

>Os08g0446200 (OsPEPR1) (SEQ ID NO: 154)

ATGAGGCTGGTTGTGTGGCACTGGTTTTTCTTCTTCTTCTTCACTTCTGTTTCATCGTCT
TGGAGTTTGACTTCAGATGGTCTAGCCCTTCTTTCTCTGTCTAGGGATCTCATATTACCT
CATTCCATAAGCTCCACTTGGAAAGCTTCTGATACAACTCCTTGTAATTGGGATGGGGTT
TCCTGCAACAAAAAGAATAGTGTGGTTTCTCTTGACCTGTCATCTTCTGGAGTTTCTGGT
TCTCTTGGACCCCAAATAGGACTTATGAAGAGCCTACAAGTACTCAGTTTGTCAAATAAC
AGCATATCTGGTTCAATCCCTCAAGAATTGGGCAATTGTAGCATGCTTGATCAATTGGAT
TTGTCCAGTAACAGTTTTTCTGGTGAGATACCAGCATCCCTTGGTGACATCAAAAAGCTT
TCGTCTCTCTCTTTGTACAGTAACTCCCTCACTGGTGAAATACCAGAGGGGTTGTTCAAG
AATCAGTTTCTGGAGCAAGTGTACCTCCATTACAATAAACTCAGTGGTTCTATCCCCTTG
ACAGTTGGAGAAATGACTAGCCTTAGGTACCTGTGGCTGCATGGCAATAAATTATCTGGA
GTTCTACCAGATTCAATTGGCAACTGCACCAAGTTGGAGGAGCTCTATCTACTAGATAAT
CAATTGAGTGGGAGTCTTCCGAAAACCTTGAGCTATATCAAAGGACTGAAGATTTTCGAT
ATTACCGCAAATAGTTTCACAGGTGAGATCACATTTAGTTTTGAGGATTGCAAGCTTGAG
GTATTCATATTGTCATTCAATCAGATTAGCAACGAAATTCCATCATGGCTAGGGAATTGT

FIGURE 11B(8)

AGTAGCTTGACACAGCTTGCATTTGTCAACAATAATATATCTGGCCAGATTCCATCGTCT
CTGGGTTTATTGAGAAACCTCTCTCAACTTTTACTTTCTGAGAACTCACTTTCTGGGCCA
ATTCCTCCTGAGATAGGTAACTGCCAGTTGCTGGTGTGGCTGGAGTTGGATGCAAACCAG
CTCAATGGCACTGTTCCTAAAGAGCTGGCAAATCTGAGAAAATTGGAGAAACTCTTTCTG
TTTGAAAACCGCCTCATTGGGGAGTTCCCTGAGGATATTTGGAGCATCAAGAGCCTGCAA
AGTGTCCTTATCTATGAAAACAGTTTTACTGGGAGGCTACCTCCAGTGCTAGCTGAGCTG
AAGTTCCTGAAGAACATTACACTTTTCAACAATTTCTTCACTGGAGTTATACCACCAGAT
TTGGGTGTTAATAGTCGTTTAACCCAAATTGATTTCACAAACAACAGTTTTGTTGGTGGA
ATCCCGCCTAACATTTGTTCAGGGAAAAGATTGAGAATTTTGGACTTGGGGCTTAATCTT
CTCAATGGTAGCATCCCATCCAATGTTATGGACTGCCCAAGTTTGGAACGATTTATTCTC
CAAAACAACAATCTAAGTGGGCCCATTCCACAATTTAGGAACTGTGCAAATCTGAGCTAT
ATAGATCTGAGTCATAATTCCTTAAGTGGCAACATTCCAGCAAGCTTGGGGAGATGTGTA
AATATTACGATGATAAAATGGTCAGAAAACAAGTTGGTTGGTCCAATACCATCTGAAATT
AGAGACTTGGTGAATTTGAGAGTGCTAAACCTCTCGCAAAACAGCCTGCAAGGTGTTCTT
CCAGTGCAGATTTCTAGTTGCTCCAAGCTGTACTTGCTTGACTTGAGTTTCAACTCTTTG
AATGGTTCGGCACTCACAACCGTAAGCAACCTTAAGTTTCTGTCACAACTACGGTTACAA
GAGAATAAATTCAGTGGAGGCATACCTGATTCCCTCTCGCAGTTGGATATGCTTATTGAG
CTGCAACTTGGTGGCAACGTTCTTGGGGGCAGTATCCCTTCATCGTTAGGAAGGTTGGTA
AAACTGGGCATTGCATTGAATATTTGTAGCAATGGACTCGTTGGTGGCATTCCGCCATTA
TTGAGCAATTTGGTGGAGCTGCAAAGTTTAGATTTGTCACTTAATGGCCTCACTGGAGAC
CTAGACATGTTAGGAAACTTACAATTACTGCATGTATTGAATGTTTCCTACAATAGATTC
AGTGGTCCGGTCCCAGAAAATCTTCTGAATTTTCTGGTTTCCTCACCGAGCTCCTTTAAT
GGCAATCCAGACCTCTGTATCTCTTGCCATACCAATGGTTCTTATTGCAAGGGGTCTAAT
GTTTTGAAACCTTGTGGAGAGACCAAAAAACTACACAAACACGTCAAGATTGCTGTTATA
GTTATTGGTTCATTGTTCGTTGGAGCAGTTTCCATACTTATACTGAGTTGCATCCTTTTA
AAGTTTTATCATCCAAAGACAAAAAATTTAGAATCAGTCAGTACTCTGTTTGAAGGTTCT
TCTTCTAAATTAAATGAGGTTATAGAGGCTACTGAAAACTTTGATGACAAGTATATCATC
GGTACTGGTGCTCATGGAACTGTTTACAAGGCAACACTGAGGTCAGGAGAAGTATATGCT
GTAAAGAAGCTTGCAATATCTGCACAGAAAGGTTCGTACAAAAGCATGATCAGAGAACTG
AAGACATTAGGCAAAATCAAGCATCGGAACTTGATAAAGCTGAAAGAGTTTTGGTTAAGA
AGTGAGTATGGGTTCATGCTTTATGTTTATATGGAGCAAGGTAGCCTTCAAGATGTTCTG
CATGGGATCCAACCTCCTCCAAGTTTGGACTGGAGTGTGCGCTATACCATAGCTCTTGGT
ACTGCCCATGGGCTAGCGTATCTTCATGATGACTGTCAACCTGCAATTATTCACCGAGAT
ATTAAGCCCAGTAATATACTTCTGAATGGGGACATGGTTCCACATATAGCAGATTTTGGC
ATTGCAAAGCTCATGGACCAGTCTTCTTCTGCTCCACAGACTACTGGAGTTATTGGCACC
TTTGGATATATGGCCCCAGAGTTGGCATTTTCCACCAGGAGTAGTATCGAGTCCGATGTA
TACAGCTACGGCGTCATACTCCTTGAGCTGCTAACAAAAAAACAGGTGGTGGATCCCTCG
TTCCCCGACAACATGGACATTGTCGGTTGGGTGACCGCAACGCTCAACGGCACCGACCAA
ATCGAACTCGTCTGCGACTCGACGCTGATGGAGGAAGTCTATGGCACGGTGGAAATAGAG
GAAGTCAGCAAGGTCCTGTCCTTGGCTCTTAGGTGCGCAGCGAAGGAAGCGAGCCGAAGG
CCGCCCATGGCCGATGTTGTGAAGGAGCTGACTGATGTCAGGAAATCCGCCGGGAAGTTG
TCCAAGCCGGAGAAGACGGCCTCCCGGAGCTCGTCCTGA

>Os08g0446200 (OsPEPR1) (SEQ ID NO: 155)

MRLVVWHWFFFFFFTSVSSSWSLTSDGLALLSLSRDLILPHSISSTWKASDTTPCNWDGV
SCNKKNSVVSLDLSSSGVSGSLGPQIGLMKSLQVLSLSNNSISGSIPQELGNCSMLDQLD
LSSNSFSGEIPASLGDIKKLSSLSLYSNSLTGEIPEGLFKNQFLEQVYLHYNKLSGSIPL
TVGEMTSLRYLWLHGNKLSGVLPDSIGNCTKLEELYLLDNQLSGSLPKTLSYIKGLKIFD
ITANSFTGEITFSFEDCKLEVFILSFNQISNEIPSWLGNCSSLTQLAFVNNNISGQIPSS
LGLLRNLSQLLLSENSLSGPIPPEIGNCQLLVWLELDANQLNGTVPKELANLRKLEKLFL
FENRLIGEFPEDIWSIKSLQSVLIYENSFTGRLPPVLAELKFLKNITLFNNFFTGVIPPD
LGVNSRLTQIDFTNNSFVGGIPPNICSGKRLRILDLGLNLLNGSIPSNVMDCPSLERFIL
QNNNLSGPIPQFRNCANLSYIDLSHNSLSGNIPASLGRCVNITMIKWSENKLVGPIPSEI
RDLVNLRVLNLSQNSLQGVLPVQISSCSKLYLLDLSFNSLNGSALTTVSNLKFLSQLRLQ
ENKFSGGIPDSLSQLDMLIELQLGGNVLGGSIPSSLGRLVKLGIALNICSNGLVGGIPPL
LSNLVELQSLDLSLNGLTGDLDMLGNLQLLHVLNVSYNRFSGPVPENLLNFLVSSPSSFN
GNPDLCISCHTNGSYCKGSNVLKPCGETKKLHKHVKIAVIVIGSLFVGAVSILILSCILL
KFYHPKTKNLESVSTLFEGSSSKLNEVIEATENFDDKYIIGTGAHGTVYKATLRSGEVYA
VKKLAISAQKGSYKSMIRELKTLGKIKHRNLIKLKEFWLRSEYGFMLYVYMEQGSLQDVL
HGIQPPPSLDWSVRYTIALGTAHGLAYLHDDCQPAIIHRDIKPSNILLNGDMVPHIADFG

FIGURE 11B(9)

IAKLMDQSSSAPQTTGVIGTFGYMAPELAFSTRSSIESDVYSYGVILLELLTKKQVVDPS
FPDNMDIVGWVTATLNGTDQIELVCDSTLMEEVYGTVEIEEVSKVLSLALRCAAKEASRR
PPMADVVKELTDVRKSAGKLSKPEKTASRSSS

>Os08g0446400 (OsPEPR2) (SEQ ID NO: 156)

ATGGGACTGCACATATGGTGTTGGTTGGTTGTCTTGTTCAGCTTGGCCCCATTGTGTTGT
AGTTTGAGCGCAGATGGCCTGGCTCTTCTGGATCTAGCCAAGACTCTGATACTGCCCAGC
TCCATAAGCTCGAATTGGAGTGCTGATGATGCAACTCCGTGTACATGGAAAGGAGTTGAT
TGTGATGAAATGAGCAATGTGGTTTCTCTTAACTTATCATATTCTGGATTGTCTGGTTCT
CTAGGTCCTCAGATAGGACTCATGAAGCACCTGAAAGTCATTGATTTATCAGGTAATGGT
ATATCAGGACCAATGCCCAGTTCCATTGGCAACTGCACCAAACTGGAGGTGCTCCATCTA
CTACGTAATCGATTGAGTGGGATCCTTCCAGATACATTGAGCAATATTGAAGCATTAAGG
GTTTTTGATCTCTCCCGCAATAGCTTCACAGGCAAGGTCAATTTCAGATTTGAGAACTGC
AAGCTTGAGGAGTTCATCTTGTCATTCAATTATCTCAGAGGCGAAATCCCGGTGTGGATA
GGGAATTGCAGCAGCTTGACACAGCTTGCATTTGTCAACAATAGTATCACCGGTCAAATA
CCAAGTTCAATCGGTTTATTGAGAAACCTTTCTTACCTTGTACTTTCCCAGAACTCCTTG
TCTGGCACAATCCCTCCTGAGATTGGTAACTGCCAATTGCTGATATGGCTGCATCTAGAT
GCAAACCAGCTCGAGGGCACTATACCAAAAGAACTAGCAAACCTGAGGAACTTGCAGAAG
CTCTATCTTTTTGAGAATTGCCTCACTGGGGAGTTTCCTGAAGATATATGGGGAATCCAA
AGCCTACTATCTGTCGACATCTATAAAAACAATTTCACTGGGCAGCTGCCTATAGTGTTG
GCTGAGATGAAGCAGCTCCAGCAAATTACGCTATTCAATAATTCATTCACTGGTGTCATA
CCACAGGGGTTGGGTGTAAATAGCAGTTTGTCCGTAATTGATTTCATAAACAATAGTTTT
GTTGGCACAATCCCTCCAAAAATTTGTTCAGGGGGAAGATTGGAAGTTTTGAACTTGGGT
TCAAATCTTCTCAATGGTAGCATCCCCTCTGGTATCGCTGACTGCCCAACTTTGAGACGA
GTAATTCTCAACCAAAATAATCTCATTGGATCAATTCCACAATTTGTAAATTGTAGCAGT
CTTAATTATATTGATCTCAGCTATAATTTATTAAGTGGGGACATTCCTGCTAGCTTGAGC
AAATGTATCAATGTTACATTTGTGAACTGGTCATGGAACAAGCTTGCTGGTCTAATACCA
TCAGAAATTGGGAACTTAGGGAACTTAAGTAGTCTTAACCTCTCAGGAAACAGACTATAT
GGTGAACTCCCTGTGGAAATTTCTGGATGCTCCAAGTTATATAAGCTTGATTTGAGCTAC
AACTCTTTGAACGGTTCGGCACTCACAACTGTAAGTAGCCTTAAATTTCTGTCACAGCTA
CGGTTGCAGGAGAATAAATTCAGTGGAGGTATACCTGATTCTTTATCTCAGTTGGATATG
CTTATTGAACTGCAACTTGGTGGCAACATTCTTGGGGGTAGTATCCCTTCATCGTTAGGA
AAGTTAGTTAAACTGGGCATTGCATTAAACCTCAGTAGAAATGGACTAGTTGGTGACATT
CCACCACTAGGCAATTTGGTGGAGCTGCAGAGTTTAGATTTGTCATTTAATAACCTCACC
GGAGGTCTTGCTTCATTAGGAAACCTACAGTTTTTGTATTTCTTGAATGTTTCCTACAAC
ATGTTTAGTGGACCAGTACCAAAAAATCTTGTGAGGTTTCTGAATTCCACTCCAAGTTCA
TTTAGTGGAAATGCAGATCTATGTATCTCTTGCCATGAAAATGATTCATCTTGCACAGGT
TCTAATGTTTTGAGACCTTGTGGTTCAATGAGTAAAAAAAGTGCACTCACACCACTCAAG
GTTGCTATGATAGTTCTTGGTTCGGTTTTTGCTGGTGCATTTCTGATACTCTGTGTCCTT
CTAAAATATAATTTCAAGCCTAAGATTAACAGTGATTTAGGTATATTATTTCAAGGATCT
TCTTCTAAATTAAATGAGGCTGTAGAAGTGACTGAAAACTTCAATAACAAGTACATTATC
GGTTCCGGGGCCCATGGAATTGTCTACAAGGCAGTACTGAGGTCAGGAGAAGTATATGCT
GTAAAGAAGCTTGTACATGCTGCTCACAAGGGCTCAAATGCAAGCATGATCCGCGAGCTG
CAGACGCTTGGTCAAATTAGGCACAGGAACCTGATAAGACTTAATGAATTCTTGTTTAAG
CATGAGTATGGTTTGATCCTATATGATTTTATGGAGAATGGTAGCCTGTATGATGTGTTG
CATGGGACTGAGCCCACTCCAACTTTGGACTGGAGCATCCGCTACAGCATAGCTCTTGGA
ACAGCCCATGGTCTAGCATATCTCCATAATGACTGTCACCCTGCTATCATACATCGAGAT
ATTAAACCAAAAAATATATTGCTGGACAACGACATGGTACCGCATATCTCAGATTTTGGC
ATTGCAAAGCTCATGGATCAATATCCTGCTGCTTTACAGACCACAGGAATCGTTGGTACT
ATTGGATATATGGCCCCAGAAATGGCCTTTTCAACCAAGGCTACCACAGAATTCGATGTG
TACAGTTACGGTGTGGTATTACTTGAGTTGATCACCAGAAAGATGGCTGTGGATTCCTCA
TTCCCTGGCAACATGGACATAGTTAGCTGGGTATCCTCCAAGTTGAATGAGACTAATCAG
ATCGAAACTATTTGCGACCCAGCTCTCATTACTGAAGTATATGGAACACATGAAATGGAA
GAAGTGCGCAAGCTGTTGTCATTAGCTCTTAGATGCACAGCAAAGGAGGCAAGCCAAAGG
CCTTCCATGGCCGTTGTTGTCAAAGAGCTGACAGATGCAAGACATGTTGCTGGCTCATAC
TCGAAGCAGAATTCAGGCCCCAGCAATTCTTGA

>Os08g0446400 (OsPEPR2) (SEQ ID NO: 157)

MGLHIWCWLVVLFSLAPLCCSLSADGLALLDLAKTLILPSSISSNWSADDATPCTWKGVD

FIGURE 11B(10)

CDEMSNVVSLNLSYSGLSGSLGPQIGLMKHLKVIDLSGNGISGPMPSSIGNCTKLEVLHL
LRNRLSGILPDTLSNIEALRVFDLSRNSFTGKVNFRFENCKLEEFILSFNYLRGEIPVWI
GNCSSLTQLAFVNNSITGQIPSSIGLLRNLSYLVLSQNSLSGTIPPEIGNCQLLIWLHLD
ANQLEGTIPKELANLRNLQKLYLFENCLTGEFPEDIWGIQSLLSVDIYKNNFTGQLPIVL
AEMKQLQQITLFNNSFTGVIPQGLGVNSSLSVIDFINNSFVGTIPPKICSGGRLEVLNLG
SNLLNGSIPSGIADCPTLRRVILNQNNLIGSIPQFVNCSSLNYIDLSYNLLSGDIPASLS
KCINVTFVNWSWNKLAGLIPSEIGNLGNLSSLNLSGNRLYGELPVEISGCSKLYKLDLSY
NSLNGSALTTVSSLKFLSQLRLQENKFSGGIPDSLSQLDMLIELQLGGNILGGSIPSSLG
KLVKLGIALNLSRNGLVGDIPPLGNLVELQSLDLSFNNLTGGLASLGNLQFLYFLNVSYN
MFSGPVPKNLVRFLNSTPSSFSGNADLCISCHENDSSCTGSNVLRPCGSMSKKSALTPLK
VAMIVLGSVFAGAFLILCVLLKYNFKPKINSDLGILFQGSSSKLNEAVEVTENFNNKYII
GSGAHGIVYKAVLRSGEVYAVKKLVHAAHKGSNASMIRELQTLGQIRHRNLIRLNEFLFK
HEYGLILYDFMENGSLYDVLHGTEPTPTLDWSIRYSIALGTAHGLAYLHNDCHPAIIHRD
IKPKNILLDNDMVPHISDFGIAKLMDQYPAALQTTGIVGTIGYMAPEMAFSTKATTEFDV
YSYGVVLLELITRKMAVDSSFPGNMDIVSWVSSKLNETNQIETICDPALITEVYGTHEME
EVRKLLSLALRCTAKEASQRPSMAVVVKELTDARHVAGSYSKQNSGPSNS

>P93194 (In) (SEQ ID NO: 158)

ATGAAGGTTGCTGTGAACACATTCTTGTTGTTTTTGTGCTCCACTTCATCAATCTATGCT
GCTTTTGCTTTGAATTCTGATGGAGCAGCTCTGCTCTCACTCACTAGACATTGGACTTCA
ATCCCTTCTGACATAACCCAGAGCTGGAATGCTTCAGATTCCACTCCTTGTTCATGGCTG
GGAGTAGAATGTGACAGGAGACAATTTGTTGATACTCTGAACCTCTCCTCCTATGGAATC
TCAGGCGAATTCGGGCCCGAAATCTCGCATTTGAAGCATTTGAAGAAGGTTGTTCTCAGT
GGCAATGGTTTCTTTGGCTCAATTCCTTCCCAGCTAGGCAATTGCAGTCTTCTTGAACAC
ATAGATCTGTCCTCCAACAGCTTTACTGGTAATATCCCTGACACCCTTGGAGCTTTGCAG
AATTTAAGGAACTTAAGCCTGTTCTTTAATTCTCTGATTGGCCCATTTCCTGAGTCTTTA
CTTTCAATTCCACATTTAGAAACTGTTTATTTCACTGGCAATGGTCTTAATGGTTCAATC
CCTTCAAATATTGGAAACATGAGTGAGCTTACAACTCTGTGGCTTGATGATAATCAATTT
TCAGGGCCAGTGCCTTCATCCTTAGGAAACATTACCACCCTGCAAGAACTTTATTTGAAT
GATAACAATCTTGTTGGAACCTTGCCTGTCACTTTAAATAATCTCGAGAACCTTGTTTAC
TTAGATGTAAGGAATAACAGTTTAGTGGGAGCTATTCCTTTGGACTTTGTTAGTTGCAAA
CAGATTGACACGATTAGCTTGTCCAACAACCAATTCACGGGAGGACTCCCACCTGGTTTG
GGAAATTGCACTAGCTTAAGGGAATTCGGTGCCTTTTCTTGTGCCTTGAGTGGTCCTATA
CCTTCCTGTTTTGGCCAACTCACTAAGTTAGACACTCTTTACCTTGCTGGAAACCATTTT
TCGGGAAGAATACCACCCGAGCTAGGCAAGTGCAAGTCCATGATTGATTTGCAACTTCAA
CAAAATCAACTTGAGGGTGAAATTCCGGGTGAACTAGGGATGCTCAGTCAATTGCAATAT
CTCCATCTATATACCAACAATTTATCTGGTGAAGTTCCACTCAGCATTTGGAAAATTCAA
AGCCTCCAAAGTCTTCAGTTGTACCAAAACAATCTCTCCGGGGAGCTACCTGTTGATATG
ACCGAGCTAAAGCAACTAGTGAGCCTTGCCTTATATGAAAACCATTTTACTGGAGTTATT
CCTCAAGATTTGGGGGCTAACAGCAGTTTAGAGGTTCTAGATTTGACCAGAAACATGTTC
ACAGGTCATATTCCACCGAACCTATGCTCCCAAAAGAAACTGAAGAGACTGCTCTTGGGT
TATAACTATCTGGAAGGTAGTGTTCCTTCTGATTTGGGGGGCTGTTCCACTTTGGAAAGG
CTAATTCTCGAAGAGAATAACCTCAGAGGTGGCCTCCCAGATTTTGTTGAGAAGCAAAAT
CTTCTGTTCTTTGATCTTAGTGGCAATAACTTCACTGGACCGATACCTCCAAGCTTAGGA
AACCTAAAAAATGTTACTGCCATTTACTTGTCATCGAATCAGCTCTCAGGGAGTATCCCA
CCCGAGCTTGGTAGCCTTGTGAAACTTGAACATTTGAACCTTTCTCACAACATCCTTAAA
GGTATACTTCCATCTGAACTGTCGAACTGTCATAAACTGTCAGAACTTGATGCGAGTCAC
AATTTGTTGAATGGCTCTATTCCATCCACTTTAGGAAGCTTGACAGAACTGACCAAATTG
AGTCTCGGTGAGAACAGTTTCTCAGGAGGTATTCCAACTTCATTGTTCCAATCCAATAAG
CTCTTAAATCTGCAGCTCGGTGGAAATTTACTAGCTGGAGATATTCCACCAGTGGGAGCT
TTGCAGGCACTGAGGTCATTAAATTTGAGCAGTAACAAACTGAATGGTCAACTCCCTATA
GATCTAGGGAAATTAAAGATGCTAGAGGAATTGGATGTATCTCACAACAATCTATCTGGT
ACGTTGAGAGTTTTGTCTACAATCCAATCATTGACATTCATCAACATTTCTCACAATCTG
TTTTCTGGCCCCGTACCACCTTCATTGACCAAGTTCTTGAACTCATCTCCCACTTCATTT
TCCGGGAACTCTGACCTTTGTATTAACTGCCCTGCTGATGGCTTAGCTTGCCCGGAGAGC
AGCATTTTGCGACCATGTAATATGCAATCCAACACTGGGAAGGGTGGCCTTAGTACTTTG
GGAATAGCAATGATAGTTCTTGGGGCATTGTTATTTATCATCTGTCTATTCCTTTTCTCT
GCTTTCCTGTTTCTACATTGCAAAAAATCAGTACAAGAAATAGCAATTTCTGCTCAAGAG
GGTGATGGTTCCTTGCTCAATAAAGTATTGGAAGCTACAGAGAATCTAAATGATAAGTAT
GTTATTGGGAAGGGAGCACATGGAACAATATACAAGGCCACATTAAGTCCAGATAAAGTG

FIGURE 11B(11)

TATGCTGTGAAAAAGCTTGTGTTTACTGGGATCAAGAATGGAAGTGTAAGCATGGTTCGG
GAAATTGAAACAATTGGGAAAGTCAGGCACCGGAATCTTATTAAACTGGAAGAGTTTTGG
CTGAGAAAGGAGTATGGACTAATTCTATACACTTATATGGAAAATGGCAGCCTTCATGAT
ATCCTCCATGAGACAAATCCTCCTAAGCCGTTAGATTGGAGCACACGTCATAATATTGCT
GTAGGGACTGCCCATGGACTTGCGTATCTCCATTTTGACTGTGATCCTGCCATTGTGCAT
CGAGATATTAAACCGATGAATATCCTGTTAGACTCTGATCTCGAGCCTCACATTTCAGAC
TTTGGCATTGCCAAGCTTCTGGATCAGTCTGCTACTTCAATCCCGTCCAACACAGTTCAA
GGGACAATCGGCTATATGGCTCCAGAAAATGCATTCACTACTGTGAAGAGCAGAGAGTCA
GATGTATACAGTTATGGGGTCGTTCTGTTGGAATTGATAACTCGTAAGAAGGCCTTGGAT
CCTTCGTTCAATGGTGAAACCGATATTGTTGGCTGGGTTAGGTCGGTTTGGACACAAACT
GGAGAAATTCAGAAGATAGTGGATCCGAGCCTTTTGGATGAATTGATAGATTCCAGCGTG
ATGGAACAAGTAACTGAAGCGCTTTCACTGGCTTTGAGGTGTGCAGAGAAGGAGGTGGAC
AAAAGACCCACAATGAGAGATGTAGTGAAGCAACTAACACGCTGGAGCATACGCTCCTAT
TCGTCGAGTGTTAGAAACAAGTCTAAGTAG

>P93194 (In) (SEQ ID NO: 159)

MKVAVNTFLLFLCSTSSIYAAFALNSDGAALLSLTRHWTSIPSDITQSWNASDSTPCSWL
GVECDRRQFVDTLNLSSYGISGEFGPEISHLKHLKKVVLSGNGFFGSIPSQLGNCSLLEH
IDLSSNSFTGNIPDTLGALQNLRNLSLFFNSLIGPFPESLLSIPHLETVYFTGNGLNGSI
PSNIGNMSELTTLWLDDNQFSGPVPSSLGNITTLQELYLNDNNLVGTLPVTLNNLENLVY
LDVRNNSLVGAIPLDFVSCKQIDTISLSNNQFTGGLPPGLGNCTSLREFGAFSCALSGPI
PSCFGQLTKLDTLYLAGNHFSGRIPPELGKCKSMIDLQLQQNQLEGEIPGELGMLSQLQY
LHLYTNNLSGEVPLSIWKIQSLQSLQLYQNNLSGELPVDMTELKQLVSLALYENHFTGVI
PQDLGANSSLEVLDLTRNMFTGHIPPNLCSQKKLKRLLLGYNYLEGSVPSDLGGCSTLER
LILEENNLRGGLPDFVEKQNLLFFDLSGNNFTGPIPPSLGNLKNVTAIYLSSNQLSGSIP
PELGSLVKLEHLNLSHNILKGILPSELSNCHKLSELDASHNLLNGSIPSTLGSLTELTKL
SLGENSFSGGIPTSLFQSNKLLNLQLGGNLLAGDIPPVGALQALRSLNLSSNKLNGQLPI
DLGKLKMLEELDVSHNNLSGTLRVLSTIQSLTFINISHNLFSGPVPPSLTKFLNSSPTSF
SGNSDLCINCPADGLACPESSILRPCNMQSNTGKGGLSTLGIAMIVLGALLFIICLFLFS
AFLFLHCKKSVQEIAISAQEGDGSLLNKVLEATENLNDKYVIGKGAHGTIYKATLSPDKV
YAVKKLVFTGIKNGSVSMVREIETIGKVRHRNLIKLEEFWLRKEYGLILYTYMENGSLHD
ILHETNPPKPLDWSTRHNIAVGTAHGLAYLHFDCDPAIVHRDIKPMNILLDSDLEPHISD
FGIAKLLDQSATSIPSNTVQGTIGYMAPENAFTTVKSRESDVYSYGVVLLELITRKKALD
PSFNGETDIVGWVRSVWTQTGEIQKIVDPSLLDELIDSSVMEQVTEALSLALRCAEKEVD
KRPTMRDVVKQLTRWSIRSYSSSVRNKSK

>803073 (Pt) (SEQ ID NO: 160)

ATGTCACTCTTGAGGAAATGGGATTCTGTGCCTACTTCCATTACTTCAAGTTGGAATTCT
TCAGACTCGACTCCTTGTTCTTGGCTAGGTATAGGATGTGATCATAGAAGTCATTGTGTG
GTTTCTTTGAACCTTTCTGGCTTAGGAATTTCTGGTCCTTTGGGACCTGAAACTGGGCAG
TTAAAGCAGTTAAAGACTGTTGATTTGAACACCAATTATTTCTCTGGTGATATACCCTCA
CAGTTGGGAAATTGTAGTCTCCTTGAGTACTTGGATTTGTCTGCAAATAGCTTTACTGGT
GGAATACCTGATAGCTTTAAGTACTTGCAAAATTTACAAACATTGATTATTTTCTCGAAT
TCACTGTCTGGTGAAATACCTGAATCATTGTTCCAAGATTTGGCTTTACAAGTTTTGTAT
TTGGACACCAATAAATTCAATGGTTCCATTCCTAGGAGTGTTGGTAACTTGACTGAGCTT
TTAGAACTGTCCTTATTTGGAAATCAATTATCTGGGACAATCCCTGAGTCTATTGGAAAT
TGTAGAAAATTGCAATCTCTCCCTCTGAGTTATAACAAGTTAAGTGGTTCTTTGCCTGAG
ATTCTAACCAATCTTGAAAGCCTTGTTGAATTATTTGTTAGTCATAATAGTCTTGAGGGT
AGAATTCCTTTAGGTTTCGGCAAATGCAAGAATTTGGAAACCTTAGATTTGTCATTCAAT
AGCTATAGTGGGGGTCTTCCACCAGATTTAGGCAATTGTAGTAGCTTAGCAACCTTGGCC
ATTATCCATAGCAACTTAAGAGGCGCTATCCCATCTTCCTTTGGCCAACTGAAAAAGCTT
TCTGTGCTCGACCTTTCTGAGAATCGACTGTCTGGGACGATTCCTCCTGAACTTAGTAAT
TGCAAGTCCTTGATGACCTTAAATTTATACACAAATGAGCTTGAGGGAAAGATTCCGAGT
GAGTTGGGGAGGCTAAACAAATTGGAGGACCTCGAATTGTTCAACAATCATTTGAGTGGT
GCAATTCCTATTAGCATCTGGAAGATTGCGAGCCTTAAGTACCTCCTTGTGTATAACAAC
AGTCTTTCTGGTGAATTGCCTCTTGAGATCACTCATCTCAAGAACCTAAAGAACTTGTCA
CTATACAACAACCAGTTCTTTGGTGTCATACCCCAAAGTTTGGGAATCAACAGCAGTTTG
TTGCAGCTGGACTTCACAGATAATAAGTTCACAGGTGAAATTCCCCCAAACCTTTGCCAT
GGAAAGCAGTTGAGAGTTCTTAATATGGGCCGGAACCAACTTCAAGGCAGCATTCCTTCT

FIGURE 11B(12)

GATGTGGGAGGCTGCTTAACGCTCTGGAGATTGATCCTCAAGGAGAACAACCTCTCAGGT
GCCCTTCCAGAATTTTCAGAAAATCCAATCCTCTATCACATGGACGTCAGCAAAAATAAT
ATTACAGGTCCAATTCCACCCAGCATTGGGAACTGTTCTGGTCTCACTTCCATTCATCTT
TCCATGAACAAGCTTACAGGGTTTATACCCTCAGAGCTAGGAAATCTTGTAAACCTTCTG
GTAGTGGATCTTTCATCCAACCAACTGGAAGGTTCTTTGCCATCGCAGCTGTCAAAGTGT
CACAACTTAGGCAAGTTTGATGTAGGGTTCAATTCACTGAACGGCTCAGTTCCATCGAGT
TTAAGGAACTGGACCAGCTTGTCCACTTTGATTTTAAAAGAGAATCATTTTATTGGGGGA
ATTCCACCTTTCCTCTCAGAACTTGAAAAGCTTACAGAGATACAACTTGGTGGAAATTTT
CTGGGAGGTGAGATTCCTTCATGGATTGGGTCTTTACAGAGTCTGCAATATGCATTGAAT
CTCAGCAGTAATGGATTGTTTGGAGAGCTTCCTTCAGAGCTGGGGAACTTGATCAAGCTT
GAACAGCTTCAGTTATCAAACAATAATCTGACAGGAACTCTAGCACCTCTTGATAAAATC
CATTCGTTGGTCCAGGTCGATATTTCATACAATCACTTCAGTGGTCCAATACCAGAAACA
CTAATGAACTTGCTTAACTCATCGCCGTCATCATTCTGGGGCAATCCCGATCTATGTGTC
AGTTGTCTTCCATCAGGTGGCTTAACATGCACCAAAAACAGAAGTATCAAGCCATGTGAC
TCTCAGTCAAGCAAGCGAGACAGCTTTTCTAGAGTGGCTGTCGCGCTGATAGCTATTGCT
TCTGTGGTTGCTGTTTTCATGCTTGTTGGACTGGTTTGCATGTTTATCTTGTGCAGAAGA
TGTAAGCAGGATCTTGGGATCGACCATGATGTTGAAATTGCTGCTCAAGAGGGCCCTTCT
TCCCTACTCAACAAAGTGATGCAAGCTACTGAGAATCTAAATGACAGACATATAGTTGGG
AGGGGAACCCATGGAACCGTTTATAAGGCTTCATTGGGTGGAGACAAAATATTTGCAGTT
AAGAAGATAGTATTTACAGGCCACAAAGGAGGAAACAAAAGTATGGTTACAGAAATTCAA
ACCATTGGGAAAATCAGGCACCGGAATCTGCTCAAATTGGAAAACTTTTGGTTACGGAAG
GATTATGGTCTGATCCTGTATGCCTACATGCAAAATGGGAGCGTTCATGATGTCTTACAT
GGGAGCACACCACCGCAAACCCTGGAGTGGAGCATACGCCATAAAATAGCTTTAGGAACT
GCCCATGGTTTGGAATATCTCCACTATGATTGCAATCCTCCTATTGTGCATCGAGACATC
AAACCAGAAAACATTCTCTTAGACTCTGATATGGAGCCTCATATCTCTGATTTCGGTATA
GCTAAGCTACTTGATCAGTCTTCTGCTTCAGCACAGTCTTTCCTGGTTGCAGGCACAATT
GGATATATAGCACCAGAAAACGCCTTGTCGACAATAAAGAGCAAGGAATCGGATGTTTAT
AGCTACGGGGTTGTTTTGCTTGAGCTGATAACTAGAAAGAAGGCATTGGATCCATTATTT
GTGGGGGAAACAGATATTGTAGAGTGGGTCAGATCTGTTTGGAGCAGCACAGAAGACATC
AACAAGATTGCTGATTCAAGCCTAAGGGAGGAGTTTTTGGATTCAAATATCATGAATCAA
GCCATTGATGTGCTTTTGGTGGCTTTGAGATGCACTGAAAAGGCGCCTAGGAGAAGACCC
ACAATGAGAGATGTTGTCAAGCGATTAGTAAAAAGAGATGCCAGCATTAGAGGCAAACGC
AGCTGA

>803073 (Pt) (SEQ ID NO: 161)

MSLLRKWDSVPTSITSSWNSSDSTPCSWLGIGCDHRSHCVVSLNLSGLGISGPLGPETGQ
LKQLKTVDLNTNYFSGDIPSQLGNCSLLEYLDLSANSFTGGIPDSFKYLQNLQTLIIFSN
SLSGEIPESLFQDLALQVLYLDTNKFNGSIPRSVGNLTELLELSLFGNQLSGTIPESIGN
CRKLQSLPLSYNKLSGSLPEILTNLESLVELFVSHNSLEGRIPLGFGKCKNLETLDLSFN
SYSGGLPPDLGNCSSLATLAIIHSNLRGAIPSSFGQLKKLSVLDLSENRLSGTIPPELSN
CKSLMTLNLYTNELEGKIPSELGRLNKLEDLELFNNHLSGAIPISIWKIASLKYLLVYNN
SLSGELPLEITHLKNLKNLSLYNNQFFGVIPQSLGINSSLLQLDFTDNKFTGEIPPNLCH
GKQLRVLNMGRNQLQGSIPSDVGGCLTLWRLILKENNLSGALPEFSENPILYHMDVSKNN
ITGPIPPSIGNCSGLTSIHLSMNKLTGFIPSELGNLVNLLVVDLSSNQLEGSLPSQLSKC
HNLGKFDVGFNSLNGSVPSSLRNWTSLSTLILKENHFIGGIPPFLSELEKLTEIQLGGNF
LGGEIPSWIGSLQSLQYALNLSSNGLFGELPSELGNLIKLEQLQLSNNNLTGTLAPLDKI
HSLVQVDISYNHFSGPIPETLMNLLNSSPSSFWGNPDLCVSCLPSGGLTCTKNRSIKPCD
SQSSKRDSFSRVAVALIAIASVVAVFMLVGLVCMFILCRRCKQDLGIDHDVEIAAQEGPS
SLLNKVMQATENLNDRHIVGRGTHGTVYKASLGGDKIFAVKKIVFTGHKGGNKSMVTEIQ
TIGKIRHRNLLKLENFWLRKDYGLILYAYMQNGSVHDVLHGSTPPQTLEWSIRHKIALGT
AHGLEYLHYDCNPPIVHRDIKPENILLDSDMEPHISDFGIAKLLDQSSASAQSFLVAGTI
GYIAPENALSTIKSKESDVYSYGVVLLELITRKKALDPLFVGETDIVEWVRSVWSSTEDI
NKIADSSLREEFLDSNIMNQAIDVLLVALRCTEKAPRRRPTMRDVVKRLVKRDASIRGKR
S

>765043 (Pt) (SEQ ID NO: 162)

ATGAGTTCTGTTTTGAATCATGTCTTGCTGTTATGTTGGTACTTTGTGTCTGTCTATACC
GTGTCTGGCTTGAACTATGATGGGTCGACTCTGTTGTCACTCTTGAGGCAGTGGAATTCT
GTGCCTCCTTCCATAACTTCAAGCTGGAATGCATCAGACTCAACTCCATGTTCTTGGCTA

FIGURE 11B(13)

GGTATAGGATGTGATAGTAGAACCCATAGTGTAGTTTCTTTGAACCTCTCTGGTTATGCA
ACTTCTGGTCAATTGGGACCAGAGATTGGACTCTTAAAGCATTTGAAAACCATCGATTTG
CACACCAGTAATTTCTCTGGTGACATACCCTCACAGTTAGGCAATTGTAGTCTACTTGAG
CACTTGGATTTGTCCATAAATAGCTTTACGCGAAAAATACCTGATGGCTTTAAGTACCTT
CAAAATTTGCAGTATTTGAGTCTTTCCTTTAATTCACTCTCTGGTGAGATACCTGAGAGT
CTAACCAAGCTTGAAAGCCTTGCCGAGTTGCTTCTCGATCATAATAGTCTTGAGGGTAGA
ATTCCTACAGGTTTCAGCAATTGCAAGAATTTGGACACCTTAGATTTGTCCTTCAATAGC
TTTAGTGGGGGTTTCCCTTCAGACCTTGGCAATTTTAGCAGCTTAGCAATCTTGGCCATT
ATTAATAGTCACTTAAGAGGTGCCATCCCATCTTCCTTTGGCCACCTAAAAAAGCTTTCT
TACCTTGACCTCTCCCAGAATCAATTGTCTGGGAGGATTCCTCCTGAACTTGGGGATTGC
GAGTCGTTGACGACCTTAAACTTGTACACAAATCAACTCGAGGGAGAGATTCCGGGTGAA
TTGGGGAGGCTAAGCAAATTAGAGAACCTGGAATTGTTTGACAATCGCTTGAGTGGTGAA
ATTCCTATCAGCATTTGGAAGATTGCAAGTCTTAAGAGCATCTATGTGTACAACAACAGT
CTTTCTGGTGAATTACCGCTTGAGATGACTGAGCTCAGGCAACTACAGAATATCTCACTG
GCACAAAATCAATTCTACGGGGTCATTCCCCAAACTTTGGGAATCAACAGCAGCTTATTG
TGGCTCGATTTCTTTGGCAATAAGTTCACTGGTGAAATTCCGCCAAATCTTTGCTACGGG
CAGCAATTGAGAATTCTTGTTATGGGTTCCAACCAACTTCAAGGCAGCATTCCTTCTGAT
GTGGGAGGCTGCCCAACACTCTGGAGATTGACCCTCGAGGAGAACAACCTCTCAGGTACC
CTTCCACAGTTCGCAGAAAATCCTATCCTCCTGTACATGGACATCAGCAAAAATAATATT
ACAGGCCCAATTCCGCCCAGCATTGGGAATTGTAGTGGTCTCACTTTCATTCGTCTTTCC
ATGAACAAGCTTACAGGGTCCATACCCTCAGAGCTAGGTAATCTTATAAACCTTCTGGTA
GTGGATCTTTCATCCAACCAACTGGAAGGTTCTTTGCCATCTCAGCTGTCAAGGTGTTAC
AAATTAGGCCAGTTTGATGTGGGGTTTAATTCACTGAATGGCACAATTCCGTCAAGTTTG
AGGAACTGGACGAGCTTATCCACTTTGGTTTTAAGTGAGAATCATTTTACCGGGGGCATT
CCACCTTTCCTGCCAGAACTTGGAATGCTTACAGAGCTACAACTTGGTGGGAATATTCTA
GGAGGTGTGATTCCTTCATCCATTGGATCGGTGCGGAGTCTGAAGTATGCCTTGAATCTC
AGCAGCAATGGATTCGTCGGAAAACTTCCTTCCGAGCTAGGGAACTTGAAAATGCTTGAA
AGACTTGATATATCAAACAATAATCTGACAGGAACTCTAGCAATTCTTGATTATATCCTT
TCATGGGACAAGGTCAATGTTTCAAACAATCATTTCACAGGTGCAATACCGGAAACACTG
ATGGACTTGCTTAACTATTCTCCGTCATCATTCTTGGGCAATCCTGGCCTATGTGTCATG
TGTTCTCCATCAAGCCGCATAGCATGCCCCAAGAACAGAAATTTCTTGCCATGTGACAGT
CAAACAAGCAATCAAAATGGACTATCTAAAGTGGCAATCGTAATGATAGCCCTTGCTCCT
GTTGCTGCTGTTTCTGTGCTTCTTGGAGTGGTTTACTTGTTTATCAGGCGCAGAAGATAT
AATCAGGATGTTGAGATCACTTCTCTAGATGGTCCATCTTCACTACTCAACAAGGTGCTG
GAAGTTACTGAGAATCTAAATGACAGACATATCATTGGGAGGGGAGCTCATGGAACAGTT
TATAAGGCTTCATTGGGAGGAGACAAAATCTTTGCAGTAAAAAAATTGTATTTGCAGGC
CACAAAGAAAGGAACAAAAGCATGGTTAGAGAAATTCAGACCATTGGGAAAATCAAGCAC
CGGAATCTGATCAAATTGGAGGAGTTTTGGTTTCAAAAGGACTACGGTCTAATCCTGTAT
ACTTACATGCAAAATGGGAGCCTCTATGATGTCTTACATGGAACCAGAGCACCACCAATC
CTGGATTGGGAAATGCGGTATAAGATAGCTATTGGAATTGCACATGGATTGGAATATATC
CATTATGATTGTGATCCTCCTATAGTGCATAGAGACATCAAACCAGAAAACATTCTTTTA
GACTCTGATATGGAGCCTCATATCTCTGATTTTGGCATAGCTAAGCTAATGGATCAGTCT
TCTGCTTCAGCACAGTCCCTCTCTGTTGCGGGAACTATTGGATATATAGCTCCAGAAAAC
GCATTTACGACAATAAAGACGAAGGAATCTGATGTTTATAGTTATGGGGTTGTTTTGCTT
GTGCTTATAACTAGAAAGAAGGCACTGGATCCCTCATTTACGGAGGGAACAGCTATTGTA
GGGTGGGTTAGGTCTGTTTGGAACATCACGGAAGACATCAACAGGATTGCTGATTCAAGT
CTTGGAGAGGAATTTTTGAGTTCTTACAGCATCAAGGATCAAGTCATTAACGTGCTTTTG
ATGGCTTTGAGATGTACTGAAGAAGAGCCTAGCAAAAGACCCTCAATGAGAGATGTTGTC
AGGCAATTAGTAAAAGCAAACGATCGCAGAAGGAGGAGGTGA

>765043 (Pt) (SEQ ID NO: 163)

MSSVLNHVLLLCWYFVSVYTVSGLNYDGSTLLSLLRQWNSVPPSITSSWNASDSTPCSWL
GIGCDSRTHSVVSLNLSGYATSGQLGPEIGLLKHLKTIDLHTSNFSGDIPSQLGNCSLLE
HLDLSINSFTRKIPDGFKYLQNLQYLSLSFNSLSGEIPESLTKLESLAELLLDHNSLEGR
IPTGFSNCKNLDTLDLSFNSFSGGFPSDLGNFSSLAILAIINSHLRGAIPSSFGHLKKLS
YLDLSQNQLSGRIPPELGDCESLTTLNLYTNQLEGEIPGELGRLSKLENLELFDNRLSGE
IPISIWKIASLKSIYVYNNSLSGELPLEMTELRQLQNISLAQNQFYGVIPQTLGINSSLL
WLDFFGNKFTGEIPPNLCYGQQLRILVMGSNQLQGSIPSDVGGCPTLWRLTLEENNLSGT
LPQFAENPILLYMDISKNNITGPIPPSIGNCSGLTFIRLSMNKLTGSIPSELGNLINLLV
VDLSSNQLEGSLPSQLSRCYKLGQFDVGFNSLNGTIPSSLRNWTSLSTLVLSENHFTGGI

FIGURE 11B(14)

PPFLPELGMLTELQLGGNILGGVIPSSIGSVRSLKYALNLSSNGFVGKLPSELGNLKMLE
RLDISNNNLTGTLAILDYILSWDKVNVSNNHFTGAIPETLMDLLNYSPSSFLGNPGLCVM
CSPSSRIACPKNRNFLPCDSQTSNQNGLSKVAIVMIALAPVAAVSVLLGVVYLFIRRRRY
NQDVEITSLDGPSSLLNKVLEVTENLNDRHIIGRGAHGTVYKASLGGDKIFAVKKIVFAG
HKERNKSMVREIQTIGKIKHRNLIKLEEFWFQKDYGLILYTYMQNGSLYDVLHGTRAPPI
LDWEMRYKIAIGIAHGLEYIHYDCDPPIVHRDIKPENILLDSDMEPHISDFGIAKLMDQS
SASAQSLSVAGTIGYIAPENAFTTIKTKESDVYSYGVVLLVLITRKKALDPSFTEGTAIV
GWVRSVWNITEDINRIADSSLGEEFLSSYSIKDQVINVLLMALRCTEEEPSKRPSMRDVV
RQLVKANDRRRRR

>CAO23192 (Vv) (SEQ ID NO: 164)

ATGGCTCTCAAGAGCAAATGGGCAGTGCCCACTTTCATGGAAGAGAGCTGGAACGCCTCT
CATTCCACCCCATGTTCATGGGTTGGAGTTTCATGTGATGAAACCCACATTGTGGTTTCT
CTTAACGTCTCCGGTTTGGGAATATCCGGCCATTTGGGTCCGGAGATTGCAGATTTGAGG
CACTTGACCAGTGTCGATTTCAGCTACAACAGTTTCTCAGGTCCAATTCCGCCGGAGTTT
GGAAATTGCAGTCTTCTGATGGATTTAGACCTGTCTGTGAATGGTTTTGTTGGTGAAATA
CCCCAAAACTTGAACAGTTTGGGGAAGTTAGAATATCTGAGCTTTTGTAATAATTCATTG
ACTGGTGCAGTCCCTGAATCCTTGTTTCGGATTCCGAATTTGGAAATGCTTTACCTGAAT
TCCAACAAACTCAGTGGTTCAATCCCTTTGAATGTTGGAAATGCTACTCAGATTATAGCC
CTATGGTTGTATGATAATGCATTATCAGGCGACATTCCTTCTTCCATTGGAAATTGTAGT
GAATTGGAGGAGCTTTACTTGAATCACAACCAATTTTTAGGGGTTTTGCCTGAAAGTATA
AACAATCTTGAGAACCTAGTTTATTTAGATGTGAGCAATAACAATTTAGAGGGTAAAATT
CCTTTGGGTTCAGGCTATTGCAAGAAATTGGATACTTTGGTTCTGTCAATGAATGGTTTT
GGTGGCGAAATTCCACCAGGTTTGGGCAACTGCACTAGCTTATCGCAGTTTGCTGCTTTG
AACAATAGGTTATCAGGTAGTATTCCATCTTCCTTTGGACTGCTACATAAGCTCTTGCTT
TTGTACCTCTCTGAAAATCATTTGTCGGGAAAGATACCACCTGAGATTGGGCAATGCAAG
TCCTTGAGAAGCTTGCATTTATACATGAACCAACTTGAGGGGGAAATCCCAAGTGAATTA
GGGATGTTGAATGAGTTACAAGACCTCCGTTTATTTAATAACCGGTTAACTGGTGAGATT
CCTATTAGTATTTGGAAGATTCCAAGCCTCGAGAATGTTCTTGTGTACAATAACACTCTT
TCTGGAGAACTGCCTGTAGAGATAACTGAGCTCAAGCACCTGAAGAACATTTCCTTGTTC
AACAATCGGTTCTCTGGAGTCATACCTCAACGTTTGGGGATTAACAGTAGTTTGGTGCAG
TTGGATGTTACAAATAATAAGTTCACTGGTGAAATCCCAAAAAGTATTTGCTTTGGAAAA
CAACTGAGCGTGCTGAATATGGGTCTGAATCTACTTCAAGGTAGTATTCCTTCTGCTGTA
GGAAGCTGTTCAACTTTGAGAAGATTGATTCTTAGGAAGAATAATCTGACTGGGGTTCTT
CCCAATTTTGCAAAAAATCCTAACCTTTTGTTGTTGGACCTCAGCGAGAATGGCATCAAT
GGAACAATTCCATTAAGCTTGGGGAACTGTACCAATGTCACCTCCATCAACTTGTCAATG
AACAGGCTTTCAGGACTAATACCCCAAGAGCTAGGAAACCTTAATGTTCTTCAGGCTTTG
AATCTTTCTCATAATGATTTAGGAGGTCCATTGCCATCTCAACTGTCAAATTGTAAGAAT
TTGTTTAAATTTGATGTGGGGTTTAATTCATTGAATGGTTCATTCCCATCAAGTTTAAGG
AGCTTAGAAAATTTGTCAGTTTTGATTTTGAGGGAGAATCGTTTTACTGGGGGTATTCCA
TCTTTCTTGTCTGAACTACAATATCTTTCAGAGATACAGCTTGGTGGAAATTTTCTGGGA
GGAAATATCCCTTCATCGATTGGAATGTTGCAGAATCTAATCTATTCATTGAATATCAGT
CATAACAGATTGACAGGTTCACTTCCCTTAGAGCTTGGGAAGTTGATCATGCTAGAGCGA
TTAGATATATCTCACAACAATCTTTCAGGGACTCTATCAGCTCTTGATGGACTCCATTCG
TTGGTCGTGGTTGATGTTTCATACAATCTTTTCAATGGTCCTCTCCCAGAAACTCTACTT
TTGTTTTTGAATTCATCTCCTTCATCACTTCAGGGCAATCCTGACCTTTGTGTCAAATGT
CCTCAAACTGGTGGCTTAACTTGCATCCAGAATAGGAATTTCAGACCATGTGAGCATTAC
TCAAGCAACCGGAGAGCCCTTGGAAAAATTGAAATTGCATGGATAGCTTTCGCATCATTG
CTCTCATTTCTTGTGCTTGTTGGACTTGTTTGCATGTTTCTCTGGTACAAAAGAACAAAA
CAGGAAGACAAGATCACTGCTCAAGAGGGTTCATCTTCTCTACTCAACAAAGTAATAGAA
GCTACTGAGAATCTCAAAGAATGCTATATCGTTGGAAAAGGAGCCCATGGAACTGTTTAT
AAGGCTTCGCTGGGTCCAAATAATCAGTATGCCTTAAAGAAACTTGTGTTTGCAGGGCTT
AAAGGAGGAAGTATGGCTATGGTTACAGAAATTCAAACAGTTGGAAAGATCAGACACCGG
AATTTGGTCAAGTTGGAAGATTTCTGGATAAGAAAGGAATATGGTTTTATCTTGTACAGG
TACATGGAAAATGGAAGCCTTCATGATGTTTTACATGAGAGGAATCCCCCACCAATTTTG
AAGTGGGATGTTCGCTACAAGATAGCCATTGGAACAGCCCATGGATTAACATATCTGCAC
TATGACTGTGATCCTGCAATTGTGCATCGAGATGTCAAACCAGATAACATACTTCTAGAC
TCAGATATGGAGCCTCATATCTCTGATTTTGGTATTGCTAAGCTGCTGGATCAGTCCTCT
TCTTTGTCACCATCCATCTCAGTTGTGGGTACAATTGGATATATTGCACCAGAGAATGCA
TTTACAACAACAAAGAGCAAAGAGTCTGATGTGTATAGCTTTGGGGTTGTCCTGCTTGAA

FIGURE 11B(15)

CTGATTACCAGAAAAAGGGCACTGGATCCTTCATTTATGGAGGAAACTGACATTGTGGGG
TGGGTTCAGTCTATTTGGAGGAACTTGGAAGAAGTTGATAAGATTGTTGACCCAAGCCTT
CTGGAGGAATTTATAGATCCAAATATCATGGATCAAGTGGTTTGTGTGCTTTTAGTAGCT
TTAAGATGTACGCAAAAGGAGGCAAGCAAAAGGCCTACAATGAGAGATGTTGTTAATCAG
TTAACAGATGCAAACGCTCCTGCCAGAGGCAAAAACAGCTAG

>CAO23192 (Vv) (SEQ ID NO: 165)

MALKSKWAVPTFMEESWNASHSTPCSWVGVSCDETHIVVSLNVSGLGISGHLGPEIADLR
HLTSVDFSYNSFSGPIPPEFGNCSLLMDLDLSVNGFVGEIPQNLNSLGKLEYLSFCNNSL
TGAVPESLFRIPNLEMLYLNSNKLSGSIPLNVGNATQIIALWLYDNALSGDIPSSIGNCS
ELEELYLNHNQFLGVLPESINNLENLVYLDVSNNNLEGKIPLGSGYCKKLDTLVLSMNGF
GGEIPPGLGNCTSLSQFAALNNRLSGSIPSSFGLLHKLLLLYLSENHLSGKIPPEIGQCK
SLRSLHLYMNQLEGEIPSELGMLNELQDLRLFNNRLTGEIPISIWKIPSLENVLVYNNTL
SGELPVEITELKHLKNISLFNNRFSGVIPQRLGINSSLVQLDVTNNKFTGEIPKSICFGK
QLSVLNMGLNLLQGSIPSAVGSCSTLRRLILRKNNLTGVLPNFAKNPNLLLLDLSENGIN
GTIPLSLGNCTNVTSINLSMNRLSGLIPQELGNLNVLQALNLSHNDLGGPLPSQLSNCKN
LFKFDVGFNSLNGSFPSSLRSLENLSVLILRENRFTGGIPSFLSELQYLSEIQLGGNFLG
GNIPSSIGMLQNLIYSLNISHNRLTGSLPLELGKLIMLERLDISHNNLSGTLSALDGLHS
LVVVDVSYNLFNGPLPETLLLFLNSSPSSLQGNPDLCVKCPQTGGLTCIQNRNFRPCEHY
SSNRRALGKIEIAWIAFASLLSFLVLVGLVCMFLWYKRTKQEDKITAQEGSSSLLNKVIE
ATENLKECYIVGKGAHGTVYKASLGPNNQYALKKLVFAGLKGGSMAMVTEIQTVGKIRHR
NLVKLEDFWIRKEYGFILYRYMENGSLHDVLHERNPPPILKWDVRYKIAIGTAHGLTYLH
YDCDPAIVHRDVKPDNILLDSDMEPHISDFGIAKLLDQSSSLSPSISVVGTIGYIAPENA
FTTTKSKESDVYSFGVVLLELITRKRALDPSFMEETDIVGWVQSIWRNLEEVDKIVDPSL
LEEFIDPNIMDQVVCVLLVALRCTQKEASKRPTMRDVVNQLTDANAPARGKNS

>GRMZM2G011806 (Zm) (SEQ ID NO: 166)

ATGAAGCTGGTTTTCTGGCATTGGATTTTTCTATTCTTCGTGTTGCTTTCAACATCACAG
GGTATGAGTTCAGATGGCCTAGCTCTTCTTGCTCTGTCCAAAACCCTAATACTACCAAGT
TTCATAAGGACCAACTGGAGTGCTTCTGATGCAACTCCTTGTACATGGAACGGTGTTGGC
TGCAATGGAAGGAACAGAGTGATTTCTCTCGACCTATCGTCATCAGAGGTCTCAGGTTTT
ATAGGACCTGAAATAGGGCGTCTGAAATACCTGCAGGTTCTCATTTTATCTGCTAACAAC
ATATCTGGTTTGATCCCTCTAGAATTGGGCAACTGCAGTATGCTTGAACAATTGGATCTG
TCCCAAAACTTGCTTTCTGGCAATATACCGGCATCAATGGGCAGCCTCAAGAAATTGTCA
TCACTGTCGCTGTACTACAACTCTTTCCATGGAACAATACCAGAGGAGTTGTTCAAGAAC
CAGTTTCTGGAGCAAGTGTACCTACATGGAAATCAGCTCAGTGGTTGGATACCCTTCTCG
GTTGGTGAAATGACAAGCCTTAAGTCATTGTGGTTGCACGAAAATATGTTGTCCGGAGTT
TTGCCCAGTTCAATTGGCAACTGCACCAAGTTGGAGGAGCTGTATCTACTCCATAATCAA
CTGAGTGGCAGTATTCCAGAAACCTTGAGTAAGATCGAAGGCCTCAAGGTTTTTGATGCC
ACTGCCAATAGTTTCACGGGCGAGATCTCTTTCAGTTTTGAGAACTGCAAGCTGGAAATA
TTCATCTTGTCATTCAATAATATAAAGGGTGAAATTCCGTCATGGCTAGGGAATTGCAGG
AGCTTGCAACAACTTGGATTTGTCAATAATAGTCTGTCTGGCAAAATTCCAAATTTTATA
GGCTTATTCAGCAACCTCACGTATCTTTTACTTTCACAGAACTCCCTGACTGGGCTGATC
CCACCTGAGATTGGTAACTGTCGGTTGCTGCAGTGGCTAGAGCTAGATGCAAATCAGCTG
GAGGGCACTGTTCCTGAAGAATTTGCAAATTTAAGGTATTTGTCAAAGCTCTTTCTTTTC
GAGAATCACCTCATGGGAGACTTCCCTGAGAGTATTTGGAGTATCCAAACCCTCGAGAGT
GTCCTTCTTTATAGCAACAAATTCACAGGGAGGCTACCTTCAGTGTTAGCTGAGCTGAAG
TCCCTAAAGAACATCACACTGTTTGATAATTTCTTCACTGGAGTCATACCACAGGAGCTG
GGTGTTAATAGCCCCTTGGTCCAGATAGATTTCACAAATAACAGTTTTGTTGGTGGTATC
CCACCAAACATTTGTTCAGGAAAAGCATTGAGAATTTTGGACTTGGGGTTTAATCATCTC
AACGGTAGCATCCCATCCAGTGTTCTGGACTGCCCAAGTCTGGAGCGAGTCATTGTCGAA
AACAATAACCTTGTTGGGTCTATTCCGCAATTTATAAACTGTGCAAATCTAAGTTATATG
GATCTGAGCCACAATTCCTTGAGTGGTAACATACCATCAAGTTTCAGCAGGTGTGTAAAA
ATTGCTGAGATAAACTGGTCAGAGAACAATATTTTTGGGGCAATACCACCAGAAATTGGA
AAGTTGGTGAATCTGAAAAGGCTTGACCTCTCACACAATCTATTGCATGGTTCGATCCCT
GTGCAAATTTCTAGTTGCTCCAAGTTGTATTCACTTGATTTGGGTTTTAACTCTTTGAAT
GGTTCGGCCCTCAGCACAGTAAGCAGCCTGAAGTTTCTGACACAGCTACGATTGCAAGAG
AATAGATTCAGCGGAGGTTTGCCTGATCCTTTCTCACAATTGGAAATGCTTATTGAGCTG
CAACTTGGTGGAAATATTCTTGGGGGCAGTATCCCTTCATCATTAGGACAGCTGGTGAAA

FIGURE 11B(16)

CTGGGTACAACCTTGAACCTTAGTAGCAATGGTCTAGTGGGTGACATTCCATCACAATTC
GGTAATTTGGTGGAGTTGCAAAACTTAGATTTGTCATTTAATAATCTCACAGGAGGCCTT
GCTACATTGCGAAGTCTACGCTTTTTGCAGGCCTTGAATGTTTCTTACAACCAATTTAGT
GGACCAGTTCCAGATAATCTTGTGAAGTTTCTGAGTTCCACAACAAATTCTTTTGATGGA
AACCCAGGCCTCTGTATCTCTTGCAGCACCAGTGATTCTTCTTGCATGGGAGCTAATGTT
CTGAAACCTTGTGGCGGGTCAAAGAAAAGAGCAGTGCATGGCCGATTCAAAATTGTTCTC
ATAGTTCTTGGCTCATTATTTGTGGGAGCAGTTCTGGTACTCATACTCTGGTGCATCCTT
CTGAAATCTCGAGATCAGAAGAAGAATAGTGAGGAAGCAGTCAGTCATATGTTTGAAGGT
TCCTCATCTAAATTAAATGAGGTTATAGAGGCAACTGAATGTTTTGATGACAAGTATATC
ATTGGTAAAGGTGGTCACGGAACCGTTTACAAGGCAACACTGAGGTCAGGGGATGTTTAT
GCTATAAAGAAACTTGTGATTTCTGCACACAAAGGTTCATACAAAAGCATGGTTGGAGAA
CTGAAGACACTAGGTAAAATCAAGCACAGGAACTTGATTAAGCTGAAAGAATCTTGGTTG
AGAAATGACAATGGATTCATACTGTATGATTTTATGGAAAAAGGTAGCCTTCATGATGTT
CTACATGTAGTTCAGCCAGCACCAGCCTTAGACTGGTGTGTGCGGTATGACATAGCCCTC
GGCACTGCCCATGGGTTAGCATATCTACATGATGACTGCCGCCCTGCGATCATTCATCGC
GACATCAAGCCAAGTAATATACTGCTGGACAAGGACATGGTGCCACATATTTCAGATTTT
GGCATTGCAAAGCTCTTGGAGCAGCCTTCTACTGCTCCTCAGACCACTGGTGTTGTTGGC
ACCATTGGATATATGGCCCCAGAGTTAGCGTTCTCCACCAAGAGCAGCATGGAGTCCGAC
GTGTACAGCTACGGCGTGGTGCTGCTGGAGCTGCTCACGAGGAGGGCGGCGGTGGATCCC
TCGTTTCCCGACGGCACGGACATAGTCAGCTGGGCGTCGTCCGCCCTGAACGGCACTGAC
AAAATCGAGGCCGTCTGCGACCCGGCCCTCATGGAGGAAGTCTTCGGCACGGTGGAGATG
GAGGAGGTGAGTAAGGTCCTGTCAGTGGCGCTGCGGTGCGCGGCCAGGGAGGCGAGCCAA
AGGCCCTCCATGACCGCGGTCGTGAAGGAGCTGACGGATGCACGGCCTGCCACTGGCGGC
GGCCGGTCGTTGTCCAAGTCGAAGCAGGGGAAACCAGGATCGCAATCCAACAGCAGCGCC
TACCGGCAGTAG

>GRMZM2G011806 (Zm) (SEQ ID NO: 167)

MKLVFWHWIFLFFVLLSTSQGMSSDGLALLALSKTLILPSFIRTNWSASDATPCTWNGVG
CNGRNRVISLDLSSSEVSGFIGPEIGRLKYLQVLILSANNISGLIPLELGNCSMLEQLDL
SQNLLSGNIPASMGSLKKLSSLSLYYNSFHGTIPEELFKNQFLEQVYLHGNQLSGWIPFS
VGEMTSLKSLWLHENMLSGVLPSSIGNCTKLEELYLLHNQLSGSIPETLSKIEGLKVFDA
TANSFTGEISFSFENCKLEIFILSFNNIKGEIPSWLGNCRSLQQLGFVNNSLSGKIPNFI
GLFSNLTYLLLSQNSLTGLIPPEIGNCRLLQWLELDANQLEGTVPEEFANLRYLSKLFLF
ENHLMGDFPESIWSIQTLESVLLYSNKFTGRLPSVLAELKSLKNITLFDNFFTGVIPQEL
GVNSPLVQIDFTNNSFVGGIPPNICSGKALRILDLGFNHLNGSIPSSVLDCPSLERVIVE
NNNLVGSIPQFINCANLSYMDLSHNSLSGNIPSSFSRCVKIAEINWSENNIFGAIPPEIG
KLVNLKRLDLSHNLLHGSIPVQISSCSKLYSLDLGFNSLNGSALSTVSSLKFLTQLRLQE
NRFSGGLPDPFSQLEMLIELQLGGNILGGSIPSSLGQLVKLGTTLNLSSNGLVGDIPSQF
GNLVELQNLDLSFNNLTGGLATLRSLRFLQALNVSYNQFSGPVPDNLVKFLSSTTNSFDG
NPGLCISCSTSDSSCMGANVLKPCGGSKKRAVHGRFKIVLIVLGSLFVGAVLVLILWCIL
LKSRDQKKNSEEAVSHMFEGSSSKLNEVIEATECFDDKYIIGKGGHGTVYKATLRSGDVY
AIKKLVISAHKGSYKSMVGELKTLGKIKHRNLIKLKESWLRNDNGFILYDFMEKGSLHDV
LHVVQPAPALDWCVRYDIALGTAHGLAYLHDDCRPAIIHRDIKPSNILLDKDMVPHISDF
GIAKLLEQPSTAPQTTGVVGTIGYMAPELAFSTKSSMESDVYSYGVVLLELLTRRAAVDP
SFPDGTDIVSWASSALNGTDKIEAVCDPALMEEVFGTVEMEEVSKVLSVALRCAAREASQ
RPSMTAVVKELTDARPATGGGRSLSKSKQGKPGSQSNSSAYRQ

>GRMZM2G128602 (Zm) (SEQ ID NO: 168)

ATGAAGCTGGTTTTATGGCATCAGTTTTTTCTCTTCTTCGTGTTAGTTTCAACATCACAG
GGTATGAGTTCAGATGGCCTAGCTCTTCTTGCTCTGTCCAAAAGCCTCATACTACCAAGT
CCCATAAGAACCAACTGGAGTGATTCTGATGCAACTCCCTGTACATGGAGCGGTGTTGGT
TGCAATGGAAGGAACAGAGTCATCTCTCTCGACCTATCATCGTCAGGTGTTTCGGGTTCT
ATAGGACCTGCAATAGGGCGTCTGAAATACCTGCGGATTCTCATCTTATCAGCTAACAAC
ATATCTGGTTTGATCCCTCTAGAATTGGGAGACTGCAATATGCTTGAAGAACTGGATTTG
TCCCAAAACCTGTTTTCTGGCAATATACCAGCATCATTGGGCAACCTCAAGAAATTGTCA
TCACTGTCACTGTACCGCAACTCCTTCAATGGAACAATACCAGAGGAGTTGTTCAAGAAC
CAGTTTCTGGAGCAAGTGTACCTACATGACAATCAGCTCAGTGGTTCGGTGCCCTTATCG
GTTGGTGAAATGACAAGCCTTAAGTCACTGTGGTTACAGGAAAATATGTTGTCTGGAGTT
TTGCCCAGTTCAATTGGAAACTGCACCAAGTTGGAGGATCTGTATCTACTCGATAATCAA

FIGURE 11B(17)

CTGAGTGGCAGTATTCCTGAAACCTTGGGTATGATCAAAGGTCTCAAGGTTTTTGATGCT
ACTACCAATAGTTTCACAGGTGAGATCTCTTTCAGTTTTGAGGACTGCAAGCTAGAAATA
TTCATCTTGTCTTTCAATAATATAAAAGGTGAAATTCCATCATGGCTGGGGAACTGCATG
AGCTTGCAACAACTTGGATTTGTCAATAATAGTTTGTATGGCAAAATTCCAAATTCTCTT
GGCTTATTGAGCAACCTCACATATCTTTTACTTTCACAGAACTCCCTTTCTGGGCCGATC
CCACCTGAGATTGGTAACTGTCAGTCGCTGCAGTGGCTAGAGTTAGATGCAAACCAGCTG
GATGGCACTGTTCCTGAAGAATTTGCAAATTTACGGAGTTTGTCAAAGCTCTTTCTTTTT
GAGAATCGCCTCATGGGAGACTTCCCTGAGAATATTTGGAGTATCCAAACCCTCGAGAGT
GTCCTACTTTATAGCAACAGATTCACAGGGAAGCTACCTTCAGTGTTAGCTGAGCTGAAG
TTCCTAAAGAACATCACACTGTTTGATAATTTCTTCACTGGAGTCATACCACAGGAGCTA
GGTGTTAATAGCCCCTTGGTCCAGATAGATTTCACAAACAACAGTTTTGTTGGTAGTATC
CCACCAAACATCTGTTCAAGAAAAGCATTGAGAATTTTGGACTTAGGGTTTAATCATCTC
AACGGTAGCATCCCATCCAGTGTTGTGGACTGCCCAAGTTTGAAGCGAGTCATTTTACAA
AACAATAACCTTAACGGGTCTATTCCACAATTTGTAAACTGTGCAAATCTAAGTTATATG
GACCTAAGCCACAATTCCTTGAGTGGTAACATTCCAGCAAGCTTCAGCAGATGTGTAAAC
ATTACTGAGATAAACTGGTCAGAGAACAAGCTTTTTGGAGCAATACCACCTGAAATTGGA
AACTTAGTGAATCTGAAAAGACTTGACCTCTCACACAACATATTGCATGGTTCGATCCCT
GTGCAAATTTCCAGTTGCTCCAAGTTGTACTCACTTGATTTGAGTTTTAACTCATTGAAT
GGTTCGGCCCTCCGCACCGTAAGCAACTTGAAGTTTCTGACACAGCTACGATTGCAAGAG
AATAGATTCAGCGGAGGCTTGCCTGATTCTCTCTCACAATTGGAAATGCTTATTGAGCTG
CAACTTGGTGGAAATATTCTTGGGGGTAGTATCCCTTCGTCATTAGGACAGCTGGTGAAA
CTGGGCACAGCCTTGAACCTTAGTAGCAATGGCCTAATGGGTGACATTCCAACACAATTG
GGTAATTTGGTGGAGTTGCAAAACTTAGATTTTTCATTTAATAATCTCACAGGAGGCCTT
GCTACATTGAGAAGTCTAGGCTTTTTGCAGGCCTTGAATGTTTCTTACAACCAATTTAGT
GGACCAGTCCCAGATAATCTTCTGAAGTTTCTGAGTTCCACACCATATTCTTTTGATGGA
AACCCAGGCCTCTGTATCTCCTGCAGCACCAGTGGCTCTTCTTGCATGGGAGCTAATGTT
TTGAAACCTTGTGGTGGGTCGAAGAAAAGAGGAGTACATGGCCAATTGAAAATTGTTCTC
ATAGTTCTCGGTTCATTATTTGTGGGAGGAGTTCTTGTACTTGTACTGTGTTGCATCCTT
CTGAAATCTCGAGATTGGAAGAAAAATAAAGTCAGTAACATGTTTGAAGGTTCCTCATCT
AAATTAAATGAGGTTACAGAGGCCACTGAAAATTTCGATGACAAGTATATCATCGGTACA
GGTGCTCACGGAACTGTTTACAAGGCAACACTGAGGTCAGGGGATGTTTATGCTATAAAG
AAGCTTGCGATTTCTGCACACAAAGGTTCATACAAAAGCATGGTTAGAGAACTGAAGACA
CTGGGTGAAATTAAGCACAGAAACTTGATAAAGCTGAAAGAATTTTGGTTGAGAAGTGAT
AATGGATTCATACTGTATGATTTTATGGAAAAGGGCAGCCTCCATGATATTCTGCATGTA
ATTCAGCCAGCACCAGCTTTGGACTGGTGTGTGAGGTATGACATAGCTCTTGGCACCGCC
CATGGGTTAGCATATCTTCATGATGACTGCCGCCCTGCGATCATTCACCGTGATATTAAA
CCAAGAAATATACTGCTCGACAAGGACATGGTGCCACATATTTCAGATTTTGGCATTGCA
AAGCACATGGACCAGTCTTCTACTACTGCTCCACAGACCACTGGAATCGTTGGCACTATT
GGATATATGGCCCCAGAATACACACCGATGACCGACGCATACTTACATTGCATGCGCTGT
CTTGCAGAATTGGCGTTTTCCACCAAGAGCAGCATGGAGTCTGACGTGTACAGCTACGGT
GTGGTGCTACTGGAGCTGTTGACCAGGAGGACGGCGGTGGATCCTTTGTTCCCCGACAGC
GCGGACATAGTCGGCTGGGTGTCGTCCGTGCTGGACGGCACCGACAAAATCGAGGCCGTC
TGTGACCCGGCCCTCATGGAGGAAGTCTTCGGCACGGTGGAGATGGAGGAGGTGCGTAAG
GTCCTGTCGGTGGCGCTCCGGTGCGCGGCCAGGGAGGTGAGCCAAAGGCCCTCCATGACT
GCCGTCGTGAAGGAGCTGACGGATGCGCGGCCAGCCTCTGCCAGCAGCGGCAGCCGGTCG
TTGTCCAAGTCGAGGGAAGGGAAACCGGGATTGCAATCCAGCAGCAGCGCGTACTGGCAG
TAG

>GRMZM2G128602 (Zm) (SEQ ID NO: 169)

MKLVLWHQFFLFFVLVSTSQGMSSDGLALLALSKSLILPSPIRTNWSDSDATPCTWSGVG
CNGRNRVISLDLSSSGVSGSIGPAIGRLKYLRILILSANNISGLIPLELGDCNMLEELDL
SQNLFSGNIPASLGNLKKLSSLSLYRNSFNGTIPEELFKNQFLEQVYLHDNQLSGSVPLS
VGEMTSLKSLWLQENMLSGVLPSSIGNCTKLEDLYLLDNQLSGSIPETLGMIKGLKVFDA
TTNSFTGEISFSFEDCKLEIFILSFNNIKGEIPSWLGNCMSLQQLGFVNNSLYGKIPNSL
GLLSNLTYLLLSQNSLSGPIPPEIGNCQSLQWLELDANQLDGTVPEEFANLRSLSKLFLF
ENRLMGDFPENIWSIQTLESVLLYSNRFTGKLPSVLAELKFLKNITLFDNFFTGVIPQEL
GVNSPLVQIDFTNNSFVGSIPPNICSRKALRILDLGFNHLNGSIPSSVVDCPSLKRVILQ
NNNLNGSIPQFVNCANLSYMDLSHNSLSGNIPASFSRCVNITEINWSENKLFGAIPPEIG
NLVNLKRLDLSHNILHGSIPVQISSCSKLYSLDLSFNSLNGSALRTVSNLKFLTQLRLQE
NRFSGGLPDSLSQLEMLIELQLGGNILGGSIPSSLGQLVKLGTALNLSSNGLMGDIPTQL

FIGURE 11B(18)

GNLVELQNLDFSFNNLTGGLATLRSLGFLQALNVSYNQFSGPVPDNLLKFLSSTPYSFDG
NPGLCISCSTSGSSCMGANVLKPCGGSKKRGVHGQLKIVLIVLGSLFVGGVLVLVLCCIL
LKSRDWKKNKVSNMFEGSSSKLNEVTEATENFDDKYIIGTGAHGTVYKATLRSGDVYAIK
KLAISAHKGSYKSMVRELKTLGEIKHRNLIKLKEFWLRSDNGFILYDFMEKGSLHDILHV
IQPAPALDWCVRYDIALGTAHGLAYLHDDCRPAIIHRDIKPRNILLDKDMVPHISDFGIA
KHMDQSSTTAPQTTGIVGTIGYMAPELAFSTKSSMESDVYSYGVVLLELLTRRTAVDPLF
PDSADIVGWVSSVLDGTDKIEAVCDPALMEEVFGTVEMEEVRKVLSVALRCAAREVSQRP
SMTAVVKELTDARPASASSGSRSLSKSREGKPGLQSSSSAYWQ

>Sb07g021950 (Sb) (SEQ ID NO: 170)

ATGAAGCTGGTTTGGCATTGGGTTTTTCTATTCTTCCTGTTAGTCTCAACATCACAGGGT
ATGAGTTCAGATGGCCTAGCTCTTCTTGCTCTGTCCAAAAGCCTCATACTACCAAGTTCC
ATAAGATCCAACTGGAGCACTTCTGCAAATCCTTGTACATGGAGCGGTGTTGATTGCAAT
GGAAGGAACAGAGTCATTTCTCTCGACCTATCATCATCAGAGGTTTCAGGATCTATAGGA
CCAGATATAGGGCGTCTGAAATACCTGCAAGTTCTCATTTTGTCTACTAACAACATATCT
GGTTCGATTCCTCTAGAATTAGGCAACTGCAGTATGCTTGAACAATTGGATTTGTCCCAA
AACTTGCTTTCTGGCAATATACCAGCATCAATGGGCAACCTCAAGAAATTGTCATCACTG
TCACTGTACTCTAACTCTTTGAATGGATCAATACCAGAGGAGTTGTTCAAGAACCAGTTT
CTGGAGGAAGTGTACCTACATGACAATCAGCTCAGTGGTTCGATACCCTTCGCGGTTGGT
GAAATGACAAGCCTTAAGTCATTGTGGTTGCATGTAAATATGTTGTCTGGAGTTTTGCCC
AGTTCAATTGGCAACTGCACCAAGTTGGAGGAGCTGTATCTACTCTATAATCAACTGAGT
GGCAGTCTTCCAGAAACCTTGAGTGAGATCAAAGGCCTCAGGGTTTTTGATGCCACTAGC
AACAGCTTCACAGGCGAGATCAATTTCAGTTTCGAGAACTGCAAGCTGGAAATATTCATC
TTGTCATTCAATTATATAAAGGGAGAAATTCCATCATGGCTGGTGAATTGCAGGAGCATG
CAACAGCTTGGATTTGTCAATAATAGTCTGTCTGGCAAGATTCCAAATTCTCTAGGGTTA
TTGAGCAACCTCACACATCTTTTACTTTCTCAGAATTCCCTGTCTGGGCCAATCCCTCCT
GAGATTAGTAACTGTCGGTTGCTGCAGTGGCTAGAGTTGGATGCAAACCAGCTGGAGGGC
ACTGTTCCTGAAGGGTTGGCAAATTTACGGAACCTCTCAAGGCTCTTTCTGTTTGAGAAT
CATCTCATGGGAGAGTTTCCTGAGAGTATTTGGAGTATCCAAACCCTCGAGAGTGTGCTT
CTTTATAGAAACAGATTCACTGGGAAGCTACCTTCAGTGTTAGCTGAGCTGAAGTACCTG
GAGAACATTACACTGTTTGATAATTTCTTCACTGGAGTCATACCACAGGAGCTGGGTGTT
AATAGCCCCTTGGTGCAGATAGATTTCACAAATAACAGTTTTGTTGGTGGTATCCCACCA
AAAATTTGTTCAGGAAAAGCATTGAGAATTCTGGACTTGGGGTTTAATCATCTCAACGGT
AGCATCCCATCCAATGTTGTGGACTGCCCAAGTCTGGAGAGAGTCATTGTCGAAAACAAT
AACCTTGATGGGTCTATTCCGCAATTTAAAAACTGTGCAAATCTAAGTTATATGGATCTG
AGCCACAATTCCTTAAGTGGTAACATTCCTGCAAGCTTCAGCAGATGTGTAAACATTACT
GAGATAAACTGGTCAGAGAACAAGCTATCTGGGGCAATACCACCTGAAATTGGAAACTTA
GTGAATCTGAAAAGACTTGACCTCTCACACAACGTATTACATGGTTCAGTTCCTGTGCAG
ATTTCCAGTTGCTCCAAGTTGTATTCACTTGATTTGAGTTTTAACTCTTTGAATGGTTCG
GCCCTTAGCACAGTAAGCAACTTGAAGTATCTGACACAACTACGATTGCAAGAGAATAGA
TTCAGCGGAGGCTTTCCTAAGTCTCTCTCCCAATTGGAAATGCTTATTGAGCTGCAACTT
GGTGGAAATATTATTGGGGGTAGTATCCCTTCATCATTAGGACAGCTGGTGAAACTGGGC
ACAGCCTTGAACCTTAGTAGCAATGGTCTAATTGGTGATATTCCACCACAATTGGGCAAT
TTAGTGGACTTGCAAAACTTAGATTTGTCATTTAATAATCTCACAGGAGGCCTTGCTACA
TTGAGAAGTCTAGGTTTTTTGCATGCCTTGAATGTTTCTTACAACCAATTTAGTGGACCT
GTCCCAGATAATCTTCTGAAGTTTCTGAGTTCGACACCAAATTCTTTTAATGGAAACCCA
GGCCTCTGTGTCTCTTGCAGCACCAGTGATTCTTCTTGCATGGGAGCTAATGTTTTGAAA
CCTTGTGGTGGGTCGAAGAATAGGGGTGTGCATGGCCGATTCAAAATTGTCCTCATAGTT
CTTGGTTCATTATTTGTGGGAGCAGTTTTGGTACTTGTACTGTGTTGCATCTTTCTGAAA
TCTCGAGATCGGAAGAAAAATACTGAGGAAGCAGTCAGTAGTATGTTTGAAGGTTCCTCA
TCTAAATTAAATGAGATTATAGAGGCTACTGAAAATTTTGATGACAAGTATATCATCGGT
ACAGGTGGTCACGGAACTGTTTACAAGGCAACACTGAGGTCAGGAGATGTTTATGCTATA
AAGAAACTTGTGATTTCTGCACACAAAGGTTCATACAAAAGCATGGTTAGGGAACTGAAG
ACACTAGGAAAAATTAAGCACAGAAACTTGATAAAGTTGAAAGAATTTTGGTTCAGACGT
GATAATGGATTCATACTGTATGATTTTATGGAAAAAGGTAGCCTTCATGATGTGCTGCAT
GTAATTCAGCCAGCACCAACTTTGGACTGGTGTGTGAGGTATGACATAGCCCTCGGCACC
GCCCATGGGTTAGCATATCTTCACGATGACTGCCGCCCTGCGATCATTCACCGTGATATC
AAGCCAAGTAATATACTGCTGGACAAGGACATGGTGCCACATATTTCAGACTTTGGCATT
GCAAAGCTCATGGACCAGCCTTCTACTGCTTCACAGACCACTGGAATCGTTGGAACCATT
GGATATATGGCCCCAGAATTGGCGTTTTCCACCAAGAGCAGCATGGAGTCCGACGTATAC

FIGURE 11B(19)

AGCTACGGCGTGGTGCTACTGGAGCTGCTCACCAGGAGGACGGCGGTGGATCCTTCGTTC
CCCGACAGCACGGACATAGTTGGCTGGGTGTCGTCCGCGCTAAACGGCACCGACAAAATC
GAGGCCGTCTGCGACCCAGCCCTCATGGAGGAAGTCTTCGGCACGGTGGAGATGGAGGAG
GTGCGCAAGGTGCTGTCGGTGGCGCTGCGGTGCGCGGCCAGGGAGGCGAGCCAAAGGCCG
TCCATGGCCGACGTCGTGAAGGAGCTGACGGGCGTACGGCTTGCCACTGGCAGTGGCGGC
GGCCGGTCGTTGTCCAAGTCGAAGCAGGGGAAACCGGGATCGCAATCCCACAGCAGCGCG
TACTAG

>Sb07g021950 (Sb) (SEQ ID NO: 171)

MKLVWHWVFLFFLLVSTSQGMSSDGLALLALSKSLILPSSIRSNWSTSANPCTWSGVDCN
GRNRVISLDLSSSEVSGSIGPDIGRLKYLQVLILSTNNISGSIPLELGNCSMLEQLDLSQ
NLLSGNIPASMGNLKKLSSLSLYSNSLNGSIPEELFKNQFLEEVYLHDNQLSGSIPFAVG
EMTSLKSLWLHVNMLSGVLPSSIGNCTKLEELYLLYNQLSGSLPETLSEIKGLRVFDATS
NSFTGEINFSFENCKLEIFILSFNYIKGEIPSWLVNCRSMQQLGFVNNSLSGKIPNSLGL
LSNLTHLLLSQNSLSGPIPPEISNCRLLQWLELDANQLEGTVPEGLANLRNLSRLFLFEN
HLMGEFPESIWSIQTLESVLLYRNRFTGKLPSVLAELKYLENITLFDNFFTGVIPQELGV
NSPLVQIDFTNNSFVGGIPPKICSGKALRILDLGFNHLNGSIPSNVVDCPSLERVIVENN
NLDGSIPQFKNCANLSYMDLSHNSLSGNIPASFSRCVNITEINWSENKLSGAIPPEIGNL
VNLKRLDLSHNVLHGSVPVQISSCSKLYSLDLSFNSLNGSALSTVSNLKYLTQLRLQENR
FSGGFPKSLSQLEMLIELQLGGNIIGGSIPSSLGQLVKLGTALNLSSNGLIGDIPPQLGN
LVDLQNLDLSFNNLTGGLATLRSLGFLHALNVSYNQFSGPVPDNLLKFLSSTPNSFNGNP
GLCVSCSTSDSSCMGANVLKPCGGSKNRGVHGRFKIVLIVLGSLFVGAVLVLVLCCIFLK
SRDRKKNTEEAVSSMFEGSSSKLNEIIEATENFDDKYIIGTGGHGTVYKATLRSGDVYAI
KKLVISAHKGSYKSMVRELKTLGKIKHRNLIKLKEFWFRRDNGFILYDFMEKGSLHDVLH
VIQPAPTLDWCVRYDIALGTAHGLAYLHDDCRPAIIHRDIKPSNILLDKDMVPHISDFGI
AKLMDQPSTASQTTGIVGTIGYMAPELAFSTKSSMESDVYSYGVVLLELLTRRTAVDPSF
PDSTDIVGWVSSALNGTDKIEAVCDPALMEEVFGTVEMEEVRKVLSVALRCAAREASQRP
SMADVVKELTGVRLATGSGGGRSLSKSKQGKPGSQSHSSAY

Figure 12

LN(K/E)XXXXTXXXXXX(Y/H)X(I/V)GXGXXGX(V/I)Y(K/R)AX(L/I/V)XXXXXXAXK
(K/R)XXXXXXXXXXXXMXXE(I/L)XT(I/L)GX(I/V)(R/K)HRNL(I/L/V)(K/R)LXXX
XX(R/K/Q)XXXGX(M/I)XY(Y/F)MXXGS(L/V)XXXLHXXXXXXXLXWXXRXX(I/V)A(L/
V/I)GX(A/S)HGLXY(L/I)HXDCXPXI(I/V)HRD(I/V)KXXNIL(L/M)(D/N)X(D/E)(
(M/L)XPHIXDFG(I/L)(A/S)(K/R)X(L/M)(D/E)XXXXXXXXXX(V/I)XGTXGY(M/I)
APEX(A/S)XXTXXXXEXGVYS(Y/F)GV(V/I)LLXL(I/L/V)(T/S)X(K/R)XXXDXXFXX
XXX(I/V)VXWXX(S/A)XXXXXXXXXX(I/V)XDXX(L/M)XXEXXXXXXXXXXXXXXX(L/V/
M)ALXCXXXXXXXXRPXMXXXXXXLXXXXXXXX

PLANT DEFENSE SIGNAL PEPTIDES

CROSS-REFERENCE TO RELATED APPLICATIONS

This application is a continuation of co-pending U.S. patent application Ser. No. 12/386,247, filed Apr. 14, 2009, which is a Continuation-in-Part of U.S. patent application Ser. No. 11/795,733, filed Jun. 4, 2008, which is a national stage entry of PCT/US2006/002661, filed Jan. 24, 2006, which claims priority to U. S. Provisional Patent Application No. 60/647,708, filed Jan. 26, 2005. This application also claims the benefit of U. S. Provisional Patent Application No. 61/124,199, filed Apr. 14, 2008, all of which are hereby incorporated by reference in their entirety.

FIELD

The present invention relates to materials and methods for enhancing plant disease resistance.

BACKGROUND

Plants are exposed to numerous denizens of their environment, including bacteria, viruses, fungi, and nematodes. Although many of the interactions between these organisms and plants, particularly via the roots of the plants, are beneficial, many of the interactions are harmful to the plants. The decimation of agricultural crops, ornamental plants, and other plants by diseases caused by plant pathogens is a worldwide problem that has enormous economic impact.

Damage to plants is caused by pathogens of multiple genera. These genera include *Alternaria, Ascochyta, Aspergillus, Botrytis, Cercospora, Colletotrichum, Diplodia, Erwinia, Erysiphe, Fusarium, Gaeumanomyces, Helminthosporium, Macrophomina, Magnaporthe, Mycosphaerella, Nectria, Peronospora, Phoma, Phymatotrichum, Phytophthora, Plasmopara, Podosphaera, Pseudomonas, Puccinia, Puthium, Pyrenophora, Pyricularia, Pythium, Rhizoctonia, Scerotium, Sclerotinia, Septoria, Thielaviopsis, Uncinula, Venturia, Verticillium*, and *Xanthomonas*.
*Macrophomina, Magnaporthe, Mycosphaerella, Nectria, Peronospora, Phoma, Phymatotrichum, Phytophthora, Plasmopara, Podosphaera, Pseudomonas, Puccinia, Puthium, Pyrenophora, Pyricularia, Pythium, Rhizoctonia, Scerotium, Sclerotinia, Septoria, Thielaviopsis, Uncinula, Venturia, Verticillium*, and *Xanthomonas*.

Many chemical compounds have been developed to combat these various pathogens. The activity of these compounds is typically limited to several species. As a consequence of the large number and diversity of plant pathogens, these compounds have not provided an effective solution to limiting infections in plants.

An alternative approach to controlling pathogenic infections in plants involves exploiting the natural defense mechanisms of plants to confer resistance. Many plants have developed natural resistance to some pathogens. However, resistance may be limited to certain genera of pathogens, or crops of agronomic interest may not exhibit sufficient resistance. Thus, natural plant defenses often do not provide sufficient protection against pathogens. By broadening the spectrum of pathogen defense or strengthening the defense response, it may be possible to enhance existing resistance mechanisms and promote pathogen defense in otherwise susceptible plants.

When present and active, the natural defense mechanisms of plants can be highly effective in preventing pathogen colonization and disease. Resistance is multi-tiered, with passive and active, constitutive and inducible elements.

Following the invasion of a plant by a potential pathogen, the pathogen either successfully proliferates in the host, causing associated disease symptoms, or its growth is halted by the defenses of the host plant. One such defense is the hypersensitive response (HR), rapid apoptotic cell death near the site of the infection that correlates with the generation of activated oxygen species, production of antimicrobial compounds, and reinforcement of host cell walls (Dixon and Lamb, Annu. Rev. Plant Physiol. Plant Mol. Biol. 41:339-367, 1990). Other defenses include systemic acquired resistance, which effectively protects the plant against subsequent attack by a broad range of pathogens (Ryals et al., Proc. Natl. Acad. Sci. USA 92:4202-4205, 1995).

Pathogens that elicit an HR on a given host are "avirulent" on that host, the host is "resistant," and the plant-pathogen interaction is "incompatible." If a pathogen proliferates and causes disease to the host, the pathogen is "virulent," the host is "susceptible," and the plant-pathogen interaction is "compatible."

In many cases in which strains ("races") of a particular fungal or bacterial pathogen differ regarding virulence on various cultivars (or wild accessions) of a particular host species, avirulent strains of the pathogen, but not virulent strains, possess one or more avirulence (avr) genes corresponding to "resistance" genes in the host. Resistance gene products are activated in response to pathogen signal molecules termed elicitors, production of which is controlled by pathogen avirulence genes. This observation is the basis for the "gene-for-gene" model of plant disease resistance (Crute et al., pp. 197-309 in Mechanisms of Resistance to Plant Disease, Fraser, ed., 1985; Ellingboe, Annu. Rev. Phytopathol. 19:125-143, 1981; Flor, Annu. Rev. Phytopathol. 9:275-296, 1971; and Keen et al., in Application of Biotechnology to Plant Pathogen Control, Chet, ed., John Wiley & Sons, 1993, pp. 65-88).

Normally avirulence and resistance genes are organized in functional pairs. A given resistance gene is generally effective only against pathogen strains that express a specific cognate avirulence gene (Flor, Annu. Rev. Phytopathol. 9:275-296, 1971; Keen, Annu. Rev. Genet. 24:447-463, 1990). However, exceptions to this rule exist. For example the *Arabidopsis* RPM1 gene product (Grant et al., Science 269:843-846, 1995) is involved in the recognition of elicitors produced by *P. syringae* expressing the avirulence genes avrRpm1 or avrB (Bisgrove et al., Plant Cell 6:927-933, 1994), suggesting that resistance gene products may function as common points in transduction of distinct pathogen signals.

A number of avirulence genes have been cloned. Many cloned avirulence genes have been shown to correspond to individual resistance genes in the cognate host plants and confer an avirulent phenotype when transferred to an otherwise virulent strain. A number of plant disease resistance genes have also been cloned. Similar features have been discovered among many of these resistance genes, in spite of the diversity of pathogens against which they act. These features include a leucine-rich-repeat (LRR), a motif found in a multitude of eukaryotic proteins with roles in signal transduction (Kobe and Deisenhofer, Trends Biochem. Sci. 19:415-421, 1994). The LRR motif is thought to be involved in protein-protein interactions and may allow interaction with other proteins that are involved in plant disease resistance. In addition, sequences predicted to encode nucleotide binding sites and leucine zippers are shared among many resistance genes (Dangl, Cell 80:383-386, 1995; Staskawicz et al., Science 268:661-667, 1995). These motifs are present and similarly organized among resistance gene products from plants as diverse as tobacco, tomato, rice, flax, and *Arabidopsis*, suggesting a common mechanism underlying disease resistance signal transduction throughout the plant kingdom.

The local perception of pathogen attack is conveyed to distant tissues via a transmissible signal that involves salicylic acid (SA), further activating gene expression and conditioning a state known as systemic acquired resistance (SAR). It has subsequently been found that resistance can be expressed near the region of pathogen attack, as local acquired resistance, or can be induced systemically, depending on triggering signal and plant species. Thus, the systemic and local responses collectively are referred to as acquired resistance (AR). Establishment of AR is a powerful line of plant defense because it can provide broad-spectrum resistance against viral, bacterial, and fungal challenges that would otherwise cause disease. The AR response triggers the transcriptional activation of a suite of genes encoding pathogenesis-related (PR) proteins. Included among these are hydrolases, cell-wall strengthening proteins, proteins involved in oxidative burst, the combination of which are believed to promote heightened resistance. Biochemical and genetic analyses have identified genes and molecular signals associated with acquired resistance. The Npr1/Nim1 gene plays a key regulatory role in the AR defense in *Arabidopsis* against a broad spectrum of fungal and bacterial pathogens (WO 98/06748; WO 94/16077; WO 98/26082). The central importance of Npr1 in dicots was further substantiated by transgenic overexpression of the cloned gene, which led to heightened disease resistance in *Arabidopsis* against both fungal and bacterial pathogens (WO 98/06748).

Although the bulk of AR research has defined the pathway in dicotyledonous plants, monocotyledonous plants, such as wheat, rice, and barley, have an inducible pathway that protects against pathogen attack. Acquired resistance can be conditioned by different external stimuli, including avirulent pathogen challenge, pathogen elicitor exposure, and chemical treatments, including application of SA or SA analogs, such as 2,6-dichloroisonicotinic acid (INA) or benzo(1,2,3) thiodiazole-7-carbothioic acid S-methyl ester (BTH). Given the inducibility of the AR pathway by the same classes of activating compounds in monocot and dicot plants, there is likely to be partial conservation of signaling pathways, as subsets of PR genes appear to be induced in both groups. In monocots, induced acquired resistance is broad-spectrum, extending to fungal and bacterial pests, irrespective of pathogen race, with activated resistance persisting for weeks to months. Thus, manipulation of the AR pathway in plants may promote resistance to pathogens for which there exists no genetic source of resistance.

Thus, there is a need to identify genes that may play key roles in disease defense. Expression of these genes in transgenic plants may enhance the level of disease resistance against certain pathogens.

Within the past decade, the mechanisms by which plants activate innate immunity have been found to share a number of similarities with the innate immune responses of animals (Nimchuk et al., Annu. Rev. Gen. 37:579-609, 2003; Jones and Takemoto, Curr. Opin. Immun. 16:48-62, 2004; Nürnberger and Scheel, Trends Plant Sci. 8:372-379, 2001; Nürnberger et al., Immun. Rev. 198:249-266, 2004; Guttman, Biotech. Adv. 22:363-382, 2004; Staskawicz et al., Science 292: 2285-2289, 2001; Nürnberger and Brunner, Curr. Opin. Plant Biol. 5:1-7, 2002). Innate immunity is initiated in animals and plants through the recognition of a variety of pathogen associated molecules that in animals are called "pathogen-associated molecular patterns," or PAMPS, and in plants are called elicitors. Peptides derived from pathogens can be powerful elicitors of plant defense responses (Hahlbrock et al., Proc. Natl. Acad. Sci. USA 92:4150-4157, 1995; van den Askerveken et al. Plant Physiol. 103:91-96, 1993; Kammpren, Curr. Opin. Plant Biol. 4:295-300, 2001; Kunze et al., Plant Cell, 16:3496-3507, 2004; Navarro et al., Plant Physiol. 135:1113-1128, 2004; Fellbrich et al., Plant J. 32:375-390, 2002); He et al., Cell 73:1255-1266, 1993).

We previously identified a number of novel defense signal peptides from dicot and monocot plant species that are useful for enhancing plant resistance against various biotic or abiotic stresses, including, but not limited to, disease resistance. See U.S. provisional patent application Ser. No. 06/647,708, filed Jan. 26, 2005, and PCT/US2006/002661, filed Jan. 24, 2006.

BRIEF SUMMARY

An embodiment provides for an isolated polynucleotide that encodes a polypeptide comprising a 10 amino acid peptide motif, where the 10 amino acid peptide motif consists of a glycine residue at position C-7 of the peptide, and the polypeptide causes a change of at least 0.2 pH units at a concentration of 25 pM/ml in a plant cell suspension. The polynucleotide may be isolated from genomic DNA, or synthesized based on genomic DNA, where the genomic DNA encodes three or more structural elements including a first EDKR repeat, a 1-5-10 helix motif, a serine repeat, a second EDKR repeat, and a K/R positive charge region, where the structural elements are positioned 5' upstream of the polynucleotide. An additional embodiment provides for a transgenic plant comprising the isolated polynucleotide.

According to another embodiment, the isolated polynucleotide may encode one more defense signal peptides including TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b. OsPep5c, OsPep6b, ZmPep4b, ZmPep4c, TaPep3b, TaPep3c, HvPep1b, HvPep1c, SoPep1b, SoPep1c, SoPep1d, SoPep1e, SoPep1f, SoPep2b, SoPep2c. SoPep2d, and SoPep2e. An additional embodiment provides for a transgenic plant comprising one or more of the defense signal peptides.

According to another aspect, an isolated polypeptide is provided that comprises a 10 amino acid peptide motif, where the 10 amino acid peptide motif consists of a glycine residue at position C-7 of the peptide, and the polypeptide causes a change of at least 0.2 pH units at a concentration of 25 pM/ml in a plant cell suspension. An additional embodiment provides for a transgenic plant comprising the isolated polypeptide.

According to another embodiment, the isolated polypeptide may encode one more defense signal peptides including TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b, ZmPep4b, ZmPep4c, TaPep3b, TaPep3c, HvPep1b, HvPep1c, SoPep1b, SoPep1c, SoPep1d, SoPep1e, SoPep1f, SoPep2b, SoPep2c, SoPep2d, and SoPep2e. An additional embodiment provides for a transgenic plant comprising one or more of the defense signal peptides.

According to a further embodiment, the polypeptide is a propeptide. In a preferred embodiment, the propeptide is between 75 and 154 amino acid residues in length and may comprise one or more defense signal peptides including TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b, ZmPep4b, ZmPep4c, TaPep3b, TaPep3c, HvPep 1b, HvPep1c, SoPep1b, SoPep1c, SoPep1d, SoPep1e, SoPep1f, SoPep2b, SoPep2c, SoPep2d, and SoPep2e. An additional embodiment provides for a transgenic plant comprising the propeptide.

According to another embodiment, the propeptide may be processed in a plant to produced one or more defense signal peptides including TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c. OsPep5b, OsPep5c, OsPep6b, ZmPep4b, ZmPep4c, TaPep3b, TaPep3c, HvPep1b, HvPep1c, SoPep1b, SoPep1c, SoPep1d, SoPep1e, SoPep1f, SoPep2b, SoPep2c, SoPep2d, and SoPep2e.

According to another aspect, an isolated polynucleotide is provided that encodes a polypeptide comprising a defense signal peptide receptor protein, where the defense signal peptide receptor protein may include AtPepR1, AtPepR2, GmPepR1a, GmPepR1b, GmPepR2, P93194 (In), 803073 (Pt), 765043 (Pt), CAO23192 (Vv), OsPepR1, OsPepR2, GRMZM2G011806 (Zm), GRMZM2G128602 (Zm), and Sb07g021950 (Sb). An additional embodiment provides for a transgenic plant comprising the isolated polynucleotide.

According to an additional embodiment, an isolated polypeptide is provided that comprises a defense signal peptide receptor protein, where the defense signal peptide receptor protein may include AtPepR1, AtPepR2, GmPepR1a, GmPepR1b, GmPepR2, P93194 (In), 803073 (Pt), 765043 (Pt), CAO23192 (Vv), OsPepR1, OsPepR2, GRMZM2G011806 (Zm), GRMZM2G128602 (Zm), and Sb07g021950 (Sb). An additional embodiment provides for a transgenic plant comprising the isolated polypeptide.

According to a further embodiment, the transgenic plant may further comprise one or more defense signal peptides including TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b, ZmPep4b, ZmPep4c, TaPep3b, TaPep3c, HvPep1b, HvPep1c, SoPep1 b, SoPep1c, SoPep1d, SoPep1e, SoPep1f, SoPep2b, SoPep2c, SoPep2d, and SoPep2e.

According to another embodiment, an isolated polynucleotide is provided that encodes a polypeptide comprising a 10 amino acid peptide motif, where the 10 amino acid peptide motif consists of a glycine residue at position C-7 of the peptide, and the polypeptide causes a change of at least 0.2 pH units at a concentration of 25 pM/ml in a plant cell suspension, where the isolated polynucleotide further comprises a promoter, where the expression of the isolated polynucleotide in a cell of a plant causes the plant to exhibit an improvement compared to a control plant lacking the polynucleotide. The improvement may be an improved yield of plant product, reduced disease symptoms, or enhanced resistance to disease infestation.

According to an additional embodiment, a composition is provided comprising one or more defense signal peptides and a biologically acceptable carrier. The one or more defense signal peptides may include TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b, ZmPep4b, ZmPep4c, TaPep3b, TaPep3c, HvPep1b, HvPep1c, SoPep1b, SoPep1c. SoPep1d, SoPep1e, SoPep1f, SoPep2b, SoPep2c, SoPep2d, and SoPep2e. In a further embodiment, a plant is provided where a surface of the plant has been treated with the composition. In yet a further embodiment, a seed is provided where the surface of the seed has been treated with the composition.

According to another aspect, compositions are provided that comprise one or more isolated defense signal peptides that are 10 or more amino acid residues in length and that have substantial defense signal peptide activity. Such defense signal peptides may be longer, e.g., 15, 20, 23 or more amino acid residues in length. For example, they are more easily synthesized. Accordingly, according to various embodiments, the defense signal peptide is between about 10 and about 50 amino acid residues in length, or between about 15 and about 50 amino acid residues in length. However, longer defense signal peptides may be made and used in the practice.

According to another embodiment, compositions are provided that comprise one or more polypeptides that are processed in a plant cell to produce defense signal peptides, for example, a defense signal peptide that comprises a sequence having at least 75 percent homology, or 80 percent homology, or 85 percent homology, or 90 percent homology, or complete homology with a polypeptide selected from the group consisting of TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b. ZmPep4b, ZmPep4c, TaPep3b, TaPep3c, HvPep1b, HvPep1c, SoPep1b, SoPep1c, SoPep1d, SoPep1e, SoPep1f, SoPep2b, SoPep2c, SoPep2d, and SoPep2e, that is, any of the plant defense peptides provided in Tables 2 and 3. Alternatively, the defense signal peptide comprises a sequence having at least 90 percent homology, or complete homology, with a dicot or monocot defense signal peptide consensus sequence, as discussed herein.

Such compositions comprising peptide or polypeptide compositions may further comprise biologically acceptable carriers and/or other substances used in formulating peptides and polypeptides. For example, such compositions may be agricultural formulations that are suitable for application to plants. Accordingly, in another embodiment, plants or seeds of plants are provided that comprise such a composition applied to a plant or seed surface, respectively. When applied to plants under suitable conditions, such compositions induce the plants' innate immunity and enhance their defense against attack by pathogens.

According to another aspect, polynucleotides that express defense signal peptides (or polypeptides, including, for example, pro-forms of defense signal peptides that are processed in plant cells to produce defense signal peptides) in plants are provided. Transgenic expression of such defense signal peptides induces the plants' innate immunity. Accordingly, one embodiment is an isolated polynucleotide comprising a sequence that encodes a defense signal peptide (as described above) operably linked to a plant promoter. Expression of the polynucleotide in a cell of a plant causes the plant to exhibit an improvement compared to a control plant lacking the polynucleotide that is selected from the group consisting of improved yield of plant product, reduced disease symptoms, and enhanced resistance to disease infestation. The encoded defense signal peptide is 10 or more, or 15 or more, or 20 or more, 23 or more amino acid residues in length. Alternatively, such a polynucleotide comprises a sequence that encodes a polypeptide that is processed in a plant cell to produce the defense signal peptide.

According to one embodiment, such polynucleotides encoding defense signal peptides have at least 80 percent, or at least 90 percent, or at least 95 percent, or complete sequence similarity to a polynucleotide sequence that encodes a plant defense signal peptide selected from the group consisting of TcPep1, GhPep2, SePep1, PtPep2, VvPep2, VvPep3, HaPep1, HaPep2, OsPep3b, OsPep8, SoPep1a, SoPep2a, PvPep1, OsPep3c, OsPep4b, OsPep4c, OsPep5b, OsPep5c, OsPep6b, ZmPep4b, ZmPep4c, TaPep3b, TaPep3c, HvPep1b, HvPep1c, SoPep1b, SoPep1c, SoPep1d, SoPep1e, SoPep1f, SoPep2b, SoPep2c, SoPep2d, and SoPep2e, that is, any of the plant defense peptides provided in Tables 2 and 3.

According to another embodiment, an isolated polynucleotide is provided that comprises a sequence that encodes a defense signal peptide operably linked to a heterologous promoter. Polynucleotides for expression in plant, bacterial, fungal (including yeast), insect, and other types of cells are contemplated. In one embodiment, expression of the polynucleotide in a cell of a plant causes the plant to exhibit an improvement compared to a control plant lacking the polynucleotide that is selected from the group consisting of improved yield of plant product, reduced disease symptoms, and enhanced resistance to disease infestation. The heterologous promoter may, for example, be a constitutive promoter or a non-constitutive promoter, including, but not limited to, an organ- or tissue-specific promoter or an inducible promoter.

According to another embodiment, cells are provided that comprise one or more of the above-mentioned polynucleotides, including, but not limited to, plant, bacterial, fungal (including yeast), and insect cells. According to another embodiment, plants that comprise such cells are provided, including, but not limited to, plants such as: acacia, alfalfa, aneth, apple, apricot, artichoke, arugula, asparagus, avocado, banana, barley, beans, beet, blackberry, blueberry, broccoli, brussels sprouts, cabbage, cantaloupe, carrot, cassaya, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf grass, turnip, a vine, watermelon, wheat, yams, and zucchini. According to another embodiment, such a plant exhibits reduced symptoms from, or enhanced resistance to, a disease caused by an organism of a genus selected from the group consisting of *Alternaria, Ascochyta, Aspergillus, Botrytis, Cercospora, Colletotrichum, Diplodia, Erwinia, Erysiphe, Fusarium, Gaeumanomyces, Helm inthosporium, Macrophomina, Magnaporthe, Mycosphaerella, Nectria, Peronospora, Phoma, Phymatotrichum, Phytophthora, Plasmopara, Podosphaera, Pseudomonas, Puccinia, Pythium; Pyrenophora, Pyricularia, Pythium, Rhizoctonia, Scerotium, Sclerotinia, Septoria, Thielaviopsis, Uncinula, Venturia, Verticillium*, and *Xanthomonas*. An embodiment further encompasses parts of such plants, including, but not limited to, seeds, seed pods, flowers, fruit, tubers, stems, cuttings, and pollen. Products resulting from processing of such plants or parts thereof are also encompassed.

Formulations of such polynucleotides are also provided. Therefore, according to another aspect, a composition is provided that comprises one or more of the above-described polynucleotides and a biologically acceptable carrier.

According to another embodiment, methods are provided for making a defense signal peptide comprising expressing in a cell a polynucleotide as described above. Included are, for example, plant cells, bacterial cells, fungal cells, and insect cells. Such methods may further comprise purifying the defense signal peptide.

According to an additional embodiment, methods are provided for making a transgenic plant, comprising introducing into a cell of a plant one or more of the above-described polynucleotides, thereby producing a transformed cell, and regenerating a transgenic plant from the transformed cell, wherein, compared to a control plant lacking the polynucleotide, the transgenic plant exhibits a characteristic selected from the group consisting of substantially improved yield of plant product, substantially reduced disease symptoms, and substantially enhanced resistance to disease infestation.

According to another embodiment, methods are provided for making a plant that comprises a transgene comprising a sequence that encodes a defense signal peptide operably linked to a plant promoter, such methods comprising sexually crossing a plant that comprises the transgene with a plant that lacks the transgene, thereby producing a plurality of progeny plants, and selecting a progeny plant comprising the transgene.

According to another embodiment, methods are provided for making a plant that comprises a transgene comprising a sequence that encodes a defense signal peptide operably linked to a plant promoter, the method comprising asexually reproducing a plant that comprises the transgene, thereby producing a plurality of progeny plants, and selecting a progeny plant comprising the transgene.

According to an additional embodiment, methods are provided for growing a plant comprising planting a seed that comprises one or more of the above-mentioned polynucleotides, and growing the seed to produce a plant, wherein, compared to a control plant lacking said polynucleotide sequence, the plant grown from the seed exhibits a characteristic selected from the group consisting of substantially improved yield of plant product, substantially reduced disease symptoms, and substantially enhanced resistance to disease infestation.

According to another embodiment, methods are provided for detecting a plant cell comprising one or more of the above-mentioned polynucleotides of the disclosure in a biological sample, the method comprising contacting the biological sample with a probe that binds specifically to the polynucleotide, and detecting said binding. One such probe is a PCR primer, in which case the method comprises performing PCR on the sample and detecting said binding by detecting an amplification product diagnostic of the presence of the polynucleotide in the sample.

According to another embodiment, kits are provided for detecting a plant cell comprising a polynucleotide in a biological sample, the kit comprising one or more probes that bind specifically to the polynucleotide, or to the defense signal peptide encoded by the polynucleotide, and instructions for use.

According to another embodiment, methods are provided for detecting a plant cell comprising a polynucleotide in a biological sample, the method comprising contacting the biological sample with a probe that binds specifically to the polynucleotide, or with a probe that binds to the defense signal peptide encoded by the polypeptide (such as, for example, an antibody probe), and detecting said binding.

According to another embodiment, plant cells are provided that comprise an insertion of a foreign promoter upstream of a coding sequence for a defense signal protein, wherein the foreign promoter is operably linked to the coding sequence for the defense signal protein and the plant is characterized by a substantially enhanced resistance to a disease compared to a control plant lacking the insertion of the foreign promoter.

According to another embodiment, methods of making a transgenic plant are provided that comprise (a) introducing into cells of a plant a polynucleotide that comprises a heterologous promoter, thereby producing a cell comprising an insertion of the heterologous promoter upstream of a coding sequence for a defense signal protein, wherein expression of the defense signal protein is controlled by the foreign promoter, and (b) regenerating a transgenic plant from said cell comprising the insertion.

According to another embodiment, methods of identifying a defense signal peptide are provided, such methods comprising: (a) providing a plurality of candidate peptides having a length of at least 10 amino acids; (b) assaying said plurality of candidate peptides for defense signal peptide activity in an alkalinization assay; and (c) selecting a candidate peptide that has substantial defense signal peptide activity. The candidate peptides may be provided for such methods by, for example, chemically synthesizing the candidate peptides. Such methods may further comprise administering the candidate peptide to a plant by applying a composition comprising the candidate peptide to the plant. Alternatively, such methods may comprise administering the candidate peptide to a plant by expressing within a cell of the plant a polynucleotide that comprises a sequence that encodes the candidate peptide, thereby producing the candidate peptide within the cell of the plant.

According to another embodiment, methods are provided for identifying a substance that enhances defense of a plant against a disease comprising (a) contacting an isolated AtPep1 receptor with a plurality of candidate substances (e.g., peptides or non-peptide compounds); (b) selecting a candidate substance that has a detectable interaction with the isolated AtPep1 receptor; and (c) applying the selected candidate substance to a plant to determine whether the selected candidate substance enhances defense of the plant against a disease.

According to another embodiment, methods are provided for conferring on a plant cell a response to a plant defense signal peptide to which the plant cell would not normally respond, the method comprising expressing in the plant cell a polynucleotide comprising a sequence encoding a receptor for the plant defense signal peptide (including, for example, AtPepR1 or AtPepR2) operably linked to a promoter that is expressible in the plant cell. The plant cell response could include, for example, alkalinization of the plant cell in response to administration of the plant defense signal peptide, transcription of pathogen defense genes, enhanced resistance to a pathogen, etc.

According to another embodiment, plant cells are provided that comprise a polynucleotide comprising a sequence encoding a receptor for the plant defense signal peptide operably linked to a promoter that is expressible in the plant cell, wherein expression of the polynucleotide confers on the plant cell a response to a plant defense signal peptide to which the plant cell would otherwise be unresponsive.

The foregoing and other aspects of the preferred embodiments will become more apparent from the following detailed description, accompanying drawings, and the claims.

Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described below. In addition, the materials, methods, and examples are illustrative only and not intended to be limiting.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 provides the nucleotide and deduced amino acid sequences for the precursor protein for AtPep1, AtproPep1, and a number of paralogs and orthologs. Sequences that correspond to AtPep1 are underlined.

Figure 4:
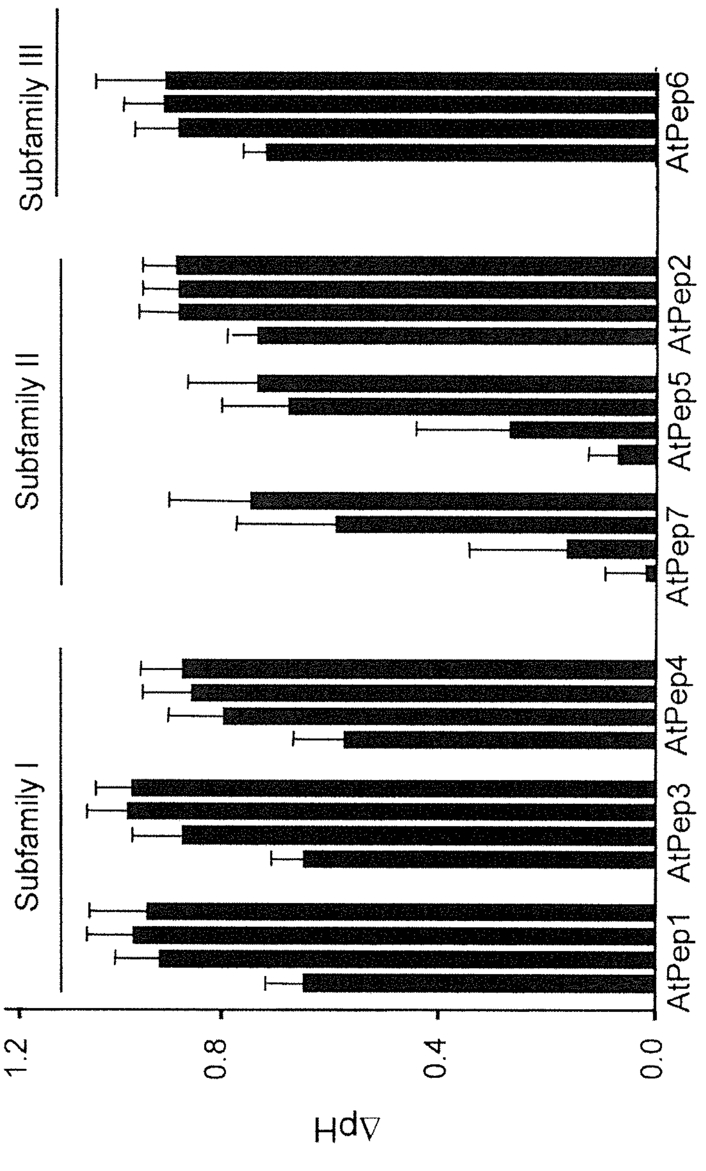

(a) AtproPep1 nucleotide (SEQ ID NO: 81) and amino acid (SEQ ID NO: 82) sequences (Locus tag At5g64900; Gene: GenBank GeneID: 836613, *Arabidopsis thaliana* Chromosome V [GenBank ID#AB019236], region 25954396-25955302; mRNA: NCBI RefSeq ID#NM_125888-499 bp; Protein: NCBI RefSeq ID#NP_569001-92 aa)

Paralogs (*Arabidopsis thaliana*):

(b) AtproPep3 nucleotide (SEQ ID NO: 83) and amino acid (SEQ ID NO: 84) sequences (Locus tag At5g64890; Gene: GenBank GeneID: 836612, *Arabidopsis thaliana* Chromosome V [GenBank ID#AB019236], region 25951798-25952735; mRNA: NCBI RefSeq ID#NM_125887-568 bp; Protein: NCBI RefSeq ID#NP_569000-109 aa)

(c) AtproPep4 nucleotide (SEQ ID NO: 85) and amino acid (SEQ ID NO: 86) sequences (Locus tag At5g64905; Gene: GenBank GeneID: 836614, *Arabidopsis thaliana* Chromosome V [GenBank ID#AB019236], region 25956800-25957285; mRNA: NCBI RefSeq ID#NM_125889-486 bp; Protein: NCBI RefSeq ID#NP_569002-96 aa)

(d) AtproPep5 nucleotide (SEQ ID NO: 87) and amino acid (SEQ ID NO: 88) sequences (Locus tag At5g09980; Gene: GenBank GeneID: 830859, *Arabidopsis thaliana* Chromosome V [GenBank ID#AB019236], region 3122757-3123909; mRNA: NCBI RefSeq ID#NM_121035-460 bp; Protein: NCBI RefSeq ID#NP_568223-81 aa)

(e) AtproPep2 nucleotide (SEQ ID NO: 89) and amino acid (SEQ ID NO: 90) sequences (Locus tag At5g09990; Gene: GenBank GeneID: 830860, *Arabidopsis thaliana* Chromosome V [GenBank ID#AB019236], region 3124569-3125073; mRNA: NCBI RefSeq ID#NM_121036-412 bp; Protein: NCBI RefSeq ID#NP_568224-86 aa)

(f) AtproPep6 nucleotide (SEQ ID NO: 91) and amino acid (SEQ ID NO: 92) sequences (Locus tag At2g22000; Gene: GenBank GeneID: 816736, *Arabidopsis thaliana* Chromosome II [GenBank ID#AC007019], region 9369406-9370082; mRNA: NCBI RefSeq ID#NM_127769-397 bp; Protein: NCBI RefSeq ID#NP_179791-104 aa)

(g) AtproPep7 nucleotide (SEQ ID NO: 93) and amino acid (SEQ ID NO: 94) sequences (Unannotated AtproPep; Gene: No GenBank GeneID, located on *Arabidopsis thaliana* Chromosome V [GenBank ID#AB019236], region 3121350-3121577; mRNA: No mRNA predicted, therefore no ID#; a 228 bp open reading frame (ORF) is encoded in genomic DNA as shown; Protein: Not predicted, therefore no ID #, Translation of ORF encoded on chromosome V yields the 75 aa sequence shown.)

Orthologs:

(h) BnproPep1 from canola (*Brassica napus*) (SEQ ID NO: 95; GenBank ID#CD816645, Protein: 95 aa)

(i) StproPep1 from potato (*Solanum tuberosum*) (SEQ ID NO: 96; GenBank ID#CV505388, Protein: 116 aa)

(j) PbproPep1 from poplar (*Populus balsamifera*) (SEQ ID NO: 97; GenBank ID#CV230975, Protein: 121 aa)

(k) BeproPep1 from birch (SEQ ID NO: 98; GenBank ID#CD276952, Protein: 110 aa)

(l) GmproPep1 from soybean (*Glycine max*) (SEQ ID NO: 99; GenBank ID#CD401281, Protein: 115 aa)

(m) MsproPep1 from alfalfa (*Medicago saliva*) (SEQ ID NO: 100; GenBank ID#B1311441, Protein: 127 aa)

(n) VvproPep1 from grape (*Vitis vinifera*) (SEQ ID NO: 101; GenBank ID#CF604664, Protein: 83 aa)

(o) OsproPep1 from rice (*Oryza saliva*) (SEQ ID NO: 102; GenBank ID#CF333408; Locus tag:Os04g54590, Protein 154 aa)

(p) OsproPep2 from rice (*Oryza sativa*) (SEQ ID NO: 103; GenBank ID#AK111113; Locus tag:Os08g07600, Protein: 93 aa)

(q) TaproPep1 from wheat (*Triticum aestivum*) (SEQ ID NO: 104; GenBank ID#AL809059, Protein: 82 aa)

(r) TaproPep2 from wheat (*Triticuin aestivum*) (SEQ ID NO: 105; GenBank ID#BF201609, Protein: 75 aa)

(s) ZmproPep1 from maize (*Zea mays*) (SEQ ID NO: 106; GenBank ID#DN214793, Protein:142 aa)

(t) HvproPep1 from barley (*Hordeum vulgare*) (SEQ ID NO: 107; GenBank ID#BQ763246, Protein: 93 aa)

FIG. 2A-D shows the sequence of an AtPep1 receptor gene (SEQ ID NO: 108; At1g73080), designated as AtPEPR1, and its deduced amino acid sequence (SEQ ID NO: 109; Also noted are several features of the receptor polypeptide: a signal sequence (residues 1-24); cysteine pairs (residues 64 and 71; and residues 836 and 854); leucine-rich repeats (residues 76-827); transmembrane domain (residues 870-892); kinase domain (residues 927-1208); and an intron (between residues 1099 and 1100).

FIG. 3A-D shows the structure of a second AtPep1 receptor gene (SEQ ID NO: 110; At1g17750) designated as AtPEPR2, and its deduced amino acid sequence (SEQ ID NO: 111). Also noted are several features of the receptor polypeptide: a signal sequence (residues 1-26); cysteine pairs (residues 62 and 71; and residues 709 and 727); leucine-rich repeats (residues 99-697); transmembrane domain (residues 738-760); kinase domain (residues 793-1079); and an intron (between residues 966 and 967).

FIG. 4 shows the concentration dependence of synthetic AtPep peptides deduced from the seven members of the AtproPep1 gene family in the alkalinization assay. Peptide concentrations (left to right for each peptide): 0.25 nM, 2.5 nM, 25 nM, 250 nM.

Figure 5:
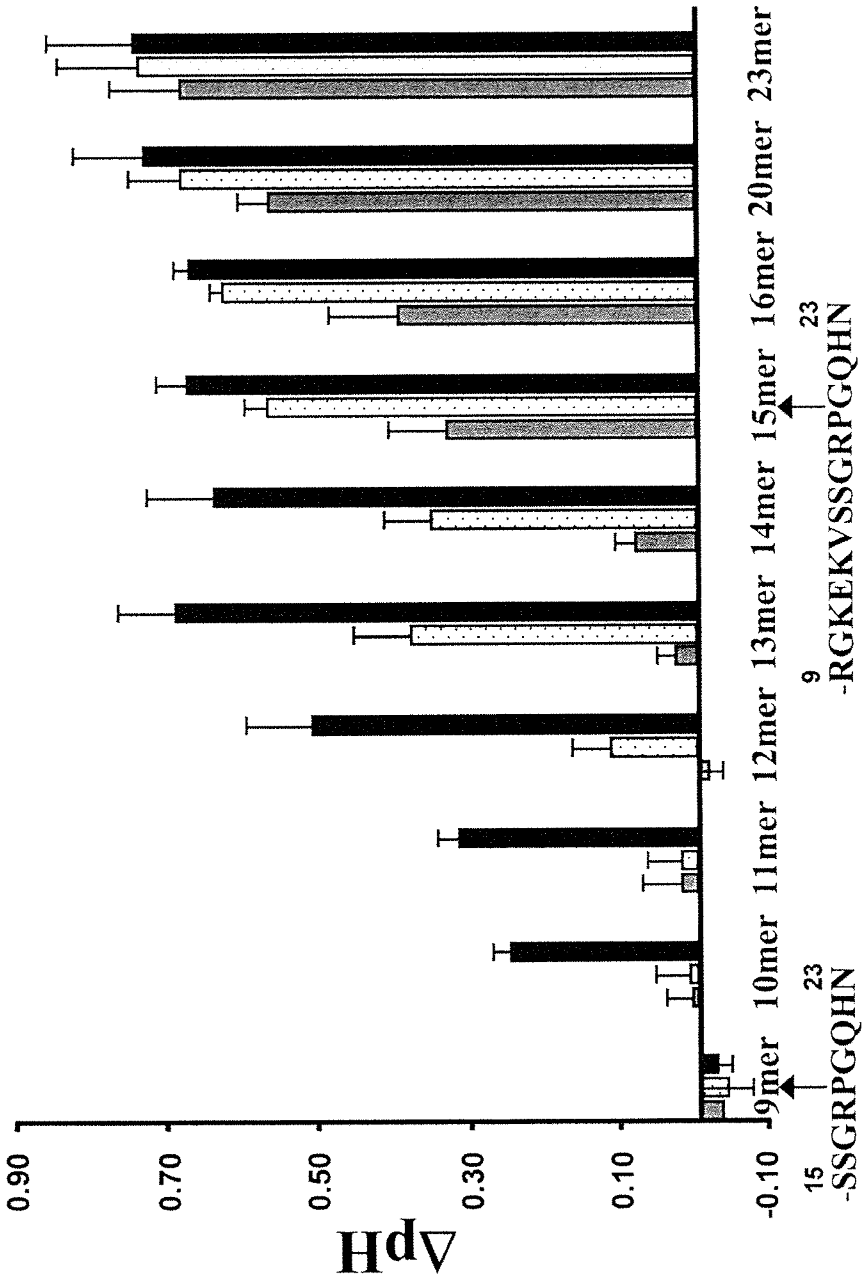

FIG. 5 shows activity of synthetic AtPep1 peptides from the C-terminus of AtPep1 in the alkalization assay, from a 9-mer (SSGRPGQHN (SEQ ID NO: 75)) to a full-length 23-mer. The 15-mer (RGKEKVSSGRPGQHN (SEQ ID NO: 78)) is also shown. Ten microliter aliquots of each peptide solution were tested for activity at 0.25 nM (gray), 2.5 nM (dotted), and 25 nM (black).

Figure 6:
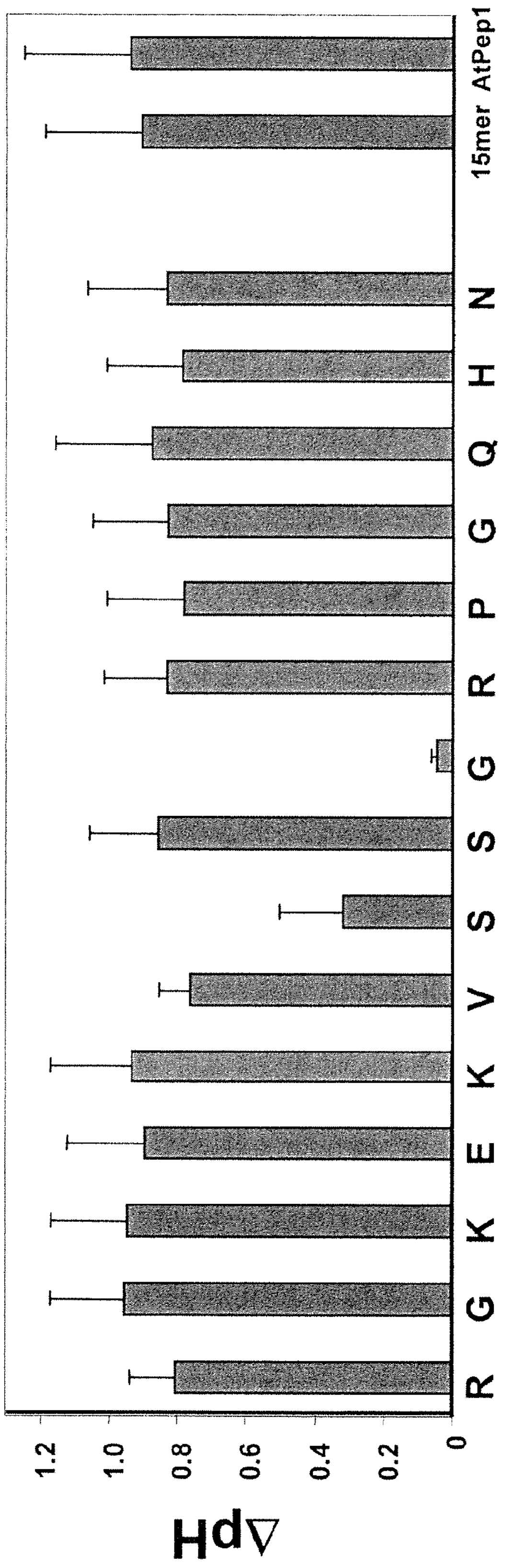

FIG. 6 shows the activity of single alanine amino acid substitutions at every position in the 15-mer peptide at the carboxy terminus of AtPep1 (RGKEKVSSGRPGQHN (SEQ ID NO: 78)) in the alkalinization assay. The set of substituted 15-mer peptides was assayed using four-day-old *Arabidopsis* cells. Ten ml of each peptide (2.5 pmoles) was added to 1 ml of cells to make a final concentration of 2.5 nM. After 20 min, the pH of the media was recorded. The data is the average of three separate experiments.

FIG. 7A-F shows nucleotide sequence information for precursors of the novel plant signal defense peptides of Table 2: OsPep8 nucleotide (SEQ ID NO: 112) and amino acid (SEQ ID NO: 113) sequences; TcPep1 nucleotide (SEQ ID NO: 114) and amino acid (SEQ ID NO: 115) sequences; GhPep2 nucleotide (SEQ ID NO: 116) and amino acid (SEQ ID NO: 117) sequences; PtPep2 nucleotide (SEQ ID NO: 118) and amino acid (SEQ ID NO: 119) sequences; VvPep2 nucleotide (SEQ ID NO: 120) and amino acid (SEQ ID NO: 121) sequences; VvPep3 nucleotide (SEQ ID NO: 122) and amino acid (SEQ ID NO: 123) sequences; HaPep1 nucleotide (SEQ ID NO: 124) and amino acid (SEQ ID NO: 125) sequences; HaPep2 nucleotide (SEQ ID NO: 126) and amino acid (SEQ ID NO: 127) sequences; SoPep1a nucleotide (SEQ ID NO: 128) and amino acid (SEQ ID NO: 129) sequences; SoPep2a nucleotide (SEQ ID NO: 130) and amino acid (SEQ ID NO: 131) sequences; PvPep1 nucleotide (SEQ ID NO: 132) and amino acid (SEQ ID NO: 133) sequences. A (*) denotes a stop codon.

FIG. 8 shows representative monocot propeptide sequences containing multiple peptides. Nucleotide sequence information for precursors of the novel plant defense signal peptides of Table 3 are shown: Barley (SEQ ID NO: 134); Sugarcane1 (SEQ ID NO: 135); Sugarcane2 (SEQ ID NO: 136). Multiple peptides from the same precursor are named using letters starting from the carboxyl end of the precursor as shown.

FIG. 9 shows (A) an amino acid sequence alignment of predicted proAtPep1 orthologs (ProAtPep1 (SEQ ID NO: 82); ProAtPep2 (SEQ ID NO: 90); At2g22000 (SEQ ID NO: 137); Canola (SEQ ID NO: 138); Potato (SEQ ID NO: 139); Rice (SEQ ID NO: 140); Poplar (SEQ ID NO: 141); Medicago (SEQ ID NO: 142); Soybean (SEQ ID NO: 143) and (B) a gene domain model for proATPep1-like genes.

Figure 10:
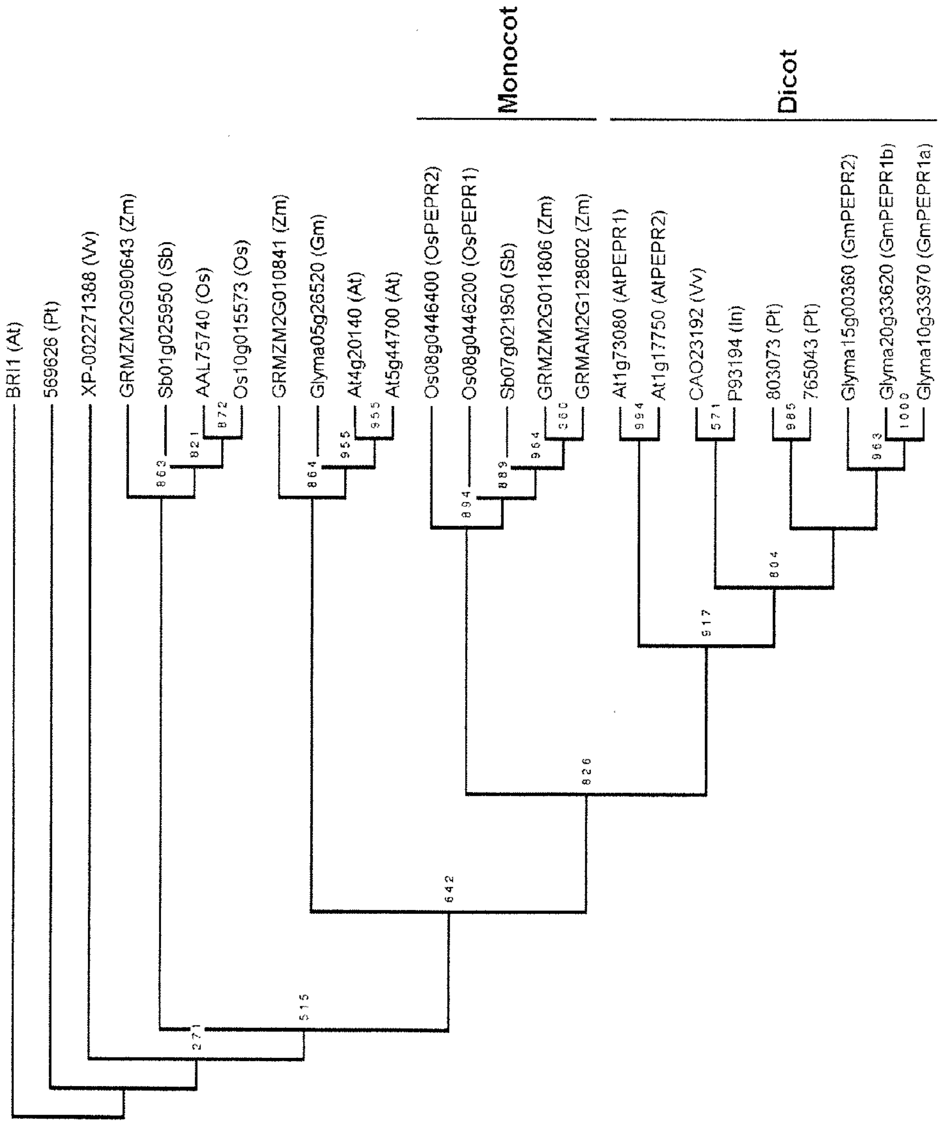

FIG. 10 shows a phylogenic tree of AtPEPRs homologues.

FIGS. 11A(1-4) and 11B(1-19) show amino acid alignment of AtPEPR homologues (A) and the DNA and amino acid sequences of identified AtPEPR homologues (B).

FIG. 12 shows a consensus amino acid sequence (SEQ ID NO: 172) of the protein kinase domain of AtPEPRs homologues.

DETAILED DESCRIPTION

We have identified defense signal peptides from *Arabidopsis* and a variety of other plants, including crop plants of commercial importance. In addition, we have identified genes that encode polypeptides, which are processed in plant cells to produce the shorter peptides, as well as receptors for the peptides. Transgenic plants in which these defense signal peptides are expressed under the control of a heterologous promoter, such as a constitutive promoter, exhibit improved yield of plant product, reduced disease symptoms, and/or enhanced resistance to disease infestation. Peptides that comprise as few as 10 amino acid residues from the carboxy-terminus of AtPep1, a 23 amino acid defense signal peptide from *Arabidopsis thaliana*, retain significant activity. In addition, individual amino acid residues that are important for activity have been defined by amino acid substitutions. Peptides and other substances that have defense signal peptide activity can be readily screened using an alkalinization assay that is described herein, and their identity can be confirmed by exogenous application to plants or transgenic expression in plants.

We have isolated novel defense peptides AtPep1 and AtPep2 from *Arabidopsis*. This is the first demonstration of the involvement of a plant-derived peptide signal in defense against pathogens. The proAtPep1 and 2 precursor genes have been identified and belong to a seven-member gene family. The DNA sequence of the gene from *Arabidopsis thaliana* that encodes AtproPep1 and the deduced amino acid sequence of AtproPep1 are provided in FIG. 1. Orthologs have been identified in such dicots as canola, potato, poplar, alfalfa, soybean, grape, and tomato, and in such monocots as rice, wheat, maize, and barley, and are likely commonly found across the plant kingdom. The sequences of several paralogs and orthologs of AtPep1 are also provided in FIG. 1.

The rapid, sensitive alkalinization assay that was used to identify and purify the AtPep1 and 2 peptides is useful for identifying defense signal peptides from any plant whose signaling pathways result from peptide-receptor interactions that initiate intracellular signaling through MAP kinases and proton pumps in the plasma membrane. Within minutes after adding systemin to cells, an ATP-driven proton pump is inhibited, causing the extracellular medium of the cells to become alkaline. When aliquots (e.g., 1-10 μL) from fractions from plant tissues that eluted from HPLC columns were added to 1 mL of suspension cultured plant cells grown at low pH (e.g., pH 5), some fractions caused the cell medium to increase in pH. The identification of a peptide as a defense signal peptide is confirmed by application of the peptide (e.g., as a plant fraction or isolated peptide) to plants or by expression of a transgene encoding the peptide, including, but not limited to, the gene encoding a pro-form of the peptide (such as, for example. AtproPep1, the pro-form of AtPep1) in plants and observation of detectable defense signal peptide activity, such as, for example, enhanced disease resistance.

We established a suspension cultured *Arabidopsis* cell line to be used in the alkalinization assay to seek novel peptides in *Arabidopsis* leaf extracts. Cells are grown unbuffered near pH 5 or less in order to record an alkalinization of about 1 pH unit in response to peptide signals. In order to establish an *Arabidopsis* suspension cell culture for use in the alkalinization assay, *Arabidopsis* cells were regularly transferred and maintained in the growth chamber room for several months, when they equilibrate at a pH of about 5.0 during exponential growth. Cell cultures that grow at low pH from several other plant species, including tomato (*Lycopersicon esculentum*), tobacco (*Nicotiana tabacum*), alfalfa (*Medicago sativa*), maize (*Zea mays*), petunia (*Petunia hybrida*), nightshade (*Solanum nigrum*), and sweet potato (*Ipomoea batatus*) have been developed for use in the alkalinization assay, and developing similar cultures from other plants is readily accomplished.

For the work described in Example 1, we used a typical purified peptide fraction from *Arabidopsis* leaves. Kilogram quantities of leaf material were extracted and peptides were separated on an HPLC column. A 10 microliter (μL) aliquot from each fraction eluting from the column was assayed with the alkalinization assay using suspension cultured *Arabidopsis* cells. Two novel peaks were identified that were called AtPep1 and AtPep2. The peptides were purified through several additional column separations until homogeneous, as verified by MALDI-MS and amino-terminal sequencing. The peptides were each 23 amino acids in length and the amino acids sequences of the two were identical at 10 residues. Neither peptide was post-translationally modified. The two peptides were chemically synthesized and, in alkalinization assays exhibited identical activities as the native peptides, in the sub-nanomolar concentration range. Searches of protein data bases revealed that the peptides were derived from the C-terminus of two members of a seven-member gene family. The deduced precursors were from 92 to more than 100 amino acids in length and did not have leader sequences at their N-termini.

These properties are similar to tomato systemin (Pearce et al., Science 253:895-897, 1991). Other similarities between proAtPep1 prosystemin were the absence of a leader sequence in the precursors, the low nanomolar concentrations needed to activate the alkalinization response, the processing of the peptides from the C-termini of their precursor proteins, and the presence of KEK motifs in the precursors that are commonly found in proteins that are involved in protein-protein interactions. The expression of the proAtPep1 gene in excised *Arabidopsis* leaves was induced by AtPep1, similar to the expression of the prosystemin gene in tomato plants being induced by systemin.

The tissue-specific expression of the proAtPep1 gene was analyzed using RT-PCR analyses. All tissues of the plant expressed the gene at low levels, which did not reveal a clue as to its function. To assess whether stresses to *Arabidopsis* plants might affect AtPep1 gene expression, the plants were subjected to cold and drought stresses and treatments with abscissic acid (ABA), methyl jasmonate (MeJA), methyl salicylate (MeSA), UV-B, and wounding. Only MeJA and wounding induced a strong expression of the gene. These results indicated that the gene was behaving in *Arabidopsis* in a similar manner as systemin in tomato plants (Ryan et al., Plant Cell. 14:251-264, 2002) and suggested that the peptide may be a defense signaling peptide.

Pathogen defense is well characterized in *Arabidopsis*, where two defense pathways have been identified in which jasmonate is a signaling component (Lorenzo and Solano, Curr. Opin. Plant Biol 8:532-540, 2005; Lorenzo et al., Plant Cell 16:1938-1950, 2004). In one pathway, wounding and jasmonate activate defensive genes through the octadecanoid pathway, with COI1 and AMYC2 playing major roles in transcription of defensive genes that includes LOX2 and VSP2 (Lorenzo et al., Plant Cell 16:1938-1950, 2004). In the second pathway jasmonate, in concert with ethylene, activates PDF1.2, and several PR proteins, with active oxygen playing a key signaling role (Lorenzo et al., Plant Cell 15:165-178, 2003; Penninckx et al., Plant Cell 10:2103-2113, 1998; Penninckx et al., Plant Cell 8:2309-2323, 1996; Coego et al., Plant Cell 17:2123-2137, 2005; Mackerness et al., Plant Cell Environ. 22:1413-1423, 1999). To assess the possible involvement of AtPep1 with the known pathways, *Arabidopsis* plants were excised and supplied with the AtPep1 peptide at 10 nM concentrations, and several known wound-inducible genes and pathogen defense genes were assayed for expression levels two hours later. Only the pathogen defense genes were induced, with PDF2.2 and PR-1 being most strongly expressed, with PR-3, PR-4, and TAT expressed at lower levels. LOX2 and VSP2 genes were not induced by the peptide.

*Arabidopsis* plants were transformed with a 35S-AtPep1 fused gene, and many stable transformants that strongly expressed the gene were recovered. The overexpression of the gene did not visibly affect the growth of the transgenic plants compared to wild type plants. The progeny of a stable transformant that strongly expressed the gene was analyzed to determine if the overexpression of the gene would affect the expression of defense genes. Plants constitutively overexpressing the proAtPep1 gene also constitutively overexpressed the AtPep1-inducible genes.

To determine if the transgenic plants were more resistant to a pathogen, the soil of plants in which the transgenic line was grown was inoculated with the root pathogen *Pythium irregulare* and the plants were monitored with time to assess pathogenicity. The aerial parts of the transgenic plants infected with *Pythium* were visibly more robust than infected wild type plants. However, the roots of the infected transgenic plants were much denser and healthier than roots of infected wild type plants. The transgenic plants were growing almost as well as uninfected wild type plants. These experiments indicated that overexpression of the gene was enhancing resistance to the root pathogen.

Using photoaffinity labeling of AtPep1, a high affinity binding protein for the peptide was identified on the surface of *Arabidopsis* suspension cultured cells by photoaffinity labeling. The protein was purified to homogeneity. The binding of the photoaffinity label to the receptor is strongly competed by unlabeled AtPep1, but not by tomato systemin. The binding of AtPep1 is powerfully competed by suramin, a potent inhibitor of many ligand-receptor interactions, including the binding of systemin with its receptor. Amino acid sequence analysis has shown the protein to be a leucine-rich repeat (LRR) receptor kinase. The gene (At1G73080) contains 27 LRR motifs, a 23 amino acid membrane-spanning region, and an intracellular protein kinase domain. The protein is glycosylated, as evidenced by the loss of about 20% of its mass by enzymatic deglycosylation. An ortholog (At1G17750) is present in *Arabidopsis*, and LRR receptor kinase orthologs from rice and morning glory have been reported in GenBank that share a high percentage of amino acid identity with the AtPep1 receptor. The paralog in *Arabidopsis* shares more than 90% amino acid identity with AtPep1, but it has only 24 LRRs and does not have either a transmembrane domain or a kinase domain. The DNA and deduced amino acid sequences for the AtPep1 receptors are provided in FIG. 2 (Ag1g73080) and FIG. 3 (At1g17750).

The AtPep1 peptide, like systemin, is apparently a cytosol-derived peptide that involves the jasmonate/ethylene signaling pathway. How the peptide is processed from a precursor and arrives at the cell surface to activate a signaling pathway is unknown, but, like systemin, transport of either the precursor or the processed peptide to the cell surface may occur in order for the peptide to react with its receptor.

AtPep1 is a component of the defense signaling of *Arabidopsis* plants and is therefore the first plant peptide hormone to be associated with a known pathogen defense pathway in any plant.

Table 1 shows examples of the C-terminal sequences of paralogs and orthologs of AtproPep1 that we have identified in a wide variety of plants. In addition to the examples listed in Table 1, for example, two orthologs of the AtPep1 precursor gene (called preproLePep1) have been identified in tomato plants. The tomato cDNA has been isolated and shown to code for an AtPep1-like defense peptide. Other paralogs and orthologs of AtproPep1 in these and other plant species may be found by amino acid sequence homology. Additional defense signal peptides may be identified by screening plants for peptides having defense peptide activity, as described herein.

TABLE 1

AtPep1, Paralogs, Orthologs, and Dicot and Monocot Consensus Sequences

| Peptide | Source | Alignment of C-terminal Sequences | SEQ ID NO: |
|---|---|---|---|
| AtPep1 | *Arabidopsis thaliana* | 10 \| 20 \| -ATKVK AKQRG KEKVS SGRPG QHN | 1 |
| Paralogs | | | |
| AtPep2 | *Arabidopsis thaliana* | -SLNVM RKGIR KQPVS SGKRG GVN | 2 |
| AtPep3 | *Arabidopsis thaliana* | -DNKAK SKKRD KEKPS SGRPG QTN | 3 |
| AtPep4 | *Arabidopsis thaliana* | -EIKAR GKNKT KPTPS SGKGG KHN | 4 |
| AtPep5 | *Arabidopsis thaliana* | -GLPGK KNVLK KSRES SGKPG GTN | 5 |
| AtPep6 | *Arabidopsis thaliana* | -ITAVL RRRPR PPPYS SGRPG QNN | 6 |
| AtPep7 | *Arabidopsis thaliana* | -VSGNV AARKG KQQTS SGKGG GTN | 7 |
| Orthologs | | | |
| BnPep1 | Canola (*Brassica napus*) | -VARLT RRRPR PP-YS SGQPG QIN | 8 |
| StPep1 | Potato (*Solanum tuberosum*) | -PTERR GRPPS RPKVG SGPPP QNN | 9 |
| PbPep1 | Poplar (*Populus balsamifera*) | -DAAVS ALARR TPPVS RGGGG QTN | 10 |
| BePep1 | Birch (*Betula* spp.) | -DLVMA VNAPP RPSLT PGSGA QIN | 11 |

TABLE 1-continued

AtPep1, Paralogs, Orthologs, and Dicot and Monocot Consensus Sequences

| Peptide | Source | Alignment of C-terminal Sequences | SEQ ID NO: |
|---|---|---|---|
| GmPep1 | Soybean (*Glycine max*) | -ASLMA TRGSR GSKIS DGSGP QHN | 12 |
| MsPep1 | Alfalfa (*Medicago sativa*) | -LSSMG RGGPR RTPLT QGPPP QHN | 13 |
| VvPep1 | Grape (*Vitis vinifera*) | -EKVRE KQKKG EDGES VGRPG KKN | 14 |
| Dicot consensus sequence | | 10 20<br>\| \|<br>XXXXXXXXXXXXXXSSGX (P/G) (P/G) QXN<br>Residues 2-13 are rich in K and R | 15 |
| OsPep1 | Rice (*Oryza sativa*) | -ARLRP KPPGN PREGS GGNGG HHH | 16 |
| OsPep2 | Rice (*Oryza sativa*) | -DDSKP TRPGA PAEGS GGNGG AIH | 17 |
| TaPep1 | Wheat (*Triticum aestivum*) | -AVRRP RPPTT PREGR GGGGG SHN | 18 |
| TaPep2 | Wheat (*Triticum aestivum*) | -AAPAP QRPGA PAEGA GGQGG IIH | 19 |
| ZmPep1 | Maize (*Zea mays*) | -VRRRP TTPGR PREGS GGNGG NHH | 20 |
| HvPep1 | Barley (*Hordeum vulgare*) | -QLARP RPPGP PRQGH GGDGG AIH | 21 |
| Monocot consensus sequence | | 10 20<br>\| \|<br>XXXXXXXPGXP (R/A) EGXGGXGGX (H/I) H<br>Residues 2-7 are rich in K and R | 22 |

Among the native defense signal peptides identified so far, the shortest deduced peptide sequence is 23 amino acids in length (for example, AtPep1) and the longest is 36 amino acids (AtPep3).

The dicot and monocot disease signal peptides in particular have a substantial degree of homology in the C-terminal region of the peptides, allowing us to define consensus sequences as shown in Table 1, which shows C-terminal alignments for AtPep paralogs and orthologs that correspond to the sequence of AtPep1 and dicot and monocot consensus sequences for defense signal peptides.

According to one aspect, defense signal peptides are provided that comprise a dicot or monocot consensus sequence or have a high degree of amino acid sequence homology to such a consensus sequence, e.g., 75 percent homology, or 80 percent homology, or 90 percent homology. In one embodiment, such defense signal peptides are 10 amino acid residues in length or longer and have defense signal peptide activity.

Analogs of AtPep1 were synthesized and assayed in the alkalinization assay. An analog of AtPep1 missing the carboxy-terminal amino acid was completely inactive, whereas deletions from the amino-terminus of the peptide resulted in a sequential reduction in activity, until peptides with 9 carboxy-terminal amino acids remaining (SSGRPGQHN (SEQ ID NO: 75)) were inactive. A peptide consisting of only the 15 C-terminal amino acids was nearly as active as the native peptide (at approximately 2.5 nM), but analogs of 14 amino acids and smaller were progressively less active.

AtPep1 is 23 amino acid residues in length. However, truncated forms of AtPep1 of 10 amino acid residues from the C-terminus of AtPep1 retain activity, and peptides having 15 residues retain substantially full defense signal peptide activity (Example 3). As a result of the foregoing studies of shorter defense signal peptides, according to another embodiment, defense signal peptides comprising at least 10 amino acid residues, particularly those including sequences from the C-terminus of native defense signal peptides or including consensus dicot or monocot sequences are provided. Such shorter peptides may be 11 or more, 12 or more, or 15 or more amino acid residues in length, provided that they retain substantial defense signal peptide activity.

The 15-mer was substituted with alanine in each position to assess which amino acids were necessary for the alkalinating activity. A Ser to Ala substitution at position 7, counting from the amino-terminus of the 15-mer, and a Gly to Ala substitution at position 9 exhibited little activity. Computer modeling predicted that these two amino acids would be involved in a hairpin-turn within the peptide region of -SSGR- (compare with residues 15-18 of the sequence of AtPep1 shown in Table 1). Substituting Ala for Ser (-ASGR-) abolished the predicted turn and severely reduced activity (half-maximal activity at approximately 25 nM), while substituting Ala for Gly was even less active (half-maximal activity of >250 nM). However, neither of these analogs were able to compete with the non-substituted 15-mer for receptor binding, indicating that the structural changes in this region may have severely modified the conformation without competing for the receptor binding site. Other Ala substitutions had no effect on activity.

These results will guide the skilled artisan in making desired substitutions in other defense signal peptides.

Additional Plant Signal Defense Peptides

In addition to the plant signal defense peptides that are shown in Table above, we have discovered additional plant signal defense peptides from a number of dicot and monocot plant species. These include the AtPep1 orthologs shown in Table 2.

TABLE 2

AtPep1 and Additional Dicot and Monocot Orthologs

| Peptide | Source | Alignment of C-terminal Sequences | SEQ ID NO: |
|---|---|---|---|
| AtPep1 | *Arabidopsis thaliana* | 10 \| 20 \| -ATKVK AKQRG KEKVS SGRPG QHN | 23 |
| Orthologs | | | |
| TcPep1 | Alpine pennycress (*Thlaspi caerulescens*) | -VTKFK AKMKE REKVS TGRSG QHN | 24 |
| GhPep2 | Cotton (*Gossypium hirsutum*) | -LPMVS LFTPK RPGTS AGSGP QIN | 25 |
| SePep1 | Tomato (*Solanum lycopersicum*) | -ATDRR GRPPS RPKVG SGPPP QNN | 26 |
| PtPep2 | Poplar (*Populus balsamifera*) | -AVTVS ALARR TPPVS SGSGG QIN | 27 |
| VvPep2 | Grape (*Vitis vinifera*) | -LRRGP TRPPI SFESR PGGGS QIN | 28 |
| VvPep3 | Grape (*Vitis vinifera*) | -KMSSD FRQPP RPPID PGQGG QIN | 29 |
| HaPep1 | Sunflower (*Helianthus annuus*) | -RGLTR RPPPP RGPIS SGGGG QTN | 30 |
| HaPep2 | Sunflower (*Helianthus annuus*) | -RVNLV GYDYS GYGQS TGKPS ECN | 31 |
| OsPep8 | Rice (*Oryza sativa*) | -QRNEI RSRGV DPSVS GGKQP GIN | 32 |
| SoPep1a | Sugarcane (*Saccharum officinarum*) | -ASVLM RGPAQ PVPPT EGAXG RGG | 33 |
| SoPep2a | Sugarcane (*Saccharum officinarum*) | -ASVLM RGPAQ PGPPT EGAGR RGG | 34 |
| PvPep1 | Switchgrass (*Panicum virgatum*) | -VVTRV WAVRR PREGS GGNGG VHH | 35 |

FIG. 7 shows nucleotide sequence information for precursors of the novel plant signal defense peptides of Table 2.

We have also identified additional plant signal defense peptides in precursor nucleotide sequences in which only one plant signal defense peptide had been identified previously. These are shown in Table 3.

TABLE 3

AtPep1 and Additional Monocot Orthologs from Precursor Genes that Encode Multiple Peptides

| Peptide | Source | Alignment of C-terminal Sequences | SEQ ID NO: |
|---|---|---|---|
| AtPep1 | *Arabidopsis thaliana* | 10 \| 20 \|<br>-ATKVK AKQRG KEKVS SGRPG QHN | 36 |
| Orthologs | | | |
| OsPep3b | Rice (*Oryza sativa*) | -RRPTP PGGAG PREGS GGRGG VIH | 37 |
| OsPep3c | Rice (*Oryza sativa*) | -SLAGA NVLVR DAPPE TGGGP HHN | 38 |
| OsPep4b | Rice (*Oryza sativa*) | -RRPTP PGGAG PREGS GGRGG VIH | 39 |
| OsPep4c | Rice (*Oryza sativa*) | -LAGAN VLLRD DAPPE GGRGP HHN | 40 |
| OsPep5b | Rice (*Oryza sativa*) | -RRPTP PGGAG PREGR GGRGG VIH | 41 |
| OsPep5c | Rice (*Oryza sativa*) | -QLAGA KVLVR DAPPE TGGGP HHN | 42 |
| OsPep6b | Rice (*Oryza sativa*) | -GGVRP TPPGN PREAQ KGGGV IHA | 43 |
| ZmPep4b | Maize (*Zea mays*) | -ALRGP APPAR PKEGS GGKVH VVS | 44 |
| ZmPep4c | Maize (*Zea mays*) | -LWPAP SPKGR PGAPR QGSGG QVH | 45 |
| TaPep3b | Wheat (*Triticum aestivum*) | -DASSL APQLR RTSPG EGTSG RIH | 46 |
| TaPep3c | Wheat (*Triticum aestivum*) | -IAPTL QPSSA PVEGT GGQVM VLN | 47 |
| HvPep1b | Barley (*Hordeum vulgare*) | -DASSL PLQLM RTPPG EGAGG RIH | 48 |
| HvPep1c | Barley (*Hordeum vulgare*) | -SVLPD QPPSA PAEGT GGQVM VLN | 49 |
| SoPep1b | Sugarcane (*Saccharum officinarum*) | -ASVLL RGPAP PGRPV EGSGG KVH | 50 |
| SoPep1c | Sugarcane (*Saccharum officinarum*) | -AHMVI RGPAR PGLPA QGSGG KVH | 51 |
| SoPep1d | Sugarcane (*Saccharum officinarum*) | -MATPM RRPTP PGPPA QGSGG KTN | 52 |
| SoPep1e | Sugarcane (*Saccharum officinarum*) | -SRAAP SPKGS PGAPR QGSGG HVH | 53 |

TABLE 3-continued

AtPep1 and Additional Monocot Orthologs from Precursor Genes that Encode Multiple Peptides

| Peptide | Source | Alignment of C-terminal Sequences | SEQ ID NO: |
|---|---|---|---|
| SoPep1f | Sugarcane (*Saccharum officinarum*) | -APASP LRRQL LRYVS SGLVA ALH | 54 |
| SoPep2b | Sugarcane (*Saccharum officinarum*) | -AHMVI RGPAR PGLPA QGRGG KVH | 55 |
| SoPep2c | Sugarcane (*Saccharum officinarum*) | -MATPM RRPTS PGPPA QGSGG KTN | 56 |
| SoPep2d | Sugarcane (*Saccharum officinarum*) | -SRAVP SLKGR PGAPR QGSGG HVH | 57 |
| SoPep2e | Sugarcane (*Saccharum officinarum*) | -APASP LRRQL LRYVS SGLVA ALH | 58 |

FIG. 8 shows nucleotide sequence information for precursors of the novel plant defense signal peptides of Table 3.

Definitions and Methods

The following definitions and methods are provided to better define the preferred embodiments and to guide those of ordinary skill in the art in the practice of the disclosed embodiments. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York, 1991; and Lewin, Genes V, Oxford University Press: New York, 1994. The nomenclature for DNA bases as set forth at 37 CFR 1.822 is used. The standard one- and three-letter nomenclature for amino acid residues is used.

Polynucleotides

"Polynucleotide." The term "polynucleotide" refers to a polymer of nucleotide monomers, including but not limited to ribonucleotides or deoxyribonucleotides or nucleotide analogues. Polynucleotides include, for example, DNA and RNA molecules, including cDNA, genomic DNA, primers, probes, vectors, and so on, and include single- and double-stranded forms thereof. Polynucleotides may be chemically modified by well known methods by labeling, coupling to solid supports, etc.

"Defense signal peptide (or polypeptide) polynucleotide". The term "defense signal peptide polynucleotide" refers to a polynucleotide that encodes a defense signal peptide, and a "defense signal polypeptide polynucleotide" refers to a polynucleotide that encodes a defense signal polypeptide (i.e., a polypeptide that, when processed in a plant cell, produces a defense signal peptide), whether a cDNA or genomic sequence or synthetic form thereof. Such polynucleotides may comprise wild type polynucleotides sequences encoding defense signal polypeptides, such as those listed in Table 1, operably linked to a heterologous promoter, i.e., a promoter not associated in nature with such native, or wild type, polynucleotide sequences. Alternatively, such polynucleotides may comprise non-naturally occurring recombinant polynucleotides that comprise a sequence that encodes a defense signal peptide operably linked to a suitable promoter. For expression of defense signal peptides for exogenous application to plants, a defense signal peptide polynucleotide may be operably linked to a promoter suitable for expression in a bacterial, fungal, insect, or other suitable cell. For transformation of plants or plant cells or tissues, a defense signal peptide may be operably linked to a promoter suitable for expression in a plant cell, i.e., a plant promoter. According to another embodiment, a heterologous promoter may be introduced into a plant or a plant cell or tissue for insertion into the genome, thereby producing an insertion of the promoter upstream of a sequence that encodes a defense signal peptide, operably linking the sequence encoding the defense signal peptide to the heterologous promoter. Such an expression unit, including the heterologous promoter and the sequence encoding the defense control peptide, is another embodiment of a defense signal peptide (or polypeptide) polynucleotide.

"Native." The term "native" refers to a naturally-occurring ("wild type") polynucleotide, polypeptide or peptide.

"Isolated." An "isolated" polynucleotide is one that has been substantially separated or purified away from other polynucleotide sequences in the cell of the organism in which the polynucleotide naturally occurs, i.e., other chromosomal and extrachromosomal DNA and RNA, by conventional purification methods. The term also embraces recombinant polynucleotides (including promoter insertions operably linked to a defense signal peptide gene) and chemically synthesized polynucleotides.

"Heterologous." A heterologous polynucleotide is one that is not normally present in a particular context. For example, with reference to a cell, tissue or organism, heterologous polynucleotide sequence is one that is not found in such a cell, tissue or organism in nature unless introduced into such cell, tissue or organism. As another example, a heterologous promoter is a promoter not associated in nature with a particular protein coding sequence.

Fragments, Probes, and Primers

A fragment of a polynucleotide is a portion of a polynucleotide that is less than full-length and comprises at least a minimum length capable of hybridizing specifically with a native polynucleotide sequence under stringent hybridization conditions. The length of such a fragment is preferably at least 15 nucleotides, more preferably at least 20 nucleotides, and most preferably at least 30 nucleotides of a native polynucleotide sequence.

A "probe" is an isolated polynucleotide to which is attached a conventional detectable label or reporter molecule, e.g., a radioactive isotope, ligand, chemiluminescent agent, or enzyme. "Primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a polynucleotide sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to the target polynucleotide sequence under high stringency hybridization conditions under at least moderately stringent conditions.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR-primer pairs can be derived from a known sequence, for example, by using computer programs intended for that purpose such-as Primer (Version 0.5, 1991, Whitehead Institute for Biomedical Research, Cambridge, Mass.).

Primers and probes based on the native defense signal polypeptide polynucleotide sequences that are disclosed herein can be used to confirm (and, if necessary, to correct) the disclosed polynucleotide sequences by conventional methods, e.g., by re-cloning and re-sequencing.

"Substantial similarity." A first polynucleotide is "substantially similar" to a second polynucleotide if, when optimally aligned (with appropriate nucleotide insertions or deletions) with the other polynucleotide (or its complementary strand), there is at least about 75% nucleotide sequence identity, preferably at least about 80% identity, more preferably at least about 85% identity, and most preferably at least about 90% identity. Sequence similarity can be determined by comparing the nucleotide sequences of two polynucleotides using sequence analysis software such as the Sequence Analysis Software Package of the Genetics Computer Group, University of Wisconsin Biotechnology Center, Madison, Wis.

Alternatively, two polynucleotides are substantially similar if they hybridize under stringent conditions.

"Operably Linked." A first nucleic-acid sequence is "operably linked" with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant." A "recombinant" polynucleotide is made by an artificial combination of two otherwise separated segments of sequence, e.g., by chemical synthesis or by the manipulation of isolated segments of polynucleotides by genetic engineering techniques. Techniques for nucleic-acid manipulation are well-known (see, e.g., Sambrook et al., 1989, and Ausubel et al., 1992). Methods for chemical synthesis of polynucleotides are discussed, for example, in Beaucage and Carruthers, Tetra. Letts. 22:1859-1862, 1981, and Matteucci et al., J. Am. Chem. Soc. 103:3185, 1981. Chemical synthesis of polynucleotides can be performed, for example, on commercial automated oligonucleotide synthesizers.

Preparation of Recombinant or Chemically Synthesized Polynucleotides; Vectors, Transformation, Host Cells Natural or synthetic polynucleotides according to the present disclosure can be incorporated into recombinant nucleic-acid constructs, typically DNA constructs, capable of introduction into and replication in a host cell. Such a construct preferably is a vector that includes a replication system and sequences that are capable of transcription and translation of a polypeptide-encoding sequence in a given host cell.

For the practice of the present embodiments, conventional compositions and methods for preparing and using vectors and host cells are employed, as discussed, inter alia, in Sambrook et al., 1989, or Ausubel et al., 1992.

A cell, tissue, organ, or organism into which has been introduced a foreign polynucleotide, such as a recombinant vector, is considered "transformed", "transfected", or "transgenic." A "transgenic" or "transformed" cell or organism also includes progeny of the cell or organism and progeny produced from a breeding program employing such a "transgenic" plant as a parent in a cross and exhibiting an altered phenotype resulting from the presence of a recombinant polynucleotide construct.

A number of vectors suitable for stable transfection of plant cells or for the establishment of transgenic plants have been described in, e.g., Pouwels et al., Cloning Vectors: A Laboratory Manual, 1985, supp. 1987); Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters include, but are not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989).

A variety of plant gene promoters that are regulated in response to environmental, hormonal, chemical, and/or developmental signals, also can be used for expression of defense signal peptides in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunl, Siebertz et al., Plant Cell 1:961, 1989); or (5) chemicals such as methyl jasminate, salicylic acid, or Safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989), including promoters that express specifically in the root, leaf, seed, etc.

Plant expression vectors optionally include RNA processing signals, e.g., introns, which may be positioned upstream or downstream of a polypeptide-encoding sequence in the transgene. In addition, the expression vectors may also include additional regulatory sequences from the 3'-untranslated region of plant genes (Thornburg et al., Proc. Natl. Acad. Sci. USA 84:744 (1987); An et al., Plant Cell 1:115 (1989), e.g., a 3' terminator region to increase mRNA stability of the mRNA, such as the PI-II terminator region of potato or the octopine or nopaline synthase 3' terminator regions.

Useful dominant selectable marker genes include genes encoding antibiotic resistance genes (e.g., resistance to hygromycin, kanamycin, bleomycin, G418, streptomycin, or spectinomycin); and herbicide resistance genes (e.g., phosphinothricin acetyltransferase). A useful strategy for selection of transformants for herbicide resistance is described, e.g., in Vasil, Cell Culture and Somatic Cell Genetics of Plants, Vols. I-III, Laboratory Procedures and Their Applications Academic Press, New York, 1984.

An expression vector for expression of a defense signal peptide or polypeptide in a plant may also comprise a gene encoding another polypeptide, including a herbicide-tolerance gene (e.g., tolerance to glyphosate, glufosinate, etc.); a polypeptide conferring insect resistance (e.g., a *Bacillus thuringensis* insecticidal protein or a *Xenorhabdus* insecticidal protein); a pathogen protein (e.g., virus coat protein); a trait for improving yield, drought resistance, cold tolerance, etc.; a trait for modifying the oil, protein or starch composition of seeds; or another gene that has a desirable activity when expressed in a plant. For example, U.S. Pat. No. 5,571,706 describes the introduction of the N gene into tobacco to confer resistance to tobacco mosaic virus; WO 95/28423 describes the expression of the Rps2 gene from *Arabidopsis thaliana* in plants as a means of creating resistance to bacterial pathogens including *Pseudomonas syringae*; WO 98/02545 describes the introduction of the Prf gene into plants to obtain broad-spectrum pathogen resistance; and U.S. Pat. No. 6,762,285 describes the expression of the Bs2 resistance proteins in plants to confer resistance to *Xanthomonas campestris*. Such plant defense genes may also be co-expressed on the same or a different expression vector with a defense signal polypeptide or peptide.

Nucleic-Acid Hybridization; "Stringent Conditions"; "Specific"

The term "stringent conditions" is functionally defined with regard to the hybridization of a nucleic-acid probe to a target polynucleotide (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa, Nucl. Acids Res. 12:203-213, 1984; and Wetmur and Davidson, J. Mol. Biol. 31:349-370, 1968.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild type sequence (or its complement) would bind and preferably to produce a unique amplification product.

The term "specific for (a target sequence)" indicates that a probe or primer hybridizes under given hybridization conditions only to the target sequence in a sample comprising the target sequence.

Nucleic-Acid Amplification

As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990.

See also the examples below regarding RT-PCR, for example.

Nucleotide-Sequence Variants of Native Defense Signal Polypeptide Polynucleotides and Amino Acid Sequence Variants of Native Defense Signal Proteins and Peptides Using the nucleotide and the amino-acid sequences disclosed herein, those skilled in the art can create DNA molecules, polypeptides, and peptides that have minor variations in their nucleotide or amino acid sequence, respectively.

"Variant" DNA molecules are DNA molecules containing minor changes in a native sequence, i.e., changes in which one or more nucleotides of a native sequence is deleted, added, and/or substituted, preferably while substantially maintaining a desired biological activity. Variant DNA molecules can be produced, for example, by standard DNA mutagenesis techniques or by chemically synthesizing the variant DNA molecule or a portion thereof. Such variants preferably do not change the reading frame of the protein-coding region of the polynucleotide and preferably encode a protein having no change, only a minor reduction, or an increase in a desired biological activity.

Amino-acid substitutions are preferably substitutions of single amino-acid residues. DNA insertions are preferably of about 1 to 10 contiguous nucleotides and deletions are preferably of about 1 to 30 contiguous nucleotides. Insertions and deletions are preferably insertions or deletions from an end of the protein-coding or non-coding sequence and are preferably made in adjacent base pairs. Substitutions, deletions, insertions or any combination thereof can be combined to arrive at a final construct.

Preferably, variant polynucleotides according are "silent" or "conservative" variants. "Silent" variants are variants of a native sequence or a homolog thereof in which there has been a substitution of one or more base pairs but no change in the amino-acid sequence of the polypeptide or peptide encoded by the sequence. "Conservative" variants are variants of a native (or consensus) sequence in which at least one codon in the protein-coding region of the gene has been changed, resulting in a conservative change in one or more amino acid residues of the encoded polypeptide encoded, i.e., an amino acid substitution. A number of conservative amino acid substitutions are listed below. In addition, one or more codons encoding cysteine residues can be substituted for, resulting in a loss of a cysteine residue and affecting disulfide linkages in the polypeptide.

TABLE 4

Conservative Amino-Acid Substitutions

| Original Residue | Conservative Substitutions |
|---|---|
| Ala | Ser |
| Arg | Lys |

TABLE 4-continued

| Conservative Amino-Acid Substitutions | |
|---|---|
| Original Residue | Conservative Substitutions |
| Asn | Gln, His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g. leucyl, isoleucyl, phenylalanyl, valyl, or alanyl; (b) a cysteine or proline is substituted for (or by) any other residue; (c) a residue having an electropositive side chain. e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Polypeptides and Peptides

For the polypeptide and peptide sequences presented herein, either the three-letter code or the one-letter code may be used for representing amino acid residues, as provided in Table 5 below.

TABLE 5

| Three-letter Code and One-letter Code for Amino Acids | | |
|---|---|---|
| Amino Acid | Three-Letter Code | One-Letter Code |
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |

TABLE 5-continued

| Three-letter Code and One-letter Code for Amino Acids | | |
|---|---|---|
| Amino Acid | Three-Letter Code | One-Letter Code |
| Tyrosine | Tyr | Y |
| Unknown or Unspecified | Xaa | X |

"Defense Signal Polypeptide"; "Defense Signal Peptide"

In general, a peptide is considered a short polypeptide. The term "defense signal polypeptide" (or protein) refers to a polypeptide encoded by a defense signal protein polynucleotide, including, but not limited to, the polynucleotides listed in Table 1, and other polynucleotides that encode orthologs, paralogs, homologs, and variants of a native defense signal polypeptide. Defense signal peptides result from the processing of a native defense signal polypeptide, such as AtproPep1, in a plant cell. As a result, a native defense signal polypeptide includes sequences in addition to defense signal peptide sequences. Recombinant polypeptides that are not processed intracellularly, but that have defense signal peptide activity, are also considered defense signal polypeptides or peptides.

Recombinant fusion polypeptides may be made that, when processed in a plant cell, result in the production of more than one defense signal peptide, or in the production of a defense signal peptide and another biologically active polypeptide or peptide.

The term "defense signal peptide" refers to a peptide about 10 or more amino acids in length that has substantial defense signal peptide activity. Such defense signal peptides may have a length of 11, 12, 13, 14, 15, or more amino acids. AtPep1 is a native defense signal peptide from *Arabidopsis* that is 23 amino acids in length, although sequences from the C-terminal end of AtPep1 as short as 10 amino acids retain substantial defense signal peptide activity, and such truncated peptides increase in activity with increasing length. Defense signal peptides longer than 23 amino acids retain defense signal peptide activity. The native defense signal polypeptides that we have identified range encodes propeptides of 75 to 154 amino acids that are processed intracellularly to produce the shorter defense signal peptides. Defense signal peptides up to about 160 amino acid residues, or 100, or 90, or 80, or 70, or 60, or 50, or 40, or 30, or 23, or 20 amino acid residues are included among the defense signal peptides disclosed herein.

Defense signal peptides may be produced by expression of a polynucleotide that encodes such a peptide intracellularly, e.g., in a plant cell, or in a non-plant cell, e.g., a bacterial, fungal, insect, or other cell used in recombinant production of polypeptides. Alternatively, defense signal peptides may be produced by chemical synthesis. Techniques for chemical synthesis of polypeptides are described, for example, in Merrifield, J. Amer. Chem. Soc. 85:2149-2156, 1963, and peptide synthesizers are commercially available. For chemical synthesis, shorter forms of the defense signal peptides are preferable to longer forms, including but not limited to, defense signal peptides between about 10 and about 30 amino acids in length.

Polypeptide Sequence Homology

Ordinarily, defense signal peptides encompassed by the present disclosure are at least about 75 percent homologous to a native defense signal peptide, including but not limited to any of the defense signal peptides listed in Tables 1,2, or 3 or a dicot or monocot consensus defense signal peptide sequence, or at least about 80 percent, 85 percent, 90 percent, or 100 percent (complete) homology, and that has substantial defense signal peptide activity. Such homology is considered to be "substantial homology," although more important than shared amino-acid sequence homology is the possession of characteristic structural features and highly conserved amino acid residues from the C-terminal region of native defense signal peptides or consensus sequences.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides and Peptides

An "isolated" polypeptide or peptide has been separated from the cellular components (polynucleotides, lipids, carbohydrates, and other polypeptides) that naturally accompany it. Such a polypeptide or peptide can also be referred to as "pure" or "homogeneous" or "substantially" pure or homogeneous. Thus, a polypeptide that is chemically synthesized is isolated. A defense signal peptide or polypeptide is also considered "isolated" if it is the product of the expression of a recombinant polynucleotide (even if expressed in a homologous cell type). Thus, if AtPep1, for example, is recombinantly expressed in an *Arabidopsis* plant, it is considered "isolated" if the polynucleotide that encodes it is under the control of a promoter that is different from the native AtproPep1 promoter, or if the polynucleotide encodes a polypeptide other than the wild type, or native, AtproPep1 polypeptide but, when processed in a plant cell produces a native AtPep1 peptide, or the AtPep1 peptide produced by expression of the polynucleotide and processing of the encoded polypeptide differs from that of the native AtPep1 peptide in any way, for example in length or sequence.

A monomeric polypeptide or peptide is isolated when at least 60% by weight of a sample is composed of the polypeptide or peptide, or 90% or more, or 95% or more, or more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification

The polypeptides and peptides of the present disclosure can be purified by any of the means known in the art. Various methods of protein purification are described, e.g., in Guide to Protein Purification, ed. Deutscher, Meth. Enzymol. 185, Academic Press, San Diego, 1990; and Scopes, Protein Purification: Principles and Practice, Springer Verlag, New York, 1982.

Variant and Modified Forms of Defense Signal Peptides and Polypeptides

Encompassed by the defense signal peptides and polypeptides of the present disclosure are variant peptides and polypeptides in which there have been substitutions, deletions, insertions or other modifications of a native (i.e., wild type) peptide or polypeptide. The variants substantially retain structural characteristics and biological activities of a corresponding native peptide or polypeptide and are preferably silent or conservative substitutions of one or a small number of contiguous amino acid residues.

Regarding the terms "paralog" and "ortholog", homologous polynucleotide sequences and homologous polypeptide sequences may be paralogs or orthologs of the claimed polynucleotide or polypeptide sequence. Orthologs and paralogs are evolutionarily related genes that have similar sequence and similar functions. Orthologs are structurally related genes in different species that are derived by a speciation event. Paralogs are structurally related genes within a single species that are derived by a duplication event. Sequences that are sufficiently similar to one another will be appreciated by those of skill in the art and may be based upon percentage identity of the complete sequences, percentage identity of a conserved domain or sequence within the complete sequence, percentage similarity to the complete sequence, percentage similarity to a conserved domain or sequence within the complete sequence, and/or an arrangement of contiguous nucleotides or peptides particular to a conserved domain or complete sequence. Sequences that are sufficiently similar to one another will also bind in a similar manner to the same DNA binding sites of transcriptional regulatory elements using methods well known to those of skill in the art.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) website, "tigr.org" under the heading "Terms associated with TIGRFAMs".

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

A native defense signal peptide or polypeptide sequence can be modified by conventional methods, e.g., by acetylation, carboxylation, phosphorylation, glycosylation, ubiquitination, and labeling, whether accomplished by in vivo or in vitro enzymatic treatment or by the synthesis of a defense signal peptide or polypeptide using modified amino acids.

Labeling

There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel et al., 1992.

Peptide Fragments

The present disclosure also encompasses fragments of a defense signal peptide that lacks at least one residue of a native full-length defense signal peptide. Preferably, such a fragment retains substantial defense signal peptide activity, including but not limited to substantial activity in an alkalinization assay and/or the ability to enhance disease resistance in a plant.

"Defense Signal Peptide Activity"; Biological Activity of Polypeptides or Peptides The terms "biological activity", "biologically active", "activity" and "active" refer primarily to the characteristic biological activity or activities of a native defense signal peptide or polypeptide. Defense signal peptide activity includes activity in an alkalinization assay. Substantial defense signal peptide activity in an alkalinization assay includes a change of at least 0.2 pH units when a 10 microliter aliquot of a solution having a concentration of 25 nM of the peptide is added to 1 mL of plant cells in the assay. More substantial defense signal peptide activity in the assay is the observation of a change in pH of at least 0.2 pH units using a solution having concentrations of 2.5 nM or 0.25 nM of the peptide, or when a change of at least 0.5 pH units are observed at a given peptide concentration, or when the activity is at least 25 percent, or 50 percent, or 75 percent that of a native defense signal polypeptide.

For the alkalinization assay, cells suspensions are grown in a volume of 40 ml in a 125 ml flask. Tobacco and *Arabidopsis* cells are typically grown for 3-5 days before use. Tomato cells are typically grown for 4-7 days before use. Soybean cells are generally grown for 3-7 days before use. Preferably, cells are in mid to log or log phase when they are to be used for the alkalinization assay. A 1 ml pipette tip with the end cut off (to prevent clogging of the tip with the cells) is used to aliquot 1 ml of the cells from the suspension into a well in a 24-well culture cluster plate. The flask is swirled between aliquots to ensure that the cells remain evenly dispersed throughout the cell suspension and an roughly equivalent number of cells is provided to each well. The plate(s) are then shaken at 160 rpm for 1 hour. Small aliquots (1-10 ml) of extracted peptide fractions are then added to the wells. After 20 min, the pH of the cell media is measured and recorded.

Alternatively, a substantial defense signal peptide activity is the ability to enhance plant disease resistance and substantially improve yield of plant product, with enhancement of plant disease resistance evidenced by reduced disease symptoms, enhanced resistance to disease infestation, etc., when a defense signal peptide is applied to a plant exogenously or recombinantly expressed within a plant. A defense signal peptide substantially enhances disease resistance of a plant if it increases the resistance of a plant to a pathogen of at least 10 percent as compared to a control plant under similar conditions, or more substantially, of at least 25, or 50, or 75, or 100 percent, as measured by standard quantitative measures of plant disease resistance to a given pathogen, e.g., the number or size of lesions, increased growth, survival rate, rate of disease progression, higher root mass, better seed viability, seed quantity and quality, etc. Alternatively, a substantial defense signal peptide activity is present where the peptide, when applied to a plant exogenously or recombinantly expressed within a plant, confers a substantial change in any resistance to a biotic or abiotic stress that involves the jasmonate/ethylene or salicylic acid pathways, as measured by standard methods.

Fusion Polypeptides

The present disclosure also provides fusion polypeptides including, for example, heterologous fusion polypeptides in which a defense signal polypeptide coding sequence is joined to a heterologous promoter (i.e., a promoter from gene other than the promoter that is operably linked to that coding sequence in nature), or in which the coding sequence for the defense signal peptide is joined to a fusion partner, i.e., a protein-coding sequence other than sequences with which the coding sequence for the defense signal peptide is joined in nature. Such fusion polypeptides can exhibit biological properties (such as substrate or ligand binding, enzymatic activity, antigenic determinants, etc.) derived from each of the fused sequences.

Polypeptide Sequence Determination

The sequence of a polypeptide of the present disclosure can be determined by any of the various methods known in the art.

Polypeptide Coupling to a Solid-Phase Support

The polypeptides of the present disclosure can be free in solution or coupled to a solid-phase support, e.g., nitrocellulose, nylon, column packing materials (e.g., Sepharose beads), magnetic beads, or glass wool, by conventional methods.

Antibodies

The present disclosure also encompasses polyclonal and/or monoclonal antibodies capable of specifically binding to a particular defense signal peptide and/or fragments thereof. Such antibodies are raised against a defense signal peptide or fragment thereof and are capable of distinguishing a defense signal peptide from other polypeptides, i.e., are specific for the particular defense signal peptide.

For the preparation and use of antibodies according to the present disclosure, including various immunoassay techniques and applications, see, e.g., Goding, Monoclonal Antibodies: Principles and Practice, 2d ed, Academic Press, New York, 1986; and Harlow and Lane, Antibodies: A Laboratory Manual, Cold Spring Harbor Laboratory, Cold Spring Harbor, N.Y., 1988. Defense signal peptide-specific antibodies are useful, for example in: purifying a defense signal peptide polypeptide from a biological sample, such as a host cell expressing a recombinant defense signal peptide; in cloning a paralog, ortholog, or homolog from an expression library; as antibody probes for protein blots and immunoassays; etc.

Antibodies can be labeled by any of a variety of conventional methods. Suitable labels include, but are not limited to, radionucleotides, enzymes, substrates, cofactors, inhibitors, fluorescent agents, chemiluminescent agents, magnetic particles, etc.

Obtaining Paralogs, Orthologs, and Homologs of Defense Signal Peptides

As discussed in the examples below, defense signal peptides homologous to AtPep1 and other defense signal peptides exist in many plant species. Based upon the availability of the defense signal peptide and polypeptide sequences and their corresponding gene sequences disclosed herein, paralogs and orthologs can be obtained by conventional methods, e.g., by screening a cDNA or genomic library with a probe that specifically hybridizes to a native defense signal peptide sequence under at least moderately stringent conditions, by PCR or another amplification method using a primer or primers that specifically hybridize to a native defense signal peptide or polypeptide sequence under at least moderately stringent conditions, or by screening an expression library using defense signal peptide-specific antibodies.

EDKR Repeat Regions

Highly negatively charged glutamate/aspartate repeat interrupted by lysine/arginine residues in the precursor region of the molecule.

1-5-10 Helix Motifs

The precursor genes encode a hydrophobic motif interrupted by a conserved lysine and cysteine, with a consensus sequence of xXxxxXCxxx, where x denotes some hydrophobic residue, X represents any nonhydrophobic amino acid, and x specifically designates F, I, L, or V. The protein secondary structure prediction programs SSpro version 2.0 (Pollastri et al. 2001) and SSpro8 (Baldi et al. 1999) predict that this region to be helical in gene family members. This consensus sequence coincides with the 1-5-10 calmodulin recognition domain motif, which requires an F, I, L, or V in the 1, 5 and 10 positions interspersed with cationic charges. This motif generates an amphipathic alpha helix that has the potential to interact with calmodulin in the presence of calcium (Rhoads and Friedberg 1997).

Serine Repeat

A stretch of multiple serines in a row in the precursor region. In some precursors, there are stretches of repeated alanines rather than serines. Note that this structural characteristic is common, but does not occur in every precursor.

K/R Positive Region

The region comprising the proposed amino end of the processed peptide, is positively charged, having in *Arabidopsis* between 3 and 7 lysine or arginine residues encoded in this area by each family member. Other plant species may have fewer lysines or arginines here (for instance poplar has just two), but all predicted peptides have at least on lysine or arginine in this region.

Core Peptide Motif

The carboxyl terminal of the predicted peptide region. All orthologs contain the conserved glycine residue at the C-7 position (7 amino acids prior to the predicted carboxy terminus of the peptide). Each precursor also encodes a conserved asparagine or histidine as the final amino acid in the predicted peptide followed by a stop codon. Most dicots encode a serine or threonine in the C-9 position, whereas this position is less conserved in the monocot sequences.

Plant Transformation and Regeneration; Transformed Plant Cells, Plants, and Parts and Products of Transformed Plants Various polynucleotide constructs that include a sequence that encodes a defense signal polypeptide or a defense signal peptide are useful for producing plants having enhanced disease resistance or enhanced resistance to another biotic and abiotic stress that involves the jasmonate/ethylene or salicylic acid pathways.

Polynucleotides that comprise a sequence that encodes a defense related polypeptide or a defense related peptide can be expressed in plants or plant cells under the control of an operably linked promoter that is capable of expression in the plant or plant cell. Any well-known method can be employed for plant cell transformation, culture, and regeneration in the practice of the present disclosure with regard to a particular plant species. Conventional methods for introduction of foreign DNA into plant cells include, but are not limited to: (1) *Agrobacterium*-mediated transformation (Lichtenstein and Fuller In: Genetic Engineering, Vol 6, Rigby, ed., London, Academic Press, 1987; and Lichtenstein and Draper, in: DNA Cloning, Vol II, Glover, ed., Oxford, IRI Press, 1985); (2) particle delivery (see, e.g., Gordon-Kamm et al., Plant Cell 2:603, 1990; or BioRad Technical Bulletin 1687), (3) microinjection (see, e.g., Green et al., Plant Tissue and Cell Culture, Academic Press, New York, 1987), (4) polyethylene glycol (PEG) procedures (see, e.g., Draper et al., Plant Cell Physiol. 23:451, 1982); Zhang and Wu, Theor. Appl. Genet. 76:835, 1988), (5) liposome-mediated DNA uptake (see, e.g., Freeman et al., Plant Cell Physiol. 25:1353, 1984), (6) electroporation (see, e.g., Fromm et al., Nature 319:791, 1986); and (7) vortexing method (see, e.g., Kindle, Proc. Natl. Acad. Sci. USA 87:1228, 1990).

Once a transformed plant cell or tissue has been obtained, it is possible to regenerate a full-grown plant from it. Means for regeneration vary from species to species. In one approach a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable. Plant regeneration is described, for example, in Evans, et al., *Handbook of Plant Cell Cultures, Vol,* 1: (MacMillan Publishing Co., New York, 1983); and Vasil I. R. (ed.), *Cell Culture and Somatic Cell Genetics of Plants*, Acad. Press, Orlando, Vol. I, 1984, and Vol. III, 1986). Practically all plants can be regenerated from cultured cells or tissues, including monocots, dicots, gymnosperms, etc.

After the DNA construct is stably incorporated in transgenic plants, it can be transferred to other plants by sexual crosses or by asexual propagation. With respect to sexual crossing, any of a number of standard breeding techniques can be used depending upon the species to be crossed. Cultivars can be propagated in accord with common agricultural procedures known to those in the field.

The term "plant" encompasses any higher plant and progeny thereof, including monocots, dicots, gymnosperms, and other plants and includes parts of plants, including reproductive units of a plant (e.g., seeds), fruit, flowers, etc.

A "reproductive unit" of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

According to one aspect of the disclosure, plant cells are provided that comprise a polynucleotide sequence that comprises a sequence that encodes a defense signal peptide or polypeptide operably linked to a plant promoter. Another aspect of the disclosure is directed to plants comprising such cells, i.e., transformed or transgenic plants. Another aspect is a part or product of such plants.

Agronomically and commercially important products and/or compositions of matter derived from transgenic plants according to the disclosure include, but are not limited to, animal feed, commodities, products and by-products that are intended for use as food for human consumption or for use in compositions and commodities that are intended for human consumption, including but not limited to plant parts, including but not limited to seeds, seed pods, flowers (including flower buds), fruit, tubers, stems, cuttings, pollen, and products derived from processing such plant parts, including but not limited to flour, meal, syrup, oil, starch, cakes, cereals, and the like. Such compositions may be defined as containing detectable amounts of a polynucleotide sequence as set forth herein, and thus are also diagnostic for any transgenic event containing such nucleotide sequences. These products are more likely to be derived from crops propagated with fewer pesticides and organophosphates as a result of their incorporation of the nucleotides of the present disclosure for controlling plant disease. For example, such commodities and commodity products can be produced from seed produced from a transgenic plant, wherein the transgenic plant comprises cells that express a defense signal protein of the present disclosure.

Identifying Transgenic Plants According to the Disclosure and Parts and Products Thereof Transgenic plants according to the present disclosure, parts of such plants, and products derived from the processing of such plants, can be readily identified by using probes and primers to specifically identify the presence of a transgene that encodes a defense signal peptide or the presence of a specific defense signal peptide. In order to perform such an identification, a biological sample thought to contain such a plant, part or product is contacted with a probe that binds specifically to the transgene containing a defense signal peptide- or polypeptide-encoding polynucleotide (such as one or more PCR primers, cDNA probe, etc.), and detecting such binding (e.g., by identifying the production of an amplification product of a diagnostic size after gel electrophoresis, or by autoradiography). Alternatively, one may use a probe that binds specifically to the defense signal peptide or polypeptide itself, such as an antibody probe, wherein binding can be detected by an enzyme-linked immunosorbent assay (ELISA), etc.

Conferring Resistance to Biotic and Abiotic Stresses to Plants and Enhancing Plant Growth As one aspect of the disclosure, resistance to disease resistance, or to another biotic and abiotic stress that involves the jasmonate/ethylene pathway or the salicylic acid pathway, is conferred on a plant, or resistance may be enhanced in the plant, or growth of the plant is enhanced, by expression of polynucleotides that encode one or more defense peptides in cells of the plant.

As another aspect of the disclosure, methods are provided that comprise growing a seed into a plant, wherein the plant comprises cells comprising a polynucleotide sequence comprising a sequence that encodes a defense signal protein or polypeptide, wherein the plant exhibits one or more of the following: improved yield of plant product, reduced disease symptoms, or enhanced resistance to disease infestation; compared to a control plant lacking the recombinant polynucleotide.

According to another aspect of the disclosure, improved yield, reduced disease symptoms, or enhanced resistance to disease infestation is conferred or enhanced, by application of compositions comprising one or more defense signal peptides to a plant.

Where absolute immunity against infection by a pathogen or detrimental affects or other stresses is not to be conferred, the severity of the disease is reduced and symptom development is delayed. This method of imparting resistance has the potential for enhancing plant resistance to a variety of diseases for which other approaches were ineffective in providing effective control.

The methods of the present disclosure are useful in imparting resistance to a wide variety of pathogens including viruses, bacteria, and fungi.

With regard to the use of the compositions and methods of the present disclosure to enhance plant growth, various forms of plant growth enhancement or promotion can be achieved. This can occur as early as when plant growth begins from seeds or later in the life of a plant. For example, plant growth according to the present disclosure encompasses greater yield, increased percentage of seeds germinated, increased plant size, greater biomass, more and bigger fruit, earlier fruit coloration, earlier flower opening, improved flower longevity (i.e., shelf-life), and earlier fruit and plant maturation. As a result, the present disclosure provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

To confer such enhanced resistance, one may express a single gene copy, or in order to express a defense signal peptide at high levels, e.g., expression of multiple copies of a transgene encoding such a defense signal peptide and/or the use of strong promoters to drive expression may be employed. Expression of a transgene encoding a defense signal peptide in plant cells at a sufficiently high level may initiate the plant defense response constitutively in the absence of signals from the pathogen. A constitutive plant promoter can be used. Alternatively, an inducible promoter, or an organ- or tissue-specific promoter, for example, can be used If a plant cell is selected to be transformed, it may be of any type capable of being transformed, preferably one with an agronomic, horticultural, ornamental, economic, or commercial value. Examples of such plant cells include, but are not limited to: acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf grass, turnip, a vine, watermelon, wheat, yams, and zucchini.

Compositions Comprising Defense Signal Peptides for Application to Plants

According to one embodiment, compositions for application to plants comprise an oil Plowable suspension, comprising purified defense signal peptides or unpurified forms of the peptides, including lysed or unlysed bacterial cells or fractions thereof that contain one or more of the defense signal peptides disclosed herein. Any such bacterial host cell expressing the novel polynucleotides disclosed herein and producing a defense signal peptide is contemplated to be useful, such as *Bacillus* spp., including *B. thuringiensis, B. megaterium, B. subtilis, B. cereus, Escherichia* spp., including *E. coli*, and/or *Pseudomonas* spp., including *P. cepacia, P. aeruginosa*, and *P. fluorescens*.

In another embodiment, compositions for application to plants comprise a water dispersible granule or powder comprising purified or unpurified defense signal peptides.

In another embodiment, compositions for application to plants comprise a wettable powder, spray, emulsion, colloid, aqueous or organic solution, dust, pellet, or colloidal concentrate comprising purified or unpurified defense signal peptides. Such dry forms of the insecticidal compositions may be formulated to dissolve immediately upon wetting, or alternatively, dissolve in a controlled-release, sustained-release, or other time-dependent manner. Alternatively, such a composition may consist of a combination of one or more of the following compositions: lysed or unlysed bacterial cells, spores, crystals, and/or purified crystal proteins.

In another embodiment, compositions for application to plants comprise an aqueous solution or suspension comprising purified or unpurified defense signal peptides. Such aqueous solutions or suspensions may be provided as a concentrated stock solution which is diluted prior to application, or alternatively, as a diluted solution ready-to-apply.

Such compositions may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers. Detergents may be included to facilitate uptake of the defense signal peptides by plant tissues and cells.

Regardless of the method of application, the amount of the active component(s) are applied at an amount that is effective to confer enhanced disease resistance to plants, which will vary depending on such factors as, for example, the specific disease to be controlled, the specific plant or crop to be treated, the environmental conditions, and the method, rate, and quantity of application of the composition.

Such compositions may be made by formulating purified or unpurified defense signal peptides with the desired biologically-acceptable carrier. The compositions may be formulated prior to administration in an appropriate means such as lyophilized, freeze-dried, desiccated, or in an aqueous carrier, medium or suitable diluents, such as saline or other buffer, for example. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art.

The term "biologically-acceptable carrier" refers to all carriers that are compatible with the growth and development of a cultured cell or tissue, an excised plant part, a seed, a plant grown under greenhouse or field conditions, or other biological entity, e.g., aqueous solutions, buffers, adjuvants, etc. that are ordinarily used in connection with the biological entity, including but not limited to any carrier used in bacterial or plant cell or tissue culture and agriculturally-acceptable carriers. The term "agriculturally-acceptable carrier" covers all adjuvants, e.g., inert components, dispersants, surfactants, tackifiers, binders, etc. that are ordinarily used in formulation technology for compositions used in agriculture to be applied to plants, soils, etc. The formulations may be mixed with one or more solid or liquid adjuvants and prepared by various means, e.g., by homogeneously mixing, blending and/or grinding.

Such compositions are applied to the environment of the plant for uptake into plant tissues and cells, typically onto the foliage of the plant or crop to be protected, by conventional methods, such as by spraying. The strength and duration of application will be set with regard to conditions specific to the particular pest(s), crop(s) to be treated and particular environmental conditions. The proportional ratio of active ingredient to carrier will naturally depend on the chemical nature, solubility, and stability of the defense signal protein(s), as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances.

The defense signal peptides may be employed in such compositions singly, in a mixture of defense signal peptides, or in combination with other compounds, including and not limited to other proteins or chemical compounds used for treatment of plants, including but not limited to proteins or chemical compounds used to treat plants for pathogens, insect pests, etc. The method may also be used in conjunction with other treatments such as surfactants, detergents, polymers or time-release formulations.

The compositions of the present disclosure may be formulated for either systemic or topical use. The concentration of insecticidal composition which is used for environmental, systemic, or foliar application will vary widely depending upon the nature of the particular formulation, means of application, environmental conditions, and degree of biocidal activity. Typically, the composition will be present in the applied formulation at a concentration of at least about 0.1% by weight and may be up to and including about 99% by weight. Dry formulations of the compositions may be from about 0.1% to about 99% or more by weight of the composition, while liquid formulations may generally comprise from about 0.1% to about 99% or more of the active ingredient by weight.

The formulation may be administered to a particular plant or target area in one or more applications as needed, with a typical field application rate per hectare ranging on the order of from about 0.1 g to about 1 kg, 2 kg, 5, kg, or more of active ingredient.

Identifying Defense Signal Proteins

According to one aspect of the disclosure, methods are provided for identifying native defense signal peptides from plants and also for screening synthetic peptides for defense signal peptide activity.

A sensitive, rapid "alkalinization assay" (see Examples) is useful for isolate native defense signal peptides from plants or synthetic defense signal peptides produced by chemical synthesis or other means. Cultured plant cells, for example suspension cell cultures that grow at about pH 5 are used. Several laboratories have developed such cell cultures for *Arabidopsis*, tomato (*Lycopersicon esculentum*), tobacco (*Nicotiana tabacum*), alfalfa (*Medicago saliva*), maize (*Zea mays*), petunia (*Petunia hybrida*), nightshade (*Solanum nigrum*), and sweet potato (*Ipomoea batatus*), for example. Within minutes after adding systemin to cells, an ATP-driven proton pump is inhibited, causing the extracellular medium of the cells to become alkaline. When 1-10 μL aliquots from fractions from plant tissues, e.g., leaves, that have eluted from HPLC columns were added to 1 mL of suspension cultured cells, some fractions caused the cell medium to increase in pH. In order to confirm that a candidate peptide is a defense signal peptide, the peptide is applied to a plant as described in the Examples below or a polynucleotide sequence encoding the candidate peptide is expressed in a plant in order to observe whether disease resistance is enhanced in the plant. Confirmation of the identity of a candidate peptide may be obtained by determining whether the peptide induces defense gene expression (for example, of PDF1.2 and PR-1), e.g., by supplying a solution of the peptide to excised leaves through their cut petioles then analyzing transcript levels, e.g., by semi-quantitative RT-PCR.

Identifying Compounds that Interact with Receptors for Defense Signal Proteins and that Enhance Plant Disease Resistance According to another aspect of the disclosure, substances other than peptides and polypeptides, for example, chemical compounds, are screened for their ability to enhance plant defense against diseases. In one approach, the alkalinization assay is used to screen such substances. Candidate substances are added to cultured plant cells and a rise in pH indicates that a candidate substance interacts with a receptor. In a second approach, candidate substances are assayed for binding by an AtPep1 receptor or another receptor for a defense signal peptide. A composition comprising one or more candidate substances that are selected after being screened in an alkalinization assay or receptor binding assay may then be administered to plants in a greenhouse or field trial to assess whether the candidate substance(s) confer enhanced plant defense against a disease. Substances that have activity in conferring enhanced plant defense may be formulated according to standard formulation approaches for application to plants, to seeds, to the soil, etc. The present disclosure also includes compositions comprising an amount of such substances that is effective to enhance plant defense against a disease and a biologically (including agriculturally) compatible carrier. Such compositions may also include other ingredients that are used in formulations for application to plants as detailed above.

Preferred embodiments will be better understood by reference to the following examples, which are intended to merely illustrate the best mode now known for practicing the embodiments. The scope of the disclosure is not to be considered limited thereto.

EXAMPLE 1

Isolation and Analysis of AtPep1 and Paralogs and Orthologs Thereof

Innate immunity is initiated in animals and plants through the recognition of a variety of pathogen associated molecules that in animals are called "pathogen-associated molecular patterns," or PAMPS, and in plants are called elicitors. Peptides derived from pathogens can be powerful elicitors of plant defense responses (Hahlbrock et al., Proc. Natl. Acad. Sci. USA 92:4150-4157, 1995; van den Askerveken et al., Plant Physiol. 103:91-96, 1993; Kammpren, Curr. Opin. Plant Biol. 4:295-300, 2001; Kunze et al., Plant Cell, 16:3496-3507, 2004; Navarro et al., Plant Physiol. 135:1113-1128, 2004; Fellbrich et al., Plant J. 32:375-390, 2002; He et al., Cell 73:1255-1266, 1993), but plant-derived peptides have not been identified previously that are elicitors of immune responses directed against pathogens.

We have isolated and characterized a 23 amino acid peptide, called AtPep1, that is a signaling component of the innate immune system of *Arabidopsis*. The peptide precursor gene is transcribed in response to elicitors generated by pathogens, and AtPep1 is produced to amplify the signaling pathways. Seven paralogs of the AtproPep1 gene are present in the *Arabidopsis* genome, and orthologs have been identified in species of several agriculturally important families including Solanaceae, Poaceae, Salicaceae, Vitaceae, and Fabaceae. AtPep1 and its paralogs and orthologs play important roles as endogenous signals to amplify innate immunity.

Materials and Methods

Plant growth conditions. *Arabidopsis thaliana* ecotype Columbia seeds were grown in soil in four-inch square pots for six days under low light at approximately 18° C. Germinated seedlings were then grown under day lengths of 16 hours at 21° C. Mutant plants were grown in autoclaved soil.

Alkalinization Assay. *Arabidopsis* suspension cells were grown with shaking in the dark in 125 mL flasks, using 40 mL NT media as previously described (Pearce et al. Proc. Natl. Acad. Sci. USA 98:12843-12847, 2001). The cells were transferred weekly (2.5 mL) and used for assays 3-5 days after transfer. One mL aliquots of cells were transferred to wells of 24-well culture plates and allowed to equilibrate for one hour while agitated on a rotary shaker at 160 rpm. Aliquots of 1-10 μL from extracts or fractions eluted from HPLC columns were added to cells and the pH of the media was monitored after 20 min.

Purification of AtPep1. *Arabidopsis thaliana* (Columbia ecotype), 28 days after planting, consisting of rosettes, flowers, stems and seed pods, were harvested, frozen in liquid nitrogen, ground to a powder, and stored at −20° C. Peptides were extracted from 600 g of powder as previously described (Pearce et al., Nature 411:817-820, 2001; Pearce and Ryan, J. Biol. Chem. 278:30044-30050, 2003), using 1200 mL 1% trifluoroacetic acid (TFA). The clear extract was applied to a reversed-phase C18 flash column (Bondesil, Varian Analytical Instruments, Walnut Creek, Calif.) that was equilibrated with 0.1% TFA/$H_2O$. After washing with equilibration buffer, the column was eluted with 50% methanol/0.1% TFA. The eluate was vacuum-evaporated and lyophilized to dryness. This material was dissolved in 0.1% TFA and chromatographed on a G-25 Sephadex column (2.5×33 cm), and the fractions were monitored with the alkalinization assay. The broad peak of activity that eluted between 1-1.5 void volumes was collected and lyophilized. The yield of dry powder was 109 mgs.

Two hundred forty mg of the powder was dissolved in 9 mL of 0.1% TFA/$H_2O$, centrifuged, and the clarified solution was applied to a 5 micron, 10×250 mm semi-preparative C18 column (#218TP510, Vydac, Hesperia, Calif.) with a flow rate of 2 ml/min and monitored at 225 nm. After 2 min, a gradient from 0-40% acetonitrile/0.1% TFA was applied to the column and 1 min fractions were collected and assayed as above. A defined activity peak was identified in fractions 36-37 and designated *Arabidopsis* Peptide 1 (AtPep1). AtPep1 was further purified by strong cation exchange chromatography on a 5 μm, 4.6×200 mm PolySulfoethyl Aspartamide™ column (The Nest Group, Southborough, Mass.) equilibrated with 5 mM potassium phosphate, pH 3, in 25% acetonitrile. Two min after applying AtPep1 to the column, a gradient of 0-100% elution buffer consisting of 5 mM potassium phosphate, 1 M potassium chloride, pH 3, in 25% acetonitrile was applied for 60 min. Absorbance was monitored at 214 nm and the flow rate was 1 mL/min. Fractions were collected at minute intervals and 10 μL aliquots were assayed for alkalinization activity. The fractions with activity, 58 and 59, were pooled and lyophilized. Further purification of AtPep1 was performed on a narrow-bore reversed-phase 218TP52, 5 μm, 2.1×250 mm C18 column (Vydac, Hesperia, Calif.) that had been equilibrated with 0.1% TFA/$H_2O$. The lyophilized material was dissolved in the equilibration buffer and applied to the column. After two min, a gradient of 0-50% acetonitrile in 0.1% TFA was applied over 90 min with a flow rate of 0.25 mL/min, and monitored at 214 nm. Fractions were collected at 1 min intervals and assayed as above. The activity was present in fractions 48-50, which were pooled and lyophilized. Further purification was obtained on the same narrow-bore column but using a 0-50% methanol/0.05% TFA gradient over 90 min for elution. The activity was found exclusively in fractions 63-64. These fractions were pooled and subjected to amino acid sequence analysis and MALDI-mass spectroscopy.

Peptide sequence analysis and synthesis. N-terminal sequence analysis was performed using Edman chemistry on an Applied Biosystems Procise Model 492 protein sequencer. MALDI-mass spectroscopy was performed on a PerSeptive Biosystems Voyager time-of-flight mass spectrometer equipped with a nitrogen laser (337 nm) with α-cyano-4-hydroxycinnamic acid as the matrix. Peptide synthesis was performed using Fmoc (N-(9-fluorenyl)methoxycarbonyl) chemistry by solid phase techniques using an Applied Biosystems Model 431 synthesizer. Synthetic peptides were purified by reversed-phase C18 HPLC. Peptide stocks (250 μM) were assayed for purity and the mass verified with a Finnigan LC/Q mass spectrometer using direct injection.

Plant stress and hormone treatments. To examine effects of cold stress, plants were placed in a refrigerated growth chamber set to 2° C. To simulate drought stress conditions, plants grown under standard growth chamber conditions were grown without watering. Methyl jasmonate (Bedoukian Research Inc., Danbury Conn.) was applied as a 625 μM solution in 0.1% Triton X-100 to the upper surface of leaves and the plants were incubated in plexiglass boxes. Methyl salicylate (Sigma-Aldrich, St. Louis Mo.), was applied to leaf surfaces at 2 mM in a 0.1% Triton X-100 solution. Ethephon (Phytotechnology Laboratories, Shawnee Mission Kans.) was sprayed on plants as a 7 mM solution in 0.1% Triton X-100 (Sigma-Aldrich, St. Louis Mo.). ABA effects were analyzed by spraying plants with a 100 μM solution (mixed isomer, Sigma-Aldrich, St. Louis Mo.) in 0.1% Triton X-100 (Denekamp and Smeekens, Plant Physiol. 132, 1415-1423, 2003).

Excised-leaf assays. AtPep1 peptide dissolved in double distilled water was supplied to excised leaves of 3 to 4 week old *Arabidopsis* plants. Leaves were excised and the petioles were immersed in 800 μL centrifuge tubes containing either the peptide solution or distilled water, and placed in a closed clear plexiglass box containing a thin layer of water for humidity, and a small opening to allow air to enter. Boxes were incubated in a growth chamber under the plant growth conditions described above and sprayed with a fine mist of distilled water every half hour to ensure humidity and prevent wilting. To determine variations in basal levels of the AtproPep1 transcript among assays, four different leaves from four different plants were used for each treatment, and leaves supplied with either water or AtPep1 were taken from the same plants. Assays were terminated by immersing the leaves in liquid nitrogen.

Hydrogen peroxide accumulation was visualized using diaminobenzidine (DAB) (Thordal-Christensen et al., Plant J. 11:1187-1194, 1997).

Semi-quantitative RT-PCR analysis of relative gene expression levels. RNA was isolated using Trizol reagent and manufacturer's instructions (Invitrogen. Carlsbad Calif.), and 2 μg of RNA template was reverse transcribed with a RETROscript kit (Ambion, Austin Tex.). PCR reactions were carried out with ExTaq Hot Start polymerase and reagents (Fisher Scientific, Pittsburgh Pa.). The AtproPep1 forward and reverse primers with the respective sequences of 5' CTT ATC AGA TCT CAA TGG AGA AAT C 3' (SEQ ID NO: 59) and 5' CAA TGT AAC TTA AAG TGC CTA ATT ATG 3' (SEQ ID NO: 60) generated a 310 bp intron-spanning product. Primers to β-tubulin (At5g62690) of 5' CAA CGC TAC TCT GTC TGT CC 3' (SEQ ID NO: 73) and 5' TCT GTG AAT TCC ATC TCG TC 3' (SEQ ID NO: 74) generated a 681 base pair intron-spanning product. An initial denaturing/polymerase activating step of 5 minutes at 94° C. was followed by 31 repetitions of the following three steps: a thirty second denaturation phase at 94° C., a thirty second annealing period at 55.5° C., and a one minute elongation step at 72° C. The amplification program was terminated with a 10 minute final 72° C. elongation phase.

The products of each reaction were separated by electrophoresis and were visualized on a Bio Imaging System (SynGene, Frederick Md.) using GeneSnap version 6.00.26 software (SynGene, Frederick Md.). A high resolution image of the gel was analyzed using GeneTools analysis software version 3.02.00 (SynGene, Frederick Md.). Relative band intensities for each band were normalized to the β-tubulin band. A numerical ratio of amplified AtproPep1 cDNA to amplified tubulin cDNA was obtained for every sample. To calculate average values, semi-quantitative RT-PCR assays were performed in duplicate, and RNA extractions were performed in triplicate.

Transformation of *Arabidopsis* with a CaMV 35S:proAtPep1 gene. Genomic DNA was isolated from *Arabidopsis* leaves using the DNAzol reagent (Invitrogen, Carlsbad Calif.). The genomic sequence encoding AtproPep1 was amplified using a forward primer 5' ATA AAG AGT CAC ACC CAA TAC CG 3' (SEQ ID NO: 76) and a reverse primer 5' TGA TAC TGG TTA TGA ACT TAT GAT GG 3' (SEQ ID NO: 77) to generate a 1078 base pair product. A 5' Xho I recognition site and a 3' BamH I site were amplified onto the genomic fragment for ligation into the pART-7 vector (Gleave, Plant Mol. Biol. 20:1203-1207, 1992). Both the proAtPep1 genomic product and the pART-7 vector were digested with BamH I and Xho I enzymes (Promega Biosciences Inc., San Luis Obispo Calif.), and ligated using the LigaFast rapid DNA ligation system (Promega Biosciences Inc., San Luis Obispo Calif.). The construct was transformed into chemically-competent *E. coli* TOPIOF' cells (Invitrogen, Carlsbad Calif.) that were plated out on LB-ampicillin (50 μg/mL): A plasmid clone containing the full AtproPep1 genomic DNA insert with no nucleotide errors was used to generate an AtproPep1/pBART construct. Both pBART and AprotPep1/PART-7 plasmid were digested with Not I (Promega Biosciences Inc., San Luis Obispo Calif.) to enable ligation of the CaMV 35S/AtproPep1 expression cassette into the digested pBART plasmid using the Promega LigaFast kit (Promega Biosciences Inc., San Luis Obispo Calif.). An empty pART-7 vector was digested with Not I to generate a control pBART construct. TOPIOF' chemically competent cells were transformed with the constructs and grown in Luria-Berftani media containing 100 μg/mL spectinomycin (Sigma-Aldrich, St. Louis Mo.), 40 μL of a 40 mg/mL solution of X-Gal (Sigma-Aldrich, St. Louis Mo.) and 40 μL of a 100 mM IPTG (Sigma-Aldrich, St. Louis Mo.) stock. A pBART clone containing the CaMV 35S/proAtPep1 construct, and a second clone containing the empty CaMV 35S construct, were transformed into *Agrobacterium tumefaciens* strain AGLO cells (Lazo and Ludwig, Biotechnology (N Y) 9:963-967, 1991) by electroporation using a BioRad electroporator (BioRad Laboratories, Hercules, Calif.). The transformed cells were grown on 2XYT media (Lazo et al., Biotechnology (N Y) 9:963-967, 1991) containing 100 μg/mL spectinomycin, and viable colonies were screened using RT-PCR with the pART F and pART R primers.

Liquid cultures of *Agrobacterium* carrying the CaMV 35S: AtproPep1 or empty CaMV 35S constructs were grown in 2XYT media and used for floral dip transformation of *Arabidopsis* plants (Clough and Bent, Plant J. 16:735-743, 1998). Transformed plants were grown to maturity, and the seed was collected and planted. Newly germinated seedlings were treated with a 350 μM solution of the herbicide BASTA (glufosinate ammonium, brand name Finale; Farnam Companies Inc., Phoenix Ariz.) four times at three day intervals, and healthy plants were screened for the proAtPep1 transgene via PCR. Plants that were both glufosinate-resistant and that amplified products of the appropriate size were grown to maturity and the seeds planted to recover T2 progeny.

Growth and inoculation of plants with *Pythium irregulare*. Two strains of the oomycete root pathogen *Pythium irregulare*, strain 110305) were grown on water-agar (1%) plates for maintenance of stock cultures and, after growing at room temperature in the dark for one week, were stored at 4° C. *Pythium* stocks for infection assays were grown on 1× potato dextrose agar (Sigma-Aldrich, St. Louis Mo.) in the dark for one week at room temperature.

Week-old *P. irregulare* cultures were scraped from the plates into 20 mL of sterile distilled water, the mixture was lightly ground with a mortar and pestle to produce a uniform suspension. Aliquots (250 μL) of the suspension or water were pipetted into the soil of plants having a rosette diameter of 2-3 cm. Plants were grown for 25 days as described above and assayed. The experiments were repeated five times. After two and a half weeks, the plants were photographed to show rosette morphology, and at three and a half weeks were harvested and the roots examined. The day prior to harvest, plants were not watered, so that the soil would easily separate from the roots. Soil was gently rinsed from the roots of each plant with water, taking care to minimize damage, and each plant was trimmed at the base of the rosette to fully expose the root structure, and photographed.

Identification the AtproPep1 gene and homologous genes. The gene locus encoding the AtPep1 peptide precursor was identified using the National Center for Biotechnology Information (NCBI) TBLASTN version 2.2.7 algorithm (Altschul et al., Nucleic Acids Res. 25:3389-3402, 1997) to search genomic sequences from *Arabidopsis thaliana*. To determine possible localization of the protein in the cell, several predictive programs were employed, including pSORT (Nakai and Kanehisa, Proteins 11:95-110, 1991), ChloroP41 and MitoProt (Emanuelsson et al., J. Mol. Biol. 300:1005-1016, 2000; Emanuelsson et al., Prot. Sci. 8:978-984, 1999). Orthologs to the AtproPep1 gene were identified using the NCBI TBLASTN version 2.2.7 and Institute of Genomic Research (TIGR) TBLASTN 2.0 MP algorithms (Gish, TBLASTN 2.0 MP-WashU [27 Aug. 2000] [linux-i686 21:46:47 28 Aug. 2000] Copyright1996-2000 Washington University, Saint Louis, Mo. USA. [http://blast.wustl.edu]). The predicted protein sequence for each was aligned using the program Clustal W version 1.8, available at the Baylor College of Medicine Search Launcher website.

Analysis of gene expression using RT-PCR. Gene expression was analyzed using RT-PCR (Nishimura et al., Plant Cell 16:1365-1377, 2004). Forward and reverse primers used for RT-PCR analysis are shown in Table 6.

Results

We have isolated a 23 amino acid peptide called AtPep1 from extracts of *Arabidopsis* leaves that exhibits characteristics of an elicitor of the innate immune response. Endogenous peptide elicitors of innate immunity have not been previously known. The identification and isolation of the peptide from soluble extracts of *Arabidopsis* leaves was facilitated by its ability, at sub-nanomolar concentrations, to cause an alkalinization response that is typical of elicitors (Moyen and Johannes, Plant Cell Environ. 19:464-470, 1996; Felix and Boller, Plant J. 7:381-389, 1999; Pearce et al.; Proc. Natl. Acad. Sci. USA 98:12843-12847, 2001; Pearce et al., Nature 411:817-820, 2001; Pearce and Ryan, J. Biol. Chem. 278: 30044-30050, 2003).

A bioactive component, AtPep1, was identified and purified to homogeneity. Peptides present in a 1% TFA/water extract of *Arabidopsis* tissues were passed through a reverse phase semi-preparative C18 flash chromatography column and separated on a G-25 Sepharose column. The breakthrough peak was applied to a C18 HPLC column and 10 μL from 2 mL fractions from the column were assayed for alkalinization activity. The peak identified as AtPep1 was further purified through two additional chromatography steps and finally purified by narrow bore HPLC. Fractions were assayed for alkalinization activity and the active peak was analyzed by MALDI mass spectroscopy. The amino acid sequence of the purified peptide was determined by Edman degradation. Its identity as a peptide was established by its molecular mass (M/Z, 2492.65) and amino acid sequence (from amino terminus to carboxy terminus, ATKVKAKQRGKEKVSSGRPGQHN (SEQ ID NO: 1; see Table 1) with a calculated molecular mass of 2491.8). The kD determined by mass spectroscopy matched the kD calculated from the amino acid sequence, indicating that the peptide was not post-translationally modified. The chemically synthesized peptide was found to be as active as the native AtPep1, with a ½ maximal activity of 0.25 nM.

The sequence of AtPep1 was identified in GenBank as being derived from the accession At5g64900, which encodes a small protein of 92 amino acids, with its C-terminal 23 amino acids comprising AtPep1. FIG. 1 shows the amino acid sequence of the AtPep1 precursor protein, AtproPep1, deduced from the protein encoded by the gene At5g64900. The AtPep1 sequence at the carboxyl terminus of the precursor protein, is underlined. The amino acid sequence of the precursor protein is highly charged and lacks a leader sequence, indicating that it is not synthesized through the secretory pathway, but rather on cytoplasmic ribosomes.

Expression analysis of AtproPep1 in response to abiotic and biotic cues. As a first step in seeking a possible function for AtproPep1 and its encoded peptide, the basal expression level of the gene was assessed in leaves, stems, roots and flowers of *Arabidopsis* plants was studied using semi-quantitative RT-PCR analysis of AtproPep1 gene expression in response to treatment of leaves with MeJA, ethephon, MeSA, and AtPep1. The relative abundance of the proAtPep1 transcript was estimated from the expression of the β-tubulin gene as a control. Leaves were wounded by crushing once across the mid-vein with a hemostat. Plants were sprayed with a 250 μM solution of MeJA in 0.1% Triton X-100; with a 2 μM solution of MeSA in 0.1% Triton X-100 or with a 7 mM solution of ethephon in 0.1% Triton X-100. AtPep1 peptide (10 nM in water) was supplied through cut petioles of excised leaves. Total RNA was extracted and analyzed. The forward and reverse primers for real-time PCR (RT-PCR) analysis are shown in Table 6 below.

TABLE 6

RT-PCR primers

| Gene | Primers | Product size |
|---|---|---|
| AtproPep1 | SEQ ID NO: 59: 5' CTTATCAGATCTCAATGGAGAAATC 3' (F*) | 310 bP |
| (At5g64900) | SEQ ID NO: 60: 5' CAATGTAACTTAAAGTGCCTAATTATG 3' (R) | |
| PDF1.2 | SEQ ID NO: 61: 5' ATGGCTAAGTTTGCTTCCA 3' (F) | 243 bP |
| (At5g44420) | SEQ ID NO: 62: 5' TTAACATGGGACGTAACAGATAC 3' (R) | |
| PR-1 | SEQ ID NO: 63: 5' GGAGCTACGCAGAACAACTA 3' (F) | 306 bP |
| (At2g14610) | SEQ ID NO: 64: 5' AGTATGGCTTCTCGTTCACA 3' (R) | |
| TAT3 | SEQ ID NO: 65: 5' TACAGGGGTAGTTCAAGCAA 3' (F) | 330 bp |
| (At2g24850) | SEQ ID NO: 66: 5' CCTAGAGCCACTCCTGGTAT 3' (R) | |
| LOX2 | SEQ ID NO: 67: 5' ACGGTAGAAGACTACGCACA 3' (F) | 312 bp |
| (At3g45140) | SEQ ID NO: 68: 5' TAAGGTCTCGAGCTCCTCTT 3' (R) | |
| VSP2 | SEQ ID NO: 69: 5' CAAAATATGGATACGGGACA 3' (F) | 317 bp |
| (At5g24770) | SEQ ID NO: 70: 5' ATTGCCAACGATGTTGTATC 3' (R) | |
| ATTI3 | SEQ ID NO: 71: 5' TGGCAATGAAGTCAGTTTCT 3' (F) | 231 bp |
| (At2g43530) | SEQ ID NO: 72: 5'AGAAGTCGCAGAAGCACTTA 3' (R) | |
| β-tubulin | SEQ ID NO: 73: 5' CAACGCTACTCTGTCTGTCC 3' (F) | 681 bp |
| (At5g62690) | SEQ ID NO: 74: 5' TCTGTGAATTCCATCTCGTC 3' (R) | |

*F = Forward primers; R = Reverse primers.

The AtproPep1 gene was expressed at low levels in all tissues, giving no clues as to its possible function. Monitoring the expression of AtproPep1 in intact plants exposed to different environmental conditions and chemicals, including drought and cold stress, UV-B irradiation, wounding, methyl jasmonate (MeJA), methyl salicylate (MeSA), abscissic acid (ABA) and Ethephon®, provided more definitive clues. Whereas most treatments did not cause changes in expression of AtproPep, wounding, MeJA, ethephon, and AtPep1 all induced expression of AtproPep1, indicating a possible relationship of the gene and its encoded peptide in plant defense. Transcription of the gene in response to wounding was detected within about 8 h, whereas spraying the plants with a 250 μM solution of MeJA or 7 mM ethephon induced a strong expression of the gene within an hour. Supplying 10 nM AtPep1 through cut petioles of excised leaves induced expression of the AtproPep1 gene within two hours.

AtPep1 regulates transcription of pathogen defense genes. The expression of AtproPep1 in response to MeJA and ethylene (Et) suggested that the encoded peptide might have a role in activating innate immunity in *Arabidopsis*, although an endogenous peptide had not previously been reported in the innate immune system of any plant. The jasmonic acid (JA)/Et signaling pathway in *Arabidopsis* activates the expression of defensive genes including PDF1.2 (defensin), while the salicylic acid (SA) pathway activates several pathogen-related (PR) genes (Penninckx et al., Plant Cell 8:2309-2323, 1996; Lorenzo et al., Plant Cell 15:165-178, 2003; Zimmerli et al., Plant J. 40:633-646, 2004; Penninckx et al., Plant Cell 10:2103-2113, 1998; Hammond-Kosack and Parker, Curr. Opin. Biotechnol. 14:177-193, 2003; Mauch-Mass and Matreau, Ann. Bot. 82:535-540, 1998).

In order to determine whether AtPep1 regulates defense gene expression, we determined the fold induction of defense related genes in excised *Arabidopsis* leaves in response to 10 nM AtPep1 supplied through their cut petioles. After 2 hr, transcript levels were analyzed for expression levels of PDF1.2 (defensin), PR-1 (pathogenesis-related 1) LOX2 (lipoxygenase 2), VSP2 (vegetative storage protein2) and ATTI3 (*Arabidopsis thaliana* trypsin inhibitor 3), relative to levels in untreated excised leaves. Expression was determined by semi-quantitative RT-PCR using a β-tubulin gene as a control. Supplying excised *Arabidopsis* leaves with solutions of AtPep1 through their cut petioles induced a strong expression of PDF1.2 and PR-1.

We also performed similar assays with an *Arabidopsis* triple mutant (fad3-2, fad7-2, fad8; McConn and Browse, Plant Cell 8:403-416, 1996) that is incapable of synthesizing jasmonic acid, and a mutant (ein2-1; Guzman and Ecker, Plant Cell 2:513-523, 1990) that is incapable of perceiving ethylene. AtPep1 was supplied at 10 nM for 2 hr, and RNA isolated and assayed by semi-quantitative RT-PCR for gene expression levels. AtPep1 did not induce the expression of AtproPep1, PDF1.2 or PR-1. These experiments suggested that AtPep1 acts upstream from the JA/Et and SA pathways to activate PDF1.2, PR-1 and AtproPep1.

We also studied the accumulation of $H_2O_2$ in leaves supplied for 2 hr with water, 10 nM AtPep1, or with 10 nM AtPep1, all containing 1 mg/mL of DAB to visualize $H_2O_2$ accumulation. Leaves treated with AtPep1 and DAB were also co-supplied with 100 μM DPI, an inhibitor of NADPH oxidase. We also studied the transcription of PDF1.2 and PR-1 in leaves of wild type plants in response to supplying with 10 nM AtPep1 in the presence or absence of DPI (diphenylene iodonium chloride), an inhibitor of NADPH oxidase in both plants and animals (O'Donnell et al., Biochem. J. 290:41-49, 1993). The expression of each gene was analyzed by RT-PCR and compared to expression in excised plants treated only with water. The results indicated that reactive oxygen species (ROS) generated in both the JA/Et and SA pathways is required for PDF1.2 and PR-1 transcription (Penninckx et al., Plant Cell 8:2309-2323, 1996; Hammond-Kosack and Parker, Curr. Opin. Biotechnol. 14:177-193, 2003; Mackerness et al., Plant Cell and Environ. 22:1413-1423, 1999).

AtproPep1 over-expression in *Arabidopsis* enhances innate immunity. *Arabidopsis* plants were transformed with a CaMV-35S-AtproPep1 transgene in order to assess the effects of the constitutive synthesis of AtPep1 on the expression of defense genes using semi-quantitative RT-PCR. In previous studies, overexpression of the tomato prosystemin precursor gene (McGurl et al., Proc. Natl. Acad. Sci. USA 91:9799-9802, 1994) caused a constitutive over-expression of defense genes. This is apparently due to the constitutive synthesis of prosystemin in the cytoplasm of cells (prosystemin, like AtproPep1, lacks a leader sequence) where it is processed to systemin. Analysis of transgenic *Arabidopsis* plants overexpressing AtproPep1 behaved in a similar manner as the prosystemin gene in that it caused an over-expression of defense genes, in this case of PDF1.2 and PR-1. The fold expression of the various genes (compared to wild type) was found to be: AtproPep1, 12.7±6.4; PDF1.2, 4.4±0.5; PR-1, 2.1±0.4; LOX2, 1.0 ±0.2; VSP-2, 0.9±0.1; and ATTI3, 1.2±0.1. These results indicated that plants over-expressing AtproPep1 were synthesizing AtPep1 in the absence of pathogen attacks or elicitors, constitutively signaling the defense response.

Transgenic *Arabidopsis* plants constitutively over-expressing AtproPep1 were assayed for enhanced resistance against a root pathogen, *Pythium irregulare*, an oomycete that has been employed previously to demonstrate the effects of signaling mutants of *Arabidopsis* on disease resistance (Staswick et al., Plant J. 15:747-754, 1998; Vijayan et al., Proc. Natl. Acad. Sci. USA 95:7209-7214, 1998). The soils of young wild type (Columbia) and transgenic plants overexpressing a 35S:AtproPep1 gene (having rosette diameters of 2-3 cm) were inoculated with either a suspension of *Pythium irregulare* strain 110305 propagules, or with sterile water, and the plants were grown for 25 days post-inoculation. Five repetitions were performed with 16 plants of each genotype in each experiment. The aerial parts of the wild type plants inoculated with *Pythium* were slightly smaller than uninoculated wild type or transgenic plants. However, the roots of plants from duplicate experiments in which the root masses of uninoculated wild type and transgenic plants are compared to the roots of inoculated wild type and transgenic plants clearly showed that the over-expression of AtproPep1 had enhanced the resistance of the plants toward the root pathogen.

AtProPep1 paralogs. AtproPep1 belongs to a seven-member gene family in *Arabidopsis* of which one gene is unannotated. Three paralogs, At5g64890, At5g64900 (AtproPep1), and At5g64905, are sequentially encoded in a 5.5 kilobase region of chromosome V (NCBI *Arabidopsis* Genome Database). Paralogs At5g09980 and At5g09990 and the unannotated gene are also found on chromosome V, but in a 3.8 kb region at a distal region on the second arm of the chromosome. At2g22000 is found on chromosome II. In comparing the amino acid sequences of the open reading frames of the paralogs, a low overall amino acid sequence identity was found, but within the C-terminal region of each gene where the putative AtPep1 sequences reside, the amino acid identities ranged from 35% to 65%. Four genes, At5g64905, At5g64900, At5g64890 and At5g09980, are expressed relatively strongly in excised *Arabidopsis* leaves in response to supplying either AtPep1 through cut petioles, or by spraying with MeJA. However, spraying plants with MeSA strongly induced only two of the genes that are induced by AtPep1 and MeJA, i.e. At5g64890 and At5g64905. This differential regulation of AtproPep1 paralogs suggests that a complex signaling network is at play in the leaves, and that cross-talk occurs between the JA/Et and SA pathways, regulating the expression levels of the paralogs. This differential expression of AtproPep1 paralogs was also found in the results from several recent microarray analyses of *Arabidopsis* genes transcribed in response to pathogens and elicitors. In these analyses the AtproPep1 paralogs were included without any knowledge of their possible signaling roles.

We performed a transcript analysis in order to determine the increases in transcription of AtproPep1 paralogs in *Arabidopsis* leaves in response to the pathogens *P. infestans* (oomycete), *B. cineria* (fungus), and *Ps. syringae* DC 3000 (bacteria) (Toufighi et al., Plant J. 43:153-163, 2005; Craigon et al., Nucleic Acids Res. 32:D575-577, 2004), and to the elicitors NPP1, HrpZ, flg22, and elf18, derived from oomycetes, and bacteria, respectively (Kammpren, Curr. Opin. Plant Biol. 4:295-300, 2001; Kunze et al., Plant Cell, 16:3496-3507, 2004; Navarro et al., Plant Physiol. 135:1113-1128, 2004; Felibrich et al., Plant J. 32:375-390, 2002); He et al., Cell 73:1255-1266, 1993). All of these treatments strongly induce the transcription of At5g64890 and At5g64905, the two paralogs that are strongly induced by treating leaves with MeJA, MeSA and AtPep1. However, the lack of induction of At5g64900 by the pathogens, a gene induced by MeJA and AtPep1, and the induction of At5g64900, At5g64890 and At5g64905 by elicitors as well as by the pathogens, indicates that differential induction of the AtproPep family of genes may be governed by the types of elicitors related to individual pathogens. The data presented herein supports a model in which the paralogs At5g64900, At5g64905, and At5g64890 are transcribed in response to elicitors of the JA/Et signaling pathway, while the genes At5g64905, and At5g64890 are transcribed in response to elicitors of SA. The nascent proproteins or processed peptides are transported to the apoplast, where they interact with a cell surface receptor(s) to amplify the immune response. Thus, the AtproPep1 paralogs are components of an amplification system for a broad spectrum of elicitors that activate the innate immune response.

Discussion

Some fundamental similarities are found among signaling components of animal and plant innate immune systems, including the recognition of PAMPS and/or elicitors from pathogens, the involvement of LRR receptor kinases that monitor the signals, and the resulting activation of defense gene transcription of genes involved in early steps of innate immunity. Several peptides originating from plant pathogens can activate the plant innate immune response, including Pep13, AVR9, and elicitins derived from fungi (Hahlbrock et al., Proc. Natl. Acad. Sci. USA 92:4150-4157, 1995; van den Askerveken et al., Plant Physiol. 103:91-96, 1993; Kammpren, Curr. Opin. Plant Biol. 4:295-300, 2001), and the peptides hrpZ, NPP1, flg22 and elf13 from bacteria (Kunze et al., Plant Cell, 16:3496-3507, 2004; Navarro et al., Plant Physiol. 135:1113-1128, 2004; Fellbrich et al., Plant J. 32:375-390, 2002; He et al., Cell 73:1255-1266, 1993), as examples. However until this report endogenous plant peptides have not been reported that are involved with signaling roles directed against pathogen attacks. We have discovered a family of genes that encode small peptides are rapidly and are strongly transcribed along with defense genes in response to pathogens and their elicitors, appearing to assure a rapid, strong amplification of the innate immune response. The low expression or lack of expression of some of the AtproPep genes demonstrates that the paralogs are differentially expressed in response to pathogen infections and elicitors. Fusions of all paralogs with green fluorescent protein (GFP) and beta-glucuronidase (GUS) are used to investigate expression of the paralogs to determine their tissue-specific expression and their roles in defense responses.

The induction of the defense responses by AtPep1 is mediated by a binding protein on the cell surface of *Arabidopsis* suspension cultured cells that interacts with AtPep1 with the characteristics of a receptor, further supporting the fundamental concept proposed in the model described above in which the AtproPep1 paralogs serve as components of an amplification system for a broad spectrum of elicitors that activate the innate immune response.

Searches of plant genomic databases and EST collections identified AtproPep orthologs in species from several plant families. Table 1, supra, shows the C-terminal sequences of paralogs and orthologs of AtproPep1 aligned with the AtPep1 peptide sequence. Paralogs are grouped above and dicot and monocot orthologs are grouped below.

The regions with the highest amino acid identities among the deduced proteins occur within the C-terminal residues of each where the AtPep homologs are found. The deduced canola peptide exhibited the highest identity with the AtPep peptides, being a Brassicaceae species. All of the putative AtPep homologs have a conserved glycine at residue #17 (numbers aligned with AtPep1), and all but paralogs from the Poeceae family contain an asparagine at residue #23. Each peptide contains several proline, glycine, and serine residues within a 10 amino acid C-terminal region that may be important for receptor recognition.

The chemical and physiological properties of the AtPep1 family members, their precursor proteins, and their genes, are strikingly similar to the properties of the 18 amino acid peptide signal systemin, its precursor prosystemin, and its gene, that are components of the signaling pathway for defense against herbivorous pests of the Solanaceae family (Ryan and Pearce, "Peptide hormones/systemins," in Encyclopedia of Biological Chemistry, ed. Lennarz and Lane, vol 3, pp. 381-384, Elsevier, 2004). Both AtPep1 homologs and tomato systemin homologs are cleaved from the carboxy (C)-termini of precursor proteins that lack leader peptides, both precursors are small, highly positively charged proteins, and each activates defense genes. The mechanism for processing AtPep1 is not known, nor is it known if it is the AtPep1 or its peptide precursor that is transported to the apoplast, or if more than one receptor is involved in recognizing the different peptides.

These results indicate that the major role for receptor-mediated defense-signaling peptides in plants is to amplify signaling that is initiated by wounding and elicitors to mount a rapid, strong defense against herbivores and pathogens. If AtproPep orthologs behave in the same manner when over-expressed in other plant species by constitutively expressing defense genes, they may provide an important new approach to enhance innate immunity in a broad spectrum of agriculturally important crops.

EXAMPLE 2

An LRR Receptor Kinase is a Component of AtPep1 Amplification of Innate Immunity in *Arabidopsis*

Over 200 LRR receptor kinases are present in the *Arabidopsis* genome. Only a few LRR receptor kinases have been identified that interact with the peptide signals in plants. This includes the receptor for the defense peptide signal, systemin (Scheer and Ryan, Proc. Natl. Acad. Sci. 99:9585-9590, 2002) and receptors for the developmental peptide signals CLAVATA1 (Clark and Meyerowitz, Cell 89:575-585, 1997), phytosulfokine-alpha (Matsubayashi et al., Science 296: 1470-1472, 2002) and the pathogen-derived peptide flg22 (Gomez-Gomez and Boller, Trends Plant Sci. 7:251-256, 2000).

The discovery that the AtPep family of endogenous peptides from *Arabidopsis* leaf extracts cause an alkalinization of the medium of *Arabidopsis* suspension cultured cells indicates that the peptide plays a role in plant cells by interacting with a cell surface receptor. Investigations of the biological role of the peptide in *Arabidopsis* plants indicated that it activates the innate immune system of the plants and functions through an interaction with a cell surface receptor.

We have isolated from *Arabidopsis* a cell surface LRR Thr/Ser kinase receptor for AtPep1, a 23 amino acid signal that that amplifies defense genes for innate immunity. The interaction of AtPep1 with the receptor is saturable and exhibits a Kd of 0.25 nM. Two SALK mutant lines with T-DNA insertions in exons of At1g73080 do not express the receptor gene and are not labeled by an AtPep1 photoaffinity analog that was used to identify and isolate the receptor protein. However, in contrast to wild type plants, the SALK insertional lines constitutively expressed high levels of PDF1.2 and PR-1, indicting that the receptor was negatively regulating defense gene expression in the absence of AtPep1. The AtPep1 receptor plays a central role in amplifying innate immunity activating defense gene expression when interacting with AtPep peptides that are synthesized in response to elicitors.

Methods

Synthesis of AtPep1 analogs. AtPep1, Cys-AtPep1 and Tyr-AtPep1 were synthesized using solid-phase instrumentation, (peptide synthesizer Model 431A; Applied Biosystems, Foster City, Calif.). After synthesis, the polypeptides were purified using C18 reverse-phase, high-performance liquid chromatography (HPLC), as previously described (Pearce and Ryan, J. Biol. Chem. 278:30044-30050, 2003; Pearce et al., Proc. Natl. Acad. Sci. USA 98:12843-12847, 2001; Pearce et al., Nature 411:817-820, 2001; Scheer and Ryan, The Plant Cell 11:1525-1535, 1999; Shevchenko et al., Anal. Chem. 68:850-858, 1996). Stock solutions of the peptides (2.5 mM) were prepared in water and stored at −20° C. Iodination of Tyr-AtPep1 was performed using IODO-GEN Pre-Coated Iodination Tubes (Pierce, Rockford, Ill.). Two hundred μl of NaI (20 mM in 0.1 M phosphate buffer, pH 8.0) solution was oxidized in the IODO-GEN Pre-Coated Iodination Tube for 6 min. Oxidized NaI solution was transferred into a 1.5 ml tube containing 100 nmol Tyr-AtPep1, and maintained at room temperature for 6 min in the dark gently agitating the tube every 30 sec. Iodinated Tyr-AtPep1 was purified using HPLC as described previously (Scheer and Ryan, The Plant Cell 11:1525-1535, 1999), and quantified with bicinchoninic acid (Pierce, Rockford, Ill.). All analogs were analyzed by LCQ ion trap mass spectrometry (Finnigan, San Jose, Calif.). Cys-AtPep1 was coupled through a disulfide bond to the photoaffinity cross-linker, N-(4-[p-azidosalicylamido]butyl)-3'-(2'-pyridyldithio)propionamide (APDP) (Pierce, Rockford, Ill.) to produce azido-Cys-AtPep1, which was purified by HPLC by methods previously described (Scheer and Ryan, Proc. Natl. Acad. Sci. 99:9585-9590, 2002).

Radioactive iodinations of Tyr-AtPep1 and azido-Cys-AtPep1 were performed using 2 mCi of $Na^{125}I$ and 12.5 nmol and the products were purified by HPLC (Scheer and Ryan, Proc. Natl. Acad. Sci. 99:9585-9590, 2002). The specific activity of the purified mono-iodinated Tyr-AtPep1 and azido-Cys-AtPep1 were 2.58 mCi/nmol, while the specific activity of the diiodinated forms was 5.15 mCi/nmol. The mono-iodinated analog of azido-Cys-AtPep1 was found to comprise 90% of the iodinated analog and was employed for photoaffinity labeling.

Alkalinization assay. Medium alkalinization activity of *Arabidopsis* suspension cultured cells by AtPep1 analogs was analyzed as previously described for systemin (Pearce et al., Science 253:895-897, 1991), RALF (Pearce et al. Proc. Natl. Acad. Sci. USA 98:12843-12847, 2001), HypSys peptides (Pearce and Ryan. J. Biol. Chem. 278:30044-30050, 2003; Pearce et al., Nature 411:817-820, 2001), and AtPep1 (supra). The alkalinization activity of azido-Cys-AtPep1 were carried out after incubation the analog with cells in darkness for 10 min, when the pH was recorded.

Binding assays. Binding assays of *Arabidopsis* cells with $^{125}I_1$-Tyr-AtPep1 were performed by the methods of Scheer and Ryan (Pearce et al., Nature 411:817-820, 2001) modified as follows: *Arabidopsis* suspension cultured cells were subcultured and grown for 4-5 days, washed with culture medium, and diluted with medium to a level of 0.2 mg fresh weight/ml. Two mL of cells were aliquoted into each well of 12-well culture plates and allowed to equilibrate on an orbital shaker (160 rpm) at room temperature for 1 hr. $^{125}I_1$-Tyr-AtPep1 was added to the medium, and 500 μL of cells were removed at selected times and filtered through a 2.5 cm Type A/E Glass Fiber Filter (Pall Corporation, Ann Arbor, Mich.) using a 12-well vacuum filtration manifold (Millipore, Bedford, Mass.). The filtered cells were washed three times with 5 mL of cold MS medium containing 3% sucrose, suspended in 1 mL MS medium containing 3% sucrose in a glass test tube, and analyzed for total radioactivity in a gamma-ray counter (Isodata 2020; Isodata Inc., Palatine, Ill.). Specific binding was calculated by subtracting nonspecific binding (binding in the presence of 250-fold native AtPep1) from total binding. $^{125}I_1$-Tyr-AtPep1 bound to the cell surface within a minute, and equilibrated within 4 min.

Photoaffinity labeling. To 1 mL of cultured cells in darkness was added $^{125}I$-azido-Cys-AtPep1 (0.25 nM final concentration as described above) and the cells were shaken for 10 min on an orbital shaker (160 rpm) at room temperature. The cells were transferred to a 1.5 mL glass tube, centrifuged at 10,000×g and the sedimented cells were dispersed in 1 mL cold MS medium containing 3% sucrose and centrifuged as above. This wash was repeated twice. The cells were resuspended in 1 mL MS medium and irradiated with UV-B for 10 min on ice to photoactivate the azido group to effect the crosslinking. The cells were washed with 1 mL MS medium, centrifuged as above, and resuspended in 400 μL of 5% SDS. The cells were disrupted by boiling for 30 min, and the insoluble debris was removed by centrifugation at 10,000×g. Proteins in the clear supernatant were precipitated by adding 1.25 volumes of methanol/chloroform (vol/vol). After centrifugation at 10,000×g, the pellet was recovered and dissolved in 100 μL of Laemmli sample buffer containing 5% SDS, boiled for 10 min, and separated using 8% SDS-PAGE. The gels were dried and exposed to X-ray film for 50 hr to visualize labeled proteins. In competition assays, unlabeled AtPep1 and suramin were added to the cells and incubated for 10 min before adding $^{125}I$-azido-Cys-AtPep1. The same procedures described above were employed to detect labeled proteins.

Purification of AtPep1-binding protein. $^{125}I$-azido-Cys-AtPep1 (0.25 nM) was added to 1 L of *Arabidopsis* suspension cultured cells and incubated for 10 min in the dark as described above, and collected on Miracloth (Calbiochem, San Diego, Calif.). After washing the cells with 1 L of cold water, the cells were suspended in 500 ml of MS medium containing 3% sucrose, and irradiated with UV-B for 15 min while being mixed on an orbital shaker at 160 rpm. The cells were again collected on Miracloth and washed with 1 L cold water. Microsomal fractions were prepared by differential centrifugation as previously described (Pearce et al., Proc. Natl. Acad. Sci. USA 98:12843-12847, 2001), and stored at −80° C. This process was repeated three times and the microsomal proteins were pooled. Protein was measured by Bio-Rad Protein Assay reagent (BIO-RAD. Hercules, Calif.) using bovine serum albumin as a standard.

Purification of AtPep1-binding protein from the membranes was performed as described previously with modifications (Pearce et al., Proc. Natl. Acad. Sci. USA 98:12843-12847, 2001). Briefly, 25 and 55 mg of radiolabeled and unlabeled microsomal proteins, respectively, were mixed and separated by 2 sets of 7.5% SDS-PAGE (0.6×14×9 cm) for 16 with 37 V at room temperature. The gels were sliced horizontally into 5 mm width and the radioactivity measured with a gamma-counter (Isodata 2020; Isodata Inc., Palatine, Ill.). The gel slices near 180 kD, containing the highest radioactivity were pooled. The gel slices were mascerated and the proteins were recovered by incubating the mascerate three times for 30 min with 25 mL of 20 mM Tris-HCl, 0.5 M NaCl, pH 7.5. The eluted proteins were pooled and incubated with 75 μL of Conconavalin A-Sepharose 4B (Amersham Bioscience, Piscataway, N.J.) for 6 h at room temperature to trap the Con A-protein complexes. The Con A-Sepharose was washed with 50 mL of 0.5 M alpha-methyl-D-glucoside three times, followed by 50 mL of $H_2O$ three times, to elute loosely bound proteins. Bound proteins were eluted by boiling the Con A-Sepharose in 500 μL of 5% SDS, and the eluted proteins were precipitated by adding 1.25 volumes of methanol/chloroform (2:1, vol/vol). Half of the eluted proteins were separated using 7.5% SDS-PAGE (0.15×14×8.5 cm) at 100 V for 8 h at room temperature. The gel was sliced horizontally into 1 mm widths, and the gel slice containing highest radioactivity was digested with trypsin (Promega, Madison, Wis.) according to Shevchenko et al. (Anal. Chem. 68:850-858, 1996). The other half of the eluted proteins were digested with Peptide-N-Glycosidase F (PNGase F) (Prozyme, San Leandro, Calif.), separated by 7.5% SDS-PAGE, recovered as above, and digested with trypsin. Peptides generated in the trypsin digests were analyzed by matrix-assisted laser desorption ionization time-of-flight mass spectrometer (MALDI-TOF MS), Voyager-DE RP Biospectrometry Workstation (Applied Biosystems, Framingham, Mass.). Protein was identified by searching in the National Center for Biotechnology Information database using Mascot (www.matrixscience.com).

Analysis of T-DNA insertional lines. *Arabidopsis thaliana* T-DNA insertional lines, SALK 014538, SALK 059281 and SALK 064539, were obtained from ABRC (Ohio State University) through The *Arabidopsis* Information Resource. The plants were screened by RT-PCR using gene-specific primer pairs and a primer specific for the T-DNA left border. Total RNA was purified from rosette leaves.

Microsomal fractions were prepared from one-month-old plants by differential centrifugation as previously described (Scheer and Ryan, Proc. Natl. Acad. Sci. 99:9585-9590, 2002). The membranes were photoaffinity labeled (Takayama et al, Nature 413:534-538, 2001) using the radiolabeled azido analog used with suspension cultured cells. The membranes were incubated for 60 min at approximately 4° C., irradiated with UV-B for 15 min, separated by SDS-PAGE, dried and analyzed by radioautography to identify labeled proteins.

Results

An analog of AtPep1 was synthesized with a Tyr residue attached to its N-terminus and radiolabeled with $^{125}$I to quantify binding. The Tyr analog and mono- and di-iodo-Tyr-AtPep1 analogs were separated by HPLC, and the concentration-dependent activities of AtPep1 and these analogs where tested in the alkalinization assay. All were found to be as fully active as AtPep1 in the alkalinization assay. The mono-iodinated Tyr-AtPep1 comprised about 95% of the iodinated proteins and was employed for binding studies. Saturation kinetics of the binding of mono-$^{125}$I-Tyr-AtPep1 with *Arabidopsis* suspension cultured cells (six repetitions using $10^6$ cells/assay) showed that the $^{125}$I-labeled peptide was maximally bound to *Arabidopsis* cells within about 10 min, saturating the sites at about 0.1 nM peptide. A Kd of 0.25 nM was estimated from Scatchard analysis of the saturation data, which is typical of ligand-receptor interactions and indicates that AtPep1 was interacting with a cell surface binding protein with the characteristics of a receptor.

A photoaffinity labeled AtPep1 was prepared by synthesizing an analog with a Cys residue at its N-terminus so that an $^{125}$I-labeled azido adduct, APDP, could be crosslinked to the peptide through a disulfide bond. All procedures were in darkness unless otherwise specified. The azido-Cys-AtPep1 was purified by HPLC and assayed for its alkalinization response under red light to avoid photoactivating the azido group. The analog was as fully active as the native peptide in the alkalinization assay. The azido analog was iodinated with $^{125}$I and incubated with *Arabidopsis* suspension cultured cells for 10 min and subjected to UV-B irradiation to activate the azido group for crosslinking with binding proteins. SDS-PAGE analyses of the radiolabeled membrane proteins revealed a single labeled protein band of Mr approximately 180 kD. Pre-incubation of 2.5 nM AtPep1 to cells totally abolished labeling. Tomato systemin (LeSys), a nonhomologous 18 amino acid peptide signal from tomato plants (Pearce et al., Science 253:895-897, 1991) did not compete for binding with the labeled analog and had not effect on photoaffinity labeling. Suramin, a polycyclic non-specific inhibitor of peptide hormone-receptor interactions in both animals and plants (Stratmann et al., Proc. Natl. Acad. Sci. USA, 97:8862-8867, 2000), inhibited the labeling of the 180 kD protein by the photoaffinity AtPep1 analog at 100 nM, supporting a membrane association for the 180 kD labeled protein. The labeled protein band from SDS-PAGE gels was eluted and incubated with the carbohydrase PNGaseF to enzymatically remove covalently bound carbohydrates. This enzyme caused a decrease in the kD of the photoaffinity labeled protein from about 180 kD to about 150 kD, indicating that the binding protein was glycosylated.

Purification of the radiolabeled protein from 1 L of *Arabidopsis* cells in late log phase was achieved using final steps of ConA-Sepharose affinity chromatography followed by SDS-PAGE. After electrophoresis, the labeled 180 kD protein band was excised from the gel and the protein recovered. Half of the protein was digested with trypsin and the fragments were analyzed by MALDI-TOF mass spectroscopy. The other half of the eluted protein was treated with the enzyme PNGase F to remove carbohydrate and was subjected to gel electrophoresis. The protein in the 150 kD band was recovered, digested with trypsin, and was also analyzed by mass spectroscopy. The amino acid sequences of 18 tryptic fragments from the 180 kD peptide exactly matched sequences of the *Arabidopsis* LRR receptor kinase gene, At1g73080. The deglycosylated protein yielded three large fragments of from 12 to 18 amino acids in length that were also exact matches to sequences within the At1g73080 gene. The nucleotide sequence of the AtPep1 receptor gene (At1g73080) the deduced receptor polypeptide is provided in FIG. 2 shows the structure of the At1g73080 gene, which is comprised of an 646 amino acid extracellular domain containing 27 LRR motifs; a 22 amino acid transmembrane domain; and a 280 amino acid Ser/Thr receptor kinase domain.

The leaves of two SALK T-DNA insertional lines having insertions in the exons of the gene At1g73080, SALK 014538 and SALK 059281, did not express the gene when analyzed by RT-PCR, using wild type plants and a SALK 059281 insertional mutant of gene At5g55480 as controls. Microsomal membrane proteins from the two At1g73080 mutant lines, and from wild type plants and the control SALK 059281 line, were analyzed for proteins that were specifically photoaffinity labeled by $^{125}$I-azido-Cys-AtPep1. A protein was labeled in the membranes from wild type plants and the SALK 059281 plants, but not from the SALK mutants unable to express the receptor gene. The label was found in a 180 kD protein band and in a slightly lower doublet band that appears to be degradation products of the receptor protein, since they were labeled. The proteins labeled in the wild type and SALK 059281 microsomal membranes were absent when the membranes were preincubated with 2.5 nM AtPep1 and then photoaffinity labeled, indicating that the proteins labeled in the membranes of wild type and SALK 059281, and not in membranes from the lines with mutants in the At1g73080 gene, were the AtPep1 receptor and its biologically active fragments.

To further investigate the role of the 180 kD protein as the receptor of AtPep1, competition experiments were performed between the $^{125}I_1$-Tyr-AtPep1 analog and synthetic peptide homologs derived from sequences at the N-termini of all seven of the AtPep family members that corresponded to the 23 amino acid AtPep1 (gene At5g684900). The peptides were purified after synthesis on HPLC and each assayed for biological activities at increasing concentrations in the alkalinization assay to determine the concentration of each that caused maximal activity. FIG. 4 shows the concentration dependence of synthetic AtPep peptides deduced from the seven members of the AtproPep1 gene family in the alkalinization assay. All peptides except those derived from At1g09980 gene and the unannotated gene were fully active at about 2.5 nM concentrations. The two genes with diminished activity were from Subfamily 11, which reside relatively close together on Chromosome V. All seven synthetic peptides competed with the $^{125}I_1$-Tyr-AtPep1 analog for binding with *Arabidopsis* suspension cultured cells, with a pattern similar to their biological activities in the alkalinization response. As in the alkalinization assay, the peptides derived from the At5g09980 gene and the unannotated gene were much weaker competitors than peptides derived from the other genes.

EXAMPLE 3

Shorter Peptides from the C-Terminus of Atpep1 Possess Substantial Defense Signal Peptide Activity Analogs of AtPep1 from the C-terminus of AtPep1 were synthesized and assayed in the alkalinization assay. One mL aliquots of 4 day old *Arabidopsis* cells were allowed to equilibrate on an orbital shaker at 180 rpm for one hour. A 10 μL aliquot of each peptide solution was added to the cells. Peptide concentrations of 0.25 nM, 2.5 nM, and 25 nM were tested. After 20 min, the pH of the media was recorded. The results are shown in FIG. 5. An analog of AtPep1 missing the carboxy-terminal amino acid was completely inactive, whereas deletions from the amino-terminus of the peptide resulted in a sequential reduction in activity, until peptides with 9 carboxy-terminal amino acids remaining (SSGRPGQHN (SEQ ID NO: 75)) were inactive. A peptide with 10 carboxy-terminal amino acids remaining had substantial defense signal peptide activity at the 25 nM peptide concentration, causing a change in pH of over 0.20 units, and longer analogs had progressively greater activity. A peptide consisting of only the 15 C-terminal amino acids was nearly as active as the native peptide at approximately 2.5 nM and had substantial activity even at the lowest concentration tested. It is expected that substantial defense signal peptide activity will be retained by analogs of other defense signal peptides that comprise sequences from the C-terminus of the peptides.

EXAMPLE 4

Alanine Substitutions in Residues of a 15-mer Analogs from the C-Terminus of AtPep1

The 15-mer from the carboxy-terminus of AtPep1 (RGKEKVSSGRPGQHN (SEQ ID NO: 78)) was substituted with alanine at each position to assess which amino acids were necessary for the alkalinizing activity. FIG. 6 shows the effect of these single alanine amino acid substitutions on the activity of the 15-mer peptide in the alkalinization assay. The set of substituted 15-mer peptides was assayed using four-day-old *Arabidopsis* cells. Ten ml of each peptide (2.5 pmoles) was added to 1 ml of cells to make a final concentration of 2.5 nM. After 20 min, the pH of the media was recorded. The data is the average of three separate experiments.

A Ser to Ala substitution at position 7, counting from the amino-terminus of the 15-mer, and a Gly to Ala substitution at position 9, exhibited little activity. Computer modeling predicted that these two amino acids would be involved in a beta-turn within the peptide region of -SSGR- (SEQ ID NO:

79) (compare with residues 15-18 of the sequence of AtPep1 shown in Table 1). Substituting Ala for Ser (-ASGR-) (SEQ ID NO: 80) abolished the predicted turn and severely abolished activity (half-maximal activity at ~250 nM), while substituting Ala for Gly was even less active (half-maximal activity of >250 nM. However, neither of these analogs were able to compete with the non-substituted 15-mer for receptor binding, indicating that the structural changes in this region may have severely modified the conformation without competing for the receptor binding site. Peptides with alanine substitutions at all residues were synthesized and assayed, with most showing no differences in activity than the native AtPep1.

EXAMPLE 5

Identification of Additional Plant Defense Signal Peptides from Various Dicot and Monocot Plant Species Additional searching of nucleotide sequence databases has revealed additional plant defense signal peptides, shown in Table 2. In addition, it was discovered that a single precursor gene may encode multiple plant defense signal peptides. Additional plant defense signal peptides shown in Table 3 are encoded by such precursor genes.

Identification of orthologs of the proAtPep1 gene in other plant species. To search for orthologs to the proAtPep1 gene in other plants, the NCBI protein query versus translated database (TBLASTN version 2.2.7) search algorithm (Altschul et al. 1997) was employed to search both plant genomic sequence and EST databases. For these searches no search filter was used and the expect value was set for either 10,000 or 20,000. Additionally, each individual plant EST database maintained by the Institute of Genomic Research (TIGR) was searched using the algorithm TBLASTN 2.0 MP (Gish) with no filter and an expect value of 10,000. Each member of the *Arabidopsis* proAtPep1 family was used as the input sequence for the database searches, and as orthologs in other plants were identified, they were also used as input sequences to search for other orthologous genes.

In order for a gene found in database searches to be classified as a proAtPep1 ortholog, the sequence had to fulfill several criteria. First, the gene had to encode a small protein—the proAtPep1 orthologs identified encode proteins ranging in size from 95 amino acids (canola) tolyl amino acids (rice). Next, each ortholog had to have a region in the encoded precursor protein that was glutamate or aspartate and lysine or arginine rich (designated E/DK/R repeats). The precursor region of the protein was required to contain some variation of the amphipathic helical hydrophobic/cationic 1-5-10 motif Finally, each predicted protein was required to have several conserved characteristics in the carboxyl region from which the active peptide would likely be cleaved. A high concentration of cationic charges in the amino end of the peptide region was a criterion, and in the carboxyl end a conserved glycine residue at position C-7 was required. In addition to these obligatory elements, several distinguishing features helped identify a gene as orthologous, but were not absolutely required. Most proteins encoded by the orthologs have repetitive serine residues in the precursor region. Additionally, in most predicted proteins a conserved asparagine is found as the carboxyl-terminal amino acid (C-1 position), immediately followed by a stop codon. Also, two residues prior to the conserved glycine in the peptide, all but one of the predicted proteins contain a serine or threonine residue.

Predicting secondary structure of proteins encoded by proAtPep1 and homologs. To predict secondary structure of the proAtPep1 protein and predicted proteins encoded by homologous genes, the SCRATCH server from the Institute for Genomics and Bioinformatics at the University of California at Irvine, Calif. was used. This server simultaneously integrates predictions from four different programs into a single output. One of these programs is SSpro version 2.0 (Pollastri et al. 2002a), which predicts three different classes of secondary structure; helix, strand, or neither. A second program SSpro8 (Baldi et al. 1999) further refines predictions into eight classifications, including three different types of helix, extended strand, β-bridge, turn, bend or none of the above. To predict whether the number of contacts each residue is involved in is above or below average for that residue, the program CONpro (Pollastri et al. 2001) was used. Finally, the ACCpro program (Pollastri et al. 2002b) was employed to estimate the relative solvent accessibility of each residue.

FIG. 7 shows nucleotide sequence information for precursors of the novel plant signal defense peptides of Table 2.

FIG. 8 shows nucleotide sequence information for precursors of the novel plant defense signal peptides of Table 3.

FIG. 9 shows an amino acid sequence alignment of predicted proAtPep1 orthologs (A) and a gene domain model for proATPep1-like genes (B).

EXAMPLE 6

PROPEP Family Regulation of Pathogen Defense in *Arabidopsis Thaliana*

AtPep1 is a 23 amino acid peptide derived from the carboxyl terminus of a precursor protein encoded by the PROPEP1 gene of *Arabidopsis thaliana*. Expression of the PROPEP1 gene is induced by methyl jasmonate and wounding, and the AtPep1 peptide specifically interacts with an LRR-RK, PEPR1, to regulate expression of genes encoding the pathogen-defense proteins PDF1.2 (plant defensin) and PR-1 (pathogenesis response protein 1). Transgenic plants constitutively expressing the PROPEP1 gene also express PDF1.2 and PR-1 at levels higher than in wild type plants and are more resistant to the root pathogen *Pythium irregulare*. *Arabidopsis* encodes five other PROPEP genes, raising the question of whether these genes act redundantly, synergistically or differ functionally. Expression studies of the individual PROPEP gene family members reveal differential induction in response to pathogens, elicitors and the defense-related hormones methyl salicylate, methyl jasmonate and ethylene. The AtPep peptides encoded by these PROPEP genes differentially regulate expression of PDF1.2 and PR-1. To better understand the regulatory role of individual PROPEP genes, we are employing microarray analysis of global gene expression patterns in transgenic plants overexpressing the different PROPEP genes. Additionally, we are investigating the role of individual AtPeps PROPEP genes in salicylate-associated defense responses by studying resistance of PROPEP-overexpression plants to infection with *Pseudomonas syringae* pv. tomato DC3000. Based on our studies we hypothesize that peptides encoded by the PROPEP gene family enhance pathogen defense responses by acting as endogenous signals to amplify defense signaling initiated by pathogens through both the jasmonate/ethylene and salicylate pathways.

EXAMPLE 7

Tobacco Transgenic Cells Expressing AtPEPR1

To further investigate the role of AtPEPR1 as the AtPep1 receptor, gain-of-function experiments were carried out with tobacco suspension-cultured cells that do not respond to AtPep1 by alkalinating the cell medium. Tobacco cells were transformed with a CaMV-35S-AtPEPR1 gene to determine whether the foreign receptor protein was targeted to the cell surface, where, in response to AtPep1, it would activate intracellular signaling to effect the alkalinization of the medium of the transgenic tobacco cells. Expression of the AtPEPR1 gene was confirmed by RT-PCR analysis of RNA from three independently transformed tobacco cell lines. All three of the tobacco lines responded to the addition of nanomolar concentrations of AtPep1 by producing a strong, reproducible alkalinization of the cell culture medium, whereas no alkalinization was detected in the culture medium of wild type cells challenged with AtPep1. These results not only confirm the identity of AtPEPR1 as the AtPep1 receptor, but they indicate that the receptor-mediated intracellular signaling pathway in tobacco cells that regulates alkalinization in response to peptide ligands can accommodate signaling by AtPEPR1 and its peptide ligand. AtPep2-7 was also supplied to the transgenic tobacco cells expressing AtPEPR1. At 2.5 nanomolar, AtPep2, AtPep3, AtPep5 and AtPep6 caused a change in pH of up to 0.6 units. But AtPep4 and AtPep7 did not increase medium pH. This is a similar pattern to their activities in the alkalinization response and in the competition with $^{125}I_1$-Tyr-AtPep1 analog for binding with *Arabidopsis* suspension-cultured cells.

Expression analysis of AtPEPR1 and AtPEPR2. In the *Arabidopsis* genome, there is a gene encoding a receptor kinase, which is very similar to AtPEPR1 (At1g73080) with 72% amino acid similarity for the entire sequence and was designated as AtPEPR2 (At1g17750). In order to elucidate the role of AtPEPR2 in AtPeps signal transduction, the gene expression patterns were analyzed in comparison with AtPEPR1. Northern hybridization and quantitative RT-PCR analysis showed that the expression patterns of AtPEPR1 and AtPEPR2 were very similar. The transcripts of AtPEPR1 and AtPEPR2 were induced by wounding, methyl jasmonate and AtPep supplying within 30 min, but not by methyl salicylate or aminocyclopropanecarboxylic acid, a precursor of ethylene. Of the 6 AtPeps, AtPep1, AtPep2 and AtPep3 were strong inducer of AtPEPR1 and AtPEPR2 transcripts.

The induction of AtproPep1 and MPK3 gene expression upon supplying AtPep1 using T-DNA insertional mutants. In addition to T-DNA insertional mutants of AtPEPR1 (SALK_059281 and SALK_014538), T-DNA insertional mutants of AtPEPR2 (SALK_036564 and SALK_004447) were obtained from The *Arabidopsis* Information Resource (http://www.arabidopsis.org/index.jsp). In order to elucidate how much AtPEPR1 and AtPEPR2 contribute to the AtPeps perception, SALK_014538 and SALK_004447 were crossed to obtain a double mutant. Another double mutant of AtPEPR1 and AtPEPR2 (SALK_059281 and SALK_036564) was provided by Dr. Frans Tax (Arizona University). It was confirmed that full length mRNAs of AtPEPR1 and/or AtPERP2 are not transcribed in the mutant lines by RT-PCR.

Using AtproPep1 and MPK3 as marker genes, the response to AtPep1 of the T-DNA insertional mutants was analyzed. Two-week-old seedlings grown in liquid medium were supplied with 10 nM AtPep1 for 30 min. The AtPEPR1 mutants (SALK_059281 and SALK_014538) showed more than a 50% reduction of AtproPep1 and MPK3 induction when supplied with AtPep1, but still responded, indicating that AtPEPR1 is not a sole receptor for AtPep1. The AtPEPR2 mutants (SALK_036564 and SALK_004447) did not show the clear reduction of the response to AtPep1. However, the double mutants of AtPEPR1 and AtPEPR2 completely lost the response when supplied with AtPep1. These data indicated that AtPEPR1 is the primary receptor for AtPep1, and AtPEPR2 is also involved in AtPep1 perception and signal transduction in *Arabidopsis*.

EXAMPLE 8

Identification of Orthologs of the AtPEPR Gene in Other Plant Species

Proteins and putative proteins, which are highly homologous to AtPEPR, were searched from several databases including NCBI, PlantGDB, and Phytozome by the BLAST program. Secondly, a phylogenic tree was made using these proteins and members of *Arabidopsis* leucine-rich repeat receptor-like kinase (LRR-RLK) XI subfamily. Then the proteins, which belong to same Glade with AtPEPR1 and AtPEPR2, were selected as AtPEPR homologues.

FIG. 10 is a simplified version of the AtPEPRs homolog phylogenic tree. Among them, OsPEPR1 and OsPEPR2 were confirmed their ability for perception of monocot defense peptides. Amino acid sequences were compared by the Clustal W program and phylogenic tree was drawn by the Tree View program. AtPEPR homologues are indicated in color. The numbers indicate bootstrap values. *Arabidopsis* BRI1 was used as an out group. At, *Arabidopsis thaliana*. Pt, *Populus* trichocarpa. Vv, *Vitis vinifera*. Zm, *Zea mays*. Sb, *Sorghum bicolor*. Os, *Oriza sativa*. Gm, *Glycine max*. In, *Ipomoea nill.*

The plant LRR-RLK family is a very large family, and more than 200 and 600 LRR-RLKs were predicted in the *Arabidopsis* and rice, respectively. All of them have an N-terminal signal sequence, an extracellular LRR region, two sets of cystein pairs around the LRR region, a transmembrane region, and an intracellular protein kinase domain. LRR regions are repeats of a leucine-rich motif consisted of 24 amino acids, and vary in length.

FIG. 11 is an amino acid alignment of AtPEPR homologues. Conserved amino acids are written in white letter with black background, and conserved similar amino acids are written with gray background. The intracellular protein kinase domain was indicated by red ruler.

FIG. 12 is a consensus amino acid sequence of the protein kinase domain of AtPEPRs homologues.

EXAMPLE 9

AtPEPR1 is a Receptor for all AtPep Peptides and AtPEPR2 for AtPep1 and AtPep2

AtPEPR1 and AtPEPR2 mutants are unable to respond to AtPEP1. To further examine the importance of AtPEPR1 and AtPEPR2 in AtPep1 signaling, the expression level of WRKY transcription factor genes, WRKY22, WRKY29, WRKY33. WRKY53 and WRKY55, were monitored by qRT-PCR after supplying AtPep1 to wild type *Arabidopsis* and T-DNA insertional mutants of AtPEPR1 and AtPEPR2. These WRKY genes were reported to be induced by the fungal PAMP, chitin (Wan et al., Plant Cell 20: 471-481, 2008), and the bacterial PAMPs, flg22 and elf18 (Zipfel et al., Cell 125:749-760, 2006). Two-week-old seedlings grown in liquid medium were incubated with AtPep1 (10 nM) for 30 min and subjected to qRT-PCR analysis. WRKY33, WRKY53, WRKY22, WRKY29 and WRKY55 were highly induced by 10 nM AtPep1 within 30 min in wild type. In pepr2-1 and pepr2-2 (SALK_059281 and SALK_014538, respectively) seedlings, these genes were induced by AtPep1 to similar levels as wild type seedlings. A 50% lower induction of these genes by AtPep1 was observed with pepr1-1 and pepr1-2 (SALK_036564 and SALK_004447) seedlings. In the double mutants, pepr1-1/pepr2-1 and pepr1-2/pepr2-2, the responses were completely abolished. We also examined the effect of supplying AtPep1 to the double mutants on the expression of the antimicrobial protein genes, defensin (PDF1.2) and pathogenesis related protein (PR-1) genes, since AtPep peptides are known to induced these genes (Huffaker and Ryan, Proc. Natl. Acad. Sci. USA 104: 10732-10736, 2007). Since the expression levels of PDF1.2 and PR-1 gene in *Arabidopsis* seedlings grown in liquid medium were already high, the method of supplying AtPep1 was changed. Four-week-old *Arabidopsis* plants grown in soil were sprayed with 1 μM AtPep1 in 0.01% Silwet L-77, and subjected to qRT-PCR analysis after 6 hours. The PDF1.2 and PR-1 genes were induced by 30- and 60-fold, respectively in wild type plants, and were not induced by AtPep1 in the double mutants.

AtPEPR2 binds to AtPep1. The results shown above strongly suggested that AtPEPR2 was also a receptor for AtPep1 in addition to AtPEPR1, whose ability to bind AtPep peptides was confirmed by loss of function and gain of function experiments (Yamaguchi et al., Proc. Natl. Acad. Sci. USA 103: 10104-10109, 2006). In these experiments, photoaffinity labeling using microsomal fractions of the T-DNA insertional mutants of AtPEPR1, pepr1-1 and pepr1-2, did not show any AtPep1 binding proteins (Yamaguchi et al., Proc. Natl. Acad. Sci. USA 103: 10104-10109, 2006). However, if the protein level of AtPEPR2 or binding capacity of AtPEPR2 to AtPep1 is much lower than AtPEPR1, it would be difficult to detect binding between AtPEPR2 and AtPep1 using *Arabidopsis* plants grown under normal condition. To clarify whether AtPEPR2 binds to AtPep1, the AtPEPR2 coding region was fused to the CaMV 35S promoter and introduced into tobacco suspension-cultured cells by *Agrobacterium*. Tobacco cells expressing AtPEPR1 and GUS genes were also created as positive and negative controls, respectively. RT-PCR analysis revealed that transgenic cells selected on kanamycin-containing medium expressed each transgene. These transgenic lines were analyzed for alkalinizing activity as previously described (Pearce et al., Proc. Natl. Acad. Sci. USA 98, 12843-12847, 2001). The cells expressing AtPEPR1 and AtPEPR2 caused alkalinization of the media in response to AtPep1, whereas wild type tobacco and GUS expressing cells did not respond to AtPep1. The level of response to AtPep1 for the AtPEPR2-expressing cells was similar to that of AtPEPR1-expressing cells and to *Arabidopsis* cells (Yamaguchi et al., Proc. Natl. Acad. Sci. USA 103: 10104-10109, 2006, Huffaker et al., Proc. Natl. Acad. Sci. USA 103: 10098-10103, 2006), with a maximal change of 1-1.2 pH units and a half-maximal peptide activity of ≈0.25 nM.

For final confirmation, a photoaffinity-labeling experiment was performed using the transgenic tobacco cells. The transgenic cells were incubated with 0.25 nM $^{125}I_1$-azido-Cys-AtPep1 (Yamaguchi et al., Proc. Natl. Acad. Sci. USA 103: 10104-10109, 2006) and irradiated with UV-B to cross-link the AtPep1-binding proteins. After separation of extracted proteins by SDS-PAGE, the labeled proteins were detected on X-ray film. A major protein band of 170 kDa, consistent with the size of AtPEPR1 in *Arabidopsis* (Yamaguchi et al., Proc. Natl. Acad. Sci. USA 103: 10104-10109, 2006), and 150 kDa were labeled in AtPEPR1 and AtPEPR2 expressing cells, respectively, but not in the cells incubated with 50 nM unlabeled AtPep1 as a competitor in addition to $^{125}I_1$-azido-Cys-AtPep1. The intensity of the 170 kDa protein was greater than that of the 150 kDa protein, requiring a one-tenth dilution of extract from AtPEPR1 expressing cells for use in SDS-PAGE to give comparable intensities to undiluted AtPEPR2 expressing cell extract. Since no specific labeling was detected in wild type tobacco and GUS expressing cells, the proteins labeled specifically by $^{125}I_1$-azido-Cys-AtPep1 in AtPEPR1 and AtPEPR2 expressing cells were products from the AtPEPR1 and AtPEPR2 genes.

AtPEPR2 contributes to AtPep1 and AtPep2 perception. The response to all AtPep peptides in transgenic tobacco cells expressing either AtPEPR1 or AtPEPR2 was analyzed by the medium alkalinization assay. As reported previously, for AtPEPR1 expressing cells, AtPep1, AtPep2, AtPep3, AtPep5 and AtPep6 showed strong activity with a maximal change of 1.2 pH units and a half-maximal activity of ≈0.25 nM, and AtPep4 and AtPep7 showed weaker activity with a half-maximal activity of nM. In contrast, only AtPep1 and AtPep2 showed strong activity to the AtPEPR2 expressing cells with a maximal change of 1.2 pH unit and a half-maximal activity at ≈0.25 nM with the other peptides showing very weak or no activity, indicating that AtPEPR2 contributes to AtPep1 and AtPep2 perception by itself.

EXAMPLE 10

AtPep Peptides Pre-Infiltration Reduces Symptom Development by *P. Syringae*

Overexpression of AtPROPEP1 showed increased resistance to a root pathogen, *Pythium irregulare* (Huffaker et al., Proc. Natl. Acad. Sci. USA 103: 10098-10103, 2006). The resistance to *P. irregulare* requires the JA signaling pathway in *Arabidopsis* (Staswick et al, Plant J. 15: 747-754, 1998), and AtPep peptides induced PDF1.2, a marker gene for the JA response (Huffaker et al., Proc. Natl. Acad. Sci. USA 103: 10098-10103, Huffaker and Ryan, Proc. Natl. Acad. Sci. USA 104: 10732-10736, 2007). In addition to PDF1.2, supplying AtPep peptides also induced expression of the PR-1 gene, a marker gene for the SA response (Huffaker et al., Proc. Natl. Acad. Sci. USA 103: 10098-10103, Huffaker and Ryan, Proc. Natl. Acad. Sci. USA 104: 10732-10736, 2007), suggesting that AtPep peptides may be involved in the SA signaling pathway, which increases resistance to *Pseudomonas syringae*. In order to examine this possibility, *Arabidopsis* plants were inoculated with *P. syringae* pv. tomato DC3000 (Pst DC3000) with or without AtPep1 pre-infiltration. Pst DC3000 was extracted from the infected leaves 4 days after infection and colony forming units (cfu/cm$^2$) were calculated. Pre-infiltration of a 10 nM solution of AtPep1 reduced Pst DC3000 growth in leaves and this reduction was concentration-dependent. AtPep1 pre-infiltration was more effective than flg22 pre-infiltration, which was reported to cause growth reduction of Pst DC3000 (Zipfel et al., Nature 428: 764-767, 2004). The reduction of Pst DC3000 growth was not observed when [A$^{17}$]AtPep1(9-23), an inactive derivative of AtPep1 (Pearce et al., Peptides. 29: 2083-2089, 2008) was pre-infiltrated. The reduction of Pst DC3000 growth was also not observed when the double mutant, pepr1-1/pepr2-1, was pre-infiltrated with AtPep1. These results indicated that reduction of Pst DC3000 growth by AtPep1 was specific. Pre-infiltration of AtPep2-6 also attenuated Pst DC3000 growth to different degrees. The attenuation of Pst DC3000 by AtPep1 pre-infiltration was differentially diminished in leaves of JA deficient (fad3,7,8), SA signaling (npr1-1) and SA biosynthesis (sid2-2) mutants, indicating that JA and SA signaling pathway are required for full activity of AtPep1.

To assess the importance of AtPEPR1 and AtPEPR2 in the resistance to Pst DC3000 after infiltration of AtPep1, T-DNA insertional mutants were inoculated. When 1 μM AtPep1 was infiltrated into leaves one day prior to Pst DC3000 inoculation, the size of the necrotic regions were reduced in both wild type and single mutant lines, pepr1-1 and pepr2-1. On the other hand, AtPep1 pre-infiltration did not affect symptom development by Pst DC3000 infection in double mutants, pepr1-1/pepr2-1. The bacterial growth was reduced to 1/100 in wild type and pepr2-1, and to 1/25 in pepr1-1 by AtPep1 pre-infiltration, but no decrease in colony growth was observed with the double mutants. Similar results were obtained when another set of mutant lines, pepr1-2, pepr2-2 and pepr1-2/pepr2-2, was used. These results were consistent with the results obtained in the analysis of defense gene induction by AtPep1 in the mutant lines, and indicated that AtPEPR1 contributed more to AtPep1 signaling than AtPEPR2.

EXAMPLE 11

Rice Homologues of AtPEPR1 are Receptors for Rice Peptides

We identified rice homologues of AtPEPR1 in the Rice Annotation Project database (see the website located at www.rapdb.dna.affrc.go.jp). The rice homologues, OsPEPR1 (Os08g0446200) and OsPEPR2 (Os08g0446400), have 60% and 62% amino acid similarities, respectively. The OsPEPR1 has 26 LRRs in the extracellular region, which is the same as AtPEPR1. The OsPEPR2 has a shorter extracellular region with 22 LRRs. Transgenic tobacco cells expressing either OsPEPR1 or OsPEPR2 were created to examine the possibility of receptor binding to monocot peptides. OsPep3a, OsPep3b, OsPep3c, ZmPep1 and ZmPep4a were supplied to suspension cultured transgenic tobacco cells, and medium pH was measured. OsPep3a, OsPep3b, ZmPep1 and ZmPep4a caused medium alkalinization in OsPEPR1 expressing cells with a 1.2 pH unit increase and a half-maximal activity of 0.25 nM. OsPep3c did not show any activity to OsPEPR1 expressing cells. However, OsPep3c showed weak activity to OsPEPR2 expressing cell with a 0.5 pH unit increase when the cells were incubated with peptide at 250 nM. These results indicated that OsPEPR1 and OsPEPR2 are receptors for monocot peptides.

EXAMPLE 12

Soybean homologues of AtPep Peptide and AtPEPR

Precursor gene expression of soybean homologues of the AtPep peptide, GmPROPEP1, GmPROPEP2 and GmPROPEP3, were analyzed by semi-quantitative RT-PCR. GmPROPEP2 and GmPROPEP3 were expressed in leaves, stems and roots. GmPROPEP1 was expressed mainly in roots, and very weakly in leaves and stems. The transcripts of GmPROPEP1 increased 4-fold 1 hour after supplying MeJA and 3-fold 8 hours after wounding. The transcripts of GmPROPEP2 increased 5-fold 2 hours after supplying MeJA. GmPep1-3 also affected the precursor gene expression. The GmPROPEP1 was induced by infiltration of GmPep1-3 (50 nM), and GmPROPEP2 was induced by GmPep2 (50 nM) and GmPep3 (50 nM) infiltration.

To examine whether GmPep1-3 are involved in defense responses, expression of soybean defense-related genes were analyzed by semi-quantitative RT-PCR after GmPep1-3 infiltration. The transcripts of D6aH/CYP93a1, a biosynthetic enzyme of the soybean phytoalexin glyceollin (Schopfer et al., FEBS Lett. 432: 182-1860, 1998), were induced 2 to 3-fold by GmPep1-3 infiltration. The expression of three chitinase genes, Chib1-b, Chi III and Chi 1 (Watanabe et al., Biosci. Biotechnol. Bioche. 63: 251-256, 1999, Gijzen et al., J. Exp. Bot. 52: 2283-2289, 2001), was also induced 3 to 15-fold by GmPep1-3 infiltration.

We found soybean homologues of AtPEPR1 and AtPEPR2, GmPEPR1a (Glymal0g33970), GmPEPR b (Glyma20g33620) and GmPEPR2 (Glyma15g00360), which have more than 60% amino acid similarities with AtPEPR1, in the soybean genome database (see the website located at www.phytozome.net/soybean.php). The GmPEPR1a and GmPEPR1b have 26 leucine-rich repeats in the extracellular region, similar to the AtPEPR1. The GmPEPR2 has a shorter extracellular region with 25 leucine-rich repeats, similar to AtPEPR2. A phylogenetic analysis of amino acid sequences revealed that GmPEPRs are more closely related to AtPEPRs than OsPEPRs, indicating that soybean homologues of AtPEPR1 and AtPEPR2 are possible receptors for soybean defense peptides.

What claimed is

1. An isolated polypeptide consisting of i) consensus amino acid sequence

```
                                        (SEQ ID NO: 22)
X-X-X-X-X-X-X-P-G-X-P-(R/A)-E-G-
|       |         |
1       5         10
                                   -X-G-G-X-G-G-X-(H/I)-H
                                    |         |
                                    15        20
``` wherein

X is any amino acid;

residue 12 is Arg or Ala;

residue 22 is His or Ile;

and residues 2-7 include at least one Lys or Arg wherein the sequence has defense signal peptide activity or ii, a 10, 12, 13, 14, or 15 amino acid carboxy terminal fragment of said consensus amino acid sequence of part i), wherein said 10, 11, 12, 13, 14, or 15 amino acid carboxy terminal fragment has defense signal peptide activity.

2. The polypeptide of claim 1, wherein said consensus sequence has a sequence selected from the group consisting of

```
ARLRP KPPGN PREGS GGNGG HHH,      (SEQ ID NO: 16)

DDSKP TRPGA PAEGS GGNGG AIH,      (SEQ ID NO: 17)

AAPAP QRPGA PAEGA GGQGG IIH,      (SEQ ID NO: 19)

VRRRP TTPGR PREGS GGNGG NHH,      (SEQ ID NO: 20)
and

QLARP RPPGP PRQGH GGDGG AIH.      (SEQ ID NO: 21)
```

3. A transgenic plant comprising a polypeptide consisting of i) a consensus amino acid sequence

```
                                                   (SEQ ID NO: 22)
X-X-X-X-X-X-X-P-G-X-P-(R/A)-E-G-X-G-G-X-G-G-X-(H/I)-H
|       |         |                |         |
1       5         10               15        20
``` wherein

X is any amino acid;

residue 12 is Arg or Ala;

residue 22 is His or Ile;

and residues 2-7 include at least one Lys or Arg wherein the sequence has defense signal peptide activity 2nd instance or ii) a 10, 11, 12, 13, 14, or 15 amino acid carboxy terminal fragment of said consensus amino acid sequence of part i), wherein said 10, 11, 12, 13, 14, or 15 amino acid carboxy terminal fragment has defense signal peptide activity.

4. An isolated polynucleotide encoding a polypeptide consisting of i) a consensus amino acid sequence (SEQ ID NO: 22)

```
X-X-X-X-X-X-X-P-G-X-P-(R/A)-E-G-X-G-G-X-G-G-X-(H/I)-H
|       |         |             |         |
1       5         10            15        20
``` wherein

X is any amino acid;

residue 12 is Arg or Ala;

residue 22 is His or Ile:

and residues 2-7 include at least one Lys or Arg wherein the sequence has defense signal peptide activity 2nd instance or ii) a 10, 11, 12, 13, 14, or 15 amino add carboxy terminal fragment of said consensus amino acid sequence of part i) wherein said 10, 11, 12, 13, 14, or 15 amino acid carboxy terminal fragment has defense signal peptide activity.

5. The isolated polypeptide of claim 1, wherein said isolated polypeptide consists of said consensus amino acid sequence (SEQ ID NO: 22)

```
X-X-X-X-X-X-X-P-G-X-P-(R/A)-E-G-X-G-G-X-G-G-X-(H/I)-H
|       |         |             |         |
1       5         10            15        20
``` wherein

X is any amino acid;

residue 12 is Arg or Ala;

residue 22 is His or lle;

and residues 2-7 include at least one Lys or Arg wherein the sequence has defense signal peptide activity.

6. A heterologous fusion polypeptide comprising i) a consensus amino acid sequence (SEQ ID NO: 22)

```
X-X-X-X-X-X-X-P-G-X-P-(R/A)-E-G-X-G-G-X-G-G-X-(H/I)-H
|       |         |             |         |
1       5         10            15        20
``` wherein

X is any amino acid residue 12 is Arg or Ala;

residue 22 is His or Ile;

and residues 2-7 include at least one Lys or Arg wherein the sequence has defense signal peptide activity 2nd instance;

or ii) a 10, 11, 12, 13, 14, or 15 amino acid carboxy terminal fragment of said consensus amino acid sequence of part i), wherein said 10, 11, 12, 13, 14, or 15 amino acid carboxy terminal fragment has defense signal peptide activity.

7. The heterologous fusion polypeptide of claim 6, wherein said heterologous fusion polypeptide comprises said consensus amino acid sequence (SEQ ID NO: 22)

```
X-X-X-X-X-X-X-P-G-X-P-(R/A)-E-G-X-G-G-X-G-G-X-(H/I)-H
|       |         |             |         |
1       5         10            15        20
``` wherein

X is any amino acid;

residue 12 is Arg or Ala;

residue 22 is His or Ile;

and residues 2-7 include at least one Lys or Arg where the sequence has defense signal peptide activity.

8. A composition comprising at least one isolated polypeptide of claim 1.

9. A method of treating a plant or a seed to increase plant defense signaling activity, comprising applying to a surface of said plant or said seed the composition of claim 1.

10. A plant comprising the isolated polypeptide of claim 1 applied to a surface of said plant wherein the plant has enhanced disease resistance.

11. A seed comprising the isolated polypeptide of claim 1 applied to a surface of said seed wherein the seed has enhanced disease resistance.

* * * * *

SEQUENCE LISTING

```
<160> NUMBER OF SEQ ID NOS: 172

<210> SEQ ID NO 1
<211> LENGTH: 23
<212> TYPE: PRT
<213> ORGANISM: Arabidopsis thaliana

<400> SEQUENCE: 1

Ala Thr Lys Val Lys Ala Lys Gln Arg Gly Lys Glu Lys Val Ser Ser
1               5                   10                  15

Gly Arg Pro Gly Gln His Asn
            20

<210> SEQ ID NO 2
<211> LENGTH: 23
<212> TYPE: PRT
<213> ORGANISM: Arabidopsis thaliana

<400> SEQUENCE: 2

Ser Leu Asn Val Met Arg Lys Gly Ile Arg Lys Gln Pro Val Ser Ser
1               5                   10                  15

Gly Lys Arg Gly Gly Val Asn
            20

<210> SEQ ID NO 3
<211> LENGTH: 23
<212> TYPE: PRT
<213> ORGANISM: Arabidopsis thaliana

<400> SEQUENCE: 3

Asp Asn Lys Ala Lys Ser Lys Lys Arg Asp Lys Glu Lys Pro Ser Ser
1               5                   10                  15

Gly Arg Pro Gly Gln Thr Asn
            20

<210> SEQ ID NO 4
<211> LENGTH: 23
<212> TYPE: PRT
<213> ORGANISM: Arabidopsis thaliana

<400> SEQUENCE: 4

Glu Ile Lys Ala Arg Gly Lys Asn Lys Thr Lys Pro Thr Pro Ser Ser
1               5                   10                  15

Gly Lys Gly Gly Lys His Asn
            20

<210> SEQ ID NO 5
<211> LENGTH: 23
<212> TYPE: PRT
<213> ORGANISM: Arabidopsis thaliana

<400> SEQUENCE: 5
```

```
Gly Leu Pro Gly Lys Lys Asn Val Leu Lys Lys Ser Arg Glu Ser Ser
1               5                   10                  15

Gly Lys Pro Gly Gly Thr Asn
            20

<210> SEQ ID NO 6
<211> LENGTH: 23
<212> TYPE: PRT
<213> ORGANISM: Arabidopsis thaliana

<400> SEQUENCE: 6

Ile Thr Ala Val Leu Arg Arg Arg Pro Arg Pro Pro Pro Tyr Ser Ser
1               5                   10                  15

Gly Arg Pro Gly Gln Asn Asn
            20

<210> SEQ ID NO 7
<211> LENGTH: 23
<212> TYPE: PRT
<213> ORGANISM: Arabidopsis thaliana

<400> SEQUENCE: 7

Val Ser Gly Asn Val Ala Ala Arg Lys Gly Lys Gln Gln Thr Ser Ser
1               5                   10                  15

Gly Lys Gly Gly Gly Thr Asn
            20

<210> SEQ ID NO 8
<211> LENGTH: 22
<212> TYPE: PRT
<213> ORGANISM: Brassica napus

<400> SEQUENCE: 8

Val Ala Arg Leu Thr Arg Arg Arg Pro Arg Pro Pro Tyr Ser Ser Gly
1               5                   10                  15

Gln Pro Gly Gln Ile Asn
            20

<210> SEQ ID NO 9
<211> LENGTH: 23
<212> TYPE: PRT
<213> ORGANISM: Solanum tuberosum

<400> SEQUENCE: 9

Pro Thr Glu Arg Arg Gly Arg Pro Pro Ser Arg Pro Lys Val Gly Ser
1               5                   10                  15

Gly Pro Pro Pro Gln Asn Asn
            20

<210> SEQ ID NO 10
<211> LENGTH: 23
<212> TYPE: PRT
<213> ORGANISM: Populus balsamifera

<400> SEQUENCE: 10

Asp Ala Ala Val Ser Ala Leu Ala Arg Arg Thr Pro Pro Val Ser Arg
1               5                   10                  15

Gly Gly Gly Gly Gln Thr Asn
            20

<210> SEQ ID NO 11
<211> LENGTH: 23
<212> TYPE: PRT
```

<213> ORGANISM: Betula spp.

<400> SEQUENCE: 11

Asp Leu Val Met Ala Val Asn Ala Pro Pro Arg Pro Ser Leu Thr Pro
1 5 10 15

Gly Ser Gly Ala Gln Ile Asn
20

<210> SEQ ID NO 12
<211> LENGTH: 23
<212> TYPE: PRT
<213> ORGANISM: Glycine max

<400> SEQUENCE: 12

Ala Ser Leu Met Ala Thr Arg Gly Ser Arg Gly Ser Lys Ile Ser Asp
1 5 10 15

Gly Ser Gly Pro Gln His Asn
20

<210> SEQ ID NO 13
<211> LENGTH: 23
<212> TYPE: PRT
<213> ORGANISM: Medicago sativa

<400> SEQUENCE: 13

Leu Ser Ser Met Gly Arg Gly Gly Pro Arg Arg Thr Pro Leu Thr Gln
1 5 10 15

Gly Pro Pro Pro Gln His Asn
20

<210> SEQ ID NO 14
<211> LENGTH: 23
<212> TYPE: PRT
<213> ORGANISM: Vitis vinifera

<400> SEQUENCE: 14

Glu Lys Val Arg Glu Lys Gln Lys Lys Gly Glu Asp Gly Glu Ser Val
1 5 10 15

Gly Arg Pro Gly Lys Lys Asn
20

<210> SEQ ID NO 15
<211> LENGTH: 23
<212> TYPE: PRT
<213> ORGANISM: Artificial Sequence
<220> FEATURE:
<223> OTHER INFORMATION: Dicot concensus sequence
<220> FEATURE:
<221> NAME/KEY: VARIANT
<222> LOCATION: 1, 2, 3, 4, 5, 6, 7, 8, 9, 10, 11, 12, 13, 14, 18, 22
<223> OTHER INFORMATION: Xaa = Any Amino Acid
<220> FEATURE:
<221> NAME/KEY: VARIANT
<222> LOCATION: 2, 3, 4, 5, 6, 7, 8, 9, 10, 11, 12, 13
<223> OTHER INFORMATION: Xaa = Rich in Lysine and Arginine
<220> FEATURE:
<221> NAME/KEY: VARIANT
<222> LOCATION: 19, 20
<223> OTHER INFORMATION: Xaa = Proline or Glycine

<400> SEQUENCE: 15

Xaa Xaa Xaa Xaa Xaa Xaa Xaa Xaa Xaa Xaa Xaa Xaa Xaa Xaa Ser Ser
1 5 10 15

Gly Xaa Xaa Xaa Gln Xaa Asn
20

<210> SEQ ID NO 16
<211> LENGTH: 23
<212> TYPE: PRT
<213> ORGANISM: Oryza sativa

<400> SEQUENCE: 16

Ala Arg Leu Arg Pro Lys Pro Pro Gly Asn Pro Arg Glu Gly Ser Gly
1 5 10 15

Gly Asn Gly Gly His His His
20

<210> SEQ ID NO 17
<211> LENGTH: 23
<212> TYPE: PRT
<213> ORGANISM: Oryza sativa

<400> SEQUENCE: 17

Asp Asp Ser Lys Pro Thr Arg Pro Gly Ala Pro Ala Glu Gly Ser Gly
1 5 10 15

Gly Asn Gly Gly Ala Ile His
20

<210> SEQ ID NO 18
<211> LENGTH: 23
<212> TYPE: PRT
<213> ORGANISM: Triticum aestivum

<400> SEQUENCE: 18

Ala Val Arg Arg Pro Arg Pro Pro Thr Thr Pro Arg Glu Gly Arg Gly
1 5 10 15

Gly Gly Gly Gly Ser His Asn
20

<210> SEQ ID NO 19
<211> LENGTH: 23
<212> TYPE: PRT
<213> ORGANISM: Triticum aestivum

<400> SEQUENCE: 19

Ala Ala Pro Ala Pro Gln Arg Pro Gly Ala Pro Ala Glu Gly Ala Gly
1 5 10 15

Gly Gln Gly Gly Ile Ile His
20

<210> SEQ ID NO 20
<211> LENGTH: 23
<212> TYPE: PRT
<213> ORGANISM: Zea mays

<400> SEQUENCE: 20

Val Arg Arg Arg Pro Thr Thr Pro Gly Arg Pro Arg Glu Gly Ser Gly
1 5 10 15

Gly Asn Gly Gly Asn His His
20

<210> SEQ ID NO 21
<211> LENGTH: 23
<212> TYPE: PRT
<213> ORGANISM: Hordeum vulgare

<400> SEQUENCE: 21

Gln Leu Ala Arg Pro Arg Pro Pro Gly Pro Pro Arg Gln Gly His Gly
1 5 10 15

Gly Asp Gly Gly Ala Ile His
20

<210> SEQ ID NO 22
<211> LENGTH: 23
<212> TYPE: PRT
<213> ORGANISM: Artificial Sequence
<220> FEATURE:
<223> OTHER INFORMATION: Monocot consensus sequence
<220> FEATURE:
<221> NAME/KEY: VARIANT
<222> LOCATION: 1, 2, 3, 4, 5, 6, 7, 10, 15, 18, 21
<223> OTHER INFORMATION: Xaa = Any Amino Acid
<220> FEATURE:
<221> NAME/KEY: VARIANT
<222> LOCATION: 2, 3, 4, 5, 6, 7
<223> OTHER INFORMATION: Xaa = Rich in Lysine and Arginine
<220> FEATURE:
<221> NAME/KEY: VARIANT
<222> LOCATION: 12
<223> OTHER INFORMATION: Xaa = Arginine or Alanine
<220> FEATURE:
<221> NAME/KEY: VARIANT
<222> LOCATION: 22
<223> OTHER INFORMATION: Xaa = Histidine or Isoleucine

<400> SEQUENCE: 22

Xaa Xaa Xaa Xaa Xaa Xaa Xaa Pro Gly Xaa Pro Xaa Glu Gly Xaa Gly
1 5 10 15

Gly Xaa Gly Gly Xaa Xaa His
20

<210> SEQ ID NO 23
<211> LENGTH: 23
<212> TYPE: PRT
<213> ORGANISM: Arabidopsis thaliana

<400> SEQUENCE: 23

Ala Thr Lys Val Lys Ala Lys Gln Arg Gly Lys Glu Lys Val Ser Ser
1 5 10 15

Gly Arg Pro Gly Gln His Asn
20

<210> SEQ ID NO 24
<211> LENGTH: 23
<212> TYPE: PRT
<213> ORGANISM: Thlaspi caerulescens

<400> SEQUENCE: 24

Val Thr Lys Phe Lys Ala Lys Met Lys Glu Arg Glu Lys Val Ser Thr
1 5 10 15

Gly Arg Ser Gly Gln His Asn
20

<210> SEQ ID NO 25
<211> LENGTH: 23
<212> TYPE: PRT
<213> ORGANISM: Gossypium hirsutum

<400> SEQUENCE: 25

Leu Pro Met Val Ser Leu Phe Thr Pro Lys Arg Pro Gly Thr Ser Ala
1 5 10 15

Gly Ser Gly Pro Gln Ile Asn
20

<210> SEQ ID NO 26

<211> LENGTH: 23
<212> TYPE: PRT
<213> ORGANISM: Solanum lycopersicum

<400> SEQUENCE: 26

```
Ala Thr Asp Arg Arg Gly Arg Pro Pro Ser Arg Pro Lys Val Gly Ser
1               5                   10                  15

Gly Pro Pro Pro Gln Asn Asn
            20
```

<210> SEQ ID NO 27
<211> LENGTH: 23
<212> TYPE: PRT
<213> ORGANISM: Populus balsamifera

<400> SEQUENCE: 27

```
Ala Val Thr Val Ser Ala Leu Ala Arg Arg Thr Pro Pro Val Ser Ser
1               5                   10                  15

Gly Ser Gly Gly Gln Ile Asn
            20
```

<210> SEQ ID NO 28
<211> LENGTH: 23
<212> TYPE: PRT
<213> ORGANISM: Vitis vinifera

<400> SEQUENCE: 28

```
Leu Arg Arg Gly Pro Thr Arg Pro Pro Ile Ser Phe Glu Ser Arg Pro
1               5                   10                  15

Gly Gly Gly Ser Gln Ile Asn
            20
```

<210> SEQ ID NO 29
<211> LENGTH: 23
<212> TYPE: PRT
<213> ORGANISM: Vitis vinifera

<400> SEQUENCE: 29

```
Lys Met Ser Ser Asp Phe Arg Gln Pro Pro Arg Pro Pro Ile Asp Pro
1               5                   10                  15

Gly Gln Gly Gly Gln Ile Asn
            20
```

<210> SEQ ID NO 30
<211> LENGTH: 23
<212> TYPE: PRT
<213> ORGANISM: Helianthus annuus

<400> SEQUENCE: 30

```
Arg Gly Leu Thr Arg Arg Pro Pro Pro Pro Arg Gly Pro Ile Ser Ser
1               5                   10                  15

Gly Gly Gly Gly Gln Thr Asn
            20
```

<210> SEQ ID NO 31
<211> LENGTH: 23
<212> TYPE: PRT
<213> ORGANISM: Helianthus annuus

<400> SEQUENCE: 31

```
Arg Val Asn Leu Val Gly Tyr Asp Tyr Ser Gly Tyr Gly Gln Ser Thr
1               5                   10                  15

Gly Lys Pro Ser Glu Cys Asn
```

20

<210> SEQ ID NO 32
<211> LENGTH: 23
<212> TYPE: PRT
<213> ORGANISM: Oryza sativa

<400> SEQUENCE: 32

Gln Arg Asn Glu Ile Arg Ser Arg Gly Val Asp Pro Ser Val Ser Gly
1 5 10 15

Gly Lys Gln Pro Gly Ile Asn
20

<210> SEQ ID NO 33
<211> LENGTH: 23
<212> TYPE: PRT
<213> ORGANISM: Saccharum officinarum
<220> FEATURE:
<221> NAME/KEY: VARIANT
<222> LOCATION: 19
<223> OTHER INFORMATION: Xaa = Any Amino Acid

<400> SEQUENCE: 33

Ala Ser Val Leu Met Arg Gly Pro Ala Gln Pro Val Pro Pro Thr Glu
1 5 10 15

Gly Ala Xaa Gly Arg Gly Gly
20

<210> SEQ ID NO 34
<211> LENGTH: 23
<212> TYPE: PRT
<213> ORGANISM: Saccharum officinarum

<400> SEQUENCE: 34

Ala Ser Val Leu Met Arg Gly Pro Ala Gln Pro Gly Pro Pro Thr Glu
1 5 10 15

Gly Ala Gly Arg Arg Gly Gly
20

<210> SEQ ID NO 35
<211> LENGTH: 23
<212> TYPE: PRT
<213> ORGANISM: Panicum virgatum

<400> SEQUENCE: 35

Val Val Thr Arg Val Trp Ala Val Arg Arg Pro Arg Glu Gly Ser Gly
1 5 10 15

Gly Asn Gly Gly Val His His
20

<210> SEQ ID NO 36
<211> LENGTH: 23
<212> TYPE: PRT
<213> ORGANISM: Arabidopsis thaliana

<400> SEQUENCE: 36

Ala Thr Lys Val Lys Ala Lys Gln Arg Gly Lys Glu Lys Val Ser Ser
1 5 10 15

Gly Arg Pro Gly Gln His Asn
20

<210> SEQ ID NO 37
<211> LENGTH: 23
<212> TYPE: PRT

<213> ORGANISM: Oryza sativa

<400> SEQUENCE: 37

Arg Arg Pro Thr Pro Pro Gly Gly Ala Gly Pro Arg Glu Gly Ser Gly
1               5                   10                  15

Gly Arg Gly Gly Val Ile His
            20

<210> SEQ ID NO 38
<211> LENGTH: 23
<212> TYPE: PRT
<213> ORGANISM: Oryza sativa

<400> SEQUENCE: 38

Ser Leu Ala Gly Ala Asn Val Leu Val Arg Asp Ala Pro Pro Glu Thr
1               5                   10                  15

Gly Gly Gly Pro His His Asn
            20

<210> SEQ ID NO 39
<211> LENGTH: 23
<212> TYPE: PRT
<213> ORGANISM: Oryza sativa

<400> SEQUENCE: 39

Arg Arg Pro Thr Pro Pro Gly Gly Ala Gly Pro Arg Glu Gly Ser Gly
1               5                   10                  15

Gly Arg Gly Gly Val Ile His
            20

<210> SEQ ID NO 40
<211> LENGTH: 23
<212> TYPE: PRT
<213> ORGANISM: Oryza sativa

<400> SEQUENCE: 40

Leu Ala Gly Ala Asn Val Leu Leu Arg Asp Asp Ala Pro Pro Glu Gly
1               5                   10                  15

Gly Arg Gly Pro His His Asn
            20

<210> SEQ ID NO 41
<211> LENGTH: 23
<212> TYPE: PRT
<213> ORGANISM: Oryza sativa

<400> SEQUENCE: 41

Arg Arg Pro Thr Pro Pro Gly Gly Ala Gly Pro Arg Glu Gly Arg Gly
1               5                   10                  15

Gly Arg Gly Gly Val Ile His
            20

<210> SEQ ID NO 42
<211> LENGTH: 23
<212> TYPE: PRT
<213> ORGANISM: Oryza sativa

<400> SEQUENCE: 42

Gln Leu Ala Gly Ala Lys Val Leu Val Arg Asp Ala Pro Pro Glu Thr
1               5                   10                  15

Gly Gly Gly Pro His His Asn
            20

<210> SEQ ID NO 43
<211> LENGTH: 23
<212> TYPE: PRT
<213> ORGANISM: Oryza sativa

<400> SEQUENCE: 43

Gly Gly Val Arg Pro Thr Pro Pro Gly Asn Pro Arg Glu Ala Gln Lys
1 5 10 15

Gly Gly Gly Val Ile His Ala
20

<210> SEQ ID NO 44
<211> LENGTH: 23
<212> TYPE: PRT
<213> ORGANISM: Zea mays

<400> SEQUENCE: 44

Ala Leu Arg Gly Pro Ala Pro Pro Ala Arg Pro Lys Glu Gly Ser Gly
1 5 10 15

Gly Lys Val His Val Val Ser
20

<210> SEQ ID NO 45
<211> LENGTH: 23
<212> TYPE: PRT
<213> ORGANISM: Zea mays

<400> SEQUENCE: 45

Leu Trp Pro Ala Pro Ser Pro Lys Gly Arg Pro Gly Ala Pro Arg Gln
1 5 10 15

Gly Ser Gly Gly Gln Val His
20

<210> SEQ ID NO 46
<211> LENGTH: 23
<212> TYPE: PRT
<213> ORGANISM: Triticum aestivum

<400> SEQUENCE: 46

Asp Ala Ser Ser Leu Ala Pro Gln Leu Arg Arg Thr Ser Pro Gly Glu
1 5 10 15

Gly Thr Ser Gly Arg Ile His
20

<210> SEQ ID NO 47
<211> LENGTH: 23
<212> TYPE: PRT
<213> ORGANISM: Triticum aestivum

<400> SEQUENCE: 47

Ile Ala Pro Thr Leu Gln Pro Ser Ser Ala Pro Val Glu Gly Thr Gly
1 5 10 15

Gly Gln Val Met Val Leu Asn
20

<210> SEQ ID NO 48
<211> LENGTH: 23
<212> TYPE: PRT
<213> ORGANISM: Hordeum vulgare

<400> SEQUENCE: 48

Asp Ala Ser Ser Leu Pro Leu Gln Leu Met Arg Thr Pro Pro Gly Glu
1 5 10 15

Gly Ala Gly Gly Arg Ile His
20

<210> SEQ ID NO 49
<211> LENGTH: 23
<212> TYPE: PRT
<213> ORGANISM: Hordeum vulgare

<400> SEQUENCE: 49

Ser Val Leu Pro Asp Gln Pro Pro Ser Ala Pro Ala Glu Gly Thr Gly
1 5 10 15

Gly Gln Val Met Val Leu Asn
20

<210> SEQ ID NO 50
<211> LENGTH: 23
<212> TYPE: PRT
<213> ORGANISM: Saccharum officinarum

<400> SEQUENCE: 50

Ala Ser Val Leu Leu Arg Gly Pro Ala Pro Pro Gly Arg Pro Val Glu
1 5 10 15

Gly Ser Gly Gly Lys Val His
20

<210> SEQ ID NO 51
<211> LENGTH: 23
<212> TYPE: PRT
<213> ORGANISM: Saccharum officinarum

<400> SEQUENCE: 51

Ala His Met Val Ile Arg Gly Pro Ala Arg Pro Gly Leu Pro Ala Gln
1 5 10 15

Gly Ser Gly Gly Lys Val His
20

<210> SEQ ID NO 52
<211> LENGTH: 23
<212> TYPE: PRT
<213> ORGANISM: Saccharum officinarum

<400> SEQUENCE: 52

Met Ala Thr Pro Met Arg Arg Pro Thr Pro Pro Gly Pro Pro Ala Gln
1 5 10 15

Gly Ser Gly Gly Lys Thr Asn
20

<210> SEQ ID NO 53
<211> LENGTH: 23
<212> TYPE: PRT
<213> ORGANISM: Saccharum officinarum

<400> SEQUENCE: 53

Ser Arg Ala Ala Pro Ser Pro Lys Gly Ser Pro Gly Ala Pro Arg Gln
1 5 10 15

Gly Ser Gly Gly His Val His
20

<210> SEQ ID NO 54
<211> LENGTH: 23
<212> TYPE: PRT
<213> ORGANISM: Saccharum officinarum

<400> SEQUENCE: 54

Ala Pro Ala Ser Pro Leu Arg Arg Gln Leu Leu Arg Tyr Val Ser Ser
1 5 10 15

Gly Leu Val Ala Ala Leu His
20

<210> SEQ ID NO 55
<211> LENGTH: 23
<212> TYPE: PRT
<213> ORGANISM: Saccharum officinarum

<400> SEQUENCE: 55

Ala His Met Val Ile Arg Gly Pro Ala Arg Pro Gly Leu Pro Ala Gln
1 5 10 15

Gly Arg Gly Gly Lys Val His
20

<210> SEQ ID NO 56
<211> LENGTH: 23
<212> TYPE: PRT
<213> ORGANISM: Saccharum officinarum

<400> SEQUENCE: 56

Met Ala Thr Pro Met Arg Arg Pro Thr Ser Pro Gly Pro Pro Ala Gln
1 5 10 15

Gly Ser Gly Gly Lys Thr Asn
20

<210> SEQ ID NO 57
<211> LENGTH: 23
<212> TYPE: PRT
<213> ORGANISM: Saccharum officinarum

<400> SEQUENCE: 57

Ser Arg Ala Val Pro Ser Leu Lys Gly Arg Pro Gly Ala Pro Arg Gln
1 5 10 15

Gly Ser Gly Gly His Val His
20

<210> SEQ ID NO 58
<211> LENGTH: 23
<212> TYPE: PRT
<213> ORGANISM: Saccharum officinarum

<400> SEQUENCE: 58

Ala Pro Ala Ser Pro Leu Arg Arg Gln Leu Leu Arg Tyr Val Ser Ser
1 5 10 15

Gly Leu Val Ala Ala Leu His
20

<210> SEQ ID NO 59
<211> LENGTH: 25
<212> TYPE: DNA
<213> ORGANISM: Artificial Sequence
<220> FEATURE:
<223> OTHER INFORMATION: Synthesized Construct

<400> SEQUENCE: 59
cttatcagat ctcaatggag aaatc 25

<210> SEQ ID NO 60
<211> LENGTH: 27
<212> TYPE: DNA

<213> ORGANISM: Artificial Sequence
<220> FEATURE:
<223> OTHER INFORMATION: Synthesized Construct

<400> SEQUENCE: 60
caatgtaact taaagtgcct aattatg 27

<210> SEQ ID NO 61
<211> LENGTH: 19
<212> TYPE: DNA
<213> ORGANISM: Artificial Sequence
<220> FEATURE:
<223> OTHER INFORMATION: Synthesized Construct

<400> SEQUENCE: 61
atggctaagt ttgcttcca 19

<210> SEQ ID NO 62
<211> LENGTH: 23
<212> TYPE: DNA
<213> ORGANISM: Artificial Sequence
<220> FEATURE:
<223> OTHER INFORMATION: Synthesized Construct

<400> SEQUENCE: 62
ttaacatggg acgtaacaga tac 23

<210> SEQ ID NO 63
<211> LENGTH: 20
<212> TYPE: DNA
<213> ORGANISM: Artificial Sequence
<220> FEATURE:
<223> OTHER INFORMATION: Synthesized Construct

<400> SEQUENCE: 63
ggagctacgc agaacaacta 20

<210> SEQ ID NO 64
<211> LENGTH: 20
<212> TYPE: DNA
<213> ORGANISM: Artificial Sequence
<220> FEATURE:
<223> OTHER INFORMATION: Synthesized Construct

<400> SEQUENCE: 64
agtatggctt ctcgttcaca 20

<210> SEQ ID NO 65
<211> LENGTH: 20
<212> TYPE: DNA
<213> ORGANISM: Artificial Sequence
<220> FEATURE:
<223> OTHER INFORMATION: Synthesized Construct

<400> SEQUENCE: 65
tacaggggta gttcaagcaa 20

<210> SEQ ID NO 66
<211> LENGTH: 20
<212> TYPE: DNA
<213> ORGANISM: Artificial Sequence
<220> FEATURE:
<223> OTHER INFORMATION: Synthesized Construct

<400> SEQUENCE: 66
cctagagcca ctcctggtat 20

-continued

<210> SEQ ID NO 67
<211> LENGTH: 20
<212> TYPE: DNA
<213> ORGANISM: Artificial Sequence
<220> FEATURE:
<223> OTHER INFORMATION: Synthesized Construct

<400> SEQUENCE: 67
acggtagaag actacgcaca 20

<210> SEQ ID NO 68
<211> LENGTH: 20
<212> TYPE: DNA
<213> ORGANISM: Artificial Sequence
<220> FEATURE:
<223> OTHER INFORMATION: Synthesized Construct

<400> SEQUENCE: 68
taaggtctcg agctcctctt 20

<210> SEQ ID NO 69
<211> LENGTH: 20
<212> TYPE: DNA
<213> ORGANISM: Artificial Sequence
<220> FEATURE:
<223> OTHER INFORMATION: Synthesized Construct

<400> SEQUENCE: 69
caaaatatgg atacgggaca 20

<210> SEQ ID NO 70
<211> LENGTH: 20
<212> TYPE: DNA
<213> ORGANISM: Artificial Sequence
<220> FEATURE:
<223> OTHER INFORMATION: Synthesized Construct

<400> SEQUENCE: 70
attgccaacg atgttgtatc 20

<210> SEQ ID NO 71
<211> LENGTH: 20
<212> TYPE: DNA
<213> ORGANISM: Artificial Sequence
<220> FEATURE:
<223> OTHER INFORMATION: Synthesized Construct

<400> SEQUENCE: 71
tggcaatgaa gtcagtttct 20

<210> SEQ ID NO 72
<211> LENGTH: 20
<212> TYPE: DNA
<213> ORGANISM: Artificial Sequence
<220> FEATURE:
<223> OTHER INFORMATION: Synthesized Construct

<400> SEQUENCE: 72
agaagtcgca gaagcactta 20

<210> SEQ ID NO 73
<211> LENGTH: 20
<212> TYPE: DNA
<213> ORGANISM: Artificial Sequence
<220> FEATURE:
<223> OTHER INFORMATION: Synthesized Construct

<400> SEQUENCE: 73
caacgctact ctgtctgtcc 20

<210> SEQ ID NO 74
<211> LENGTH: 20
<212> TYPE: DNA
<213> ORGANISM: Artificial Sequence
<220> FEATURE:
<223> OTHER INFORMATION: Synthesized Construct

<400> SEQUENCE: 74
tctgtgaatt ccatctcgtc 20

<210> SEQ ID NO 75
<211> LENGTH: 9
<212> TYPE: PRT
<213> ORGANISM: Arabidopsis thaliana

<400> SEQUENCE: 75

Ser Ser Gly Arg Pro Gly Gln His Asn
1 5

<210> SEQ ID NO 76
<211> LENGTH: 23
<212> TYPE: DNA
<213> ORGANISM: Artificial Sequence
<220> FEATURE:
<223> OTHER INFORMATION: Synthesized Construct

<400> SEQUENCE: 76
ataaagagtc acacccaata ccg 23

<210> SEQ ID NO 77
<211> LENGTH: 26
<212> TYPE: DNA
<213> ORGANISM: Artificial Sequence
<220> FEATURE:
<223> OTHER INFORMATION: Synthesized Construct

<400> SEQUENCE: 77
tgatactggt tatgaactta tgatgg 26

<210> SEQ ID NO 78
<211> LENGTH: 15
<212> TYPE: PRT
<213> ORGANISM: Arabidopsis thaliana

<400> SEQUENCE: 78

Arg Gly Lys Glu Lys Val Ser Ser Gly Arg Pro Gly Gln His Asn
1 5 10 15

<210> SEQ ID NO 79
<211> LENGTH: 4
<212> TYPE: PRT
<213> ORGANISM: Artificial Sequence
<220> FEATURE:
<223> OTHER INFORMATION: Synthesized Construct

<400> SEQUENCE: 79

Ser Ser Gly Arg
1

<210> SEQ ID NO 80
<211> LENGTH: 4
<212> TYPE: PRT
<213> ORGANISM: Artificial Sequence
<220> FEATURE:
<223> OTHER INFORMATION: Synthesized Construct

<400> SEQUENCE: 80

Ala Ser Gly Arg
1

<210> SEQ ID NO 81
<211> LENGTH: 499
<212> TYPE: DNA
<213> ORGANISM: Arabidopsis thaliana

<400> SEQUENCE: 81
actcacatat aaaaaacagc ttcactcctc tcaccaaaac taatcagatt aataaaagtt 60
ttcctctgtc ttatcagatc tcaatggaga aatcagatag acgaagcgaa gaaagtcacc 120
tatggattcc tcttcagtgc ctcgaccaaa ccctcagagc tatcttgaaa tgccttggtc 180
tttttcatca agattctccg acaacgtcct ctcccggaac ttcgaaacag ccgaaggagg 240
aaaaagaaga cgttaccatg gaaaaggagg aggtcgttgt gacgagtaga gccacaaagg 300
tcaaggcaaa gcaaaggggg aaggagaaag ttagctcagg ccgtcctggc caacataatt 360
aggcacttta agttacattg tttagtctaa ttatttgcag tcgaaatgtg ttaatttaat 420
atcactgttt tactttttta ttatatcaac aatctacaga caaacaaaat ttcattaagt 480
tcttgttcac tatacgagt 499

<210> SEQ ID NO 82
<211> LENGTH: 92
<212> TYPE: PRT
<213> ORGANISM: Arabidopsis thaliana

<400> SEQUENCE: 82

Met Glu Lys Ser Asp Arg Arg Ser Glu Glu Ser His Leu Trp Ile Pro
1 5 10 15

Leu Gln Cys Leu Asp Gln Thr Leu Arg Ala Ile Leu Lys Cys Leu Gly
20 25 30

Leu Phe His Gln Asp Ser Pro Thr Thr Ser Ser Pro Gly Thr Ser Lys
35 40 45

Gln Pro Lys Glu Glu Lys Glu Asp Val Thr Met Glu Lys Glu Glu Val
50 55 60

Val Val Thr Ser Arg Ala Thr Lys Val Lys Ala Lys Gln Arg Gly Lys
65 70 75 80

Glu Lys Val Ser Ser Gly Arg Pro Gly Gln His Asn
85 90

<210> SEQ ID NO 83
<211> LENGTH: 568
<212> TYPE: DNA
<213> ORGANISM: Arabidopsis thaliana

<400> SEQUENCE: 83
acattgagag atacaaagtt gtctctctga catataccta gctgctcgat aactcaccaa 60
actattggat ttcaatggag aaattagata aacggaggga agaagaaact tatctatgga 120
ttccagttca gtttctcgac caagctctca tagctgtctt gaaatgtatt ggtcttcttt 180
gtcagccagc gaagaaaact gcgccgtctc cggtaacttt taaccagccg gaggaacaag 240
aggaagacta tggtgttgct ctgaaagacg atgatgtcgt tgtgttgctt agggacaaca 300
aggccaaatc aaagaaaagg gataaagaaa agcctagttc aggtcgtcct ggccaaacta 360

-continued

```
atagtgtacc caacgcggca atacaagttt ataaggagga ttaagaagtc aaaaattgag    420
tcgaaaaatc caagaggcca atgagtcagt cattgctcct ttttttttt tactcaaact    480 tctatgaaaa actcgtacgt agtttatttt ggtttcctca tttttcaaga cagcaaaatt    540
gaccagaatg tatatacttt tgaatcgg                                       568
```

<210> SEQ ID NO 84
<211> LENGTH: 109
<212> TYPE: PRT
<213> ORGANISM: Arabidopsis thaliana

<400> SEQUENCE: 84

```
Met Glu Lys Leu Asp Lys Arg Arg Glu Glu Glu Thr Tyr Leu Trp Ile
1               5                   10                  15

Pro Val Gln Phe Leu Asp Gln Ala Leu Ile Ala Val Leu Lys Cys Ile
            20                  25                  30

Gly Leu Leu Cys Gln Pro Ala Lys Lys Thr Ala Pro Ser Pro Val Thr
        35                  40                  45

Phe Asn Gln Pro Glu Glu Gln Glu Glu Asp Tyr Gly Val Ala Leu Lys
    50                  55                  60

Asp Asp Asp Val Val Val Leu Leu Arg Asp Asn Lys Ala Lys Ser Lys
65                  70                  75                  80

Lys Arg Asp Lys Glu Lys Pro Ser Ser Gly Arg Pro Gly Gln Thr Asn
                85                  90                  95

Ser Val Pro Asn Ala Ala Ile Gln Val Tyr Lys Glu Asp
            100                 105
```

<210> SEQ ID NO 85
<211> LENGTH: 486
<212> TYPE: DNA
<213> ORGANISM: Arabidopsis thaliana

<400> SEQUENCE: 85

```
atcaacctaa taacacacaa cactaaatct ctttcccaaa aaaagattaa gaagtcaacg     60
atggagaatc tcagaaatgg agaagataac ggttctttga tcccatttac gttctttgat    120
caatcttcag tgacgattcc tctcttgaag tgttccggtc tcgaaagttc atcatcatca    180
tcttcttctt gcgatctttc gtcatcacac agcgaggaag atgagagtat cgatataaag    240
gaggaggaag aagaagaaga agaagatggc atgaccattg aaatcaaagc gagagggaag    300
aacaagacta agcctacgcc aagttcagga aaaggaggca aacacaatta gagttcattc    360
atataccgag gaaattaaac aaataaatgc atttgtataa aatacttaga gctataatac    420
agtggagttt ttttatagtc atttgtttcg aatatgaatt ggattaataa agatcgagtt    480
ttattt                                                               486
```

<210> SEQ ID NO 86
<211> LENGTH: 96
<212> TYPE: PRT
<213> ORGANISM: Arabidopsis thaliana

<400> SEQUENCE: 86

```
Met Glu Asn Leu Arg Asn Gly Glu Asp Asn Gly Ser Leu Ile Pro Phe
1               5                   10                  15

Thr Phe Phe Asp Gln Ser Ser Val Thr Ile Pro Leu Leu Lys Cys Ser
            20                  25                  30

Gly Leu Glu Ser Ser Ser Ser Ser Ser Ser Ser Cys Asp Leu Ser Ser
        35                  40                  45
```

```
Ser His Ser Glu Glu Asp Glu Ser Ile Asp Ile Lys Glu Glu Glu Glu
    50                  55                  60

Glu Glu Glu Glu Asp Gly Met Thr Ile Glu Ile Lys Ala Arg Gly Lys
65                  70                  75                  80

Asn Lys Thr Lys Pro Thr Pro Ser Ser Gly Lys Gly Gly Lys His Asn
                85                  90                  95

<210> SEQ ID NO 87
<211> LENGTH: 460
<212> TYPE: DNA
<213> ORGANISM: Arabidopsis thaliana

<400> SEQUENCE: 87
acttagctct cacgaagcag aattgaagaa aaacatggag agaggagttt cttattatct     60
atggattcct tttaagttca tccaccaaac tttcggatct cttttactca agcttctcgg    120
tttgcgatct ccatctgatc atagttttcc ggaggatggg gaggaggaag ttaaggttgt    180
ggaagtgtcg tcgaggggtc ttcccgggaa aaagaatgta ctaaagaagt cgagagaaag    240
ttccggcaag ccgggaggca ccaacaagaa gccgttttag tttttcactt caactaataa    300
tatttgacgg agaaattctt ccttacattt tcatctattt agtgtaagat ctaagagaat    360
agtttcatat ttgtatcgta taattcctga agattgcaac tcctacgagt cctttatttt    420
ttttctttaa gacaataact aaagagagac gtgaatcata                          460

<210> SEQ ID NO 88
<211> LENGTH: 81
<212> TYPE: PRT
<213> ORGANISM: Arabidopsis thaliana

<400> SEQUENCE: 88

Met Glu Arg Gly Val Ser Tyr Tyr Leu Trp Ile Pro Phe Lys Phe Ile
1               5                   10                  15

His Gln Thr Phe Gly Ser Leu Leu Leu Lys Leu Leu Gly Leu Arg Ser
            20                  25                  30

Pro Ser Asp His Ser Phe Pro Glu Asp Gly Glu Glu Glu Val Lys Val
        35                  40                  45

Val Glu Val Ser Ser Arg Gly Leu Pro Gly Lys Lys Asn Val Leu Lys
    50                  55                  60

Lys Ser Arg Glu Ser Ser Gly Lys Pro Gly Gly Thr Asn Lys Lys Pro
65                  70                  75                  80

Phe

<210> SEQ ID NO 89
<211> LENGTH: 412
<212> TYPE: DNA
<213> ORGANISM: Arabidopsis thaliana

<400> SEQUENCE: 89
acaaagaaaa tttgaggaga aagtcacata tagaggaact tagaagatag cgaagatgca     60
gcaagagaga gatcacaaaa gagattgttg caagctcatg cctcaaactg tcaaggcttt    120
cttcaagtgt ctgagattca gacgttcttc ttcttcttct tcagacatgg tgaaagctag    180
agcaagaaat gaagagaaag aagaaccttc atctatcgaa acttcaacta ggagtctcaa    240
cgtaatgagg aaagggataa ggaaacaacc agttagctcg ggaaaacgag gtggagttaa    300
cgactacgac atgtaactag aatcttgatg tagaattgga taatcttgtt tggtagttac    360
tctacaacat actttctttg catctcatga atcatcatga tatattgata tt            412
```

<210> SEQ ID NO 90
<211> LENGTH: 86
<212> TYPE: PRT
<213> ORGANISM: Arabidopsis thaliana

<400> SEQUENCE: 90

```
Met Gln Gln Glu Arg Asp His Lys Arg Asp Cys Cys Lys Leu Met Pro
1               5                   10                  15

Gln Thr Val Lys Ala Phe Phe Lys Cys Leu Arg Phe Arg Arg Ser Ser
            20                  25                  30

Ser Ser Ser Ser Asp Met Val Lys Ala Arg Ala Arg Asn Glu Glu Lys
        35                  40                  45

Glu Glu Pro Ser Ser Ile Glu Thr Ser Thr Arg Ser Leu Asn Val Met
    50                  55                  60

Arg Lys Gly Ile Arg Lys Gln Pro Val Ser Ser Gly Lys Arg Gly Gly
65                  70                  75                  80

Val Asn Asp Tyr Asp Met
                85
```

<210> SEQ ID NO 91
<211> LENGTH: 397
<212> TYPE: DNA
<213> ORGANISM: Arabidopsis thaliana

<400> SEQUENCE: 91

```
ggtcaaacta gacacaacac ttaatgcatt gagcagaaga agaagaagaa gaagaattaa     60
gaagagaaag aaaacaaaaa acatggaagt taatggagaa gaagagagaa gaagtagaag    120
agaagatgaa gaaaaagaag attactacta ctctcttctc aactctccat gttctgtttg    180
taacaaattt gttcaagcca tattgaagtg tcttggtctt gagtcatcat caataccacc    240
atcttcatca tcatcatcac catccttagt agaagaagaa gattcaggaa ctgaaactgt    300
tgaagaaaca ggatttatgg cgaggataac agcagtgtta agaaggagac caagaccacc    360
accttatagc tcaggacgac ctggtcaaaa caattga                             397
```

<210> SEQ ID NO 92
<211> LENGTH: 104
<212> TYPE: PRT
<213> ORGANISM: Arabidopsis thaliana

<400> SEQUENCE: 92

```
Met Glu Val Asn Gly Glu Glu Glu Arg Arg Ser Arg Arg Glu Asp Glu
1               5                   10                  15

Glu Lys Glu Asp Tyr Tyr Tyr Ser Leu Leu Asn Ser Pro Cys Ser Val
            20                  25                  30

Cys Asn Lys Phe Val Gln Ala Ile Leu Lys Cys Leu Gly Leu Glu Ser
        35                  40                  45

Ser Ser Ile Pro Pro Ser Ser Ser Ser Ser Ser Pro Ser Leu Val Glu
    50                  55                  60

Glu Glu Asp Ser Gly Thr Glu Thr Val Glu Glu Thr Gly Phe Met Ala
65                  70                  75                  80

Arg Ile Thr Ala Val Leu Arg Arg Arg Pro Arg Pro Pro Pro Tyr Ser
                85                  90                  95

Ser Gly Arg Pro Gly Gln Asn Asn
            100
```

<210> SEQ ID NO 93
<211> LENGTH: 228

<212> TYPE: DNA
<213> ORGANISM: Arabidopsis thaliana

<400> SEQUENCE: 93
atgaatgttt tttttttgt ttctgaatta ttgtcacatc tttcttttca atatgaaatt 60
tctaatggaa aatgtgtata tgtaataatg ttggtgacga agatatcaca agaagtagag 120
gaagagacag aggtagtgaa tataccgagg agtgtggtgt cggggaacgt tgcagcgcga 180
aagggtaagc agcaaacgag ttccgggaag ggtggaggta ccaactag 228

<210> SEQ ID NO 94
<211> LENGTH: 75
<212> TYPE: PRT
<213> ORGANISM: Arabidopsis thaliana

<400> SEQUENCE: 94

Met Asn Val Phe Phe Phe Val Ser Glu Leu Leu Ser His Leu Ser Phe
1 5 10 15

Gln Tyr Glu Ile Ser Asn Gly Lys Cys Val Tyr Val Ile Met Leu Val
20 25 30

Thr Lys Ile Ser Gln Glu Val Glu Glu Glu Thr Glu Val Val Asn Ile
35 40 45

Pro Arg Ser Val Val Ser Gly Asn Val Ala Ala Arg Lys Gly Lys Gln
50 55 60

Gln Thr Ser Ser Gly Lys Gly Gly Gly Thr Asn
65 70 75

<210> SEQ ID NO 95
<211> LENGTH: 95
<212> TYPE: PRT
<213> ORGANISM: Brassica napus

<400> SEQUENCE: 95

Met Glu Val Asn Gly Glu Glu Lys Arg Ser Tyr Arg Arg Glu Asp Glu
1 5 10 15

Glu Lys Glu Val Tyr Tyr Pro Leu Leu Asn Ser Pro Cys Ser Ala Phe
20 25 30

His Lys Thr Val Gln Ala Ile Leu Lys Cys Leu Gly Leu Glu Ser Ser
35 40 45

Ser Ile Ser Pro Ser Ser Ser Ser Ser Gln Asp Pro Gly Thr Glu Thr
50 55 60

Val Gln Glu Thr Gly Phe Met Ala Met Val Ala Arg Leu Thr Arg Arg
65 70 75 80

Arg Pro Arg Pro Pro Tyr Ser Ser Gly Gln Pro Gly Gln Ile Asn
85 90 95

<210> SEQ ID NO 96
<211> LENGTH: 116
<212> TYPE: PRT
<213> ORGANISM: Solanum tuberosum

<400> SEQUENCE: 96

Met Phe Tyr Leu Gln Glu Gly Ile Lys Ala Ile Leu Lys Cys Leu Gly
1 5 10 15

Phe Glu Ser Ser Lys Leu Val His Gln Ala Ser Ser Ser Ser Ser Ser
20 25 30

Ser Ser Met Ser Asp Ile Asn Lys Asn Glu Glu Glu Glu Ser Glu Lys
35 40 45

Gln Glu Gln Glu Cys Val Leu Phe Gln Glu Asp Gly Asn Lys Gln Gly

```
    50                  55                  60

Ser Asp Ser Thr Asn Asp Asn Tyr Lys Asn Asp Pro Pro Val Glu Asn
65                  70                  75                  80

Asp Asp Glu Asp Pro Pro Gln Ser Glu Thr Leu Ile Leu Pro Thr Glu
                85                  90                  95

Arg Arg Gly Arg Pro Pro Ser Arg Pro Lys Val Gly Ser Gly Pro Pro
            100                 105                 110

Pro Gln Asn Asn
        115

<210> SEQ ID NO 97
<211> LENGTH: 121
<212> TYPE: PRT
<213> ORGANISM: Populus balsamifera

<400> SEQUENCE: 97

Met Asp Lys Gly Ser Ser Thr Lys Glu Glu Ile Gln Gly Asp Val Leu
1               5                   10                  15

Gln Ile Ser His Ser Pro Ser Ile Phe Val Glu Ala Phe Asn Ala Leu
            20                  25                  30

Leu Arg Cys Leu Gly Leu Gly Thr Val Asp His Gln Arg Ile Thr Gln
        35                  40                  45

Glu Ser Ser Ser Thr Ser Ser Ser Lys Gln Glu Asp Asp Glu Lys Ala
    50                  55                  60

Ser Glu Glu Ser Pro Gln Tyr Pro Pro Pro Thr Arg Thr Ser Asp Pro
65                  70                  75                  80

Gln Ala Asp Pro Pro Thr Asp Thr Ser Glu Asp Pro Ser Thr Asp Ala
                85                  90                  95

Ala Val Ser Ala Leu Ala Arg Arg Thr Pro Pro Val Ser Arg Gly Gly
            100                 105                 110

Gly Gly Gln Thr Asn Thr Thr Thr Ser
        115                 120

<210> SEQ ID NO 98
<211> LENGTH: 110
<212> TYPE: PRT
<213> ORGANISM: Betula spp.

<400> SEQUENCE: 98

Met Glu Glu Ser Ser Ala Asn Asp Gln Ala Thr Thr Ala His Thr Lys
1               5                   10                  15

Val Val Tyr Phe Leu Glu Glu Ala Leu Arg Ala Ile Phe Lys Cys Leu
            20                  25                  30

Gly Leu Glu Thr Lys Pro Gln Asp Asp Pro Pro Ser Ser Gln Leu Glu
        35                  40                  45

Asp Ala Ser Ser Thr Thr Lys Gln Ala Val Ala Asp Asn Ser Ser Thr
    50                  55                  60

Ala Asp Pro Glu Leu Ala Asp Pro Pro Ser Thr Thr Glu Thr Ser Glu
65                  70                  75                  80

Val Ala Ala Thr Ala Ser Ile Asp Leu Val Met Ala Val Asn Ala Pro
                85                  90                  95

Pro Arg Pro Ser Leu Thr Pro Gly Ser Gly Ala Gln Ile Asn
            100                 105                 110

<210> SEQ ID NO 99
<211> LENGTH: 115
<212> TYPE: PRT
<213> ORGANISM: Glycine max
```

<400> SEQUENCE: 99

Met Glu Gly Ser Ser Pro Ser Ile Glu Glu Glu Arg Thr Ala Thr Phe
1 5 10 15

Tyr Val Tyr His Pro Cys Tyr Phe Leu Gln Gln Ala Leu Arg Ala Leu
20 25 30

Leu Lys Cys Val Gly Ile Asp Glu Ser Glu Asn Thr Met Cys Ser Gln
35 40 45

Ala Asn Lys Gln Glu Lys Ser Ser Leu Pro Gln Thr Pro Ser Ala Asp
50 55 60

Asp Pro Ile Thr Asn Ser Pro Thr His Lys Ser Ser Pro Asp Ala Ala
65 70 75 80

Asp Pro Pro Ser Thr Thr Asn Gln Thr Ile Ile Ile Ala Ser Leu Met
85 90 95

Ala Thr Arg Gly Ser Arg Gly Ser Lys Ile Ser Asp Gly Ser Gly Pro
100 105 110

Gln His Asn
115

<210> SEQ ID NO 100
<211> LENGTH: 127
<212> TYPE: PRT
<213> ORGANISM: Medicago sativa

<400> SEQUENCE: 100

Met Glu Glu Thr Thr Glu Arg Leu Ser Thr Lys Lys Glu Glu Lys Thr
1 5 10 15

Met Thr Phe Tyr Val Tyr His Pro Cys Tyr Cys Leu Glu Glu Ile Phe
20 25 30

Lys Thr Phe Leu Arg Cys Phe Gly Ile Glu Ser Thr Gln Thr Lys Glu
35 40 45

Glu Glu Asp Ser Ser Thr Ser Leu Leu Lys Pro His Ala Cys Ala Cys
50 55 60

Ala Ser Asp Ser Asn Val Ala Leu Lys Asp Arg Tyr Tyr Ser Ser Ser
65 70 75 80

Ser Asn Lys Lys Ser Ser Gln Glu Glu Gly Val Ala Asp Pro Pro Pro
85 90 95

Ser Thr Ser Thr Gln Thr Ile Asn Leu Ser Ser Met Gly Arg Gly Gly
100 105 110

Pro Arg Arg Thr Pro Leu Thr Gln Gly Pro Pro Pro Gln His Asn
115 120 125

<210> SEQ ID NO 101
<211> LENGTH: 84
<212> TYPE: PRT
<213> ORGANISM: Vitis vinifera

<400> SEQUENCE: 101

Met Asn Asp Asp Ala Glu Gln Arg Gln Arg Ser His Ala Gly Asp Asp
1 5 10 15

Gly Gln Glu Gly Leu Asp Leu Gly Arg Leu Pro Pro Asn Pro Cys Gly
20 25 30

His Gly Val Asp Arg Ser Ser Trp Arg Pro His Gly Gly Gly Pro Phe
35 40 45

Val Phe Cys Phe Cys Pro Cys Leu Ala Gly Glu Lys Val Arg Glu Lys
50 55 60

Gln Lys Lys Gly Glu Asp Gly Glu Ser Val Gly Arg Pro Gly Lys Lys

```
65                  70                  75                  80

Asn Glu Ile Leu

<210> SEQ ID NO 102
<211> LENGTH: 154
<212> TYPE: PRT
<213> ORGANISM: Oryza sativa

<400> SEQUENCE: 102

Met Asp Arg Val Glu Glu Lys Glu Gly Asn Arg Phe Gln Glu Pro Ala
1               5                   10                  15

Ser Asp Arg Cys Glu Asp Asn Glu Asp Lys Glu Gln Asp Asn Ser Glu
            20                  25                  30

Glu Ser Ser Ser Val Asp Gln Arg Lys Glu Glu Glu Glu Glu Glu Lys
        35                  40                  45

Glu Gly Cys Glu Glu Ala Thr Pro Ala Ala Ala Ala Ala Ala Ala Ala
    50                  55                  60

Pro Ser Phe Phe Ala His Pro Cys Ser Leu Leu Gln Tyr Ile Ala Arg
65                  70                  75                  80

Val Cys Ala Cys Cys Leu Gly Leu Ser Asp Ser Phe Cys Asp Pro Lys
                85                  90                  95

Ala Ser Ser Val Leu Val Pro Glu Pro Glu Pro Ala Ala Ala Asp Pro
            100                 105                 110

Ser Gln Glu Gly Glu Glu Asp Met Lys Ser Ser Glu Ala Thr Thr Arg
        115                 120                 125

Val Arg Ala Ala Arg Leu Arg Pro Lys Pro Pro Gly Asn Pro Arg Glu
    130                 135                 140

Gly Ser Gly Gly Asn Gly Gly His His His
145                 150

<210> SEQ ID NO 103
<211> LENGTH: 93
<212> TYPE: PRT
<213> ORGANISM: Oryza sativa

<400> SEQUENCE: 103

Met Ala Met Ser Ser Ser Pro Ala Ser Pro Pro Pro Ser Phe Leu Ile
1               5                   10                  15

Gly Gly Ala Gln Ala Gln Leu Leu Arg His Arg Glu Glu Met Leu Leu
            20                  25                  30

Val Leu Pro Ser Pro Pro Ser Gly Arg Gln Leu Pro Ser Glu Glu Glu
        35                  40                  45

Glu Ala Ala Pro Cys Ala Val Asn Gly Arg Ser Thr Ile Leu Ala Ala
    50                  55                  60

Ala Asp Asp Ser Lys Pro Thr Arg Pro Gly Ala Pro Ala Glu Gly Ser
65                  70                  75                  80

Gly Gly Asn Gly Gly Ala Ile His Thr Ala Ala Ser Ser
                85                  90

<210> SEQ ID NO 104
<211> LENGTH: 82
<212> TYPE: PRT
<213> ORGANISM: Triticum aestivum

<400> SEQUENCE: 104

Met Gly Met Ala Asp Trp Phe Gly Gly Gly Gly Thr Arg Pro Ser Ala
1               5                   10                  15

Ala Pro Ala Ala Ser Leu Asn Ser Ser Arg Glu Glu Ala Gly Glu Ala
```

-continued

```
            20                  25                  30

Ala Asp Ile Gly Thr Arg Glu Ile Ser Lys Thr Thr Thr Gly Arg Gly
        35                  40                  45

Phe Tyr Met Arg Glu Val Ile Met Arg Val Arg Ala Val Arg Arg Pro
    50                  55                  60

Arg Pro Pro Thr Thr Pro Arg Glu Gly Arg Gly Gly Gly Gly Gly Ser
65                  70                  75                  80

His Asn

<210> SEQ ID NO 105
<211> LENGTH: 75
<212> TYPE: PRT
<213> ORGANISM: Triticum aestivum

<400> SEQUENCE: 105

Met Ala Ser Pro Ser Pro Ser Phe Leu Leu Gln Leu Val Arg Tyr Val
1               5                   10                  15

Trp Ser Leu Pro Ser Gln Phe Met Gly Ala Thr Ala Arg Ala Leu Pro
            20                  25                  30

Ala Ser Arg Glu Gly Ala Gly Gly Ala Ile Arg Pro Ser Phe Ala Ala
        35                  40                  45

Pro Ala Pro Gln Arg Pro Gly Ala Pro Ala Glu Gly Ala Gly Gly Gln
    50                  55                  60

Gly Gly Ile Ile His Glu Ala Ser Pro Val Pro
65                  70                  75

<210> SEQ ID NO 106
<211> LENGTH: 142
<212> TYPE: PRT
<213> ORGANISM: Zea mays

<400> SEQUENCE: 106

Met Asp Glu Arg Gly Glu Lys Glu Glu Glu His Gly Val Val Glu Glu
1               5                   10                  15

Glu Thr Ala Ala Val Val Leu Lys Glu Val Glu Val Glu Met Glu Met
            20                  25                  30

Val Gly Gly Ser Glu Glu Ala Ser Ala Ala Pro Leu Leu Leu Ala His
        35                  40                  45

Pro Cys Ser Leu Leu Gln Leu Leu Leu Arg Ala Cys Ala Gly Cys Leu
    50                  55                  60

Val Arg Leu Leu His Gly His Cys Ser Asp Gly Ala Asn Asp Asp Pro
65                  70                  75                  80

Lys Ala Ala Ala Asp Asp Asp Asp Ala Ala Pro Glu Ala Ala Ala Ala
                85                  90                  95

Ala Ala Ala Ala Ala Gly Asp Gly Gly Asp Lys Ala Ala Thr Tyr Leu
            100                 105                 110

Tyr Met Gln Glu Val Trp Ala Val Arg Arg Arg Pro Thr Thr Pro Gly
        115                 120                 125

Arg Pro Arg Glu Gly Ser Gly Gly Asn Gly Gly Asn His His
    130                 135                 140

<210> SEQ ID NO 107
<211> LENGTH: 93
<212> TYPE: PRT
<213> ORGANISM: Hordeum vulgare

<400> SEQUENCE: 107

Met Ala Ser Ser Ala Pro Pro Ala Phe Leu Pro Gln Leu Val Gln Pro
```

-continued

```
1               5                   10                  15

Val Ser Val Leu Pro Asp Gln Pro Pro Ser Ala Pro Ala Glu Gly Thr
            20                  25                  30

Gly Gly Gln Val Met Val Leu Asn Asp Ala Ser Ser Leu Pro Leu Gln
        35                  40                  45

Leu Met Arg Thr Pro Pro Gly Glu Gly Ala Gly Gly Arg Ile His Arg
    50                  55                  60

Gln Leu Ala Arg Pro Arg Pro Pro Gly Pro Pro Arg Gln Gly His Gly
65                  70                  75                  80

Gly Asp Gly Gly Ala Ile His Ala Ile Leu Leu Glu Leu
                85                  90

<210> SEQ ID NO 108
<211> LENGTH: 4509
<212> TYPE: DNA
<213> ORGANISM: Arabidopsis thaliana

<400> SEQUENCE: 108
tgaaagaccc aaacctaatg aatgttaacc actaattgac cattcaccaa ccaattattt      60
aatgaaatat ctttgttagt ttcgttattt agtattgtta acggtttctt actctttttg     120
actacatcag acggacgtaa aacgacatcg ttgtcgaata ttcaaaagat tcacaatttg     180
acaaagagaa acagagacga cttgtttcta aaaaaaccac gtgtgtctga aaacggaaaa     240
aaagaagact gaatgagaaa cggcgtgtaa aaagaaaacg cgttgaaggt taggctctca     300
caatcgttgg tatacagaga gaccaaacat ctcgtcataa aaaacggcaa gaatcatcag     360
ttactttata cccatcaatc aagtcttgtc ctttttctcc ttctctctct catacgagct     420
tctttcctgc tgatgaggct tgagctttaa attttcaatc ttgattgaga ttctgcatgt     480
ttctcgatct ttaaactcag atgaagaatc ttggggggtt gttcaaaatt cttctgcttt     540
tcttctgtct ctttctatcg acccacataa tttccgtttc ttgtttaaac tcagatgggc     600
taactctact ctctcttctg aagcatttgg atagagtacc accacaagtt acttcgacat     660
ggaaaataaa cgcatctgaa gcaactccat gtaactggtt cggtatcact tgtgacgatt     720
ctaagaatgt tgcgtctctc aacttcactc gttctagggt ttcaggtcaa ttgggtccgg     780
aaattgggga gctcaaaagc ttgcagattt tggatctgag tactaacaat ttctccggga     840
ctataccttc cactttagga aactgtacca aactcgctac tctagatttg tctgaaaatg     900
gattctctga taagatccca gatactctcg atagcttgaa gaggttggag gtgctttatc     960
tttacataaa cttcctcact ggtgagttac ctgaatcctt gtttcgaatt ccgaagctgc    1020
aggttttata tcttgactat aacaatctca ccggtccgat tcctcaaagt attggtgatg    1080
ctaaggagct tgtggagctg agtatgtatg cgaatcagtt ctctggtaac atccctgagt    1140
cgattgggaa tagcagtagt ctgcagattc tttatttgca caggaacaag ttagttggtt    1200
cattacctga aagtctcaat cttttgggga atctcactac tctgtttgtt ggtaacaaca    1260
gtctacaagg gccggttcgt ttcggatcac ctaattgcaa gaatttgttg actttagatt    1320
tgtcatacaa tgaattcgaa ggcggtgttc cacctgcatt gggaaattgc agtagccttg    1380
acgctttagt cattgtgagt ggtaacttgt caggtacaat cccttcctca ttgggtatgt    1440
tgaagaatct cacaattctt aacctttccg agaatcgtct ctctgggagt atccccgcag    1500
agctcgggaa ctgcagtagc ttgaacttgt tgaagctgaa cgataaccag cttgtaggcg    1560
gaataccgag tgcattaggt aagctgagga agctagaaag tctggagctt ttcgaaaacc    1620
ggttttcggg tgagattcct attgagatat ggaagagtca gagtcttacg cagttgctag    1680
```

-continued

```
tttatcaaaa caatctcact ggtgaactac ctgtggaaat gactgagatg aagaagctaa   1740
agatcgctac gctgttcaac aacagctttt atggagcgat accaccgggt ttaggtgtga   1800
acagcagctt agaagaggtt gactttattg gtaacaaact tacaggagag ataccgccaa   1860
atctatgcca tggaaggaag ttgagaatac tcaacttggg ttctaatctg cttcatggta   1920
caataccagc ttctattggt cactgtaaga ccatcaggag attcatcctt agagaaaata   1980
acctttcagg tcttcttcct gagttttctc aggatcatag tctttctttt cttgatttca   2040
atagcaacaa cttcgaagga ccaatcccgg gcagcctcgg aagctgtaag aatctctcga   2100
gtattaacct atctcgaaac agattcacgg ggcagatacc tccacaactt gggaatctac   2160
aaaaccttgg ttacatgaat ctttctcgta atcttcttga agggtctcta ccagctcagc   2220
tatctaactg tgtgagttta gagcgttttg atgttggctt caactcatta aacggttcag   2280
ttccttcaaa ctttagtaac tggaaaggct tgacgacttt agttctcagc gagaaccggt   2340
tttcaggagg tattccacag ttcttgcctg agcttaagaa gctgtcaact ctgcagattg   2400
ctagaaatgc ttttggtggt gagattcctt cgtcgattgg gttgatagag gatctgatct   2460
atgacttgga ccttagtgga aacggattga caggtgaaat tccagccaag ttgggagatc   2520
tcatcaagtt aacaagactc aacatatcta acaacaattt gacaggatct ttatcggttc   2580
tcaaaggtct tacctcattg ctacatgttg atgtctccaa caatcagttc acaggtccaa   2640
taccagataa cttggagggt cagttgttat ctgagccgtc gtcgttttca ggaaatccaa   2700
acctctgcat tccacattcc ttctctgcta gcaacaatag ccgcagcgcg ttaaagtact   2760
gtaaagatca atctaaaagc aggaagagtg gccttagcac ctggcaaatc gtgctaatag   2820
cggtcttatc gtctttatta gtcttggttg tggtccttgc tcttgttttc atttgcctac   2880
gtcgtcgcaa aggaagacca gagaaagatg cttatgtctt cactcaggag gaaggcccat   2940
ctttgttgtt gaacaaagtt cttgcagcaa ctgacaatct aaatgaaaag tacaccattg   3000
gaagaggagc tcatggaatt gtgtacagag cttctttagg ctccggaaag gtctacgctg   3060
tgaagagact tgtattcgcg tctcacatcc gcgctaacca gagtatgatg agggagattg   3120
atacaatcgg taaagtcagg cacaggaatc tgattaagtt agaagggttt tggctgagga   3180
aagacgacgg tttaatgctg tatagataca tgccaaaagg aagtctttac gacgttctcc   3240
acggtgttag cccgaaagaa aatgtgctag actggtctgc acggtacaat gtagcacttg   3300
gtgtcgctca tggactagcc tatctacact atgactgcca tcccccgatt gttcaccgtg   3360
acatcaaacc agagaacata ctcatggact cagatttgga gcctcacatt ggggatttcg   3420
gtttggctcg ccttcttgat gactcaacgg tttcaactgc aactgttaca ggcaccaccg   3480
gctacattgc accaggtaat gcatcttctc attatacata gtggacttgg tataatctgg   3540
tttagtgttc aaaccgagtt agttaccggt taaaaaagtc tgttaggaag atactctgtt   3600
tcttattagc taatttcaca attaaactgc agaaaacgct ttcaaaaccg tgaggggaag   3660
agaatcagac gtttacagtt atggagtcgt gttacttgag ctggttacga ggaagagagc   3720
ggtggacaaa tctttcccgg aaagtacaga tatagtaagc tgggtgagat ctgccttgag   3780
cagcagcaac aacaatgtgg aggatatggt aacaacaatc gtcgatccga ttctcgtgga   3840
cgagcttctg gattcgagtc ttagggagca ggtgatgcaa gtgacggaac tggcactgag   3900
ttgtacacag caagatccgg caatgagacc aacgatgaga gatgcggtga aactgttgga   3960
agatgtgaaa catctggcaa gaagctgctc ctctgattca gttcggtaat ctcgttactt   4020
tgtgcagagc agaaggagga aactaaagga ctgttatcag tggtaacgta actgggctta   4080
```

```
ccggtaatgt aactgggcca ataatgtaaa atatggctta ttgaaggccc aaatatgacg   4140
gccctttaat tgtaaccgtg tttgtttgtg aaataaaatc tcgtttatca aatttctgtt   4200
tcctatttta tttttaaaaa aagtgttggg aaaattttcg tttggccgga gatgaagata   4260
ggggcggttc aggagagttg gcttatacgg actccggtac ttaggccggc ggttcaaggc   4320
tcaattcgcc ggaatggaaa gccgcagctt gagtttcctc tctcgaacag tgagcttaag   4380
ctcttctttc ttccattgaa ttttttttt gggaacgcat tatcttgtgc acacttgtag   4440
taacttggtc tatatcaaat tgaggttgaa gatgaaagtt cagttatttc ctgtgatttg   4500
caatttcct                                                           4509

<210> SEQ ID NO 109
<211> LENGTH: 1123
<212> TYPE: PRT
<213> ORGANISM: Arabidopsis thaliana

<400> SEQUENCE: 109

Met Lys Asn Leu Gly Gly Leu Phe Lys Ile Leu Leu Leu Phe Phe Cys
1               5                   10                  15

Leu Phe Leu Ser Thr His Ile Ile Ser Val Ser Cys Leu Asn Ser Asp
            20                  25                  30

Gly Leu Thr Leu Leu Ser Leu Leu Lys His Leu Asp Arg Val Pro Pro
        35                  40                  45

Gln Val Thr Ser Thr Trp Lys Ile Asn Ala Ser Glu Ala Thr Pro Cys
    50                  55                  60

Asn Trp Phe Gly Ile Thr Cys Asp Asp Ser Lys Asn Val Ala Ser Leu
65                  70                  75                  80

Asn Phe Thr Arg Ser Arg Val Ser Gly Gln Leu Gly Pro Glu Ile Gly
                85                  90                  95

Glu Leu Lys Ser Leu Gln Ile Leu Asp Leu Ser Thr Asn Asn Phe Ser
            100                 105                 110

Gly Thr Ile Pro Ser Thr Leu Gly Asn Cys Thr Lys Leu Ala Thr Leu
        115                 120                 125

Asp Leu Ser Glu Asn Gly Phe Ser Asp Lys Ile Pro Asp Thr Leu Asp
    130                 135                 140

Ser Leu Lys Arg Leu Glu Val Leu Tyr Leu Tyr Ile Asn Phe Leu Thr
145                 150                 155                 160

Gly Glu Leu Pro Glu Ser Leu Phe Arg Ile Pro Lys Leu Gln Val Leu
                165                 170                 175

Tyr Leu Asp Tyr Asn Asn Leu Thr Gly Pro Ile Pro Gln Ser Ile Gly
            180                 185                 190

Asp Ala Lys Glu Leu Val Glu Leu Ser Met Tyr Ala Asn Gln Phe Ser
        195                 200                 205

Gly Asn Ile Pro Glu Ser Ile Gly Asn Ser Ser Ser Leu Gln Ile Leu
    210                 215                 220

Tyr Leu His Arg Asn Lys Leu Val Gly Ser Leu Pro Glu Ser Leu Asn
225                 230                 235                 240

Leu Leu Gly Asn Leu Thr Thr Leu Phe Val Gly Asn Asn Ser Leu Gln
                245                 250                 255

Gly Pro Val Arg Phe Gly Ser Pro Asn Cys Lys Asn Leu Leu Thr Leu
            260                 265                 270

Asp Leu Ser Tyr Asn Glu Phe Glu Gly Gly Val Pro Pro Ala Leu Gly
        275                 280                 285

Asn Cys Ser Ser Leu Asp Ala Leu Val Ile Val Ser Gly Asn Leu Ser
```

```
    290                 295                 300

Gly Thr Ile Pro Ser Ser Leu Gly Met Leu Lys Asn Leu Thr Ile Leu
305                 310                 315                 320

Asn Leu Ser Glu Asn Arg Leu Ser Gly Ser Ile Pro Ala Glu Leu Gly
                325                 330                 335

Asn Cys Ser Ser Leu Asn Leu Leu Lys Leu Asn Asp Asn Gln Leu Val
            340                 345                 350

Gly Gly Ile Pro Ser Ala Leu Gly Lys Leu Arg Lys Leu Glu Ser Leu
        355                 360                 365

Glu Leu Phe Glu Asn Arg Phe Ser Gly Glu Ile Pro Ile Glu Ile Trp
    370                 375                 380

Lys Ser Gln Ser Leu Thr Gln Leu Leu Val Tyr Gln Asn Asn Leu Thr
385                 390                 395                 400

Gly Glu Leu Pro Val Glu Met Thr Glu Met Lys Lys Leu Lys Ile Ala
                405                 410                 415

Thr Leu Phe Asn Asn Ser Phe Tyr Gly Ala Ile Pro Pro Gly Leu Gly
            420                 425                 430

Val Asn Ser Ser Leu Glu Glu Val Asp Phe Ile Gly Asn Lys Leu Thr
        435                 440                 445

Gly Glu Ile Pro Pro Asn Leu Cys His Gly Arg Lys Leu Arg Ile Leu
    450                 455                 460

Asn Leu Gly Ser Asn Leu Leu His Gly Thr Ile Pro Ala Ser Ile Gly
465                 470                 475                 480

His Cys Lys Thr Ile Arg Arg Phe Ile Leu Arg Glu Asn Asn Leu Ser
                485                 490                 495

Gly Leu Leu Pro Glu Phe Ser Gln Asp His Ser Leu Ser Phe Leu Asp
            500                 505                 510

Phe Asn Ser Asn Asn Phe Glu Gly Pro Ile Pro Gly Ser Leu Gly Ser
        515                 520                 525

Cys Lys Asn Leu Ser Ser Ile Asn Leu Ser Arg Asn Arg Phe Thr Gly
    530                 535                 540

Gln Ile Pro Pro Gln Leu Gly Asn Leu Gln Asn Leu Gly Tyr Met Asn
545                 550                 555                 560

Leu Ser Arg Asn Leu Leu Glu Gly Ser Leu Pro Ala Gln Leu Ser Asn
                565                 570                 575

Cys Val Ser Leu Glu Arg Phe Asp Val Gly Phe Asn Ser Leu Asn Gly
            580                 585                 590

Ser Val Pro Ser Asn Phe Ser Asn Trp Lys Gly Leu Thr Thr Leu Val
        595                 600                 605

Leu Ser Glu Asn Arg Phe Ser Gly Gly Ile Pro Gln Phe Leu Pro Glu
    610                 615                 620

Leu Lys Lys Leu Ser Thr Leu Gln Ile Ala Arg Asn Ala Phe Gly Gly
625                 630                 635                 640

Glu Ile Pro Ser Ser Ile Gly Leu Ile Glu Asp Leu Ile Tyr Asp Leu
                645                 650                 655

Asp Leu Ser Gly Asn Gly Leu Thr Gly Glu Ile Pro Ala Lys Leu Gly
            660                 665                 670

Asp Leu Ile Lys Leu Thr Arg Leu Asn Ile Ser Asn Asn Leu Thr
        675                 680                 685

Gly Ser Leu Ser Val Leu Lys Gly Leu Thr Ser Leu Leu His Val Asp
    690                 695                 700

Val Ser Asn Asn Gln Phe Thr Gly Pro Ile Pro Asp Asn Leu Glu Gly
705                 710                 715                 720
```

```
Gln Leu Leu Ser Glu Pro Ser Ser Phe Ser Gly Asn Pro Asn Leu Cys
                725                 730                 735

Ile Pro His Ser Phe Ser Ala Ser Asn Asn Ser Arg Ser Ala Leu Lys
            740                 745                 750

Tyr Cys Lys Asp Gln Ser Lys Ser Arg Lys Ser Gly Leu Ser Thr Trp
        755                 760                 765

Gln Ile Val Leu Ile Ala Val Leu Ser Ser Leu Leu Val Leu Val Val
    770                 775                 780

Val Leu Ala Leu Val Phe Ile Cys Leu Arg Arg Arg Lys Gly Arg Pro
785                 790                 795                 800

Glu Lys Asp Ala Tyr Val Phe Thr Gln Glu Glu Gly Pro Ser Leu Leu
                805                 810                 815

Leu Asn Lys Val Leu Ala Ala Thr Asp Asn Leu Asn Glu Lys Tyr Thr
            820                 825                 830

Ile Gly Arg Gly Ala His Gly Ile Val Tyr Arg Ala Ser Leu Gly Ser
        835                 840                 845

Gly Lys Val Tyr Ala Val Lys Arg Leu Val Phe Ala Ser His Ile Arg
    850                 855                 860

Ala Asn Gln Ser Met Met Arg Glu Ile Asp Thr Ile Gly Lys Val Arg
865                 870                 875                 880

His Arg Asn Leu Ile Lys Leu Glu Gly Phe Trp Leu Arg Lys Asp Asp
                885                 890                 895

Gly Leu Met Leu Tyr Arg Tyr Met Pro Lys Gly Ser Leu Tyr Asp Val
            900                 905                 910

Leu His Gly Val Ser Pro Lys Glu Asn Val Leu Asp Trp Ser Ala Arg
        915                 920                 925

Tyr Asn Val Ala Leu Gly Val Ala His Gly Leu Ala Tyr Leu His Tyr
    930                 935                 940

Asp Cys His Pro Pro Ile Val His Arg Asp Ile Lys Pro Glu Asn Ile
945                 950                 955                 960

Leu Met Asp Ser Asp Leu Glu Pro His Ile Gly Asp Phe Gly Leu Ala
                965                 970                 975

Arg Leu Leu Asp Asp Ser Thr Val Ser Thr Ala Thr Val Thr Gly Thr
            980                 985                 990

Thr Gly Tyr Ile Ala Pro Glu Asn  Ala Phe Lys Thr Val  Arg Gly Arg
        995                 1000                 1005

Glu Ser  Asp Val Tyr Ser Tyr  Gly Val Val Leu Leu  Glu Leu Val
    1010                 1015                 1020

Thr Arg  Lys Arg Ala Val Asp  Lys Ser Phe Pro Glu  Ser Thr Asp
    1025                 1030                 1035

Ile Val  Ser Trp Val Arg Ser  Ala Leu Ser Ser Ser  Asn Asn Asn
    1040                 1045                 1050

Val Glu  Asp Met Val Thr Thr  Ile Val Asp Pro Ile  Leu Val Asp
    1055                 1060                 1065

Glu Leu  Leu Asp Ser Ser Leu  Arg Glu Gln Val Met  Gln Val Thr
    1070                 1075                 1080

Glu Leu  Ala Leu Ser Cys Thr  Gln Gln Asp Pro Ala  Met Arg Pro
    1085                 1090                 1095

Thr Met  Arg Asp Ala Val Lys  Leu Leu Glu Asp Val  Lys His Leu
    1100                 1105                 1110

Ala Arg  Ser Cys Ser Ser Asp  Ser Val Arg
    1115                 1120
```

<210> SEQ ID NO 110

<211> LENGTH: 4353
<212> TYPE: DNA
<213> ORGANISM: Arabidopsis thaliana

<400> SEQUENCE: 110
attctagtgt agacgacaga taccagagat cttgattaaa ttccaatata taatgtttat 60
gaaagattta aatctaacaa agtaacagta ggatgaaatg tcaatagaaa attagcgtcc 120
aaagaagctt tctcttgaat aagctaagaa aacaaaacgt ggaaaatgga atatttaaaa 180
ccacgaaaca gtctccgagt agtaatggaa atagcgagaa agaaacacga aacagcgttg 240
aaggtcgcca attcgtaaag ttaggttcac aatctctgac gaagagttaa ccaaaaagcg 300
cgctcttttt ctctctcacc aaactcatcg atcgtttctt aaataatgca atctgttcct 360
gtcactaaat ccagataccc tttcaaatcc aaaagctctc tcttttttt ttccgcctct 420 cattctgggt tcaagggttg ttgagtgagg ttactacgta cgagtgtttc atatttcagt 480
ctcttgagct ctaatctcaa atgaggaatc ttgggttact cgaaattact ctgctttgct 540
ctctctttgt ctatttccgt atagattctg tctctagttt aaactcagat ggtttggctt 600
tactctcgct tctcaagcac tttgataaag tcccacttga agtagcttcg acgtggaagg 660
agaacacatc tgaaaccact ccatgtaata ataactggtt tggtgtcatt tgtgatcttt 720
ctggtaatgt cgtcgagacc cttaatttgt ctgcttctgg gctttcaggc caattaggtt 780
ctgaaattgg ggagcttaag agcttggtca cattggatct cagtcttaac agtttctctg 840
gtttattgcc ttccacttta ggaaactgta cttcacttga gtatttggat ttgtctaaca 900 atgattttc tggagaagtt cctgatattt ttggtagctt gcagaatttg acgtttctgt 960
atcttgatcg caataatctt agtggtctca ttcctgcaag tgttggtggg ttgatagagc 1020
tcgtagatct gaggatgtca tataataact tgtctggtac cattccagag ttgcttggga 1080
actgtagtaa gctggaatat ctggctttga acaacaacaa gttaaatggt tctttgccag 1140
caagtctcta tctactcgag aatcttggtg agctatttgt cagtaacaac agccttggag 1200
ggaggcttca ttttggttct agcaactgca agaaattggt ttctttagat ctctcgttca 1260
atgatttcca aggcggtgtt ccacctgaga taggcaactg cagtagcctt cactctttag 1320
tcatggtgaa atgcaacttg acaggtacaa tcccatcatc aatgggtatg ttgagaaagg 1380
tttcggttat tgacctttcc gataatcgtc tctcggggaa tatccctcaa gagcttggga 1440
actgcagcag cttggaaacc ttgaagctga acgacaacca gctccaaggc gagataccac 1500
ctgcattgag taagctaaag aagctacaaa gcctggagct ttttttaat aagctgtccg 1560 gtgagattcc tattggcata tggaagattc agagtctgac acagatgctc gtttataaca 1620
acactctcac cggggaacta ccagttgaag taactcagct gaagcacctt aagaagctta 1680
cactgtttaa caacggcttt tatggagata taccaatgag tttaggcctg aatcgaagct 1740
tagaggaggt ggaccttctt ggtaaccgtt ttacagggga gataccaccc catctctgcc 1800
atggacagaa gttgagattg ttcatcttgg gttctaatca gcttcatggt aagataccag 1860
cgtctattcg tcagtgtaag acccttgagc gagtcagact tgaagataac aaactttcag 1920
gtgttcttcc ggaattccct gagagtctta gtctttccta tgtgaacctc ggaagcaata 1980
gctttgaagg atccatcccg cgcagcttgg gaagctgtaa aaatctcttg actattgacc 2040
tttctcaaaa caaactcacg ggtctgatac ctccagaact gggaaatctg caaagccttg 2100
gactgttgaa cctttcacat aattatctgg aaggtcctct gccatcccag ctatcaggct 2160
gtgcgagact tctgtatttt gatgttggat ccaactcatt gaacggttct attccatcaa 2220
gcttcagaag ctggaaaagc ttgtccactt tagttctcag tgacaataat tttctaggag 2280
ctattccaca gttcttggca gagcttgacc gactctcaga tctgcggata gctcgaaatg 2340
cttttggagg taagattcct tcctcggttg gcttgttgaa gagtctacgc tatggcttag 2400
acctcagtgc gaacgtattt acgggtgaga ttccaaccac actgggggct cttatcaatc 2460
ttgaacgtct caacatatcc aacaacaagt tgacagggcc tttatcggtt cttcaaagtc 2520
ttaagtcatt gaatcaagtt gacgtctcgt ataatcagtt cacgggtcca atacccgtaa 2580
atctgttatc aaattcttca aagttttctg gaaatccaga cctctgcatt caagcttctt 2640
actcagtgag tgccataatc cgcaaagagt ttaaatcttg caaaggtcaa gtcaaactta 2700
gcacgtggaa gatcgccctt atagcagctg ggtcctcact atccgtattg gctttgcttt 2760
ttgctctctt tttggtttta tgccggtgca aaagaggaac caagacagaa gatgctaata 2820
tcctcgcaga ggaaggtctg tccttgttgc tgaacaaagt tctagcagcc actgacaatc 2880
tagatgacaa gtacatcatt ggaagaggag ctcatggagt tgtttacaga gcttctttag 2940
gatcaggcga agaatacgcc gtgaagaaac tcatctttgc ggaacacatt cgcgcaaacc 3000
aaaatatgaa gcgggagatc gaaacaatcg ggctagtcag gcacagaaat ctcattcggt 3060
tagaaagatt ttggatgagg aaagaagatg gcttaatgct gtatcagtac atgcccaatg 3120
gaagcctaca cgacgttttg cacagaggta atcaaggaga agcagttctt gactggtctg 3180
cacggttcaa catagccctt gggatttcac atggactggc gtatttacat catgattgtc 3240
atccaccaat aattcaccgc gacatcaaac cagagaacat actcatggac tcggatatgg 3300
agcctcacat tggagatttc ggattggctc ggattctaga tgactcaaca gtttcaacgg 3360
ccactgttac tggcacaact gggtacattg caccaggtat atatacttct caacataaca 3420
cgttcgtatt ttgttcaccg ttaccttatt catgctctga tgaccatatt tctatcaaac 3480
agaaaatgcg tacaagacgg tgaggagcaa ggaatcagat gtttacagtt atggagttgt 3540
tttgctcgag ctggtaacag gaaagagagc actggacaga tctttcccgg aagatatcaa 3600
cattgtgagc tgggtcagat ctgtattaag cagctacgag gatgaagacg atactgctgg 3660
tccaatcgtt gatccaaaac ttgtggatga gcttctggat acgaagctca gggaacaagc 3720
aatccaagtc acagacttgg ctcttagatg tacagacaag aggccggaga acagaccatc 3780
gatgagagat gtggtgaaag atttgactga tttggaaagt tttgtaagaa gcacttcggg 3840
ttcagttcac tagtttcata agttgcaggt ttatatagtg tactgttctt tgaaaccact 3900
aatataattg taactaccat tgaataccgt gaagatttga gaaacatata tatccaaaga 3960
gacttaattt tattgcataa gttggaattg ttgggggaaa taaattacaa gtattaagag 4020
aggcttcaca aatttgccaa tctcagtata ttttagccag tgctaccaga aagctcgcca 4080
gagaaggcac taccatacga tgtggaaccg gttggtgtct gtgatgatgt tgcgatccct 4140
cgagctttcc gcatctgcct tagtctgaaa acatctgtgg gcaaaggctg gctttgtaca 4200
gttgctgtat catcttcttc ttgccctgtt aacagagaga tagaataaga taagtaacta 4260
tcatttaacg gttgttctaa gggatagtag aagttatatg catctgcagc taagaagtgc 4320
caaacatttg agtgatgaca tagtcatgag cca 4353

<210> SEQ ID NO 111
<211> LENGTH: 1088
<212> TYPE: PRT
<213> ORGANISM: Arabidopsis thaliana

<400> SEQUENCE: 111

-continued

```
Met Arg Asn Leu Gly Leu Leu Glu Ile Thr Leu Leu Cys Ser Leu Phe
1               5                   10                  15

Val Tyr Phe Arg Ile Asp Ser Val Ser Ser Leu Asn Ser Asp Gly Leu
            20                  25                  30

Ala Leu Leu Ser Leu Leu Lys His Phe Asp Lys Val Pro Leu Glu Val
        35                  40                  45

Ala Ser Thr Trp Lys Glu Asn Thr Ser Glu Thr Thr Pro Cys Asn Asn
    50                  55                  60

Asn Trp Phe Gly Val Ile Cys Asp Leu Ser Gly Asn Val Val Glu Thr
65                  70                  75                  80

Leu Asn Leu Ser Ala Ser Gly Leu Ser Gly Gln Leu Gly Ser Glu Ile
                85                  90                  95

Gly Glu Leu Lys Ser Leu Val Thr Leu Asp Leu Ser Leu Asn Ser Phe
            100                 105                 110

Ser Gly Leu Leu Pro Ser Thr Leu Gly Asn Cys Thr Ser Leu Glu Tyr
        115                 120                 125

Leu Asp Leu Ser Asn Asn Asp Phe Ser Gly Glu Val Pro Asp Ile Phe
    130                 135                 140

Gly Ser Leu Gln Asn Leu Thr Phe Leu Tyr Leu Asp Arg Asn Asn Leu
145                 150                 155                 160

Ser Gly Leu Ile Pro Ala Ser Val Gly Gly Leu Ile Glu Leu Val Asp
                165                 170                 175

Leu Arg Met Ser Tyr Asn Asn Leu Ser Gly Thr Ile Pro Glu Leu Leu
            180                 185                 190

Gly Asn Cys Ser Lys Leu Glu Tyr Leu Ala Leu Asn Asn Asn Lys Leu
        195                 200                 205

Asn Gly Ser Leu Pro Ala Ser Leu Tyr Leu Leu Glu Asn Leu Gly Glu
    210                 215                 220

Leu Phe Val Ser Asn Asn Ser Leu Gly Gly Arg Leu His Phe Gly Ser
225                 230                 235                 240

Ser Asn Cys Lys Lys Leu Val Ser Leu Asp Leu Ser Phe Asn Asp Phe
                245                 250                 255

Gln Gly Gly Val Pro Pro Glu Ile Gly Asn Cys Ser Ser Leu His Ser
            260                 265                 270

Leu Val Met Val Lys Cys Asn Leu Thr Gly Thr Ile Pro Ser Ser Met
        275                 280                 285

Gly Met Leu Arg Lys Val Ser Val Ile Asp Leu Ser Asp Asn Arg Leu
    290                 295                 300

Ser Gly Asn Ile Pro Gln Glu Leu Gly Asn Cys Ser Ser Leu Glu Thr
305                 310                 315                 320

Leu Lys Leu Asn Asp Asn Gln Leu Gln Gly Glu Ile Pro Pro Ala Leu
                325                 330                 335

Ser Lys Leu Lys Lys Leu Gln Ser Leu Glu Leu Phe Phe Asn Lys Leu
            340                 345                 350

Ser Gly Glu Ile Pro Ile Gly Ile Trp Lys Ile Gln Ser Leu Thr Gln
        355                 360                 365

Met Leu Val Tyr Asn Asn Thr Leu Thr Gly Glu Leu Pro Val Glu Val
    370                 375                 380

Thr Gln Leu Lys His Leu Lys Lys Leu Thr Leu Phe Asn Asn Gly Phe
385                 390                 395                 400

Tyr Gly Asp Ile Pro Met Ser Leu Gly Leu Asn Arg Ser Leu Glu Glu
                405                 410                 415

Val Asp Leu Leu Gly Asn Arg Phe Thr Gly Glu Ile Pro Pro His Leu
            420                 425                 430
```

-continued

```
Cys His Gly Gln Lys Leu Arg Leu Phe Ile Leu Gly Ser Asn Gln Leu
        435                 440                 445

His Gly Lys Ile Pro Ala Ser Ile Arg Gln Cys Lys Thr Leu Glu Arg
    450                 455                 460

Val Arg Leu Glu Asp Asn Lys Leu Ser Gly Val Leu Pro Glu Phe Pro
465                 470                 475                 480

Glu Ser Leu Ser Leu Ser Tyr Val Asn Leu Gly Ser Asn Ser Phe Glu
                485                 490                 495

Gly Ser Ile Pro Arg Ser Leu Gly Ser Cys Lys Asn Leu Leu Thr Ile
            500                 505                 510

Asp Leu Ser Gln Asn Lys Leu Thr Gly Leu Ile Pro Pro Glu Leu Gly
        515                 520                 525

Asn Leu Gln Ser Leu Gly Leu Leu Asn Leu Ser His Asn Tyr Leu Glu
    530                 535                 540

Gly Pro Leu Pro Ser Gln Leu Ser Gly Cys Ala Arg Leu Leu Tyr Phe
545                 550                 555                 560

Asp Val Gly Ser Asn Ser Leu Asn Gly Ser Ile Pro Ser Ser Phe Arg
                565                 570                 575

Ser Trp Lys Ser Leu Ser Thr Leu Val Leu Ser Asp Asn Asn Phe Leu
            580                 585                 590

Gly Ala Ile Pro Gln Phe Leu Ala Glu Leu Asp Arg Leu Ser Asp Leu
        595                 600                 605

Arg Ile Ala Arg Asn Ala Phe Gly Gly Lys Ile Pro Ser Ser Val Gly
    610                 615                 620

Leu Leu Lys Ser Leu Arg Tyr Gly Leu Asp Leu Ser Ala Asn Val Phe
625                 630                 635                 640

Thr Gly Glu Ile Pro Thr Thr Leu Gly Ala Leu Ile Asn Leu Glu Arg
                645                 650                 655

Leu Asn Ile Ser Asn Asn Lys Leu Thr Gly Pro Leu Ser Val Leu Gln
            660                 665                 670

Ser Leu Lys Ser Leu Asn Gln Val Asp Val Ser Tyr Asn Gln Phe Thr
        675                 680                 685

Gly Pro Ile Pro Val Asn Leu Leu Ser Asn Ser Ser Lys Phe Ser Gly
    690                 695                 700

Asn Pro Asp Leu Cys Ile Gln Ala Ser Tyr Ser Val Ser Ala Ile Ile
705                 710                 715                 720

Arg Lys Glu Phe Lys Ser Cys Lys Gly Gln Val Lys Leu Ser Thr Trp
                725                 730                 735

Lys Ile Ala Leu Ile Ala Ala Gly Ser Ser Leu Ser Val Leu Ala Leu
            740                 745                 750

Leu Phe Ala Leu Phe Leu Val Leu Cys Arg Cys Lys Arg Gly Thr Lys
        755                 760                 765

Thr Glu Asp Ala Asn Ile Leu Ala Glu Glu Gly Leu Ser Leu Leu Leu
    770                 775                 780

Asn Lys Val Leu Ala Ala Thr Asp Asn Leu Asp Asp Lys Tyr Ile Ile
785                 790                 795                 800

Gly Arg Gly Ala His Gly Val Val Tyr Arg Ala Ser Leu Gly Ser Gly
                805                 810                 815

Glu Glu Tyr Ala Val Lys Lys Leu Ile Phe Ala Glu His Ile Arg Ala
            820                 825                 830

Asn Gln Asn Met Lys Arg Glu Ile Glu Thr Ile Gly Leu Val Arg His
        835                 840                 845

Arg Asn Leu Ile Arg Leu Glu Arg Phe Trp Met Arg Lys Glu Asp Gly
```

850 855 860

Leu Met Leu Tyr Gln Tyr Met Pro Asn Gly Ser Leu His Asp Val Leu
865 870 875 880

His Arg Gly Asn Gln Gly Glu Ala Val Leu Asp Trp Ser Ala Arg Phe
885 890 895

Asn Ile Ala Leu Gly Ile Ser His Gly Leu Ala Tyr Leu His His Asp
900 905 910

Cys His Pro Pro Ile Ile His Arg Asp Ile Lys Pro Glu Asn Ile Leu
915 920 925

Met Asp Ser Asp Met Glu Pro His Ile Gly Asp Phe Gly Leu Ala Arg
930 935 940

Ile Leu Asp Asp Ser Thr Val Ser Thr Ala Thr Val Thr Gly Thr Thr
945 950 955 960

Gly Tyr Ile Ala Pro Glu Asn Ala Tyr Lys Thr Val Arg Ser Lys Glu
965 970 975

Ser Asp Val Tyr Ser Tyr Gly Val Val Leu Leu Glu Leu Val Thr Gly
980 985 990

Lys Arg Ala Leu Asp Arg Ser Phe Pro Glu Asp Ile Asn Ile Val Ser
995 1000 1005

Trp Val Arg Ser Val Leu Ser Ser Tyr Glu Asp Glu Asp Asp Thr
1010 1015 1020

Ala Gly Pro Ile Val Asp Pro Lys Leu Val Asp Glu Leu Leu Asp
1025 1030 1035

Thr Lys Leu Arg Glu Gln Ala Ile Gln Val Thr Asp Leu Ala Leu
1040 1045 1050

Arg Cys Thr Asp Lys Arg Pro Glu Asn Arg Pro Ser Met Arg Asp
1055 1060 1065

Val Val Lys Asp Leu Thr Asp Leu Glu Ser Phe Val Arg Ser Thr
1070 1075 1080

Ser Gly Ser Val His
1085

<210> SEQ ID NO 112
<211> LENGTH: 249
<212> TYPE: DNA
<213> ORGANISM: Oryza sativa

<400> SEQUENCE: 112
atggccagct acgcggcgca gctcaaggac atgttcttcg gcctcgtcga gcgcgtcacc 60
ggctacggac gcggcgagga caaggacgtc gctgcaggtg tagatgagcc cagcaagttg 120
gcatctgaag aggttgcagt aagcagcgaa gaggttgtga ttgtacagcg caatgagatc 180
agatcaagag gcgtagatcc ctccgtgtca ggcgggaaac agccagggat caatgcggcc 240
ggtatctag 249

<210> SEQ ID NO 113
<211> LENGTH: 82
<212> TYPE: PRT
<213> ORGANISM: Oryza sativa

<400> SEQUENCE: 113

Met Ala Ser Tyr Ala Ala Gln Leu Lys Asp Met Phe Phe Gly Leu Val
1 5 10 15

Glu Arg Val Thr Gly Tyr Gly Arg Gly Glu Asp Lys Asp Val Ala Ala
20 25 30

Gly Val Asp Glu Pro Ser Lys Leu Ala Ser Glu Glu Val Ala Val Ser

```
        35                  40                  45

Ser Glu Glu Val Val Ile Val Gln Arg Asn Glu Ile Arg Ser Arg Gly
    50                  55                  60

Val Asp Pro Ser Val Ser Gly Gly Lys Gln Pro Gly Ile Asn Ala Ala
65                  70                  75                  80

Gly Ile

<210> SEQ ID NO 114
<211> LENGTH: 534
<212> TYPE: DNA
<213> ORGANISM: Thlaspi caerulescens
<220> FEATURE:
<221> NAME/KEY: misc_feature
<222> LOCATION: 483
<223> OTHER INFORMATION: n = A, T, C or G

<400> SEQUENCE: 114
actttaattt cagatctcaa tggagaaaga gagacgaaac gaagaagaaa cttatcgatg      60
tttttctttt cagttcctcg accaaattct taaagctagc ttaaagtgtt ttggtcttct     120
tcatcatgat tcaccgccga cgacgacgaa aacagcgtcg tatcccgtac ctttaaacca     180
gccggaggaa gaagaagagg aaaatgttgg cgtgaaagac cacgtcgttg tgacgcccag     240
tggcagtaaa aacggcgtcg ttgtcacgag tagggtcaca aagttcaaag caaagatgaa     300
ggagagggaa aaagttagca ctggccggtc tggccagcat aactagcact taattaaaat     360
tgtttagttc aattaattcg cagtcaataa ttctatttat tttatagttg cacttaatat     420
aatgtttagt ggcatcattg tacttatttg tatgaattta taaatgaaat ttaacagctt     480
acnggcccca aatgataaat ctagttcatc aatatgaaaa caaccttaaa cttc           534

<210> SEQ ID NO 115
<211> LENGTH: 170
<212> TYPE: PRT
<213> ORGANISM: Thlaspi caerulescens
<220> FEATURE:
<221> NAME/KEY: VARIANT
<222> LOCATION: 156
<223> OTHER INFORMATION: Xaa = Any Amino Acid

<400> SEQUENCE: 115

Leu Phe Gln Ile Ser Met Glu Lys Glu Arg Arg Asn Glu Glu Glu Thr
1               5                   10                  15

Tyr Arg Cys Phe Ser Phe Gln Phe Leu Asp Gln Ile Leu Lys Ala Ser
            20                  25                  30

Leu Lys Cys Phe Gly Leu Leu His His Asp Ser Pro Pro Thr Thr Thr
        35                  40                  45

Lys Thr Ala Ser Tyr Pro Val Pro Leu Asn Gln Pro Glu Glu Glu Glu
    50                  55                  60

Glu Glu Asn Val Gly Val Lys Asp His Val Val Val Thr Pro Ser Gly
65                  70                  75                  80

Ser Lys Asn Gly Val Val Val Thr Ser Arg Val Thr Lys Phe Lys Ala
                85                  90                  95

Lys Met Lys Glu Arg Glu Lys Val Ser Thr Gly Arg Ser Gly Gln His
            100                 105                 110

Asn His Leu Ile Lys Ile Val Phe Asn Phe Ala Val Asn Asn Ser Ile
        115                 120                 125

Tyr Phe Ile Val Ala Leu Asn Ile Met Phe Ser Gly Ile Ile Val Leu
    130                 135                 140

Ile Cys Met Asn Leu Met Lys Phe Asn Ser Leu Xaa Ala Pro Asn Asp
```

-continued

```
145                 150                 155                 160

Lys Ser Ser Ser Ser Ile Lys Gln Pro Thr
                165                 170

<210> SEQ ID NO 116
<211> LENGTH: 675
<212> TYPE: DNA
<213> ORGANISM: Gossypium hirsutum
<220> FEATURE:
<221> NAME/KEY: misc_feature
<222> LOCATION: 600, 604, 617, 618, 619, 623, 626, 627, 628, 637, 642,
      647
<223> OTHER INFORMATION: n = A,T,C or G

<400> SEQUENCE: 116
gggaagatac ttcatcagca aaggaagtaa cgttgcaagg aactccagct aattacttcc     60
ccaggtcctt ccatgaagtt gtaggtgcca ttctcaggtg tttgggactt gaaactggat    120
tccaacaaaa ccctaatcca tgtccaaaga aagaagatga cagtaaagcc aatcataatc    180
aatctgtttc tcagaaggaa agtccagatc caccttcatc aacagacaat tcagatccat    240
caaccactgt gatcgaccca ccagctgatc ctcctccttc caccactgga gacacgaacg    300
atggcgaact tcccatggtt tctctcttta ctcctaaaag gccagggaca agcgccggca    360
gtggacctca gattaattaa cttgagttgt caagatcgac gctttgtggg caaaaacaag    420
ctttggcaac tgcagcgata ttcaagagag gtttatatgg ggtccttgac tgttgttttc    480
atcttgttct tggatgtttt ttttttagga gaatggaaaa tcgagtgagt tgtgaataat    540
ttgtataaaa tatcataaac ccatgtattt taagagtata ttaatttcaa taacgttgcn    600
gaanaaaaaa aaaaaaannna aanaannnaa aaaaaanaaa anaaaanaaa aaaaaaactc    660
ggaaagtcct tctac                                                     675

<210> SEQ ID NO 117
<211> LENGTH: 218
<212> TYPE: PRT
<213> ORGANISM: Gossypium hirsutum
<220> FEATURE:
<221> NAME/KEY: VARIANT
<222> LOCATION: 194, 195, 199, 200, 201, 202, 203, 206, 208, 209
<223> OTHER INFORMATION: Xaa = Any Amino Acid

<400> SEQUENCE: 117

Glu Asp Thr Ser Ser Ala Lys Glu Val Thr Leu Gln Gly Thr Pro Ala
1               5                   10                  15

Asn Tyr Phe Pro Arg Ser Phe His Glu Val Val Gly Ala Ile Leu Arg
            20                  25                  30

Cys Leu Gly Leu Glu Thr Gly Phe Gln Gln Asn Pro Asn Pro Cys Pro
        35                  40                  45

Lys Lys Glu Asp Asp Ser Lys Ala Asn His Asn Gln Ser Val Ser Gln
    50                  55                  60

Lys Glu Ser Pro Asp Pro Pro Ser Ser Thr Asp Asn Ser Asp Pro Ser
65                  70                  75                  80

Thr Thr Val Ile Asp Pro Pro Ala Asp Pro Pro Pro Ser Thr Thr Gly
                85                  90                  95

Asp Thr Asn Asp Gly Glu Leu Pro Met Val Ser Leu Phe Thr Pro Lys
            100                 105                 110

Arg Pro Gly Thr Ser Ala Gly Ser Gly Pro Gln Ile Asn Leu Glu Leu
        115                 120                 125

Ser Arg Ser Thr Leu Cys Gly Gln Lys Gln Ala Leu Ala Thr Ala Ala
    130                 135                 140
```

-continued

```
Ile Phe Lys Arg Gly Leu Tyr Gly Val Leu Asp Cys Cys Phe His Leu
145                 150                 155                 160

Val Leu Gly Cys Phe Phe Phe Arg Arg Met Glu Asn Arg Val Ser Cys
                165                 170                 175

Glu Val Asn Ile Ile Asn Pro Cys Ile Leu Arg Val Tyr Phe Gln Arg
            180                 185                 190

Cys Xaa Xaa Lys Lys Lys Xaa Xaa Xaa Xaa Xaa Lys Lys Xaa Lys Xaa
        195                 200                 205

Xaa Lys Lys Lys Thr Arg Lys Val Leu Leu
    210                 215

<210> SEQ ID NO 118
<211> LENGTH: 534
<212> TYPE: DNA
<213> ORGANISM: Populus balsamifera

<400> SEQUENCE: 118
atgggttcct atctctcttc cttctttatt gaagctcata atgctcttct acagttcttg      60
ggactggtta ttgttgatca tcaaagtaag acccaagaag gctcgtcaac ttccagttca     120
gagaaacaag aggatgaaaa agcctctgaa gaaagctccc aagatcctcc tccaacaaca     180
accgacccaa aagctgatcc tcccacagat aactctgaag atcctcctgc agtcactgta     240
agtgctcttg cgaggcggac tccaccagta agcagcggga gcggtggtca gattaattaa     300
ttccacctca gcttaagaat cgcagaagct caaagatctg tcggtcacac catgctagct     360
tcgctaaagt ccaaaaaatc atcttctcta tagatttcac gagtactagt tgtaattatt     420
gtgtgtgcgc ttagggatac tctccccccc cccccccccc tttttttttt ttgggggaaa     480
tgaacttgaa aatcttggac ccgttatacc tatatgaata ttacatatgt ttag           534

<210> SEQ ID NO 119
<211> LENGTH: 173
<212> TYPE: PRT
<213> ORGANISM: Populus balsamifera

<400> SEQUENCE: 119

Met Gly Ser Tyr Leu Ser Ser Phe Phe Ile Glu Ala His Asn Ala Leu
1               5                   10                  15

Leu Gln Phe Leu Gly Leu Val Ile Val Asp His Gln Ser Lys Thr Gln
            20                  25                  30

Glu Gly Ser Ser Thr Ser Ser Ser Glu Lys Gln Glu Asp Glu Lys Ala
        35                  40                  45

Ser Glu Glu Ser Ser Gln Asp Pro Pro Pro Thr Thr Thr Asp Pro Lys
    50                  55                  60

Ala Asp Pro Pro Thr Asp Asn Ser Glu Asp Pro Pro Ala Val Thr Val
65                  70                  75                  80

Ser Ala Leu Ala Arg Arg Thr Pro Pro Val Ser Ser Gly Ser Gly Gly
                85                  90                  95

Gln Ile Asn Phe His Leu Ser Leu Arg Ile Ala Glu Ala Gln Arg Ser
            100                 105                 110

Val Gly His Thr Met Leu Ala Ser Leu Lys Ser Lys Lys Ser Ser Ser
        115                 120                 125

Leu Ile Ser Arg Val Leu Val Val Ile Ile Val Cys Ala Leu Arg Asp
    130                 135                 140

Thr Leu Pro Pro Pro Pro Pro Leu Phe Phe Phe Trp Gly Lys Thr Lys
145                 150                 155                 160
```

```
Ser Trp Thr Arg Tyr Thr Tyr Met Asn Ile Thr Tyr Val
                165                 170

<210> SEQ ID NO 120
<211> LENGTH: 495
<212> TYPE: DNA
<213> ORGANISM: Vitis vinifera
<400> SEQUENCE: 120
atgtgtcaaa aactgaagca gtatagcatt cattcaaaag aaggtacacc accaaacccc      60
attaaagagc tagatattga aggaggagga ggagaagaag aagaaaaata tgatctagag     120
atggaggagc catcaaccgg ggagatgaca cagagaccaa caactgttta ctactctcac     180
aatccatgct attatcttca agaagctata agggctattc tcaagtgttt gggcctggaa     240
tcttctactt ctagggactc ttcgtcaagc agttcagaac aaaaggatga tgacgacact     300
gaagcaagtc cccaacaatc tcgttcttct acacaacaag gagcacactc atcgtcagct     360
gactctcctt caactacaca acaagataac aacaccttcg aggatgctga aagtgcgcgt     420
gtattgagga gagggcctac aaggccacca ataagttttg aaagcaggcc tggaggtggt     480
tctcagatta actga                                                      495

<210> SEQ ID NO 121
<211> LENGTH: 164
<212> TYPE: PRT
<213> ORGANISM: Vitis vinifera
<400> SEQUENCE: 121

Met Cys Gln Lys Leu Lys Gln Tyr Ser Ile His Ser Lys Glu Gly Thr
1               5                   10                  15

Pro Pro Asn Pro Ile Lys Glu Leu Asp Ile Glu Gly Gly Gly Gly Glu
            20                  25                  30

Glu Glu Glu Lys Tyr Asp Leu Glu Met Glu Glu Pro Ser Thr Gly Glu
        35                  40                  45

Met Thr Gln Arg Pro Thr Thr Val Tyr Tyr Ser His Asn Pro Cys Tyr
    50                  55                  60

Tyr Leu Gln Glu Ala Ile Arg Ala Ile Leu Lys Cys Leu Gly Leu Glu
65                  70                  75                  80

Ser Ser Thr Ser Arg Asp Ser Ser Ser Ser Ser Ser Glu Gln Lys Asp
                85                  90                  95

Asp Asp Asp Thr Glu Ala Ser Pro Gln Gln Ser Arg Ser Ser Thr Gln
            100                 105                 110

Gln Gly Ala His Ser Ser Ser Ala Asp Ser Pro Ser Thr Thr Gln Gln
        115                 120                 125

Asp Asn Asn Thr Phe Glu Asp Ala Glu Ser Ala Arg Val Leu Arg Arg
    130                 135                 140

Gly Pro Thr Arg Pro Pro Ile Ser Phe Glu Ser Arg Pro Gly Gly Gly
145                 150                 155                 160

Ser Gln Ile Asn

<210> SEQ ID NO 122
<211> LENGTH: 237
<212> TYPE: DNA
<213> ORGANISM: Vitis vinifera
<400> SEQUENCE: 122
atgaagtctt gtgcagagaa gtggataaaa gtagtagagt tcaaccagag ccggggctat      60
ctcctgaaac tagtcttgaa gcctttcttg aagcgccttg gagctcatgc ctcaactact     120
```

```
gatcaagcca agcaagaaaa gcttgcaagc aagtctaaaa tgtcttcaga tttcagacag    180
ccaccaagac cgccaataga ccctggtcaa ggtgggcaga tcaactcttc atcttaa       237

<210> SEQ ID NO 123
<211> LENGTH: 78
<212> TYPE: PRT
<213> ORGANISM: Vitis vinifera

<400> SEQUENCE: 123

Met Lys Ser Cys Ala Glu Lys Trp Ile Lys Val Val Glu Phe Asn Gln
1               5                   10                  15

Ser Arg Gly Tyr Leu Leu Lys Leu Val Leu Lys Pro Phe Leu Lys Arg
            20                  25                  30

Leu Gly Ala His Ala Ser Thr Thr Asp Gln Ala Lys Gln Glu Lys Leu
        35                  40                  45

Ala Ser Lys Ser Lys Met Ser Ser Asp Phe Arg Gln Pro Pro Arg Pro
    50                  55                  60

Pro Ile Asp Pro Gly Gln Gly Gly Gln Ile Asn Ser Ser Ser
65                  70                  75

<210> SEQ ID NO 124
<211> LENGTH: 581
<212> TYPE: DNA
<213> ORGANISM: Helianthus annuus

<400> SEQUENCE: 124
gcgggggatt tacatatcta accttccctt cattctattc attctctttg acttgaaaaa     60
agatatatgc aaacacatat ataaaataat ggtggaggaa agggctgaag ttgtgtatga    120
tattggatat ggttatggta acccttgtag gtatttacaa gaagttttta gaagcttttt    180
aaggtgtttg gggttagaga aacaagaagg aaaagaaaga aacactagtg gtggtgttgg    240
tggcggcgac acaggcggtg gtgacggtga cggtgacggt gacggtgacg gaggtggagg    300
tgaggtggat ccacctacaa cttctcctat tatggatcct actgatgaac ctatgtctac    360
aaggggactc acaagaagac cccctccgcc aagggggccg attagctctg gaggaggcgg    420
tcaaaccaac taactagtta gatcgttcgc ttttctcccc ttcaaccagt atatcaatgt    480
cgtaattgtc gtttttaatg ttctgaaatt taggatttct taaactatca tatccgattt    540
catcgtaaat atgattatat gtgcttgatt tcaaaaaaac c                        581

<210> SEQ ID NO 125
<211> LENGTH: 191
<212> TYPE: PRT
<213> ORGANISM: Helianthus annuus

<400> SEQUENCE: 125

Met Arg Gly Ile Tyr Ile Ser Asn Leu Pro Phe Ile Leu Phe Ile Leu
1               5                   10                  15

Phe Asp Leu Lys Lys Asp Ile Cys Lys His Ile Tyr Lys Ile Met Val
            20                  25                  30

Glu Glu Arg Ala Glu Val Val Tyr Asp Ile Gly Tyr Gly Tyr Gly Asn
        35                  40                  45

Pro Cys Arg Tyr Leu Gln Glu Val Phe Arg Ser Phe Leu Arg Cys Leu
    50                  55                  60

Gly Leu Glu Lys Gln Glu Gly Lys Glu Arg Asn Thr Ser Gly Gly Val
65                  70                  75                  80

Gly Gly Gly Asp Thr Gly Gly Gly Asp Gly Asp Gly Asp Gly Asp Gly
```

```
                85                  90                  95

Asp Gly Gly Gly Gly Glu Val Asp Pro Pro Thr Thr Ser Pro Ile Met
            100                 105                 110

Asp Pro Thr Asp Glu Pro Met Ser Thr Arg Gly Leu Thr Arg Arg Pro
        115                 120                 125

Pro Pro Pro Arg Gly Pro Ile Ser Ser Gly Gly Gly Gly Gln Thr Asn
    130                 135                 140

Leu Val Arg Ser Phe Ala Phe Leu Pro Phe Asn Gln Tyr Ile Asn Val
145                 150                 155                 160

Val Ile Val Val Phe Asn Val Leu Lys Phe Arg Ile Ser Thr Ile Ile
                165                 170                 175

Ser Asp Phe Ile Val Asn Met Ile Ile Cys Ala Phe Gln Lys Asn
            180                 185                 190

<210> SEQ ID NO 126
<211> LENGTH: 931
<212> TYPE: DNA
<213> ORGANISM: Helianthus annuus

<400> SEQUENCE: 126
gggacaagcg ttggcattcg ccgccacctc tacaacaccc cacgcgccaa tcatccaaac      60
cccacgcgcc gcccccacca ccaccacata gcagctcacc accatctccc cacacccttt     120
tgccctcaca tctccaaacc cacctcaaaa ccaagatctg aacactccaa ttctcataaa     180
gtttcaaact ttatttatga acaacaacaa caacaacaac aataatcaat gggaggagtg     240
acgtcatcaa ttgctgcaaa gtttgcattt ttccctccca ctccgccgtc gtacacggtg     300
gaggacgacg gtggtggtca gctggttatc ccggaggtgc cacggaggga gggtgtggat     360
gtgttgaagc ttagaactaa aaaggggaat gagattgtga ctgtttatat taagcatcct     420
aaagctaatg ctaccctttt gtattctcat ggtaatgctg ctgatttggg tcaaatgttt     480 gagcttttttg tggagttgag ccttcgtctc cgagttaatc ttgttggata cgactactct     540
ggctatgggc aatcaaccgg aaagccatcc gagtgcaata catacgcgga cgttgacgca     600
gtgtataaat gcctcaagga gaaatacggt gttaaagatg accaactaat cgtatacggt     660
caatctgttg gtagcggtcc caccattgat cttgcatcac gtatacccga cttaagaggt     720
gtggttctac acagtcccat cctctcgggc ctgagggtgc tatatcctgt caaaagaacc     780
tattggtttg atatttataa gaacattgac aagatcggtt tagttaactg cccggttctt     840
gtcatacacg gtacggcaga tgaagttgtt gatcattctc atgggaaaca gctatgggaa     900
ctttgcaaga acaagtatga accgttgtgg c                                    931

<210> SEQ ID NO 127
<211> LENGTH: 309
<212> TYPE: PRT
<213> ORGANISM: Helianthus annuus

<400> SEQUENCE: 127

Gly Thr Ser Val Gly Ile Arg Arg His Leu Tyr Asn Thr Pro Arg Ala
1               5                   10                  15

Asn His Pro Asn Pro Thr Arg Arg Pro His His His His Ile Ala Ala
            20                  25                  30

His His His Leu Pro Thr Pro Phe Cys Pro His Ile Ser Lys Pro Thr
        35                  40                  45

Ser Lys Pro Arg Ser Glu His Ser Asn Ser His Lys Val Ser Asn Phe
    50                  55                  60
```

```
Ile Tyr Glu Gln Gln Gln Gln Gln Gln Gln Ser Met Gly Gly Val Thr
65                  70                  75                  80

Ser Ser Ile Ala Ala Lys Phe Ala Phe Phe Pro Pro Thr Pro Pro Ser
                85                  90                  95

Tyr Thr Val Glu Asp Asp Gly Gly Gly Gln Leu Val Ile Pro Glu Val
            100                 105                 110

Pro Arg Arg Glu Gly Val Asp Val Leu Lys Leu Arg Thr Lys Lys Gly
        115                 120                 125

Asn Glu Ile Val Thr Val Tyr Ile Lys His Pro Lys Ala Asn Ala Thr
    130                 135                 140

Leu Leu Tyr Ser His Gly Asn Ala Ala Asp Leu Gly Gln Met Phe Glu
145                 150                 155                 160

Leu Phe Val Glu Leu Ser Leu Arg Leu Arg Val Asn Leu Val Gly Tyr
                165                 170                 175

Asp Tyr Ser Gly Tyr Gly Gln Ser Thr Gly Lys Pro Ser Glu Cys Asn
            180                 185                 190

Thr Tyr Ala Asp Val Asp Ala Val Tyr Lys Cys Leu Lys Glu Lys Tyr
        195                 200                 205

Gly Val Lys Asp Asp Gln Leu Ile Val Tyr Gly Gln Ser Val Gly Ser
    210                 215                 220

Gly Pro Thr Ile Asp Leu Ala Ser Arg Ile Pro Asp Leu Arg Gly Val
225                 230                 235                 240

Val Leu His Ser Pro Ile Leu Ser Gly Leu Arg Val Leu Tyr Pro Val
                245                 250                 255

Lys Arg Thr Tyr Trp Phe Asp Ile Tyr Lys Asn Ile Asp Lys Ile Gly
            260                 265                 270

Leu Val Asn Cys Pro Val Leu Val Ile His Gly Thr Ala Asp Glu Val
        275                 280                 285

Val Asp His Ser His Gly Lys Gln Leu Trp Glu Leu Cys Lys Asn Lys
    290                 295                 300

Tyr Glu Pro Leu Trp
305
```

<210> SEQ ID NO 128
<211> LENGTH: 612
<212> TYPE: DNA
<213> ORGANISM: Saccharum officinarum
<220> FEATURE:
<221> NAME/KEY: misc_feature
<222> LOCATION: 592
<223> OTHER INFORMATION: n = A,T,C or G

<400> SEQUENCE: 128

```
atggcgttgt cgccgtctgc gccagctagc ccgctccggc ggcagctgtt gcgctacgtg      60
tcgtccggcc ttgtcgccgc ccttcaccgc ccagctccaa tcatcagtct tccgattgcg     120
ctgcggggag tggaagcggc ggcgtcccag cggctccaaa ccgcgagcag agccgctcct     180
tccccgaaag ggagccccgg cgcgccgagg caaggcagtg gcggacatgt ccatgccgcc     240
gctccggcga tggcgacgat agcgcgcatg gctacgccta tgcgacggcc cacgccgcct     300
ggtcccccgg cacagggcag cggtggcaaa acgaacgccg tgacgacggc gacgactgcg     360
cacatggtga tacgaggacc cgcccggcct ggtctccctg cacaaggcag cggtggaaaa     420
gttcatgccg tgtcgctggc ggcgacggcg agtgtgcttc tgcgagggcc tgctccgcca     480
ggtcgccctg tggaaggcag cggcggaaaa gttcatgctg tgtcgccggc agcgacggcc     540
agtgtgctta tgcgagggcc cgcccagcct gttcccccga cagaaggcgc cngcgggcgt     600
```
ggtggagtca tc 612

<210> SEQ ID NO 129
<211> LENGTH: 204
<212> TYPE: PRT
<213> ORGANISM: Saccharum officinarum
<220> FEATURE:
<221> NAME/KEY: VARIANT
<222> LOCATION: 198
<223> OTHER INFORMATION: Xaa = Any Amino Acid

<400> SEQUENCE: 129

Met Ala Leu Ser Pro Ser Ala Pro Ala Ser Pro Leu Arg Arg Gln Leu
1 5 10 15

Leu Arg Tyr Val Ser Ser Gly Leu Val Ala Ala Leu His Arg Pro Ala
20 25 30

Pro Ile Ile Ser Leu Pro Ile Ala Leu Arg Gly Val Glu Ala Ala Ala
35 40 45

Ser Gln Arg Leu Gln Thr Ala Ser Arg Ala Ala Pro Ser Pro Lys Gly
50 55 60

Ser Pro Gly Ala Pro Arg Gln Gly Ser Gly Gly His Val His Ala Ala
65 70 75 80

Ala Pro Ala Met Ala Thr Ile Ala Arg Met Ala Thr Pro Met Arg Arg
85 90 95

Pro Thr Pro Pro Gly Pro Pro Ala Gln Gly Ser Gly Gly Lys Thr Asn
100 105 110

Ala Val Thr Thr Ala Thr Thr Ala His Met Val Ile Arg Gly Pro Ala
115 120 125

Arg Pro Gly Leu Pro Ala Gln Gly Ser Gly Gly Lys Val His Ala Val
130 135 140

Ser Leu Ala Ala Thr Ala Ser Val Leu Leu Arg Gly Pro Ala Pro Pro
145 150 155 160

Gly Arg Pro Val Glu Gly Ser Gly Gly Lys Val His Ala Val Ser Pro
165 170 175

Ala Ala Thr Ala Ser Val Leu Met Arg Gly Pro Ala Gln Pro Val Pro
180 185 190

Pro Thr Glu Gly Ala Xaa Gly Arg Gly Gly Val Ile
195 200

<210> SEQ ID NO 130
<211> LENGTH: 539
<212> TYPE: DNA
<213> ORGANISM: Saccharum officinarum

<400> SEQUENCE: 130
atggcgttgt cgccgtctgc gccagctagc ccgctccggc ggcagctgct gcgctacgtg 60
tcctccggcc ttgtcgccgc cctccaccgc ccagctccaa tcatcagtct gccgattgcg 120
ccgcggggag tggattcgtc ggcgtcccag cggctccaaa ccgcgagcag agccgttcct 180
tccctgaaag ggcgccccgg cgcgccgagg caaggcagcg gcggacatgt ccatgccgcc 240
gctccggcgt tggcgacgat agcgcgcatg gctacgccta tgcgacggcc cacgtcgcct 300
ggtcccccgg cacagggcag cggtggcaaa acgaacgccg tgacgacggc ggcgactgcg 360
cacatggtga tacgaggacc cgcccggcct ggtctccctg cacaaggcag aggtggaaaa 420
gttcatgtcg tgtcgccggc agcaacggcg agtgtgctta tgcgagggcc cgcccagcct 480
ggtcccccga cagaaggcgc tggacggcgt ggtggagtca tccatgcaat tgcttcttg 539

<210> SEQ ID NO 131
<211> LENGTH: 179
<212> TYPE: PRT
<213> ORGANISM: Saccharum officinarum

<400> SEQUENCE: 131

```
Met Ala Leu Ser Pro Ser Ala Pro Ala Ser Pro Leu Arg Arg Gln Leu
1               5                   10                  15

Leu Arg Tyr Val Ser Ser Gly Leu Val Ala Ala Leu His Arg Pro Ala
            20                  25                  30

Pro Ile Ile Ser Leu Pro Ile Ala Pro Arg Gly Val Asp Ser Ser Ala
        35                  40                  45

Ser Gln Arg Leu Gln Thr Ala Ser Arg Ala Val Pro Ser Leu Lys Gly
    50                  55                  60

Arg Pro Gly Ala Pro Arg Gln Gly Ser Gly Gly His Val His Ala Ala
65                  70                  75                  80

Ala Pro Ala Leu Ala Thr Ile Ala Arg Met Ala Thr Pro Met Arg Arg
                85                  90                  95

Pro Thr Ser Pro Gly Pro Pro Ala Gln Gly Ser Gly Gly Lys Thr Asn
            100                 105                 110

Ala Val Thr Thr Ala Ala Thr Ala His Met Val Ile Arg Gly Pro Ala
        115                 120                 125

Arg Pro Gly Leu Pro Ala Gln Gly Arg Gly Gly Lys Val His Val Val
    130                 135                 140

Ser Pro Ala Ala Thr Ala Ser Val Leu Met Arg Gly Pro Ala Gln Pro
145                 150                 155                 160

Gly Pro Pro Thr Glu Gly Ala Gly Arg Arg Gly Gly Val Ile His Ala
                165                 170                 175

Ile Ala Ser
```

<210> SEQ ID NO 132
<211> LENGTH: 591
<212> TYPE: DNA
<213> ORGANISM: Panicum virgatum

<400> SEQUENCE: 132

```
gctccgcgcc tgcgccggct gcctgggcct gcacggctac tgcagcagcg acgagcccga      60
cccgaagccg gccgctgtcg ctgcgccgga cgccgcggcg gatgcggcgt cgaaggaagg     120
agagggcggc ggcgaggagg ctaataactt cttgtacatg caggaggagg tggtgaccag     180
ggtgtgggcg gtgaggaggc cgagggaggg cagcgggggc aatggcggag tacaccacta     240
gacggcgcga acaaaacaag ccggtgatga aactacggtg acgcgtcggc ctccgcggca     300
ggcggcagct gatgtatttt gttcgtcgaa gctatggccg tgtgtagcat cttttaactt     360
ggtataaata aagtagtagg tgtggctatg gggttcttgt ttgcgtaggc ttctctgatc     420
tgaacttgaa ataagactct gaaagtgtgt agttatctgt atagttatct tcgtgtttaa     480
gctgcaatac ccgatacgtg cgtttgctac tcgatgtgtg tgggtggtag aattaattgt     540
ttgttgtctt cagaattcag atcatagttt gttgctgctg gtgtatatat a              591
```

<210> SEQ ID NO 133
<211> LENGTH: 135
<212> TYPE: PRT
<213> ORGANISM: Panicum virgatum

<400> SEQUENCE: 133

```
Leu Arg Ala Cys Ala Gly Cys Leu Gly Leu His Gly Tyr Cys Ser Ser
1               5                   10                  15
```

```
Asp Glu Pro Asp Pro Lys Pro Ala Ala Val Ala Ala Pro Asp Ala Ala
            20                  25                  30

Ala Asp Ala Ala Ser Lys Glu Gly Glu Gly Gly Gly Glu Glu Ala Asn
        35                  40                  45

Asn Phe Leu Tyr Met Gln Glu Glu Val Val Thr Arg Val Trp Ala Val
    50                  55                  60

Arg Arg Pro Arg Glu Gly Ser Gly Gly Asn Gly Gly Val His His Thr
65                  70                  75                  80

Ala Arg Thr Lys Gln Ala Gly Asp Glu Thr Thr Val Thr Arg Arg Pro
                85                  90                  95

Pro Arg Gln Ala Ala Ala Asp Val Phe Cys Ser Ser Lys Leu Trp Pro
            100                 105                 110

Cys Val Ala Ser Phe Asn Leu Val Ile Lys Val Trp Leu Trp Gly Ser
        115                 120                 125

Cys Leu Arg Arg Leu Leu Ser
    130                 135

<210> SEQ ID NO 134
<211> LENGTH: 93
<212> TYPE: PRT
<213> ORGANISM: Hordeum vulgare

<400> SEQUENCE: 134

Met Ala Ser Ser Ala Pro Pro Ala Phe Leu Pro Gln Leu Val Gln Pro
1               5                   10                  15

Val Ser Val Leu Pro Asp Gln Pro Pro Ser Ala Pro Ala Glu Gly Thr
            20                  25                  30

Gly Gly Gln Val Met Val Leu Asn Asp Ala Ser Ser Leu Pro Leu Gln
        35                  40                  45

Leu Met Arg Thr Pro Pro Gly Glu Gly Ala Gly Gly Arg Ile His Arg
    50                  55                  60

Gln Leu Ala Arg Pro Arg Pro Pro Gly Pro Pro Arg Gln Gly His Gly
65                  70                  75                  80

Gly Asp Gly Gly Ala Ile His Ala Ile Leu Leu Glu Leu
                85                  90

<210> SEQ ID NO 135
<211> LENGTH: 204
<212> TYPE: PRT
<213> ORGANISM: Saccharum officinarum
<220> FEATURE:
<221> NAME/KEY: VARIANT
<222> LOCATION: 198
<223> OTHER INFORMATION: Xaa = Any Amino Acid

<400> SEQUENCE: 135

Met Ala Leu Ser Pro Ser Ala Pro Ala Ser Pro Leu Arg Arg Gln Leu
1               5                   10                  15

Leu Arg Tyr Val Ser Ser Gly Leu Val Ala Ala Leu His Arg Pro Ala
            20                  25                  30

Pro Ile Ile Ser Leu Pro Ile Ala Leu Arg Gly Val Glu Ala Ala Ala
        35                  40                  45

Ser Gln Arg Leu Gln Thr Ala Ser Arg Ala Ala Pro Ser Pro Lys Gly
    50                  55                  60

Ser Pro Gly Ala Pro Arg Gln Gly Ser Gly Gly His Val His Ala Ala
65                  70                  75                  80

Ala Pro Ala Met Ala Thr Ile Ala Arg Met Ala Thr Pro Met Arg Arg
                85                  90                  95
```

```
Pro Thr Pro Pro Gly Pro Pro Ala Gln Gly Ser Gly Gly Lys Thr Asn
            100                 105                 110

Ala Val Thr Thr Ala Thr Thr Ala His Met Val Ile Arg Gly Pro Ala
        115                 120                 125

Arg Pro Gly Leu Pro Ala Gln Gly Ser Gly Gly Lys Val His Ala Val
    130                 135                 140

Ser Leu Ala Ala Thr Ala Ser Val Leu Leu Arg Gly Pro Ala Pro Pro
145                 150                 155                 160

Gly Arg Pro Val Glu Gly Ser Gly Gly Lys Val His Ala Val Ser Pro
                165                 170                 175

Ala Ala Thr Ala Ser Val Leu Met Arg Gly Pro Ala Gln Pro Val Pro
            180                 185                 190

Pro Thr Glu Gly Ala Xaa Gly Arg Gly Gly Val Ile
        195                 200

<210> SEQ ID NO 136
<211> LENGTH: 179
<212> TYPE: PRT
<213> ORGANISM: Saccharum officinarum

<400> SEQUENCE: 136

Met Ala Leu Ser Pro Ser Ala Pro Ala Ser Pro Leu Arg Arg Gln Leu
1               5                   10                  15

Leu Arg Tyr Val Ser Ser Gly Leu Val Ala Ala Leu His Arg Pro Ala
            20                  25                  30

Pro Ile Ile Ser Leu Pro Ile Ala Pro Arg Gly Val Asp Ser Ser Ala
        35                  40                  45

Ser Gln Arg Leu Gln Thr Ala Ser Arg Ala Val Pro Ser Leu Lys Gly
    50                  55                  60

Arg Pro Gly Ala Pro Arg Gln Gly Ser Gly Gly His Val His Ala Ala
65                  70                  75                  80

Ala Pro Ala Leu Ala Thr Ile Ala Arg Met Ala Thr Pro Met Arg Arg
                85                  90                  95

Pro Thr Ser Pro Gly Pro Pro Ala Gln Gly Ser Gly Gly Lys Thr Asn
            100                 105                 110

Ala Val Thr Thr Ala Ala Thr Ala His Met Val Ile Arg Gly Pro Ala
        115                 120                 125

Arg Pro Gly Leu Pro Ala Gln Gly Arg Gly Gly Lys Val His Val Val
    130                 135                 140

Ser Pro Ala Ala Thr Ala Ser Val Leu Met Arg Gly Pro Ala Gln Pro
145                 150                 155                 160

Gly Pro Pro Thr Glu Gly Ala Gly Arg Arg Gly Gly Val Ile His Ala
                165                 170                 175

Ile Ala Ser

<210> SEQ ID NO 137
<211> LENGTH: 104
<212> TYPE: PRT
<213> ORGANISM: Arabidopsis thaliana

<400> SEQUENCE: 137

Met Glu Val Asn Gly Glu Glu Glu Arg Arg Ser Arg Arg Glu Asp Glu
1               5                   10                  15

Glu Lys Glu Asp Tyr Tyr Tyr Ser Leu Leu Asn Ser Pro Cys Ser Val
            20                  25                  30

Cys Asn Lys Phe Val Gln Ala Ile Leu Lys Cys Leu Gly Leu Glu Ser
```

```
        35                  40                  45

Ser Ser Ile Pro Pro Ser Ser Ser Ser Ser Ser Pro Ser Leu Val Glu
    50                  55                  60

Glu Glu Asp Ser Gly Thr Glu Thr Val Glu Glu Thr Gly Phe Met Ala
65                  70                  75                  80

Arg Ile Thr Ala Val Leu Arg Arg Arg Pro Arg Pro Pro Pro Tyr Ser
                85                  90                  95

Ser Gly Arg Pro Gly Gln Asn Asn
            100

<210> SEQ ID NO 138
<211> LENGTH: 95
<212> TYPE: PRT
<213> ORGANISM: Brassica napus

<400> SEQUENCE: 138

Met Glu Val Asn Gly Glu Glu Lys Arg Ser Tyr Arg Arg Glu Asp Glu
1               5                   10                  15

Glu Lys Glu Val Tyr Tyr Pro Leu Leu Asn Ser Pro Cys Ser Ala Phe
            20                  25                  30

His Lys Thr Val Gln Ala Ile Leu Lys Cys Leu Gly Leu Glu Ser Ser
        35                  40                  45

Ser Ile Ser Pro Ser Ser Ser Ser Ser Gln Asp Pro Gly Thr Glu Thr
    50                  55                  60

Val Gln Glu Thr Gly Phe Met Ala Met Val Ala Arg Leu Thr Arg Arg
65                  70                  75                  80

Arg Pro Arg Pro Pro Tyr Ser Ser Gly Gln Pro Gly Gln Ile Asn
                85                  90                  95

<210> SEQ ID NO 139
<211> LENGTH: 116
<212> TYPE: PRT
<213> ORGANISM: Solanum tuberosum

<400> SEQUENCE: 139

Met Phe Tyr Leu Gln Glu Gly Ile Lys Ala Ile Leu Lys Cys Leu Gly
1               5                   10                  15

Phe Glu Ser Ser Lys Leu Val His Gln Ala Ser Ser Ser Ser Ser Ser
            20                  25                  30

Ser Ser Met Ser Asp Ile Asn Lys Asn Glu Glu Glu Glu Ser Glu Lys
        35                  40                  45

Gln Glu Gln Glu Cys Val Leu Phe Gln Glu Asp Gly Asn Lys Gln Gly
    50                  55                  60

Ser Asp Ser Thr Asn Asp Asn Tyr Lys Asn Asp Pro Pro Val Glu Asn
65                  70                  75                  80

Asp Asp Glu Asp Pro Pro Gln Ser Glu Thr Leu Ile Leu Pro Thr Glu
                85                  90                  95

Arg Arg Gly Arg Pro Pro Ser Arg Pro Lys Val Gly Ser Gly Pro Pro
            100                 105                 110

Pro Gln Asn Asn
        115

<210> SEQ ID NO 140
<211> LENGTH: 154
<212> TYPE: PRT
<213> ORGANISM: Oryza sativa

<400> SEQUENCE: 140
```

```
Met Asp Arg Val Glu Glu Lys Glu Gly Asn Arg Phe Gln Glu Pro Ala
1               5                   10                  15

Ser Asp Arg Cys Glu Asp Asn Glu Asp Lys Glu Gln Asp Asn Ser Glu
            20                  25                  30

Glu Ser Ser Ser Val Asp Gln Arg Lys Glu Glu Glu Glu Glu Glu Lys
        35                  40                  45

Glu Gly Cys Glu Glu Ala Thr Pro Ala Ala Ala Ala Ala Ala Ala Ala
    50                  55                  60

Pro Ser Phe Phe Ala His Pro Cys Ser Leu Leu Gln Tyr Ile Ala Arg
65                  70                  75                  80

Val Cys Ala Cys Cys Leu Gly Leu Ser Asp Ser Phe Cys Asp Pro Lys
                85                  90                  95

Ala Ser Ser Val Leu Val Pro Glu Pro Glu Pro Ala Ala Ala Asp Pro
            100                 105                 110

Ser Gln Glu Gly Glu Glu Asp Met Lys Ser Ser Glu Ala Thr Thr Arg
        115                 120                 125

Val Arg Ala Ala Arg Leu Arg Pro Lys Pro Pro Gly Asn Pro Arg Glu
    130                 135                 140

Gly Ser Gly Gly Asn Gly Gly His His His
145                 150
```

<210> SEQ ID NO 141
<211> LENGTH: 121
<212> TYPE: PRT
<213> ORGANISM: Populus balsamifera

<400> SEQUENCE: 141

```
Met Asp Lys Gly Ser Ser Thr Lys Glu Glu Ile Gln Gly Asp Val Leu
1               5                   10                  15

Gln Ile Ser His Ser Pro Ser Ile Phe Val Glu Ala Phe Asn Ala Leu
            20                  25                  30

Leu Arg Cys Leu Gly Leu Gly Thr Val Asp His Gln Arg Ile Thr Gln
        35                  40                  45

Glu Ser Ser Ser Thr Ser Ser Ser Lys Gln Glu Asp Asp Glu Lys Ala
    50                  55                  60

Ser Glu Glu Ser Pro Gln Tyr Pro Pro Pro Thr Arg Thr Ser Asp Pro
65                  70                  75                  80

Gln Ala Asp Pro Pro Thr Asp Thr Ser Glu Asp Pro Ser Thr Asp Ala
                85                  90                  95

Ala Val Ser Ala Leu Ala Arg Arg Thr Pro Pro Val Ser Arg Gly Gly
            100                 105                 110

Gly Gly Gln Thr Asn Thr Thr Thr Ser
        115                 120
```

<210> SEQ ID NO 142
<211> LENGTH: 111
<212> TYPE: PRT
<213> ORGANISM: Medicago sativa

<400> SEQUENCE: 142

```
Met Thr Phe Tyr Val Tyr His Pro Cys Tyr Cys Leu Glu Glu Ile Phe
1               5                   10                  15

Lys Thr Phe Leu Arg Cys Phe Gly Ile Glu Ser Thr Gln Thr Lys Glu
            20                  25                  30

Glu Glu Asp Ser Ser Thr Ser Leu Leu Lys Pro His Ala Cys Ala Cys
        35                  40                  45

Ala Ser Asp Ser Asn Val Ala Leu Lys Asp Arg Tyr Tyr Ser Ser Ser
```

```
    50                  55                  60

Ser Asn Lys Lys Ser Ser Gln Glu Glu Gly Val Ala Asp Pro Pro Pro
65                  70                  75                  80

Ser Thr Ser Thr Gln Thr Ile Asn Leu Ser Ser Met Gly Arg Gly Gly
                85                  90                  95

Pro Arg Arg Thr Pro Leu Thr Gln Gly Pro Pro Pro Gln His Asn
            100                 105                 110

<210> SEQ ID NO 143
<211> LENGTH: 115
<212> TYPE: PRT
<213> ORGANISM: Glycine max

<400> SEQUENCE: 143

Met Glu Gly Ser Ser Pro Ser Ile Glu Glu Glu Arg Thr Ala Thr Phe
1               5                   10                  15

Tyr Val Tyr His Pro Cys Tyr Phe Leu Gln Gln Ala Leu Arg Ala Leu
            20                  25                  30

Leu Lys Cys Val Gly Ile Asp Glu Ser Glu Asn Thr Met Cys Ser Gln
        35                  40                  45

Ala Asn Lys Gln Glu Lys Ser Ser Leu Pro Gln Thr Pro Ser Ala Asp
    50                  55                  60

Asp Pro Ile Thr Asn Ser Pro Thr His Lys Ser Ser Pro Asp Ala Ala
65                  70                  75                  80

Asp Pro Pro Ser Thr Thr Asn Gln Thr Ile Ile Ile Ala Ser Leu Met
                85                  90                  95

Ala Thr Arg Gly Ser Arg Gly Ser Lys Ile Ser Asp Gly Ser Gly Pro
            100                 105                 110

Gln His Asn
        115

<210> SEQ ID NO 144
<211> LENGTH: 3372
<212> TYPE: DNA
<213> ORGANISM: Arabidopsis thaliana

<400> SEQUENCE: 144
atgaagaatc ttgggggtt gttcaaaatt cttctgcttt tcttctgtct ctttctatcg     60
acccacataa tttccgtttc ttgtttaaac tcagatgggc taactctact ctctcttctg    120
aagcatttgg atagagtacc accacaagtt acttcgacat ggaaaaataa cgcatctgaa    180
gcaactccat gtaactggtt cggtatcact tgtgacgatt ctaagaatgt tgcgtctctc    240
aacttcactc gttctagggt ttcaggtcaa ttgggtccgg aaattgggga gctcaaaagc    300
ttgcagattt tggatctgag tactaacaat ttctccggga ctataccttc cactttagga    360
aactgtacca aactcgctac tctagatttg tctgaaaatg gattctctga taagatccca    420
gatactctcg atagcttgaa gaggttggag gtgctttatc tttacataaa cttcctcact    480
ggtgagttac ctgaatcctt gtttcgaatt ccgaagctgc aggttttata tcttgactat    540
aacaatctca ccggtccgat tcctcaaagt attggtgatg ctaaggagct tgtggagctg    600
agtatgtatg cgaatcagtt ctctggtaac atccctgagt cgattgggaa tagcagtagt    660
ctgcagattc tttatttgca caggaacaag ttagttggtt cattacctga aagtctcaat    720
cttttgggga atctcactac tctgtttgtt ggtaacaaca gtctacaagg gccggttcgt    780
ttcggatcac ctaattgcaa gaatttgttg actttagatt tgtcatacaa tgaattcgaa    840
ggcggtgttc cacctgcatt gggaaattgc agtagccttg acgctttagt cattgtgagt    900
```

```
ggtaacttgt caggtacaat cccttcctca ttgggtatgt tgaagaatct cacaattctt    960
aacctttccg agaatcgtct ctctgggagt atccccgcag agctcgggaa ctgcagtagc   1020
ttgaacttgt tgaagctgaa cgataaccag cttgtaggcg gaataccgag tgcattaggt   1080
aagctgagga agctagaaag tctggagctt ttcgaaaacc ggttttcggg tgagattcct   1140
attgagatat ggaagagtca gagtcttacg cagttgctag tttatcaaaa caatctcact   1200
ggtgaactac ctgtggaaat gactgagatg aagaagctaa agatcgctac gctgttcaac   1260
aacagctttt atggagcgat accaccgggt ttaggtgtga acagcagctt agaagaggtt   1320
gactttattg gtaacaaact tacaggagag ataccgccaa atctatgcca tggaaggaag   1380
ttgagaatac tcaacttggg ttctaatctg cttcatggta caataccagc ttctattggt   1440
cactgtaaga ccatcaggag attcatcctt agagaaaata acctttcagg tcttcttcct   1500
gagttttctc aggatcatag tctttctttt cttgatttca atagcaacaa cttcgaagga   1560
ccaatcccgg gcagcctcgg aagctgtaag aatctctcga gtattaacct atctcgaaac   1620
agattcacgg ggcagatacc tccacaactt gggaatctac aaaaccttgg ttacatgaat   1680
ctttctcgta atcttcttga agggtctcta ccagctcagc tatctaactg tgtgagttta   1740
gagcgttttg atgttggctt caactcatta aacggttcag ttccttcaaa ctttagtaac   1800
tggaaaggct tgacgacttt agttctcagc gagaaccggt tttcaggagg tattccacag   1860
ttcttgcctg agcttaagaa gctgtcaact ctgcagattg ctagaaatgc ttttggtggt   1920
gagattcctt cgtcgattgg gttgatagag gatctgatct atgacttgga ccttagtgga   1980
aacggattga caggtgaaat tccagccaag ttgggagatc tcatcaagtt aacaagactc   2040
aacatatcta acaacaattt gacaggatct ttatcggttc tcaaaggtct tacctcattg   2100
ctacatgttg atgtctccaa caatcagttc acaggtccaa taccagataa cttggagggt   2160
cagttgttat ctgagccgtc gtcgttttca ggaaatccaa acctctgcat tccacattcc   2220
ttctctgcta gcaacaatag ccgcagcgcg ttaaagtact gtaaagatca atctaaaagc   2280
aggaagagtg gccttagcac ctggcaaatc gtgctaatag cggtcttatc gtctttatta   2340
gtcttggttg tggtccttgc tcttgttttc atttgcctac gtcgtcgcaa aggaagacca   2400
gagaaagatg cttatgtctt cactcaggag gaaggcccat ctttgttgtt gaacaaagtt   2460
cttgcagcaa ctgacaatct aaatgaaaag tacaccattg gaagaggagc tcatggaatt   2520
gtgtacagag cttctttagg ctccggaaag gtctacgctg tgaagagact tgtattcgcg   2580
tctcacatcc gcgctaacca gagtatgatg agggagattg atacaatcgg taaagtcagg   2640
cacaggaatc tgattaagtt agaagggttt tggctgagga aagacgacgg tttaatgctg   2700
tatagataca tgccaaaagg aagtctttac gacgttctcc acggtgttag cccgaaagaa   2760
aatgtgctag actggtctgc acggtacaat gtagcacttg gtgtcgctca tggactagcc   2820
tatctacact atgactgcca tcccccgatt gttcaccgtg acatcaaacc agagaacata   2880
ctcatggact cagatttgga gcctcacatt ggggatttcg gtttggctcg ccttcttgat   2940
gactcaacgg tttcaactgc aactgttaca ggcaccaccg gctacattgc accagaaaac   3000
gctttcaaaa ccgtgagggg aagagaatca gacgtttaca gttatggagt cgtgttactt   3060
gagctggtta cgaggaagag agcggtggac aaatctttcc cggaaagtac agatatagta   3120
agctgggtga gatctgcctt gagcagcagc aacaacaatg tggaggatat ggtaacaaca   3180
atcgtcgatc cgattctcgt ggacgagctt ctggattcga gtcttaggga gcaggtgatg   3240
caagtgacgg aactggcact gagttgtaca cagcaagatc cggcaatgag accaacgatg   3300
```
agagatgcgg tgaaactgtt ggaagatgtg aaacatctgg caagaagctg ctcctctgat 3360
tcagttcggt aa 3372

<210> SEQ ID NO 145
<211> LENGTH: 1123
<212> TYPE: PRT
<213> ORGANISM: Arabidopsis thaliana

<400> SEQUENCE: 145

Met Lys Asn Leu Gly Gly Leu Phe Lys Ile Leu Leu Leu Phe Phe Cys
1 5 10 15

Leu Phe Leu Ser Thr His Ile Ile Ser Val Ser Cys Leu Asn Ser Asp
20 25 30

Gly Leu Thr Leu Leu Ser Leu Leu Lys His Leu Asp Arg Val Pro Pro
35 40 45

Gln Val Thr Ser Thr Trp Lys Ile Asn Ala Ser Glu Ala Thr Pro Cys
50 55 60

Asn Trp Phe Gly Ile Thr Cys Asp Asp Ser Lys Asn Val Ala Ser Leu
65 70 75 80

Asn Phe Thr Arg Ser Arg Val Ser Gly Gln Leu Gly Pro Glu Ile Gly
85 90 95

Glu Leu Lys Ser Leu Gln Ile Leu Asp Leu Ser Thr Asn Asn Phe Ser
100 105 110

Gly Thr Ile Pro Ser Thr Leu Gly Asn Cys Thr Lys Leu Ala Thr Leu
115 120 125

Asp Leu Ser Glu Asn Gly Phe Ser Asp Lys Ile Pro Asp Thr Leu Asp
130 135 140

Ser Leu Lys Arg Leu Glu Val Leu Tyr Leu Tyr Ile Asn Phe Leu Thr
145 150 155 160

Gly Glu Leu Pro Glu Ser Leu Phe Arg Ile Pro Lys Leu Gln Val Leu
165 170 175

Tyr Leu Asp Tyr Asn Asn Leu Thr Gly Pro Ile Pro Gln Ser Ile Gly
180 185 190

Asp Ala Lys Glu Leu Val Glu Leu Ser Met Tyr Ala Asn Gln Phe Ser
195 200 205

Gly Asn Ile Pro Glu Ser Ile Gly Asn Ser Ser Ser Leu Gln Ile Leu
210 215 220

Tyr Leu His Arg Asn Lys Leu Val Gly Ser Leu Pro Glu Ser Leu Asn
225 230 235 240

Leu Leu Gly Asn Leu Thr Thr Leu Phe Val Gly Asn Asn Ser Leu Gln
245 250 255

Gly Pro Val Arg Phe Gly Ser Pro Asn Cys Lys Asn Leu Leu Thr Leu
260 265 270

Asp Leu Ser Tyr Asn Glu Phe Glu Gly Gly Val Pro Pro Ala Leu Gly
275 280 285

Asn Cys Ser Ser Leu Asp Ala Leu Val Ile Val Ser Gly Asn Leu Ser
290 295 300

Gly Thr Ile Pro Ser Ser Leu Gly Met Leu Lys Asn Leu Thr Ile Leu
305 310 315 320

Asn Leu Ser Glu Asn Arg Leu Ser Gly Ser Ile Pro Ala Glu Leu Gly
325 330 335

Asn Cys Ser Ser Leu Asn Leu Leu Lys Leu Asn Asp Asn Gln Leu Val
340 345 350

Gly Gly Ile Pro Ser Ala Leu Gly Lys Leu Arg Lys Leu Glu Ser Leu

```
        355                 360                 365

Glu Leu Phe Glu Asn Arg Phe Ser Gly Glu Ile Pro Ile Glu Ile Trp
    370                 375                 380

Lys Ser Gln Ser Leu Thr Gln Leu Leu Val Tyr Gln Asn Asn Leu Thr
385                 390                 395                 400

Gly Glu Leu Pro Val Glu Met Thr Glu Met Lys Lys Leu Lys Ile Ala
                405                 410                 415

Thr Leu Phe Asn Asn Ser Phe Tyr Gly Ala Ile Pro Pro Gly Leu Gly
            420                 425                 430

Val Asn Ser Ser Leu Glu Glu Val Asp Phe Ile Gly Asn Lys Leu Thr
        435                 440                 445

Gly Glu Ile Pro Pro Asn Leu Cys His Gly Arg Lys Leu Arg Ile Leu
    450                 455                 460

Asn Leu Gly Ser Asn Leu Leu His Gly Thr Ile Pro Ala Ser Ile Gly
465                 470                 475                 480

His Cys Lys Thr Ile Arg Arg Phe Ile Leu Arg Glu Asn Asn Leu Ser
                485                 490                 495

Gly Leu Leu Pro Glu Phe Ser Gln Asp His Ser Leu Ser Phe Leu Asp
            500                 505                 510

Phe Asn Ser Asn Asn Phe Glu Gly Pro Ile Pro Gly Ser Leu Gly Ser
        515                 520                 525

Cys Lys Asn Leu Ser Ser Ile Asn Leu Ser Arg Asn Arg Phe Thr Gly
    530                 535                 540

Gln Ile Pro Pro Gln Leu Gly Asn Leu Gln Asn Leu Gly Tyr Met Asn
545                 550                 555                 560

Leu Ser Arg Asn Leu Leu Glu Gly Ser Leu Pro Ala Gln Leu Ser Asn
                565                 570                 575

Cys Val Ser Leu Glu Arg Phe Asp Val Gly Phe Asn Ser Leu Asn Gly
            580                 585                 590

Ser Val Pro Ser Asn Phe Ser Asn Trp Lys Gly Leu Thr Thr Leu Val
        595                 600                 605

Leu Ser Glu Asn Arg Phe Ser Gly Gly Ile Pro Gln Phe Leu Pro Glu
    610                 615                 620

Leu Lys Lys Leu Ser Thr Leu Gln Ile Ala Arg Asn Ala Phe Gly Gly
625                 630                 635                 640

Glu Ile Pro Ser Ser Ile Gly Leu Ile Glu Asp Leu Ile Tyr Asp Leu
                645                 650                 655

Asp Leu Ser Gly Asn Gly Leu Thr Gly Glu Ile Pro Ala Lys Leu Gly
            660                 665                 670

Asp Leu Ile Lys Leu Thr Arg Leu Asn Ile Ser Asn Asn Asn Leu Thr
        675                 680                 685

Gly Ser Leu Ser Val Leu Lys Gly Leu Thr Ser Leu Leu His Val Asp
    690                 695                 700

Val Ser Asn Asn Gln Phe Thr Gly Pro Ile Pro Asp Asn Leu Glu Gly
705                 710                 715                 720

Gln Leu Leu Ser Glu Pro Ser Ser Phe Ser Gly Asn Pro Asn Leu Cys
                725                 730                 735

Ile Pro His Ser Phe Ser Ala Ser Asn Asn Ser Arg Ser Ala Leu Lys
            740                 745                 750

Tyr Cys Lys Asp Gln Ser Lys Ser Arg Lys Ser Gly Leu Ser Thr Trp
        755                 760                 765

Gln Ile Val Leu Ile Ala Val Leu Ser Ser Leu Leu Val Leu Val Val
    770                 775                 780
```

-continued

```
Val Leu Ala Leu Val Phe Ile Cys Leu Arg Arg Arg Lys Gly Arg Pro
785                 790                 795                 800

Glu Lys Asp Ala Tyr Val Phe Thr Gln Glu Glu Gly Pro Ser Leu Leu
                805                 810                 815

Leu Asn Lys Val Leu Ala Ala Thr Asp Asn Leu Asn Glu Lys Tyr Thr
            820                 825                 830

Ile Gly Arg Gly Ala His Gly Ile Val Tyr Arg Ala Ser Leu Gly Ser
        835                 840                 845

Gly Lys Val Tyr Ala Val Lys Arg Leu Val Phe Ala Ser His Ile Arg
    850                 855                 860

Ala Asn Gln Ser Met Met Arg Glu Ile Asp Thr Ile Gly Lys Val Arg
865                 870                 875                 880

His Arg Asn Leu Ile Lys Leu Glu Gly Phe Trp Leu Arg Lys Asp Asp
                885                 890                 895

Gly Leu Met Leu Tyr Arg Tyr Met Pro Lys Gly Ser Leu Tyr Asp Val
            900                 905                 910

Leu His Gly Val Ser Pro Lys Glu Asn Val Leu Asp Trp Ser Ala Arg
        915                 920                 925

Tyr Asn Val Ala Leu Gly Val Ala His Gly Leu Ala Tyr Leu His Tyr
    930                 935                 940

Asp Cys His Pro Pro Ile Val His Arg Asp Ile Lys Pro Glu Asn Ile
945                 950                 955                 960

Leu Met Asp Ser Asp Leu Glu Pro His Ile Gly Asp Phe Gly Leu Ala
                965                 970                 975

Arg Leu Leu Asp Asp Ser Thr Val Ser Thr Ala Thr Val Thr Gly Thr
            980                 985                 990

Thr Gly Tyr Ile Ala Pro Glu Asn  Ala Phe Lys Thr Val  Arg Gly Arg
        995                 1000                1005

Glu Ser  Asp Val Tyr Ser Tyr  Gly Val Val Leu Leu  Glu Leu Val
    1010                 1015                 1020

Thr Arg  Lys Arg Ala Val Asp  Lys Ser Phe Pro Glu  Ser Thr Asp
    1025                 1030                 1035

Ile Val  Ser Trp Val Arg Ser  Ala Leu Ser Ser Ser  Asn Asn Asn
    1040                 1045                 1050

Val Glu  Asp Met Val Thr Thr  Ile Val Asp Pro Ile  Leu Val Asp
    1055                 1060                 1065

Glu Leu  Leu Asp Ser Ser Leu  Arg Glu Gln Val Met  Gln Val Thr
    1070                 1075                 1080

Glu Leu  Ala Leu Ser Cys Thr  Gln Gln Asp Pro Ala  Met Arg Pro
    1085                 1090                 1095

Thr Met  Arg Asp Ala Val Lys  Leu Leu Glu Asp Val  Lys His Leu
    1100                 1105                 1110

Ala Arg  Ser Cys Ser Ser Asp  Ser Val Arg
    1115                 1120
```

<210> SEQ ID NO 146
<211> LENGTH: 3267
<212> TYPE: DNA
<213> ORGANISM: Arabidopsis thaliana

<400> SEQUENCE: 146

```
atgaggaatc ttgggttact cgaaattact ctgctttgct ctctctttgt ctatttccgt      60
atagattctg tctctagttt aaactcagat ggtttggctt tactctcgct tctcaagcac     120
tttgataaag tcccacttga agtagcttcg acgtggaagg agaacacatc tgaaaccact     180
```

-continued

```
ccatgtaata ataactggtt tggtgtcatt tgtgatcttt ctggtaatgt cgtcgagacc    240
cttaatttgt ctgcttctgg gctttcaggc caattaggtt ctgaaattgg ggagcttaag    300
agcttggtca cattggatct cagtcttaac agtttctctg gtttattgcc ttccacttta    360
ggaaactgta cttcacttga gtatttggat ttgtctaaca atgatttttc tggagaagtt    420
cctgatattt ttggtagctt gcagaatttg acgtttctgt atcttgatcg caataatctt    480
agtggtctca ttcctgcaag tgttggtggg ttgatagagc tcgtagatct gaggatgtca    540
tataataact tgtctggtac cattccagag ttgcttggga actgtagtaa gctggaatat    600
ctggctttga acaacaacaa gttaaatggt tctttgccag caagtctcta tctactcgag    660
aatcttggtg agctatttgt cagtaacaac agccttggag ggaggcttca ttttggttct    720
agcaactgca agaaattggt ttctttagat ctctcgttca atgatttcca aggcggtgtt    780
ccacctgaga taggcaactg cagtagcctt cactctttag tcatggtgaa atgcaacttg    840
acaggtacaa tcccatcatc aatgggtatg ttgagaaagg tttcggttat tgacctttcc    900
gataatcgtc tctcggggaa tatccctcaa gagcttggga actgcagcag cttggaaacc    960
ttgaagctga acgacaacca gctccaaggc gagataccac ctgcattgag taagctaaag   1020
aagctacaaa gcctggagct ttttttttaat aagctgtccg gtgagattcc tattggcata   1080
tggaagattc agagtctgac acagatgctc gtttataaca acactctcac cggggaacta   1140
ccagttgaag taactcagct gaagcacctt aagaagctta cactgtttaa caacggcttt   1200
tatggagata taccaatgag tttaggcctg aatcgaagct tagaggaggt ggaccttctt   1260
ggtaaccgtt ttacagggga gataccaccc catctctgcc atggacagaa gttgagattg   1320
ttcatcttgg gttctaatca gcttcatggt aagataccag cgtctattcg tcagtgtaag   1380
acccttgagc gagtcagact tgaagataac aaactttcag gtgttcttcc ggaattccct   1440
gagagtctta gtctttccta tgtgaacctc ggaagcaata gctttgaagg atccatcccg   1500
cgcagcttgg gaagctgtaa aaatctcttg actattgacc tttctcaaaa caaactcacg   1560
ggtctgatac ctccagaact gggaaatctg caaagccttg gactgttgaa cctttcacat   1620
aattatctgg aaggtcctct gccatcccag ctatcaggct gtgcgagact tctgtatttt   1680
gatgttggat ccaactcatt gaacggttct attccatcaa gcttcagaag ctggaaaagc   1740
ttgtccactt tagttctcag tgacaataat tttctaggag ctattccaca gttcttggca   1800
gagcttgacc gactctcaga tctgcggata gctcgaaatg cttttggagg taagattcct   1860
tcctcggttg gcttgttgaa gagtctacgc tatggcttag acctcagtgc gaacgtattt   1920
acgggtgaga ttccaaccac actgggggct cttatcaatc ttgaacgtct caacatatcc   1980
aacaacaagt tgacagggcc tttatcggtt cttcaaagtc ttaagtcatt gaatcaagtt   2040
gacgtctcgt ataatcagtt cacgggtcca atacccgtaa atctgttatc aaattcttca   2100
aagttttctg gaaatccaga cctctgcatt caagcttctt actcagtgag tgccataatc   2160
cgcaaagagt ttaaatcttg caaaggtcaa gtcaaactta gcacgtggaa gatcgccctt   2220
atagcagctg ggtcctcact atccgtattg gctttgcttt ttgctctctt tttggtttta   2280
tgccggtgca aaagaggaac caagacagaa gatgctaata tcctcgcaga ggaaggtctg   2340
tccttgttgc tgaacaaagt tctagcagcc actgacaatc tagatgacaa gtacatcatt   2400
ggaagaggag ctcatggagt tgtttacaga gcttctttag gatcaggcga agaatacgcc   2460
gtgaagaaac tcatctttgc ggaacacatt cgcgcaaacc aaaatatgaa gcgggagatc   2520
gaaacaatcg ggctagtcag gcacagaaat ctcattcggt tagaaagatt ttggatgagg   2580
```

-continued

```
aaagaagatg gcttaatgct gtatcagtac atgcccaatg gaagcctaca cgacgttttg   2640
cacagaggta atcaaggaga agcagttctt gactggtctg cacggttcaa catagcccct   2700
gggatttcac atggactggc gtatttacat catgattgtc atccaccaat aattcaccgc   2760
gacatcaaac cagagaacat actcatggac tcggatatgg agcctcacat tggagatttc   2820
ggattggctc ggattctaga tgactcaaca gtttcaacgg ccactgttac tggcacaact   2880
gggtacattg caccagaaaa tgcgtacaag acggtgagga gcaaggaatc agatgtttac   2940
agttatggag ttgttttgct cgagctggta acaggaaaga gagcactgga cagatctttc   3000
ccggaagata tcaacattgt gagctgggtc agatctgtat taagcagcta cgaggatgaa   3060
gacgatactg ctggtccaat cgttgatcca aaacttgtgg atgagcttct ggatacgaag   3120
ctcagggaac aagcaatcca agtcacagac ttggctctta gatgtacaga caagaggccg   3180
gagaacagac catcgatgag agatgtggtg aaagatttga ctgatttgga aagttttgta   3240
agaagcactt cgggttcagt tcactag                                         3267
```

```
<210> SEQ ID NO 147
<211> LENGTH: 1088
<212> TYPE: PRT
<213> ORGANISM: Arabidopsis thaliana

<400> SEQUENCE: 147

Met Arg Asn Leu Gly Leu Leu Glu Ile Thr Leu Leu Cys Ser Leu Phe
1               5                   10                  15

Val Tyr Phe Arg Ile Asp Ser Val Ser Ser Leu Asn Ser Asp Gly Leu
            20                  25                  30

Ala Leu Leu Ser Leu Leu Lys His Phe Asp Lys Val Pro Leu Glu Val
        35                  40                  45

Ala Ser Thr Trp Lys Glu Asn Thr Ser Glu Thr Thr Pro Cys Asn Asn
    50                  55                  60

Asn Trp Phe Gly Val Ile Cys Asp Leu Ser Gly Asn Val Val Glu Thr
65                  70                  75                  80

Leu Asn Leu Ser Ala Ser Gly Leu Ser Gly Gln Leu Gly Ser Glu Ile
                85                  90                  95

Gly Glu Leu Lys Ser Leu Val Thr Leu Asp Leu Ser Leu Asn Ser Phe
            100                 105                 110

Ser Gly Leu Leu Pro Ser Thr Leu Gly Asn Cys Thr Ser Leu Glu Tyr
        115                 120                 125

Leu Asp Leu Ser Asn Asn Asp Phe Ser Gly Glu Val Pro Asp Ile Phe
    130                 135                 140

Gly Ser Leu Gln Asn Leu Thr Phe Leu Tyr Leu Asp Arg Asn Asn Leu
145                 150                 155                 160

Ser Gly Leu Ile Pro Ala Ser Val Gly Gly Leu Ile Glu Leu Val Asp
                165                 170                 175

Leu Arg Met Ser Tyr Asn Asn Leu Ser Gly Thr Ile Pro Glu Leu Leu
            180                 185                 190

Gly Asn Cys Ser Lys Leu Glu Tyr Leu Ala Leu Asn Asn Asn Lys Leu
        195                 200                 205

Asn Gly Ser Leu Pro Ala Ser Leu Tyr Leu Leu Glu Asn Leu Gly Glu
    210                 215                 220

Leu Phe Val Ser Asn Asn Ser Leu Gly Gly Arg Leu His Phe Gly Ser
225                 230                 235                 240

Ser Asn Cys Lys Lys Leu Val Ser Leu Asp Leu Ser Phe Asn Asp Phe
                245                 250                 255
```

-continued

```
Gln Gly Gly Val Pro Pro Glu Ile Gly Asn Cys Ser Ser Leu His Ser
            260                 265                 270

Leu Val Met Val Lys Cys Asn Leu Thr Gly Thr Ile Pro Ser Ser Met
        275                 280                 285

Gly Met Leu Arg Lys Val Ser Val Ile Asp Leu Ser Asp Asn Arg Leu
    290                 295                 300

Ser Gly Asn Ile Pro Gln Glu Leu Gly Asn Cys Ser Ser Leu Glu Thr
305                 310                 315                 320

Leu Lys Leu Asn Asp Asn Gln Leu Gln Gly Glu Ile Pro Pro Ala Leu
                325                 330                 335

Ser Lys Leu Lys Lys Leu Gln Ser Leu Glu Leu Phe Phe Asn Lys Leu
            340                 345                 350

Ser Gly Glu Ile Pro Ile Gly Ile Trp Lys Ile Gln Ser Leu Thr Gln
        355                 360                 365

Met Leu Val Tyr Asn Asn Thr Leu Thr Gly Glu Leu Pro Val Glu Val
    370                 375                 380

Thr Gln Leu Lys His Leu Lys Lys Leu Thr Leu Phe Asn Asn Gly Phe
385                 390                 395                 400

Tyr Gly Asp Ile Pro Met Ser Leu Gly Leu Asn Arg Ser Leu Glu Glu
                405                 410                 415

Val Asp Leu Leu Gly Asn Arg Phe Thr Gly Glu Ile Pro Pro His Leu
            420                 425                 430

Cys His Gly Gln Lys Leu Arg Leu Phe Ile Leu Gly Ser Asn Gln Leu
        435                 440                 445

His Gly Lys Ile Pro Ala Ser Ile Arg Gln Cys Lys Thr Leu Glu Arg
    450                 455                 460

Val Arg Leu Glu Asp Asn Lys Leu Ser Gly Val Leu Pro Glu Phe Pro
465                 470                 475                 480

Glu Ser Leu Ser Leu Ser Tyr Val Asn Leu Gly Ser Asn Ser Phe Glu
                485                 490                 495

Gly Ser Ile Pro Arg Ser Leu Gly Ser Cys Lys Asn Leu Leu Thr Ile
            500                 505                 510

Asp Leu Ser Gln Asn Lys Leu Thr Gly Leu Ile Pro Pro Glu Leu Gly
        515                 520                 525

Asn Leu Gln Ser Leu Gly Leu Leu Asn Leu Ser His Asn Tyr Leu Glu
    530                 535                 540

Gly Pro Leu Pro Ser Gln Leu Ser Gly Cys Ala Arg Leu Leu Tyr Phe
545                 550                 555                 560

Asp Val Gly Ser Asn Ser Leu Asn Gly Ser Ile Pro Ser Ser Phe Arg
                565                 570                 575

Ser Trp Lys Ser Leu Ser Thr Leu Val Leu Ser Asp Asn Asn Phe Leu
            580                 585                 590

Gly Ala Ile Pro Gln Phe Leu Ala Glu Leu Asp Arg Leu Ser Asp Leu
        595                 600                 605

Arg Ile Ala Arg Asn Ala Phe Gly Gly Lys Ile Pro Ser Ser Val Gly
    610                 615                 620

Leu Leu Lys Ser Leu Arg Tyr Gly Leu Asp Leu Ser Ala Asn Val Phe
625                 630                 635                 640

Thr Gly Glu Ile Pro Thr Thr Leu Gly Ala Leu Ile Asn Leu Glu Arg
                645                 650                 655

Leu Asn Ile Ser Asn Asn Lys Leu Thr Gly Pro Leu Ser Val Leu Gln
            660                 665                 670

Ser Leu Lys Ser Leu Asn Gln Val Asp Val Ser Tyr Asn Gln Phe Thr
        675                 680                 685
```

```
Gly Pro Ile Pro Val Asn Leu Leu Ser Asn Ser Ser Lys Phe Ser Gly
    690                 695                 700

Asn Pro Asp Leu Cys Ile Gln Ala Ser Tyr Ser Val Ser Ala Ile Ile
705                 710                 715                 720

Arg Lys Glu Phe Lys Ser Cys Lys Gly Gln Val Lys Leu Ser Thr Trp
                725                 730                 735

Lys Ile Ala Leu Ile Ala Ala Gly Ser Ser Leu Ser Val Leu Ala Leu
            740                 745                 750

Leu Phe Ala Leu Phe Leu Val Leu Cys Arg Cys Lys Arg Gly Thr Lys
        755                 760                 765

Thr Glu Asp Ala Asn Ile Leu Ala Glu Glu Gly Leu Ser Leu Leu Leu
    770                 775                 780

Asn Lys Val Leu Ala Ala Thr Asp Asn Leu Asp Asp Lys Tyr Ile Ile
785                 790                 795                 800

Gly Arg Gly Ala His Gly Val Val Tyr Arg Ala Ser Leu Gly Ser Gly
                805                 810                 815

Glu Glu Tyr Ala Val Lys Lys Leu Ile Phe Ala Glu His Ile Arg Ala
            820                 825                 830

Asn Gln Asn Met Lys Arg Glu Ile Glu Thr Ile Gly Leu Val Arg His
        835                 840                 845

Arg Asn Leu Ile Arg Leu Glu Arg Phe Trp Met Arg Lys Glu Asp Gly
    850                 855                 860

Leu Met Leu Tyr Gln Tyr Met Pro Asn Gly Ser Leu His Asp Val Leu
865                 870                 875                 880

His Arg Gly Asn Gln Gly Glu Ala Val Leu Asp Trp Ser Ala Arg Phe
                885                 890                 895

Asn Ile Ala Leu Gly Ile Ser His Gly Leu Ala Tyr Leu His His Asp
            900                 905                 910

Cys His Pro Pro Ile Ile His Arg Asp Ile Lys Pro Glu Asn Ile Leu
        915                 920                 925

Met Asp Ser Asp Met Glu Pro His Ile Gly Asp Phe Gly Leu Ala Arg
    930                 935                 940

Ile Leu Asp Asp Ser Thr Val Ser Thr Ala Thr Val Thr Gly Thr Thr
945                 950                 955                 960

Gly Tyr Ile Ala Pro Glu Asn Ala Tyr Lys Thr Val Arg Ser Lys Glu
                965                 970                 975

Ser Asp Val Tyr Ser Tyr Gly Val Val Leu Leu Glu Leu Val Thr Gly
            980                 985                 990

Lys Arg Ala Leu Asp Arg Ser Phe  Pro Glu Asp Ile Asn  Ile Val Ser
        995                 1000                 1005

Trp Val  Arg Ser Val Leu Ser  Ser Tyr Glu Asp Glu  Asp Asp Thr
    1010                 1015                 1020

Ala Gly  Pro Ile Val Asp Pro  Lys Leu Val Asp Glu  Leu Leu Asp
    1025                 1030                 1035

Thr Lys  Leu Arg Glu Gln Ala  Ile Gln Val Thr Asp  Leu Ala Leu
    1040                 1045                 1050

Arg Cys  Thr Asp Lys Arg Pro  Glu Asn Arg Pro Ser  Met Arg Asp
    1055                 1060                 1065

Val Val  Lys Asp Leu Thr Asp  Leu Glu Ser Phe Val  Arg Ser Thr
    1070                 1075                 1080

Ser Gly  Ser Val His
    1085
```

-continued

<210> SEQ ID NO 148
<211> LENGTH: 3252
<212> TYPE: DNA
<213> ORGANISM: Glycine max

<400> SEQUENCE: 148

```
atggggtatc tgtatctctt gctgcttcta tgtttttctt ccttgttata tgctgcttct     60
gcattgaact ctgatggttt ggctttgttg tccctcttga gggattggac tactgtgcct    120
agtgacataa actccacatg gaggttgtct gattccactc catgctcatc ttgggcagga    180
gtgcattgtg ataatgccaa caatgtggtt tctctaaacc tcactagtta ttcgattttg    240
ggtcaattag gacctgatct tggacgtttg gttcacttgc aaaccataga cttatcatat    300
aatgatttct ttgggaaaat ccccccagaa ttagagaact gtagcatgct tgagtacttg    360
aacctttctg taaacaactt tagcggagga atacctgaga gcttcaaaag cttgcaaaat    420
ttgaagcata tataccttt atctaatcac cttaatggtg aaattcctga atccttgttt    480
gaaatttctc acctggaaga agtggatctt agcagaaaca gtttaactgg ttcaatcccc    540
ttaagtgttg ggaatatcac taagcttgtc actctggatc tttcttataa tcagttgtca    600
gggacaattc caatatccat tggaaattgt agtaacttag agaatctgta tttggaaagg    660
aatcaattag agggagttat tcctgagagt ctaaataatc tcaaaaatct tcaagagtta    720
tatctcaatt ataataacct tggaggtact gttcaattgg gatctggata ttgcaaaaag    780
ttgtctattt tgagtatttc ttacaataac tttagtgggg gtataccatc aagcttgggg    840
aattgtagtg gtctaataga gttttatgct tcagggaata acttagttgg cactatacca    900
tcaaccttcg gcctcctgcc caacctttct atgttattca ttccggagaa cctattgtca    960
gggaaaatac ctccacagat tggtaattgc aaatcactga aagagttgag tttgaattcc   1020
aatcaacttg aaggagaaat tccaagcgaa ttaggaaact tgagtaaatt gcgtgatctt   1080
agattgtttg aaaaccattt gacaggagaa attccacttg gcatatggaa aattcaaagc   1140
cttgagcaga tccatatgta cattaataac ctctcgggcg agctaccact tgagatgaca   1200
gagcttaaac atcttaagaa tgtctccttg tttaacaacc agttctccgg agtcatacct   1260
caaagcttag gaatcaatag cagtttggtg gtgttagatt ttatgtataa taatttcact   1320
ggtaccctcc caccaaatct ttgttttgga aagcacctgg tcaggctgaa tatgggtggc   1380
aatcaattta ttggcagcat acctcctgat gtaggaaggt gtacaactct tacaaggttg   1440
agacttgaag ataataattt aactggggca cttcctgatt ttgaaactaa tccaaacctc   1500
tcttacatga gcatcaacaa caacaatatc agtggagcaa ttccatcaag tttgggaaac   1560
tgcacaaatc tctctctttt agatttgtcc atgaacagct tgacgggtct tgtaccttca   1620
gagctaggaa accttgtgaa tcttcagact ttggatcttt ctcacaataa cttgcaaggt   1680
cctttgccac atcagctgtc aaactgtgcc aaaatgatca agtttaatgt cggattcaat   1740
tctttgaatg gttcggttcc ttcaagtttt cagagctgga caacattaac aactttaatt   1800
ctctcagaga atcgttttaa tggtggtatt ccagctttct tgtcagaatt taaaaagctc   1860
aacgagttac gacttggtgg aaatacgttt ggaggaaaca ttcctagatc aattggagaa   1920
ttggtgaatt tgatatatga gctaaattta agtgctaatg ggctgatagg tgaacttcct   1980
agggagattg gaaacctgaa gaatctgcta agcctggatc tatcttggaa caatttgaca   2040
ggaagtatac aagttcttga tgagctcagt tcattatctg aattcaacat ctcatttaat   2100
tcttttgaag gtcctgtgcc acaacagcta acaacattac caaattcttc tttatcattt   2160
ttgggcaatc ctggtctgtg tgactcgaat ttcactgtga gcagctattt acagccatgt   2220
```

```
agcacaaatt caaaaaagtc aaaaaagctg agtaaagttg aagctgtgat gatagcactt   2280
ggatccttag tatttgttgt tctgctgctg gggttaatct gtatattctt tatcagaaaa   2340
attaagcagg aagccataat cattgaggag gatgattttc caacacttct taatgaagta   2400
atggaagcga cagaaaatct aaatgatcaa tatattattg gcagaggagc tcaaggagtg   2460
gtttacaaag cagcaatagg tccagacaaa attttggcta taaagaaatt tgtatttgct   2520
catgatgaag ggaaaagctc aagcatgacc agagaaattc aaaccattgg aaagattagg   2580
catcgaaatt tggtcaaatt ggaagggtgc tggttgagag aaaactatgg tctaattgca   2640
tacaaataca tgccaaatgg aagccttcat ggtgctttgc atgagaggaa tccaccatac   2700
tccttagaat ggaatgtccg gaataggata gctcttggaa ttgctcatgg attggcttat   2760
ctccattatg actgtgatcc tgtcatagtg cacagagaca tcaaaaccag caatatactt   2820
ctagattctg acatggagcc tcatattgca gattttggta tttccaagct tttagatcag   2880
ccttctacct caacacagtc gtcatctgtt actggtacac ttggatatat agcaccagag   2940
aaatcctata caacaacaaa gggtaaggaa tctgatgtat acagttatgg ggtagttttg   3000
ctggaactga tatccagaaa gaagccattg gatgcatcat ttatggaagg gacggatata   3060
gttaattggg ctagatctgt ctgggaggaa acaggagtta ttgacgaaat tgttgatcca   3120
gagatggctg atgaaatttc aaattctgat gtgatgaaac aagttgccaa ggtgcttttg   3180
gtggctttga gatgcacatt aaaggatcca cgcaagagac ctacgatgag ggatgttatc   3240
aagcatttgt ag                                                       3252
```

<210> SEQ ID NO 149
<211> LENGTH: 1083
<212> TYPE: PRT
<213> ORGANISM: Glycine max

<400> SEQUENCE: 149

```
Met Gly Tyr Leu Tyr Leu Leu Leu Leu Leu Cys Phe Ser Ser Leu Leu
1               5                   10                  15

Tyr Ala Ala Ser Ala Leu Asn Ser Asp Gly Leu Ala Leu Leu Ser Leu
            20                  25                  30

Leu Arg Asp Trp Thr Thr Val Pro Ser Asp Ile Asn Ser Thr Trp Arg
        35                  40                  45

Leu Ser Asp Ser Thr Pro Cys Ser Ser Trp Ala Gly Val His Cys Asp
    50                  55                  60

Asn Ala Asn Asn Val Val Ser Leu Asn Leu Thr Ser Tyr Ser Ile Leu
65                  70                  75                  80

Gly Gln Leu Gly Pro Asp Leu Gly Arg Leu Val His Leu Gln Thr Ile
                85                  90                  95

Asp Leu Ser Tyr Asn Asp Phe Phe Gly Lys Ile Pro Pro Glu Leu Glu
            100                 105                 110

Asn Cys Ser Met Leu Glu Tyr Leu Asn Leu Ser Val Asn Asn Phe Ser
        115                 120                 125

Gly Gly Ile Pro Glu Ser Phe Lys Ser Leu Gln Asn Leu Lys His Ile
    130                 135                 140

Tyr Leu Leu Ser Asn His Leu Asn Gly Glu Ile Pro Glu Ser Leu Phe
145                 150                 155                 160

Glu Ile Ser His Leu Glu Glu Val Asp Leu Ser Arg Asn Ser Leu Thr
                165                 170                 175

Gly Ser Ile Pro Leu Ser Val Gly Asn Ile Thr Lys Leu Val Thr Leu
            180                 185                 190
```

Asp Leu Ser Tyr Asn Gln Leu Ser Gly Thr Ile Pro Ile Ser Ile Gly
195 200 205

Asn Cys Ser Asn Leu Glu Asn Leu Tyr Leu Glu Arg Asn Gln Leu Glu
210 215 220

Gly Val Ile Pro Glu Ser Leu Asn Asn Leu Lys Asn Leu Gln Glu Leu
225 230 235 240

Tyr Leu Asn Tyr Asn Asn Leu Gly Gly Thr Val Gln Leu Gly Ser Gly
245 250 255

Tyr Cys Lys Lys Leu Ser Ile Leu Ser Ile Ser Tyr Asn Asn Phe Ser
260 265 270

Gly Gly Ile Pro Ser Ser Leu Gly Asn Cys Ser Gly Leu Ile Glu Phe
275 280 285

Tyr Ala Ser Gly Asn Asn Leu Val Gly Thr Ile Pro Ser Thr Phe Gly
290 295 300

Leu Leu Pro Asn Leu Ser Met Leu Phe Ile Pro Glu Asn Leu Leu Ser
305 310 315 320

Gly Lys Ile Pro Pro Gln Ile Gly Asn Cys Lys Ser Leu Lys Glu Leu
325 330 335

Ser Leu Asn Ser Asn Gln Leu Glu Gly Glu Ile Pro Ser Glu Leu Gly
340 345 350

Asn Leu Ser Lys Leu Arg Asp Leu Arg Leu Phe Glu Asn His Leu Thr
355 360 365

Gly Glu Ile Pro Leu Gly Ile Trp Lys Ile Gln Ser Leu Glu Gln Ile
370 375 380

His Met Tyr Ile Asn Asn Leu Ser Gly Glu Leu Pro Leu Glu Met Thr
385 390 395 400

Glu Leu Lys His Leu Lys Asn Val Ser Leu Phe Asn Asn Gln Phe Ser
405 410 415

Gly Val Ile Pro Gln Ser Leu Gly Ile Asn Ser Ser Leu Val Val Leu
420 425 430

Asp Phe Met Tyr Asn Asn Phe Thr Gly Thr Leu Pro Pro Asn Leu Cys
435 440 445

Phe Gly Lys His Leu Val Arg Leu Asn Met Gly Gly Asn Gln Phe Ile
450 455 460

Gly Ser Ile Pro Pro Asp Val Gly Arg Cys Thr Thr Leu Thr Arg Leu
465 470 475 480

Arg Leu Glu Asp Asn Asn Leu Thr Gly Ala Leu Pro Asp Phe Glu Thr
485 490 495

Asn Pro Asn Leu Ser Tyr Met Ser Ile Asn Asn Asn Asn Ile Ser Gly
500 505 510

Ala Ile Pro Ser Ser Leu Gly Asn Cys Thr Asn Leu Ser Leu Leu Asp
515 520 525

Leu Ser Met Asn Ser Leu Thr Gly Leu Val Pro Ser Glu Leu Gly Asn
530 535 540

Leu Val Asn Leu Gln Thr Leu Asp Leu Ser His Asn Asn Leu Gln Gly
545 550 555 560

Pro Leu Pro His Gln Leu Ser Asn Cys Ala Lys Met Ile Lys Phe Asn
565 570 575

Val Gly Phe Asn Ser Leu Asn Gly Ser Val Pro Ser Ser Phe Gln Ser
580 585 590

Trp Thr Thr Leu Thr Thr Leu Ile Leu Ser Glu Asn Arg Phe Asn Gly
595 600 605

Gly Ile Pro Ala Phe Leu Ser Glu Phe Lys Lys Leu Asn Glu Leu Arg

-continued 610 615 620

Leu Gly Gly Asn Thr Phe Gly Gly Asn Ile Pro Arg Ser Ile Gly Glu
625 630 635 640

Leu Val Asn Leu Ile Tyr Glu Leu Asn Leu Ser Ala Asn Gly Leu Ile
645 650 655

Gly Glu Leu Pro Arg Glu Ile Gly Asn Leu Lys Asn Leu Leu Ser Leu
660 665 670

Asp Leu Ser Trp Asn Asn Leu Thr Gly Ser Ile Gln Val Leu Asp Glu
675 680 685

Leu Ser Ser Leu Ser Glu Phe Asn Ile Ser Phe Asn Ser Phe Glu Gly
690 695 700

Pro Val Pro Gln Gln Leu Thr Thr Leu Pro Asn Ser Ser Leu Ser Phe
705 710 715 720

Leu Gly Asn Pro Gly Leu Cys Asp Ser Asn Phe Thr Val Ser Ser Tyr
725 730 735

Leu Gln Pro Cys Ser Thr Asn Ser Lys Lys Ser Lys Lys Leu Ser Lys
740 745 750

Val Glu Ala Val Met Ile Ala Leu Gly Ser Leu Val Phe Val Val Leu
755 760 765

Leu Leu Gly Leu Ile Cys Ile Phe Phe Ile Arg Lys Ile Lys Gln Glu
770 775 780

Ala Ile Ile Ile Glu Glu Asp Asp Phe Pro Thr Leu Leu Asn Glu Val
785 790 795 800

Met Glu Ala Thr Glu Asn Leu Asn Asp Gln Tyr Ile Ile Gly Arg Gly
805 810 815

Ala Gln Gly Val Val Tyr Lys Ala Ala Ile Gly Pro Asp Lys Ile Leu
820 825 830

Ala Ile Lys Lys Phe Val Phe Ala His Asp Glu Gly Lys Ser Ser Ser
835 840 845

Met Thr Arg Glu Ile Gln Thr Ile Gly Lys Ile Arg His Arg Asn Leu
850 855 860

Val Lys Leu Glu Gly Cys Trp Leu Arg Glu Asn Tyr Gly Leu Ile Ala
865 870 875 880

Tyr Lys Tyr Met Pro Asn Gly Ser Leu His Gly Ala Leu His Glu Arg
885 890 895

Asn Pro Pro Tyr Ser Leu Glu Trp Asn Val Arg Asn Arg Ile Ala Leu
900 905 910

Gly Ile Ala His Gly Leu Ala Tyr Leu His Tyr Asp Cys Asp Pro Val
915 920 925

Ile Val His Arg Asp Ile Lys Thr Ser Asn Ile Leu Leu Asp Ser Asp
930 935 940

Met Glu Pro His Ile Ala Asp Phe Gly Ile Ser Lys Leu Leu Asp Gln
945 950 955 960

Pro Ser Thr Ser Thr Gln Ser Ser Ser Val Thr Gly Thr Leu Gly Tyr
965 970 975

Ile Ala Pro Glu Lys Ser Tyr Thr Thr Thr Lys Gly Lys Glu Ser Asp
980 985 990

Val Tyr Ser Tyr Gly Val Val Leu Leu Glu Leu Ile Ser Arg Lys Lys
995 1000 1005

Pro Leu Asp Ala Ser Phe Met Glu Gly Thr Asp Ile Val Asn Trp
1010 1015 1020

Ala Arg Ser Val Trp Glu Glu Thr Gly Val Ile Asp Glu Ile Val
1025 1030 1035

```
Asp Pro  Glu Met Ala Asp Glu  Ile Ser Asn Ser Asp  Val Met Lys
    1040                 1045                 1050

Gln Val  Ala Lys Val Leu Leu  Val Ala Leu Arg Cys  Thr Leu Lys
    1055                 1060                 1065

Asp Pro  Arg Lys Arg Pro Thr  Met Arg Asp Val Ile  Lys His Leu
    1070                 1075                 1080

<210> SEQ ID NO 150
<211> LENGTH: 3186
<212> TYPE: DNA
<213> ORGANISM: Glycine max

<400> SEQUENCE: 150
atggggtatt tgtatctctt gctgatttca tatttgtctg ccttgttgta tgctgcttct     60
gcattgaact ctgatgggtt ggctttgttg tccctcttga gggactggac tattgtgcct    120
agtgacataa actccacatg gaagttgtct gattccactc cgtgctcatc ttgggcagga    180
gtgcattgtg ataatgccaa taatgtggtt tctctaaacc tcactaactt atcatataat    240
gatctatttg gaaaaattcc cccagaatta gacaactgta ccatgcttga gtacttggac    300
ctttctgtaa acaactttag tggaggaata cctcagagct tcaaaaactt gcaaaatttg    360
aagcatatag acctttcatc taatccgctg aatggtgaaa ttcctgaacc cttgtttgac    420
atttatcacc tggaagaagt gtatcttagc aacaacagtt tgactggttc aatttcctca    480
agtgttggga atatcactaa gcttgtcaca ctggatcttt cttataatca gctgtcaggg    540
acaattccca tgtccattgg aaattgtagt aacttagaga atctatattt ggaaaggaat    600
caattagagg gagttattcc tgagagtcta aataatctca aaaatcttca ggagttattt    660
ctcaattata ataaccttgg aggcactgtt caattgggaa ctggaaattg caaaaagttg    720
tctagtttaa gtctttctta caataacttc agtgggggta taccatcaag cttggggaat    780
tgtagcggtc taatggagtt ttatgctgca cggagtaact tagttggcag tataccatca    840
accttgggcc tcatgcccaa cctttctctt ctaatcattc cagagaacct attgtctggg    900
aaaatacctc cacagattgg taattgcaaa gcactggaag agttgcgttt gaattccaat    960
gaacttgagg gagaaattcc cagtgaattg ggaaacttga gtaaattacg cgaccttaga   1020
ttgtatgaaa accttttgac aggagaaatt ccacttggca tatggaaaat tcaaagcctt   1080
gagcagatct atctgtacat taataacctt tcgggggagc taccttttga gatgacagag   1140
ctcaaacatc ttaagaatat ctccttgttt aacaaccagt tctccggagt catacctcaa   1200
agtttaggaa tcaatagcag tttggtggtg ttagacttca tgtataataa tttcactggt   1260
acccttccac caaatctttg ttttggaaag caactggtga agctgaatat gggtgtcaat   1320
caattttatg gtaacatacc tccagatgtg ggaaggtgta caactcttac aagggtgaga   1380
cttgaagaaa atcatttcac tgggtctctt cctgattttt atattaatcc aaatctctct   1440
tacatgagca tcaacaacaa caatatcagt ggagcaattc catcaagttt gggaaaatgc   1500
acaaatctct ctcttttaaa tttgtccatg aacagcttga cgggtcttgt accttcagag   1560
cttggaaacc ttgagaatct ccagactttg gatctttctc acaataactt ggaaggtcct   1620
ttgccacatc agctgtcaaa ctgtgccaaa atgatcaagt ttgatgtcag attcaattcc   1680
ttgaatggtt cggttccatc aagttttcgg agctggacaa cattaacagc tttaattctc   1740
tcagagaatc attttaatgg tggtatccca gctttcttgt cagaatttaa aaagctcaac   1800
gagttacaac ttggtggaaa catgtttgga ggaaacattc ctagatcaat cggagagctg   1860
gtgaatttga tatatgaact aaatctaagt gctactgggc tgataggtga gcttcctagg   1920
```

```
gagattggaa acctgaagag tctgctaagc ctggatctat cttggaacaa tttgacagga   1980
agtatacaag ttcttgatgg gctcagttca ttatctgaat tcaacatctc atataattct   2040
tttgaaggtc ctgtgccaca acagctaaca acattaccaa actcttcttt atcatttttg   2100
ggcaatcctg gcctgtgtgg ctcgaatttc actgagagca gctatttaaa gccttgtgac   2160
acaaattcaa aaaagtcaaa aaagctcagt aaagttgcaa ctgtgatgat agcacttgga   2220
tctgcaatat ttgttgttct gctgctgtgg ttagtatata tattctttat cagaaaaatt   2280
aagcaagaag ccataatcat taaggaagat gattctccaa cccttcttaa cgaagtgatg   2340
gaagctacag aaaatctaaa tgatgagtat attattggca gaggagctca aggagttgtt   2400
tataaagcag caataggtcc agacaaaaca ttggctataa agaagtttgt attttctcat   2460
gaagggaaaa gctcaagcat gaccagagaa attcaaaccc ttggaaagat taggcatcga   2520
aatttagtca aattggaagg gtgctggttg agagaaaact atggtctaat tgcatacaaa   2580
tacatgccaa atggaagcct acatgatgct ttgcatgaga agaatccacc atactcctta   2640
gaatggattg ttcggaataa catagcactt ggaattgctc acggattgac ttatctccat   2700
tatgactgtg atcctgtcat agtgcacaga gatatcaaaa caagcaacat acttctagat   2760
tcagaaatgg agcctcatat tgcagatttt ggtattgcta aacttataga tcagccttct   2820
acctcaacac agttatcatc tgttgctggt acacttggtt atatagcacc agagaatgct   2880
tatacaacaa caaagggtaa ggaatctgat gtatacagtt atggggtagt tttgctggag   2940
ctgatatcca gaaagaagcc attggatgca tcatttatgg aaggaacgga tatagttaat   3000
tgggcaagat ctgtctggga ggaaacggga gttgttgatg aaattgttga tccagagctg   3060
gctgatgaaa tttcaaattc tgaagtgatg aaacaagtta ccaaggtgct tttggtggct   3120
ttgagatgca ctgaaaagga tccacgtaag agacctacga tgagggatgt tatcaggcat   3180
ttgtag                                                              3186
```

```
<210> SEQ ID NO 151
<211> LENGTH: 1082
<212> TYPE: PRT
<213> ORGANISM: Glycine max

<400> SEQUENCE: 151

Met Gly Tyr Leu Tyr Leu Leu Leu Ile Ser Tyr Leu Ser Ala Leu Leu
1               5                   10                  15

Tyr Ala Ala Ser Ala Leu Asn Ser Asp Gly Leu Ala Leu Leu Ser Leu
            20                  25                  30

Leu Arg Asp Trp Thr Ile Val Pro Ser Asp Ile Asn Ser Thr Trp Lys
        35                  40                  45

Leu Ser Asp Ser Thr Pro Cys Ser Ser Trp Ala Gly Val His Cys Asp
    50                  55                  60

Asn Ala Asn Asn Val Val Ser Leu Asn Leu Thr Ser Tyr Ser Ile Phe
65                  70                  75                  80

Gly Gln Leu Gly Pro Asp Leu Gly Arg Met Val His Leu Gln Thr Ile
                85                  90                  95

Asp Leu Ser Tyr Asn Asp Leu Phe Gly Lys Ile Pro Pro Glu Leu Asp
            100                 105                 110

Asn Cys Thr Met Leu Glu Tyr Leu Asp Leu Ser Val Asn Asn Phe Ser
        115                 120                 125

Gly Gly Ile Pro Gln Ser Phe Lys Asn Leu Gln Asn Leu Lys His Ile
    130                 135                 140
```

-continued

```
Asp Leu Ser Ser Asn Pro Leu Asn Gly Glu Ile Pro Glu Pro Leu Phe
145                 150                 155                 160

Asp Ile Tyr His Leu Glu Glu Val Tyr Leu Ser Asn Asn Ser Leu Thr
                165                 170                 175

Gly Ser Ile Ser Ser Ser Val Gly Asn Ile Thr Lys Leu Val Thr Leu
            180                 185                 190

Asp Leu Ser Tyr Asn Gln Leu Ser Gly Thr Ile Pro Met Ser Ile Gly
        195                 200                 205

Asn Cys Ser Asn Leu Glu Asn Leu Tyr Leu Glu Arg Asn Gln Leu Glu
    210                 215                 220

Gly Val Ile Pro Glu Ser Leu Asn Asn Leu Lys Asn Leu Gln Glu Leu
225                 230                 235                 240

Phe Leu Asn Tyr Asn Asn Leu Gly Gly Thr Val Gln Leu Gly Thr Gly
                245                 250                 255

Asn Cys Lys Lys Leu Ser Ser Leu Ser Leu Ser Tyr Asn Asn Phe Ser
            260                 265                 270

Gly Gly Ile Pro Ser Ser Leu Gly Asn Cys Ser Gly Leu Met Glu Phe
        275                 280                 285

Tyr Ala Ala Arg Ser Asn Leu Val Gly Ser Ile Pro Ser Thr Leu Gly
    290                 295                 300

Leu Met Pro Asn Leu Ser Leu Leu Ile Ile Pro Glu Asn Leu Leu Ser
305                 310                 315                 320

Gly Lys Ile Pro Pro Gln Ile Gly Asn Cys Lys Ala Leu Glu Glu Leu
                325                 330                 335

Arg Leu Asn Ser Asn Glu Leu Glu Gly Glu Ile Pro Ser Glu Leu Gly
            340                 345                 350

Asn Leu Ser Lys Leu Arg Asp Leu Arg Leu Tyr Glu Asn Leu Leu Thr
        355                 360                 365

Gly Glu Ile Pro Leu Gly Ile Trp Lys Ile Gln Ser Leu Glu Gln Ile
    370                 375                 380

Tyr Leu Tyr Ile Asn Asn Leu Ser Gly Glu Leu Pro Phe Glu Met Thr
385                 390                 395                 400

Glu Leu Lys His Leu Lys Asn Ile Ser Leu Phe Asn Asn Gln Phe Ser
                405                 410                 415

Gly Val Ile Pro Gln Ser Leu Gly Ile Asn Ser Ser Leu Val Val Leu
            420                 425                 430

Asp Phe Met Tyr Asn Asn Phe Thr Gly Thr Leu Pro Pro Asn Leu Cys
        435                 440                 445

Phe Gly Lys Gln Leu Val Lys Leu Asn Met Gly Val Asn Gln Phe Tyr
    450                 455                 460

Gly Asn Ile Pro Pro Asp Val Gly Arg Cys Thr Thr Leu Thr Arg Val
465                 470                 475                 480

Arg Leu Glu Glu Asn His Phe Thr Gly Ser Leu Pro Asp Phe Tyr Ile
                485                 490                 495

Asn Pro Asn Leu Ser Tyr Met Ser Ile Asn Asn Asn Asn Ile Ser Gly
            500                 505                 510

Ala Ile Pro Ser Ser Leu Gly Lys Cys Thr Asn Leu Ser Leu Leu Asn
        515                 520                 525

Leu Ser Met Asn Ser Leu Thr Gly Leu Val Pro Ser Glu Leu Gly Asn
    530                 535                 540

Leu Glu Asn Leu Gln Thr Leu Asp Leu Ser His Asn Asn Leu Glu Gly
545                 550                 555                 560

Pro Leu Pro His Gln Leu Ser Asn Cys Ala Lys Met Ile Lys Phe Asp
                565                 570                 575
```

```
Val Arg Phe Asn Ser Leu Asn Gly Ser Val Pro Ser Ser Phe Arg Ser
            580                 585                 590

Trp Thr Thr Leu Thr Ala Leu Ile Leu Ser Glu Asn His Phe Asn Gly
        595                 600                 605

Gly Ile Pro Ala Phe Leu Ser Glu Phe Lys Lys Leu Asn Glu Leu Gln
    610                 615                 620

Leu Gly Gly Asn Met Phe Gly Gly Asn Ile Pro Arg Ser Ile Gly Glu
625                 630                 635                 640

Leu Val Asn Leu Ile Tyr Glu Leu Asn Leu Ser Ala Thr Gly Leu Ile
                645                 650                 655

Gly Glu Leu Pro Arg Glu Ile Gly Asn Leu Lys Ser Leu Leu Ser Leu
            660                 665                 670

Asp Leu Ser Trp Asn Asn Leu Thr Gly Ser Ile Gln Val Leu Asp Gly
        675                 680                 685

Leu Ser Ser Leu Ser Glu Phe Asn Ile Ser Tyr Asn Ser Phe Glu Gly
    690                 695                 700

Pro Val Pro Gln Gln Leu Thr Thr Leu Pro Asn Ser Ser Leu Ser Phe
705                 710                 715                 720

Leu Gly Asn Pro Gly Leu Cys Gly Ser Asn Phe Thr Glu Ser Ser Tyr
                725                 730                 735

Leu Lys Pro Cys Asp Thr Asn Ser Lys Lys Ser Lys Lys Leu Ser Lys
            740                 745                 750

Val Ala Thr Val Met Ile Ala Leu Gly Ser Ala Ile Phe Val Val Leu
        755                 760                 765

Leu Leu Trp Leu Val Tyr Ile Phe Phe Ile Arg Lys Ile Lys Gln Glu
    770                 775                 780

Ala Ile Ile Ile Lys Glu Asp Asp Ser Pro Thr Leu Leu Asn Glu Val
785                 790                 795                 800

Met Glu Ala Thr Glu Asn Leu Asn Asp Glu Tyr Ile Ile Gly Arg Gly
                805                 810                 815

Ala Gln Gly Val Val Tyr Lys Ala Ala Ile Gly Pro Asp Lys Thr Leu
            820                 825                 830

Ala Ile Lys Lys Phe Val Phe Ser His Glu Gly Lys Ser Ser Ser Met
        835                 840                 845

Thr Arg Glu Ile Gln Thr Leu Gly Lys Ile Arg His Arg Asn Leu Val
    850                 855                 860

Lys Leu Glu Gly Cys Trp Leu Arg Glu Asn Tyr Gly Leu Ile Ala Tyr
865                 870                 875                 880

Lys Tyr Met Pro Asn Gly Ser Leu His Asp Ala Leu His Glu Lys Asn
                885                 890                 895

Pro Pro Tyr Ser Leu Glu Trp Ile Val Arg Asn Asn Ile Ala Leu Gly
            900                 905                 910

Ile Ala His Gly Leu Thr Tyr Leu His Tyr Asp Cys Asp Pro Val Ile
        915                 920                 925

Val His Arg Asp Ile Lys Thr Ser Asn Ile Leu Leu Asp Ser Glu Met
    930                 935                 940

Glu Pro His Ile Ala Asp Phe Gly Ile Ala Lys Leu Ile Asp Gln Pro
945                 950                 955                 960

Ser Thr Ser Thr Gln Leu Ser Ser Val Ala Gly Thr Leu Gly Tyr Ile
                965                 970                 975

Ala Pro Glu Asn Ala Tyr Thr Thr Thr Lys Gly Lys Glu Ser Asp Val
            980                 985                 990

Tyr Ser Tyr Gly Val Val Leu Leu  Glu Leu Ile Ser Arg  Lys Lys Pro
```

-continued

```
        995                 1000                1005

Leu Asp  Ala Ser Phe Met Glu  Gly Thr Asp Ile Val  Asn Trp Ala
    1010                 1015                1020

Arg Ser  Val Trp Glu Glu Thr  Gly Val Val Asp Glu  Ile Val Asp
    1025                 1030                1035

Pro Glu  Leu Ala Asp Glu Ile  Ser Asn Ser Glu Val  Met Lys Gln
    1040                 1045                1050

Val Thr  Lys Val Leu Leu Val  Ala Leu Arg Cys Thr  Glu Lys Asp
    1055                 1060                1065

Pro Arg  Lys Arg Pro Thr Met  Arg Asp Val Ile Arg  His Leu
    1070                 1075                1080
```

<210> SEQ ID NO 152
<211> LENGTH: 3261
<212> TYPE: DNA
<213> ORGANISM: Glycine max

<400> SEQUENCE: 152

```
atgtccatga tttggattgt tttcttttcc ttgtcttgca tgtcttgtgc tgttgtttct     60
tcactcacct ccgatggggt gactctcttg tcactcttga ggcactggac atccgtgcct    120
ccttccataa acgccacctg gcttgcctcc gataccactc catgctcctc ctgggtagga    180
gtacaatgtg accattccca ccatgtcgtc aaccttaccc tcccagatta tggtattgct    240
ggtcaattag gacctgaaat tggaaattta agtcgcctag agtacttaga acttgctagc    300
aacaacctta ctggtcaaat acctgacgcc ttcaaaaaca tgcacaacct caatttactc    360
agccttccat ataatcaact gtctggtgaa attccagatt ccttgactca tgctccccaa    420
ctaaatcttg ttgatctttc tcataacact ttaagtggat ccatccccac aagtattggg    480
aacatgactc agctcttgca gttgtatctt cagagtaacc agttgtctgg gacaattccc    540
tcatccattg ggaactgcag caaattacaa gaattgtttt tggataaaaa tcacttggag    600
ggtatcctgc ctcagagtct taacaatctc aatgatcttg cttattttga tgttgccagc    660
aatagactta agggtaccat tccttttggt tctgctgcca gttgtaaaaa tttgaagaat    720
ttggatctct cattcaatga ctttagtgga ggccttccct caagcttggg gaactgtagc    780
gctttatctg aatttttctgc cgtgaactgc aatttggatg gcaatattcc tccctccttt    840
ggtctactga ccaagctttc tattctatac cttcccgaga accacttatc tggaaaagta    900
cctccagaaa ttggcaactg catgtctttg acagagttac atctgtattc caatcaactt    960
gagggaaaca ttccaagtga actgggaaaa ctaagaaaac tagtggatct tgaattgttt   1020
tcaaatcaat tgacgggtga aattccactc agcatctgga agattaaatc tctgaagcat   1080
ctccttgtgt ataataacag tctttctggg gaacttcctt tggagatgac agagctcaag   1140
caactgaaaa acatctcatt gtttagcaac cagttctccg gagtcatacc gcaaagcttg   1200
ggaattaaca gcagtttagt tcttttggat tttacaaata ataaattcac tggcaacatc   1260
ccaccaaatc tgtgttttgg caagaaatta aacatcctga atttgggcat caaccaactt   1320
caaggcagca ttcctcctga tgttgggaga tgtacaaccc ttagaaggtt aattcttcaa   1380
caaaataact ttactgggcc tcttcctgat ttcaaaagca atccaaatct cgaacatatg   1440
gatatcagca gcaacaaaat ccatggtgaa attccatcaa gtttgcgaaa ttgcagacat   1500
atcactcacc taattttgtc catgaacaaa tttaatgggc ctataccctc agagctaggg   1560
aacattgtca atcttcaaac tttgaatctc gctcacaaca acttagaagg tcctttgccc   1620
tctcagctgt caaagtgtac caaaatggac aggtttgatg ttggatttaa tttcctaaat   1680
```

```
ggttcattgc catcaggtct gcagagctgg acaaggctaa ccacattaat tttgagtgag   1740
aatcacttta gtgggggcct cccagctttc ttgtcggaat ataaaatgct ttctgaacta   1800
caacttggtg gcaatatgtt tggtggcaga attcctagat cggttggagc attgcagagt   1860
ttgaggtatg gtatgaatct gagttcaaat gggctgatag gagacattcc tgttgagatt   1920
ggaaacttga actttttgga aagactggat ctgtctcaga acaatttgac cggaagcata   1980
gaagttcttg gtgaactcct ctccttagtt gaagtcaata tttcatacaa ttcttttcat   2040
ggtcgtgtac caaagaagct aatgaaattg ctcaagtctc ccttgtcatc atttttgggc   2100
aatcctggcc tatgtaccac caccaggtgt tcagcatctg atggcttggc ttgcactgca   2160
agaagctcta taaaaccatg tgatgacaaa tctactaaac agaaaggcct cagtaaagtt   2220
gaaattgtga tgatagctct cgggtcctca atacttgttg ttttgctgtt gctgggatta   2280
gtttatattt tttattttgg aagaaaagct taccaggaag tccatatctt tgctgaaggg   2340
ggttcttctt cccttcttaa cgaagtcatg gaggctacag caaacctaaa tgatcggtat   2400
attattggca gaggagccta tggagttgtt tataaagccc tggtgggtcc agacaaagcc   2460
tttgctgcga agaagatagg atttgctgcg agcaaaggta agaacttgag catggccaga   2520
gaaattgaaa cccttgggaa aattcggcat cgaaatctgg tcaaattgga agacttttgg   2580
ttgagagaag attatggtat aattttgtac agctacatgg caaatggaag tcttcatgat   2640
gttttgcacg aaaagacacc accactaacc ttagagtgga atgtccggaa taagatagct   2700
gttggaattg ctcatggatt ggcttatctc cattatgact gtgatcctcc catagtgcac   2760
cgagacatca agccaagcaa tatacttcta gactctgata tggagcctca cattgctgac   2820
tttggtattg ccaaacttct ggatcagtct tctgcttcaa atccttccat ttctgttccg   2880
ggtacaattg gttatattgc accagagaat gcttatacaa caacaaatag tagggagtct   2940
gatgtataca gttacggggt agttttgctt gagctgataa ccagaaagaa ggcagcagaa   3000
tcagatcctt ccttcatgga gggtactata gtagtggatt gggttaggtc tgtgtggagg   3060
gaaacaggag acattaatca aattgttgat tcaagccttg cagaggaatt tctagatatc   3120
catataatgg aaaatattac caaagtgctt atggtggctc tgagatgtac tgagaaggat   3180
ccacacaaga gacccacaat gagagatgtt accaagcagt tagcagatgc taatccacgg   3240
gcaagaagta caaagggcta g                                              3261
```

<210> SEQ ID NO 153
<211> LENGTH: 1086
<212> TYPE: PRT
<213> ORGANISM: Glycine max

<400> SEQUENCE: 153

```
Met Ser Met Ile Trp Ile Val Phe Phe Ser Leu Ser Cys Met Ser Cys
1               5                   10                  15

Ala Val Val Ser Ser Leu Thr Ser Asp Gly Val Thr Leu Leu Ser Leu
            20                  25                  30

Leu Arg His Trp Thr Ser Val Pro Pro Ser Ile Asn Ala Thr Trp Leu
        35                  40                  45

Ala Ser Asp Thr Thr Pro Cys Ser Ser Trp Val Gly Val Gln Cys Asp
    50                  55                  60

His Ser His His Val Val Asn Leu Thr Leu Pro Asp Tyr Gly Ile Ala
65                  70                  75                  80

Gly Gln Leu Gly Pro Glu Ile Gly Asn Leu Ser Arg Leu Glu Tyr Leu
                85                  90                  95
```

```
Glu Leu Ala Ser Asn Asn Leu Thr Gly Gln Ile Pro Asp Ala Phe Lys
            100                 105                 110

Asn Met His Asn Leu Asn Leu Leu Ser Leu Pro Tyr Asn Gln Leu Ser
        115                 120                 125

Gly Glu Ile Pro Asp Ser Leu Thr His Ala Pro Gln Leu Asn Leu Val
    130                 135                 140

Asp Leu Ser His Asn Thr Leu Ser Gly Ser Ile Pro Thr Ser Ile Gly
145                 150                 155                 160

Asn Met Thr Gln Leu Leu Gln Leu Tyr Leu Gln Ser Asn Gln Leu Ser
                165                 170                 175

Gly Thr Ile Pro Ser Ser Ile Gly Asn Cys Ser Lys Leu Gln Glu Leu
            180                 185                 190

Phe Leu Asp Lys Asn His Leu Glu Gly Ile Leu Pro Gln Ser Leu Asn
        195                 200                 205

Asn Leu Asn Asp Leu Ala Tyr Phe Asp Val Ala Ser Asn Arg Leu Lys
    210                 215                 220

Gly Thr Ile Pro Phe Gly Ser Ala Ala Ser Cys Lys Asn Leu Lys Asn
225                 230                 235                 240

Leu Asp Leu Ser Phe Asn Asp Phe Ser Gly Gly Leu Pro Ser Ser Leu
                245                 250                 255

Gly Asn Cys Ser Ala Leu Ser Glu Phe Ser Ala Val Asn Cys Asn Leu
            260                 265                 270

Asp Gly Asn Ile Pro Pro Ser Phe Gly Leu Leu Thr Lys Leu Ser Ile
        275                 280                 285

Leu Tyr Leu Pro Glu Asn His Leu Ser Gly Lys Val Pro Pro Glu Ile
    290                 295                 300

Gly Asn Cys Met Ser Leu Thr Glu Leu His Leu Tyr Ser Asn Gln Leu
305                 310                 315                 320

Glu Gly Asn Ile Pro Ser Glu Leu Gly Lys Leu Arg Lys Leu Val Asp
                325                 330                 335

Leu Glu Leu Phe Ser Asn Gln Leu Thr Gly Glu Ile Pro Leu Ser Ile
            340                 345                 350

Trp Lys Ile Lys Ser Leu Lys His Leu Leu Val Tyr Asn Asn Ser Leu
        355                 360                 365

Ser Gly Glu Leu Pro Leu Glu Met Thr Glu Leu Lys Gln Leu Lys Asn
    370                 375                 380

Ile Ser Leu Phe Ser Asn Gln Phe Ser Gly Val Ile Pro Gln Ser Leu
385                 390                 395                 400

Gly Ile Asn Ser Ser Leu Val Leu Leu Asp Phe Thr Asn Asn Lys Phe
                405                 410                 415

Thr Gly Asn Ile Pro Pro Asn Leu Cys Phe Gly Lys Lys Leu Asn Ile
            420                 425                 430

Leu Asn Leu Gly Ile Asn Gln Leu Gln Gly Ser Ile Pro Pro Asp Val
        435                 440                 445

Gly Arg Cys Thr Thr Leu Arg Arg Leu Ile Leu Gln Gln Asn Asn Phe
    450                 455                 460

Thr Gly Pro Leu Pro Asp Phe Lys Ser Asn Pro Asn Leu Glu His Met
465                 470                 475                 480

Asp Ile Ser Ser Asn Lys Ile His Gly Glu Ile Pro Ser Ser Leu Arg
                485                 490                 495

Asn Cys Arg His Ile Thr His Leu Ile Leu Ser Met Asn Lys Phe Asn
            500                 505                 510

Gly Pro Ile Pro Ser Glu Leu Gly Asn Ile Val Asn Leu Gln Thr Leu
```

-continued

```
        515                 520                 525

Asn Leu Ala His Asn Asn Leu Glu Gly Pro Leu Pro Ser Gln Leu Ser
    530                 535                 540

Lys Cys Thr Lys Met Asp Arg Phe Asp Val Gly Phe Asn Phe Leu Asn
545                 550                 555                 560

Gly Ser Leu Pro Ser Gly Leu Gln Ser Trp Thr Arg Leu Thr Thr Leu
                565                 570                 575

Ile Leu Ser Glu Asn His Phe Ser Gly Gly Leu Pro Ala Phe Leu Ser
            580                 585                 590

Glu Tyr Lys Met Leu Ser Glu Leu Gln Leu Gly Gly Asn Met Phe Gly
        595                 600                 605

Gly Arg Ile Pro Arg Ser Val Gly Ala Leu Gln Ser Leu Arg Tyr Gly
    610                 615                 620

Met Asn Leu Ser Ser Asn Gly Leu Ile Gly Asp Ile Pro Val Glu Ile
625                 630                 635                 640

Gly Asn Leu Asn Phe Leu Glu Arg Leu Asp Leu Ser Gln Asn Asn Leu
                645                 650                 655

Thr Gly Ser Ile Glu Val Leu Gly Glu Leu Leu Ser Leu Val Glu Val
            660                 665                 670

Asn Ile Ser Tyr Asn Ser Phe His Gly Arg Val Pro Lys Lys Leu Met
        675                 680                 685

Lys Leu Leu Lys Ser Pro Leu Ser Ser Phe Leu Gly Asn Pro Gly Leu
    690                 695                 700

Cys Thr Thr Thr Arg Cys Ser Ala Ser Asp Gly Leu Ala Cys Thr Ala
705                 710                 715                 720

Arg Ser Ser Ile Lys Pro Cys Asp Asp Lys Ser Thr Lys Gln Lys Gly
                725                 730                 735

Leu Ser Lys Val Glu Ile Val Met Ile Ala Leu Gly Ser Ser Ile Leu
            740                 745                 750

Val Val Leu Leu Leu Leu Gly Leu Val Tyr Ile Phe Tyr Phe Gly Arg
        755                 760                 765

Lys Ala Tyr Gln Glu Val His Ile Phe Ala Glu Gly Gly Ser Ser Ser
    770                 775                 780

Leu Leu Asn Glu Val Met Glu Ala Thr Ala Asn Leu Asn Asp Arg Tyr
785                 790                 795                 800

Ile Ile Gly Arg Gly Ala Tyr Gly Val Val Tyr Lys Ala Leu Val Gly
                805                 810                 815

Pro Asp Lys Ala Phe Ala Ala Lys Lys Ile Gly Phe Ala Ala Ser Lys
            820                 825                 830

Gly Lys Asn Leu Ser Met Ala Arg Glu Ile Glu Thr Leu Gly Lys Ile
        835                 840                 845

Arg His Arg Asn Leu Val Lys Leu Glu Asp Phe Trp Leu Arg Glu Asp
    850                 855                 860

Tyr Gly Ile Ile Leu Tyr Ser Tyr Met Ala Asn Gly Ser Leu His Asp
865                 870                 875                 880

Val Leu His Glu Lys Thr Pro Pro Leu Thr Leu Glu Trp Asn Val Arg
                885                 890                 895

Asn Lys Ile Ala Val Gly Ile Ala His Gly Leu Ala Tyr Leu His Tyr
            900                 905                 910

Asp Cys Asp Pro Pro Ile Val His Arg Asp Ile Lys Pro Ser Asn Ile
        915                 920                 925

Leu Leu Asp Ser Asp Met Glu Pro His Ile Ala Asp Phe Gly Ile Ala
    930                 935                 940
```

```
Lys Leu Leu Asp Gln Ser Ser Ala Ser Asn Pro Ser Ile Ser Val Pro
945                 950                 955                 960

Gly Thr Ile Gly Tyr Ile Ala Pro Glu Asn Ala Tyr Thr Thr Thr Asn
                965                 970                 975

Ser Arg Glu Ser Asp Val Tyr Ser Tyr Gly Val Val Leu Leu Glu Leu
            980                 985                 990

Ile Thr Arg Lys Lys Ala Ala Glu  Ser Asp Pro Ser Phe  Met Glu Gly
        995                 1000                 1005

Thr Ile  Val Val Asp Trp Val  Arg Ser Val Trp Arg  Glu Thr Gly
    1010                 1015                 1020

Asp Ile  Asn Gln Ile Val Asp  Ser Ser Leu Ala Glu  Glu Phe Leu
    1025                 1030                 1035

Asp Ile  His Ile Met Glu Asn  Ile Thr Lys Val Leu  Met Val Ala
    1040                 1045                 1050

Leu Arg  Cys Thr Glu Lys Asp  Pro His Lys Arg Pro  Thr Met Arg
    1055                 1060                 1065

Asp Val  Thr Lys Gln Leu Ala  Asp Ala Asn Pro Arg  Ala Arg Ser
    1070                 1075                 1080

Thr Lys  Gly
    1085
```

<210> SEQ ID NO 154
<211> LENGTH: 3339
<212> TYPE: DNA
<213> ORGANISM: Oryza sativa

<400> SEQUENCE: 154

```
atgaggctgg ttgtgtggca ctggtttttc ttcttcttct tcacttctgt ttcatcgtct     60
tggagtttga cttcagatgg tctagccctt ctttctctgt ctagggatct catattacct    120
cattccataa gctccacttg gaaagcttct gatacaactc cttgtaattg ggatggggtt    180
tcctgcaaca aaaagaatag tgtggtttct cttgacctgt catcttctgg agtttctggt    240
tctcttggac cccaaatagg acttatgaag agcctacaag tactcagttt gtcaaataac    300
agcatatctg gttcaatccc tcaagaattg ggcaattgta gcatgcttga tcaattggat    360
ttgtccagta acagtttttc tggtgagata ccagcatccc ttggtgacat caaaaagctt    420
tcgtctctct ctttgtacag taactccctc actggtgaaa taccagaggg gttgttcaag    480
aatcagtttc tggagcaagt gtacctccat tacaataaac tcagtggttc tatccccttg    540
acagttggag aaatgactag ccttaggtac ctgtggctgc atggcaataa attatctgga    600
gttctaccag attcaattgg caactgcacc aagttggagg agctctatct actagataat    660
caattgagtg ggagtcttcc gaaaaccttg agctatatca aaggactgaa gatttttcgat   720 attaccgcaa atagtttcac aggtgagatc acatttagtt ttgaggattg caagcttgag    780
gtattcatat tgtcattcaa tcagattagc aacgaaattc catcatggct agggaattgt    840
agtagcttga cacagcttgc atttgtcaac aataatatat ctggccagat tccatcgtct    900
ctgggtttat tgagaaacct ctctcaactt ttactttctg agaactcact ttctgggcca    960
attcctcctg agataggtaa ctgccagttg ctggtgtggc tggagttgga tgcaaaccag   1020
ctcaatggca ctgttcctaa agagctggca aatctgagaa aattggagaa actctttctg   1080
tttgaaaacc gcctcattgg ggagttccct gaggatattt ggagcatcaa gagcctgcaa   1140
agtgtcctta tctatgaaaa cagttttact gggaggctac ctccagtgct agctgagctg   1200
aagttcctga agaacattac acttttcaac aatttcttca ctggagttat accaccagat   1260
```

-continued

```
ttgggtgtta atagtcgttt aacccaaatt gatttcacaa acaacagttt tgttggtgga   1320
atcccgccta acatttgttc agggaaaaga ttgagaattt tggacttggg gcttaatctt   1380
ctcaatggta gcatcccatc caatgttatg gactgcccaa gtttggaacg atttattctc   1440
caaaacaaca atctaagtgg gcccattcca caatttagga actgtgcaaa tctgagctat   1500
atagatctga gtcataattc cttaagtggc aacattccag caagcttggg gagatgtgta   1560
aatattacga tgataaaatg gtcagaaaac aagttggttg gtccaatacc atctgaaatt   1620
agagacttgg tgaatttgag agtgctaaac ctctcgcaaa acagcctgca aggtgttctt   1680
ccagtgcaga tttctagttg ctccaagctg tacttgcttg acttgagttt caactctttg   1740
aatggttcgg cactcacaac cgtaagcaac cttaagtttc tgtcacaact acggttacaa   1800
gagaataaat tcagtggagg catacctgat tccctctcgc agttggatat gcttattgag   1860
ctgcaacttg gtggcaacgt tcttgggggc agtatccctt catcgttagg aaggttggta   1920
aaactgggca ttgcattgaa tatttgtagc aatggactcg ttggtggcat tccgccatta   1980
ttgagcaatt tggtggagct gcaaagttta gatttgtcac ttaatggcct cactggagac   2040
ctagacatgt taggaaactt acaattactg catgtattga atgtttccta caatagattc   2100
agtggtccgg tcccagaaaa tcttctgaat tttctggttt cctcaccgag ctcctttaat   2160
ggcaatccag acctctgtat ctcttgccat accaatggtt cttattgcaa ggggtctaat   2220
gttttgaaac cttgtggaga gaccaaaaaa ctacacaaac acgtcaagat tgctgttata   2280
gttattggtt cattgttcgt tggagcagtt tccatactta tactgagttg catcctttta   2340
aagttttatc atccaaagac aaaaaattta gaatcagtca gtactctgtt tgaaggttct   2400
tcttctaaat taaatgaggt tatagaggct actgaaaact ttgatgacaa gtatatcatc   2460
ggtactggtg ctcatggaac tgtttacaag gcaacactga ggtcaggaga agtatatgct   2520
gtaaagaagc ttgcaatatc tgcacagaaa ggttcgtaca aaagcatgat cagagaactg   2580
aagacattag gcaaaatcaa gcatcggaac ttgataaagc tgaaagagtt ttggttaaga   2640
agtgagtatg ggttcatgct ttatgtttat atggagcaag gtagccttca agatgttctg   2700
catgggatcc aacctcctcc aagtttggac tggagtgtgc gctataccat agctcttggt   2760
actgcccatg ggctagcgta tcttcatgat gactgtcaac ctgcaattat tcaccgagat   2820
attaagccca gtaatatact tctgaatggg gacatggttc cacatatagc agattttggc   2880
attgcaaagc tcatggacca gtcttcttct gctccacaga ctactggagt tattggcacc   2940
tttggatata tggccccaga gttggcattt tccaccagga gtagtatcga gtccgatgta   3000
tacagctacg gcgtcatact ccttgagctg ctaacaaaaa aacaggtggt ggatccctcg   3060
ttccccgaca acatggacat tgtcggttgg gtgaccgcaa cgctcaacgg caccgaccaa   3120
atcgaactcg tctgcgactc gacgctgatg gaggaagtct atggcacggt ggaaatagag   3180
gaagtcagca aggtcctgtc cttggctctt aggtgcgcag cgaaggaagc gagccgaagg   3240
ccgcccatgg ccgatgttgt gaaggagctg actgatgtca ggaaatccgc cgggaagttg   3300
tccaagccgg agaagacggc ctcccggagc tcgtcctga                          3339
```

<210> SEQ ID NO 155
<211> LENGTH: 1112
<212> TYPE: PRT
<213> ORGANISM: Oryza sativa

<400> SEQUENCE: 155

```
Met Arg Leu Val Val Trp His Trp Phe Phe Phe Phe Phe Phe Thr Ser
1               5                   10                  15
```

-continued

```
Val Ser Ser Ser Trp Ser Leu Thr Ser Asp Gly Leu Ala Leu Leu Ser
            20                  25                  30

Leu Ser Arg Asp Leu Ile Leu Pro His Ser Ile Ser Ser Thr Trp Lys
        35                  40                  45

Ala Ser Asp Thr Thr Pro Cys Asn Trp Asp Gly Val Ser Cys Asn Lys
    50                  55                  60

Lys Asn Ser Val Val Ser Leu Asp Leu Ser Ser Ser Gly Val Ser Gly
65                  70                  75                  80

Ser Leu Gly Pro Gln Ile Gly Leu Met Lys Ser Leu Gln Val Leu Ser
                85                  90                  95

Leu Ser Asn Asn Ser Ile Ser Gly Ser Ile Pro Gln Glu Leu Gly Asn
            100                 105                 110

Cys Ser Met Leu Asp Gln Leu Asp Leu Ser Ser Asn Ser Phe Ser Gly
        115                 120                 125

Glu Ile Pro Ala Ser Leu Gly Asp Ile Lys Lys Leu Ser Ser Leu Ser
    130                 135                 140

Leu Tyr Ser Asn Ser Leu Thr Gly Glu Ile Pro Glu Gly Leu Phe Lys
145                 150                 155                 160

Asn Gln Phe Leu Glu Gln Val Tyr Leu His Tyr Asn Lys Leu Ser Gly
                165                 170                 175

Ser Ile Pro Leu Thr Val Gly Glu Met Thr Ser Leu Arg Tyr Leu Trp
            180                 185                 190

Leu His Gly Asn Lys Leu Ser Gly Val Leu Pro Asp Ser Ile Gly Asn
        195                 200                 205

Cys Thr Lys Leu Glu Glu Leu Tyr Leu Leu Asp Asn Gln Leu Ser Gly
    210                 215                 220

Ser Leu Pro Lys Thr Leu Ser Tyr Ile Lys Gly Leu Lys Ile Phe Asp
225                 230                 235                 240

Ile Thr Ala Asn Ser Phe Thr Gly Glu Ile Thr Phe Ser Phe Glu Asp
                245                 250                 255

Cys Lys Leu Glu Val Phe Ile Leu Ser Phe Asn Gln Ile Ser Asn Glu
            260                 265                 270

Ile Pro Ser Trp Leu Gly Asn Cys Ser Ser Leu Thr Gln Leu Ala Phe
        275                 280                 285

Val Asn Asn Asn Ile Ser Gly Gln Ile Pro Ser Ser Leu Gly Leu Leu
    290                 295                 300

Arg Asn Leu Ser Gln Leu Leu Leu Ser Glu Asn Ser Leu Ser Gly Pro
305                 310                 315                 320

Ile Pro Pro Glu Ile Gly Asn Cys Gln Leu Leu Val Trp Leu Glu Leu
                325                 330                 335

Asp Ala Asn Gln Leu Asn Gly Thr Val Pro Lys Glu Leu Ala Asn Leu
            340                 345                 350

Arg Lys Leu Glu Lys Leu Phe Leu Phe Glu Asn Arg Leu Ile Gly Glu
        355                 360                 365

Phe Pro Glu Asp Ile Trp Ser Ile Lys Ser Leu Gln Ser Val Leu Ile
    370                 375                 380

Tyr Glu Asn Ser Phe Thr Gly Arg Leu Pro Pro Val Leu Ala Glu Leu
385                 390                 395                 400

Lys Phe Leu Lys Asn Ile Thr Leu Phe Asn Asn Phe Phe Thr Gly Val
                405                 410                 415

Ile Pro Pro Asp Leu Gly Val Asn Ser Arg Leu Thr Gln Ile Asp Phe
            420                 425                 430

Thr Asn Asn Ser Phe Val Gly Gly Ile Pro Pro Asn Ile Cys Ser Gly
```

-continued

```
        435                 440                 445

Lys Arg Leu Arg Ile Leu Asp Leu Gly Leu Asn Leu Leu Asn Gly Ser
    450                 455                 460

Ile Pro Ser Asn Val Met Asp Cys Pro Ser Leu Glu Arg Phe Ile Leu
465                 470                 475                 480

Gln Asn Asn Asn Leu Ser Gly Pro Ile Pro Gln Phe Arg Asn Cys Ala
                485                 490                 495

Asn Leu Ser Tyr Ile Asp Leu Ser His Asn Ser Leu Ser Gly Asn Ile
            500                 505                 510

Pro Ala Ser Leu Gly Arg Cys Val Asn Ile Thr Met Ile Lys Trp Ser
        515                 520                 525

Glu Asn Lys Leu Val Gly Pro Ile Pro Ser Glu Ile Arg Asp Leu Val
    530                 535                 540

Asn Leu Arg Val Leu Asn Leu Ser Gln Asn Ser Leu Gln Gly Val Leu
545                 550                 555                 560

Pro Val Gln Ile Ser Ser Cys Ser Lys Leu Tyr Leu Leu Asp Leu Ser
                565                 570                 575

Phe Asn Ser Leu Asn Gly Ser Ala Leu Thr Thr Val Ser Asn Leu Lys
            580                 585                 590

Phe Leu Ser Gln Leu Arg Leu Gln Glu Asn Lys Phe Ser Gly Gly Ile
        595                 600                 605

Pro Asp Ser Leu Ser Gln Leu Asp Met Leu Ile Glu Leu Gln Leu Gly
    610                 615                 620

Gly Asn Val Leu Gly Gly Ser Ile Pro Ser Ser Leu Gly Arg Leu Val
625                 630                 635                 640

Lys Leu Gly Ile Ala Leu Asn Ile Cys Ser Asn Gly Leu Val Gly Gly
                645                 650                 655

Ile Pro Pro Leu Leu Ser Asn Leu Val Glu Leu Gln Ser Leu Asp Leu
            660                 665                 670

Ser Leu Asn Gly Leu Thr Gly Asp Leu Asp Met Leu Gly Asn Leu Gln
        675                 680                 685

Leu Leu His Val Leu Asn Val Ser Tyr Asn Arg Phe Ser Gly Pro Val
    690                 695                 700

Pro Glu Asn Leu Leu Asn Phe Leu Val Ser Ser Pro Ser Ser Phe Asn
705                 710                 715                 720

Gly Asn Pro Asp Leu Cys Ile Ser Cys His Thr Asn Gly Ser Tyr Cys
                725                 730                 735

Lys Gly Ser Asn Val Leu Lys Pro Cys Gly Glu Thr Lys Lys Leu His
            740                 745                 750

Lys His Val Lys Ile Ala Val Ile Val Ile Gly Ser Leu Phe Val Gly
        755                 760                 765

Ala Val Ser Ile Leu Ile Leu Ser Cys Ile Leu Leu Lys Phe Tyr His
    770                 775                 780

Pro Lys Thr Lys Asn Leu Glu Ser Val Ser Thr Leu Phe Glu Gly Ser
785                 790                 795                 800

Ser Ser Lys Leu Asn Glu Val Ile Glu Ala Thr Glu Asn Phe Asp Asp
                805                 810                 815

Lys Tyr Ile Ile Gly Thr Gly Ala His Gly Thr Val Tyr Lys Ala Thr
            820                 825                 830

Leu Arg Ser Gly Glu Val Tyr Ala Val Lys Lys Leu Ala Ile Ser Ala
        835                 840                 845

Gln Lys Gly Ser Tyr Lys Ser Met Ile Arg Glu Leu Lys Thr Leu Gly
    850                 855                 860
```

-continued

Lys Ile Lys His Arg Asn Leu Ile Lys Leu Lys Glu Phe Trp Leu Arg
865 870 875 880

Ser Glu Tyr Gly Phe Met Leu Tyr Val Tyr Met Glu Gln Gly Ser Leu
885 890 895

Gln Asp Val Leu His Gly Ile Gln Pro Pro Pro Ser Leu Asp Trp Ser
900 905 910

Val Arg Tyr Thr Ile Ala Leu Gly Thr Ala His Gly Leu Ala Tyr Leu
915 920 925

His Asp Asp Cys Gln Pro Ala Ile Ile His Arg Asp Ile Lys Pro Ser
930 935 940

Asn Ile Leu Leu Asn Gly Asp Met Val Pro His Ile Ala Asp Phe Gly
945 950 955 960

Ile Ala Lys Leu Met Asp Gln Ser Ser Ser Ala Pro Gln Thr Thr Gly
965 970 975

Val Ile Gly Thr Phe Gly Tyr Met Ala Pro Glu Leu Ala Phe Ser Thr
980 985 990

Arg Ser Ser Ile Glu Ser Asp Val Tyr Ser Tyr Gly Val Ile Leu Leu
995 1000 1005

Glu Leu Leu Thr Lys Lys Gln Val Val Asp Pro Ser Phe Pro Asp
1010 1015 1020

Asn Met Asp Ile Val Gly Trp Val Thr Ala Thr Leu Asn Gly Thr
1025 1030 1035

Asp Gln Ile Glu Leu Val Cys Asp Ser Thr Leu Met Glu Glu Val
1040 1045 1050

Tyr Gly Thr Val Glu Ile Glu Glu Val Ser Lys Val Leu Ser Leu
1055 1060 1065

Ala Leu Arg Cys Ala Ala Lys Glu Ala Ser Arg Arg Pro Pro Met
1070 1075 1080

Ala Asp Val Val Lys Glu Leu Thr Asp Val Arg Lys Ser Ala Gly
1085 1090 1095

Lys Leu Ser Lys Pro Glu Lys Thr Ala Ser Arg Ser Ser Ser
1100 1105 1110

<210> SEQ ID NO 156
<211> LENGTH: 3033
<212> TYPE: DNA
<213> ORGANISM: Oryza sativa

<400> SEQUENCE: 156
atgggactgc acatatggtg ttggttggtt gtcttgttca gcttggcccc attgtgttgt 60
agtttgagcg cagatggcct ggctcttctg gatctagcca agactctgat actgcccagc 120
tccataagct cgaattggag tgctgatgat gcaactccgt gtacatggaa aggagttgat 180
tgtgatgaaa tgagcaatgt ggtttctctt aacttatcat attctggatt gtctggttct 240
ctaggtcctc agataggact catgaagcac ctgaaagtca ttgatttatc aggtaatggt 300
atatcaggac caatgcccag ttccattggc aactgcacca aactggaggt gctccatcta 360
ctacgtaatc gattgagtgg gatccttcca gatacattga gcaatattga agcattaagg 420
gtttttgatc tctcccgcaa tagcttcaca ggcaaggtca atttcagatt tgagaactgc 480
aagcttgagg agttcatctt gtcattcaat tatctcagag gcgaaatccc ggtgtggata 540
gggaattgca gcagcttgac acagcttgca tttgtcaaca atagtatcac cggtcaaata 600
ccaagttcaa tcggtttatt gagaaacctt tcttaccttg tactttccca gaactccttg 660
tctggcacaa tccctcctga gattggtaac tgccaattgc tgatatggct gcatctagat 720

```
gcaaaccagc tcgagggcac tataccaaaa gaactagcaa acctgaggaa cttgcagaag    780
ctctatcttt ttgagaattg cctcactggg gagtttcctg aagatatatg gggaatccaa    840
agcctactat ctgtcgacat ctataaaaac aatttcactg ggcagctgcc tatagtgttg    900
gctgagatga agcagctcca gcaaattacg ctattcaata attcattcac tggtgtcata    960
ccacaggggt tgggtgtaaa tagcagtttg tccgtaattg atttcataaa caatagtttt   1020
gttggcacaa tccctccaaa aatttgttca gggggaagat tggaagtttt gaacttgggt   1080
tcaaatcttc tcaatggtag catcccctct ggtatcgctg actgcccaac tttgagacga   1140
gtaattctca accaaaataa tctcattgga tcaattccac aatttgtaaa ttgtagcagt   1200
cttaattata ttgatctcag ctataattta ttaagtgggg acattcctgc tagcttgagc   1260
aaatgtatca atgttacatt tgtgaactgg tcatggaaca agcttgctgg tctaatacca   1320
tcagaaattg ggaacttagg gaacttaagt agtcttaacc tctcaggaaa cagactatat   1380
ggtgaactcc ctgtggaaat ttctggatgc tccaagttat ataagcttga tttgagctac   1440
aactctttga acggttcggc actcacaact gtaagtagcc ttaaatttct gtcacagcta   1500
cggttgcagg agaataaatt cagtggaggt atacctgatt ctttatctca gttggatatg   1560
cttattgaac tgcaacttgg tggcaacatt cttgggggta gtatcccttc atcgttagga   1620
aagttagtta aactgggcat tgcattaaac ctcagtagaa atggactagt tggtgacatt   1680
ccaccactag gcaatttggt ggagctgcag agtttagatt tgtcatttaa taacctcacc   1740
ggaggtcttg cttcattagg aaacctacag tttttgtatt tcttgaatgt ttcctacaac   1800
atgtttagtg gaccagtacc aaaaaatctt gtgaggtttc tgaattccac tccaagttca   1860
tttagtggaa atgcagatct atgtatctct tgccatgaaa atgattcatc ttgcacaggt   1920
tctaatgttt tgagaccttg tggttcaatg agtaaaaaaa gtgcactcac accactcaag   1980
gttgctatga tagttcttgg ttcggttttt gctggtgcat ttctgatact ctgtgtcctt   2040
ctaaaatata atttcaagcc taagattaac agtgatttag gtatattatt tcaaggatct   2100
tcttctaaat taaatgaggc tgtagaagtg actgaaaact tcaataacaa gtacattatc   2160
ggttccgggg cccatggaat tgtctacaag gcagtactga ggtcaggaga agtatatgct   2220
gtaaagaagc ttgtacatgc tgctcacaag ggctcaaatg caagcatgat ccgcgagctg   2280
cagacgcttg gtcaaattag gcacaggaac ctgataagac ttaatgaatt cttgtttaag   2340
catgagtatg gtttgatcct atatgatttt atggagaatg gtagcctgta tgatgtgttg   2400
catgggactg agcccactcc aactttggac tggagcatcc gctacagcat agctcttgga   2460
acagcccatg gtctagcata tctccataat gactgtcacc ctgctatcat acatcgagat   2520
attaaaccaa aaaatatatt gctggacaac gacatggtac cgcatatctc agattttggc   2580
attgcaaagc tcatggatca atatcctgct gctttacaga ccacaggaat cgttggtact   2640
attggatata tggccccaga aatggccttt tcaaccaagg ctaccacaga attcgatgtg   2700
tacagttacg gtgtggtatt acttgagttg atcaccagaa agatggctgt ggattcctca   2760
ttccctggca acatggacat agttagctgg gtatcctcca agttgaatga gactaatcag   2820
atcgaaacta tttgcgaccc agctctcatt actgaagtat atggaacaca tgaaatggaa   2880
gaagtgcgca agctgttgtc attagctctt agatgcacag caaaggaggc aagccaaagg   2940
ccttccatgg ccgttgttgt caaagagctg acagatgcaa gacatgttgc tggctcatac   3000
tcgaagcaga attcaggccc cagcaattct tga                                3033
```

<210> SEQ ID NO 157

```
<211> LENGTH: 1010
<212> TYPE: PRT
<213> ORGANISM: Oryza sativa

<400> SEQUENCE: 157

Met Gly Leu His Ile Trp Cys Trp Leu Val Val Leu Phe Ser Leu Ala
1               5                   10                  15

Pro Leu Cys Cys Ser Leu Ser Ala Asp Gly Leu Ala Leu Leu Asp Leu
            20                  25                  30

Ala Lys Thr Leu Ile Leu Pro Ser Ser Ile Ser Ser Asn Trp Ser Ala
        35                  40                  45

Asp Asp Ala Thr Pro Cys Thr Trp Lys Gly Val Asp Cys Asp Glu Met
    50                  55                  60

Ser Asn Val Val Ser Leu Asn Leu Ser Tyr Ser Gly Leu Ser Gly Ser
65                  70                  75                  80

Leu Gly Pro Gln Ile Gly Leu Met Lys His Leu Lys Val Ile Asp Leu
                85                  90                  95

Ser Gly Asn Gly Ile Ser Gly Pro Met Pro Ser Ser Ile Gly Asn Cys
            100                 105                 110

Thr Lys Leu Glu Val Leu His Leu Leu Arg Asn Arg Leu Ser Gly Ile
        115                 120                 125

Leu Pro Asp Thr Leu Ser Asn Ile Glu Ala Leu Arg Val Phe Asp Leu
    130                 135                 140

Ser Arg Asn Ser Phe Thr Gly Lys Val Asn Phe Arg Phe Glu Asn Cys
145                 150                 155                 160

Lys Leu Glu Glu Phe Ile Leu Ser Phe Asn Tyr Leu Arg Gly Glu Ile
                165                 170                 175

Pro Val Trp Ile Gly Asn Cys Ser Ser Leu Thr Gln Leu Ala Phe Val
            180                 185                 190

Asn Asn Ser Ile Thr Gly Gln Ile Pro Ser Ser Ile Gly Leu Leu Arg
        195                 200                 205

Asn Leu Ser Tyr Leu Val Leu Ser Gln Asn Ser Leu Ser Gly Thr Ile
    210                 215                 220

Pro Pro Glu Ile Gly Asn Cys Gln Leu Leu Ile Trp Leu His Leu Asp
225                 230                 235                 240

Ala Asn Gln Leu Glu Gly Thr Ile Pro Lys Glu Leu Ala Asn Leu Arg
                245                 250                 255

Asn Leu Gln Lys Leu Tyr Leu Phe Glu Asn Cys Leu Thr Gly Glu Phe
            260                 265                 270

Pro Glu Asp Ile Trp Gly Ile Gln Ser Leu Leu Ser Val Asp Ile Tyr
        275                 280                 285

Lys Asn Asn Phe Thr Gly Gln Leu Pro Ile Val Leu Ala Glu Met Lys
    290                 295                 300

Gln Leu Gln Gln Ile Thr Leu Phe Asn Asn Ser Phe Thr Gly Val Ile
305                 310                 315                 320

Pro Gln Gly Leu Gly Val Asn Ser Ser Leu Ser Val Ile Asp Phe Ile
                325                 330                 335

Asn Asn Ser Phe Val Gly Thr Ile Pro Pro Lys Ile Cys Ser Gly Gly
            340                 345                 350

Arg Leu Glu Val Leu Asn Leu Gly Ser Asn Leu Leu Asn Gly Ser Ile
        355                 360                 365

Pro Ser Gly Ile Ala Asp Cys Pro Thr Leu Arg Arg Val Ile Leu Asn
    370                 375                 380

Gln Asn Asn Leu Ile Gly Ser Ile Pro Gln Phe Val Asn Cys Ser Ser
385                 390                 395                 400
```

```
Leu Asn Tyr Ile Asp Leu Ser Tyr Asn Leu Leu Ser Gly Asp Ile Pro
                405                 410                 415

Ala Ser Leu Ser Lys Cys Ile Asn Val Thr Phe Val Asn Trp Ser Trp
            420                 425                 430

Asn Lys Leu Ala Gly Leu Ile Pro Ser Glu Ile Gly Asn Leu Gly Asn
        435                 440                 445

Leu Ser Ser Leu Asn Leu Ser Gly Asn Arg Leu Tyr Gly Glu Leu Pro
    450                 455                 460

Val Glu Ile Ser Gly Cys Ser Lys Leu Tyr Lys Leu Asp Leu Ser Tyr
465                 470                 475                 480

Asn Ser Leu Asn Gly Ser Ala Leu Thr Thr Val Ser Ser Leu Lys Phe
                485                 490                 495

Leu Ser Gln Leu Arg Leu Gln Glu Asn Lys Phe Ser Gly Gly Ile Pro
            500                 505                 510

Asp Ser Leu Ser Gln Leu Asp Met Leu Ile Glu Leu Gln Leu Gly Gly
        515                 520                 525

Asn Ile Leu Gly Gly Ser Ile Pro Ser Ser Leu Gly Lys Leu Val Lys
    530                 535                 540

Leu Gly Ile Ala Leu Asn Leu Ser Arg Asn Gly Leu Val Gly Asp Ile
545                 550                 555                 560

Pro Pro Leu Gly Asn Leu Val Glu Leu Gln Ser Leu Asp Leu Ser Phe
                565                 570                 575

Asn Asn Leu Thr Gly Gly Leu Ala Ser Leu Gly Asn Leu Gln Phe Leu
            580                 585                 590

Tyr Phe Leu Asn Val Ser Tyr Asn Met Phe Ser Gly Pro Val Pro Lys
        595                 600                 605

Asn Leu Val Arg Phe Leu Asn Ser Thr Pro Ser Ser Phe Ser Gly Asn
    610                 615                 620

Ala Asp Leu Cys Ile Ser Cys His Glu Asn Asp Ser Ser Cys Thr Gly
625                 630                 635                 640

Ser Asn Val Leu Arg Pro Cys Gly Ser Met Ser Lys Lys Ser Ala Leu
                645                 650                 655

Thr Pro Leu Lys Val Ala Met Ile Val Leu Gly Ser Val Phe Ala Gly
            660                 665                 670

Ala Phe Leu Ile Leu Cys Val Leu Leu Lys Tyr Asn Phe Lys Pro Lys
        675                 680                 685

Ile Asn Ser Asp Leu Gly Ile Leu Phe Gln Gly Ser Ser Ser Lys Leu
    690                 695                 700

Asn Glu Ala Val Glu Val Thr Glu Asn Phe Asn Asn Lys Tyr Ile Ile
705                 710                 715                 720

Gly Ser Gly Ala His Gly Ile Val Tyr Lys Ala Val Leu Arg Ser Gly
                725                 730                 735

Glu Val Tyr Ala Val Lys Lys Leu Val His Ala Ala His Lys Gly Ser
            740                 745                 750

Asn Ala Ser Met Ile Arg Glu Leu Gln Thr Leu Gly Gln Ile Arg His
        755                 760                 765

Arg Asn Leu Ile Arg Leu Asn Glu Phe Leu Phe Lys His Glu Tyr Gly
    770                 775                 780

Leu Ile Leu Tyr Asp Phe Met Glu Asn Gly Ser Leu Tyr Asp Val Leu
785                 790                 795                 800

His Gly Thr Glu Pro Thr Pro Thr Leu Asp Trp Ser Ile Arg Tyr Ser
                805                 810                 815

Ile Ala Leu Gly Thr Ala His Gly Leu Ala Tyr Leu His Asn Asp Cys
```

-continued

```
            820                 825                 830

His Pro Ala Ile Ile His Arg Asp Ile Lys Pro Lys Asn Ile Leu Leu
        835                 840                 845

Asp Asn Asp Met Val Pro His Ile Ser Asp Phe Gly Ile Ala Lys Leu
    850                 855                 860

Met Asp Gln Tyr Pro Ala Ala Leu Gln Thr Thr Gly Ile Val Gly Thr
865                 870                 875                 880

Ile Gly Tyr Met Ala Pro Glu Met Ala Phe Ser Thr Lys Ala Thr Thr
                885                 890                 895

Glu Phe Asp Val Tyr Ser Tyr Gly Val Val Leu Leu Glu Leu Ile Thr
            900                 905                 910

Arg Lys Met Ala Val Asp Ser Ser Phe Pro Gly Asn Met Asp Ile Val
        915                 920                 925

Ser Trp Val Ser Ser Lys Leu Asn Glu Thr Asn Gln Ile Glu Thr Ile
    930                 935                 940

Cys Asp Pro Ala Leu Ile Thr Glu Val Tyr Gly Thr His Glu Met Glu
945                 950                 955                 960

Glu Val Arg Lys Leu Leu Ser Leu Ala Leu Arg Cys Thr Ala Lys Glu
                965                 970                 975

Ala Ser Gln Arg Pro Ser Met Ala Val Val Val Lys Glu Leu Thr Asp
            980                 985                 990

Ala Arg His Val Ala Gly Ser Tyr  Ser Lys Gln Asn Ser  Gly Pro Ser
        995                 1000                1005

Asn Ser
    1010

<210> SEQ ID NO 158
<211> LENGTH: 3330
<212> TYPE: DNA
<213> ORGANISM: Ipomoea nil

<400> SEQUENCE: 158
atgaaggttg ctgtgaacac attcttgttg tttttgtgct ccacttcatc aatctatgct      60
gcttttgctt tgaattctga tggagcagct ctgctctcac tcactagaca ttggacttca     120
atcccttctg acataaccca gagctggaat gcttcagatt ccactccttg ttcatggctg     180
ggagtagaat gtgacaggag acaatttgtt gatactctga acctctcctc ctatggaatc     240
tcaggcgaat tcgggcccga aatctcgcat ttgaagcatt tgaagaaggt tgttctcagt     300
ggcaatggtt tctttggctc aattccttcc cagctaggca attgcagtct tcttgaacac     360
atagatctgt cctccaacag ctttactggt aatatccctg acacccttgg agctttgcag     420
aatttaagga acttaagcct gttctttaat tctctgattg gcccatttcc tgagtcttta     480
ctttcaattc cacatttaga aactgtttat ttcactggca atggtcttaa tggttcaatc     540
ccttcaaata ttggaaacat gagtgagctt acaactctgt ggcttgatga taatcaattt     600
tcagggccag tgccttcatc cttaggaaac attaccaccc tgcaagaact ttatttgaat     660
gataacaatc ttgttggaac cttgcctgtc actttaaata atctcgagaa ccttgtttac     720
ttagatgtaa ggaataacag tttagtggga gctattcctt tggactttgt tagttgcaaa     780
cagattgaca cgattagctt gtccaacaac caattcacgg gaggactccc acctggtttg     840
ggaaattgca ctagcttaag ggaattcggt gccttttctt gtgccttgag tggtcctata     900
ccttcctgtt ttggccaact cactaagtta gacactcttt accttgctgg aaaccatttt     960
tcgggaagaa taccacccga gctaggcaag tgcaagtcca tgattgattt gcaacttcaa    1020
```

-continued

```
caaaatcaac ttgagggtga aattccgggt gaactaggga tgctcagtca attgcaatat   1080
ctccatctat ataccaacaa tttatctggt gaagttccac tcagcatttg gaaaattcaa   1140
agcctccaaa gtcttcagtt gtaccaaaac aatctctccg ggagctacc tgttgatatg   1200
accgagctaa agcaactagt gagccttgcc ttatatgaaa accattttac tggagttatt   1260
cctcaagatt tgggggctaa cagcagttta gaggttctag atttgaccag aaacatgttc   1320
acaggtcata ttccaccgaa cctatgctcc caaaagaaac tgaagagact gctcttgggt   1380
tataactatc tggaaggtag tgttccttct gatttggggg gctgttccac tttggaaagg   1440
ctaattctcg aagagaataa cctcagaggt ggcctcccag attttgttga gaagcaaaat   1500
cttctgttct ttgatcttag tggcaataac ttcactggac cgatacctcc aagcttagga   1560
aacctaaaaa atgttactgc catttacttg tcatcgaatc agctctcagg gagtatccca   1620
cccgagcttg gtagccttgt gaaacttgaa catttgaacc tttctcacaa catccttaaa   1680
ggtatacttc catctgaact gtcgaactgt cataaactgt cagaacttga tgcgagtcac   1740
aatttgttga atggctctat tccatccact ttaggaagct tgacagaact gaccaaattg   1800
agtctcggtg agaacagttt ctcaggaggt attccaactt cattgttcca atccaataag   1860
ctcttaaatc tgcagctcgg tggaaattta ctagctggag atattccacc agtgggagct   1920
ttgcaggcac tgaggtcatt aaatttgagc agtaacaaac tgaatggtca actccctata   1980
gatctaggga aattaaagat gctagaggaa ttggatgtat ctcacaacaa tctatctggt   2040
acgttgagag ttttgtctac aatccaatca ttgacattca tcaacatttc tcacaatctg   2100
ttttctggcc ccgtaccacc ttcattgacc aagttcttga actcatctcc cacttcattt   2160
tccgggaact ctgacctttg tattaactgc cctgctgatg gcttagcttg cccggagagc   2220
agcattttgc gaccatgtaa tatgcaatcc aacactggga agggtggcct tagtactttg   2280
ggaatagcaa tgatagttct tggggcattg ttatttatca tctgtctatt cctttttctct  2340
gctttcctgt ttctacattg caaaaaatca gtacaagaaa tagcaatttc tgctcaagag   2400
ggtgatggtt ccttgctcaa taaagtattg gaagctacag agaatctaaa tgataagtat   2460
gttattggga agggagcaca tggaacaata tacaaggcca cattaagtcc agataaagtg   2520
tatgctgtga aaaagcttgt gtttactggg atcaagaatg gaagtgtaag catggttcgg   2580
gaaattgaaa caattgggaa agtcaggcac cggaatctta ttaaactgga agagttttgg   2640
ctgagaaagg agtatggact aattctatac acttatatgg aaaatggcag ccttcatgat   2700
atcctccatg agacaaatcc tcctaagccg ttagattgga gcacacgtca taatattgct   2760
gtagggactg cccatggact tgcgtatctc cattttgact gtgatcctgc cattgtgcat   2820
cgagatatta aaccgatgaa tatcctgtta gactctgatc tcgagcctca catttcagac   2880
tttggcattg ccaagcttct ggatcagtct gctacttcaa tcccgtccaa cacagttcaa   2940
gggacaatcg gctatatggc tccagaaaat gcattcacta ctgtgaagag cagagagtca   3000
gatgtataca gttatggggt cgttctgttg gaattgataa ctcgtaagaa ggccttggat   3060
ccttcgttca atggtgaaac cgatattgtt ggctgggtta ggtcggtttg gacacaaact   3120
ggagaaattc agaagatagt ggatccgagc cttttggatg aattgataga ttccagcgtg   3180
atggaacaag taactgaagc gctttcactg gctttgaggt gtgcagagaa ggaggtggac   3240
aaaagaccca caatgagaga tgtagtgaag caactaacac gctggagcat acgctcctat   3300
tcgtcgagtg ttagaaacaa gtctaagtag                                    3330
```

<210> SEQ ID NO 159

<211> LENGTH: 1109
<212> TYPE: PRT
<213> ORGANISM: Ipomoea nil

<400> SEQUENCE: 159

```
Met Lys Val Ala Val Asn Thr Phe Leu Leu Phe Leu Cys Ser Thr Ser
1               5                   10                  15

Ser Ile Tyr Ala Ala Phe Ala Leu Asn Ser Asp Gly Ala Ala Leu Leu
            20                  25                  30

Ser Leu Thr Arg His Trp Thr Ser Ile Pro Ser Asp Ile Thr Gln Ser
        35                  40                  45

Trp Asn Ala Ser Asp Ser Thr Pro Cys Ser Trp Leu Gly Val Glu Cys
    50                  55                  60

Asp Arg Arg Gln Phe Val Asp Thr Leu Asn Leu Ser Ser Tyr Gly Ile
65                  70                  75                  80

Ser Gly Glu Phe Gly Pro Glu Ile Ser His Leu Lys His Leu Lys Lys
                85                  90                  95

Val Val Leu Ser Gly Asn Gly Phe Phe Gly Ser Ile Pro Ser Gln Leu
            100                 105                 110

Gly Asn Cys Ser Leu Leu Glu His Ile Asp Leu Ser Ser Asn Ser Phe
        115                 120                 125

Thr Gly Asn Ile Pro Asp Thr Leu Gly Ala Leu Gln Asn Leu Arg Asn
    130                 135                 140

Leu Ser Leu Phe Phe Asn Ser Leu Ile Gly Pro Phe Pro Glu Ser Leu
145                 150                 155                 160

Leu Ser Ile Pro His Leu Glu Thr Val Tyr Phe Thr Gly Asn Gly Leu
                165                 170                 175

Asn Gly Ser Ile Pro Ser Asn Ile Gly Asn Met Ser Glu Leu Thr Thr
            180                 185                 190

Leu Trp Leu Asp Asp Asn Gln Phe Ser Gly Pro Val Pro Ser Ser Leu
        195                 200                 205

Gly Asn Ile Thr Thr Leu Gln Glu Leu Tyr Leu Asn Asp Asn Asn Leu
    210                 215                 220

Val Gly Thr Leu Pro Val Thr Leu Asn Asn Leu Glu Asn Leu Val Tyr
225                 230                 235                 240

Leu Asp Val Arg Asn Asn Ser Leu Val Gly Ala Ile Pro Leu Asp Phe
                245                 250                 255

Val Ser Cys Lys Gln Ile Asp Thr Ile Ser Leu Ser Asn Asn Gln Phe
            260                 265                 270

Thr Gly Gly Leu Pro Pro Gly Leu Gly Asn Cys Thr Ser Leu Arg Glu
        275                 280                 285

Phe Gly Ala Phe Ser Cys Ala Leu Ser Gly Pro Ile Pro Ser Cys Phe
    290                 295                 300

Gly Gln Leu Thr Lys Leu Asp Thr Leu Tyr Leu Ala Gly Asn His Phe
305                 310                 315                 320

Ser Gly Arg Ile Pro Pro Glu Leu Gly Lys Cys Lys Ser Met Ile Asp
                325                 330                 335

Leu Gln Leu Gln Gln Asn Gln Leu Glu Gly Glu Ile Pro Gly Glu Leu
            340                 345                 350

Gly Met Leu Ser Gln Leu Gln Tyr Leu His Leu Tyr Thr Asn Asn Leu
        355                 360                 365

Ser Gly Glu Val Pro Leu Ser Ile Trp Lys Ile Gln Ser Leu Gln Ser
    370                 375                 380

Leu Gln Leu Tyr Gln Asn Asn Leu Ser Gly Glu Leu Pro Val Asp Met
385                 390                 395                 400
```

-continued

```
Thr Glu Leu Lys Gln Leu Val Ser Leu Ala Leu Tyr Glu Asn His Phe
                405                 410                 415

Thr Gly Val Ile Pro Gln Asp Leu Gly Ala Asn Ser Ser Leu Glu Val
            420                 425                 430

Leu Asp Leu Thr Arg Asn Met Phe Thr Gly His Ile Pro Pro Asn Leu
        435                 440                 445

Cys Ser Gln Lys Lys Leu Lys Arg Leu Leu Leu Gly Tyr Asn Tyr Leu
    450                 455                 460

Glu Gly Ser Val Pro Ser Asp Leu Gly Gly Cys Ser Thr Leu Glu Arg
465                 470                 475                 480

Leu Ile Leu Glu Glu Asn Asn Leu Arg Gly Gly Leu Pro Asp Phe Val
                485                 490                 495

Glu Lys Gln Asn Leu Leu Phe Phe Asp Leu Ser Gly Asn Asn Phe Thr
            500                 505                 510

Gly Pro Ile Pro Pro Ser Leu Gly Asn Leu Lys Asn Val Thr Ala Ile
        515                 520                 525

Tyr Leu Ser Ser Asn Gln Leu Ser Gly Ser Ile Pro Pro Glu Leu Gly
    530                 535                 540

Ser Leu Val Lys Leu Glu His Leu Asn Leu Ser His Asn Ile Leu Lys
545                 550                 555                 560

Gly Ile Leu Pro Ser Glu Leu Ser Asn Cys His Lys Leu Ser Glu Leu
                565                 570                 575

Asp Ala Ser His Asn Leu Leu Asn Gly Ser Ile Pro Ser Thr Leu Gly
            580                 585                 590

Ser Leu Thr Glu Leu Thr Lys Leu Ser Leu Gly Glu Asn Ser Phe Ser
        595                 600                 605

Gly Gly Ile Pro Thr Ser Leu Phe Gln Ser Asn Lys Leu Leu Asn Leu
    610                 615                 620

Gln Leu Gly Gly Asn Leu Leu Ala Gly Asp Ile Pro Pro Val Gly Ala
625                 630                 635                 640

Leu Gln Ala Leu Arg Ser Leu Asn Leu Ser Ser Asn Lys Leu Asn Gly
                645                 650                 655

Gln Leu Pro Ile Asp Leu Gly Lys Leu Lys Met Leu Glu Glu Leu Asp
            660                 665                 670

Val Ser His Asn Asn Leu Ser Gly Thr Leu Arg Val Leu Ser Thr Ile
        675                 680                 685

Gln Ser Leu Thr Phe Ile Asn Ile Ser His Asn Leu Phe Ser Gly Pro
    690                 695                 700

Val Pro Pro Ser Leu Thr Lys Phe Leu Asn Ser Ser Pro Thr Ser Phe
705                 710                 715                 720

Ser Gly Asn Ser Asp Leu Cys Ile Asn Cys Pro Ala Asp Gly Leu Ala
                725                 730                 735

Cys Pro Glu Ser Ser Ile Leu Arg Pro Cys Asn Met Gln Ser Asn Thr
            740                 745                 750

Gly Lys Gly Gly Leu Ser Thr Leu Gly Ile Ala Met Ile Val Leu Gly
        755                 760                 765

Ala Leu Leu Phe Ile Ile Cys Leu Phe Leu Phe Ser Ala Phe Leu Phe
    770                 775                 780

Leu His Cys Lys Lys Ser Val Gln Glu Ile Ala Ile Ser Ala Gln Glu
785                 790                 795                 800

Gly Asp Gly Ser Leu Leu Asn Lys Val Leu Glu Ala Thr Glu Asn Leu
                805                 810                 815

Asn Asp Lys Tyr Val Ile Gly Lys Gly Ala His Gly Thr Ile Tyr Lys
```

```
        820                 825                 830

Ala Thr Leu Ser Pro Asp Lys Val Tyr Ala Val Lys Lys Leu Val Phe
    835                 840                 845

Thr Gly Ile Lys Asn Gly Ser Val Ser Met Val Arg Glu Ile Glu Thr
    850                 855                 860

Ile Gly Lys Val Arg His Arg Asn Leu Ile Lys Leu Glu Glu Phe Trp
865                 870                 875                 880

Leu Arg Lys Glu Tyr Gly Leu Ile Leu Tyr Thr Tyr Met Glu Asn Gly
                885                 890                 895

Ser Leu His Asp Ile Leu His Glu Thr Asn Pro Pro Lys Pro Leu Asp
            900                 905                 910

Trp Ser Thr Arg His Asn Ile Ala Val Gly Thr Ala His Gly Leu Ala
        915                 920                 925

Tyr Leu His Phe Asp Cys Asp Pro Ala Ile Val His Arg Asp Ile Lys
    930                 935                 940

Pro Met Asn Ile Leu Leu Asp Ser Asp Leu Glu Pro His Ile Ser Asp
945                 950                 955                 960

Phe Gly Ile Ala Lys Leu Leu Asp Gln Ser Ala Thr Ser Ile Pro Ser
                965                 970                 975

Asn Thr Val Gln Gly Thr Ile Gly Tyr Met Ala Pro Glu Asn Ala Phe
            980                 985                 990

Thr Thr Val Lys Ser Arg Glu Ser  Asp Val Tyr Ser Tyr  Gly Val Val
        995                 1000                1005

Leu Leu  Glu Leu Ile Thr Arg  Lys Lys Ala Leu Asp  Pro Ser Phe
    1010                1015                1020

Asn Gly  Glu Thr Asp Ile Val  Gly Trp Val Arg Ser  Val Trp Thr
    1025                1030                1035

Gln Thr  Gly Glu Ile Gln Lys  Ile Val Asp Pro Ser  Leu Leu Asp
    1040                1045                1050

Glu Leu  Ile Asp Ser Ser Val  Met Glu Gln Val Thr  Glu Ala Leu
    1055                1060                1065

Ser Leu  Ala Leu Arg Cys Ala  Glu Lys Glu Val Asp  Lys Arg Pro
    1070                1075                1080

Thr Met  Arg Asp Val Val Lys  Gln Leu Thr Arg Trp  Ser Ile Arg
    1085                1090                1095

Ser Tyr  Ser Ser Ser Val Arg  Asn Lys Ser Lys
    1100                1105

<210> SEQ ID NO 160
<211> LENGTH: 3246
<212> TYPE: DNA
<213> ORGANISM: Populus trichocarpa

<400> SEQUENCE: 160
atgtcactct tgaggaaatg ggattctgtg cctacttcca ttacttcaag ttggaattct      60
tcagactcga ctccttgttc ttggctaggt ataggatgtg atcatagaag tcattgtgtg     120
gtttctttga acctttctgg cttaggaatt tctggtcctt tgggacctga aactgggcag     180
ttaaagcagt taaagactgt tgatttgaac accaattatt tctctggtga tataccctca     240
cagttgggaa attgtagtct ccttgagtac ttggatttgt ctgcaaatag ctttactggt     300
ggaatacctg atagctttaa gtacttgcaa aatttacaaa cattgattat tttctcgaat     360
tcactgtctg gtgaaatacc tgaatcattg ttccaagatt tggctttaca agttttgtat     420
ttggacacca ataaattcaa tggttccatt cctaggagtg ttggtaactt gactgagctt     480
```

-continued

```
ttagaactgt ccttatttgg aaatcaatta tctgggacaa tccctgagtc tattggaaat    540
tgtagaaaat tgcaatctct ccctctgagt tataacaagt taagtggttc tttgcctgag    600
attctaacca atcttgaaag ccttgttgaa ttatttgtta gtcataatag tcttgagggt    660
agaattcctt taggtttcgg caaatgcaag aatttggaaa ccttagattt gtcattcaat    720
agctatagtg gggtcttcc accagattta ggcaattgta gtagcttagc aaccttggcc    780
attatccata gcaacttaag aggcgctatc ccatcttcct ttggccaact gaaaaagctt    840
tctgtgctcg acctttctga gaatcgactg tctgggacga ttcctcctga acttagtaat    900
tgcaagtcct tgatgacctt aaatttatac acaaatgagc ttgagggaaa gattccgagt    960
gagttgggga ggctaaacaa attggaggac ctcgaattgt tcaacaatca tttgagtggt   1020
gcaattccta ttagcatctg gaagattgcg agccttaagt acctccttgt gtataacaac   1080
agtctttctg gtgaattgcc tcttgagatc actcatctca agaacctaaa gaacttgtca   1140
ctatacaaca accagttctt tggtgtcata ccccaaagtt tgggaatcaa cagcagtttg   1200
ttgcagctgg acttcacaga taataagttc acaggtgaaa ttccccaaaa cctttgccat   1260
ggaaagcagt tgagagttct taatatgggc cggaaccaac ttcaaggcag cattccttct   1320
gatgtgggag gctgcttaac gctctggaga ttgatcctca aggagaacaa cctctcaggt   1380
gcccttccag aattttcaga aaatccaatc ctctatcaca tggacgtcag caaaaataat   1440
attacaggtc caattccacc cagcattggg aactgttctg gtctcacttc cattcatctt   1500
tccatgaaca agcttacagg gtttataccc tcagagctag gaaatcttgt aaaccttctg   1560
gtagtggatc tttcatccaa ccaactggaa ggttctttgc catcgcagct gtcaaagtgt   1620
cacaacttag gcaagtttga tgtagggttc aattcactga acggctcagt tccatcgagt   1680
ttaaggaact ggaccagctt gtccactttg attttaaaag agaatcattt tattgggga   1740
attccacctt tcctctcaga acttgaaaag cttacagaga tacaacttgg tggaaatttt   1800
ctgggaggtg agattccttc atggattggg tctttacaga gtctgcaata tgcattgaat   1860
ctcagcagta atggattgtt tggagagctt ccttcagagc tggggaactt gatcaagctt   1920
gaacagcttc agttatcaaa caataatctg acaggaactc tagcacctct tgataaaatc   1980
cattcgttgg tccaggtcga tatttcatac aatcacttca gtggtccaat accagaaaca   2040
ctaatgaact tgcttaactc atcgccgtca tcattctggg gcaatcccga tctatgtgtc   2100
agttgtcttc catcaggtgg cttaacatgc accaaaaaca gaagtatcaa gccatgtgac   2160
tctcagtcaa gcaagcgaga cagcttttct agagtggctg tcgcgctgat agctattgct   2220
tctgtggttg ctgttttcat gcttgttgga ctggtttgca tgtttatctt gtgcagaaga   2280
tgtaagcagg atcttgggat cgaccatgat gttgaaattg ctgctcaaga gggcccttct   2340
tccctactca acaaagtgat gcaagctact gagaatctaa atgacagaca tatagttggg   2400
aggggaaccc atggaaccgt ttataaggct tcattgggtg gagacaaaat atttgcagtt   2460
aagaagatag tatttacagg ccacaaagga ggaaacaaaa gtatggttac agaaattcaa   2520
accattggga aaatcaggca ccggaatctg ctcaaattgg aaaacttttg gttacggaag   2580
gattatggtc tgatcctgta tgcctacatg caaaatggga gcgttcatga tgtcttacat   2640
gggagcacac caccgcaaac cctggagtgg agcatacgcc ataaaatagc tttaggaact   2700
gcccatggtt tggaatatct ccactatgat tgcaatcctc ctattgtgca tcgagacatc   2760
aaaccagaaa acattctctt agactctgat atggagcctc atatctctga tttcggtata   2820
gctaagctac ttgatcagtc ttctgcttca gcacagtctt tcctggttgc aggcacaatt   2880
```

-continued

```
ggatatatag caccagaaaa cgccttgtcg acaataaaga gcaaggaatc ggatgtttat   2940
agctacgggg ttgttttgct tgagctgata actagaaaga aggcattgga tccattattt   3000
gtgggggaaa cagatattgt agagtgggtc agatctgttt ggagcagcac agaagacatc   3060
aacaagattg ctgattcaag cctaagggag gagtttttgg attcaaatat catgaatcaa   3120
gccattgatg tgcttttggt ggctttgaga tgcactgaaa aggcgcctag gagaagaccc   3180
acaatgagag atgttgtcaa gcgattagta aaaagagatg ccagcattag aggcaaacgc   3240
agctga                                                              3246

<210> SEQ ID NO 161
<211> LENGTH: 1081
<212> TYPE: PRT
<213> ORGANISM: Populus trichocarpa

<400> SEQUENCE: 161

Met Ser Leu Leu Arg Lys Trp Asp Ser Val Pro Thr Ser Ile Thr Ser
1               5                   10                  15

Ser Trp Asn Ser Ser Asp Ser Thr Pro Cys Ser Trp Leu Gly Ile Gly
            20                  25                  30

Cys Asp His Arg Ser His Cys Val Val Ser Leu Asn Leu Ser Gly Leu
        35                  40                  45

Gly Ile Ser Gly Pro Leu Gly Pro Glu Thr Gly Gln Leu Lys Gln Leu
    50                  55                  60

Lys Thr Val Asp Leu Asn Thr Asn Tyr Phe Ser Gly Asp Ile Pro Ser
65                  70                  75                  80

Gln Leu Gly Asn Cys Ser Leu Leu Glu Tyr Leu Asp Leu Ser Ala Asn
                85                  90                  95

Ser Phe Thr Gly Gly Ile Pro Asp Ser Phe Lys Tyr Leu Gln Asn Leu
            100                 105                 110

Gln Thr Leu Ile Ile Phe Ser Asn Ser Leu Ser Gly Glu Ile Pro Glu
        115                 120                 125

Ser Leu Phe Gln Asp Leu Ala Leu Gln Val Leu Tyr Leu Asp Thr Asn
    130                 135                 140

Lys Phe Asn Gly Ser Ile Pro Arg Ser Val Gly Asn Leu Thr Glu Leu
145                 150                 155                 160

Leu Glu Leu Ser Leu Phe Gly Asn Gln Leu Ser Gly Thr Ile Pro Glu
                165                 170                 175

Ser Ile Gly Asn Cys Arg Lys Leu Gln Ser Leu Pro Leu Ser Tyr Asn
            180                 185                 190

Lys Leu Ser Gly Ser Leu Pro Glu Ile Leu Thr Asn Leu Glu Ser Leu
        195                 200                 205

Val Glu Leu Phe Val Ser His Asn Ser Leu Glu Gly Arg Ile Pro Leu
    210                 215                 220

Gly Phe Gly Lys Cys Lys Asn Leu Glu Thr Leu Asp Leu Ser Phe Asn
225                 230                 235                 240

Ser Tyr Ser Gly Gly Leu Pro Pro Asp Leu Gly Asn Cys Ser Ser Leu
                245                 250                 255

Ala Thr Leu Ala Ile Ile His Ser Asn Leu Arg Gly Ala Ile Pro Ser
            260                 265                 270

Ser Phe Gly Gln Leu Lys Lys Leu Ser Val Leu Asp Leu Ser Glu Asn
        275                 280                 285

Arg Leu Ser Gly Thr Ile Pro Pro Glu Leu Ser Asn Cys Lys Ser Leu
    290                 295                 300

Met Thr Leu Asn Leu Tyr Thr Asn Glu Leu Glu Gly Lys Ile Pro Ser
```

```
305                 310                 315                 320

Glu Leu Gly Arg Leu Asn Lys Leu Glu Asp Leu Glu Leu Phe Asn Asn
                325                 330                 335

His Leu Ser Gly Ala Ile Pro Ile Ser Ile Trp Lys Ile Ala Ser Leu
            340                 345                 350

Lys Tyr Leu Leu Val Tyr Asn Asn Ser Leu Ser Gly Glu Leu Pro Leu
        355                 360                 365

Glu Ile Thr His Leu Lys Asn Leu Lys Asn Leu Ser Leu Tyr Asn Asn
    370                 375                 380

Gln Phe Phe Gly Val Ile Pro Gln Ser Leu Gly Ile Asn Ser Ser Leu
385                 390                 395                 400

Leu Gln Leu Asp Phe Thr Asp Asn Lys Phe Thr Gly Glu Ile Pro Pro
                405                 410                 415

Asn Leu Cys His Gly Lys Gln Leu Arg Val Leu Asn Met Gly Arg Asn
            420                 425                 430

Gln Leu Gln Gly Ser Ile Pro Ser Asp Val Gly Gly Cys Leu Thr Leu
        435                 440                 445

Trp Arg Leu Ile Leu Lys Glu Asn Asn Leu Ser Gly Ala Leu Pro Glu
    450                 455                 460

Phe Ser Glu Asn Pro Ile Leu Tyr His Met Asp Val Ser Lys Asn Asn
465                 470                 475                 480

Ile Thr Gly Pro Ile Pro Pro Ser Ile Gly Asn Cys Ser Gly Leu Thr
                485                 490                 495

Ser Ile His Leu Ser Met Asn Lys Leu Thr Gly Phe Ile Pro Ser Glu
            500                 505                 510

Leu Gly Asn Leu Val Asn Leu Leu Val Val Asp Leu Ser Ser Asn Gln
        515                 520                 525

Leu Glu Gly Ser Leu Pro Ser Gln Leu Ser Lys Cys His Asn Leu Gly
    530                 535                 540

Lys Phe Asp Val Gly Phe Asn Ser Leu Asn Gly Ser Val Pro Ser Ser
545                 550                 555                 560

Leu Arg Asn Trp Thr Ser Leu Ser Thr Leu Ile Leu Lys Glu Asn His
                565                 570                 575

Phe Ile Gly Gly Ile Pro Pro Phe Leu Ser Glu Leu Glu Lys Leu Thr
            580                 585                 590

Glu Ile Gln Leu Gly Gly Asn Phe Leu Gly Gly Glu Ile Pro Ser Trp
        595                 600                 605

Ile Gly Ser Leu Gln Ser Leu Gln Tyr Ala Leu Asn Leu Ser Ser Asn
    610                 615                 620

Gly Leu Phe Gly Glu Leu Pro Ser Glu Leu Gly Asn Leu Ile Lys Leu
625                 630                 635                 640

Glu Gln Leu Gln Leu Ser Asn Asn Asn Leu Thr Gly Thr Leu Ala Pro
                645                 650                 655

Leu Asp Lys Ile His Ser Leu Val Gln Val Asp Ile Ser Tyr Asn His
            660                 665                 670

Phe Ser Gly Pro Ile Pro Glu Thr Leu Met Asn Leu Leu Asn Ser Ser
        675                 680                 685

Pro Ser Ser Phe Trp Gly Asn Pro Asp Leu Cys Val Ser Cys Leu Pro
    690                 695                 700

Ser Gly Gly Leu Thr Cys Thr Lys Asn Arg Ser Ile Lys Pro Cys Asp
705                 710                 715                 720

Ser Gln Ser Ser Lys Arg Asp Ser Phe Ser Arg Val Ala Val Ala Leu
                725                 730                 735
```

```
Ile Ala Ile Ala Ser Val Val Ala Val Phe Met Leu Val Gly Leu Val
            740                 745                 750

Cys Met Phe Ile Leu Cys Arg Arg Cys Lys Gln Asp Leu Gly Ile Asp
        755                 760                 765

His Asp Val Glu Ile Ala Ala Gln Glu Gly Pro Ser Ser Leu Leu Asn
    770                 775                 780

Lys Val Met Gln Ala Thr Glu Asn Leu Asn Asp Arg His Ile Val Gly
785                 790                 795                 800

Arg Gly Thr His Gly Thr Val Tyr Lys Ala Ser Leu Gly Gly Asp Lys
                805                 810                 815

Ile Phe Ala Val Lys Lys Ile Val Phe Thr Gly His Lys Gly Gly Asn
            820                 825                 830

Lys Ser Met Val Thr Glu Ile Gln Thr Ile Gly Lys Ile Arg His Arg
        835                 840                 845

Asn Leu Leu Lys Leu Glu Asn Phe Trp Leu Arg Lys Asp Tyr Gly Leu
    850                 855                 860

Ile Leu Tyr Ala Tyr Met Gln Asn Gly Ser Val His Asp Val Leu His
865                 870                 875                 880

Gly Ser Thr Pro Pro Gln Thr Leu Glu Trp Ser Ile Arg His Lys Ile
                885                 890                 895

Ala Leu Gly Thr Ala His Gly Leu Glu Tyr Leu His Tyr Asp Cys Asn
            900                 905                 910

Pro Pro Ile Val His Arg Asp Ile Lys Pro Glu Asn Ile Leu Leu Asp
        915                 920                 925

Ser Asp Met Glu Pro His Ile Ser Asp Phe Gly Ile Ala Lys Leu Leu
    930                 935                 940

Asp Gln Ser Ser Ala Ser Ala Gln Ser Phe Leu Val Ala Gly Thr Ile
945                 950                 955                 960

Gly Tyr Ile Ala Pro Glu Asn Ala Leu Ser Thr Ile Lys Ser Lys Glu
                965                 970                 975

Ser Asp Val Tyr Ser Tyr Gly Val Val Leu Leu Glu Leu Ile Thr Arg
            980                 985                 990

Lys Lys Ala Leu Asp Pro Leu Phe  Val Gly Glu Thr Asp  Ile Val Glu
        995                 1000                1005

Trp Val  Arg Ser Val Trp Ser  Ser Thr Glu Asp Ile  Asn Lys Ile
    1010                1015                1020

Ala Asp  Ser Ser Leu Arg Glu  Glu Phe Leu Asp Ser  Asn Ile Met
    1025                1030                1035

Asn Gln  Ala Ile Asp Val Leu  Leu Val Ala Leu Arg  Cys Thr Glu
    1040                1045                1050

Lys Ala  Pro Arg Arg Arg Pro  Thr Met Arg Asp Val  Val Lys Arg
    1055                1060                1065

Leu Val  Lys Arg Asp Ala Ser  Ile Arg Gly Lys Arg  Ser
    1070                1075                1080

<210> SEQ ID NO 162
<211> LENGTH: 3102
<212> TYPE: DNA
<213> ORGANISM: Populus trichocarpa

<400> SEQUENCE: 162
atgagttctg ttttgaatca tgtcttgctg ttatgttggt actttgtgtc tgtctatacc      60
gtgtctggct tgaactatga tgggtcgact ctgttgtcac tcttgaggca gtggaattct     120
gtgcctcctt ccataacttc aagctggaat gcatcagact caactccatg ttcttggcta     180
```

-continued

```
ggtataggat gtgatagtag aacccatagt gtagtttctt tgaacctctc tggttatgca    240
acttctggtc aattgggacc agagattgga ctcttaaagc atttgaaaac catcgatttg    300
cacaccagta atttctctgg tgacataccc tcacagttag gcaattgtag tctacttgag    360
cacttggatt tgtccataaa tagctttacg cgaaaaatac ctgatggctt taagtacctt    420
caaaatttgc agtatttgag tctttccttt aattcactct ctggtgagat acctgagagt    480
ctaaccaagc ttgaaagcct tgccgagttg cttctcgatc ataatagtct tgagggtaga    540
attcctacag gtttcagcaa ttgcaagaat ttggacacct tagatttgtc cttcaatagc    600
tttagtgggg gtttcccttc agaccttggc aattttagca gcttagcaat cttggccatt    660
attaatagtc acttaagagg tgccatccca tcttcctttg gccacctaaa aaagctttct    720
taccttgacc tctcccagaa tcaattgtct gggaggattc ctcctgaact tggggattgc    780
gagtcgttga cgaccttaaa cttgtacaca aatcaactcg agggagagat tccgggtgaa    840
ttggggaggc taagcaaatt agagaacctg gaattgtttg acaatcgctt gagtggtgaa    900
attcctatca gcatttggaa gattgcaagt cttaagagca tctatgtgta caacaacagt    960
ctttctggtg aattaccgct tgagatgact gagctcaggc aactacagaa tatctcactg   1020
gcacaaaatc aattctacgg ggtcattccc caaactttgg gaatcaacag cagcttattg   1080
tggctcgatt tctttggcaa taagttcact ggtgaaattc cgccaaatct ttgctacggg   1140
cagcaattga gaattcttgt tatgggttcc aaccaacttc aaggcagcat tccttctgat   1200
gtgggaggct gcccaacact ctggagattg accctcgagg agaacaacct ctcaggtacc   1260
cttccacagt tcgcagaaaa tcctatcctc ctgtacatgg acatcagcaa aaataatatt   1320
acaggcccaa ttccgcccag cattgggaat tgtagtggtc tcactttcat tcgtctttcc   1380
atgaacaagc ttacagggtc cataccctca gagctaggta atcttataaa ccttctggta   1440
gtggatcttt catccaacca actggaaggt tctttgccat ctcagctgtc aaggtgttac   1500
aaattaggcc agtttgatgt ggggtttaat tcactgaatg gcacaattcc gtcaagtttg   1560
aggaactgga cgagcttatc cactttggtt ttaagtgaga atcattttac cgggggcatt   1620
ccacctttcc tgccagaact tggaatgctt acagagctac aacttggtgg gaatattcta   1680
ggaggtgtga ttccttcatc cattggatcg gtgcggagtc tgaagtatgc cttgaatctc   1740
agcagcaatg gattcgtcgg aaaacttcct tccgagctag ggaacttgaa aatgcttgaa   1800
agacttgata tatcaaacaa taatctgaca ggaactctag caattcttga ttatatcctt   1860
tcatgggaca aggtcaatgt ttcaaacaat catttcacag gtgcaatacc ggaaacactg   1920
atggacttgc ttaactattc tccgtcatca ttcttgggca atcctggcct atgtgtcatg   1980
tgttctccat caagccgcat agcatgcccc aagaacagaa atttcttgcc atgtgacagt   2040
caaacaagca atcaaaatgg actatctaaa gtggcaatcg taatgatagc ccttgctcct   2100
gttgctgctg tttctgtgct tcttggagtg gtttacttgt ttatcaggcg cagaagatat   2160
aatcaggatg ttgagatcac ttctctagat ggtccatctt cactactcaa caaggtgctg   2220
gaagttactg agaatctaaa tgacagacat atcattggga ggggagctca tggaacagtt   2280
tataaggctt cattgggagg agacaaaatc tttgcagtaa aaaaaattgt atttgcaggc   2340
cacaaagaaa ggaacaaaag catggttaga gaaattcaga ccattgggaa aatcaagcac   2400
cggaatctga tcaaattgga ggagttttgg tttcaaaagg actacggtct aatcctgtat   2460
acttacatgc aaaatgggag cctctatgat gtcttacatg gaaccagagc accaccaatc   2520
ctggattggg aaatgcggta taagatagct attggaattg cacatggatt ggaatatatc   2580
```

-continued

```
cattatgatt gtgatcctcc tatagtgcat agagacatca aaccagaaaa cattctttta   2640
gactctgata tggagcctca tatctctgat tttggcatag ctaagctaat ggatcagtct   2700
tctgcttcag cacagtccct ctctgttgcg ggaactattg gatatatagc tccagaaaac   2760
gcatttacga caataaagac gaaggaatct gatgtttata gttatggggt tgttttgctt   2820
gtgcttataa ctagaaagaa ggcactggat ccctcattta cggagggaac agctattgta   2880
gggtgggtta ggtctgtttg gaacatcacg gaagacatca acaggattgc tgattcaagt   2940
cttggagagg aatttttgag ttcttacagc atcaaggatc aagtcattaa cgtgcttttg   3000
atggctttga gatgtactga agaagagcct agcaaaagac cctcaatgag agatgttgtc   3060
aggcaattag taaaagcaaa cgatcgcaga aggaggaggt ga                      3102
```

```
<210> SEQ ID NO 163
<211> LENGTH: 1033
<212> TYPE: PRT
<213> ORGANISM: Populus trichocarpa

<400> SEQUENCE: 163

Met Ser Ser Val Leu Asn His Val Leu Leu Leu Cys Trp Tyr Phe Val
1               5                   10                  15

Ser Val Tyr Thr Val Ser Gly Leu Asn Tyr Asp Gly Ser Thr Leu Leu
            20                  25                  30

Ser Leu Leu Arg Gln Trp Asn Ser Val Pro Pro Ser Ile Thr Ser Ser
        35                  40                  45

Trp Asn Ala Ser Asp Ser Thr Pro Cys Ser Trp Leu Gly Ile Gly Cys
    50                  55                  60

Asp Ser Arg Thr His Ser Val Val Ser Leu Asn Leu Ser Gly Tyr Ala
65                  70                  75                  80

Thr Ser Gly Gln Leu Gly Pro Glu Ile Gly Leu Leu Lys His Leu Lys
                85                  90                  95

Thr Ile Asp Leu His Thr Ser Asn Phe Ser Gly Asp Ile Pro Ser Gln
            100                 105                 110

Leu Gly Asn Cys Ser Leu Leu Glu His Leu Asp Leu Ser Ile Asn Ser
        115                 120                 125

Phe Thr Arg Lys Ile Pro Asp Gly Phe Lys Tyr Leu Gln Asn Leu Gln
    130                 135                 140

Tyr Leu Ser Leu Ser Phe Asn Ser Leu Ser Gly Glu Ile Pro Glu Ser
145                 150                 155                 160

Leu Thr Lys Leu Glu Ser Leu Ala Glu Leu Leu Leu Asp His Asn Ser
                165                 170                 175

Leu Glu Gly Arg Ile Pro Thr Gly Phe Ser Asn Cys Lys Asn Leu Asp
            180                 185                 190

Thr Leu Asp Leu Ser Phe Asn Ser Phe Ser Gly Gly Phe Pro Ser Asp
        195                 200                 205

Leu Gly Asn Phe Ser Ser Leu Ala Ile Leu Ala Ile Ile Asn Ser His
    210                 215                 220

Leu Arg Gly Ala Ile Pro Ser Ser Phe Gly His Leu Lys Lys Leu Ser
225                 230                 235                 240

Tyr Leu Asp Leu Ser Gln Asn Gln Leu Ser Gly Arg Ile Pro Pro Glu
                245                 250                 255

Leu Gly Asp Cys Glu Ser Leu Thr Thr Leu Asn Leu Tyr Thr Asn Gln
            260                 265                 270

Leu Glu Gly Glu Ile Pro Gly Glu Leu Gly Arg Leu Ser Lys Leu Glu
        275                 280                 285
```

-continued

```
Asn Leu Glu Leu Phe Asp Asn Arg Leu Ser Gly Glu Ile Pro Ile Ser
    290                 295                 300

Ile Trp Lys Ile Ala Ser Leu Lys Ser Ile Tyr Val Tyr Asn Asn Ser
305                 310                 315                 320

Leu Ser Gly Glu Leu Pro Leu Glu Met Thr Glu Leu Arg Gln Leu Gln
                325                 330                 335

Asn Ile Ser Leu Ala Gln Asn Gln Phe Tyr Gly Val Ile Pro Gln Thr
            340                 345                 350

Leu Gly Ile Asn Ser Ser Leu Leu Trp Leu Asp Phe Phe Gly Asn Lys
        355                 360                 365

Phe Thr Gly Glu Ile Pro Pro Asn Leu Cys Tyr Gly Gln Gln Leu Arg
    370                 375                 380

Ile Leu Val Met Gly Ser Asn Gln Leu Gln Gly Ser Ile Pro Ser Asp
385                 390                 395                 400

Val Gly Gly Cys Pro Thr Leu Trp Arg Leu Thr Leu Glu Glu Asn Asn
                405                 410                 415

Leu Ser Gly Thr Leu Pro Gln Phe Ala Glu Asn Pro Ile Leu Leu Tyr
            420                 425                 430

Met Asp Ile Ser Lys Asn Asn Ile Thr Gly Pro Ile Pro Pro Ser Ile
        435                 440                 445

Gly Asn Cys Ser Gly Leu Thr Phe Ile Arg Leu Ser Met Asn Lys Leu
    450                 455                 460

Thr Gly Ser Ile Pro Ser Glu Leu Gly Asn Leu Ile Asn Leu Leu Val
465                 470                 475                 480

Val Asp Leu Ser Ser Asn Gln Leu Glu Gly Ser Leu Pro Ser Gln Leu
                485                 490                 495

Ser Arg Cys Tyr Lys Leu Gly Gln Phe Asp Val Gly Phe Asn Ser Leu
            500                 505                 510

Asn Gly Thr Ile Pro Ser Ser Leu Arg Asn Trp Thr Ser Leu Ser Thr
        515                 520                 525

Leu Val Leu Ser Glu Asn His Phe Thr Gly Gly Ile Pro Pro Phe Leu
    530                 535                 540

Pro Glu Leu Gly Met Leu Thr Glu Leu Gln Leu Gly Gly Asn Ile Leu
545                 550                 555                 560

Gly Gly Val Ile Pro Ser Ser Ile Gly Ser Val Arg Ser Leu Lys Tyr
                565                 570                 575

Ala Leu Asn Leu Ser Ser Asn Gly Phe Val Gly Lys Leu Pro Ser Glu
            580                 585                 590

Leu Gly Asn Leu Lys Met Leu Glu Arg Leu Asp Ile Ser Asn Asn Asn
        595                 600                 605

Leu Thr Gly Thr Leu Ala Ile Leu Asp Tyr Ile Leu Ser Trp Asp Lys
    610                 615                 620

Val Asn Val Ser Asn Asn His Phe Thr Gly Ala Ile Pro Glu Thr Leu
625                 630                 635                 640

Met Asp Leu Leu Asn Tyr Ser Pro Ser Ser Phe Leu Gly Asn Pro Gly
                645                 650                 655

Leu Cys Val Met Cys Ser Pro Ser Ser Arg Ile Ala Cys Pro Lys Asn
            660                 665                 670

Arg Asn Phe Leu Pro Cys Asp Ser Gln Thr Ser Asn Gln Asn Gly Leu
        675                 680                 685

Ser Lys Val Ala Ile Val Met Ile Ala Leu Ala Pro Val Ala Ala Val
    690                 695                 700

Ser Val Leu Leu Gly Val Val Tyr Leu Phe Ile Arg Arg Arg Arg Tyr
705                 710                 715                 720
```

```
Asn Gln Asp Val Glu Ile Thr Ser Leu Asp Gly Pro Ser Ser Leu Leu
                725                 730                 735

Asn Lys Val Leu Glu Val Thr Glu Asn Leu Asn Asp Arg His Ile Ile
            740                 745                 750

Gly Arg Gly Ala His Gly Thr Val Tyr Lys Ala Ser Leu Gly Gly Asp
        755                 760                 765

Lys Ile Phe Ala Val Lys Lys Ile Val Phe Ala Gly His Lys Glu Arg
    770                 775                 780

Asn Lys Ser Met Val Arg Glu Ile Gln Thr Ile Gly Lys Ile Lys His
785                 790                 795                 800

Arg Asn Leu Ile Lys Leu Glu Glu Phe Trp Phe Gln Lys Asp Tyr Gly
                805                 810                 815

Leu Ile Leu Tyr Thr Tyr Met Gln Asn Gly Ser Leu Tyr Asp Val Leu
            820                 825                 830

His Gly Thr Arg Ala Pro Pro Ile Leu Asp Trp Glu Met Arg Tyr Lys
        835                 840                 845

Ile Ala Ile Gly Ile Ala His Gly Leu Glu Tyr Ile His Tyr Asp Cys
    850                 855                 860

Asp Pro Pro Ile Val His Arg Asp Ile Lys Pro Glu Asn Ile Leu Leu
865                 870                 875                 880

Asp Ser Asp Met Glu Pro His Ile Ser Asp Phe Gly Ile Ala Lys Leu
                885                 890                 895

Met Asp Gln Ser Ser Ala Ser Ala Gln Ser Leu Ser Val Ala Gly Thr
            900                 905                 910

Ile Gly Tyr Ile Ala Pro Glu Asn Ala Phe Thr Thr Ile Lys Thr Lys
        915                 920                 925

Glu Ser Asp Val Tyr Ser Tyr Gly Val Val Leu Leu Val Leu Ile Thr
    930                 935                 940

Arg Lys Lys Ala Leu Asp Pro Ser Phe Thr Glu Gly Thr Ala Ile Val
945                 950                 955                 960

Gly Trp Val Arg Ser Val Trp Asn Ile Thr Glu Asp Ile Asn Arg Ile
                965                 970                 975

Ala Asp Ser Ser Leu Gly Glu Glu Phe Leu Ser Ser Tyr Ser Ile Lys
            980                 985                 990

Asp Gln Val Ile Asn Val Leu Leu  Met Ala Leu Arg Cys  Thr Glu Glu
        995                 1000                 1005

Glu Pro  Ser Lys Arg Pro Ser  Met Arg Asp Val Val  Arg Gln Leu
    1010                 1015                 1020

Val Lys  Ala Asn Asp Arg Arg  Arg Arg Arg
    1025                 1030
```

<210> SEQ ID NO 164
<211> LENGTH: 3222
<212> TYPE: DNA
<213> ORGANISM: Vitis vinifera

<400> SEQUENCE: 164

```
atggctctca agagcaaatg ggcagtgccc actttcatgg aagagagctg gaacgcctct      60
cattccaccc catgttcatg ggttggagtt tcatgtgatg aaacccacat tgtggtttct     120
cttaacgtct ccggtttggg aatatccggc catttgggtc cggagattgc agatttgagg     180
cacttgacca gtgtcgattt cagctacaac agtttctcag gtccaattcc gccggagttt     240
ggaaattgca gtcttctgat ggatttagac ctgtctgtga atggttttgt tggtgaaata     300
ccccaaaact tgaacagttt ggggaagtta gaatatctga gcttttgtaa taattcattg     360
```

```
actggtgcag tccctgaatc cttgtttcgg attccgaatt tggaaatgct ttacctgaat    420
tccaacaaac tcagtggttc aatccctttg aatgttggaa atgctactca gattatagcc    480
ctatggttgt atgataatgc attatcaggc gacattcctt cttccattgg aaattgtagt    540
gaattggagg agctttactt gaatcacaac caatttttag gggttttgcc tgaaagtata    600
aacaatcttg agaacctagt ttatttagat gtgagcaata acaatttaga gggtaaaatt    660
cctttgggtt caggctattg caagaaattg gatactttgg ttctgtcaat gaatggtttt    720
ggtggcgaaa ttccaccagg tttgggcaac tgcactagct tatcgcagtt tgctgctttg    780
aacaataggt tatcaggtag tattccatct tcctttggac tgctacataa gctcttgctt    840
ttgtacctct ctgaaaatca tttgtcggga aagataccac ctgagattgg gcaatgcaag    900
tccttgagaa gcttgcattt atacatgaac caacttgagg gggaaatccc aagtgaatta    960
gggatgttga atgagttaca agacctccgt ttatttaata accggttaac tggtgagatt   1020
cctattagta tttggaagat tccaagcctc gagaatgttc ttgtgtacaa taacactctt   1080
tctggagaac tgcctgtaga gataactgag ctcaagcacc tgaagaacat ttccttgttc   1140
aacaatcggt tctctggagt catacctcaa cgtttgggga ttaacagtag tttggtgcag   1200
ttggatgtta caaataataa gttcactggt gaaatcccaa aaagtatttg ctttggaaaa   1260
caactgagcg tgctgaatat gggtctgaat ctacttcaag gtagtattcc ttctgctgta   1320
ggaagctgtt caactttgag aagattgatt cttaggaaga ataatctgac tggggttctt   1380
cccaatttg caaaaaatcc taacctttg ttgttggacc tcagcgagaa tggcatcaat     1440
ggaacaattc cattaagctt ggggaactgt accaatgtca cctccatcaa cttgtcaatg   1500
aacaggcttt caggactaat accccaagag ctaggaaacc ttaatgttct tcaggctttg   1560
aatctttctc ataatgattt aggaggtcca ttgccatctc aactgtcaaa ttgtaagaat   1620
ttgtttaaat ttgatgtggg gtttaattca ttgaatggtt cattcccatc aagtttaagg   1680
agcttagaaa atttgtcagt tttgattttg agggagaatc gttttactgg gggtattcca   1740
tctttcttgt ctgaactaca atatctttca gagatacagc ttggtggaaa ttttctggga   1800
ggaaatatcc cttcatcgat tggaatgttg cagaatctaa tctattcatt gaatatcagt   1860
cataacagat tgacaggttc acttccctta gagcttggga agttgatcat gctagagcga   1920
ttagatatat ctcacaacaa tctttcaggg actctatcag ctcttgatgg actccattcg   1980
ttggtcgtgg ttgatgtttc atacaatctt ttcaatggtc ctctcccaga aactctactt   2040
ttgtttttga attcatctcc ttcatcactt cagggcaatc ctgacctttg tgtcaaatgt   2100
cctcaaactg gtggcttaac ttgcatccag aataggaatt tcagaccatg tgagcattac   2160
tcaagcaacc ggagagccct tggaaaaatt gaaattgcat ggatagcttt cgcatcattg   2220
ctctcatttc ttgtgcttgt tggacttgtt tgcatgtttc tctggtacaa aagaacaaaa   2280
caggaagaca agatcactgc tcaagagggt tcatcttctc tactcaacaa agtaatagaa   2340
gctactgaga atctcaaaga atgctatatc gttggaaaag gagcccatgg aactgtttat   2400
aaggcttcgc tgggtccaaa taatcagtat gccttaaaga aacttgtgtt tgcagggctt   2460
aaaggaggaa gtatggctat ggttacagaa attcaaacag ttggaaagat cagacaccgg   2520
aatttggtca agttggaaga tttctggata agaaaggaat atggttttat cttgtacagg   2580
tacatggaaa atggaagcct tcatgatgtt ttacatgaga ggaatccccc accaattttg   2640
aagtgggatg ttcgctacaa gatagccatt ggaacagccc atggattaac atatctgcac   2700
tatgactgtg atcctgcaat tgtgcatcga gatgtcaaac cagataacat acttctagac   2760
```

```
tcagatatgg agcctcatat ctctgatttt ggtattgcta agctgctgga tcagtcctct   2820
tctttgtcac catccatctc agttgtgggt acaattggat atattgcacc agagaatgca   2880
tttacaacaa caaagagcaa agagtctgat gtgtatagct ttggggttgt cctgcttgaa   2940
ctgattacca gaaaaagggc actggatcct tcatttatgg aggaaactga cattgtgggg   3000
tgggttcagt ctatttggag gaacttggaa gaagttgata agattgttga cccaagcctt   3060
ctggaggaat ttatagatcc aaatatcatg gatcaagtgg tttgtgtgct tttagtagct   3120
ttaagatgta cgcaaaagga ggcaagcaaa aggcctacaa tgagagatgt tgttaatcag   3180
ttaacagatg caaacgctcc tgccagaggc aaaaacagct ag                      3222
```

```
<210> SEQ ID NO 165
<211> LENGTH: 1073
<212> TYPE: PRT
<213> ORGANISM: Vitis vinifera

<400> SEQUENCE: 165

Met Ala Leu Lys Ser Lys Trp Ala Val Pro Thr Phe Met Glu Glu Ser
1               5                   10                  15

Trp Asn Ala Ser His Ser Thr Pro Cys Ser Trp Val Gly Val Ser Cys
            20                  25                  30

Asp Glu Thr His Ile Val Val Ser Leu Asn Val Ser Gly Leu Gly Ile
        35                  40                  45

Ser Gly His Leu Gly Pro Glu Ile Ala Asp Leu Arg His Leu Thr Ser
    50                  55                  60

Val Asp Phe Ser Tyr Asn Ser Phe Ser Gly Pro Ile Pro Pro Glu Phe
65                  70                  75                  80

Gly Asn Cys Ser Leu Leu Met Asp Leu Asp Leu Ser Val Asn Gly Phe
                85                  90                  95

Val Gly Glu Ile Pro Gln Asn Leu Asn Ser Leu Gly Lys Leu Glu Tyr
            100                 105                 110

Leu Ser Phe Cys Asn Asn Ser Leu Thr Gly Ala Val Pro Glu Ser Leu
        115                 120                 125

Phe Arg Ile Pro Asn Leu Glu Met Leu Tyr Leu Asn Ser Asn Lys Leu
    130                 135                 140

Ser Gly Ser Ile Pro Leu Asn Val Gly Asn Ala Thr Gln Ile Ile Ala
145                 150                 155                 160

Leu Trp Leu Tyr Asp Asn Ala Leu Ser Gly Asp Ile Pro Ser Ser Ile
                165                 170                 175

Gly Asn Cys Ser Glu Leu Glu Glu Leu Tyr Leu Asn His Asn Gln Phe
            180                 185                 190

Leu Gly Val Leu Pro Glu Ser Ile Asn Asn Leu Glu Asn Leu Val Tyr
        195                 200                 205

Leu Asp Val Ser Asn Asn Asn Leu Glu Gly Lys Ile Pro Leu Gly Ser
    210                 215                 220

Gly Tyr Cys Lys Lys Leu Asp Thr Leu Val Leu Ser Met Asn Gly Phe
225                 230                 235                 240

Gly Gly Glu Ile Pro Pro Gly Leu Gly Asn Cys Thr Ser Leu Ser Gln
                245                 250                 255

Phe Ala Ala Leu Asn Asn Arg Leu Ser Gly Ser Ile Pro Ser Ser Phe
            260                 265                 270

Gly Leu Leu His Lys Leu Leu Leu Leu Tyr Leu Ser Glu Asn His Leu
        275                 280                 285

Ser Gly Lys Ile Pro Pro Glu Ile Gly Gln Cys Lys Ser Leu Arg Ser
```

```
    290                 295                 300

Leu His Leu Tyr Met Asn Gln Leu Glu Gly Glu Ile Pro Ser Glu Leu
305                 310                 315                 320

Gly Met Leu Asn Glu Leu Gln Asp Leu Arg Leu Phe Asn Asn Arg Leu
                325                 330                 335

Thr Gly Glu Ile Pro Ile Ser Ile Trp Lys Ile Pro Ser Leu Glu Asn
            340                 345                 350

Val Leu Val Tyr Asn Asn Thr Leu Ser Gly Glu Leu Pro Val Glu Ile
        355                 360                 365

Thr Glu Leu Lys His Leu Lys Asn Ile Ser Leu Phe Asn Asn Arg Phe
    370                 375                 380

Ser Gly Val Ile Pro Gln Arg Leu Gly Ile Asn Ser Ser Leu Val Gln
385                 390                 395                 400

Leu Asp Val Thr Asn Asn Lys Phe Thr Gly Glu Ile Pro Lys Ser Ile
                405                 410                 415

Cys Phe Gly Lys Gln Leu Ser Val Leu Asn Met Gly Leu Asn Leu Leu
            420                 425                 430

Gln Gly Ser Ile Pro Ser Ala Val Gly Ser Cys Ser Thr Leu Arg Arg
        435                 440                 445

Leu Ile Leu Arg Lys Asn Asn Leu Thr Gly Val Leu Pro Asn Phe Ala
    450                 455                 460

Lys Asn Pro Asn Leu Leu Leu Leu Asp Leu Ser Glu Asn Gly Ile Asn
465                 470                 475                 480

Gly Thr Ile Pro Leu Ser Leu Gly Asn Cys Thr Asn Val Thr Ser Ile
                485                 490                 495

Asn Leu Ser Met Asn Arg Leu Ser Gly Leu Ile Pro Gln Glu Leu Gly
            500                 505                 510

Asn Leu Asn Val Leu Gln Ala Leu Asn Leu Ser His Asn Asp Leu Gly
        515                 520                 525

Gly Pro Leu Pro Ser Gln Leu Ser Asn Cys Lys Asn Leu Phe Lys Phe
    530                 535                 540

Asp Val Gly Phe Asn Ser Leu Asn Gly Ser Phe Pro Ser Ser Leu Arg
545                 550                 555                 560

Ser Leu Glu Asn Leu Ser Val Leu Ile Leu Arg Glu Asn Arg Phe Thr
                565                 570                 575

Gly Gly Ile Pro Ser Phe Leu Ser Glu Leu Gln Tyr Leu Ser Glu Ile
            580                 585                 590

Gln Leu Gly Gly Asn Phe Leu Gly Gly Asn Ile Pro Ser Ser Ile Gly
        595                 600                 605

Met Leu Gln Asn Leu Ile Tyr Ser Leu Asn Ile Ser His Asn Arg Leu
    610                 615                 620

Thr Gly Ser Leu Pro Leu Glu Leu Gly Lys Leu Ile Met Leu Glu Arg
625                 630                 635                 640

Leu Asp Ile Ser His Asn Asn Leu Ser Gly Thr Leu Ser Ala Leu Asp
                645                 650                 655

Gly Leu His Ser Leu Val Val Val Asp Val Ser Tyr Asn Leu Phe Asn
            660                 665                 670

Gly Pro Leu Pro Glu Thr Leu Leu Leu Phe Leu Asn Ser Ser Pro Ser
        675                 680                 685

Ser Leu Gln Gly Asn Pro Asp Leu Cys Val Lys Cys Pro Gln Thr Gly
    690                 695                 700

Gly Leu Thr Cys Ile Gln Asn Arg Asn Phe Arg Pro Cys Glu His Tyr
705                 710                 715                 720
```

```
Ser Ser Asn Arg Arg Ala Leu Gly Lys Ile Glu Ile Ala Trp Ile Ala
                725                 730                 735

Phe Ala Ser Leu Leu Ser Phe Leu Val Leu Val Gly Leu Val Cys Met
            740                 745                 750

Phe Leu Trp Tyr Lys Arg Thr Lys Gln Glu Asp Lys Ile Thr Ala Gln
        755                 760                 765

Glu Gly Ser Ser Ser Leu Leu Asn Lys Val Ile Glu Ala Thr Glu Asn
    770                 775                 780

Leu Lys Glu Cys Tyr Ile Val Gly Lys Gly Ala His Gly Thr Val Tyr
785                 790                 795                 800

Lys Ala Ser Leu Gly Pro Asn Asn Gln Tyr Ala Leu Lys Lys Leu Val
                805                 810                 815

Phe Ala Gly Leu Lys Gly Gly Ser Met Ala Met Val Thr Glu Ile Gln
            820                 825                 830

Thr Val Gly Lys Ile Arg His Arg Asn Leu Val Lys Leu Glu Asp Phe
        835                 840                 845

Trp Ile Arg Lys Glu Tyr Gly Phe Ile Leu Tyr Arg Tyr Met Glu Asn
    850                 855                 860

Gly Ser Leu His Asp Val Leu His Glu Arg Asn Pro Pro Pro Ile Leu
865                 870                 875                 880

Lys Trp Asp Val Arg Tyr Lys Ile Ala Ile Gly Thr Ala His Gly Leu
                885                 890                 895

Thr Tyr Leu His Tyr Asp Cys Asp Pro Ala Ile Val His Arg Asp Val
            900                 905                 910

Lys Pro Asp Asn Ile Leu Leu Asp Ser Asp Met Glu Pro His Ile Ser
        915                 920                 925

Asp Phe Gly Ile Ala Lys Leu Leu Asp Gln Ser Ser Ser Leu Ser Pro
    930                 935                 940

Ser Ile Ser Val Val Gly Thr Ile Gly Tyr Ile Ala Pro Glu Asn Ala
945                 950                 955                 960

Phe Thr Thr Thr Lys Ser Lys Glu Ser Asp Val Tyr Ser Phe Gly Val
                965                 970                 975

Val Leu Leu Glu Leu Ile Thr Arg Lys Arg Ala Leu Asp Pro Ser Phe
            980                 985                 990

Met Glu Glu Thr Asp Ile Val Gly  Trp Val Gln Ser Ile  Trp Arg Asn
        995                 1000                1005

Leu Glu  Glu Val Asp Lys Ile  Val Asp Pro Ser Leu  Leu Glu Glu
    1010                1015                1020

Phe Ile  Asp Pro Asn Ile Met  Asp Gln Val Val Cys  Val Leu Leu
    1025                1030                1035

Val Ala  Leu Arg Cys Thr Gln  Lys Glu Ala Ser Lys  Arg Pro Thr
    1040                1045                1050

Met Arg  Asp Val Val Asn Gln  Leu Thr Asp Ala Asn  Ala Pro Ala
    1055                1060                1065

Arg Gly  Lys Asn Ser
    1070
```

<210> SEQ ID NO 166
<211> LENGTH: 3372
<212> TYPE: DNA
<213> ORGANISM: Zea mays

<400> SEQUENCE: 166

```
atgaagctgg ttttctggca ttggattttt ctattcttcg tgttgctttc aacatcacag      60
ggtatgagtt cagatggcct agctcttctt gctctgtcca aaaccctaat actaccaagt     120
```

-continued

```
ttcataagga ccaactggag tgcttctgat gcaactcctt gtacatggaa cggtgttggc    180
tgcaatggaa ggaacagagt gatttctctc gacctatcgt catcagaggt ctcaggtttt    240
ataggacctg aaatagggcg tctgaaatac ctgcaggttc tcattttatc tgctaacaac    300
atatctggtt tgatccctct agaattgggc aactgcagta tgcttgaaca attggatctg    360
tcccaaaact tgctttctgg caatataccg gcatcaatgg gcagcctcaa gaaattgtca    420
tcactgtcgc tgtactacaa ctctttccat ggaacaatac cagaggagtt gttcaagaac    480
cagtttctgg agcaagtgta cctacatgga aatcagctca gtggttggat acccttctcg    540
gttggtgaaa tgacaagcct taagtcattg tggttgcacg aaaatatgtt gtccggagtt    600
ttgcccagtt caattggcaa ctgcaccaag ttggaggagc tgtatctact ccataatcaa    660
ctgagtggca gtattccaga aaccttgagt aagatcgaag gcctcaaggt ttttgatgcc    720
actgccaata gtttcacggg cgagatctct ttcagttttg agaactgcaa gctggaaata    780
ttcatcttgt cattcaataa tataaagggt gaaattccgt catggctagg gaattgcagg    840
agcttgcaac aacttggatt tgtcaataat agtctgtctg gcaaaattcc aaattttata    900
ggcttattca gcaacctcac gtatctttta ctttcacaga actccctgac tgggctgatc    960
ccacctgaga ttggtaactg tcggttgctg cagtggctag agctagatgc aaatcagctg   1020
gagggcactg ttcctgaaga atttgcaaat ttaaggtatt tgtcaaagct ctttcttttc   1080
gagaatcacc tcatgggaga cttccctgag agtatttgga gtatccaaac cctcgagagt   1140
gtccttcttt atagcaacaa attcacaggg aggctacctt cagtgttagc tgagctgaag   1200
tccctaaaga acatcacact gtttgataat ttcttcactg gagtcatacc acaggagctg   1260
ggtgttaata gccccttggt ccagatagat ttcacaaata acagttttgt tggtggtatc   1320
ccaccaaaca tttgttcagg aaaagcattg agaattttgg acttggggtt taatcatctc   1380
aacggtagca tcccatccag tgttctggac tgcccaagtc tggagcgagt cattgtcgaa   1440
aacaataacc ttgttgggtc tattccgcaa tttataaact gtgcaaatct aagttatatg   1500
gatctgagcc acaattcctt gagtggtaac ataccatcaa gtttcagcag gtgtgtaaaa   1560
attgctgaga taaactggtc agagaacaat atttttgggg caataccacc agaaattgga   1620
aagttggtga atctgaaaag gcttgacctc tcacacaatc tattgcatgg ttcgatccct   1680
gtgcaaattt ctagttgctc caagttgtat tcacttgatt tgggttttaa ctctttgaat   1740
ggttcggccc tcagcacagt aagcagcctg aagtttctga cacagctacg attgcaagag   1800
aatagattca gcggaggttt gcctgatcct ttctcacaat tggaaatgct tattgagctg   1860
caacttggtg gaaatattct tgggggcagt atcccttcat cattaggaca gctggtgaaa   1920
ctgggtacaa ccttgaacct tagtagcaat ggtctagtgg gtgacattcc atcacaattc   1980
ggtaatttgg tggagttgca aaacttagat ttgtcattta ataatctcac aggaggcctt   2040
gctacattgc gaagtctacg ctttttgcag gccttgaatg tttcttacaa ccaatttagt   2100
ggaccagttc cagataatct tgtgaagttt ctgagttcca caacaaattc ttttgatgga   2160
aacccaggcc tctgtatctc ttgcagcacc agtgattctt cttgcatggg agctaatgtt   2220
ctgaaacctt gtggcgggtc aaagaaaaga gcagtgcatg gccgattcaa aattgttctc   2280
atagttcttg gctcattatt tgtgggagca gttctggtac tcatactctg gtgcatcctt   2340
ctgaaatctc gagatcagaa gaagaatagt gaggaagcag tcagtcatat gtttgaaggt   2400
tcctcatcta aattaaatga ggttatagag gcaactgaat gttttgatga caagtatatc   2460
attggtaaag gtggtcacgg aaccgtttac aaggcaacac tgaggtcagg ggatgtttat   2520
```

```
gctataaaga aacttgtgat ttctgcacac aaaggttcat acaaaagcat ggttggagaa   2580
ctgaagacac taggtaaaat caagcacagg aacttgatta agctgaaaga atcttggttg   2640
agaaatgaca atggattcat actgtatgat tttatggaaa aaggtagcct tcatgatgtt   2700
ctacatgtag ttcagccagc accagcctta gactggtgtg tgcggtatga catagccctc   2760
ggcactgccc atgggttagc atatctacat gatgactgcc gccctgcgat cattcatcgc   2820
gacatcaagc caagtaatat actgctggac aaggacatgg tgccacatat ttcagatttt   2880
ggcattgcaa agctcttgga gcagccttct actgctcctc agaccactgg tgttgttggc   2940
accattggat atatggcccc agagttagcg ttctccacca agagcagcat ggagtccgac   3000
gtgtacagct acggcgtggt gctgctggag ctgctcacga ggagggcggc ggtggatccc   3060
tcgtttcccg acggcacgga catagtcagc tgggcgtcgt ccgccctgaa cggcactgac   3120
aaaatcgagg ccgtctgcga cccggccctc atggaggaag tcttcggcac ggtggagatg   3180
gaggaggtga gtaaggtcct gtcagtggcg ctgcggtgcg cggccaggga ggcgagccaa   3240
aggccctcca tgaccgcggt cgtgaaggag ctgacggatg cacggcctgc cactggcggc   3300
ggccggtcgt tgtccaagtc gaagcagggg aaaccaggat cgcaatccaa cagcagcgcc   3360
taccggcagt ag                                                       3372
```

```
<210> SEQ ID NO 167
<211> LENGTH: 1123
<212> TYPE: PRT
<213> ORGANISM: Zea mays

<400> SEQUENCE: 167

Met Lys Leu Val Phe Trp His Trp Ile Phe Leu Phe Phe Val Leu Leu
1               5                   10                  15

Ser Thr Ser Gln Gly Met Ser Ser Asp Gly Leu Ala Leu Leu Ala Leu
            20                  25                  30

Ser Lys Thr Leu Ile Leu Pro Ser Phe Ile Arg Thr Asn Trp Ser Ala
        35                  40                  45

Ser Asp Ala Thr Pro Cys Thr Trp Asn Gly Val Gly Cys Asn Gly Arg
    50                  55                  60

Asn Arg Val Ile Ser Leu Asp Leu Ser Ser Ser Glu Val Ser Gly Phe
65                  70                  75                  80

Ile Gly Pro Glu Ile Gly Arg Leu Lys Tyr Leu Gln Val Leu Ile Leu
                85                  90                  95

Ser Ala Asn Asn Ile Ser Gly Leu Ile Pro Leu Glu Leu Gly Asn Cys
            100                 105                 110

Ser Met Leu Glu Gln Leu Asp Leu Ser Gln Asn Leu Leu Ser Gly Asn
        115                 120                 125

Ile Pro Ala Ser Met Gly Ser Leu Lys Lys Leu Ser Ser Leu Ser Leu
    130                 135                 140

Tyr Tyr Asn Ser Phe His Gly Thr Ile Pro Glu Glu Leu Phe Lys Asn
145                 150                 155                 160

Gln Phe Leu Glu Gln Val Tyr Leu His Gly Asn Gln Leu Ser Gly Trp
                165                 170                 175

Ile Pro Phe Ser Val Gly Glu Met Thr Ser Leu Lys Ser Leu Trp Leu
            180                 185                 190

His Glu Asn Met Leu Ser Gly Val Leu Pro Ser Ser Ile Gly Asn Cys
        195                 200                 205

Thr Lys Leu Glu Glu Leu Tyr Leu Leu His Asn Gln Leu Ser Gly Ser
    210                 215                 220
```

```
Ile Pro Glu Thr Leu Ser Lys Ile Glu Gly Leu Lys Val Phe Asp Ala
225                 230                 235                 240

Thr Ala Asn Ser Phe Thr Gly Glu Ile Ser Phe Ser Phe Glu Asn Cys
                245                 250                 255

Lys Leu Glu Ile Phe Ile Leu Ser Phe Asn Asn Ile Lys Gly Glu Ile
            260                 265                 270

Pro Ser Trp Leu Gly Asn Cys Arg Ser Leu Gln Gln Leu Gly Phe Val
        275                 280                 285

Asn Asn Ser Leu Ser Gly Lys Ile Pro Asn Phe Ile Gly Leu Phe Ser
    290                 295                 300

Asn Leu Thr Tyr Leu Leu Leu Ser Gln Asn Ser Leu Thr Gly Leu Ile
305                 310                 315                 320

Pro Pro Glu Ile Gly Asn Cys Arg Leu Leu Gln Trp Leu Glu Leu Asp
                325                 330                 335

Ala Asn Gln Leu Glu Gly Thr Val Pro Glu Glu Phe Ala Asn Leu Arg
            340                 345                 350

Tyr Leu Ser Lys Leu Phe Leu Phe Glu Asn His Leu Met Gly Asp Phe
        355                 360                 365

Pro Glu Ser Ile Trp Ser Ile Gln Thr Leu Glu Ser Val Leu Leu Tyr
    370                 375                 380

Ser Asn Lys Phe Thr Gly Arg Leu Pro Ser Val Leu Ala Glu Leu Lys
385                 390                 395                 400

Ser Leu Lys Asn Ile Thr Leu Phe Asp Asn Phe Phe Thr Gly Val Ile
                405                 410                 415

Pro Gln Glu Leu Gly Val Asn Ser Pro Leu Val Gln Ile Asp Phe Thr
            420                 425                 430

Asn Asn Ser Phe Val Gly Gly Ile Pro Pro Asn Ile Cys Ser Gly Lys
        435                 440                 445

Ala Leu Arg Ile Leu Asp Leu Gly Phe Asn His Leu Asn Gly Ser Ile
    450                 455                 460

Pro Ser Ser Val Leu Asp Cys Pro Ser Leu Glu Arg Val Ile Val Glu
465                 470                 475                 480

Asn Asn Asn Leu Val Gly Ser Ile Pro Gln Phe Ile Asn Cys Ala Asn
                485                 490                 495

Leu Ser Tyr Met Asp Leu Ser His Asn Ser Leu Ser Gly Asn Ile Pro
            500                 505                 510

Ser Ser Phe Ser Arg Cys Val Lys Ile Ala Glu Ile Asn Trp Ser Glu
        515                 520                 525

Asn Asn Ile Phe Gly Ala Ile Pro Pro Glu Ile Gly Lys Leu Val Asn
    530                 535                 540

Leu Lys Arg Leu Asp Leu Ser His Asn Leu Leu His Gly Ser Ile Pro
545                 550                 555                 560

Val Gln Ile Ser Ser Cys Ser Lys Leu Tyr Ser Leu Asp Leu Gly Phe
                565                 570                 575

Asn Ser Leu Asn Gly Ser Ala Leu Ser Thr Val Ser Ser Leu Lys Phe
            580                 585                 590

Leu Thr Gln Leu Arg Leu Gln Glu Asn Arg Phe Ser Gly Gly Leu Pro
        595                 600                 605

Asp Pro Phe Ser Gln Leu Glu Met Leu Ile Glu Leu Gln Leu Gly Gly
    610                 615                 620

Asn Ile Leu Gly Gly Ser Ile Pro Ser Ser Leu Gly Gln Leu Val Lys
625                 630                 635                 640

Leu Gly Thr Thr Leu Asn Leu Ser Ser Asn Gly Leu Val Gly Asp Ile
```

```
                645                 650                 655

Pro Ser Gln Phe Gly Asn Leu Val Glu Leu Gln Asn Leu Asp Leu Ser
            660                 665                 670

Phe Asn Asn Leu Thr Gly Gly Leu Ala Thr Leu Arg Ser Leu Arg Phe
        675                 680                 685

Leu Gln Ala Leu Asn Val Ser Tyr Asn Gln Phe Ser Gly Pro Val Pro
    690                 695                 700

Asp Asn Leu Val Lys Phe Leu Ser Ser Thr Thr Asn Ser Phe Asp Gly
705                 710                 715                 720

Asn Pro Gly Leu Cys Ile Ser Cys Ser Thr Ser Asp Ser Ser Cys Met
                725                 730                 735

Gly Ala Asn Val Leu Lys Pro Cys Gly Gly Ser Lys Lys Arg Ala Val
            740                 745                 750

His Gly Arg Phe Lys Ile Val Leu Ile Val Leu Gly Ser Leu Phe Val
        755                 760                 765

Gly Ala Val Leu Val Leu Ile Leu Trp Cys Ile Leu Leu Lys Ser Arg
    770                 775                 780

Asp Gln Lys Lys Asn Ser Glu Glu Ala Val Ser His Met Phe Glu Gly
785                 790                 795                 800

Ser Ser Ser Lys Leu Asn Glu Val Ile Glu Ala Thr Glu Cys Phe Asp
                805                 810                 815

Asp Lys Tyr Ile Ile Gly Lys Gly Gly His Gly Thr Val Tyr Lys Ala
            820                 825                 830

Thr Leu Arg Ser Gly Asp Val Tyr Ala Ile Lys Lys Leu Val Ile Ser
        835                 840                 845

Ala His Lys Gly Ser Tyr Lys Ser Met Val Gly Glu Leu Lys Thr Leu
    850                 855                 860

Gly Lys Ile Lys His Arg Asn Leu Ile Lys Leu Lys Glu Ser Trp Leu
865                 870                 875                 880

Arg Asn Asp Asn Gly Phe Ile Leu Tyr Asp Phe Met Glu Lys Gly Ser
                885                 890                 895

Leu His Asp Val Leu His Val Val Gln Pro Ala Pro Ala Leu Asp Trp
            900                 905                 910

Cys Val Arg Tyr Asp Ile Ala Leu Gly Thr Ala His Gly Leu Ala Tyr
        915                 920                 925

Leu His Asp Asp Cys Arg Pro Ala Ile Ile His Arg Asp Ile Lys Pro
    930                 935                 940

Ser Asn Ile Leu Leu Asp Lys Asp Met Val Pro His Ile Ser Asp Phe
945                 950                 955                 960

Gly Ile Ala Lys Leu Leu Glu Gln Pro Ser Thr Ala Pro Gln Thr Thr
                965                 970                 975

Gly Val Val Gly Thr Ile Gly Tyr Met Ala Pro Glu Leu Ala Phe Ser
            980                 985                 990

Thr Lys Ser Ser Met Glu Ser Asp  Val Tyr Ser Tyr Gly  Val Val Leu
        995                 1000                1005

Leu Glu  Leu Leu Thr Arg Arg  Ala Ala Val Asp Pro  Ser Phe Pro
    1010                1015                1020

Asp Gly  Thr Asp Ile Val Ser  Trp Ala Ser Ser Ala  Leu Asn Gly
    1025                1030                1035

Thr Asp  Lys Ile Glu Ala Val  Cys Asp Pro Ala Leu  Met Glu Glu
    1040                1045                1050

Val Phe  Gly Thr Val Glu Met  Glu Glu Val Ser Lys  Val Leu Ser
    1055                1060                1065
```

```
Val Ala  Leu Arg Cys Ala Ala  Arg Glu Ala Ser Gln  Arg Pro Ser
    1070                 1075                 1080

Met Thr  Ala Val Val Lys Glu  Leu Thr Asp Ala Arg  Pro Ala Thr
    1085                 1090                 1095

Gly Gly  Gly Arg Ser Leu Ser  Lys Ser Lys Gln Gly  Lys Pro Gly
    1100                 1105                 1110

Ser Gln  Ser Asn Ser Ser Ala  Tyr Arg Gln
    1115                 1120

<210> SEQ ID NO 168
<211> LENGTH: 3423
<212> TYPE: DNA
<213> ORGANISM: Zea mays

<400> SEQUENCE: 168
atgaagctgg ttttatggca tcagtttttt ctcttcttcg tgttagtttc aacatcacag     60
ggtatgagtt cagatggcct agctcttctt gctctgtcca aaagcctcat actaccaagt    120
cccataagaa ccaactggag tgattctgat gcaactccct gtacatggag cggtgttggt    180
tgcaatggaa ggaacagagt catctctctc gacctatcat cgtcaggtgt ttcgggttct    240
ataggacctg caatagggcg tctgaaatac ctgcggattc tcatcttatc agctaacaac    300
atatctggtt tgatccctct agaattggga gactgcaata tgcttgaaga actggatttg    360
tcccaaaacc tgttttctgg caatatacca gcatcattgg gcaacctcaa gaaattgtca    420
tcactgtcac tgtaccgcaa ctccttcaat ggaacaatac cagaggagtt gttcaagaac    480
cagtttctgg agcaagtgta cctacatgac aatcagctca gtggttcggt gcccttatcg    540
gttggtgaaa tgacaagcct taagtcactg tggttacagg aaaatatgtt gtctggagtt    600
ttgcccagtt caattggaaa ctgcaccaag ttggaggatc tgtatctact cgataatcaa    660
ctgagtggca gtattcctga aaccttgggt atgatcaaag gtctcaaggt ttttgatgct    720
actaccaata gtttcacagg tgagatctct ttcagttttg aggactgcaa gctagaaata    780
ttcatcttgt ctttcaataa tataaaaggt gaaattccat catggctggg gaactgcatg    840
agcttgcaac aacttggatt tgtcaataat agtttgtatg gcaaaattcc aaattctctt    900
ggcttattga gcaacctcac atatctttta ctttcacaga actccctttc tgggccgatc    960
ccacctgaga ttggtaactg tcagtcgctg cagtggctag agttagatgc aaaccagctg   1020
gatggcactg ttcctgaaga atttgcaaat ttacggagtt tgtcaaagct ctttcttttt   1080
gagaatcgcc tcatgggaga cttccctgag aatatttgga gtatccaaac cctcgagagt   1140
gtcctacttt atagcaacag attcacaggg aagctacctt cagtgttagc tgagctgaag   1200
ttcctaaaga acatcacact gtttgataat ttcttcactg gagtcatacc acaggagcta   1260
ggtgttaata gccccttggt ccagatagat ttcacaaaca acagttttgt tggtagtatc   1320
ccaccaaaca tctgttcaag aaaagcattg agaattttgg acttaggggtt taatcatctc   1380 aacggtagca tcccatccag tgttgtggac tgcccaagtt tgaagcgagt catttttacaa   1440 aacaataacc ttaacgggtc tattccacaa tttgtaaact gtgcaaatct aagttatatg   1500
gacctaagcc acaattcctt gagtggtaac attccagcaa gcttcagcag atgtgtaaac   1560
attactgaga taaactggtc agagaacaag ctttttggag caataccacc tgaaattgga   1620
aacttagtga atctgaaaag acttgacctc tcacacaaca tattgcatgg ttcgatccct   1680
gtgcaaattt ccagttgctc caagttgtac tcacttgatt tgagttttaa ctcattgaat   1740
ggttcggccc tccgcaccgt aagcaacttg aagtttctga cacagctacg attgcaagag   1800
```
aatagattca gcggaggctt gcctgattct ctctcacaat tggaaatgct tattgagctg 1860
caacttggtg gaaatattct tgggggtagt atcccttcgt cattaggaca gctggtgaaa 1920
ctgggcacag ccttgaacct tagtagcaat ggcctaatgg gtgacattcc aacacaattg 1980
ggtaatttgg tggagttgca aaacttagat ttttcattta ataatctcac aggaggcctt 2040
gctacattga gaagtctagg ctttttgcag gccttgaatg tttcttacaa ccaatttagt 2100
ggaccagtcc cagataatct tctgaagttt ctgagttcca caccatattc ttttgatgga 2160
aacccaggcc tctgtatctc ctgcagcacc agtggctctt cttgcatggg agctaatgtt 2220
ttgaaacctt gtggtgggtc gaagaaaaga ggagtacatg gccaattgaa aattgttctc 2280
atagttctcg gttcattatt tgtgggagga gttcttgtac ttgtactgtg ttgcatcctt 2340
ctgaaatctc gagattggaa gaaaaataaa gtcagtaaca tgtttgaagg ttcctcatct 2400
aaattaaatg aggttacaga ggccactgaa aatttcgatg acaagtatat catcggtaca 2460
ggtgctcacg gaactgttta caaggcaaca ctgaggtcag gggatgttta tgctataaag 2520
aagcttgcga tttctgcaca caaaggttca tacaaaagca tggttagaga actgaagaca 2580
ctgggtgaaa ttaagcacag aaacttgata aagctgaaag aattttggtt gagaagtgat 2640
aatggattca tactgtatga ttttatggaa aagggcagcc tccatgatat tctgcatgta 2700
attcagccag caccagcttt ggactggtgt gtgaggtatg acatagctct tggcaccgcc 2760
catgggttag catatcttca tgatgactgc cgccctgcga tcattcaccg tgatattaaa 2820
ccaagaaata tactgctcga caaggacatg gtgccacata tttcagattt tggcattgca 2880
aagcacatgg accagtcttc tactactgct ccacagacca ctggaatcgt tggcactatt 2940
ggatatatgg ccccagaata cacaccgatg accgacgcat acttacattg catgcgctgt 3000
cttgcagaat tggcgttttc caccaagagc agcatggagt ctgacgtgta cagctacggt 3060
gtggtgctac tggagctgtt gaccaggagg acggcggtgg atcctttgtt ccccgacagc 3120
gcggacatag tcggctgggt gtcgtccgtg ctggacggca ccgacaaaat cgaggccgtc 3180
tgtgacccgg ccctcatgga ggaagtcttc ggcacggtgg agatggagga ggtgcgtaag 3240
gtcctgtcgg tggcgctccg gtgcgcggcc agggaggtga gccaaaggcc ctccatgact 3300
gccgtcgtga aggagctgac ggatgcgcgg ccagcctctg ccagcagcgg cagccggtcg 3360
ttgtccaagt cgagggaagg gaaaccggga ttgcaatcca gcagcagcgc gtactggcag 3420
tag 3423

<210> SEQ ID NO 169
<211> LENGTH: 1123
<212> TYPE: PRT
<213> ORGANISM: Zea mays

<400> SEQUENCE: 169

Met Lys Leu Val Leu Trp His Gln Phe Phe Leu Phe Phe Val Leu Val
1 5 10 15

Ser Thr Ser Gln Gly Met Ser Ser Asp Gly Leu Ala Leu Leu Ala Leu
20 25 30

Ser Lys Ser Leu Ile Leu Pro Ser Pro Ile Arg Thr Asn Trp Ser Asp
35 40 45

Ser Asp Ala Thr Pro Cys Thr Trp Ser Gly Val Gly Cys Asn Gly Arg
50 55 60

Asn Arg Val Ile Ser Leu Asp Leu Ser Ser Ser Gly Val Ser Gly Ser
65 70 75 80

Ile Gly Pro Ala Ile Gly Arg Leu Lys Tyr Leu Arg Ile Leu Ile Leu

```
                85                  90                  95

Ser Ala Asn Asn Ile Ser Gly Leu Ile Pro Leu Glu Leu Gly Asp Cys
            100                 105                 110

Asn Met Leu Glu Glu Leu Asp Leu Ser Gln Asn Leu Phe Ser Gly Asn
        115                 120                 125

Ile Pro Ala Ser Leu Gly Asn Leu Lys Lys Leu Ser Ser Leu Ser Leu
    130                 135                 140

Tyr Arg Asn Ser Phe Asn Gly Thr Ile Pro Glu Glu Leu Phe Lys Asn
145                 150                 155                 160

Gln Phe Leu Glu Gln Val Tyr Leu His Asp Asn Gln Leu Ser Gly Ser
                165                 170                 175

Val Pro Leu Ser Val Gly Glu Met Thr Ser Leu Lys Ser Leu Trp Leu
            180                 185                 190

Gln Glu Asn Met Leu Ser Gly Val Leu Pro Ser Ser Ile Gly Asn Cys
        195                 200                 205

Thr Lys Leu Glu Asp Leu Tyr Leu Leu Asp Asn Gln Leu Ser Gly Ser
    210                 215                 220

Ile Pro Glu Thr Leu Gly Met Ile Lys Gly Leu Lys Val Phe Asp Ala
225                 230                 235                 240

Thr Thr Asn Ser Phe Thr Gly Glu Ile Ser Phe Ser Phe Glu Asp Cys
                245                 250                 255

Lys Leu Glu Ile Phe Ile Leu Ser Phe Asn Asn Ile Lys Gly Glu Ile
            260                 265                 270

Pro Ser Trp Leu Gly Asn Cys Met Ser Leu Gln Gln Leu Gly Phe Val
        275                 280                 285

Asn Asn Ser Leu Tyr Gly Lys Ile Pro Asn Ser Leu Gly Leu Leu Ser
    290                 295                 300

Asn Leu Thr Tyr Leu Leu Leu Ser Gln Asn Ser Leu Ser Gly Pro Ile
305                 310                 315                 320

Pro Pro Glu Ile Gly Asn Cys Gln Ser Leu Gln Trp Leu Glu Leu Asp
                325                 330                 335

Ala Asn Gln Leu Asp Gly Thr Val Pro Glu Glu Phe Ala Asn Leu Arg
            340                 345                 350

Ser Leu Ser Lys Leu Phe Leu Phe Glu Asn Arg Leu Met Gly Asp Phe
        355                 360                 365

Pro Glu Asn Ile Trp Ser Ile Gln Thr Leu Glu Ser Val Leu Leu Tyr
    370                 375                 380

Ser Asn Arg Phe Thr Gly Lys Leu Pro Ser Val Leu Ala Glu Leu Lys
385                 390                 395                 400

Phe Leu Lys Asn Ile Thr Leu Phe Asp Asn Phe Phe Thr Gly Val Ile
                405                 410                 415

Pro Gln Glu Leu Gly Val Asn Ser Pro Leu Val Gln Ile Asp Phe Thr
            420                 425                 430

Asn Asn Ser Phe Val Gly Ser Ile Pro Pro Asn Ile Cys Ser Arg Lys
        435                 440                 445

Ala Leu Arg Ile Leu Asp Leu Gly Phe Asn His Leu Asn Gly Ser Ile
    450                 455                 460

Pro Ser Ser Val Val Asp Cys Pro Ser Leu Lys Arg Val Ile Leu Gln
465                 470                 475                 480

Asn Asn Asn Leu Asn Gly Ser Ile Pro Gln Phe Val Asn Cys Ala Asn
                485                 490                 495

Leu Ser Tyr Met Asp Leu Ser His Asn Ser Leu Ser Gly Asn Ile Pro
            500                 505                 510
```

-continued

```
Ala Ser Phe Ser Arg Cys Val Asn Ile Thr Glu Ile Asn Trp Ser Glu
        515                 520                 525

Asn Lys Leu Phe Gly Ala Ile Pro Pro Glu Ile Gly Asn Leu Val Asn
    530                 535                 540

Leu Lys Arg Leu Asp Leu Ser His Asn Ile Leu His Gly Ser Ile Pro
545                 550                 555                 560

Val Gln Ile Ser Ser Cys Ser Lys Leu Tyr Ser Leu Asp Leu Ser Phe
                565                 570                 575

Asn Ser Leu Asn Gly Ser Ala Leu Arg Thr Val Ser Asn Leu Lys Phe
            580                 585                 590

Leu Thr Gln Leu Arg Leu Gln Glu Asn Arg Phe Ser Gly Gly Leu Pro
        595                 600                 605

Asp Ser Leu Ser Gln Leu Glu Met Leu Ile Glu Leu Gln Leu Gly Gly
    610                 615                 620

Asn Ile Leu Gly Gly Ser Ile Pro Ser Ser Leu Gly Gln Leu Val Lys
625                 630                 635                 640

Leu Gly Thr Ala Leu Asn Leu Ser Ser Asn Gly Leu Met Gly Asp Ile
                645                 650                 655

Pro Thr Gln Leu Gly Asn Leu Val Glu Leu Gln Asn Leu Asp Phe Ser
            660                 665                 670

Phe Asn Asn Leu Thr Gly Gly Leu Ala Thr Leu Arg Ser Leu Gly Phe
        675                 680                 685

Leu Gln Ala Leu Asn Val Ser Tyr Asn Gln Phe Ser Gly Pro Val Pro
    690                 695                 700

Asp Asn Leu Leu Lys Phe Leu Ser Ser Thr Pro Tyr Ser Phe Asp Gly
705                 710                 715                 720

Asn Pro Gly Leu Cys Ile Ser Cys Ser Thr Ser Gly Ser Ser Cys Met
                725                 730                 735

Gly Ala Asn Val Leu Lys Pro Cys Gly Gly Ser Lys Lys Arg Gly Val
            740                 745                 750

His Gly Gln Leu Lys Ile Val Leu Ile Val Leu Gly Ser Leu Phe Val
        755                 760                 765

Gly Gly Val Leu Val Leu Val Leu Cys Cys Ile Leu Leu Lys Ser Arg
    770                 775                 780

Asp Trp Lys Lys Asn Lys Val Ser Asn Met Phe Glu Gly Ser Ser Ser
785                 790                 795                 800

Lys Leu Asn Glu Val Thr Glu Ala Thr Glu Asn Phe Asp Asp Lys Tyr
                805                 810                 815

Ile Ile Gly Thr Gly Ala His Gly Thr Val Tyr Lys Ala Thr Leu Arg
            820                 825                 830

Ser Gly Asp Val Tyr Ala Ile Lys Lys Leu Ala Ile Ser Ala His Lys
        835                 840                 845

Gly Ser Tyr Lys Ser Met Val Arg Glu Leu Lys Thr Leu Gly Glu Ile
    850                 855                 860

Lys His Arg Asn Leu Ile Lys Leu Lys Glu Phe Trp Leu Arg Ser Asp
865                 870                 875                 880

Asn Gly Phe Ile Leu Tyr Asp Phe Met Glu Lys Gly Ser Leu His Asp
                885                 890                 895

Ile Leu His Val Ile Gln Pro Ala Pro Ala Leu Asp Trp Cys Val Arg
            900                 905                 910

Tyr Asp Ile Ala Leu Gly Thr Ala His Gly Leu Ala Tyr Leu His Asp
        915                 920                 925

Asp Cys Arg Pro Ala Ile Ile His Arg Asp Ile Lys Pro Arg Asn Ile
    930                 935                 940
```

Leu Leu Asp Lys Asp Met Val Pro His Ile Ser Asp Phe Gly Ile Ala
945 950 955 960

Lys His Met Asp Gln Ser Ser Thr Thr Ala Pro Gln Thr Thr Gly Ile
965 970 975

Val Gly Thr Ile Gly Tyr Met Ala Pro Glu Leu Ala Phe Ser Thr Lys
980 985 990

Ser Ser Met Glu Ser Asp Val Tyr Ser Tyr Gly Val Val Leu Leu Glu
995 1000 1005

Leu Leu Thr Arg Arg Thr Ala Val Asp Pro Leu Phe Pro Asp Ser
1010 1015 1020

Ala Asp Ile Val Gly Trp Val Ser Ser Val Leu Asp Gly Thr Asp
1025 1030 1035

Lys Ile Glu Ala Val Cys Asp Pro Ala Leu Met Glu Glu Val Phe
1040 1045 1050

Gly Thr Val Glu Met Glu Glu Val Arg Lys Val Leu Ser Val Ala
1055 1060 1065

Leu Arg Cys Ala Ala Arg Glu Val Ser Gln Arg Pro Ser Met Thr
1070 1075 1080

Ala Val Val Lys Glu Leu Thr Asp Ala Arg Pro Ala Ser Ala Ser
1085 1090 1095

Ser Gly Ser Arg Ser Leu Ser Lys Ser Arg Glu Gly Lys Pro Gly
1100 1105 1110

Leu Gln Ser Ser Ser Ser Ala Tyr Trp Gln
1115 1120

<210> SEQ ID NO 170
<211> LENGTH: 3366
<212> TYPE: DNA
<213> ORGANISM: Sorghum bicolor

<400> SEQUENCE: 170
atgaagctgg tttggcattg ggtttttcta ttcttcctgt tagtctcaac atcacagggt 60
atgagttcag atggcctagc tcttcttgct ctgtccaaaa gcctcatact accaagttcc 120
ataagatcca actggagcac ttctgcaaat ccttgtacat ggagcggtgt tgattgcaat 180
ggaaggaaca gagtcatttc tctcgaccta tcatcatcag aggtttcagg atctatagga 240
ccagatatag ggcgtctgaa atacctgcaa gttctcattt tgtctactaa caacatatct 300
ggttcgattc ctctagaatt aggcaactgc agtatgcttg aacaattgga tttgtcccaa 360
aacttgcttt ctggcaatat accagcatca atgggcaacc tcaagaaatt gtcatcactg 420
tcactgtact ctaactcttt gaatggatca ataccagagg agttgttcaa gaaccagttt 480
ctggaggaag tgtacctaca tgacaatcag ctcagtggtt cgataccctt cgcggttggt 540
gaaatgacaa gccttaagtc attgtggttg catgtaaata tgttgtctgg agttttgccc 600
agttcaattg gcaactgcac caagttggag gagctgtatc tactctataa tcaactgagt 660
ggcagtcttc cagaaacctt gagtgagatc aaaggcctca gggtttttga tgccactagc 720
aacagcttca caggcgagat caatttcagt ttcgagaact gcaagctgga aatattcatc 780
ttgtcattca attatataaa gggagaaatt ccatcatggc tggtgaattg caggagcatg 840
caacagcttg gatttgtcaa taatagtctg tctggcaaga ttccaaattc tctagggtta 900
ttgagcaacc tcacacatct tttactttct cagaattccc tgtctgggcc aatccctcct 960
gagattagta actgtcggtt gctgcagtgg ctagagttgg atgcaaacca gctggagggc 1020
actgttcctg aagggttggc aaatttacgg aacctctcaa ggctctttct gtttgagaat 1080

-continued

```
catctcatgg gagagtttcc tgagagtatt tggagtatcc aaaccctcga gagtgtgctt   1140
ctttatagaa acagattcac tgggaagcta ccttcagtgt tagctgagct gaagtacctg   1200
gagaacatta cactgtttga taatttcttc actggagtca taccacagga gctgggtgtt   1260
aatagcccct tggtgcagat agatttcaca aataacagtt ttgttggtgg tatcccacca   1320
aaaatttgtt caggaaaagc attgagaatt ctggacttgg ggtttaatca tctcaacggt   1380
agcatcccat ccaatgttgt ggactgccca agtctggaga gagtcattgt cgaaaacaat   1440
aaccttgatg ggtctattcc gcaatttaaa aactgtgcaa atctaagtta tatggatctg   1500
agccacaatt ccttaagtgg taacattcct gcaagcttca gcagatgtgt aaacattact   1560
gagataaact ggtcagagaa caagctatct ggggcaatac cacctgaaat tggaaactta   1620
gtgaatctga aaagacttga cctctcacac aacgtattac atggttcagt tcctgtgcag   1680
atttccagtt gctccaagtt gtattcactt gatttgagtt ttaactcttt gaatggttcg   1740
gcccttagca cagtaagcaa cttgaagtat ctgacacaac tacgattgca agagaataga   1800
ttcagcggag gctttcctaa gtctctctcc caattggaaa tgcttattga gctgcaactt   1860
ggtggaaata ttattggggg tagtatccct tcatcattag gacagctggt gaaactgggc   1920
acagccttga accttagtag caatggtcta attggtgata ttccaccaca attgggcaat   1980
ttagtggact tgcaaaactt agatttgtca tttaataatc tcacaggagg ccttgctaca   2040
ttgagaagtc taggtttttt gcatgccttg aatgtttctt acaaccaatt tagtggacct   2100
gtcccagata atcttctgaa gtttctgagt tcgacaccaa attcttttaa tggaaaccca   2160
ggcctctgtg tctcttgcag caccagtgat tcttcttgca tgggagctaa tgttttgaaa   2220
ccttgtggtg ggtcgaagaa taggggtgtg catggccgat tcaaaattgt cctcatagtt   2280
cttggttcat tatttgtggg agcagttttg gtacttgtac tgtgttgcat ctttctgaaa   2340
tctcgagatc ggaagaaaaa tactgaggaa gcagtcagta gtatgtttga aggttcctca   2400
tctaaattaa atgagattat agaggctact gaaaattttg atgacaagta tatcatcggt   2460
acaggtggtc acggaactgt ttacaaggca acactgaggt caggagatgt ttatgctata   2520
aagaaacttg tgatttctgc acacaaaggt tcatacaaaa gcatggttag ggaactgaag   2580
acactaggaa aaattaagca cagaaacttg ataaagttga aagaattttg gttcagacgt   2640
gataatggat tcatactgta tgattttatg gaaaaaggta gccttcatga tgtgctgcat   2700
gtaattcagc cagcaccaac tttggactgg tgtgtgaggt atgacatagc cctcggcacc   2760
gcccatgggt tagcatatct tcacgatgac tgccgccctg cgatcattca ccgtgatatc   2820
aagccaagta atatactgct ggacaaggac atggtgccac atatttcaga ctttggcatt   2880
gcaaagctca tggaccagcc ttctactgct tcacagacca ctggaatcgt tggaaccatt   2940
ggatatatgg ccccagaatt ggcgttttcc accaagagca gcatggagtc cgacgtatac   3000
agctacggcg tggtgctact ggagctgctc accaggagga cggcggtgga tccttcgttc   3060
cccgacagca cggacatagt tggctgggtg tcgtccgcgc taaacggcac cgacaaaatc   3120
gaggccgtct gcgacccagc cctcatggag gaagtcttcg gcacggtgga gatggaggag   3180
gtgcgcaagg tgctgtcggt ggcgctgcgg tgcgcggcca gggaggcgag ccaaaggccg   3240
tccatggccg acgtcgtgaa ggagctgacg ggcgtacggc ttgccactgg cagtggcggc   3300
ggccggtcgt tgtccaagtc gaagcagggg aaaccgggat cgcaatccca cagcagcgcg   3360
tactag                                                              3366
```

<210> SEQ ID NO 171
<211> LENGTH: 1121
<212> TYPE: PRT
<213> ORGANISM: Sorghum bicolor

<400> SEQUENCE: 171

```
Met Lys Leu Val Trp His Trp Val Phe Leu Phe Phe Leu Leu Val Ser
1               5                   10                  15

Thr Ser Gln Gly Met Ser Ser Asp Gly Leu Ala Leu Leu Ala Leu Ser
            20                  25                  30

Lys Ser Leu Ile Leu Pro Ser Ser Ile Arg Ser Asn Trp Ser Thr Ser
        35                  40                  45

Ala Asn Pro Cys Thr Trp Ser Gly Val Asp Cys Asn Gly Arg Asn Arg
    50                  55                  60

Val Ile Ser Leu Asp Leu Ser Ser Ser Glu Val Ser Gly Ser Ile Gly
65                  70                  75                  80

Pro Asp Ile Gly Arg Leu Lys Tyr Leu Gln Val Leu Ile Leu Ser Thr
                85                  90                  95

Asn Asn Ile Ser Gly Ser Ile Pro Leu Glu Leu Gly Asn Cys Ser Met
            100                 105                 110

Leu Glu Gln Leu Asp Leu Ser Gln Asn Leu Leu Ser Gly Asn Ile Pro
        115                 120                 125

Ala Ser Met Gly Asn Leu Lys Lys Leu Ser Ser Leu Ser Leu Tyr Ser
    130                 135                 140

Asn Ser Leu Asn Gly Ser Ile Pro Glu Glu Leu Phe Lys Asn Gln Phe
145                 150                 155                 160

Leu Glu Glu Val Tyr Leu His Asp Asn Gln Leu Ser Gly Ser Ile Pro
                165                 170                 175

Phe Ala Val Gly Glu Met Thr Ser Leu Lys Ser Leu Trp Leu His Val
            180                 185                 190

Asn Met Leu Ser Gly Val Leu Pro Ser Ser Ile Gly Asn Cys Thr Lys
        195                 200                 205

Leu Glu Glu Leu Tyr Leu Leu Tyr Asn Gln Leu Ser Gly Ser Leu Pro
    210                 215                 220

Glu Thr Leu Ser Glu Ile Lys Gly Leu Arg Val Phe Asp Ala Thr Ser
225                 230                 235                 240

Asn Ser Phe Thr Gly Glu Ile Asn Phe Ser Phe Glu Asn Cys Lys Leu
                245                 250                 255

Glu Ile Phe Ile Leu Ser Phe Asn Tyr Ile Lys Gly Glu Ile Pro Ser
            260                 265                 270

Trp Leu Val Asn Cys Arg Ser Met Gln Gln Leu Gly Phe Val Asn Asn
        275                 280                 285

Ser Leu Ser Gly Lys Ile Pro Asn Ser Leu Gly Leu Leu Ser Asn Leu
    290                 295                 300

Thr His Leu Leu Leu Ser Gln Asn Ser Leu Ser Gly Pro Ile Pro Pro
305                 310                 315                 320

Glu Ile Ser Asn Cys Arg Leu Leu Gln Trp Leu Glu Leu Asp Ala Asn
                325                 330                 335

Gln Leu Glu Gly Thr Val Pro Glu Gly Leu Ala Asn Leu Arg Asn Leu
            340                 345                 350

Ser Arg Leu Phe Leu Phe Glu Asn His Leu Met Gly Glu Phe Pro Glu
        355                 360                 365

Ser Ile Trp Ser Ile Gln Thr Leu Glu Ser Val Leu Leu Tyr Arg Asn
    370                 375                 380

Arg Phe Thr Gly Lys Leu Pro Ser Val Leu Ala Glu Leu Lys Tyr Leu
```

-continued

```
385                 390                 395                 400

Glu Asn Ile Thr Leu Phe Asp Asn Phe Phe Thr Gly Val Ile Pro Gln
                405                 410                 415

Glu Leu Gly Val Asn Ser Pro Leu Val Gln Ile Asp Phe Thr Asn Asn
            420                 425                 430

Ser Phe Val Gly Gly Ile Pro Pro Lys Ile Cys Ser Gly Lys Ala Leu
        435                 440                 445

Arg Ile Leu Asp Leu Gly Phe Asn His Leu Asn Gly Ser Ile Pro Ser
    450                 455                 460

Asn Val Val Asp Cys Pro Ser Leu Glu Arg Val Ile Val Glu Asn Asn
465                 470                 475                 480

Asn Leu Asp Gly Ser Ile Pro Gln Phe Lys Asn Cys Ala Asn Leu Ser
                485                 490                 495

Tyr Met Asp Leu Ser His Asn Ser Leu Ser Gly Asn Ile Pro Ala Ser
            500                 505                 510

Phe Ser Arg Cys Val Asn Ile Thr Glu Ile Asn Trp Ser Glu Asn Lys
        515                 520                 525

Leu Ser Gly Ala Ile Pro Pro Glu Ile Gly Asn Leu Val Asn Leu Lys
    530                 535                 540

Arg Leu Asp Leu Ser His Asn Val Leu His Gly Ser Val Pro Val Gln
545                 550                 555                 560

Ile Ser Ser Cys Ser Lys Leu Tyr Ser Leu Asp Leu Ser Phe Asn Ser
                565                 570                 575

Leu Asn Gly Ser Ala Leu Ser Thr Val Ser Asn Leu Lys Tyr Leu Thr
            580                 585                 590

Gln Leu Arg Leu Gln Glu Asn Arg Phe Ser Gly Gly Phe Pro Lys Ser
        595                 600                 605

Leu Ser Gln Leu Glu Met Leu Ile Glu Leu Gln Leu Gly Gly Asn Ile
    610                 615                 620

Ile Gly Gly Ser Ile Pro Ser Ser Leu Gly Gln Leu Val Lys Leu Gly
625                 630                 635                 640

Thr Ala Leu Asn Leu Ser Ser Asn Gly Leu Ile Gly Asp Ile Pro Pro
                645                 650                 655

Gln Leu Gly Asn Leu Val Asp Leu Gln Asn Leu Asp Leu Ser Phe Asn
            660                 665                 670

Asn Leu Thr Gly Gly Leu Ala Thr Leu Arg Ser Leu Gly Phe Leu His
        675                 680                 685

Ala Leu Asn Val Ser Tyr Asn Gln Phe Ser Gly Pro Val Pro Asp Asn
    690                 695                 700

Leu Leu Lys Phe Leu Ser Ser Thr Pro Asn Ser Phe Asn Gly Asn Pro
705                 710                 715                 720

Gly Leu Cys Val Ser Cys Ser Thr Ser Asp Ser Ser Cys Met Gly Ala
                725                 730                 735

Asn Val Leu Lys Pro Cys Gly Gly Ser Lys Asn Arg Gly Val His Gly
            740                 745                 750

Arg Phe Lys Ile Val Leu Ile Val Leu Gly Ser Leu Phe Val Gly Ala
        755                 760                 765
```

```
Val Leu Val Leu Val Leu Cys Cys Ile Phe Leu Lys Ser Arg Asp Arg
    770                 775                 780

Lys Lys Asn Thr Glu Glu Ala Val Ser Ser Met Phe Glu Gly Ser Ser
785                 790                 795                 800

Ser Lys Leu Asn Glu Ile Ile Glu Ala Thr Glu Asn Phe Asp Asp Lys
                805                 810                 815

Tyr Ile Ile Gly Thr Gly Gly His Gly Thr Val Tyr Lys Ala Thr Leu
            820                 825                 830

Arg Ser Gly Asp Val Tyr Ala Ile Lys Lys Leu Val Ile Ser Ala His
        835                 840                 845

Lys Gly Ser Tyr Lys Ser Met Val Arg Glu Leu Lys Thr Leu Gly Lys
    850                 855                 860

Ile Lys His Arg Asn Leu Ile Lys Leu Lys Glu Phe Trp Phe Arg Arg
865                 870                 875                 880

Asp Asn Gly Phe Ile Leu Tyr Asp Phe Met Glu Lys Gly Ser Leu His
                885                 890                 895

Asp Val Leu His Val Ile Gln Pro Ala Pro Thr Leu Asp Trp Cys Val
            900                 905                 910

Arg Tyr Asp Ile Ala Leu Gly Thr Ala His Gly Leu Ala Tyr Leu His
        915                 920                 925

Asp Asp Cys Arg Pro Ala Ile Ile His Arg Asp Ile Lys Pro Ser Asn
    930                 935                 940

Ile Leu Leu Asp Lys Asp Met Val Pro His Ile Ser Asp Phe Gly Ile
945                 950                 955                 960

Ala Lys Leu Met Asp Gln Pro Ser Thr Ala Ser Gln Thr Thr Gly Ile
                965                 970                 975

Val Gly Thr Ile Gly Tyr Met Ala Pro Glu Leu Ala Phe Ser Thr Lys
            980                 985                 990

Ser Ser Met Glu Ser Asp Val Tyr  Ser Tyr Gly Val Val  Leu Leu Glu
        995                 1000                1005

Leu Leu  Thr Arg Arg Thr Ala  Val Asp Pro Ser Phe  Pro Asp Ser
    1010                1015                1020

Thr Asp  Ile Val Gly Trp Val  Ser Ser Ala Leu Asn  Gly Thr Asp
    1025                1030                1035

Lys Ile  Glu Ala Val Cys Asp  Pro Ala Leu Met Glu  Glu Val Phe
    1040                1045                1050

Gly Thr  Val Glu Met Glu Glu  Val Arg Lys Val Leu  Ser Val Ala
    1055                1060                1065

Leu Arg  Cys Ala Ala Arg Glu  Ala Ser Gln Arg Pro  Ser Met Ala
    1070                1075                1080

Asp Val  Val Lys Glu Leu Thr  Gly Val Arg Leu Ala  Thr Gly Ser
    1085                1090                1095

Gly Gly  Gly Arg Ser Leu Ser  Lys Ser Lys Gln Gly  Lys Pro Gly
    1100                1105                1110

Ser Gln  Ser His Ser Ser Ala  Tyr
    1115                1120
```

<210> SEQ ID NO 172
<211> LENGTH: 294
<212> TYPE: PRT
<213> ORGANISM: Arabidopsis thaliana
<220> FEATURE:
<221> NAME/KEY: Variant
<222> LOCATION: 3
<223> OTHER INFORMATION: Xaa = Lysine or Glutamic Acid
<220> FEATURE:
<221> NAME/KEY: Variant
<222> LOCATION: 15
<223> OTHER INFORMATION: Xaa = Tyrosine or Histidine
<220> FEATURE:
<221> NAME/KEY: Variant
<222> LOCATION: 17
<223> OTHER INFORMATION: Xaa = Isoleucine or Valine
<220> FEATURE:
<221> NAME/KEY: Variant
<222> LOCATION: 25
<223> OTHER INFORMATION: Xaa = Valine or Isoleucine
<220> FEATURE:
<221> NAME/KEY: Variant
<222> LOCATION: 27
<223> OTHER INFORMATION: Xaa = Lysine or Arginine
<220> FEATURE:
<221> NAME/KEY: Variant
<222> LOCATION: 30
<223> OTHER INFORMATION: Xaa = Leucine or Isoleucine or Valine
<220> FEATURE:
<221> NAME/KEY: Variant
<222> LOCATION: 40
<223> OTHER INFORMATION: Xaa = Lysine or Arginine
<220> FEATURE:
<221> NAME/KEY: Variant
<222> LOCATION: 57
<223> OTHER INFORMATION: Xaa = Leucine or Isoleucine
<220> FEATURE:
<221> NAME/KEY: Variant
<222> LOCATION: 60
<223> OTHER INFORMATION: Xaa = Leucine or Isoleucine
<220> FEATURE:
<221> NAME/KEY: Variant
<222> LOCATION: 63
<223> OTHER INFORMATION: Xaa = Valine or Isoleucine
<220> FEATURE:
<221> NAME/KEY: Variant
<222> LOCATION: 64
<223> OTHER INFORMATION: Xaa = Arginine or Lysine
<220> FEATURE:
<221> NAME/KEY: Variant
<222> LOCATION: 69
<223> OTHER INFORMATION: Xaa = Leucine or Isoleucine or Valine
<220> FEATURE:
<221> NAME/KEY: Variant
<222> LOCATION: 70
<223> OTHER INFORMATION: Xaa = Arginine or Lysine
<220> FEATURE:
<221> NAME/KEY: Variant
<222> LOCATION: 77
<223> OTHER INFORMATION: Xaa = Arginine or Lysine or Glutamine
<220> FEATURE:
<221> NAME/KEY: Variant
<222> LOCATION: 83
<223> OTHER INFORMATION: Xaa = Methionine or Isoleucine
<220> FEATURE:
<221> NAME/KEY: Variant
<222> LOCATION: 86
<223> OTHER INFORMATION: Xaa = Tyrosine or Phenylalanine
<220> FEATURE:
<221> NAME/KEY: Variant
<222> LOCATION: 92
<223> OTHER INFORMATION: Xaa = Leucine or Valine
<220> FEATURE:
<221> NAME/KEY: Variant
<222> LOCATION: 113
<223> OTHER INFORMATION: Xaa = Isoleucine or Valine
<220> FEATURE:
<221> NAME/KEY: Variant
<222> LOCATION: 115
<223> OTHER INFORMATION: Xaa = Leucine or Isoleucine or Valine
<220> FEATURE:
<221> NAME/KEY: Variant
<222> LOCATION: 118
<223> OTHER INFORMATION: Xaa = Alanine or Serine
<220> FEATURE:
<221> NAME/KEY: Variant
<222> LOCATION: 124
<223> OTHER INFORMATION: Xaa = Isoleucine or Leucine
<220> FEATURE:
<221> NAME/KEY: Variant
<222> LOCATION: 133
<223> OTHER INFORMATION: Xaa = Isoleucine or Valine
<220> FEATURE:
<221> NAME/KEY: Variant
<222> LOCATION: 137
<223> OTHER INFORMATION: Xaa = Isoleucine or Valine
<220> FEATURE:
<221> NAME/KEY: Variant
<222> LOCATION: 144
<223> OTHER INFORMATION: Xaa = Leucine or Methionine
<220> FEATURE:
<221> NAME/KEY: Variant
<222> LOCATION: 145
<223> OTHER INFORMATION: Xaa = Aspartic Acid or Asparagine
<220> FEATURE:
<221> NAME/KEY: Variant
<222> LOCATION: 147
<223> OTHER INFORMATION: Xaa = Aspartic Acid or Glutamic Acid
<220> FEATURE:
<221> NAME/KEY: Variant
<222> LOCATION: 148
<223> OTHER INFORMATION: Xaa = Methionine or Leucine
<220> FEATURE:
<221> NAME/KEY: Variant
<222> LOCATION: 157
<223> OTHER INFORMATION: Xaa = Isoleucine or Leucine
<220> FEATURE:
<221> NAME/KEY: Variant
<222> LOCATION: 158
<223> OTHER INFORMATION: Xaa = Alanine or Serine
<220> FEATURE:
<221> NAME/KEY: Variant
<222> LOCATION: 159
<223> OTHER INFORMATION: Xaa = Lysine or Arginine
<220> FEATURE:
<221> NAME/KEY: Variant
<222> LOCATION: 161
<223> OTHER INFORMATION: Xaa = Leucine or Methionine
<220> FEATURE:
<221> NAME/KEY: Variant
<222> LOCATION: 162
<223> OTHER INFORMATION: Xaa = Aspartic Acid or Glutamic Acid
<220> FEATURE:
<221> NAME/KEY: Variant
<222> LOCATION: 173
<223> OTHER INFORMATION: Xaa = Valine or Isoleucine
<220> FEATURE:
<221> NAME/KEY: Variant
<222> LOCATION: 180
<223> OTHER INFORMATION: Xaa = Methionine or Isoleucine
<220> FEATURE:
<221> NAME/KEY: Variant
<222> LOCATION: 185
<223> OTHER INFORMATION: Xaa = Alanine or Serine
<220> FEATURE:
<221> NAME/KEY: Variant
<222> LOCATION: 199
<223> OTHER INFORMATION: Xaa = Tyrosine or Phenylalanine
<220> FEATURE:
<221> NAME/KEY: Variant
<222> LOCATION: 202
<223> OTHER INFORMATION: Xaa = Valine or Isoleucine
<220> FEATURE:
<221> NAME/KEY: Variant
<222> LOCATION: 207
<223> OTHER INFORMATION: Xaa = Valine or Isoleucine or Leucine
<220> FEATURE:
<221> NAME/KEY: Variant
<222> LOCATION: 208
<223> OTHER INFORMATION: Xaa = Threonine or Serine
<220> FEATURE:
<221> NAME/KEY: Variant
<222> LOCATION: 210
<223> OTHER INFORMATION: Xaa = Lysine or Arginine
<220> FEATURE:
<221> NAME/KEY: Variant
<222> LOCATION: 223
<223> OTHER INFORMATION: Xaa = Valine or Isoleucine
<220> FEATURE:
<221> NAME/KEY: Variant
<222> LOCATION: 229
<223> OTHER INFORMATION: Xaa = Serine or Alanine
<220> FEATURE:
<221> NAME/KEY: Variant
<222> LOCATION: 240
<223> OTHER INFORMATION: Xaa = Valine or Isoleucine
<220> FEATURE:
<221> NAME/KEY: Variant
<222> LOCATION: 245
<223> OTHER INFORMATION: Xaa = Leucine or Methionine
<220> FEATURE:
<221> NAME/KEY: Variant
<222> LOCATION: 264
<223> OTHER INFORMATION: Xaa = Valine or Leucine or Methionine
<220> FEATURE:
<221> NAME/KEY: Variant
<222> LOCATION: 4, 5, 6, 7, 9, 10, 11, 12, 13, 14, 16, 19, 21, 22, 24, 29, 31, 32, 33, 34, 35, 36, 38, 41, 42, 43, 44, 45, 46, 47, 48, 49, 50, 51, 52, 54, 55, 58, 62, 72, 73, 74, 75, 76, 78, 79, 80, 82, 84, 88, 89, 93, 94, 95, 98, 99, 100, 101, 102
<223> OTHER INFORMATION: Xaa = Any Amino Acid
<220> FEATURE:
<221> NAME/KEY: Variant
<222> LOCATION: 103, 104, 106, 108, 109, 111, 112, 117, 122, 126, 129, 131, 139, 140, 146, 149, 153, 160, 163, 164, 165, 166, 167, 168, 169, 170, 171, 172, 174, 177, 184, 186, 187, 189, 190, 191, 192, 194, 205, 209, 211, 212, 213, 215, 216, 218, 219
<223> OTHER INFORMATION: Xaa = Any Amino Acid
<220> FEATURE:
<221> NAME/KEY: VARIANT
<222> LOCATION: 220, 221, 222, 225, 227, 228, 230, 231, 232, 233, 234, 235, 236, 237, 238, 239, 241, 243, 244, 246, 247, 249, 250, 251, 252, 253, 254, 255, 256, 257, 258, 259, 260, 261, 262, 263, 267, 269, 270, 271, 272, 273, 274, 275, 278, 280, 281, 282, 283, 284, 285,
<223> OTHER INFORMATION: Xaa = Any Amino Acid
<220> FEATURE:
<221> NAME/KEY: VARIANT
<222> LOCATION: 287, 288, 289, 290, 291, 292, 293, 294
<223> OTHER INFORMATION: Xaa = Any Amino Acid

<400> SEQUENCE: 172

Leu Asn Xaa Xaa Xaa Xaa Xaa Thr Xaa Xaa Xaa Xaa Xaa Xaa Xaa Xaa
1               5                   10                  15

Xaa Gly Xaa Gly Xaa Xaa Gly Xaa Xaa Tyr Xaa Ala Xaa Xaa Xaa Xaa
            20                  25                  30

Xaa Xaa Xaa Xaa Ala Xaa Lys Xaa Xaa Xaa Xaa Xaa Xaa Xaa Xaa Xaa
        35                  40                  45

Xaa Xaa Xaa Xaa Met Xaa Xaa Glu Xaa Xaa Thr Xaa Gly Xaa Xaa Xaa
    50                  55                  60

His Arg Asn Leu Xaa Xaa Leu Xaa Xaa Xaa Xaa Xaa Xaa Xaa Xaa Xaa
65                  70                  75                  80

Gly Xaa Xaa Xaa Tyr Xaa Met Xaa Xaa Gly Ser Xaa Xaa Xaa Xaa Leu
                85                  90                  95

His Xaa Xaa Xaa Xaa Xaa Xaa Xaa Leu Xaa Trp Xaa Xaa Arg Xaa Xaa
            100                 105                 110

-continued

```
Xaa Ala Xaa Gly Xaa Xaa His Gly Leu Xaa Tyr Xaa His Xaa Asp Cys
        115                 120                 125

Xaa Pro Xaa Ile Xaa His Arg Asp Xaa Lys Xaa Xaa Asn Ile Leu Xaa
    130                 135                 140

Xaa Xaa Xaa Xaa Xaa Pro His Ile Xaa Asp Phe Gly Xaa Xaa Xaa Xaa
145                 150                 155                 160

Xaa Xaa Xaa Xaa Xaa Xaa Xaa Xaa Xaa Xaa Xaa Xaa Xaa Xaa Gly Thr
                165                 170                 175

Xaa Gly Tyr Xaa Ala Pro Glu Xaa Xaa Xaa Xaa Thr Xaa Xaa Xaa Xaa
            180                 185                 190

Glu Xaa Gly Val Tyr Ser Xaa Gly Val Xaa Leu Leu Xaa Leu Xaa Xaa
        195                 200                 205

Xaa Xaa Xaa Xaa Xaa Asp Xaa Xaa Phe Xaa Xaa Xaa Xaa Xaa Xaa Val
    210                 215                 220

Xaa Trp Xaa Xaa Xaa Xaa Xaa Xaa Xaa Xaa Xaa Xaa Xaa Xaa Xaa Xaa
225                 230                 235                 240

Xaa Asp Xaa Xaa Xaa Xaa Xaa Glu Xaa Xaa Xaa Xaa Xaa Xaa Xaa Xaa
                245                 250                 255

Xaa Xaa Xaa Xaa Xaa Xaa Xaa Xaa Ala Leu Xaa Cys Xaa Xaa Xaa Xaa
            260                 265                 270

Xaa Xaa Xaa Arg Pro Xaa Met Xaa Xaa Xaa Xaa Xaa Xaa Leu Xaa Xaa
        275                 280                 285

Xaa Xaa Xaa Xaa Xaa Xaa
    290
```